United States Patent
Alliel et al.

(12) 
(10) Patent No.: US 6,919,438 B1
(45) Date of Patent: Jul. 19, 2005

(54) NUCLEIC SEQUENCE AND DEDUCED PROTEIN SEQUENCE FAMILY WITH HUMAN ENDOGENOUS RETROVIRAL MOTIFS, AND THEIR USES

(75) Inventors: Patrick M. Alliel, Clamart (FR); Jean-Pierre Perin, Le Plessis-Robinson (FR); François Rieger, Boulogne (FR)

(73) Assignee: Institut National de la Sante et de la Recherche Medical-Inserm, Paris (FR)

( * ) Notice: Subject to any disclaimer, the term of this patent is extended or adjusted under 35 U.S.C. 154(b) by 0 days.

(21) Appl. No.: 09/719,554

(22) PCT Filed: Jun. 23, 1999

(86) PCT No.: PCT/FR99/01513

§ 371 (c)(1),
(2), (4) Date: Jan. 18, 2001

(87) PCT Pub. No.: WO99/67395

PCT Pub. Date: Dec. 29, 1999

(30) Foreign Application Priority Data

Jun. 23, 1998 (FR) .............................. 98 07920

(51) Int. Cl.$^7$ .......................... C07H 21/04; C12Q 1/70; A61K 39/21
(52) U.S. Cl. ........................ 536/23.1; 435/5; 424/207.1
(58) Field of Search ............................ 536/23.1; 435/5; 424/207.1

(56) References Cited

U.S. PATENT DOCUMENTS 6,184,025 B1 * 2/2001 Perron et al. ............ 435/235.1

OTHER PUBLICATIONS

R.S. Fujinami, et al., *Trends in Microbiology*, vol. 7, No. 7, pp. 263–264 (1999).

I. Steiner, et al., *Current Neurology and Neuroscience Reports*, vol. 1, No. 3, pp. 271–276 (2001).

* cited by examiner

*Primary Examiner*—James Housel
*Assistant Examiner*—Stacy B. Chen
(74) *Attorney, Agent, or Firm*—Oblon, Spivak, McClelland, Maier & Neustadt, P.C.

(57) ABSTRACT

The invention concerns a novel nucleic sequence and deduced protein sequence family with whole or partial human endogenous retroviral motifs. The invention also concerns the detection and/or the use of said nucleic sequences and said corresponding protein sequences or fragments of said sequences, for diagnostic, prophylactic and therapeutic uses, in particular for neuropathological conditions with autoimmune constituent such as multiple sclerosis. Said purified nucleic acid sequences comprise all or part of a sequence coding for a human endogenous retroviral sequence having at least eny-type retroviral motifs, corresponding to the sequence SEQ ID NO:1 or to a sequence having a homology level with said sequence SEQ ID NO:1 not less than 80% of more than 190 nucleotides or not less than 70% on more than 600 nucleotides for env-type domains. The invention further concerns the use of the flanking or adjacent sequence of said sequences and controlled by the latter, as diagnostic reagents.

13 Claims, 64 Drawing Sheets

FIG. 1A

Figure 2:

```
CAAACCCAACATCTCAACTCACCTGGACTATTTTACCCCAAGGGTTCAGGGATAGTCCCCATCTATTTGGCC    5255
AGGCATTAGCCCAAGACTTGAGCCAATCCTCATACCTGGACACTTGTCCTTCGGTAGGTGGATGATTTACTT    5327
TTGGCCGCCCATTCAGAAACCTTGTGCCATCAAGCCACCCAAGCGCTCTTCAATTTCCTCGCTACCTGTGGC    5399
TACATGGTTTCCAAACCAAAGGCTCAACTCTGCTCACAGCAGGTTACTTAGGGCTAAAATTATCCAAAGGCA    5471
CCAGGGCCCTCAGTGAGGAACACATCCAGCCTATACTGGCTTATCCTCATCCCAAAACCCTAAAGCAACTAA    5543
GGGGATTCCTTGGCGTAATAGGTTTCTGCCGAAAATGGATTCCCAGGTATGGCGAAATAGCCAGGTCATTAA    5615
ATACACTAATTAAGGAAACTCAGAAAGCCAATACCCATTTAGTAAGATGGACAACTGAAGTAGAAGTGGCTT    5687
TCCAGGCCCTAACCCAAGCCCCAGTGTTAAGTTTGCCAACAGGGCAAGACTTTTCTTCATATGTCACAGAAA    5759
AAACAGGAATAGCCTCTAGGAGTCCTTACACAGATCCGAGGGATGAGCTTGCAACCTGTGGCATACCTGACTA    5831
AGGAAATTGATGTAGTGGCAAAGGGTTGACCTCATTGTTTACGGGTAGTGGTGGCAGTAGCAGTCTTAGTAT    5903
CTGAAGCAGTTAAAATAATACAGGGAAGAGATCTTACTGTGTGGACATCTCATGATGTGAATGGCATACTCA    5975
CTGCTAAAGGAGACTTGTGGCTGTCAGACAACTGTTTACTTAAATGTCAGGCTCTATTACTTGAAGGGCCAG    6047
TGCTGCGACTGTGCACTTGTGCAACTCTTAACCCAGCCACATTTCTTCCAGACAATGAAGAAAAGATAAAAC    6119
ATAACTGTCAACAAGTAATTTCTCAAACCTATGCCACTCGAGGGGACCTTTTAGAGGTTCCTTTGACTGATC    6191
CCGACCTCAACTTGTATACTGATGGAAGTTCCTTTGTAGAAAAAGGACTTCGAAAAGTGGGGTATGCAGTGG    6263
TCAGTGATAATGGAATACTTGAAAGTAATCCCCTCACTCCAGGAACTAGTGCTCAGCTAGCAGAACTAATAG    6335
CCCTCACTTGGGCACTAGAATTAGGAGAAGAAAAAGGGCAAATATATATACAGACTCTAAATATGCTTACC    6407
TAGTCCTCCATGCCCATGCAGCAATATGGAAAGAAAGGGAATTCCTAACTTCTGAGAGAACACCTATCAAAC    6479
ATCAGGAAGCCATTAGGAAATTATTATTGGCTGTACAGAAACCTAAAGAGGTGGCAGTCTTACACTGCCGGG    6551
GTCATCAGAAGGAAAGGAAAGGGAAATAGAAGAGAACTGCCAAGCAGATATTGAAGCCAAAAGAGCTGCAA    6623
GGCAGGACCCTCCATTAGAAATGCTTATAAAACAACCCCTAGTATAGGGTAATCCCCTCCGGGAAACCAAGC    6695
CCCAGTACTCAGCAGGAGAAACAGAATGGGGAACCTCACGAGGACAGTTTTCTCCCCTCGGGACGGCTAGCC    6767
ACTGAAGAAGGGAAAATACTTTTGCCTGCAACTATCCAATGAAATTACTTAAAACCCTTCATCAAACCTTT    6839
CACTTAGGCATCGATAGCACCCATCAGATGGCCAAATCATTATTTACTGGACCAGGCCTTTTCAAAACTATC    6911
AAGCAGATAGTCAGGGCCTGTGAAGTGTGCCAGAGAAATAATCCCCTGCCTTATCGCCAAGCTCCTTCAGGA    6983
GAACAAAGAACAGGCCATTACCCTGGAGAAGACTGGCAACTGATTTTACCCACAAGCCCAAACCTCAGGGAT    7055
TTCAGTATCTACTAGTCTGGGTAGATACTTTCACGGGTTGGGCAGAGGCCTTCCCCTGTAGGACAGAAAAGG    7127
CCCAAGAGGTAATAAAGGCACTAGTTCATGAAATAATTCCCAGATTCGGACTTCCCCGAGGCTTACAGAGTG    7199
ACAATAGCCCTGCTTTCCAGGCCACAGTCCTCAGGGAGTATCCCAGGCGTTAGGTATACGATATCACTTAC    7271
ACTGCGCCTGAAGGCCACAGTCCTCAGGGAAGGTCGAGAAAATGAATGAAACACTCAAAGGACATCTAAAAA    7343
AGCAAACCCAGGAAACCCACCTCACATGGCCTGCTCTGTTGCCTATAGCCTTAAAAAGAATCTGCAACTTTC    7415
CCCAAAAAGCAGGACTTAGCCCATACGAAATGCTGTATGGAAGGCCCTTCATAACCAATGACCTTGTGCTTG    7487
ACCCAAGACAGCCAACTTAGTTGCAGACATCACCTCCTTAGCCAAATATCAACAAGTTCTTAAAACATTACA    7559
AGGAACCTATCCCTGAGAAGAGGGAAAAGAACTATTCCACCCTTGTGACATGGTATTAGTCAAGTCCCTTCC    7631
CTCTAATTCCCCATCCCTAGATACATCCTGGGAAGGACCCTACCCAGTCATTTTATCTACCCCAACTGCGGT    7703
TAAAGTGGCTGGAGTGGAGTCTTGGATACATCACACTTGAGTGTCAAATCCTGGATACTGCCAAAGGAACCTGA    7775
AAATCCAGGAGACAACGCTAGCTATTCCTGTGAACCTCTAGAGGATTTGCGCCTGCTCTTCAAACAACAACC    7847
AGGAGGAAAGTAACTAAAATCATAAATCCCCATGGCCCTCCCTTATCATATTTTTCTCTTTACTGTTCTTTT    7919
ACCCTCTTTCACTCTCACTGCACCCCCTCCATGCCGCTGTATGACCAGTAGCTCCCCTTACCAAGAGTTTCT    7991
ATGGAGAATGCAGCGTCCCGGAAATATTGATGCCCATCGTATAGGAGTCTTTCTAAGGGAACCCCCACCTT    8063
CACTGCCCACACCCATATGCCCCGCAACTGCTATCACTCTGCCACTCTTTGCATGCATGCAAATACTCATTA    8135
TTGGACAGGAAAATGATTAATCCTAGTTGTCCTGGAGGACTTGGAGTCACTGTCTGTTGGACTTACTTCAC    8207
CCAAACTGGTATGTCTGATGGGGGTGGAGTTCAAGATCAGGCAAGAGAAAAACATGTAAAAGAAGTAATCTC    8279
CCAACTCACCCGGGTACATGGCACCTCTAGCCCCTACAAAGGACTAGATCTCTCAAAACTACATGAAACCCT    8351
CCGTACCCATACTCGCCTGGTAAGCTCCTATTTAATACCACCCTCACTGGGCTCCATGAGGTCTCGGCCCAAAA    8423   Env
CCCTACTAACTGTTGGATATGCCTCCCCCTGAACTTCAGGCCATATGTTTCAATCCCTGTACCTGAACAATG    8495   domain
GAACAACTTCAGCACAGAAATAAACACCACTTCCGTTTTAGTAGGACCTCTTGTTTCCAAATCTGGAAATAAC    8567
CCATACCTCAAACCTCACCTGTGTAAAATTTAGCAATACTACATACACAACCAACTCCCAATGCATCAGGTG    8639
GGTAACTCCTCCCACACAAATAGTCTGCCTACCCTCAGGAATATTTTTGTCTGTGGTACCTCAGCCTATCG    8711
TTGTTTGAATGGCTCTTCAGAATCTATGTGCTTCCTCTCATTCTTAGTGCCCCTATGACCATCTACACTGA    8783
ACAAGATTTATACAGTTATGTCATATCTAAGCCCCGCAACAAAAGAGTACCCATTCCTTCCTTTTGTTATAGG    8855
AGCAGGAGTGCTAGGTGCACTAGGTACTGGCATTGGCGGTATCACAAACCTCTACTCAGTTCTACTACAAACT    8927
ATCTCAAGAACTAAATGGGGACATGGAACGGGTCGCCGACTCCCTGGTCACCTTGCAAGATCAACTTAACTC    8999
CCTAGCAGCAGTAGTCCTTCAAAAATCGAAGAGCTTTAGACTTGCTAACCGCTGACTGAGAAAGTTAAAGAAATTCG    9071
ATTTTTAGGGGAAGATGCTGTGTTATTATGTTAATCAATCCGGAATCGTCACTGAGAAAGTTAAAGAAATTCG    9143
AGATCGAATACAACGTAGAGCAGAGGAGCTTCGAAACACTGGACCCTGGGGCCTCCTCAGCCAATGGATGCC    9215
CTGGATTCTCCCCTTCTTAGGACCTCTAGCAGCTATAATATTGCTACTCCTCTTTGGACCCTGTATCTTTAA    9287
CCTCCTTGTTAACTTTGTCTCTTCCAGAATCGAAGCTGTAAAACTACAAATGGAGCCCAAGATGCAGTCCAA    9359
GACTAAGATCTACCGGCAGACCCCTGGACCGGCCTGCTAGCCCACGATCTGATGTTAATGACATCAAAGGCAC    9431
CCCTCCTGAGGAAATCAGCTGCACAACCTCTACTACGCCCCAATTCAGCAGGAAGCAGTTAGAGCGGTC    9503
TCGGCCAACCTCCCCAACAGCACTTAGGTTTTCCTGTTGAGATGGGGACTGAGAGACAGGACTAGCTGGAT    9575
TTCCTAGGCTGACTAAGAATCCCTAAGCCTAGCTGGGAAGGTGACCACATCCACCTTTAAACACGGGGCTTG    9647
CAACTTAGCTCACACCTGACCAATCAGAGAGCTCACTAAAATGCTAATTAGGCAAAGACAGGAGGTAAAGAA    9719
ATAGCCAATCATCTATTGCCTGAGAGCACAGCACGAGGGACAATGATCGGGATATAAACCCAAGTCTTCGAG    9791
CCGGCAACGGCAACCCCCTTTGGGTCCCCTCCCTTTGTATGGGAGCTCTGTTTTCATGCTATTTCACTCTAT    9863
TAAATCTTGCAACTGCACTCTTCTGGTCCATGTTTCTTACGGCTTGAGCTGAGCTTTCGCTCGCCATCCACC    9935   Repeated
ACTGCTGTTTGCCGCCACCGCAGACCCGCCGCTGACTCCCATCCCTCTGGATCATGCAGGGTGTCCGCTGTG    10007  region
CTCCTGATCCAGCGAGGCACCCATTGCCGCTCCCAATCGGGCTAAAGGCTTGCCATTGTTCCTGCATGGCTA    10079  R1
AGTGCCTGGGTTCATCCTAATTGAGCTGAACACTAGTCACTGGGTTCCATGGTTCTCTTCTGTGACCCACAG    10151
CTTCTAATAGAGCTATAACACTCACCGCATGGCCCAAGGTTCCATTCCTTGAATCCATAAGGCCAAGAACCC    10223
CAGGTCAGAGAACACGAGGCTTGCCACCATCTTGGGAGCTCTGTGAGCAAGGACCCCCAAGTAACACAACCA    10295
TGAGGGTGCAAATGCATGGGCCACTAATGGTAGAGCAAGAAAACAGAAGGGCCCTGGTTCCTCGAAGGCATC    10367
AGTGAGCTGAAATGCCTGCCCTGGATGTCCTATTCCTAGGTGTTTTCTGCCTGAAGCAGATTAAACCCTTT    10439
GTTCACTTCTCCAAGTAGGGCTTCTATTACAGCCAAATCAATCCCCACCCCAGATGACAT    10500
```

*FIG. 1B*

```
ACTGAGAGACAGGACTAGCTGGATTTCCTAGGCCGACTAAGAATCCCTAAGCCTAGCTGGGAAGGTGACC
::::::::::::::::::::::::::::::::::::: :::::::::::::::::::::::::::::::
ACTGAGAGACAGGACTAGCTGGATTTCCTAGGCTGACTAAGAATCCCTAAGCCTAGCTGGGAAGGTGACC
ACGTCCACCTTTAAACACGGGGCTTGCAACTTAGCTCACACCTGACCAATCAGAGAGCTCACTAAAATGC
 :::::::::::::::::::::::::::::::::::::::::::::::::::::::::::::::::::
ACATCCACCTTTAAACACGGGGCTTGCAACTTAGCTCACACCTGACCAATCAGAGAGCTCACTAAAATGC
TAATTAGGCAAAGACAGGAGGTAAAGAAATAGCCAATCATCTATTGCCTGAGAGCACAGCAGGAGGGACA
::::::::::::::::::::::::::::::::::::::::::::::::::::::::::::::::::::::
TAATTAGGCAAAGACAGGAGGTAAAGAAATAGCCAATCATCTATTGCCTGAGAGCACAGCAGGAGGGACA
ACAATCGGGATATAAACCCAGGCATTCGAGCTGGCAACAGCAGCCCCCCTTTGGGTCCCTTCCCTTTGTA
 :  :::::::::::::::   :::::::: :::::::: :::::   :::::::::::::::::::::
ATGATCGGGATATAAACCCAAGTCTTCGAGCCGGCAACGGCAACCCCC-TTTGGGTCCCCTCCCTTTGTA
TGGGAGCT--GTTTTCATGCTATTTCACTCTATTAAATCTTGCAACTGCACTCTTCTGGTCCATGTTTCT
:::::::   ::::::::::::::::::::::::::: :::::::::::::::::::::::::::::::
TGGGAGCTCTGTTTTCATGCTATTTCACTCTATTAAATCTTGCAACTGCACTCTTCTGGTCCATGTTTCT
TACGGCTCGAGCTGAGCTTTTGCTCACCGTCCACCACTGCTGTTTGCCACCACCGCAGACCTGCCGCTGA
:::::::  ::::::::::::   ::::  ::  ::::::::::::::  ::::::::::::::::::::
TACGGCTTGAGCTGAGCTTTCGCTCGCCATCCACCACTGCTGTTTGCCGCCACCGCAGACCCGCCGCTGA
CTCCCATCCCTCTGGATCCTGCAGGGTGTCCGCTGTGCTCCTGATCCAGCGAGGCGCCCATTGCCGCTCC
:::::::::::::::::  ::::::::::::::::::::::::::::::::::::::::::::::::::
CTCCCATCCCTCTGGATCATGCAGGGTGTCCGCTGTGCTCCTGATCCAGCGAGGCACCCATTGCCGCTCC
CAATTGGGCTAAAGGCTTGCCATTGTTCCTGCACGGCTAAGTGCCTGGGTTTGTTCTAATTGAGCTGAAC
 ::::  ::::::::::::::::::::::::  :::::::::::::::   :  ::::::::::::::::
CAATCGGGCTAAAGGCTTGCCATTGTTCCTGCATGGCTAAGTGCCTGGGTTCATCCTAATTGAGCTGAAC
ACTAGTCACTGGGTTCCATGGTTCTCTTCTGTGACCCACGGCTTCTAATAGAACTATAACACTTACCACA
:::::::::::::::::::::::::::::::::::::::  ::::::::::: ::::::::::: :: ::
ACTAGTCACTGGGTTCCATGGTTCTCTTCTGTGACCCACAGCTTCTAATAGAGCTATAACACTCACCGCA
TGGCCCAAGATTCCATTCCTTGGAATCCGTGAGGCAAGAACTCCAGGTCAGAGAATACGAGGCTTGCCA
::::::::: :::::::::::: ::::::::::  :::::::: :::::::::::::: ::::::::::
TGGCCCAAGGTTCCATTCCTTG-AATCCATAAGGCCAAGAACCCCAGGTCAGAGAACACGAGGCTTGCCA
CCATCTTGGAAGC
::::::::: :::
CCATCTTGGGAGC
```

FIG. 3

IPMALPYHIFLFTVLLPSFTLTAPPPCRCMTSSSPYQEFLWRMQRPGNIDAPSYRSLSKG
TPTFTAHTHMPRNCYHSATLCMHANTHYWTGKMINPSCPGGLGVTVCWTYFTQTGMSDGG
GVQDQAREKHVKEVISQLTRVHGTSSPYKGLDLSKLHETLRTHTRLVSLFNTTLTGLHEV
SAQNPTNCWICLPLNFRPYVSIPVPEQWNNFSTEINTTSVLVGPLVSNLEITHTSNLTCV
KFSNTTYTTNSQCIRWVTPPTQIVCLPSCIFFVCGTSAYRCLNGSSESMCFLSFLVPPMT
IYTEQDLYSYVISKPRNKRVPILPFVIGAGVLGALGTGIGGITTSTQFYYKLSQELNGDM
ERVADSLVTLQDQLNSLAAVVLQNRRALDLLTAERGGTCLFLGEECCYYVNQSGIVTEKVKE IRDRIQRRAEELR
NTGPWGLLSQWMPWILPFLGPLAAIILLLLFGPCIFNLLVNFVSSRIEAVKLQMEPKMQSKTKIYRRPLDRPASP
RSDVNDIKGTPPEEISAAQPLLRPNSAGSS

FIG. 4

1) NSLAAVVLQNRRALDLLTAESGGTFLFLEEKC
2) NSLAAVVLQNRRALDLLTAERGGTCLFLGEEC
3) DSLAAVTLQNHQGLDLLTAEKGGLCYFLGEDC
4) DSLAAVTLQNHQGLDLLIAEKGGLCTFLGEEC
5) DSLAAVTLQNCRGLDLLTAEKGGHYTFLGEEC
6)             LQNRRGLDLLFLKEGGLC
7) DSLAKVVLQNRRGLDLLTAEQGGICLALQEKC

FIG. 5

TSFVEKANGVKCHKYKLSFHXETTHNYVKSVIYALQEAFRVYLPILPASPTPSPTNKDPPSTQMVQKEIDKRVNSEPKS
ANIPQLXPLQAVGGREFGPARVHVPFSLPDLKQIKTDLGKFSDNPDGYIDVLQGLGQFFDLTWRDIMSLLNQTLTPNER
SATITAAXEFGDLWYLSQVNDRMTTEEREXFPTGQQAVPSLDPHWDTESEHGDWCCRHLLTCVLEGLRKTRKKSMNYSM
MSTITQGREENPTAFLERLREALRKRASLSPDSSEGQLILKRKFITQSAADIRKKLQKSAVGPEQNLETLLNLATSVFY
NRDQEEQAEQDKRDXKKGHRFSHDPQASGLWRLWKREKLGKLNAXXGLLPVRSTRTLXKRLSKXKXAAPSSMPLISRES
LEGPLPQGTKVLXVRSHXPD/SSSRT

FIG. 6

```
CCTGGCACTCCTGAGGGAAGTATAAATTATAACACCATCTTACAGCTAGACCTCTTTTGTAGAAAAGGCA
:::::: :::::::::::::::::::::::::::::::::::::::::::::::::::::::::::
CCTGGC-CTCCTGAGGGAAGTATAAATTATAACACCATCTTACAGCTAGACCTCTTTTGTAGAAAAGAAG
-CAAATGGAGTGAAGTGCCATAAGTACAAACTTTCTTTTCATTAAGAGACAACTCACAATTATGTAAAAA
 :::::::::::::::::::::::::: ::::::::::::::::::::: ::::: :::::::::::::::
GCAAATGGAGTGAAGTGCCATATGTACAAACTTTCTTTTCATTAAGAGATAACTCCCAATTATGTAAAAA
GTGTGATTTATGCCCTACAGGAAGCCTTCAGAGTCTACCTCCCTATCCCAGCAT--CCCCGACTCCTTCC
:::::::::::::::::::::::::::: ::::::::::::::::: ::::::: ::::  :::::::::
GTGTGATTTATGCCCTACAGGAAGCCCTCAGAGTCTACCTCCCGACCCCAGCAAGACCCCAACTCCTTCT
CCAACTAATAAGGACCCCCCTTCAACCCAAATGGTCCAAAAGGAGATAGACAAAAGGGTAAACAGTGAAC
::::::::::::::::::::::::::::::::::::::::::::::::::::::::::::: :::::::
CCAACTAATAAGGACCCCCCTTCAACCCAAATGGTCCAAAAGGAGATAGACAAAGGGGTAAACAATGAAC
CAAAGAGTGCCAATATTCCCCAATTATGACCC-CTCCAAGCAGTGGGAGGAACAGAATTCGGCCCAGCCA
:::::::::::::::: : : ::::: :::: :::::::::::::::: :: :: ::::::::::
CAAAGAGTGCCAATATTACACGATTAT-ACTCGCTCCAAGCAGTGGGAGGA-GA-ATTT-GGCCCAGCCA
GAGTGCATGTGCCTTTTTCTCTCCCAGACTTAAAGCAAATAAAAACAGACTTAGGTAAATTCTCAGATAA
: :::::::::: :::::::::::: :::: :::::::::: ::::  ::::::::AATTCTCAGATAA
GCGTGCATGTACCTTTTTCTCTCTCAGATTTAAAGCAAATTAAAATAGACCTAGGTAAATTCTCAGATAA
CCCTGATGGCTATATTGATGTTTTACAAGGGTTAGGACAATTCTTTGATCTGACATGGAGAGATATAATG
::::::::::::::::::::::::::::::::::::::::: ::::::::::::::::::::::::::::
CCCTGATGGCTATATTGATGTTTTACAAGGGTTAGGACAATCCTTTGATCTGACATGGAGAGATATAATG
TCACTGCTAAATCAGACACTAACCCCAAATGAGAGAAGTGCCACCATAACTGCAGCCTGAGAGTTTGGCG
: :::::::::::::::::::::::::: : ::::::: ::::::: ::::::::::::::::::::::
TTACTGCTAAATCAGACACTAACCCCAAATGAAAAAAGTGCTGCCATAACAGCAGCCTGAGAGTTTGGCG
ATCTCTGGTATCTCAGTCAGGTCAATGATAGGATGACAACAGAGGAAAGAGAATGATTCCCCACAGGCCA
: :::::::::::::::::::::::::::::::::::::::::::::::: :::::::::::::::::
AACTCTGGTATCTCAGTCAGGTCAATGATAGGATGACAACAGATGAAAGAGAATGATTCCCCACAGGCCA
GCAGGCAGTTCCCAGTCTAGACCCTCATTGGGACACAGAATCAGAACATGGACATTGGTGCTGCAGACAT
:::::::::::::::: :::::::::::: ::::::::::::::: ::::::::::: ::::::::
GCAGGCAGTTCCCAGTGTAGACCCTCATTAGGACACAGAATCAGAACTTGGAGATTGGTGCCACAGACAT
TTGCTAACTTGTGTGCTAGAAGGACTAAGGAAAACTAGGAAGAAGTCTATGAATTACTCAATGATGTCCA
:::::::::::: :::::::::::::::::::::::::::::::: : :::::::: ::::::::::::
TTGCTAACTTGCGTGCTAGAAGGACTAAGGAAAACTAGGAAGAAGCCCATGAATTATTCAATGATGTCCC
CCATAACACAGGGAAGGGAAGAAAATCCTACTGCCTTTCTGGAGAGACTAAGCGAGGCATTGAGGAAGCG
: ::::::::::::  ::::::::::::::::::::::::::::::::::::::::: :: ::::::::
CTATAACACAGGGAAAGGAAGAAAATCCTACTGCCTTTCTGGAGAGACTAAGGGAAGGATTGAGGAAGCA
TGCCTCTCTGTCACCTGACTCTTCTGAAGGCCAACTAATCTTAAAGCGTAAGTTTATCACTCAGTCAGCT
: :::: :::::::::::::::: : :::::::::::::::::: :::::::::::::::::::::::
TACCTCCCTGTCACCTGACTCTATTAAAGGCCAACTAATCTTAAAGGATAAGTTTATCACTCAGTCAGCT
GCAGACATTAGAAAAAAACTTCAAAAGTCTGCCGTAGGCCCGGAGCAAAACTTAGAAACCCTATTGAACT
::::: :::: ::::::::::::::: :::::::::::: :::::::::::::::::::: :::::
GCAGAGATTAAGAAAAAACTTCAAAAGTATGCCTTAGGCCCAGAGCAAAACTTAGAAACCCTACTGAACT
TGGCAACCTCGGTTTTTTATAATAGAGATCAGGAGGAGCAGGCGGAACAGGACAAACGGGATTAAAAAAA
::::::::::: :::::::::::::::::::::: :::: ::: :::::: ::::: :::::: :::
TGGCAACCTCAGTTTTTTATAATAGAGATCAGGAAGAGCAGG-GGAATGGGACAAATGGGATAAAAAAAA
A-------GGCCACCGCTTTAGTCATGACCCTCAGGCAAGTGGACTTTGGAGGCTCTGGAAAAGGGAAAA
:       ::  :: ::::::::::: :: :::::::::: :::::::::::::::: :::::::::::::
AAAAAAAGGTGACTGCTTTAGTCGTGGCCCTCAGGCAAATGGACTTTGGAGGCTCCAGAAAAGGGAAAA
GCTGGGCAAATTGAATGCCTAATAGGGCTTGCTTCCAGTGCGGTCTACAAGGACACTTTAAAAAAGATTG
:::: :::::::::::::::::: :::::::::: ::::: :::::::::::::::::: ::::::::
GCTGAGCAAATTGAATGCCTAACAGGGCTTGCTTCTAGTGTGGTCTACAAGGACACTTTAAAAAAGATTG
TCCAAGTAGAAGTAAGCCGCCCCCTCGTCCATGCCCCTTATTTCAAGGGAATCACTGGAAGGCCCACTGC
:::::::::::   :::: ::::::: ::::::::::: ::::::::::::::::::::::::::::::
TCCAAGTAGAAACAAGCTGCCCCCTTGTCCATGCCCCTTATGTCAAGGGAATCACTGGAAGGCCCACTGC
CCCAGGGGACAAAGGTCCTCTGAGTCAGAAGCCACTAACCAGATGATCCAGCAGCAGGACTGAGGGTGCC
::::: ::  :::::::::::::::::::::::::::::: :::: :::::::::::::::::  ::::
CCCAGGAGATGAAGGTCCTCTGAGTCAGAAGCCACTAACCAGATAATCCAGCAGCAGGACTGAGGATGCC
TGGGGCAAGCGCCATCCCATGCCATCACCCTCACAGAGCCCTGGGTATGCTTGACCATTGAGGGCCAGGA
 :::: ::::::::::::: :::::::::::::::::::::: :::::::::::::::::::::::::::
CAGGGCAAGCGCCAGCCCTGCCATCACCCTCACAGAGCCCTTGGGTATGCTTGACCATTGAGGGCCAGGA
GGTT----GTCTCCTGGACACTGGTGCGGTCTTCTTAGTCTTACTCTTCTGTCCCGGACAACTGTCCTCC
::::    :::::: :::::::::::: :: ::::: ::::: ::::::: ::::::: :::::::: :
GGTTCACTGTCTCTTGGACACTGGTATGGCCTTCTCAGTCTTACTCTCCTGTCCTGGACAACTGTCCTTC
```

*FIG. 7*

```
01/                              TAAATCCCCATGGCCCTCCCTTATCATATTTTTCT
02/                              TAAATCCCC-TGGCCCTCCCTTATCATATTTTTCT
03/                              TAAATCCCCATGGCCCTCCCTTATCATATTTTTCT
04/                              TAGATCCTCATGGCCCTCC-TTGTCATATTTTTT

01/CTTTACTGTTCTTTTA-CCCTCTTTCACTCTCACTGCACCCCCTCCATGCCGCTGTATGACC
02/CTTTACTGTTCTCTTACCCCCCTTTCACTCTCACTGCACCCCGTCCATGCCACTGCACCCCC
03/CTTTACTGTTCTCTTA-CCCCCTTTCTCTCTCACTGCACCCCCTCCATGCTGCTGTACAACC
04/CTTTACTGTTCTCTTA-CCCCCTTTCACTCTCACTGAACCCCCTCCATGCCACTGTACTACC

01/AGT------------------AGCTCCCCTTACCAAGAGTTTCTATGGAGAATGCAGCGT
02/GTCCATGCCCGTCTCATGCCAGTAGCTCCCCTTAGCAAGAGTTTCTATGGAGAATGCAGCGT
03/AGC------------------AGCTCCCCTTACCAAGAGTTTCTATGAAGAATGCGGCTT
04/AGT------------------AGCTCCCATTACCAAGAGCTTCTATGGACAATGCGGCTT

01/CCCGGAAATATTGATGCCCCATCGTATAGGAGTCTTTCTAAGGGAACCCCCACCTTCACTGC
02/CCCGGAAATATTGATGCCCCATTGTATAGGAGTTTATCTAAGGGAACCCCCACCTTCACTGC
03/CCCAGAAATATTGATGCCCCATCAAATAGGAGTTTACCTAAAGGAAACTCCACCTTCACTGC
04/CCTGGAAATATTGATGACCCATCGTATAGGAGTTTTTCTAAAGGAAACCCCATTTTCACCAC

01/CCACACCCATATGCCCCGCAACTGCTATCACTCTGCCACTCTTTGCATGCATGCAAATACTC
02/CCACACCCATATGCCCCACAACTGCTATAACTCTGCCACTCTTTGCATGCATGCAAATACTC
03/CCACACCCATATGCCCCACAACTGCTATAACTCTGCCACTCTTTGCATGCATGCAAATACTC
04/CCACACCTATATGACCC--------------------------------------------

01/ATTATTGGACAGGAAAAATGATTAATCCTAGTTGTCCTGGAGGACTTGGAGTCACTGTCTGT
02/ATTATTGGACAGGAAAAACGATTAATCCCAGTTGTCCTGGAGGACTTGGAG-----------
03/ATTATTGGACAGGGAAAATGATTAATCCTAGTTGTCCTGGAAGACTTGGAGCCACTGTCTGT
04/-------------------------------------------------------------

01/TGGACTTACTTCACCCAAACTGGTATGTCTGATGGGGGTGGAGTTCAAGATCAGGCAAGAGA
02/--GACTCACTTCACTCATACCAGTATGTCTGATGGGGGTGGAGTTCAAGATCAGGCAACAGA
03/CGGACTTACTTCACCCATACTGGTATGTCTGAGGGGGGTGGAGTTCAAGATCAGGCAAGAGA
04/-------------------------------------------------------------

01/AAAACATGTAAAAGAAGTAATCTCCCAACTCACCCGGGTACATGGCACCTCTAGCCCCTACA
02/AAAACACATAAAGGAAGTAATCTCCCAACTGACCTGGGTACATAGCACCCCTGGCCCCTACA
03/AAAACATGTAAAGGAAGTAACCTCCCAACTGACCCGGGTACATAGCACCCCTAGCCCCTACA
04/-------------------------------------------------------------

01/AAGGACTAGATCTCTCAAAACTACATGAAACCCTCCGTACCCATACTCGCCTGGTAAGCCTA
02/AAGGACTAGATCTCTCAAAACTACATGAAACCCTCCATACCCATACTGGCCTGGTAAGCCTA
03/AAGGACTAGATCTCTTAAAACTACATGAAACCCTCCATACCCATACTTGCCTGGTAAGCCTA
04/-------------------------------------------------------------

01/TTTAATACCACCCTCACTGGGCTCCATGAGGTCTCGGCCCAAAACCCTACTAACTGTTGGAT
02/TTTAATACCACCCTGACTGGGCTCCATGAGGTCTCGGCCCAAAACCCTACTAACTGTTGGAT
03/TTTAATACCACCCTCACTGGGCTCCATGAGGTCTCGGTCCAAAACCCTACTAACTGTTGGTT
04/-------------------------------------------------------------

01/ATGCCTCCCCCTGAACTTCAGGCCATATGTTTCAATCCCTGTACCTGAACAATGGAACAACT
02/GTGCCTCCCCCTGCACTTTAGGCCATACATTTCAATCCCTATACCTGAACAATGGAACAACT
03/GTGCCTCCCCCTGTATTTCAGGCCATGCATTTCAATCCCTGTACCTGAACAATGGAACAACT
04/-----------TGCACTTCAGGCCATACATTTCAATCCCTGTA------------------
```

*FIG. 8A*

```
01/TCAGCACAGAAATAAACACCACTTCCGTTTTAGTAGGACCTCTTGTTTCCAATCTGGAAATA
02/TCAGCACAGAAATAAACACCACTTCTGTTTTAGTAGGTCCTC---TTTCCAATCTGGAAATA
03/ACAGCACAGAAATAAACACCACTTCCGTTTTAGTAGGACCTCTTGTTTCCAATCTGGAAATA
04/--------------------------------------------------------------

01/ACCCATACCTCAAACCTCACCTGTGTAAAATTTAGCAATACTACATACACAACCAACTCCCA
02/ACCCATACCTCAAACCTCACCTGTGTAAAATTTAGCAATACTATAGACACAGCCAACTCCCA
03/ACCCATACCTCAAACCTCACCTGTGTAAAATTTAGCAATACTGTAGACACAACCAACTCCCA
04/--------------------------------------------------------------

01/ATGCATCAGGTGGGTAACTCCTCCCACACAAATAGTCTGCCTACCCTCAGGAATATTTTTTG
02/ATGCATCAGGTGGGTAACTCCTCCCACACGAATAGTCTGCCTACCCTCAGGAATATTTTTTG
03/ATGCATCAGGTGGGTAACTCCTCCCACACGAATAGTCTGCCTACCCTCAGGAATATTTTTTG
04/--------------------------------------------------------------

01/TCTGTGGTACCTCAGCCTATCGTTGTTTGAATGGCTCTTCAGAATCTATGTGCTTCCTCTCA
02/TCTGTGGTACCTCAGCCTATCATTGTTTGAATGGCTCTTCAGAATCTGTGTGCTTCCTCTCA
03/TCTGTGGTACCTTAGCCTATCGTTGTTTGAATGGCTCTTCAGAATCTATGTGCTTCCTCTCA
04/--------------------------------------------------------------

01/TTCTTAGTGCCCCCTATGACCATCTACACTGAACAAGATTTATACAGTTATGTCATATCTAA
02/TTCTTAGTGGCCCCTATGCCCATCTACACTGAACAAGATTTATACAATCATGTCATACCTAA
03/TTCTTAGTGCCCCC-ATGACCATTTACACTGAACAAGATTTATACAATTATGTTGTACCTAA
04/--------------------------------------------------------------

01/GCCCCGCAACAAAAGAGTACCCATTCTTCCTTTTGTTATAGGAGCAGGAGTGCTAGGTGCAC
02/GCCCCGCAACAAAAGAGTACCCATTCTTCCTTTTGTTATTGGAGCAGGAGTGCTAGGCGGAG
03/GCCCCACAACAAAAGAGTACTCATTCTTCCTTTTGTTATCGGAGCAGGAGTGCTAGGTGGAC
04/--------------------------------------------------------------

01/TAGGTACTGGCATTGGCGGTATCACAACCTCTACTCAGTTCTACTACAAACTATCTCAAGAA
02/TAGCTACTGGCATTGGCGGTATCACAACCTCTACTCAGTTCTACTACAAACTGTCTCAAGAA
03/TAGGTTCTGGCATTGGCGGTACCACAACCTCTACTCAGTTCTACTACAAACTATCTCAAGAA
04/--------------------------------------------------------------

01/CTAAATGGGGACATGGAACGGGTCGCCGACTCCCTGGTCACCTTGCAAGATCAACTTAACTC
02/CTTAAAGCTGACATGGAATGGGTCGCTGATACCCTGGTCACCTTGCAAGATCAACTTAACTC
03/CTCAATGGTGACATGGAATGGGTTGCCGACTCCCTGGTCACCTTGCAAGATCAACTTAACTT
04/--------------------------------------------------------------

01/CCTAGCAGCAGTAGTCCTTCAAAATCGAAGAGCTTTAGACTTGCTAACCGCTGAAAGAGGGG
02/CCTAGCAGCAGTAGTCCTTCAAAATCGAAGAGCTTTAGACTTGCTAACCGCGGAAAGCGGGG
03/CCTAGCATCAGTAGTCCTTCAAAATTGAAGAGCTTTAGACTTGCTAACCTCTGAAAGAGGGG
04/--------------------------------------------------------------

01/GAACCTGTTTATTTTTAGGGGAAGAATGCTGTTATTATGTT--------------------
02/GAACCTTTTTATTTTTAGAGGAAAAAATGCTGTTGTTATGTT--------------------
03/GAAGCTGTTTATTTTTAGGGGAAGAATGTTGTTATTATGTTATTTTAGCGGAAGAATGTTGT
04/--------------------------------------------------------------

01/---------AATCAATCCGGAATCGTCACTGAGAAAGTTAAAGAAATTCGAGATCGAATACA
02/---------AATCAATCCGGAATCATCACCGAGAAAGTTAAAGAAATTCAAGGTCGAATATA
03/TATTATGTTAATCAATCCTGAATTGTCACAGAGAAAGTTGAAGAAATTCGAGATTGAATACA
04/--------------------------------------------------------------

01/ACGTAGAGCAGAGGAGCTTCAAAA-CACTGGACCCTGGGGCCTCCTCAGCCAATGGATGCCCT
02/ACGTAGAGCAAAGGAGCTGCAAAA-CACTGGACCCTGGGGCCTCCTCAGCCAATGGATGCCCT
03/ACGTAGAACAGAGGAGCTTCAAAAACACCAGACCCTGGGGCCTCCTCAGCCAATGGATGCCCT
04/--------------------------------------------------------------
```

*FIG. 8B*

```
01/GGATTCTCCCCTTCTTAGGACCTCTAGCAGCTATAATATTGCTACTCCTCTTTGGACCCTGTA
02/GGATTCTCCCCTTCTTAGGACCTCTAGCAGCTATAATATTGTTACTCCTCTTTGGACCCTGTA
03/GGATTCTCCCCTTCTTAGGATCTCTAGCAGCTCTAATATTGATACTCCTCTTTGGACCCTGTA
04/----------------------------------------------------------------

01/TCTTTAACCTCCTTGTTAACTTTGTCTCTTCCAGAATCGAAGCTGTAAAACTA----------
02/TCTTTAACCTCCTTGTTAAGTTTGTCTTTTCCAGAATCGAAGCAGTAAAACTACAAATCGTTC
03/TCTTTAACCTCCTTGTTAAGTTTGTCTCTTCCAGAATCAAAGTTGTAAAGCTACAAATCGTTC
04/TCTTTAACCTCCTTGTTAAGCTTGTCTCTTGCAGAATCGAAGCTGTAAAACTACAAATGCTTG

01/--CAAATGGAGCCCAAGATGCAGTCCAAGACTAAGATCTACCGCAGACCCCTGGACCGGCCTG
02/TTCAAATGGAGCCCCAGATGCAGTCCATGAGTAAAATCTACCACGGACCCCTGGACCGGCCTG
03/TTCAAATGGAACCCCAGATGAAGTCCATGACTAAGATCTACCGTGGACCCCTGGACCGGCCTA
04/TTAAAATAGAGCCCCAGATGCAGTCCATGGCTAAGATCTACCACGGACCCCTGGACCGGCCTG

01/CTAGCCCACGATCTGATGTTAATGACATCAAAGGCACCCCTCCTGAGGAAATCTCAGCTGCAC
02/CTAGCCCATGCTCTGATGTTAATGACATCAAAGGCACCCCTCCCGAGGAAATCTCAACTGCAC
03/CTAGCCCATGCTCCAATTGTAATGATATCGAACGCACCCCTCCCGAGGAAATCTCAACTGCAC
04/CTAGCCCATGCTCTGATGTTGATGACATTGAAGGCACGGCTTCCGAGGAAATCTCAACTGCAC

01/AACCTCTACTACGCCCCAATTCAGCAGGAAGCAGTTAGAGCGGTCGTCGGCCAACCTCCCC
02/AACCTCTACTACGCCCCAATTCAGCAGGAAGCAGTTAGAGTGGTTGTTGGCCAACCTCCCC
03/AACCCCTACTATGCCCCAATTCCGCAGGAAGCAGTTAGACTGGTCGTCAGCCAACCTCCCC

04/GACCCCTACTACACCCCAATTTAGCGGGAAGCAATTAGAGCAGCCTATGGCCACCTCCCC
```

*FIG. 8C*

```
CTTCCCCAACTAATAAGGACCCCCCTTTCAACCCAAACAGTCCAAAAGGACATAGACAAAGGA      1
CTTCCCCAACTAATAAGGACCCCCCTTTCAACCCAAACAGTCCAAAACGACATAGACAAAGGA     3
CTTCCCCAACTAATAAGGACCCCCC-TTCAACCCAAATGGTCCAAAAGGAGATAGACAAAAGG     4
CTTCTCCAACTAATAAGGACCCCCC-TTCAACCCAAATGGTCCAAAACGAGATAGACAAAGGG     5
CTTCCCCAAATAATAAGAACCCCCC-TTCAACCCAAACGGTCCAAAAGGAGATAGACAAAGGG     6
                                                                    7

GTAAACAATGAACCAAAGAGTGCCAATATTCCCTGGTTATGCACCCTCCAAGCGGTGGGAG--     1
GTAAACAATGAACCAAAGAGTGCCAATATTCCCTGGTTATGCACCCTCCAAGCGGTGGGAG--     3
GTAAACAGTGAACCAAAGAGTGCCAATATTCCCCAATTATGACCCCTCCAAGCAGTGGGAGGA     4
GTAAACAATGAACCAAAGAGTGCCAATATTACACGATTATACTCGCTCCAAGCAGTGGGAG--     5
GTAAACAACTAACCAAAGAATGCCAATATTCCCCGATTATGCCCCCTCCAAGCGGTGGGAG--     6
                                                                    7

A-AGAATTCGGCCCAGCCAGAGTGCATGTACCTTTTTCTCTCTCAC-ACTTGAAGCAAATTAAA    1
A-AGAATTCGGCCCAGCCAGAGTGCATGTACCTTTTTCTCTCTCAC-ACTTGAAGCAAATTAAA    3
AGAGAATTCGGCCCAGCCAGAGTGCATGTGCCTTTTCTCTCCCAG-ACTTAAAGCAAATAAAA    4
-GAGAATTTGGCCCAGCCAGCGTGCATGTACCTTTTTCTCTCTCAG-ATTTAAAGCAAATTAAA    5
-GAGAATTCGGCCCAGCCAGAGTGCACGTACCTTTTTCTCTCTAGACTTTAAA----TTAAA     6
                                                                    7

ATAGACNTAGGTNAATTNTCAGATAGCCCTGATGGYTATATTGATGTTTTACAAGGATTAGGA    3
ATAGACXTAGGTXAATTXTCAGATAGCCCTGATGGXTATATTGATGTTTTACAAGGATTAGGA    4
ACAGACTTAGGTAAATTCTCAGATAACCCTGATGGCTATATTGATGTTTTACAAGGGTTAGGA    5
ATAGACCTAGGTAAATTCTCAGATAACCCTGATGGCTATATTGATGTTTTACAAGGGTTAGGA    6
ATAGACCTAGGTAAATTCTCAGATAACCCTAATGGCTATATTGATGTTTTACAAGGTTTAGGA    7

TTCCTGAGTTCTTGCACTAACCTCAAAT              1
CAATCCTTTGATCTGACATGGAGAGATATAATATTACTGCTAAATCAGACGCTAACCTCAAAT    3
CAATCCTTTGATCTGACATGGAGAGATATAATATTACTGCTAAATCAGACGCTAACCTCAAAT    4
CAATTCTTTGATCTGACATGGAGAGATATAATGTCACTGCTAAATCAGACACTAACCCCAAAT    5
CAATCCTTTGATCTGACATGGAGAGATATAATGTTACTGCTAAATCAGACACTAACCCCAAAT    6
CAATCCTTTGATCTGATATGGAGAGATATAATGTTACTGCTAAATCAGACACTAACCCCAAAT    7

GAGAGAAGTGCCGCCATAACTGCAACCCAAGAGTTTGGCGATCCCTGGTATCTCAGTCAGGTC    1
GAGAGAAGTGCTGCCATAACTGGAGCCCGAGAGTTTGGCAATCTCTGGTATCTCAGTCAGGTC    3
GAGAGAAGTGCTGCCATAACTGGAGCCCGAGAGTTTGGCAATCTCTGGTATCTCAGTCAGGTC    4
GAGAGAAGTGCCACCATAACTGCAGCCTGAGAGTTTGGCGATCTCTGGTATCTCAGTCAGGTC    5
GAAAAAGTGCTGCCATAACAGCAGCCTGAGTTTGGCGAACTCTGGTATCTCAGTCAGGTC      6
GACAGAAGTGTCGCCGTAACTGGAGCCCGAGAGTTTGGCAATCTCTGGTATCTCAGTCAGGTC    7

AATGACAGGATGACAACAGAGGAAAGATAATGATTCCCCACAGGCCAGCAGGCAGTTCCCAGT    1
AATGATAGGATGACAACGGAGGAAAGAGAACGATTCCCCACAGGGCAGCAGGCAGTTCCCAGT    3
AATGATAGGATGACAACGGAGGAAAGAGAACGATTCCCCACAGGGCAGCAGGCAGTTCCCAGT    4
AATGATAGGATGACAACAGAGGAAAGAGAATGATTCCCCACAGGCCAGCAGGCAGTTCCCAGT    5
AATGATAGGATGACAACAGATGAAAGAGAATGATTCCCCACAGGCCAGCAGGCAGTTCCCAGT    6
AATGATAGGATGACAACAGAGGAAAGAGAACGATTCCCCACAGGCCAGCAGGCAGTTCCCAGT    7

GTAGACCCTCATTAGGACACAGAATCAGAACATGGAGATTGGTGCCGCAGACATTTGCTAACT    1
                                                          AACT    2
GTAGCTCCTCATTGGGACACAGAATCAGAACATGGAGATTGGTGCCGCAGACATTTACTAACT    3
GTAGCTCCTCATTGGGACACAGAATCAGAACATGGAGATTGGTGCCGCAGACATTT          4
CTAGACCCTCATTGGGACACAGAATCAGAACATGGAGATTGGTGCTGCAGACATTTGCTAACT    5
GTAGACCCTCATTAGGACACAGAATCAGAACTTGGAGATTGGTGCCACAGACATTTGCTAACT    6
GTAGACCCTCACTGGGACACAGAATCAGAACATGGAGATTGGTGCCGCAGACATTTGCTAACT    7
```

*FIG. 9A*

```
TGCGTGCTAGAAGGACTAAGGAAAACTAGGAAGA----TATGAATTATTCAATGATGTCCACT      1
TGCGTGCTAGAAGGACTAAGGAAAACTAGGAAGA---CTATGAATTATTCAATGATGTCCACT      2
TGCGTGCTAGAAGGACTAAGGAAAACTAGGAAGA---CTATGAATTATTCAATGATGTCCACT      3
TGTGTGCTAGAAGGACTAAGGAAAACTAGGAAGAAGTCTATGAATTACTCAATGATGTCCACA      5
TGCGTGCTAGAAGGACTAAGGAAAACTAGGAAGAAGCCCATGAATTATTCAATGATGTCCCCT      6
TGCGTGCTAGAAGGACTAAGGAAAACTAGAAAGAAGCCTGTGAGTTATTCAATGATGTCCACT      7

ATAACACAGGGGAAAGGAAGAAAATCCTACTGCCTTTCTGGAGAGACTAAGGGAGGCATTGAG      1
ATAACACAGGGGAAAGGAAGAAAATCCTACTGCCTTTCTGGAGAGACTAAGGGAGGCATTGAG      2
ATAACACAGGGGAAAGGAAGAAAATCCTACTGCCTTTCTGGAGAGACTAAGGGAGGCATTGAG      3
ATAACACAGGG-AAGGGAAGAAAATCCTACTGCCTTTCTGGAGAGACTAAGGGAGGCATTGAG      5
ATAACACAGGG-AAAGGAAGAAAATCCTACTGCCTTTCTGGAGAGACTAAGGGAAGGATTGAG      6
ATAACACAGGG-AAAGGAAGAAAATCCTACCGCCTTTCTGGAGTGACTAACGGAGGCATTGAG      7

GAAGCATACC---AGGCAAGTGGACATTGGAGGCTCTGGAAAAGGGAAAAGTTGGGAAAAGTA      1
GAAGCATACC---AGGCAAGTGGACATTGGAGGCTCTGGAAAAGGGAAAAGTTGGGCAAATTG      2
GAAGCATACC---AGGCAAGTGGACATTGGAGGCTCTGGAAAAGGGAAAAGTTGGGCAAATTG      3
GAAGCGTGCC232AGGCAAGTGGACTTTGGAGGCTCTGGAAAAGGGAAAAGCTGGGCAAATTG      5
GAAGCATACC238AGGCAAATGGACTTTGGAGGCTCCAGAAAAGGGAAAAGCTGAGCAAATTG      6
GAAGCATACC233AGGCAAGCGGACTTTGGAGGCACTGGAAAAGGGAAAAGCTAGGCAAATCA      7

TATGTCTAATAGGGCTTGCTTCCAGTGTGGTCTACAAGGACACTTTAAAAAAGATTGTCC-AA      1
AATGCCTAATAGGGCTTGCTTCCAGTGCAGTCTACAAGGACGCTTTAGAAAAGATTGTCC-AA      2
AATGCCTAA                                                            3
AATGCCTAATAGGGCTTGCTTCCAGTGCGGTCTACAAGGACACTTTAAAAAAGATTGTCC-AA      5
AATGCCTAACAGGGCTTGCTTCTAGTGTGGTCTACAAGGACACTTTAAAAAAGATTGTCC-AA      6
AATGCCTAATAGGGTTTGCTTCCAGTGCGGTCTACAAGGACACTTTAAAAAAGATTGTCCAAA      7

-TAGAAATAAGCCACCACCTCGTCCATGCCCCTTATGTCAAGGGAATCACTGGAAGGCCCACT     1
GTAGAAATAAGCCGCCCC-TCGTCCATGCCCCTTATGTCAAGGGAATCACTGGAAGGCCTACT     2
GTAGAAGTAAGCCGCCCCCTCGTCCATGCCCCTTATTTCAAGGGAATCACTGGAAGGCCCACT     5
GTAGAAACAAGCTGCCCCCTTGTCCATGCCCCTTATGTCAAGGGAATCACTGGAAGGCCCACT     6
-TAGAAATAAGCCGCCCCCTCGTCCATGCACCTCGTCAAGGGAATCACTGTAAGGCCCACT      7

GCCCCAGGGGATGAAGGTCCTCTGAGTCAGAAGCCACTAACCAGATGA                     1
GCCCCAGGGGACGAAGGTCCTCTGAGTCAGAAGCCACTAACCTGATGA                     2
GCCCCAGGGGACAAAGGTCCTCTGAGTCAGAAGCCACTAACCAGATGA                     5
GCCCCAGGAGATGAAGGTCCTCTGAGTCAGAAGCCACTAACCAGATAA                     6
GCCCCAGGGGACGTAGGTCCTCTGAGTCAGAAGCCACTAACCAGATGA                     7
```

*FIG. 9B*

```
RTPLSTQTVQKDIDKGVNNEPKSANIPWLCTLQAVGEEFGPARVHVPFSLSHLKQIKIDG   SDSPII
- = === ===-=== == ========= =  ===== ============ ===== = =  == ===
KDPPSTQMVQKEIDKRVNSEPKSANIPQLPLQAVGGREFGPARVHVPFSLPDLKQIKTDLGKFSDNPCS

YIDVLQGLGQSFDLTWRDIILLLNQTLTSNERSAAITGAREFGNLWYLSQVNDRMTTEERERFPTGQC
========== ========- ====== ======-==-= ===-================= =====
YIDVLQGLGQFFDLTWRDIMSLLNQTLTPNERSATITAAXEFGDLWYLSQVNDRMTTEEREXFPTGQC

AVPSVAPHWDTESEHGDWCRRELLTCVLEGLRKTRK TMNYSMMSTITQGK
=====- ============= ===========================--================-
AVPSLDPHWDTESEHGDWCCRELLTCVLEGLRKTRKKSMNYSMMSTITQGR
```

*FIG. 10*

```
GTCTACCTAGCCA-AGGCATATTCTTCTTATGTGGAACATCAACCTATATCTGCCTTCCCACTAATGGA
::::  ::::  ::   :::  :::::  ::   :  :::::  ::  :::  :::::    ::   :    ::
GTCTGCCTACCCTCAGGAATATTTTTTGTCTGTGGTACCTCAGCCTATCGTTGTTTGA--A-TGGCTCTT
CAGGCACC-TGAACCTTAGTCT--TTCTAAGTCCCAAC-ATTAACATTGCCCCAGGAAATCAGACCC-TA
:::   :   ::    :  ::    :::    ::::   :::  ::   :   :   :::    :::
CAGAATCTATGTGC-TTCCTCTCATTCTTAGTGCCCCTATGACCATCTACACTGAACA--AGATTTATA
TTGGTACCTGTCAAAGCTAAAGTCCCGTCAGTGCAGAGCCATACAACTAATATCCCTAT-TTATAGGGTT
   :  ::  :::::  : :::: ::     ::::   ::   ::    ::  :  :::::::
CAGTTA--TGTCATATCTAA-GCCCCGCAACAAAAGAGT-ACCCAT-TC-T-TCCTTTTGTTATAGGAGC
AGGAATGGCTAC-TGCTAC-AGGAACTGGAATAGCCGGTTTATCTACTTC-ATT-A-TCCTACTACCATA
::::  ::  ::  ::::: ::   ::   :  : :::::  ::  ::  :: :: :: :::::::  :
AGGAGTG-CTAGGTGC-ACTAGGTACTGGCATTGGCGGTATCACAACCTCTACTCAGTTCTACTACAA-A
CACTCTCAAAGAATTTCTCAGACAGTTTGCAAGAAATAATCAAATCTATTCTTACTTTACAATCCCAA-T
:  :::::: :::  :          :     :  :         ::   :  ::  ::  :::     ::: :
CTATCTCAA-GAACTAAATGGGGACATGGAACGGGTCGCCGAC-TCCCTGGTCACCTTGCAAGATCAACT
TAGACTCTTTGGCAGCAAT-GACTCTCCAAAACCGCCGAGGCCCACACCTCCTCACTGCTGAGAAAGGAG
::  ::::    :  :::::::   :  ::  ::  :::::  ::    :  ::  ::  ::  ::::::::
TA-ACTCCCTAGCAGCAGTAGTC-CTTCAAAATCGAAGAGCTTTAGACTTGCTAACCGCTGAAAGAGGGG
GACTCTGCACCTTCTTAGGGGAAGAGTGTTGTTTTACACTAACCAGTCAGGGATAGT-AC-GAGAT-GC
::   :::         ::  ::::::::::::  ::   :::    :::   ::  ::  ::  ::   :::
GAACCTGTTTATTTTTAGGGGAAGAATGCTGTTATTATGTTAATCAATCCGGAATCGTCACTGAGAAAGT
CACCTGGCATTT-ACAGGAAAGGCTTCTGATATCAGACAATGCCTTTCAAACTCTTATACCAA---CCT
 :    :   :  ::  ::::    ::  :::: ::   ::  ::  ::::  ::   ::    ::
TAAA-GAAATTCGAGATCGAATA-CAACGTAGAGCAGAGGA-GC-TTCGAAACACTGGACCCTGGGGCCT
CTGGAGT---TGGGCAACATGGCTTCTTCCATTTCTAGGTCCCATGGCAGCCATCTTGCTGTTACTCACC
:    ::       :::    :  :::  :::::  ::  ::    ::::: : :::::: ::  ::::::  :
CCTCAGCCAATGGATGCCCTGGATTCTCCCCTTCTTAGGACCTCTAGCAGCTATAATATTGCTACTCCTC
TTTGGGCCCTGTATTTTTAAGCTTCTTGTCAAATTTGTTTCCTCTAGGATCGAAGCCATCAAGCTACAGA
:::::  :::::::   :::::   ::  :::::  ::   ::  ::  ::  ::  :::::::    :    :   :
TTTGGACCCTGTATCTTTAACCTCCTTGTTAACTTTGTCTCTTCCAGAATCGAAGC--T---G-TAAA-A
TGGTCTTACAAATGGAACCCCAAATG-AGTTCAACTAACAACTTCTACCAAGGACCCCTGGAACGATCCA
     ::  :::::::::::  :::  :  :::  :::   :  ::  :::::::                :: :
----CT-ACAAATGGAGCCCAAGATGCAGTCCAAG-ACTAAGATCTACCGCAGACCCCTGGACCGGCCTG
CTGGC--ACT-TCC-AC-T-A--GCC-T-AGAGATTCCCCTCTGGAAGACA-CTACAACTGCAGGGCCCC
:: ::   ::  ::  :  :  :  ::   :   : ::          ::   ::     ::  :::::::  ::
CTAGCCCACGATCTGATGTTAATGACATCAAAGGCACCCCTCCTGAGGAAATCT-CAGCTGCACAACCTC
TTCTTTGCCCCTATCCAGCAGGAAGTAGCTAGAGCGGTCATCGGCCAAATTCCC-AACAGCAGTTGGGGT
:  :::  :::::::::::::::::::::   ::  :::::::::::   ::::  :::::::: :: ::  :
TACTACGCCCCAATTCAGCAGGAAGCAGTTAGAGCGGTCGTCGGCCAACCTCCCCAACAGCACTTAGGTT
GTCCTGTTTAGAGGGGGG
:::::::: :::  :::::
TTCCTGTTGAGATGGGGG
```

*FIG. 11*

```
ACCTTGCAAGATCAACTTA-ACTCCCTAGCAGCAGT-AGTCCTTCAAAATCGAAGAGCTTTAGACTTGCT
:: :: :::    :::  : :  ::::     :  ::::::::: : :: : ::::: ::   :::    :::: : ::
ACTTTACAATCCCAAATAAGACTCTTTGGCAGCAGTGACTC-TCCAAAACCGCTGAGGCCTAGATCTCCT
AACCGCTGAAAGAGGGGGAACCTGTTTATTTTTAGGGGAAGAATGCTGTTATTATGTTAATCAATCCGA
 :: ::::::::  ::: :::   :::       :: ::::::::::: :: :::: :::    ::: :: :: ::
CACTGCTGAAAAAGGAGGACTCTGCACCTTCTTAGGGGAAGAGTGTTGTTTTTACACTAACCAGTCAGGG
ATCGTCACTGAGAAAGTTAAAGAAATTCGAGATCGAATA--CAACGTAGAGCAGAGGAGCTTCGAAACAC
:: : :: :::::   :    :     :  :: :::  :  :  : ::::: :   ::: :::    :
ATAG-CA-TGAGAT-GCCACCCAGCGTTTACAG-GAAAAGGCTTCTGAAATCAGACGCCTTTC-AAATTC
TGGACCCTGGGGCCTCCTCAGCCAATGGATGCCCTGGATTCTCCCCTTCTTAGGACCTCTAGCAGCTATA
 :   ::    ::::  ::    :::     : :::   :::::::::::    :::: ::  :  :::::: ::
TTATACCAA---CCTCTGGAGT---TGGGCAACATGGCTTCTCCCCTTTCTAGGTCCCGTGGCAGCCATC
ATATTGCTACTCCTCTTTGGACCCTGTATCTTTAACCTCCTTGTTAACTTTGTCTCTTCCAGAATCGAAG
 :  :: :::::   :::::: ::: ::::  :::::::::   :::::  ::::: :  ::  :::::::::  :
TTGCTGTTACTCGCCTTTGGGCCCCGTATTTTTAACCTTCTTGTCAAATTTGTTTGGTCTAGAATCGAGG
C--T---G-TAAA-A----CT-ACAAATGGAGCCCAAGATGCAGTCCAAG-ACTAAGATCTACCGCAGAC
:  :   : ::: : :      :: :::::::: ::: :  : ::: :::   :   :::  ::::::::: :::
CCATCAAGCTACAGATGGTCTTACAAATCGAACCCCAAATG-AGTTCAACTAACAACTTCTACCGAGGAC
CCCTGGACCGGCCTGCTAGCCCACGATCTGATGTTAATGACATCAAAG-GCACCCCTCCTGA-GGAAATC
:::::::: : :: ::: :: :: :: ::         : :::  ::   :::::: ::: ::: :
CCCTGGACTGACCAGCTGGC--ACT-TCCCCTG-----GCC-T-AGAGAGTTCCCCTC-TGAAGGACA-C
T-CAGCTGCACAACCTCTACTACGCCCCAATTCAGCAGGAAGCAGTTAGAGCGGTCGTCGGCCAACCTCC
 : :: :::::  : :: :: :: :::::: :: ::::::::::: :: :::::: :::  :::::::::   :::
TACAACTGCAAAGCCCCTTCTTCGCCCCTATCCAGCAGGAAGTAGCTAGAGCAGTCATCGGCCAAATTCC
CCAACAGCACTTAGGTTTTCCTGTTGAGATGGGGG
 : :::::::: :: :: : ::::::::   :: :::
C-AACAGCAGTTGGGGTGTCCTGTTGAT-TGAGGG
```

*FIG. 12*

```
agttgcaattccttgcctcaactctgagagaaacccagccacatctccagcaaacaaga
|||||||||||||||||||  |||  |||||  ||||||| ||||||||||||| ||||
agttgcaattccttgcctccactgtgagacaaacccagacacatctccagcacacaaga  2299 acttcaaaacacctgaactgcagcagccaggcgttcctcaggaccacctcccaggat
|||||  |||  |||  |  | |||||||| |||||||| |   ||||||||||
acttcgaaatgcctcaacctcaggtgccagggttcctccagaaccttctcccaggag  2355 cttgcttcaagtgccggaaatctgaccatgggccaaggaatgcctgcagccaggattc
||||||  ||||||||  |||| || ||||||||||||||||||  | ||||||||||
cctgctacaagtgccagaaatctggccactgggccaaggaatgccacagaccaggattc  2419 ctcctaagccacgtccattgtgcaggacccactggaaatcggactgtccaactcacc
|||||||||  |||||| | || ||||||| ||||| ||||| |||||| |||||||
ctcctaagctgtatccatctctgtgggacccactaaaaatcagactgttcaactcacc  2479 cggcagccaatcccagagccctggaactctggcccaaggctctctgactgactcctcc
||||||||  | |||||||||||||||||| |||||||||||||||||||||  ||||
tggcagccacttccagagccctggaactctagcccaaggctctctgactgacccctcc  2539 cagatcttctcggcttagcagctgaagactgacactgccgatcacttcagaagtcccct
||||||||  |||||||||||||||||||||||||||| ||| |  |  ||| |
gagatcttcttggcttagcagctgaagactgacactgccagatcgcctcggaagcctaca  2599 ggaccatcacggatactgagcttcaggtaactctcacagtggaggctaagtccatcccct
||||||||| ||    |||||||||||||||||||||| ||  ||||||| | |||||
ggaccatcacagat-----gctccaggtaactctcacagtagagggtaagtctgtccct  2654 gtttaatcgatacagcggctacccactccacatcaccttcttttcaagggcctgtttccc
|||||| ||| | |||||||||||||| | ||||| || ||||||||||||||||||||
tcttaatcaatatggaggctacccactgcacattaccttcttttcaagggcctgtttcct  2714 tttccccataactgttgtgggtattgacggccaagcttcaaaaccccttaaaactcccc
|| ||||||||||||||||||||||||||||||| ||||| ||||  ||||||||||||
ttgcctccataactgttgtgggtattgacggccaggcttctaaacctcttaaaactcccc  2774 cactctggtgccaacttggacaacattcttttatgcactcttttcagttatcctcacct
||||| || ||||||| ||||  ||| || ||| |||||   ||| |||| ||| | |
aactctagtaccaacttagacaatactcttttaagcactccttttagttatcccactt  2834 gcccagttcccttattaggccgagacattttaaccaaattatctgcttccccgactattc
|||||||||||| ||||| ||||||||| ||  ||| ||||||||||||| ||||||||
gcccagttcccttatgaggccgagacacttcaactaaattatctgcttccctgactattc  2994 ctgggctacagccacatctccttgccgcccttcttcccaacccaaagcctccttcatatc
||||||||| ||||| | |  || | ||||||||||| | |||||||||||||   |||
ctggactacagctacatctcattgctgcccttcttcccaatccaaagcctcctttgcatc  2954 ttcctctcatatcccccaccttaaccacaagtatgggacacctctactcccctccctgg
|||  |   |||||| |||||||||||||| || | ||| ||||||  ||| |||| ||
ttcttgt---atcccccaaccttaacccacaagtataagatacctctattccctccttgg  3011
```

*FIG. 13A*

```
caaccgatcacacgcccattactatcccattaaaacctaatcaccottacoctgctcaat
 ||| ||||  | |||  ||| |||  ||||||||||||||  ||||||  ||||||| 
tgaccaatcatgcacccctaccatctcattaaaacctaatcactcttaccoggctcaat 3071 gccagtatcccataccacaacaggcttcaaaggcttgaagcctgctatcacttgcctgc
 ||||  |||||||| ||||| |||||||||| ||||| || |||||||||||| |||||
gccaagatcccatccacagcatgcttaaaaggactaaaacctgttatcactcgcctgc 3131 tacagcacgggcttctaaaacctataaactctccatacaattccccatttacctgtct
|| ||||  || ||| |||| ||||||||||||||||||||||||||||||||||||||
tagagcatggcctttaaagcctataaactctccttacaattcccccatttacctgtcc 3191 aaaaaccagataagtcttacaggttagttcagaatctgcaccttatcaaccaaattgttt
 |||||||| ||| ||||||||||   ||| ||||| |||||||| ||||||||||||
tagaaccagacaagccttacaggtt----caggatctgtgtcttatcaatgaaattgttt 3247 tgcctatccaccctgtagcacccaactcgtacactcttttgtcctcaatgccttccccca
| ||||||||||||| | |  ||| | ||||||||| ||||||||||| ||| || | |
tccctatccaccctgtggtgctgaacccatatactctcctatcctcaatacctcctcta 3307 caactcactattccgttcttgatcttaaagatgcttttttcactatccctgcacccc
||||  | ||||| ||||| ||||| ||| ||||||||| |||  |||| | ||||| |
caaccattattctgttctagatctcaaacatgctttctttactatccctttacacccct 3367 catcccagcctctctttgcttttacctggactgaccctgacacccatcagtccagcagc
|| |||||||||||| |||||| |||||||||||||||||||||||||||||||||||
caacccagcctctcttcgttttcacctggactgaccctgacacccatcagtccagcagc 3427 ttacctgggctgtactgccgcaaggcttcagggacagcccctcattacttcagccaagctc
||||||||||||| || |||||| ||||||| ||||||| |||| |||||||||||||
ttacctgggctgtaatgctgcaaggtttcagggcagccctcattatttcagccaagctc 3487 tttctcatgatttactttctttccacctctctgcttctcaccttattcaatatattgatg
|||||||||||||||||| ||||||| || ||||||||||||||||||||||||||| ||
tttctcatgatttactttctttccaccoctccacttctcaccttattcaatatattggtg 3547 accttctactttgtagccoctcctttaaatcttctcaacaagacaccctcctgctccttc
|  |||| ||||||||||||||||||  |||||||||||||||||  || || |||||||
atgttcttctttgtagccoctcctttgaatcttctcaacaagacacacttctgctccttc 3607 aacattgttctccaaaggatatcgggtatcccoctccaaagctcaaatttcttctccat
| |||| ||||||||||||||||        |||||||||||||||| ||||||||||
agcatttattctccaaaggatatc-------cccctccaaagctcaaatgtcttctccat 3660 ctgttacatacctcggcataattcttcatgaaaacacatgtgctctccctgccaattgcg
| |||||  ||| |||||||||||||| || |||||||| |||| ||||||||||  | |
ccgttacctaccttggcataattcttcataaaaacacacgtgccctccctgctgatagtg 3720 tctccaactgatctctcaaatcccaacctcttctacaaaacaacaactcctttccctcct
|||   |||||||||| ||||| ||||||||||||||||||||||||||||| ||||||
tctg--actgatctctcaaacccaacccccttctacaaaacaacaactcttttccatcct 3778 aggcatggttggatactttgcctttggataccctggttttgccatcctaacaaaatcatt
|||||||||||||||||||  || |||||||||||||||||||||||||||||||| |||
aggcatggttggatactttcgtgttaggataccctggttttgccatcctaacaaaaccatt 3838
```

FIG. 13B

```
atataaactcacaaaaggaaacctagctgacccatagattctaaatcctttcccactc
|||||||||||||||||||||||||||| |||||||||||||| ||||||| ||||||||||
atataaactcacaaaaggaaacctagttgacccatagatcctaaatcgtttcccactc  3898 ctctttccattccttgaagacagctttagagactgctcccacactagctctccctgtctc
||||||||||||||||||||||||||||||||||||||||    |||| |||||||| ||| |||
ctctttccattccttgaagacagctttagagactgtctccactctagctctccctgactc  3958 atcccaaccctttcattacacacagccgaagtgcaggctgtgcagtcggaattcttac
|| ||||| |||||||||||||||||||||| |||||||||||||||||||||: ||||||||
atcccaacacttctcattacacacagctgaagtgcaggctgtgcagtcagaattcttac  4018 acaaggaccgggaccatgccctgtagccttttgtccaaacaacttgaccttactgtttt
||||||||||||| |    ||||||||||||||||||:|||||||||||||||||||||||
acaaggaccgggatcgcatcctgtagccttttgtccaaacaacttgaccttactgtttt  4078 aggctcgccatcatgtctccatgcggtagcttccgctgccctaatacttttagaggccct
|||||  |||||||||||||||||| |  |  || ||||||||||||||||||||||||||
aggctcgccatcatgtctccatgcagcgtctgctgccaccctaatactcttagaggccct  4138 caaaatcacaaactatgctcaactcactctctacagctctcacaacttccaaaatctatt
||||||||||||||||||||||||||| |||||||||||||:| || |||||||||||||
caaaatcacaaactatgctcaactcattctctacagctctcataatttccaaaatctatt  4198 ttctttctcacacctgacgcatatactttctgctcccggctccttcagctgtattcact
|||||  |||||||||| |||||||||||||||||||||||||||||| | || |||||
ttcttcctcacacctgacacatatactttctgctcccggctccttcagatatactcact  4258 ctttgttgagtctcccacaattaccattcttcctggccagacttcaatctggcctccca
|   || | |||||||||||||||| ||||||||| ||||||||||||| ||||||||
c--cattatctcccacaattaccattattcctggcctggacttcaatccggcctccca  4316 cattattctggataccacacctgaccctgatgattgtatgtctctgatctacctgacatt
|||||||||||||||| ||||||||| || || || |||||||| | ||||| |||| ||
cattattctggataccatacctgaccctcatgactgcatctctctgatccacctgacgtt  4376 cacccatttccccatatttccttcttttctgttcctcatgttgatcacatttggtttac
||||||||||||| |||||||| |||| ||||    ||||  ||||| ||||||||||||
cacccatttccccacatttccttctgccctgtttctcaccctgatcacacttggtttat  4436 tgacggcagttccaccaggcctgatcgccactcaccagcaaaggcaggctatgctat
||| ||||||||||||||||||| |||||||||||||||||||||||| ||||||||
tgatggcagttccaccaggcctaatcgccactcaccagcaaaggcaggatatgctat  4493 gaactgattgccttaactcgggccttcactcttgcaaagggactacacgtcaatatttat
|||||  |||||||||| ||  |||||||||||||||||| |||||||| |||||| |||
gaactagttgccttaattcaagccctcactcttgcaaaggactacgtgtcaatatctat  4553 actgactctaaatatgccttccatatcttgcaccaccatgctgttatatgggctgaaaga
|||||  |||||||||||| ||||| ||||||||||||||| ||||||||||||||||||
actgattctaaatatgcctttcatattctgcaccaccatgcggtcatatgggctgaaaga  4613 ggttcctcactacgcaagggtcctccatcattaatgcctctttaataaaaactcttctc
||||||||||||| ||||| ||||||||||||||||||||||||||  |||| |||
ggttcctcactacacaagtgtcctccatcattaatgcctctttaagaaaa-ctctgctc  4672
```

*FIG. 13C*

```
aaggctgctttacttccaaaggaagctggagtcacacactgcaagggccaccaaaaggcg
||||||||||||||| ||||||||||||||| |||| ||||||||||| || |||||| |
aaggctgctttacttccaaaggaagctggggtcattcactgcaaggggcatcaaaagact  4732 tcagatcccattactctaggaaatgcttatgctgataaggtagctaaagaagcacctagc
||||||||||||| ||||||| |||||||||||||||||||||| |||| | ||||| |||||
tcagatcccattgctctaggcaatgcttatgctgataaggtggctagacaagcagctagc  4792 gttccaacttctgtccctcatggccagttttctccttccatcagtcattccacctac
|||||||| |||||||||||||||||||||||||||||||| |||| |||| ||||||||
tctccaacttttgtccctcatggccagttttctccttcacatccgtcactccacctac  4852 tccccattgaaacttccgcctatcaatctcttctcacacaaggcaaatggttcttagac
||| |   ||||||||| ||||||| ||||| | | |||||| |||||!||||||||||||
tccacagctgaaacttccacctatcaagctcttcccccgcaaggtaaatggttcttagac  4912 caaggaaaatatctccttccagcctcacaggccattctattctgtcatcatttcataac
||||||||||||||||||||||||||||||||||||||||||||!|||| ||||||||||
caaggaaaatatctccttccagcctcacaggccattctattctgtcgtcatttcataac  4972 ctcttccatgtaggttacaagccactagtccacctcttagaacctctcatttcctt-cca
|| ||||||||||||||||||||||||| |    ||||||| |||!|!||!|||||| |||
cttttccatgtaggttacaagccactagcctgtctcttaggacctctcattccttcca  5032 tcgtggaaacatatcctcaaggaaatcacttctcagtgttccatctgctattctactacc
|| ||||||  ||||||||| ||||||||||||||||||||||||||||||||||| |||||
tcatggaaatctatcctcaaggagatcacttctcagtgttccatctgctattctgctacc  5092 cctcaggattgttcaggccccctcccctcctacacatcaagctcgggatttgcccct
|||||||||||||||||||||| |||||| | ||||||||| ||||||||||||||||||||
cctcaggattgttcaggcctcctcccttcctacacataaagctcgggatttgcccct  5152 gcccaggactggcaaattgactttactcacatgccctgagtcaggaaactaaaataccc
||||||||||||||||||||||||||||||||||||| | ||||| ||||||||||| |||
gcccaggactggcaaattgactttactcacatgcctcgggtcagaaaactaaaatatctc  5212 ttggtctgggtagacactgtcactggatgggtagaggcctttcccacagggtctgagaag
|| |||||||||||||||| ||||||| ||||||||||||||||||| || ||||||||||
ttagtctgggtagacactttcactgggtgggtagaggcctttcccatagagtctgagaag  5272 gccactgcagtcatttcttcccttctgtcagacataattccttgggttggccttccacc
||||| || ||||||||||||||||||||||||||||||||||||| |||||||||||| |
gccaccgcggtcatttcttcccttctgtcagacataattccttggtttggccttcccttc  5332 tctatacagtccaataacggagcagcctttattagtcaaatcacctgagcagttttcag
|||||||||| |||||||| |||||||| |||| |||||||| ||||||||| |||| ||||
tctatacagtctgataacggaccagcctttactagttaaatcacccaagcagtttctcag  5392 gctcttggtattcagtggaaccttcgtacccttactgtcctcaatcttcaggaaggta
|||||||||||||||||||||||||| |||||| |||||||||||||||||||||||||
gctcttggtattcagtggaaccttcatatcccttaacatcctcaatcttcaggaaggta  5452 gaatggactaatggtctttttaaaaacacaccccaccaaactcagcctccaacttaaaaag
|| |||||||||||||||||||| |||||||| ||||||| |||||||||||||||||||||
aaaccgactaatggtctttttaaagacacacctcaccaagctcagcctccaacttaaaaag  5512
```

*FIG. 13D*

```
TGCCTTTATTTCCGTAGGCTGGTCATATGGCGCTAGCACTCACATAAAGCTACCGAGGAG
AGCGAATGAAACCAAAATCACTTTACCTTCACAGCACGAGGCCGTCGTCCCTCTCGATAT
TTGGCCCGTGTGTCGCATACCGCCCTCTGGACGTGGTGATCAAATAAACTCCCTAGCTCC
CCGCCGCTCGACGCCATCTTGCCTACTTTGATCCTCGCAGGGAGGACAACATCCGCCCTA
CTGAGCTCCCTTTTATCCAATAAGAGAGCGGGATGAGTTAAGGAGTGCCAGGATTGGCTG
GAGAATCGACAGCGTCGGCCATCGTTTCCTGCGTGCGAAGATTTGATGAACGAGGTGCCG
CCCCCGAGCGGCTCGGCGGAGAGGCGCGGTGGGTGACAGAAGCTTTCTTGTCCCACCCAC
TACAGGCTTACGGCAGGATGCGCAGCGGGGAGAGGGGCGGGGCCGCAGGGGCGGGGCC
GATCGATCTCCTCCGGCTCCGACGTCCTCGGCCTGCCGGGTCCCGGTCCTTTGCGGCGC
TAGGGTGGGCGAACCCAGAGCGACGCTCCGGACGATGTGGGCAGCGATCGCCTGGCGG
GTGCTGGGGGAGGCGGGGCGGCAGTGACTGTGGCCTTCACCAACGCTCGCGACTGCTTCC
TCCACCTGCCGCGGCGTCTCGTGGCCCAGCTGCATCTGCTGCAGGTAACCTGCCGGCCCC
GAGCCACCTGATCTTCAGCCTGGGGTCGGACGAGGCCGAAGCCTCTCAGGGACGCGGCGG
GACACCGGCTGCCACCCGGGCGCCGCCGAAGCGCGCAGAGATCAGGGTCCCTCGACGGCA
GGGCCCTTCTGGGTAGTCTCTGGATCCCACAAGTCCAGTGCAGCCCTGGGCTCGTCTTAT
CCCAGGTCTTTTCACTTGGTGAAACTGAACCTAGAAACGTCCTAATATTCTACCACTGTT
TTTATAAATATTCCTTATTCCAGGCTGGAAAAGCTCCTGAGAAGTGGTTTGTTTTTATTA
TTTTAAAAGGTGTTTTCCTTGCCAGCCATTTCCAGTTAACCTGCGCTGCTGCCGTCCGGG
CCGCGAGAGCGGGACGCAGAGTTGTTGGCGGAGCCCCTGTCGGTTCCCGGGGACTAAGCA
CCGCGTCCCATGAGCGGGAAAGGTTAATACAATGATGGTTCTGCCCTGCGTCGCTGACGC
GGAACACAGCTGTAGTGTGTTAGGAACACATAACGTAGTTAAGATCACTTGAAGCTCTGC
GATCAGTCGCCCTTCTGGACGTTGTGGTTAGGATGTTTCACAGTTCTAACCACTGGTGGA
GATACAGCGTCCATATTTTCATAATTAAAAATAGAGGCACATGGTCTCACGAGTTTGAGT
GTACTTATGGGGGCAAAAGGACGGCGTATTTGAAATCCTCATAAATCCTGGATGCATGGT
ACCCACCAGTGGCTAATCTATGCAATGAATAGAGTTTGCAATAATTTCAAGCATCCCTTC
TTTCCACTTGAGTTACTTCCCCATACCTAGGGAAGATATTTTTGGTCCACTGAAAACAT
GAGTTCAGCAGAATCCTCCTATCATCGTCGTTATTATTTTTACCACTAAGTAGACAATC
TTTTGGTTTTTGATGGGCTTTATGGCTAGAGACAAATCAGTCACTGTCACCAAGTTCCAG
GTAGAAGTTGGTTCAGTGCTCTGTCAGCTTCGATGGGATTTTTCAACATGTTTTCAAATC
TGCACTTAATAGTAGGAATGCTTTCTTACAGTAACTCTAATTTGATCCTAAGATGTAGTT
GTTACCTTACATTCATCACTGTTTAAGAATTTAGTGGTCTTGATCTTTGTTTTAAATTTT
GAGCCTTCGGGAAGTACTTATAAGAATTAATTCATGCATATCTTTTGAAATGTAAATGT
CTTTAGCCCTGGAACAAATTGCTGTTTCTGTTCAGCCCATATTAGCAGAATAGGTCAACT
TTACTTTCTAATTATCAATGTAATAAGTTTATTACTTTATAGATTCCATAAATCTATACA
TTTATTCCTCGATGAATTATATAAATTTATAGAATTTATGTTTTATAGAAAATTTGGAAA
GCATGGAAAATTATTAACAAGAAAATAAGTTACCCATAATCCCAGAACTTAGAGGTGACT
AATGTTGACAGTTTGGATCAAATCTTCCAGTTTTGTTTCTAATCTTTATTTTAACATAA
ATGAGGTCCTGTATACACACGTACAGTTTTGTGTCCTGGTGTTTTTATTTAATGTTATTA
TGAGTGTTTTATTTTGTTAAAAGGTCATCATTTTAAGTTGTTAATTAGTATTCTAGCACA
AATTTGCCATAATTTATTTAATTGTTTACTATGATTGACCATTTAGATTGTACTTAATTT
TTAGGCATTAGAAGTGATAAACTATATTTTAATCAGACGTTGAAAATAACACATCTTTGT
TTAGAAAACATCATTTTATTTCTGGTTGTCTAGGATAGATTCCCAGAATTCTTGGGTTAG
AGGCCATAGATAATTATGAAAGCAGAAGATTCACAAGTTGGGAGTTAATACTTGAATTA
CTTTATTTGGGGTGAAGCATTGAGTGCATAATACAGATCATGCAGTAATGGGAAGAAGGG
TTGGAACAATGGTTTTCTGGCCTATGTCAGACTTACCTTGAAGCTTTTAAGAATACAGAT
GTTCTGATCAACCCTCAGACCTATTAAATCAGACCTAAAATCTTAGGGAATAGGCTTTAG
GCATCTCTAATTTTAAAAAATTTATTCAGGCTACTTGGATGCACAAAAGAGTTGAGACCT
ACTGTCCTAGAATCATAGAATTTTAATGACGATAGAGACCTTAAGCATCTAGGTCGTTTC
TGTACTTTTACATGTAAGGAAACTGGCATTCCTAGGCCAGTACCATTGCCATGCAGCTAA
TTTGCCCTCTTGTCTATAGCTCACTCTGCATCACCCAACCTACCGTTCTCACTGTTTCTT
CTATAACCAATCTCCTTCCCACTTCTGTTCTCTTACTCATGCCATTCTTCCCTCAGTCAT
TTTTCTTCCTTCCATACAAATTCCATGTCTTTAAAAAGGAATAATCCTACCTCCTCCACA
```

*FIG. 14A*

```
TAGCTTTCCAATTCTCTGTTGCCCACATTTGTCTCCCTTTCAATACTTCTCTGTTGTGTT
ATGTGACACATCACATTTGATATACTCTGTACTGTGTTTCAAGTATTGTATTCTCTTGTT
TACTCAAGTCATTATTTCAGGACTGACTACCCAGTAGATGCTTTAAGTCAGGATTTCTCA
ACCTTGGCACTGTTGACATTTTGAGCTGGATAATTTTTTGTTTTGGGGGCTCTCCTGTAC
ATTTTAAGATGTTTAACAGCACCCTTGGCCTCTATCCAGTAGACGCCTGTACTGCCTCCC
CCTATCTGTGACAACCAAAAGGTCTTCAGACATTGTCAGATGTCTACTGAAGGACAAAA
TCACCTCTGGTTGAGAACCACCGCTTCAACTAAGTTATCTTCTCTGTACTCAGAACTTGA
TGTGATTGCAGCAGGGGAGAGGATTCATATACACAGTGAATGCAAACGAACCTAAATCA
CCATTCGGATATGGCCACACAATTTTCATTTCCCTTGTGTTAGCAAGAGATACCCTAGGC
TTTGGACCTGATTATTCCTAAGGCATTCTGATGTATGGTTTTACCTGCAGATTTCCTGGT
AATACTGATACCTCAGTTTGGGTCAAAGAAGGTCAATTAATTGATTGATTTGATTTGACT
CCTGGAAAAGACGCTCCTTTCTAGCTGTCTCTTTCTTCTCTTTACCTGAATAGCCAGGGC
TCTGTGGTTCAAGTGAAGTATTTTGACATAAAAATTAACTTAGAACATTGGTCTGCAGAG
TTTGCTCAATATAACTGAGCACATATTGTGGCTTTATGGAGCTGCTTACTACTTTTTGAC
CAAATAAATAATTAGAAGTATTTTTCCTCCTCAATAAGGTTCATTTTTCCTTTTTTCAGT
GAGCTGGTAGAGTTTCCTTTTTTGATATTTCAGGGCATCTTTCATATTTCCATCTCTTAA
GTTTCTTCATATGAAGTAGAATTTATCTGGATTATGTATTGCTGACTCTGATGAAACCC
ATAGAAAGCATCTGGGGCTTGATCACCTTCATTCTTGTAATAGCTCACACGGTTACAGCT
GATATGGTAACTTAAGACTTTTGATTCCAAATCTAGGCAAAATACACTCAGTTGAAAGAA
TTTGTCAGCCAGAACAGTTGGACTGTTCTGTGAAAATTGTGAGAAAAATTACACAACTAA
GTGATACATGATGATGGCTTTCTTAAATATAAAATTGTAATAACATGGTTAATTTCCAGT
ACGTTATATTGTCCCAGAAGTGGCTCCAACATTGTTTGAAATTTGTCTCATTTAAAGAAA
CATAAGCTGGCTATGGTGGCTCACGCCTGTAATCCCAGCACTTTGGGAGGCTGAGGCAGG
CAGATCACCTGAGGTCAGGAGTTCGAGACCAGCCTGGCCAACATGGTAAAACCCCATCTC
TACTAAAAATACAAAAATTAGCCGGGCATTTGGTGGGGGCCTGTAATCCCAGCTACTTGG
GAGGCTGAGGCAGGAGAATTGCTTGAATCTGGGAGGTGGAGGTTGCAGTGAGCCGAGATT
GTGCCACTGCCCTCCAGCCTGGGTGACAGAGTGAGTCTCCGTCTCAAGAAAAAAAAAAA
AAAAGCAAGAAACATAAAGACTGGGCATGTTGGCTCATGCCTGTAATCCCAGCACTTTGA
GAGACTGAGGTGGGAAGATCACTTGAGCCCAGGAGGTTAAGGCTGCAGTGAGCCGTGATT
TTGCCACTGTACTCGAGCCTGGGCAACACAGTGAGATCCTGTCTCAGGAAAAAAAAAATT
GCATGTAAATGAATGAATTTGATATTTAATATTTTAAATTATGAAAACTGTTCTGTAGAG
ATGTAGATCTTGCCATGTTGCCCAGGCTGGCTTTGAACTTCTGGGCTCAAACAATCCTCC
TGTCTCAGTCTCCCAAAGTATAAAGATTACACATGTGAGCCACTGCACCTGGCCTAATAT
TTTTAACTTAATGAATTTATTTTGATATAAATAAATTAATAACACTGAAGCTTCCTGATA
TAATAAGTCTTTTTGTGTGTGTGACGGGTTCTCACTCTGTTGCCCAGACTGGAGTGTAAT
GGCACTATCATGGCTCACTGTAGCCTCAACCTCCCTGACTCAAGTGATCCTCCCACCTCG
GCTTCCTGAGTAGATGGGACCACAGGCGTATGCCACCACACCTGGCTGATTTTTAAAATT
TATTATTGATACATATTAATAAAATTATTTTTATTTAAAAATGATATATGTGGCTGGGC
ATGGTGGCTCATGCCTGTAATCCCGACAGTTTGGGAGGCCGAGGTGGGAGGATCACTTGA
GACCAGGAGCTTAAGACCAGCCTAAGCAACATAGTGAGATCCATCTCTATAGAAAAAAAA
AAATGGCTAGGTGTGGTGGTGTATGCCTATATTCCCAGCTACTCAGGAGACTGAGGTGAG
AGGATTGCTAGAGCCCAGGAGTTTCAAGTTACAGTGACCTATGATTGTGCCAGTGCACTC
CAGCCTGGGCAACAGAGCAAAATCCTGTCTCAAAAAAAAAAAAAGTTCGAAAATGCTTAT
GATGCAATATAAGTAGTGGAAAAGGATATTAAATTGTGCCTATATGAACACAACTATATG
AAAAACTTGCACATAGAGAAAAGGATTAACAAGAAATAGACCAAATTGTTCACATGGTTG
TCTTGTTTGTGGAGAGAATATCAGTAGTTCATTTGTTTCCTTCCAAGTTTATATGTTTTC
CGAGGTCTCTATAATGAGTTTGTAATTGTTAATCATAGAAAACCCTTTTTGGTCCTTG
GCCACAAACTTACATGTTTAATGTAATTGCTTTTTTAATGAGAATAAATGTTATATTTT
GCTTTTTTAAAACCTATATTCCCATAGTTATATGAGCCCTTACAATTATTAAGAGGCTGC
ATAATATAACGTTTCTGGAAGGGTACAGAAGAAACAGCAGTAATTACCTCTGAGAACAGA
GACATGGCTTCACATTTTACCCTTTTGTACGTTTTGTGCTTTTGCCACATGCATTTATTA
TTCTTCCAATAAATAAGTAAATAAATATGGATTGTATACTCCATCTGGTTGGTGTTTCAT
AATTCTAAAATTATATTGCTACATTTTTAAAGATGATATGTGTTTCTACTTATTAACGTA
```

*FIG. 14B*

```
TATGTTAAAATAGTAAATTTATATCTTATTTAATAATTTCCCTATTGATAGACATTTAAG
ACAGTCTCAAGTGTTCACTATCATAGAAAATACTGCACAGATAGCTTTTGCTATAGTTTC
TTTTTTCTTTGAATCGTTAATTGGGAATAAATGCTCAAATAGTTATATGTGGCTCAACTG
CTATTTAAGTTTATTGACTGACTGCTGCCATTTTGAATTCTGAAGGGGTTGATTAAATTT
ATAATGCTGCCATAAGAATATAAGGGTATTGGCTTCATTAGCATCCACCAGCATTGGGTG
TTGGAAATGATTATAGATTTTTAAATGCTACAACAAATGTAGATAACAGAGAACTATCTA
TAGAACTCTTTTTGGACATGTGAATTGTAATAATAGTTTATTTTCATGTGAATCCAGAAA
AATGTATACGAAAACCTTTTTCCTCTCATTTCTTATATGAATAGAATCAAGCTATAGAA
GTGGTCTGGAGTCACCAGCCTGCATTCTTGAGCTGGGTGGAAGGCAGGCATTTTAGTGAT
GGGGGACAGGTAAGCACATGTGATGGCAATAACTTTCTTCTAATATCACATAATATAGCA
ATAGAAATAAAATTAAAAGTTTAGATTTTTTGTTAAAGGAGGTGAGATGTCACCTAATTT
GTATGCTATTATGTAACTAGTCTAGGATATTGAAGCTGACTATACTCTGTTTTTAGGTCA
TTATCTTGTAGTTTACCATACTCCCTACTTGCTTCTTATTCTACTATTTAACTCATTTTC
CACATCCCTAATTTTGGTTTCATGAAATTATTTTTCCTTCTGAATTACTAGGTTCTACT
TACTATTATTAAACTTTATTTCTGACATATTTTATAACCTTCCATGGTCTCACTTGATTA
AAAATAAAAAATTCAGCTGGGTGCGGTGGCTCACACCTATAATCCCAGCACTTTGGGAGG
CCAAGGTGGGCGGATAATTTGAGGTCAGGAGTTGGAGACCAGCCTGCCCAACGTGGTGAA
ACCCCCCCTCTCTACTAAAAATTCAAAAATTAGCTGGGCATGGTGGCAGGTGCCTGTAAT
CCCAGCTACTCAGGAGGCTGAGGCAGGAGAATTGCTTGAACCTGGGAGGTGGAGGTTGCA
GTGAGCTGAGATTGCACTGCTGCACTTCAGCTGGGTGACAAGAGCGAAACAATGTCTTGA
AAAAAAATAAAAAATAAAAAATTCTACAACACAGGGTTATTATTTTCCATTTTTGTTTT
CCCTTATGAGTTTAATATGTTTAGATTATAAACCTGAAAGCTTGAATACCTATGTCTATC
TTTTGTTTTCTTATGTTTATCAAGTTATTCCTTTAAACATTTTCTAAACTGTAAGAATAA
TGTGAGGCTGGGCTCAATGGCTTATGCCTGTAATCCCAGTGCTTTGGGAGGCCAAGGTGG
GAGGACCACTTGAGGCCACGAGTTCAAGATTAGCCTGGCTAGGCAACATAGCAAGACCCT
ATCTCTATAAAAAAATTAAAAAAATTAGCTGGGCATGGTAGCAAATGCTTGTAGTCCCAG
CTACTCAGCAGACTGAGGTAGGAGGAATGCTTGAGACCAGGAATTTGAGTGACCTATGAT
TATGCACTCCAGCCCGGGCAATAGCAAGACCCTATCTCTTAAAGAAGAAGATGTAGTAA
TAATACATATTCATTATAACTATTTTACCATTGAAAGTAAAAAATGAGTTTTTACCTTTT
CCCAGTCCCATCCTCAGAATGGGGATCTCAGTAGACCTTTAGGATTGGAAGAATGAGATC
ATTCATATTTTCTGCAATTATTACCCCACAAAATATTTCAGATACCTTTCCATGTATTAC
AAACAATGTGCATTTAACATGTCTCTCTCTTTCTCTCTCTCTGTGTGCGTCTTCATGA
TCCTCTGTTGCAGCCCTGCCAGTAAGACACTATCTCCTGAAGAATCACTGATAGGAACAG
AAAGTGGACTGGCTAGGCCAGGAGTCCTTAGCTTCTTAGGGGGCAGGAGCTGCTTTGTGC
TTTCTCAGAATCAGATATATATGTGGACTGAAACATTTAAAAACAGAATAGCCAAGGGTG
CTATACGTTTAAAACTTATATAGATGGGGCTACATTGCTCTCTATTACTAATTTCCCATG
ACAATACACGAGAGTGCCATGTCTTTTTAACTTGTTTTGAGCACAGACTAATCTTGTTTA
TGCATGTTTTTTGATGAGAATAGGCTACTCATGAGAAATCTGTAAACCTAACACTAGTCC
CTTGCATACTCTAAATTGTTGCTAGAATCTTAAAATTTTAGCACCAGACGGACCTTAGAA
ATCATTAACTTTGGTGCTTTGTTCTACAATACAAGGAGATGGAATATTTTACCCAGGATT
GCTTAGCAGGTTACAGTTCTGCCCTCTGAGTACCCAGCACTTCCCTGTGGGCAACATCAA
CTTCCTGATTTTCAAGTCTTAATTAGTACTCTGAAGAATCCTACTTGTTTTTAACTCCCA
TTTGCTTTGAAGTGACTTTACCTGATTTTTTTAGATCCCTTATTGCAGCAATGCCACTAA
GAAACTGAGTCTCTAGCTTCTTGGTGGGCAGGAGCTGCTTTGTGCTTGCTCAGAATCATC
CTTTTCAGTAAGGGAGATATTGAAGAGAAATCTACTGAGGAGTCTGGGGGTGAGGCACTC
AGGGAAATCCTGCTCCAGTCCACAAAAGCAGAGAGGAAGGGTTGGTTACCTAGAGTATTT
AACATGCAGAGGCTTTGGATTTTACTCCTTTAATCCTTGGAAATGCCTATGGAAGGGGAA
AGGAAGTAAGATGGTGACTCCAGCTTATAGACATACTAGTGTTACATATATTTAAACTAT
AATAGGAGGGTATTATTAGTTTTACTTAACTTTCAACTGTGAAGGATTATACTTCTCAAT
ATTTGTCTCCAGTGTCTATTTCAGTGTATTTTTCACTTTTCTTGAAGCAGCATGTCTGTT
GCAAAACTTCTAGAAATAATGAGAATATTTATATATTAGATCAAGCCATAACTTGATGAT
ATAGTCATTTCTTCTTATATTTTTACTTACATTTTTACATTTTAATGATTACTTTCATT
TTTGAAAAACATGTCATGCTGAGATGTATTTTTCTTCATTCTGTAATTAGTTATGAAACA
```

*FIG. 14C*

```
GTTTTTCCTAAAATGCTGAGTATATCAAGTCTTGGCTAAGAATAAGTAATAAATATTTGC
CACATGAAAGACTACACATATAGCCAGGTGCAGTGGCTTGCACCTGTTTTCCCAGCTACC
CAGGAGGCTGAGGCAGGAGGATTGCTTGAGCCCAGGGTTTCCAGGCTGCAGTGAACTATG
ATTGTACCACTCTACTCCAGAATGGGTGACAGAGCCAGGCCCCATCTCTCAAAACAGAAA
AGAAAGATTACATAGACTACATATACACCCCCATCCAAAACATACACACACATCTACTTA
ACCTAAAATGGTAAGAAGATAACTTCTTATTTTCTAATATATGACACAGAAAAGTTTTTT
TAAAGTAGTTTTAAATTTTTAATTTTTTCTAGGTATTTCTCAAGCCATGTTCCCATGTGG
TATCTTGTCAACAAGTTGAGGTGGAACCCCTCTCAGCAGATGATTGGGAGATACTGGTAA
AGAAAACCAAATAAGAACTATCTCATTTAAGGTTAAATTACTTCACAATATCAATGTCTT
TAGCTTTCTCTAAGCTTTATTATATATTCTGAGTTGGTTTTGAATTATAAGAATGAATTG
GGGCCAGGCACAGTAGCTCATGCCTATAGTCCCAGCACTTTGGGAGGCCAAGGCAGGTGG
ATTGCTTGAGTCCAGGAGTTCAAGACCAGGCTGGGCAACATGGTGAAACCCCGTATCTAC
TAAAAATACAAAAATTAGCCAGGCATGGTAGTGCATGCCATTAGTCCCAGTCACTTGGGA
GGCTGAGGCAGGAGAATCGCTTGAGCCCGTAAAGTCAAGGCTGCAGTGAGTCAGGATCTT
GCCATTGTACTCCAGTCTGGAAAACAGAGTGAGACCTTGTCTCAAATAAAAAAAGAATGA
ATTGATAGAGATCTAATGTACAACCTGACAACTATAGGTAATAAAATTGTATTGGGGATT
CATGTTAAATGAGTAGATTTTAACTACTCTTACCACAAAAACACAAAAGTGGGTAACTGT
GAGATGATGTATATGTTAATTTACTTCACTATAGTAACCATTATACTATCTATATGTAGC
TCATAACACCATGTCGTGTATATTAAATATGCACATTAAAATTTGTTTTTTAAAAAAAGA
ATTGAGATTTTTTTTAACTAGATATGGAGTGGACAAAATGTAAAGTGAATTGATCTTTTC
GTCTGTTGGTTCTAGGAGCTGCATGCTGTTTCCCTTGAACAACATCTTCTAGATCAAATT
CGAATAGTTTTTCCAAAAGCCATTTTTCCTGTTTGGGTTGATCAACAAACGTACATATTT
ATCCAAATTGGTAGGTGCTATTGTAATATTTGCTGTCATATTCTACACTATAGCATTGAG
TCCAAAGTAGAAATGAATGTGCACTAATGAGCTTTATTTTCTACACAGTTGCACTAATAC
CAGCTGCCTCTTATGGAAGGCTGGAAACTGACACCAAACTCCTTATTCAGCCAAGACAC
GCCGAGCCAAAGAGAATACATTTTCAAAAGCTGATGCTGAATATAAAAAACTTCATAGTT
ATGGAAGAGACCAGAAAGGAATGATGAAAGAACTTCAAACCAAGCAACTTCAGTCAAATA
CTGTGGGAATCACTGAATCTAATGAAAACGAGTCAGAGATTCCAGTTGACTCATCATCAG
TAGCAAGTTTATGGACTATGATAGGAAGCATTTTTTCCTTTCAATCTGAGAAGAAACAAG
AGACATCTTGGGGTTTAACTGAAATCAATGCATTCAAAAATATGCAGTCAAAGGTTGTTC
CTCTAGACAATATTTTCAGAGTATGCAAATCTCAACCTCCTAGTATATATAACGCGTCAG
CAACCTCTGTTTTTCATAAACACTGTGCCATTCATGTATTTCCATGGGACCAGGAATATT
TTGATGTAGAGCCCAGCTTTACTGTGACATATGGAAAGCTAGTTAAGCTACTTTCTCCAA
AGCAACAGCAAAGTAAAACAAAACAAAATGTGTTATCACCTGAAAAGAGAAGCAGATGT
CAGAGCCACTAGATCAAAAAAAAATTAGGTCAGATCATAATGAAGAAGATGAGAAGGCCT
GTGTGCTACAAGTAGTCTGGAATGGACTTGAAGAATTGAACAATGCCATCAAATATACCA
AAAATGTAGAAGTTCTCCATCTTGGGAAAGTCTGGGTTAGTATAAATTTTATAACTTGGG
AGAAATTTTATGTGGCTTAAACATCCCCAAATTATGAATTAGAATAGTATTTCATATATA
AATTGAAAATCAATTAAAAAGAAACACAGTGCCTAAAGGCACTTGGGGGACACATTTACG
CTTTGCAGTAAAGTCCTTGTTTGGATAAAGATTGTATGTTTTCTGGCCAAGTAAGCTTGA
ATAGGTACAAGCTTAGATAGGTTCAGGCCAGAGAGGTCAAAATTACTTGCCTGAGATTGC
ATAGCTAGTGTTACAACTAGGATTCAAACCCAGGCAGATTGACTTGGGGGTTCATCAGGA
TGGAGTGCCCTACAAAGCCTCCCATCTTTAATGCTTGCAGATTTGTTCCCCAGTTACCGA
AAGCAACTTGTTAATATTAGGGAAAGGGCCAGTGTAGGGAGAGATCCATGGCATGAGGT
AACCTTCCTGCTGCATGTGGTGGCACCTGGATTGGAATGCATCCAGGAGCTGCTTACCCT
GCCGGTGTCTGCTCTTTAATTTGTGTATAACGGAGAGGAAGTAGACAGGGCAACTAGTGC
TCCAGCCCCTCATCCTGGCCACAAATATTAATGCTACCTTTATATGACATAAGTCACTAG
TCCATTTATTGGAACCTAAATTTGAACCACTGTAAAGTAAGACTTCATAGTGATAAAGAG
AGGAACTTGTTAGGAAAGAGAATAAAATAGAAAGAGAAGGTTGTCTCCTTTTGTAGATTT
TTTTTTTTCTCCAACAGTTTTACCTGTGACCTTTATACAAATAACTGACAAAGCATTAA
TCTCTTTGGCCTACATCATTTTCTTTTCTATTTTTTTTTTCCACAAGATGGAGTTTCACT
CTTCTTGCCCAAGCTGGAGTGCAGTGGCATGATCTGGCTCACTGCAACCTCCGCCTCCCA
```

FIG. 14D

```
CGTTCAAGTGGTTCTCCTGCCTCAGCCTCCTGAGTAGCTGGGACTACAGGCATGCACCAC
CACGCCTGGCTAATTTTTGTATTTTTAGTAGAAACTGGGTTTCACCATGTTAGCCAGCC
TGGTCTGGAACTCCTGACCTCAGGTGATCTGCCTGCCTCGGCCTCCCAAAGTGCTGGGAT
TACAGGCATGAGCCACTGCTCCTGGCCGGCCTACATCATTTTCTAAAGCTCCAGACCATT
CTTTTCTTTTCTTTTCTTTTCTTTTCTTTTCTTTTCTTTTCTTTTCTTTTCTTTTTCTC
TTCTCTTCTCTTCTCTTCTCTTCTCTTCTCTTCTCTTCTCTTTTCTTTTCTTTTTTGAG
TTAGAAGCTTGCTTTGTTGCCCAGGCTGGAGTGCAGTGGCACCACCTCCACTCACTACAA
CCTCCACCTCCCAGGTTCAAATGATTCTCCTGCCTCAGCCTTCAGAGTAGCTGGGACTAC
AAGTGTGCGCCACCACTCCTGGCTAATTTTTGTATTTTTAGTAGGGACGAGGTTTCACCA
TGTTGGCCAGGCTAGTCTTGAACTCCTGGTCTCAAGTGATCCGCCTGCCTCAGTCTCCCA
AGGTGCTGGGATTACAGGCGTGAGCCACTGTGCCTGGCCTCAGATCATTATTTTCTGTTA
GCTTTAAACTGTCCGTTCAGGAGATCCCACTGCATCCTCAAATTCAAAATATCTAACACT
GAGCTTATGATTTAGCTGGTTCTGTCATTAGATGGGAATATCCTTTTATTTCCTTGAAAT
TATATGGTGAGAACAGGGAGAAGTGCTGATGGTAAAGTCCTGTGATTAAGATAGCAATAA
GGACTCCGCCCTTCCCACTCCACTGAAGGTTGAAGAGCCATGGACAATGAGAAGTCACAG
TAGGTGAAATCAGGTACTAAAATGGACTTGGCTTGAGAGATCAAAATTGATCACTTGGTG
ATACAACTAACAAATTCATGTTAACTTGAACCTTTATTACCCTGTGAAGCATGGTGATTA
AAAAAAAACAACAAACAAACAGGAAACTTGATTGTTAAATTCTCTTTAAGTCAGAATATG
TACCTTAGAGTTTTTATTTATGCTTTTGTCTACCATTAATATGTCTGCACCTGCTCTTTA
GAAGTTAATAGACAGTAAAGTCGTCTTTATGTCTTTCAGTGCTTACTTATATTTGGGAAG
TTGAGAAAAATTTTTAACATCATTATTGATATATATATATATATATATATATATATATAT
ATATATATATATATATATATAGATAATTTTTTTTTTTTCTTGAGACGGAGTCTCACT
CTGTCGCCCAGGCCGGAGTGTGGTGGCGATCTCCACTCAATGCAAGCTCTGCCTCCCAGG
TTCAAGCGATTCTCTTGCCTCAGCCTCCCGAGTAGCTAGGATACAGGCTCCCACCACCAC
GCCTGGCTAATTTTTGTAGTTTTAGTAGAGACGAGGTTTCACCATATTGGCCACGCTGGT
CTCAAACTCCTGACCTTGTGATCCGCCCACCTCGGCCTCCCAAAGTGCTGGGATTACAGG
CGTGAGCCACTGCGCCCGGCTGAGGTAAAATTTAAAGTGTACAATTCAGTCATTTTTAGT
ATATTTATACTAGTTGTACAGCCATCACCACAATCTAAGTTTAGAACATTTTCATTAGGG
GGTGGGAGAAATTTTACTCTGCTTTTTAGATTAAGTTTCTGTCTGGATCTAATCATTTAA
TCAGACAATCAGGCAGATTGTCTGTGATTAGTTTTGGCCATTCCAGCTTCTTCATTGGTT
GTTAACTTTCACAAATAAAGGCTGCTCAAAGATTAGAAATAACATTTAATTTGAATGTAA
ATGTGCCATAGTTTAAAAGATGGGTTTGGTGAATACAGTCAAATACATACATTTAAAGCT
CTAATTCTGAAGATTATGTAAAGAAAAGGAAAGAAATGTAGGGAGAGGATTGAAATGTTC
ATGGTATAACAATATCTGAACATCCATCTGGTCACACCGTTGGTATTTGAATGTTTTGTC
CTCCTCAAATTCATATGTCGAAATCCCAACTCCCAAGGTGATCGTATTAGGAGGTGTGGT
CTTTGGGAAGTGATTAGGTCATGAAGGTGAAGCCTTCATGAATGGGATTCGTGCTCTTAT
AAAAGAGAACTGTGAGAAATAAGTTTCTGTCGTTTGTTAGCCACCCAGTTTAGGATATTT
TGATATAGCAGCCTGCATGGACTGAGACAACTATGAGTTATTATGATAGCTTCTGTTATT
TCACCTAAATTCATAGAAGCTAATATATCAATATTTATGCTATGAAATATTTCTTAACCA
AGCTTTGAATATATTTATATTTTTGTTTATTTTTAAATTTCAGATTCCAGATGACCTGAG
GAAGAGACTAAATATAGAAATGCATGCCGTAGTCAGGATAACTCCAGTGGAAGTTACCCC
TAAAATTCCAAGATCTCTAAAGTTACAACCTAGAGAGAATTTAGTGAGTTCAAATATATA
TGTTACATCAAAATTCTTTTACACGTTTTGTAAGATTTCTAGTTGCTTTAGCTAAGTAAT
AAGAATGTTGTATTCCTTTTTGATACAAATCTTTTTTTATTGTGTTAAACTATATATAAC
ATAAAATATGCCATGTTCGCCATTTTTAAGTGTATAATTCAAAGGCATTAATTACATTCA
TAATATTGTACAACCATCACCACTATCTATATCCAGAACTTTTCCATCACCCCAAAGAGA
AACTTGGTACCCATTAAACAATAATTCCCCGTCCACTCCTTTCCCCAGTCCCTGGTAATC
TCTAATGTATATTGTGTCTCTATGAATTTACTTATTCTAGATATTTCATATATAAGTAGA
AGTATGCATTTGTCTTATGTATCTGACTTATTTCATTTAACATAATGTTTTCAAGGCTCA
TCTGTGTTGTATGTATCAGAATGTTATTCCTTTTCATGGCTGAATACTATTCCATTGACT
GCATATACCACATTTGTTTATCCATTCATCTGTTGATGGACACTTGGGTTGTTTCCACAT
```

FIG. 14E

```
TTTTGGCTGCTGTGAATAATGCTACAGTGAACATTGGTGTACAAGTATCTGTTTGAGTTC
CTCTTTTCAGCTCCTTTGGGATATACCTAGGAATTATGTTTAACTTTTTGAGAAGCTGAG
AAATCTTTAATAAATGATAACACAAATACTTATATTTGCCAATGCAAATATGAATATTTT
TGGCTTTTAAGAGATTGATCATTTTGCCACGTGGTTGTAATTAAAAAAAATTGTCCCATG
TTGTTTCAGTATTAATATTGTAGCCTAAAAGAGTGCTAGACTGTTTTACTTTTTACTCAG
TTAATTCTTTGGATACTGGTAGAGTCAGGAAATGAGATATTGAACTTAAAGATCTTTGCA
GGTGGGGTCCAGTGGCTCACACCTGTAATCCTAGCACTTTGGGAAGCTGAGGTGGGAGGA
TTGCTTGAGGCCAAGAGTTTGAGAATAGCCTGGGCAACATAGCAAGACCCCATCTCTACA
AAAAAATTAAAAAAAAAATTAAGCCAGGCGTGGTAGCTCACGCCTGTATCCCAACACTT
CGGGAGGCTGAGATGGGTGGATCACTTGAGGTCAGGAGTTGGAGACCAGCCTGGCCAACA
TGGTGAAACCCCATCTCTACTAAAAATACCAAAATTATCGGGCGTGGTGCTAATCCTGT
AATCTCAGCTACTCAGGAGGCTGAGGCAGGAGAACCACTTGAACTGAGGAGGTGGAAGTT
GCAGTGAGCCTAGATCTCACCACTGCACTCCAGCCTGGGTAACAGAGCGAGACTCTATTT
CAAAAAAAGTAAAATAAAATTAGACACATGTGGTGGCACATGCCTGTAGTCCTAGCTA
CTCAGGAGGCTGACTGAAGTGGGAGGATCTCTTGAGCCCAGGAGTTCCACACTGCAGTGA
GCTATGATTGTGCCACTGCACTCCAGCCTAGGCAATATCTCAAAAAAAATTTTTTAAAT
AGATTATTAGGCCAGACGTGGTGGCTCATGCCAGTAATCCCAGCACTTTGGAAGGCCAAG
GCAGGCGGATCACCTGAGGCCAGGAGTTTGAGACCAGCCTGGCCAACATGGTGAAACCCC
ATGTCTACCAAAAATACAAAAATTAGCTGCAATGTCTATAATCCCAGCTACTTGGGAGCC
TGAGGCAAGCGAATCGCTTGAACCCGGGAGGCAGAGGTTGCAGTGAGTGGAGACTGCGCC
ACTGCACTCCAGCCTGGGCGATACAGCGAGATTCTGTCTCAAAGAAAAGGAATTTGTTT
TCCTGTCTTTATCGTAGAGGGAGGAAAGGGAGAATGGGGTTGGAATGGTTATTGAGTGAG
CCACATTATGGTAGATGTATCACTGGGCATAGAGAAAGGAGCATTTAAAACTTTTCCGC
CTAACAGATGTTTCTTCAGGCTACACTGCACTCATTGTGCTAACTGTAATGTCAAATCCC
AGACCTGTGCCTATAGAACATGAACATCCTTCATTGGATTTGTTTGGTCAGGCTTACACT
TTATTAGGAAGATCAGATGTTAAAATAAGGGTGTTAAAGTTAAGTTCAGATATGAGGATA
ATTCATTACTATTCCTTTTCTGGCAGCCTAAAGACATAAGTGAAGAAGACATAAAAACT
GTATTTTATTCATGGCTACAGCAGTCTACTACCACCATGCTTCCTTTGGTAATATCAGAG
GAAGAATTTATTAAGCTGGAAACTAAAGATGGTGAGTACATTTGTTATTTTGACTTTTTT
TTCTATTTAAATAGTTGTACATTTTTAATTGTTCTTGCAACCTGTCATACCTGTGAACAG
TATGTGAATAGTGAAATATAATTATGATAATTAAACAGTAGTTTTTATGTATTGAAAAAT
ATCTTTGGCCGGGTGCAGTGGCTCATGCCTGTAATCCCAGCACTTTGGGAGGCCGAGGCA
GGCGGATCACTTGAGGCCAGGAGTTCGAGAGCAGCCTGCCAACATGGCGCAACCCTATCT
ATACAAAAAAATACAAAAATTAGCCTGACATAGTGGTGTATGCCTGTAGTCCCAGCTACT
TGGGAGGCTGAGGCAGAAGGATCACTTGAGCCCAGGAGGTCTGTGTTCCTGCCACTGCAC
TCCAGCCTGGGCAGCAGAGTGAGACCCTGTTGGGGGGAAAAAAAAAAAGTCTTTAACTT
AAATAAATTTGACATTTAAAATCTTAAATTATTTCATCTCTGTTTCAGTACTAACTCTGC
ATTTATTACTTTCTTTTTAATAGGACTGAAGGAATTTTCTCTGAGTATAGTTCATTCTTG
GGAAAAAGAAAAAGATAAAAATATTTTTCTGTTGAGTCCCAATTTGCTGCAGAAGACTAC
AATACAAGTAATAGCATGTTATTGAATATTTAATAAAATACTATTTGTTACATATGATTG
ATAATAAAGTATGAAGTTCCTTGTAACACCTTGCATTGTGAAGTGTATTAAAAACCTGCT
AAGAGTAAGGAATAACTTGATTTAAAATATTTTATTCTGTAATCTCTTTAAATTATCTGT
ACAAATTATTGACTTAACCTAAATTTAAAAATGAATGCCTTAGCACAATTAAGTTCAAG
AATAGAGTTGATCATGTTAACTGGTAAATGGATCATGATTTAAAATTCTTCTAGGATTGA
AACAAATGAAAACGTAGTTTTAAGGGTTTGATTTTTAAATTCCTATTTTACATGCAAT
TTTACTGCACAACCCATCTTATTTTGACAGTTCTTAAATTCGCAACTCTTCAGAAATATT
ATCAGATCACTTTTCTTTGCTTCCATAAGTTTTTTTATTATTATATTATTATTTTTTTTT
TTTAAAAGACGGTGTCTCACTTTGTCGCCCAGGCTGGAGTGCAGTGGCATGATCATGGCT
CACTGCAGCCTCGACCTCCCAGGCTCAGGTGATTCTCCCACCTCAGCCTCCCAAGTAGCT
GGGACCACAGGCGAATGCCATGATGCCTGGCTAATTTTGTATGTTTTGTAGAGATAGGG
TTTCACCATGTTGCCCAGAATTGTCTTGAACTCCTGGGTTCAAGCAGTTGTTCTGCCTTG
CCCACCCAAAGTTGTGGGATTACAAGTGTGAGCCACTGCGCCCAGCTATTCTAGAAGTAT
```

*FIG. 14F*

```
TTTAAGAGTCATCTTTTTTTTTTTTGAGATGGAGTCTCACTCTGTCACCCAGGCTGGA
GTGCAGTGGCACACTCTCGGCTCACTGCAACCTCCACCTCCTGGGTTCAAGTGATTCTCC
TGCCTCAGCTTCCCTAGTAGCTAGGATTACAGGCGCATGCCACCATGCCCTGCTATTTT
TGTAGTTTTAGTAGAGACGAGATTTCACCATGTTGGCCAGGCTGCTCTTGAACTCCTGAC
CTCAAGTGATCTGCCCTCCTCAGCCTCCCAAAGTGCTGGGATTCTAAGTGTAAACCACCA
CACCCAGCCAAGAGTGGTCTTTTTACAATATTATTTTTGATTAGGACATTCATTCTTGT
CATAAAATTGAAGATACTCTAGTCATTTAGAATTTCATTGTTTTGGAACTAGACATTGTT
TCTTTATTTTTGAAATGTTATTGAAGGAATACCATTTGGAGAAGATACAAATGTAAGAAT
TGTGAAAAGGATAATTGTGACACAAATCAAAATTATAGATAAAAATATACCTGTAAAATG
TATTAAGGCAATAACATTCTTTCTGCTTGTTGACCATAAATATTTATATTCCCTGGATGG
GTACATTGTTATTGTCAAGGGTGTTTAAATAATGATCTTGCATGCATAATTTATTCTCTC
TGGTATAACAGAATCAGCAATTTAGTTTTCTGGGACCCGAGAAAAACATGCAAAAGACAT
ACTTTGAAATGTAAAACTGATTTTTCCTTGCAACTGTAG<u>GTCCTTCTAGATCCTATGGTA</u>
<u>AAAGAAGAAAACAGTGAGGAAATTGACTTTATTCTTCCTTTTTAAAGCTGAGCTCTTTG</u>
<u>GG</u>GTAAGAAGTTATGGCCAAACTAGCATGTTAGACATGTTTTAACACTATATCTGGCAG
AGTTTTCAATGTAAATATTAAAGTAGATGTTAATGTCAATAAGTGATCTTAATAATGCAT
CAGTAGATATTTTTCAAGGATTGTCTCTATCTTCACGCCTAGCTTATAATTTGCCTTGT
CGTCTTTTTTTTTTCTCTTTATTTTTATGTTTTTATCCATCCCTGGTGGTAGGGGATAA
CCTTGTCTTCTTCGATAACAAGAAGTCTGAAGCTTATTAGAAATTTTACTTTGAGAATTG
ATCGATGAGAAGAAAGCAACTAGATATCACGTGGATCATATATGCTTGAATAAAACAATA
ATTCTTAGAACAAATAAATACATTTTAAAAGTTAAAGCCAAAAACATTAGTTGAATGTTT
AAAAATATTTCAAATTAAGTTATTCCTTCACTGTCTTGTATTACTGTAATAATTTGGATT
ATTTGTGTTTTCTCAACTTTTAAAACAAATATTTAAAAAATTCCTCTTTTGATTAAGTA
GGGCTAGATAAAATATAAAAAATATTTTTAAACTCCTCTTAATTTCCATATTTCTTATA
TAATATGAGAATCTCTTATAAACACTACCTCTTAGAAGTCTCCACAGAAGCTTTGGTAGA
TGTAGTAGTAGGGATTTGATTTCTTAGAATGGTATAATCTGTAAATGTTTTAGTAAAAGG
ATTAAACGATAAAGTCAAAATGTTTATAGCACAGTGTTTATTAATATAAAATAAAATCTC
TTTTTTTTTTTTGAGATGGACTCTCACTTTGTCACTCAGGCTGGAGTGCAGTGTTGCAA
TCTCAGCTCATTGCAACCTCCGCCTCCTGGGTTCAAGCAATCCTTCCGCATCAGCCTCCT
AAGTAGCTGGGATTACAAGCATGCACCACCACACCTGCCTAATTTTTTGTATTTTTAGTA
GAGATGGGGTTTCACCATGTTGGCCAGGCTGGTCTCAAGTGATCCGCCTGCCTCAGCCTC
CCAAAGTGCTGGGATTACAGGCGTGAACCACTGTGCCCAGCATAAAGTAAAATCTCTTCA
GACTCTCATGTGATCATGTAAAGTGGCAGGCAGTCACAGTCAAGAAGTAGTTTAAAGTTC
ATGTTTGTAAAATATAATCTACAGATTGATACTGGATTTCATAGGTAATGTTTAAGAGAA
AATAAGTTTTTAGTTATCCTCAGTACTTCAAAAGCACCCATTTATGATTATGTTGATTAC
TAAACTAAATCATTTGGGGGCTAGAGGTGTTTTTTTATGTGTTAAGATTCCTTAAGGAGT
TCTATTAGGGCAAAACTTTTAGTAACTGCATATTTTAAAAGTAATAAAACTAATTTTAAA
AGCTTGGAGGCTGGGCGCGGTGGCTCACACCTGTAATTCCAGCACTTTGGGAGGCCAAGG
CGGGTGGATCACTTGAGGTCAGGAGTTTGAGACGAGCCTGAGCAACATGGTGAAACCTTG
TCTCTACTAAAAATACAGAAATTAGCCAGGTGTGGTGGTGGGCACCTGTAATCCCAGCTA
CTCGGGAGGCTAAGGCAGGAGAATTGCTCGAACTTGGGAGGCAGAGGTTGCAGTGAGCCG
AGATCATGCCACTGCACTCCAGCCTGGGTGACAGAGCAAGACTCCGTCTCAAAAAAAAAA
AAAAAAAAAAGCTTGAAGTCAGATTCGACATTAATCAGTATACTTTCTCTCAAGTAGGGG
ACAATTTCTAAGATTTTAGTCTTTTAAAATTTATTAACTAGTCTGAGCATGGTGGCTTGT
GTCTATAATCCCAGCACTTTGTGGGGCCGAGGCAGATGGATCACTTGAGCCCAGGAGTTG
GAGACTAGCCTGGGCAACATGGCAAAACCCCGTCTCTACAACAAATGCACACACAAAAAA
CCCAATCAGCTGGGTGTGGTGTTACACTCCTGAAGTCCCAGCTACTCGGGAGGCTGAGGC
AGGAGGATCACCTTTGCCAGGGCGTTTGAGGCTGCAGGGAGCTGGGTTCACACCACTGCG
CTCCAGCCTGGATGACACAGCAAGCCCCTTTCTCAAAAAAAAAAAGATAAAAATTAAAT
TAAATTAATTAACTACACTGGGAAGGCAAAATTCAGCATTTTTTATAGCTAAATTTTAT
CCTGCTTCAGTCTTTTATCATGTAACTATGTATATTTTTTACAG<u>AGGAGTGAATTCCTTA</u>
<u>GGCGTATCCTCCTTGGAGCACATCACTCACAGCCTCCTGGGACGCCCTTTGTCTCGGCAG</u>
```

FIG. 14G

CTGATGTCTCTTGTTGCAGGACTTAGGAATGGAGCTCTTTTACTCACAGGAGGAAAGGTA
AGTGGTTAAGGTGTGTTCATTTTTCTGTAACATTTAATAACTTTTCATTTATCTTTCTTT
GGGTTTTGACCATCTATTATATAGGGTGGGTTTTGACCATCTATTATATAGGGTTTATAC
GACATATGGAAAGCATTCATTTATTCACTAATATTTCTGTGTGTCTGCTTTTAGGTGTTG
GGGGAGTGATGACGAATAAGACTGATGTTCTCCATGCCCTTTTTCTGTGTCAGTTGATAC
AATTATATGGTTTTTCTTTTTTAGGCTATTAGGTGTTGATAGGGTTGAGTAACTTACAAA
TGTTGAACCAGCCTTGCATACCTGTGATAAATACCACGTAGTTGTGGTGTATCATTCTTT
CTACATTGCTGAGTTTTATCTGCTAATGTTCTGTTGAGCTTTTGTCCATTTAAGTTTGAA
AGTGATTAGTTTGCAGTTTTCTGTTTTTGTGTTGTCTTTGTCTGGTTTTGCTATCCGTGT
AAATCTGGCCTCATAAAATGAGATGGGAAGTATTCTCTCCTCTTCTTTTGTTTTTTTGGA
AGAGGTTGTATAAAATTGAGGCTGAATCTTGGTGGTTGCCACAATGACAGGAACTATTTC
TGTGACTGAATATATTGGGAATTCCTATAAAGCAATTATTTTCTAGGGAAGTGGAAAATC
AACTTTAGCCAAAGCAATCTGTAAAGAAGCATTTGACAAACTGGATGCCCATGTGGAGAG
AGTTGACTGTAAAGCTTTACGAGGTATGAGTATGGTAACACTCTATATAAATCCCTTTTT
CATTAGAAAGACAGGAATGTTATACATAATGCTGTCAATCTAATAAATACACATATCATC
TAGTCTTTAACTTTTCTGTTTATCATTTAGTCATTAAAATTTCTTTGGCTTTCTAATGTT
TTTGATAAAATTTCTAAAACTCTCCATATTTAATGGAGGCCTATTTTTTTTTCTAGCCAG
AACTTTTTGTAGACTACATTTCTGGAAGTGCTCACTGACACCACTCTGAAAAATTAGTAC
TTAGAATATACTCTAATTGGTATAAATGATCTCTGAATTGCTATGGAAAACTGGGAGAAT
GGTTGCTTCAGGGGAGAGAAAGTAGGAGGCTGTGGACAGCAATGAGGAGAATTACAGTTC
ACCATATAACACTTTTGTACTTTTAAAGTCCTTAACATTTACATTATTATCTATTCAATT
AAAAAATATTGGGAAGATTTTACTTTGAACAGTTAATTTTTCCCCCATGGGTACCGCTGT
CATATAGTTCCAACTAATCATGAACTTGTGTATTTCCTGTTCTTTGTAAATTTAAACTTT
GTAACTCACCAGGAAGTTTGAAGCCAAATTTGTGTTTCAAATATAGCAACTCCAGGATCT
CTAGGCAGATGCATTTGCATTTGATTTTAAATGAATCTTGATCCCTTACTCTCACTTATG
TTTTCCCACATCCTACTTTTTTTATTTTGTTGTAAGCCATCTAAAATTCTCAATGGGATG
AAACTGGGTATAAATGAATACATGCATACAGGAATTATAGTAGCATATTCCTTTTCTTTT
TTCTTTTTTTTTTTTTTGAGACAGAGTCTTGCTCTGTAGCCCAGGCTGGAGTGCAGTGG
TGCGATCTCGGCTCACTATAGCCTCCACCTCCCAGGTTCAAGCAATTCTCGTGCCTCAAC
CTCCCGAGTAATTGGGACTACAGGTGCATGCCACCACCTGGCTAATTTTTGTATTTTT
TAGTAGAGATGGGGTTTCACCATGTTGGCCAGGCTGATCTCAAACTCCTGACCTCAAAGT
GATCTGCCTGCCTTGGTTTCCCAAAGTGCTGGGATTACTAGCATAAGCCACTGCACCTGG
CCTCCTTTTCTGAGTTTTATAAAATTTGATACTTTACTGCACGCTTTGAGACTGTATTAA
TTGAACCATGTTGATGAACAAGTTTTTGTGATGGGTATATTAATAAAATATAGATCAAAT
TTTTATAGTTAAATCAATATCGAGCTTTTCTAGTGCTTTCAAAGGACAACCTGAATTTT
CCCAGCACTGAAATGATACTGAAACCATTTCATATCTTCTGTATTAAGGAAAAAGGCTTG
AAAACATACAAAAAACCCTAGAGGTGGCTTTCTCAGAGGCAGTGTGGATGCAGCCATCTG
TTGTCCTGCTGGATGACCTTGACCTCATTGCTGGACTGCCTGCTGTCCCGGAACATGAGC
ACAGTCCTGATGCGGTGCAGAGCCAGCGGCTTGCTCATGGTAAATGCATCCACCACTGGC
TTAAGGTCTTGTTCTTTTGTCAGTCAGCATTTTTAGTCTTAACAATAAATCTACTCTCTT
CAGAGAATAATATATGTGTTATGTTAAGTGTTGTGTTTGAGGCCCCTGATGGCATTCTAC
AGTTGTCCTATAGACTGTAATAGCAAAATTGGTAGAGTAAAAACAGTGTGAAAATTCTGC
AACTTCATGGTTAGTCCTTTAGGGTTTTTCATTCTCCCTTACTTATTGTTTAATTTACAG
ATTTACTCTTTTGTTCATTTGACAAATATTTGTCAAATGCTTGTGCACAGTCTGTATTCT
CAAATTCTAGGAGAAAAGAAGGGTGAACAGTATTAGCGCAGAACGATACTAATAATGAT
GGCTACTGTGTATGAGTAGCCAGCCCTTTCTTGGCTTTCTTGGATTGCTTTGTATTCTAC
ATGAAGATATTCCCTGGGCTTTACAGGTCAATAAATGGAAATTCAGAGAGATTAATTTGA
CCAGGGTGACCAACAAGGAGATGACAGCATACACTATGCGAGAAGTATACACAGAGTAGT
GTAGGAGCATATAACCTAAACTGGGGGTGAGGTGGGATAAGGAGTTATCAGGGAAGGCTT
TTTGGAGGAGTTGACAACTGAGCCGAGTTTTGATGGAAGAGTAGAAATTAGCATGAACCA
ATTTCATGCTAATAAAGAAGCAAAGGAAGCGTGGTCTACAGGCAAAAGCACAGAGGTACA
GGAAGTAATGATATGTTGGGGAATACCCTGTTGACTGGAGCTTAGAGTGCAAGGAGAGGA

*FIG. 14H*

```
GTGCTAGGGAGGTGAGGTTGGAGGGTTTGGCAGCATTGACTTGCTTCAAGGTTCTTAAGA
GCTGAAATAGATATAAAATGCAACTAAGAGTGGCTTGGATTATTATTACCTAGTGTGTTA
ATCTCAAATTTTGAAATCTATAGCATCTATAGGACTGGTGTTACTAATCTTACACTCGAT
CTGTTACTGTTCTTATACTAGATCTATTAGTCCAGTGTTTAAGGGAGTGGTGCAGATTTC
TAGGTCAGGACAGGACTCAGATGTACATTATTAATGCCTATTTCAGTTCTGACCTTCTCA
TATGAAACCTTATAAGACCTGGGGTAGGAAGAGATTGTTCTGGAAGTCATAGGAATATGA
ACTGTATTTTGTTTAACAAACAATACAGTATGGAAATTTATCACCCTTCCAGAATATTTA
TTTCAGAGACAAATTTTTATCATTCGTTCATTTATTTCATAAGATCCACGAGTAGGGAAC
CTCACTAGACATTGCTCTGAGTATATGGTCTGAGTTTGCAGTACCTCTTGTGTCTCCATT
AGATTTATTAGGTCCTCAATAGATAAATCAGGGAATAACTAGATGGATTCATTTTTTAAA
GACATGAAAGAGCGATACCATACATACTGCACCTTAAAGGTCAACCTTAGAGTATCATTA
TTTTTAATGAATGTATAATTTTAAATTTCATGTTTACTTTTCCTAAGCTTTTGCACTAT
ATTGCTTAATTCCAGCTTTGAATGATATGATAAAAGAGTTTATCTCCATGGGAAGTTTGG
TTGCACTGATTGCCACAAGTCAGTCTCAGCAATCTCTACATCCTTTACTTGTTTCTGCTC
AAGGAGTTCACATATTTCAGTGCGTCCAACACATTCAGCCTCCTAATCAGGTAATACACT
ACTTGTAAGGATTATTGAATTATGTCCCTTTTATAGAAATTATTTTTCAATTTTATTAGT
AATTCGTGGCTTTAAATTTATGCTTCTCTTAATGATTTTAAGGATATGTAAGTCAACATT
TGGTGCATATTGTGCTAGAGGCATAAATTATAATTTATAGCCACCTGAAATGTTAGTATG
CGCTTTCCAAGAAAATGACTTTTTTGAAAATGGTATTTCTTTGAATGAGAAAGAACAGAG
AGAAATAGATAGATGGCTTTTAAACACTTCATTAATTAAACTTTTTTTTCCACCATCAC
ATAATGGCACTTAGTCCCCTTTGGGAACTCATGAGGGTTTTAGTGGTAGTGAGCTGAAAG
AAATATGTTCCAGGACTGGCAAACATATTCTAAATTCTTTAAAATTTTCACCTAGCATCT
ACCCTAAATATTCAGACCCTGTGCTAGTTAACTGCTATTGAAGAACAAAGGTATTATATC
TATTATTAAGGATAATAGAATGGTATTTGAGATATTGGTCATTGAATATGAATATGTTTT
GAGAAATAAGTTTTATAGGAACCAAAAAAAAATTCTTAAAGGAACCATATATTACTAAAA
ATGCTTCTTATTGGAGAAAGAAATGACAATCATTTATTAATGTGATTTTTTCACAACTTT
ATTAAGATATAATTTAAGTACAACAAACTCACATAAAGTGTACAATTTGATCAGTTTTAA
CATATGTAGATGCCATGAAACCATCACCACAATTAAGGAAACAAACATTTTCATCACTCC
AGAAGTCTCCTAGCCCTTTTACTACCCATTCCTCCCCTGCTCCATCCCCAGACAACTACC
AATTTGCTTTCTGTCACTATAGATTTGTCAACCTGATTTTCTCCAAATATACATTCAAAA
ATATACAGTTGAATACAATTGGAAATTCGAATTTTGTGTTTTTTTCTTTAGGAACAAAGA
TGTGAAATTCTGTGTAATGTAATAAAAAATAAATTGGACTGTGATATAAACAAGTTCACC
GATCTTGACCTGCAGCATGTAGCTAAAGAAACTGGCGGGTTTGTGGCTAGAGATTTTACA
GTACTTGTGGATCGAGCCATACATTCTCGACTCTCTCGTCAGAGTATATCCACCAGAGAA
AGTATGTTTTACTATTAAAACCTGAACTTGGAATCTTCTTTCTATTGTGGAGAAATGTAA
TTGTAGTAAGACAAGAATTAAATATATTCCATTGTAGTATTTGAATAAGCAGTTATTTGA
GTAGAAAATTAGTGTTTCCAGCTAAGATGATGGCATATTTTGAAAATTCATATAGTGAAT
ATAACTAGTAAAGAAGTTTTGTTTATTTTTAAACAGAATTAGTTTTAACAACATTGGAC
TTCCAAAAGGCTCTCCGCGGATTTCTTCCTGCGTCTTTGCGAAGTGTCAACCTGCATAAA
CCTAGAGACCTGGGTTGGGACAAGATTGGTGGGTTACATGAAGTTAGGCAGATACTCATG
GATACTATCCAGTTACCTGCCAAGGTATGTTTAAAAAAAGAAAAGTGAATACTTACTCC
CAGAAGAACCACTGTATTATTGGCTTTGGCTTTATGTGTCAGCTTGCCCAATCTCCGTGT
GAGTCAACAAGTGTTTACTGAGTTACCAAATAAATGTCTTAACACTATTTTAGGTACTTT
AACAAATTTTAATTTTATTAATTAATTTTTATTAGAATTGAGACCTCACTCTGTCATCT
AGGCTGGAGTACACTCACAGCTCACTGCAACCTCAAACTCCTGGGCTCAAGCAATCCTCC
TGCCTCAGCCTCCCCAGTAGCTAGAACTACAGGCATGAACCACCATGCCCGGCCAACTCT
TTAATTTTCTTAGAGACGGAGTCTTGCTATGTTGCCCAGGCAGACAGATTTTAATGTGTA
TGATGCAGTCTTTGATGATAAGAAACTTATAATGGAAAGCTGAGGTGATAGTTACAGTAA
ATACATTTGATGTATAATTCTGTTTGCTTTAATCATTCAAATTGTAGTAAAGCAAGATG
AACTGTCTGCTGGGATTTGAGCAGAAATGGATAGGAATAAACTAGGAGGTAGAAGAGTTA
TCAAGGTTCACAGGACTGATGGGTGAAGCTAGATTTCCAGACCCGGGATGTCAGTCCTTG
AAAAGCAGACTTGGCAGGCATAGACGAGGCAGATAGCAGGATAAAGGAGACAAATGTAGA
```

*FIG. 14I*

```
GGCTCTACTTTGGAAGCTCTTATGAATCAGAACTTGGAAATGGAACCTCTTCTGATTTGG
TATCTTGTGCAGTCATCATTATACAGTTCTGAAATATAAAGCTATATGTTGGTGTAAAGT
TGCAGTGATTTCTCTCCTAACCAGCCCCACATATTCTTCCTGGTTGGTTGGTTCTTCAGT
AAAATAGTCTTGTTTCTTGCTTACACTAATTGGTAATTTGCATTCCTTGTTAAGATTTTC
AAGACAGGGCTGGGAGCAAGGAACCAAAGTAGCGCGTGGTTGTGATTACCTTTGGTTTCT
TTGAGGTTTCTCTTACCTAGTGGCTTTAAAACATCTTTAGGAGCAGTTCCATTTTATAGT
AAACTTAAATTCTGTTATCATGAACAGTTGAGGATAATGAATAATTTGATACAATAATGT
AAGAAATTCCTGAAAACAAAGTGTTATCTGTGATACTTTTGCTGCATAGTAAGCACAATG
AAGTGTACTGATAATGTTTCAACAGGAAAGTGTTTTGATTAAATGTGGGCAGTATCACTG
TTCTACTAGCATTCAACATCTCTTCTAAAAATTAATAGTGGTTCACTGTAATTTATTGG
TACATGTAACATCTGTACATGTGTTTGGTTATCTATATGTTTCCTGGTTTTTTGTACATT
TGCTTTATTAATTTAGGCTTTTTTTTTTTTTTTTTTTGAGACAGTCTCACTCTATCATC
CAGACTAGAGTGCAGTGGCACAATTATGGCTCACTGCAGCCTTGACCTCCTGGGCTTAGG
TGATTCTTCCACCTCAGCCTCCTGAGTAGCTGGGACTACAGGCACATGCCACCATGCCCA
GCTAATTTTTGTATGTTTTGTAGAGACGAGGTTTCACCATATTGCCCAGGCTGGTCTCAA
ACTCCTGGGCTCAAGCTATCTGCGTGCCTTGACCTCCCAAAGTGCTAGGATTACAGGTGT
GAGCCACTATGCCTAGCCTAACTCAGACTTTAAAAATATAAAAGCAATTCATTTTTATTC
CCAAGAACAGTAAGGTGGTGGTTTAATTTTAGTCTTTAATTCTGTTTTTAATTTATTCTA
TTTAGAAATGTCCCAGAAACTTAGTATAACTTTACTTTCTGAAAATGAAGAAACCTGTCC
TTGGGCATTAGTGTGTTGGATTTAAGCAACAAAGTTAAAAAAACCTACCCTGTGTTATGG
CAATTTTCACTTGATGGTGGTTCTATAACACAGGTATCAGTGAACCTTTATAAAAGATGA
ACAACTTTTCAGCTTGCTTAATTTCAGTTAATTAACATGTATACTTATCTATGTTAATGT
TTTATTGCTTAAAATGTTTAATTTTTATATTTGGTAAACAGATAGTTTTTTCTCTCCCCC
TCTTCCTTCCATCTTTCATTACTACAATTTACCATGCAGAGCTCACAATGTCTCTCTGCA
CCAAGCTCCATGACTCAGGATTTGCCTGGAGTTCCTGGGAAAGACCAGTTGTTTTCACAG
CCTCCAGTGTTAAGGACAGCTTCACAAGAGGGTTGCCAAGAACTTACACAAGAACAAAGA
GATCAACTGAGGGCAGATATCAGTATTATCAAAGGCAGATACCGGAGCCAAAGTGGAGTA
TGGCTTTTTCCCCCTCATTATAATTGTTAAAACTTCTTAAAAATTGTTTCACCCTTTTGA
TATATATTTCTTTGACTTATAAACGAGCTATATTTATAAACAAGGGACCAGAACACATTA
ACTCAGTCATGGTTATGTGCTTCCTTGCTTTCAATGTTTCATTATCTTATAAGGAAGAGA
ACGTATGGTCTCTTGAAAAAACTGACAATAAGAAGTAACAACTGGACTACCACATTTTTT
TTTACATCCTTAATTTAACTCTTCGTCAATTTCTTTTTTTACTTAAGGAGGACGAATCCA
TGAACCAACCAGGACCAATCAAAACCAGACTGGCTATTAGTCAGTCACATTTAATGACTG
CACTTGGTCACACAAGACCATCCATTAGTGAAGATGACTGGAAGAATTTTGCTGAGCTGT
AAGTAACAGATTCTGTTTTGGAAGTACAGCTACTATTACAAGTGACATAGTATTACACTT
AAACCTTTAAAGTTCGTGTTTAAAATAAAATATTTTGAATATTTAAAAGCTAATTCAAA
AAATATGTGTCGTAGCTATGCATTAAAAAACCCCAAAATGTCAGAAGTACAGAAGTCAAA
ATTGAGTTTTCATTAACCAGTTCATTTGATTATATTTGAATTATTCATAATGGACTCATT
TAATTTTAGTAACTTTGGGCTGGGTGCTGTGGCTCATGCCTGTAATCCCAGCTCTTTGGG
AGGCCAAGGCAGGTGGATCACCTGAGGTCAGGAGTTCGAGGCAAGCCTAACCAACACGGG
GAAACCCCATCTCTACTAAAAATACAAAAATTAGCCAGGTGTGGTGGCATGTGCCTGTAG
TCCCAGCTACTTGGGAGGCTGAGACAGGAGAATTGCTTGAACCCAGGAGGTGGAGGTTGC
AGTGAGCCGAGATTGCACCACTGCACTCCATCCAGCCTGGGCCACAGAGCGAGACTGTGT
CTCAAAAAAAAAAAAAAAAAATTTAGTAACTTCGAAGAAATAAGAAGGAAAATTAAAAGT
TGAAAGTGATTCTAATGTATAGTTTATAAAATTTTGTTATAAAAATACCTGTTTTGCCTT
CAAAATAATTTATATTAATATTTTATTGACCTCAAGAACATTTAAATACATTCAGATTTA
TTCATTTGTGGACCACATTTGTTATACATTGGATTTAAAGGATCCTTGCAATTGAGTTTA
TGGCCACCTATGCATCTGAGACCCATGGACTGGGAACCATTCTAGGTCAATGATTCAGTG
TGATTCAATTTAAGAGATGTTTATTCCTGGTCTTTAGAAGCTGCTACCTTTGTTATCTA
ATTTTGCAGTACTTTGAAGTATGTATGTATGTGTACATACGTTAGTGCTATGTATTTATT
AAAGAAGAATCAGAAAACAGAGGTAAGGAAAAATAAGGAAACAAATTTCTGTTAAGCCCA
CCACCTCCCAAAGCATATTTGTTTATATGCTTATATATGTTTTCCTATTATGGTAAGAAC
AGTCTGTACATATTGCTATATAGCAGTCCCCCTTTATCCACATACATCCTGAAAATTGTT
TTACATTTTAAATGTTAACTACTTTATTGTTTTTAAATGTCATTTTATAGTGTAGCTATG
```

*FIG. 14J*

```
GTGGTTGAATATTAGAAATTCCTTATTTTGGTCACATATCCTGATCAGTAGTTGGTCTTC
TGGAGATAGTGATTTTCACTAGAGATGACTTTAGGACCTATTCAGGTTTTTTTTAAGAT
CCCAATTTAAGGAAAGACTATTCTCATTATTGATTTTGCTATATGCAGGGAAATTTATTT
CGAAAGGTTTTTCAGTTGGCTTTTAGGGAAGATTATATATTCTCTTTTTTTTTTTTTGGC
CTTTTCCCACATGTTCTAAAAATGATATATTCTTTAACTCCTATGAAAATACATTGTTTC
AGTAATTGAAGATGCTGATTAAAGTCATATCTCTACACATTTTTTAAAATTTGAGATAGA
TGGGACTTTGTCCCTTCTTACACCATTCACTTATTCACTTGGAAAAACTATTATCCAATA
CTTATGTGGCAGACACTGTTTCTGGCACAAGGGATTCAGCAGTGAACAAAACTGCCTTTT
TGGAGTTTACATTCTACTAGTGGAAAGCGACAACAAGCAGATAGACACATTCAGTATATA
ATTCACTGTCAGATGGTGGTGGTAAGTCCTATGTAGGAAGAAAAGCAGGGTAAGCAGGCT
TGGAGTAACTGGAGTGAGTCATAGATGGACTTGTCAGGAAAGGGTTTCTGAAGAGGTGGT
ATTTGGGCAGAGATCTAAATAAAATGAAGCAACAAGCCATGAGAATATCCGGGGGAAAAT
GTTCTGGGCAGAAGCATCAAGCATAGAACTTGTGGTATGATATTTATTCTAGCACACATT
AATTTTAAAAATGTATAAAAGACATCCATTTAATCATATTAAAGATTTCCATGATTCATT
TAGACTTAGTCAGAAACCAAATTTATATTTTCTTTTTAAATAATTTTATCTCAACTCTTA
TTTTACCCAATAGGGGCCAGAGTTACTCAGCAAATACATTGGAGCAAGTGAACAAGCTGT
TCGGGATATTTTTATTAGGTTGGTAGCCTATGAATGTTTTTAAAGTAACTGACTCTGTTA
TTATTTATCAATCAGTGCTTTTTTTGGTCTTGTTTTTGAAGAACTGATATTTGAAACCT
GTGGTTTATGTGAATTATTAATAAGCTAGAGGACGTGGATTCTCTATTTCATCAAATAAT
ACAAAACATTTTAGATATTAAATTTGGAAATTATTTGGTTTTGTTTTACAATAGAAATA
CTCCTCAAAGTGGAATCGAAGTGGTTATTCAAAGAAATCTCAGAGTAGATTCTTATATGA
AGCAAATAATTGCCCCTAATTTATCTCTAAATTTTGTAAGTTCTAAATTCTTTTTTCCCC
CAGTTTCTAATTTATCTCTTATAAGTCAAGAGTCCATCTGGCCAATTTAATTTCAGTGAG
TGTAACTATTTTGCATATATTAAAAAACTGTATATGAATACAGAAGATGGTATTTAAGGA
TGAAAATAATTATTCAAATGTGATAGCATTATGGGGAGTTTTAAAATAAAAGTTACTGTT
TTATTCTTCCAAAAATTTTATTATAAAGTATACAGTTAAGAGAATATACATAAAATACAT
ATGCAGCTTAAGGAAGAATAATAAAATGAATACTTCATGTATTCACCACCGAGTTTACCA
GGAAAAAGCATAAACAAAATAAACCTCTTCCACGTAATTCCTGGGTTAAAGAGAAGTTAT
AGTGGAAAATATTTGGGAGCAAACGATAATGAAAATACTATCCATTAAAATTGTTAGATG
TTGCAAAACTGATTTCAAGGAAAATTTATAGTGTTAAATGTTTAGAAAAGAAAAAAGGTT
AGAAGTTAACCACTTATGTATCTATCTCATGAAATTAGGAAAATTATAGATATAAACTAA
AAAATATGTTAAAAGGGAAATAATAAAGATAAGAATGAAGTTTAATGAAACACAAAACAG
AGAAGCTCACAAAGCCAAGATTTATTTTTTGAACACCGAGTACAATTGACAAATCTCTAA
CAAGTTTGATTAAGAAAAAGAAAGCATGAATAAACAATTTAGGGATAAAAAGGGAAAC
ATCGCTAAAGATATCCCAGAAATGTAAAAGATAATAAGGGAATATTATGAAAATATTCAT
GCCAATACATTTGAAAACTTAGGTGACATAGACAAAAACAAAATTGACCAAAATTGAGCA
AAAAAGAAACAAATCTGAGTAGTCCTGTAACTTAGTAAAAATTGAGTTAGAAAAGTTAA
AGAAGTCTTTACACAAATCAAACATCAGACTCAGTTTTCTAGGAGAGTTTTGCCAAACAT
TCAAGTAGCAGATAATTCTGGTCTATTTTGGCCCCAGAAGATATATTTTACTTGCCATG
CATTTAATGAGATAGCTGTTGATTTTTTTCAATCACCGTGACAGGTGTTTTATATTAGGT
GTTATTCGCCAGACATCTAGTCCACCTGTTGCCAGATATGGAATTAATATTCACTTATTT
TGAATTAAAATTTGTTAATAAATTAATAAAACAAAGTCAAAGTTCAAATTATTAAAAAAG
TAAAAGAAATAAAATATATTTTATAGAGAGCCCTTACAAAACAGTACCAACATAATGAGC
TTTCCAAATTTTGAATGGGCAAAATAAATGAATAGGCATTTCACAAAAGAAGGAAGGGTG
GCCAATAAGTATATATTAATATAAAAATGGTTACTTGTAATAGGAATCAAAAGTGTTTGA
CTTATTGACTAAGAGTCAGTTTTTGTTTTGATCCCTGTTAGTCTATCCAGAAGGCATGGG
TCTTAATAAACACCTTGACCTCAACAGTTTACTGAATACAAGGGTAATTTCATATGCCTT
GCCTTCTTTAAGGGTTTGTTGTAAAGATTAAAATAAATACATAAATATATATAAATACAT
TTATATGTATTTATATGTAATTACATACAACTTGCCTTCTTTAAGGGTTTGTTGTAAAAA
TTAAAAGAAGTATATAAATATATATAAATACATAAAATAAATACATTCATATATGTATAT
GAAATCACTTTGCCAACTATGAAGCCTGATTCAAATATGAAATGTTGTTTGTTTTTCCCA
GAGCACAGGCTGCAAAGCCCTGCATTCTTTTCTTTGATGAATTTGAATCCATTGCTCCTC
```

FIG. 14K

```
GGCGGGGTCATGATAATACAGGAGTTACAGACCGAGTAGTTAACCAGTTGCTGACTCAGT
TGGATGGAGTAGAAGGCTTACAGGGTAATAATTATAAATACAGAAATAGAATGTTATAAC
AAAATGTCATCATGTCATCAGATTTTGGTAAAAAAATGTTCTTTTTTCCTCTAGGTGTTT
ATGTATTGGCTGCTACTAGTCGCCCTGACTTGATTGACCCTGCCCTGCTTAGGCCTGGTC
GACTAGATAAATGTGTATACTGTCCTCCTCCTGATCAGGTGACAATTTCATATTTAGAGT
CCAAAACCCAACAAATGCTACACTCTTTCCTTGTGAGCTTTACTTCTGCCAGGTAATGGC
AATTGTCCTTAGAAGACCAGCTTTCTTAGGGAAAAGCTTTAGCCACTGTTTGCTCAAAGC
ATAAAAGATTCTGAATTAGATGCAAAGCCTTTTTTTGGCCCAGTGCAAGTCTGAAAACT
TTGTAATCCTTCTGTGTTGGCTGATTGGGGAAAAAAAAATGCAAGAAACCTAATGTATTA
TATTTTCACATTATCTTCTGTTCAAAGATTACATACTTCCATTATCCTGTCAAAAAAAAA
ACTCTGATACAGAATCAAGCATGTGAATCGTAAGCATGTAAGCAGGTTTCATAGAGATAA
TTTTTCAACTCTTCCTTGTCCTGTGTTGTTCCAACTCTTATTCTCCAATTTAGAAGCAAA
CAAATAAATGAATGAAAGAACAGATAGACAAATGAATAGTCAAAGGTATAAAGTATCTGT
ATATATGTTACATGTAGCTATTATTTAAATTATTTAGATTTTCCTTTTGAAATACCTTCT
TGGCACACTTGCCTAAATCTAGAAAATAAGCACTGTGTGAATAAGAAATTATTTACACTG
AATATTTTGTAGGTTTTTGGGTTTTTGTTTTTCAGACAAGGTCTCACTTTGTCACCCAGG
CTGGAGTACACTGGTACGATCACAACTCACTGCAGCCTCTATGGCCCAGGCTCAAGCAAT
CTCCCCACCTCAGCCTCCCGAGTAGCTGGGACCACAGGCACACGCTACCATGCCCAGATA
ATTTTATTATTAATTTTTGTATAGAGATGGGGTCTCCCTGTGTTGCCCAGGCTTTCTTGA
ACTCCAGGGCTCAAGTGATCCTCCCACCTCAACCTCCCAAAGTGTTGGGATTACAGGCGT
GAGCCACCATGCCCAGCCTTAAGAGTGTTTGATTTTCATTCATTTTCCTATATATATTAT
TTCTGTTGGGGAAAAAATTCCAAGGAAGATAAATAGTAGGCTGTTGGTACATTTCTCAAC
TTACTTATAAAGCTTTTTAGATATATAAGGTTAATTTATGAAGAAAATCATAAGATACAC
AATTTAAGATAATATTTTAATTTTATTTTTATTTGTTAAATAAATTTTTCTCCTTTCA
GGTGTCACGTCTTGAAATTTTAAATGTCCTCAGTGACTCTCTACCTCTGGCAGATGATGT
TGACCTTCAGCATGTAGCATCAGTAACTGACTCCTTTACTGGAGCTGATCTGAAAGCTTT
ACTTTACAATGCCCAATTGGAGGCCTTACATGGAATGCTGCTCTCGAGTGGACTCCAGGC
AAGTTATATGAGGAAGTTGTTATGACATTTATGAGTGATAAAAGAAGTACAATGTCAAA
ATTTCCACCTTAAAAAATGCTATTTTTTAAACAACTTTGGTAAAACTGTATAGAAACATA
AATTTACCTTTAGTTGAATGTTCCATAGTTGGAATATGGGTTTTGCAGAGAATTTATAAT
TATGAAGTTTGATGTCTGTTTCTTTAACATTACCTTAATATTGGCAAAAACATGTTGGTG
TTTGCAAGGATATTATTTAAATTGGGATACCATGAATTAAATACTACAAACAAAAATAAT
TAGAGTTTTTGTTTGTTTGTACTTTAACTTTTAAAAAATAATCAGTTAAAGTTGTTGTT
TTGAAGCTCACATTGTTCCAATCTGGCCAATAGGAGCCCCTTTTGTATGGCTCCTGTATC
TTTATGACATGTCCTCATCATTCTTGAATCACTTCCTCACTTCCAGATACAGTAAGTTAT
TCTTGGCCAGGTGCAGTGGTTCACGCCTGTAATCCCAGCACTTTGGCAGGCCAAGGCAGG
AGGATCATTTGGGCCTAGTTTGAGACCAAATCATGGTTGCACAAACTGTACCCACTATGG
ACAACAGAGTGGGATCTTGTCTCTGTGAAAAATTTAAAAATTAGCTGGGCATGGTGGCAC
ATACCTGTAGTCCTAGCTTCTTGGGAGAGGCTGTGGCAGGAGGATCGCTTGAGTAAATCC
AGGATGCAGTGAGCCATGCTTGTGCCACTGCACTCCAGCATGGATGACAGAATGAGACCC
TGCCCCAAAAAGAAAATATTCTTGGTTTATCTTGTACTTTCTGTATCCCAGCCCTAG
CATCAGCCTTTTCTCTAAAGACAGTATTATGATTTAATATTTACAGTAGATATTTGAAC
TGTTACATTATAGACTTTACCATATATTTCTAGGAAGGATTATTCTATTACTCTTCTTT
ACCACATTTGTTTGGAATGTCTACAGAACCTACAGTTTCTAAATCAGAAACTCCCTAGGT
TTTTGCTATTTTGGCAAGCCATTGAAGTTCTTCCCTCTCCCTTTACTACCAGAAAGGTGT
GTATTTGTAGAGCTCTCTATAATGAGAAAGCACTCTATAACATGGTTGATTCATCATTTT
GGAGTAGAAAAGTATGAATGGAAAGTCAGAGACATAAAAATAAAGCCCAGAGGTCTGAGT
CTTAGCTTCATTACAGACTTTCTTGGGGATGGTTGGTAAATTATCTACACATTCTATCT
TGTCTTTATAATTTTAATAGTTAAATTTTTACCATGTGCCTCAAAACCGTTAGAGAATTA
ATGAGCTCTTTGAAAAATGCTTCTAAGTTTCTTGTATTGCTCTAATAGAATGCTATCTAT
GTTATTATTTATTTCTGAGACTAAAATTGTTTACATCTTTAAACTGGTTGTCCTTTTGTG
TATTTTAGGATGGAAGTTCCAGCTCTGATAGTGACCTAAGTCTGTCTTCAATGGTCTTTC
TTAACCATAGCAGTGGCTCTGACGATTCAGCTGGAGATGGAGAATGTGGCTTAGATCAGT
CCCTTGTTTCTTTAGAGATGTCCGAGATCCTTCCAGATGAATCAAAATTCAATATGTACC
```

*FIG. 14L*

```
TTGTTCTTCAGAAGATCAGATGGTAGAGTCTAGGAGGTAGTGTGTTTTAATCAGAGATCT
GAGAGGCAAAGATCATTGCATGAGATCAGGGACCCATGCAAAGGAGTGAGAAAAAAACT
GGGTTAAGGAGCCTGCTGCATGGCAACTCCTGGGAACAGTGGCCACTGGGGCCTGGGACA
TGTTGATTGCAGCCCAGGACTGTTAAAACCAGTGTGAGAGAACATGGGTATGGAAGTACT
AGCTAGCAGGATCATGACCCCGATGCTGGGATGGGGCATCAAGCATTAGTACATGGAGAT
TCAGTACATCCAGATGCAGTACATGGAGACTATATGCGTAACTGCTGACTTTGGGCTTCT
TTCAGATTGGAGCAGAGGTAGAGGTGAGTGGGAATATTCTCAATAGAGGGAACTAAATAG
GCATACCTAATAAAGGAGACCAGGATATTGCAGACAGTAGCCTCATGTTTGGCTCACCTG
TTCAAAAGTTCTCTTGTTCTTGAGCAGTGGTGCCTTAAAAGGTAACTTGAGAAGCAGTC
GATTATTTGTTCAGCCTGGAGACTCTTGGGATATTTTACTATCTTTGATTGAATAGATTT
AAATGTACACAGCTCTCATAACTTGCCCCATGAAGCATATCCATGAAAGGCACTATACTT
GTTAAAAGATTGGTTTGTACTTTTTAAATGTAGTACTTTTAATAAAACAGGAAAAATAGA
AGTTCTGATGCAGTTATATGCATTTTATATAGAATGTGTTCTTAATTGGAAAAAATTTGT
CGTAGTTCCTTTGAGTTCATTTACAGTTTTTAGTAGGAATTGTATTTTCTACTGTTGTAC
TTGCTGTTACTAAAGAAAGATGGTCGTGATTACCATCTGAATTTTTTTCTATACATTGA
TCTTTAGCTGCTACTTAGTCATTTCTGTTTAGACTTGAGCTCTTTTCATATTTTTTTTT
TTTGTTTCTCAGTATCCAGAATTATTTGCAAACTTGCCCATACGACAAAGAACAGGAATA
CTGTTGTATGGTCCGCCTGGAACAGGAAAAACCTTACTAGCTGGGTAATTGCACGAGAG
AGTAGAATGAATTTTATAAGTGTCAAGGTATGTTGTCTACTTATCTTCTTTTTTTATTTA
GGTAAAATTAACATAAATGCAGTTAGCCATTTCAAAGTGTAAATTCACTGGCATTTAGTG
CATTCACAATGCTATGCAACCACCACCTCTCTCTAATTTCAAAACTTTTTCATTCCACTC
CTCCTCTTGCTTATCCCCTGGCAACCATTCATCTGCTTTTTGTCTCTATGGATTTGCCTT
TTCTGTATATTTCATATAAACAAATCATGCAATATGTGACCTTTTTGTCTGGCTTCTT
TCACTTATGTAATGTTTTCATGGTTCATCCAGGTAGTAGCATGTATCAGTACTTCATTCC
TTTGCATGACTGAATAATGTTACCATACTTTGTTTATCCACTTATCAGTGGTGAACATTT
GAATTGTTTCTACCTTTTGACTATTATGAATAATGTTGCTGTAAATATTCATGCACAAAT
TTCTCCACGGATATGTTTTCATTTCTCTTGGGTATAAACTGAGGAGTAGAATTCTTGGGT
CTTAGGGTAATTCTCTAACTTTTCAAAGAACCACCAAACTGTCTTTCACACCAACTGCAC
CATTCCCACTAGCAGTGTGGGGGGTTCCTGATTCTCCACATCTTTACCAACACCATTATG
TTTCTCAATTGTGGGCTAGTCTCACATTTGGAAAGCTAGTGGGAGCAGCGATCCATCTAT
TAAAAGTTGTATGAAATTGAGTAATGAGCCACCTCTCTCTTGTAGGGCTTATTATGTTCT
TGCTTAAGGCAATCTTCATGCATTGTGAACAGAATTATACATAAATGCTCAGATAAAAGG
GCAAACCATTCTTAAAGGGAGTAGACAACTAGAGGCAGGAGACCATACTGAGGCAGGAAG
CTGGGGTTTTATGGTTCTGTTACTTTTGACTATATCTCACCATTGCTTTTGTCAAAGTG
AGACTAGGTCTAAGTTTTTTTCAGGTATAAGGTGAGTGTGGTAATTAAGGGGCATGCTAG
CAGATCATTTTGGGTAATGCTTCACAGTCCACCACTGGTGTGTCATTGTGGTCGCAGATC
CAGTATCTTAGCTGTGTAATTTCAGACATCAGCAATATTAGTTTAACAAAGGGCAATTAG
ATTCCAAGACAAAGGAATCGTGTATTATTCTAGCCTTATTCAAACTTGATTTATAAATCA
GTTTAGTAATTTATTTATTTGTTTCTGTATTTATTTTATTTCTTTGAGATGGAGTCTCA
CTCTATTGGCCAGGCTGGAGTGTAGTGATGCAATCTTGGCTTACTGCAACCTCTGCCTCC
TGGGTTCAAGCTATTCTCCTGCCTCAGCCTCCCGAGTAGCTGGGATTACAGGCTAATTTT
TGTATTTTTAGTAGAGATGGGGTTTCACCATGTTGGCCAGGCTGGTCTTGAACTCCTGAC
CTCGAGTGATCTGCCCGCCTTGGCCTCCCAAAGTTCTGGGATTACAGACGTGAGCTACCG
TGCCCAGCTCAGTTTAGTAATGTATAACTGGGTTTTACCCAGTTGTAAATTACTCTTTTG
TCGTGTTTTTTTGAGAACTGGCAATGACGGAGAAACTAAAAGTGCCAGGCTGTTGCCTTG
TTCCTGTTATTTTGCCTTAGTTTTTTTTTTTTTTTTTTTTCTCTGAGACTGAGTCTTG
TTGTGTTACCAGGCTAGAGTGGAGTGGCATGATCTCGGCTCACTGCAACCTCTGCCTCCT
GGGTTCAAGTGATTCCTGCCTCAGCCTCCCGAGTAGCTGGGATTACAGGCGCCTGCCACC
GCACCCGGTGAATTTTGTATTTTTAGTAGAGACGGGATTTTACCATGTTGGCCAGGCTG
GCCTCGACCTCCTGACCTCATGATCCACCAGCTTCGGCCTCCCAAAGTGCTGGGATTACA
GGCGAGAACCACCGTGCCCGGTCTTGCCTTAGTTATTTCTTGTTCCCTCCTCTAGTCCTA
TAGTTCTCTGACTGTATTGAGGAAATGTAATTAAATATTATTATGTTAATAGATATTTAT
```

*FIG. 14M*

```
CCACAATATCCAATTTTTAGACATTTAAATTGCTCCCAGGCAATGTGGTAATGAACATTC
TTGCAGCTGAATATATGCACATATCTAATTGTTTCACTAGGATAGAGGTGGAATTGTATA
ACAGGGAGCTCACATTTTTAAGGCTTTTGAAATGTATTGCCAAATTGCCTGCCAGATAT
ACTGCACCATCACTAACATTGTGTGTTGCAGTATTTTTCTAAACTTGGCCCTTTTGATTT
TAGAAAATGATATCAATAATTTACATTTCTTTGATTAAAGTGTAGAAGTTATAATTTTT
CATATTATTCATTGTCATTTGTATTTTATCTTTTCTAACTTGTCTCTTCATCCCCTTTGC
TCCGTTTTCTATTGGAGTGCAACTTTATTTGTAAGAATTCTTTTTAATTTCTGTGACTGG
AATTTTTTTTCTAGTTTGTTATTTCCCGTTCATTTCTTAAAATATAATTGTGTTTGCCA
ACAATCCATTATCTTTTGTTTGTAATGGTAGTATTTATACATATTAAATTATCTCTTTC
TTTTTTCAGATATGAAAGCTTTCAAAATCCAAAGAGGAGAAAAAATCAAAGTGGAACAAT
GTTTCGACCTGGACAGAAAGTAACTTTAGCATAAAATATACTTCTTTTTGATTTGGTTCT
GTTAAGTTTTTTGATGGCTTTTCCATATGTTGTAACAGGAAAAAATGGTGTCTATGAAT
TTCTTCTTAATTTAACAAATTTGGTTAATTTATAAAATCACAGATTGGTAAATGCTATAA
TTATGTAATGATCAGGATTGAGATTAATACTGTAGTATAAATTGGGACATTATAACAGAT
TCCATATTTTATTTCCTAAAATCTAAATTCAGTCTTTAATGAAATAATATTAGCCAAATG
GTGGAACTAATTTATTTCTTTTGAGGAAAAGATAATAAAGAATGTAATTAAATTTAAATT
TCTTGGAATTCCCAGTTGTATATTCATCACCTTTGTAGCATTTGACAAATTTTATGCTTA
GCAGCTTCTTCACTGTTTTGAAATAAAATATCCTATTACCTACTGATACAATTATCTGTT
CTTTGTATATCAAAAAATGTGAAATTTACACATAATTCAAATACATTTAATTATCCGCTC
AACCAGAAATGAAATCACATCCCTCTACTATACTACATCCAGCTCCAAGCCCAAGATATT
TAAATGACATCCATTCCTCCTAGTTCCAGTTATGATTTTATCTTGATATTCTCTCATA
TATGAACTAAATTATAAAGTTAGCCACCATCAATACAATCTGCGTATCTAATATCTTAAC
TATATAGTAATGGGGTAAGGAACAGCAAAAAGGAGAACATTAATTAAAATATACAAGTA
AGCCTGGGCAACATAGTGAGACCCCATCTCTTAAAAAAAAAATTAGCCATGCATGATGGT
ATGCCTCTAGTCCCAGCTACTTGGGAGGCTGAGGTAGGAGGATCACTTGCTCCAGGAGG
TTCAAGGTTCTAAACCAGCAAAGCTCAGAATCCCAGGGGATAGAAACAAAGACTTAGTGG
ATCACTAGTATTAAACTGAGACACGTCACCCTGCATTGCACTTTGTTTCTCAGTTCTTTG
ATGAAATCACTGAGCTGACATACCTGCCCTCTTTTCACCATAAAGTGAGTTTCATGATCA
GAAGCAATGTCTATGGGATAGCCTAACAAACAATGTAAAAACCATTTAGTAAGTTCATGA
AGGGTGGTGGTGGTAAAAATTTGGAGAACATACAAAACAAATACAATTCCAAGGTGTGTC
CCCTCCAGGAAGGACAAATTGCTGCCTGCTCTGTGATAGAAGAGGATCAGATGTAATCAA
CCTGCCGTCAGACTTGGGCTGTTCTCTCCTGGGTGTGGACTTGCCTGGTTGGTCACTGCT
GCTGACAAGTAGGCTGTCAATATAGCTGGGTTGTCATGTCAGCTGTGGTGAGGGGGAAGT
CCACATTGTGGAGGCCACATCCCTGCACTCTTGGCCAATTTGACCATGAATCTTAAGCAC
TGGGGTGGCTGGAAAAGACAGCCGATTGACATCCATACAGAGGTCATCTTGACCACTTGA
TTAGTATAAGCACTGAAGGCTTTTAACTGAGCATTCACATAGGACACAAATATTCTGATT
CTTTGGGCCCATTCCAAGAACTCTGGGCATACTTTTCCTCCAGACCTCATACCCAGTTGT
GTTCTTTCCAAATTTCTGGTCATCTGGTTATGTTATTAGCCACTATCTGTGAATCAGCAT
AGATTTTTATATCAGACATCTCTACCTCCTGACAGAATGGAGGAGATATGTTACTTAACA
ATTCTGTTCCCTTGGAAGATTTCCTGTCTCCACTGTTTGTAAGGGCTACTCCCTCAATGT
AGCAGTAATGCTTTCACTCTGATGGAAGTCACAGTGGAATTCTGGGTCTCCAAGAATTA
GTGTTAGTGCATACACAGTGTCTGATAATCCCCAGAGTGTCTGGTGCCCTTGGATCCTGT
GAAGAAGGCTTGGAGAAAAGAAGATTCATGGCAAGAACTTGTGATGTGATGACAGGGCCT
TTTCTCTGGCTCTTCATTCTTAGTCTGACCTAGGTGTGAGAATTAGGTCAGGGGCCATGA
CTATATTGTGGTGACTCAAACCAGGCCTTTGTTTACTAACTGGGAGATTTTTACATTGTA
AGAATCAAGTAGGATCTTTGCCCATGTATTTTGGTCTTAAGAACACAAATGATATGGCTC
CAATGACTGGAGGAACACCAGGGTCCTTGGTCTCACGCTGATTTAGATAAAACGACTGTC
AGGCCTCTGAGCCCAAGCTAAGCCATCCTCCCCTGTGACCTGCACGTATACATCCAGATG
GCCTGAAGTAACCAAAGAATCACAAAAGCAGTGAAAATGGCCTGTTCCTGCCTTAACTGA
TGACATTCCACCATTGTGATTTGTTCCTGCCCATCTTAACTGAGCGATTAACCTTGTGA
AATTCCTTCTCCTGGCTCAAAACCTCCCCACTGAGCACCTTGTGACCCCGCCCCTGCC
CCTAAGAGAAAACCCCCTTTGATTATAATTTTCCACTACCCACCCAAATCCTATAAAATG
GCCCCACCCCTATCTCCCTTCGCTGACTCCTTTTCGGACTCAGCCCGCCTGCACCCAGG
TGAAATAAACAGCCTTGTTGCTCACACAAAGCCTGTTTGGTGGACTCTCTTCACACGGAC
```

*FIG. 14N*

```
AAGCTTTAGTAGAGATCTCAAAATGGTTGGATGGTAGCAAATTACTAAGAACTCTCAAA
GTTTCTAAAGCCTTAGTTTCAGCTTGCTAGAAAACCTATGTTGAGTATTATGGCTAGTTC
CATAGTTGAGTTGGGAAATGTCTTTGAGGAGACACTTTTTCACTTTGTATTCATCTGTAC
ATTTTCTGTTACTTGCATTCTGTCATGCTCAGGCTATTAGAGCAGGTACATTTTTATAAC
TGGAATGTTTATGTGTAGTGAAGCTCTGAGAGGACTTTGCATTAGATCTCAGCAGCATAA
TCAGAAGGTTGTCCTTTGTCTCAGCAATTTTTAAGCTAATAGTAGCAGAAATTGCAGTGG
AAATAGACTGCTTTGCCACAACATTCAGAAAATCATTTATCTTTTATTGCAGTTCTTGT
CACCAAACAATACATTTTAGTACTTCTCAAATTGCAGAACTCTCATAGGGCTGGGAAAAT
GCCTGTAGACACATACATACTATGAATGTGCTAATGTTTTTGTATTTCATAGCCCATC
AAAGCTCCTGAGTCAGTTTCCACTATAATCACTGCAGAATCAATCTTCTACAAGGTAAGC
TTTTGTAGAGTTACTGAAGGAAGAGTTGGGCCTAGTGGGTAATGTGCCACTAAAATGTTG
GATTAGTCTAAAGGTCTCTGCTACTCTTTATTTGTATAAGGTGTGATTATACTTTTTGTT
CCCTTCTTAGCTGTTTTCCCCCATAAGTGGCTGTTATTAAAACATCTCATCTAGAGCTGA
AGTGGGAGGAGAAAGTGCCTACTGACACATGATGTCAGGATCTTAAGTATTTTTTTAG
TGTAGATTGTAGGAATTATTCTTAAAATGCTGATTGTATAGTGTGGAGCCATGGAAGACT
GAGCCGTTAGTGCGATGGCATTGAAGAATGAGAAGGACAGAGACAGGATTTGGACTAGTA
GAGGTTGTCGACTGTGGTGTCAAATGGGTAGAGTAGGCCCAGAGATTCTAAAATGCCTTT
AAGTGGAGTTGAGCTGAGTAAGGGCAGTAGTGAGGATTAACACCTACTAGAAATTCATAG
TGAGAGGAATTCCAAGATGTTTTGATAAAAGAATGAGGAGGTCAGGTTTCCCAGGGCCAA
AGTCCATGAACATCTGATACCTCAGTGAGAGAAGTGACAGATTGTTGTGTTTAAACCAGA
AGTCTTAGGAAAGGAATTAGAACATAGACCCCCAAGGCTCGGCAGGCCTGGCACGGCACA
GGCAGCAACCATTGAAGGCTATTTGGTGTTTCGGATCTGAACTGTCATTTAGGGGACAG
TGGTGTGAGTTAGTACTTTATACTTGACCCAGGTGGACTGAGAAACTCAAGTGATGATGC
CCTTAAGTATACTTTTTTTTAAGCCCACAATCTATATAGTCGAAGTCTGTTCCTCCCAAC
AGGGGTACACTGGCATTCCTCAGCAGGGCTGGGAAAAACCAACAACAAAAAAAGTCTGTA
CACAGGCAAACATCTCTCTTATTTTCCAACATTTAATACATTGTTAATAAAATATCTAA
AGTTTAGCAAACAGTTGCTGTGTATCAGTGGCTGAGCATTTGCATGCTTTATTTCATTC
AGTTCACTCTATGAGGTGGATACTACTATCCCCATTTTCTAGATGAGAACATTGAGGCAC
AGCGAGGTTAATTAACTTGTCCAAGATCACATAGCCAACAAGTCATGGAGTCAGGCAGTC
TCATGCCAGAGCTTAAGCCTAGAGCATAGTTCCTGGCTCTACAGCTTTAGCAAGTGACTG
GCTATGTGACGAGGACCAACCTCTCTAATGTCTCATCTGTAAAATAGGAATTGTAAATAG
TTACTACCTCAGTGGGTCAAATGAAATCATATGTGTTAAGCACTTAGCAGAGTAAGCACT
CAATGAATAGTAGGAGTTATCACATCTTCGTATTTGTGCATTACCTTCACAGTTTACAGA
TTAAGGCCAGAAGCAACTTGTTGAGCTACGGGTTTAGTGTACTAACAGTTTCCATGTGTG
TCTCCATGGAAGGGTGTGTGGGACCTGTTATTGTGACTGTCTGTACTTTCGTATTGTTGT
CTGCCACCCATGTTTATTAAATGATAAGGACAATAATGCAACAAAGTAGTCAAGTAATGT
TGCAAATGCCCAGTATTGTAGTGGCTATCACAGCAGTGCCACTGGCAGGCAGCACCATGG
TGGCAAGTTCAAGAGGTCACTGCCAGCCACTGAGCTAGAGCCCAGATCAGGCATGCAAGA
GGAGCCTGAGTGGGAGCCACTGGGGATCACGGCCAAGAGTGTGACCACCCAAGACCCAGA
ATGGCTGAGTGGCCTCCCTGGAGCATGGCAGTGGCAGAACAACTCCATGAACTCAGATCT
GGTGATGCCTAAACTAGTGCTGTTCTCGTGTGGACCCCTTTTCTCTACCAGAAACCTTGA
ATCCTCTCAGCAAATGAGGAGACTACTCAGATCAGTGACTTAGTCCTGTTTGGTGTTATA
TATGTGTACACAACACAGCACATATTAATAAATACCTACTATGTGCCAGGCACTGCCTAC
CACTGGAATCTTTCACTAAGACATTGTTTTTACTTTGCATTTCTGCCTTTACACTATGAA
AGTAGATGTTTTGGATTCATATTCATTCAGCATACATTTGAATATGCTGTGTTATGCATA
GTAAGCCTATGATAAGCAAGTATTCTCATTTAGAATTTGGGAATATTGATTATACATGTG
GACAAACAAACCATAAATGCAAACTATTTATATGATAAATAACTTTGGACTGATGGCTGG
GAGGAAGGACCAGCTATTGATGGGTAGGAACTAGCAAGTAGCGGACTGTGGCCTGCATAG
ACCAGACCCATCCGTAGTGATCCAGATGAAACAGCCACCCTCAGACACTTGGATAAAGGG
TCCACCAGGAAAAAACTCCTGGCCTATCAGGTGCTATGTTACAGTTCAGTTACTGGAAGT
ATTTCCTCAAAAGTGTTTTATGGTTGAGGTACACATTCCTACAGCTTTACCTGCTGCCA
```

*FIG. 15A*

```
AGTCCCTGTTTCAAGGGAAGCAGCAATGAATTACACTGTTCCCGTAGTCAAGGACAGTAT
ATCTTACCAAGAACTATACCCACTTAAGGAGGTGCTGGATGTCATAAAGATTTGGATCAA
CCATTATGGGTGTTCAGAGGAGAGATTATTTCCAGCTCAAGACCCAGGGAAGAGGACATA
GCATGGATACCAGAGTCATAGGGAGGATTTAACACAGGACATGTACACATTAGTTAGTTG
GGTATAAAGTGGAACAGAAATGAATGAGACACAAAGCCTTGAATGCCAGAAATACTAGTA
GTCCTGTTGTGGAAGGATATAAAAACTCAACTGGGAGTGGAAGAGAAAGGCAGCAGTGAGT
CTAGGAGATGTACAGTAGGTTGAGGTAAACATATCCTGAAGACTATAATCCAAAGATTAT
TTTTGGTTTGAATTTGTTTGGTTTGAATTCATGGTATCTATTTTCTTTGAGTGGATGGT
TGGGGAGGGTGGCATGTAGAATGCATTCTTACCAAATCAGCATGATTTTCAAGACAGTAC
AGAGAAAGACTGCTGAGCTGATGTAGGAGCTTTGGCTGCAGTCTCTATGGCTTTCAGCA
AGCCGTTTAACCTTACTACTGCTTCATGACTGTGGCTAACAAAGTAGGGATAGTACGGAG
CACAGAGGATTTTTAGGGCGGTGAAACTATTAATACTCTCTTTGTATGATACTATAATGG
TGGGTACATGTCATTATACATTTGCCCAACCCCACAGAATACACAGCACCAAGAGTGAAC
CCTAATGTGAACTCTGGTCTTTGATGATGCTATGTCAGTGTACGTTCATCCGTGTAACAA
GTGTACCACTCTAGTGGTGGGAGGGGTTATTGATAATAGGGGAGGATGTGCATGTGTGGG
GGCAGGAAGTATATGGGAAATCTCTCTACTTCTGCTCAATTTTGCTGTAAACCTAAAACC
TCTGTAAAAAATAAAGTCTATTTTTAAAAAGTGGGGATGGTATTACGGCAATATAAAAT
CAAATACTTTATGAACAAATCTTTTCTCCAGATGTAAACTGTCATATATGCACCCTCGT
ATGTGTATGTATAATTTTCATTCAAACGTGAAACAACTTTAGAATTGGCACCAAACATAT
AAACACTGATACATTAGACTATCTCGAACACCTTTTACTGACCACTTTGAAAACTTGCTT
ACCTATTAAGGTTCATTCATAGCTGTGATGTTCTATTTTTATTTTCAATGTGGGATTATC
TTCTGTTTCCCCAGGGAGTATATTACCAAATTGGTGATGTTGTTTCTGTGATTGATGAA
CAAGATGGAAAGCCCTACTATGCTCAAATCAGAGGTTTTATCCAGGACCAGTATTGCGAG
AAGAGTGCAGCACTGACGTGGCTCATTCCTACCCTCTCTAGCCCCAGAGACCAATTTGAT
CCCGCCTCCTATATCATAGGTAAGTTTGACAAATGGCACAGGTTTTTTTTTAACTTAGTT
AACTCTCCAATATTATGTAAAGAGTGTGTTAGTCAGCTTGGGCTGTCAGGACAAAATAT
CACAGACTGAGTGGCTTAAACAACAGAAAGTCACTTTCTCACAGTTGTGGAGGCTGAAGT
CCAACATCAAGGTGCTGGCAACACGGATTTCTGGGGAGGCTTTTCTTCCTGGCATATAGA
TGGTCACCTTCTTGCTGTGTCCTCACATGGCCTTTCATGGAGTGAGAGCTCTTTGGTGTA
TCTTCTTATAAGGACACCATTTCTGTCAGATGAGGGCCCCACCCTTATGGTTTCATTTAA
CCTTAATTGCCTCCCTAAAGGTCTCATCTCCAAGTACCATCACATTGGGGATTAGGGCTT
CAACATATAAATTTGGAGGGTGGCGGGGGGGATGCAATTCAGTCCATAACAAAAAAGC
ATGAGTATTATTAAGTACAAAAAATTAGAGAGCTTTATAGAAAATATGAGGCATTTTAT
GTAGCTGGAGTGTGAGTGCTATCAGTTATTTTGAGTTAGAGCAATGTGCATCTACTAAGA
AGTGGTATGGATAAGATTTTTTTGGAGTGACCCAGGGTTAAACTGTACTACAAGAATGTA
TTGCTCAGGAACTAGGTTATTTAGGTTACTTATTTATACAAACCTATTCAAAAATAATTT
AGGAAAGAACTATCCCAGTTATCCCATACTTGCAAATTCTCAATATGTGTGCCTCTGCAT
GCTACACATGTCATCTTAGGCCTTTATAGTATAAAGCTGATAGTTGAAATGGCAGCTGC
TGTGCTTTTGTTAATTTCAAAGCTGCCAAAACAGTTGTGAGATAGACTCACAAGAATTTA
CTGATTAATACAATTTTTAAAGTTTTCAGATTTTTACAGTTACTTCAGACTTTTTATCTT
TCTGCAGTGAGCATGCATCATTACTTTTGCATCCTGAGAACAAGCATAAGTGTGTTTTG
GAGAGAACTCCAGGGACAAATAATATACCACTGTTATTCTCACCTATATGTCAAGTTTGA
TACATTACCAAACAATTCTAGCCTTCTGCTTATAAGTATATAGAATTTTTATTTACCTTA
TCTATGGATCAGGATCTCAGCAGAGGCAGTGATGTATCAGAATCACCTTCGGGATTCCTC
TACTGCCTCCTCTTTCTAATCCCCAGATTCTGATATGCATCCTTGTCCTACAGCGAGGCA
GCATGGCATGAGGTCAGAACACCAGTTCTGGAGCCAGACTGTCTAGGTTCACAGCCTGCC
ATTTACCGGCCATGTGACTTTGGCAAGTTTCTTAGTCTCTCTTGCCTCACTTTCCTCATA
TGTAAAATGGGAATAATAATAGTGCCTACCTCAGAAGGTTGATGTGAGGAATGAAGGTAT
TGATACATGTAAACTTAGAGCAGTGTGGGTACAAAATAAACATGATGCAAGTGTTCAATC
ACTGTTTTTGGGAGAATGCCATATTCTTTAAGCCGTTAAAGAAGAAAAATGATTAAGAA
TAATTTCAAAGTAATGCATGTTTCAAGGGCTAATGCCAGGTTGCTCCCAGAGTGGTCTCT
CCCAGTGTCTAGAAATTTTAACATCTTATGAAAATGATATATATGGTCAAAAATGTATTT
```

*FIG. 15B*

```
AACCTTTCCCTTGGCTGCCTTCCAGGGCCAGAGGAAGATCTTCCAAGGAAGATGGAATAC
TTGGAATTTGTTTGTCATGCACCTTCTGAGTATTTCAAGTCACGGTCATCACCATTTCCC
ACAGTTCCCACCAGACCAGAGAAGGGCTACATATGGACTCATGTTGGGCCTACTCCTGCA
ATAACAATTAAGGAATCAGTTGCCAACCATTTGTAGTTCACAAATTAAAACTGGGTTTCC
AGGCCTGGTGTGGTGGCTCACGCCTGTAGCCCCAGCTATTGCACCACTGCTCTCCAAGCT
GGGCAATGGAGTCAGATTCTCTTTCTTAAAAAACCACAAAAAACTGGATTTCCAGTTCT
CTAATATTCTTAGTACCACAAGATATGTCATAGGTATCTTTAAATGAAATTCTTAGCTGG
AAAAGTGACTAAAAAGTTTTTCTCCTGCTACCTAGTAATAAACAAATCATTGTTTATTAC
TGGTCACTTAGAAAATTAAAAGGGATAGGGCCAGGCACAGTGGCTTATGCCTGTAATTGC
AGCACTTTTAGAGGCCGAGGCAGGCGGATCACCTGAGGTCGGGAAGTGGATCGCCTGAGG
TCAGGAGTTCGAGACCAGCCTGGCCAACATGGCGAAACCCCGTCGCTACTAAAATACAA
AAATTAGCCAGGTGTGGTGGCATGTGCCTGTAATCCCAGCTATTTGGGAGGCTGAGGCAG
GAGAATCGCCTAAACCCAGGAGGTGGAGGTTGTAGTGAGCCAAGATTGCACCGCTGTGCT
CCAGCCTGGGCAACAGAGTGAGACTCTTGTCTCGGAAAAAAAAAAAAAAAAAAGGCTG
GGCACAGTGGCTCACGCCTTTAATCCCAGCACTTTGGGAGGCTGAGGCAGATGGATCGCC
TGAGGTTGGGAGTTCGAGACCAGCCTGGCCAGCATGGTGAAACCCTGTCTCTACTAAAA
TACAAAAATTAGCCAGGTGTGGTGGCGCACACCTGTAGTCCCAGCTACTCGGGAGGCTGA
GGCAGGAGAATTGGTTGAACCCAGGAGGCGGAGGTTGCAGTGAGCAGAGATCGTGCCACT
GCACTCCAGCCTGGGTGGACAGAGCAAGACTCCGTCTCAAAGAAACAAACAAAAATTAA
AAGGGATAGAATATAATGAAATATATTTTGAACTTAAATTATATTCTATATGTGTATCTT
CCTAGGCAAAAGCTGTAATTTCCAGAGAGACCATTAGGAACAGGTAGTATCTATTTTTCT
CCATTATTTATTTCTAGAAACTCATAAAATGGATTGTATTTTTCTATAAGAACAAAATAT
TAATTAAGGTATAGATGACTGACCAAGGGCTTAATCAAATAAATGACTAACAGCATCTA
TCATAAAGCCACACAAGCCTTATGTTCTCATCTCAAAAATGCTGTGACAGCTTTTTGGCT
GCTTTAACCATAAGAAAATGATTGGTGGATGATTTATTAGCCCAGGCTTTTAAAAACT
TTCATCTAGGCCACGTGCGGTGGCTCATGCCTGTAATCCCGGCACTTTGGGAGGCCTGAG
TGGATGGATCACTTGAGGTCAGGAGTTCAGGACCAGCCTGGCCAACATGATGAAACCCTG
TCTCTACTAAATATACAAAAATTAGTTGGGTGTTATGGTGCATGCCTGTAATCCCAGCTA
CTCGGGAGGCTGAGGCAGGAGAATTGCTTGAACTCGGGAGGTGGAGATTGCAGTAAGCCG
AGATCGTGCCACTGCACTCCAGCCTGGGTGATAGAGCAAGACTGTCTCAAAAAGAAAAA
AAAGAAAAATTTTAATTTAATCCTTCTGTAGAAACAGGCATTCAGAACCATTCCATTGA
TCTTAATAAAGCTGCTCTTTACTGTTTCTAGTCAAAAATGAGACTTCGATCAAACCATAA
GATTTTATACTGCAGATAGTCAGCTTCACCAAAGCCGCAGAGGAAACATGTCGAGATCAG
GCTTCCTGCTTGATAGTCTCTTGACTACCATTAAAACGAATATTGGGAGGTCATGAAAGT
CATTGGTAGGCCATTAGCATTGATATCTTTAAAACATCTACCCTAAACCATCTGCTATGG
ACCCATAATAAGAGGCCTGTTGTATATGAAATTGTCTAGAATTCAGGTGCAGGTCTTTGC
CGGTTAAGTAAGGGAGCAACACGTAAAATGGGAGAGGAGTGGGGTGTACTCACTTGCCTC
CTCTTTTGTCCTGATTTAACCAGCATTTTCAACCCTGGGAAAATTTGCAGAATCTAAGT
TGATTGTAATGATTTTGAGCTGCAGCAGCTTTAACTCTTACCCTTTTTCCACATAGTTAT
GGTGTTTGAGTTGGAAAGAAACAACTATAGGTAGCTACACGTACATAATTATCTCTTTAT
TCACAAAGGGTATAGTAAAATTGATTGTAAATAACTTTCTAAGTGCCAATATTCAAAACT
TTTGGATTAAAATGTATTTTTCACCGTGCATTTACTTTGGATGTATTTATTTCATTTAAA
CAATTTAAATGGGGCTCTTTAACCAAAAATGGTATTTAAAACCAAAACAGTATCGTACTT
AGAATTTGGAGTAGAGGCCGGGCACAGTGGCTCACGCCTGTAATCCCAGCACTTTGGAAG
GCTGAGGCAGGCGGATCACCTGAGGTCAGGAGTTCGAGACCAGCCTGGTCAACATGAAAC
CCCGTCTCTACTAAAAATACAAAAATTAGCTGGGCGTGGTGGCGTGCGCCTATAATCCCA
GCTAGTCTACTCGGGAGGCTGAGGCAGGAGAATCGCTGGAACTCAGGAGGCAGAGACTGC
AGTGAGCCGAGATCGCGCCACTGCACTCCAGTCTGGGTGACGGCATGACTCCATCTCCAA
AAAAAAAAAAAAGATTTTGGAGTAGATTCATCATTAATAAGTAACAGATTTTAGGAAA
ATCAAAAATGGCTAATAAAATGAACACAATGTAAAACATTTATTAAAATGTAGACTTTT
AAAATCTATAAATTGATCATCTGTTTATAAATTGGCAGATGGTTGTGTACCATCTTTTA
AAATAAAGATTGAATTTCACCCAGTGTGATGGTTCCCATTGCTTATATTTCTCCTGCTGA
```

*FIG. 15C*

```
GGCCGGACCTGATATGGCCCTGGTCTGTGTTCCCAGCCTTGTTTCCTCATTACCACTAAA
ATCTTTCCCCTGTATGCCCGCCCAATTTTTCTGGCTCTGAGTCCTTGTTCATACTGTTCT
CTCCAATTCTACCTTCCAAAGGCCTTTCTTAACACCTTCGGATTCTTTCTTTGAGAACTT
TCCAGATTCCATGCCTTTTTGGAATCAATCTCTATCCTATTGTCATCACATTTAAGTTT
CTACTTCCATCATCCTCACTCCTATCCCTTTGGTCCTGGGATGACAGGGATGCTGTGTTT
TATTTACTCATCTTTGTAACTTCCACATAACCTAACCCCGGTTCTTGCTTATGGGAGATG
CTGATTGTAGGGTCTGAGTTAGATACTGTTAACTAAAATGCTTGTTGATATTTTAGTTAT
TAATTCATATTAACTTTGGCTGAAACTTTTAAATTCTATTGTGAATAGTCAAGTAAAATT
TAGATTGTTACATTCTGGGTTAGTATTAGATTGTTTTTAAGATTGTTTTAAACAAGATGT
TTTTAAGATGAGTTTTAAATAGTTCTCTTAACACAAATAAAGCTTAATATGAGTATTTGA
AGGAAATTATCCCAAACCATTCCAGTTCCTGGCTGTGAAAGGCTTTTCCAGGCCTAATAA
GTTTTCCACTTCAGCCGTAAGTAGGTGAAATCAAATGAACAATAGAGGGAAATGTATTTA
TTTGCTTTATACACATGCATGTGTGTTGTGTCTACATATAAACATTGCACACGCTTAGAA
TGAAGTTTCTGTCATGCCCAGAAAGGGAGAGGCATTTTGTGGATTTTGTCTGGCTGCC
CTGGGCATGTTTGAAGAACTGTGCTGTTTACTTCATACCAGGTGTGTGAGCCATACCTTT
GGTAGGAGGGTATACCTCCTACACCCAAGAAATATAAGCCAGGAGAAGGTCTGTGCCAAG
AGAAGGAACCCAAATGACCCACAAGAGGTGGGCCATTAATTATTGGGTCAGATGCATAAA
TGCACAGTAATTTATTTAAGCACCTCTTAATGGTGACCCACAAGGAAGATTGCTCGTAGT
AGCGGAAAGGTTCACAATAAATAAGAGAAAAAGCAGAATGTAGAACTGTATGATAGCAA
TTCTGCAAACAAGAAGCATCTTTTATAAAGATGGAAGGAGCCCAGGCACAGTAGCTCAT
GCCTGTAATCCCAGCACTTTAAGAGGCTGAGGTGGAGGATCACTTGAGCTGCAGTGACCC
ATGATTGTGCCACCACTCCAGCCTGGGTGATAGAAGTGAGACCTTCTCTCAAAAAAAAA
AAAAAAAAAAAGACGGAAATTCCTCCAGAATTTTAACATGTCAACAGAGGTTTTCTGC
AGCTACTTTTTTCAGCTTTATACTTCGCAGTATTTTCCAAATTTTCTCTAACAAGCAGTA
TTTTCCAAATTTTTTACAATAAGCACACACACACACACACGTTTGTTTGCATAAGTGCCC
AACTGGTGGTGAACAACCGCTGGCTTTTAGTCTATACATATCTAGAATATTTTATAAATA
GTAGTTCTTAAACCCTTGAAAGGGAGTGAATGACCAGCTGAGAAAATAAAGTCAGTGATT
TCATTATTTTCCTATATTCACATCATGATTCTAGGAAAGAACTTGGGAGTGACTTCCTTC
AGCTTCAGCCACTCCTGGGCCAGGCGCATGCTTAGCTCTGTGGTAAAGGTCACCAGCTTC
TTCTGCAGGGTGCCTGTATCATCTGAATTGGAGGTTTGGCGAGGGTAAGAGACTGATGTA
GGTTCAAGTTTTTCTTTCCTGTCCTCCACTTGAAATCTGTCTTCCCTTCCAGACTGCCTG
CGCTGCTGACTTAAGGCCCCAACACCAAACACAGAAGCAACAGCCTTACACAGAGTGTTC
AGCAAGCTCCAACAATTGTGTAAGGTAAAGTTTCCTTTATAGATTCCTTTTCTATATCGC
TCCTAGTGGTTCTGTTTCTCTGATCGAATTCTGGCTGATAACAGTTGCTGAGACTCTGAA
AGAGAAGGCAAGGAACTACTGTTTCTCATTATAAACTGTTTAGAATTATTTGGCCATCTT
TTTGCTATGAATATGTAGTGCTTTGATACATTTTTAAATCAAAAGTAATGAAAGAGAT
CACATAGGGAAAGATAGATTGGATTATTTTTAAAGTTTATATACTAAATTGAAAAGCAAA
GAATAAAATGGGAGAAACAGCTCCCTCATGTGGCTGTTGGCAGGAAGCTTCCATTCCTCT
CTGTGGGCCTCCACAGGTTTGCTCACAGCAAATGGTCCGTGACAGAAAGACGCAAGGGCA
GTTGCACCCAAGATGGAAGCCACCATCTTTTCTATAACCTAATCTGAAAGAAGGGACATA
CCAGCACTTCTGCCATATGCTGTTGGGTCACACAGACCAACTCTGGTACAGTGTGAACAC
AGGACCACACAAGGGCGTGAATTCCAAGGGCAGAGACCACTAGGGACCACCTCAGAGGCA
CAGAGGGACACCCTATCCAGCTGGTGGCCAATGTAAATTAACATAGCTTTTTAGAATAGC
AATATGTATCTATAATCTTAAAAGTATTAAAAGTACTTCTTGATCCAGTAATTTCATTTC
TAAGAATCCATGCTAAGAGGATTTAAAATGTGGACCAAAAAATGGGTATAAAAGAAGTT
GTTAACAGTATTTAAAGTTGTGAAAAACCAGAAACAATCTAAAGGTCCAACAATAGGAAA
ATGAATTTTGATATTTTCTAATAGAATTTATGCTGTCATCAGAAATACCATTTACAAA
TAATTTTTAATAACGCAAAAAAAGTTTATAAAATGTTTAGTGTAAAACCTGGACACAAC
TACATAATGATTCTGATTTTCTAAAAAAAAAAACAAAACACACACATATACACATGCA
TACATATGCATATAAAGAAAACTGGAACAAACAAAATAACAAGCATAGTTGGAATTACAG
TCATTTTAATATTCTTTATGCTTTTAAAAATTTTGAAGTTTGTATTACTAGCATCCACTA
CTTACGTAGTCAGGAAAAAAATACAACTTTAAAATAGATATTTAGGTCCAAAGATGGTAA
```

*FIG. 15D*

```
TCTAAATGGTGTTACAGGCTGAATGTGTGCCTGATCCCCATGCCCCAAGTTCATATGTTA
AAGCCCTGGCCCCCAAGGCAATGGTATTAGGGGAGTAGGGCCTTTGGGAGGTAATCAGAT
TTCTACGAGGTCATGAGGGTGGAGCCCGCATAGTGGAATTAGTGTCCTTTTAGGAAGAGG
AGAACAGACCAAAGCCTTCCTTTCTCTCCTCACTATGTAAGAAGACAGCCAGAAGGTGGC
CACAGCCAGGAAGAGAGCTCTCACCAGAACCCAAATCTGCTAGCACCTTGCTCTTGGGTT
CTCAGCATCCAGAACTGTGAGAAATGAATGTGTGTTGTTTAAACCACTCAGGCTACGGTA
TTTTGTTGCAGCAGCCCAAGCTGACAGAGATAGAAACAACACAAGGACCCATCAGCAGAC
GAATGGATGATCAAAACGTGGTGAGGTCGTGCAGTGGATATTATTCAGCCGTAGAAGGA
ATGAAATTCTGATACATGCTATAATGATGAACCTTGAAAACATGTTAATGGAAATAAGCC
AAACTTAAAAGGACAAATATTGTATAATTCCACTTATATGAGTTAGTTACCTAGAATAGG
CAAATTATGTCATAGATACAGAACATTAGAGGTTACCAGGGTTGTGGGAAGAGGGGTATT
GTGGGTACAAATTTTCGGTTTGGAGTGATTTTGAAAAATTCTGGAAATGGGTAGTGACA
GTAGTCAACATGATGAATGTACTTAATGACACTAAATTGTACACTTAAAAATGGTTAATA
CTGGGCTGGCGCAGTGGCTCATGGCTGTAAATCCCAGAACTTTGGGAGGCCAAGACAGGC
GGATCATGAGGTCAGGAGATTGAGACCATTCTGGCTAACATGGTGAAACCCTGTCTCTAC
TAAAAATAAAAACAAATAAAAAAAAATTAGCCGGGCATGGTGGCAGGCACCTGTAGTC
CCAGCTACTCGGGAGGCTGAGGCAGGAGAATGGTGTGACCTGGGAGTCGGAGCTTGCAGT
GAGCTGAGATCGCGCCACTGCACTCCAGCCTGGGCAACAGAGCCAGATTCCGTCTCAAAA
AAAAAAAAAAAAGGTTGATACCTGGGTGCGGTGGCTCATGCCTGTAATTTCAGCACTTT
GGGAGGCCAAGGCAGGCAGATCAGTTGAGGTCAAGAGTTAAGGACCAGCCTGGCCAACGT
GGCGAAACCCCATCTCTATTAAAAATACAAAAATTAGTCGAGTGTGGTGGTGGGTGCCTG
TAGTCCCAGCTGCTGGGAGGATGAGGCCTAGGAATTGCTTGAACCCAGGAGGCAGAGGTT
GCAGTGAGTTGAGATTGCGCCACTGCACTCCAGCCTGGGGACAGAGCGAGACTTAGTCT
CAAAAAAGGTTAAAATTGTAAGTTTTGTTATGCATATTTACCATAATCTTTAAAAAA
TAGATATATAGGAGATAAAGTCAACAGAATTTAATAACCAGTTGTAAATAGAGACTGAGT
GAGGAGGATGAATTAAGGAAGACATTGAGTACAACTTTTTGGTAGGTGAAAAACTCTTAA
AAAAATACGTGGGCAAAGATCCTACTTGATTCTTATAATTTAAAAATCTCCCAGTTAGTA
AACAAGGCTAGGTGGAGATTTGCATGTGATGTGAGGTGTGTGTTCTGTTTTGTAATGTGA
GGACTGTGAGCCATCTCCTGGACTTGAATATCCATTAGATAATTGAAAATACGGATTTGA
GAACTCAGGAGACGTGCAATGCAGTAACAAAACTCTGCACCTAGTTGATTTCTGTCTCCT
AATTTAATGCTTTTATGGGACAAACTGTTAGGCAGGTGGGCAAGATGGACAGCCATATTT
TTGTGGGTTTCTGGCCTGTGGGCCAGCCTCAGTGCTCACTCTGAGGTCATGTCCAAACTT
AGAACACATTCAGGCCTACCACAGTCAAGGCTCCCTTTCTCAACTCTAGTCCTCTGCACA
AATATCCGAAGCCTAGAAATAATAATCATCTGTCCTTGTGTCTTGCATTATGAAAGCCTA
GGAAAGGGCCTTGGGAATTAAGAAGAATGGAAAAACTGGTCTAACTGCTGCATGCTTCAG
CTTGCAGGGGAATCACTGAAATGGGGACAGGCCATAAAAGGACAACCAGAAGAGTGGCTT
CAGCAAAGGCATCGTTTTTCAGAGCAAGCTAGAGAATCCTGCCAGCGTCCTCAGGCAGGG
CCCCTGGGCACAGAGGTTAGGCAAGGGAGTGTCCCAGCATGTTGATGCCCTGAGCATCAG
AATAATGCCATAGAGGAGCTTCCAAAGAGTTCATTTCAGGTTTTGTAAGCCGAACATTTC
TAGGCAAATAAAATTTGATTTTGTGAATAAAGCTTGTTTCTTCAACTCCAGTGCAGATTC
TCATAGATTGATAGTGGCTTGTGATCCAGATAAAGAAAACAATTTTTCAAAGATTCATAT
TCTTTGTAGATGTACGGATTTAGAGACCATCTAATCTAACTCCCTCATTCTACAGATAGG
AAAAATGAGGCCTAAAGAAGTTAAGAAAATACCATGGAAATGTCACTGCTGAACTGCCAT
ACGTAGGATCCGAAAGAAATTGGGTAAATGCTACTGTGAGAAATACAGTACTAGGTCCAA
AGAATCTAATACAAATTAAAAATCTAAATGTTATTTCTAAAGCATCCCTGCACATGGCTG
AACTTACATAGTTTCATTTTCTTTCTTTTCTGTTGAAGAAGAGGCAATTGGCTGGGTGCA
GTGGCTCATGCCTGTAATCCTGGCACTTTGAGAGGCCGAGGCGGGTGGATCACCTGAGGT
CAGGAGTTTGAGACCAGCCTGGCCAACATGGTGAAACCCCATCTCTACTAAAAATACAAA
AATTAGCTGGCTGTGGTGGCCGCTGCCTGTAATCCCAGCTACTCCAGAGGCTGAGGCAGG
AGAATTACTTGAATCTGGGAGGTGGAGGTTGCAGTGAGCCAAGATCACGCCATTGCACTC
TAGCCTGGATGACAAGAGGGAAACTCCATCTCAAAAAAAAAAGAAAAAAGCAATCACT
AACCTGTGTTGTTTATTAAACATGACAGACTGGCATGAAGTAATTACCAAACTGTAAACA
```

*FIG. 15E*

```
AAAAAGCTACAATCTGCCAGGCATGGTGGCTCATGCCTGTAATCCCCACCTTGGGAGGC
CAGGTTGGGGGATCACCTGAGGCCTGGAGTTCAAGACTAGCCTGGTCAACATGGTGAAAC
CTCGTCTCTACTAAAAATACAAAAATTAGCCCGGCGTGGTGGCACATCCCTGTAATCCCA
GTTACTCAGGAGGCTGAGGCAGGAGAATCACTTGAACCTGGGCAGTGGGGAGGTTGCAGT
GAGCCAAGATCGCACCGTTGTACTCCAGTCTGGGCCGACAGAGTGAGACTCGGTCTCAAA
AAAAAGAAAAAGAAAAGCTACAACCTTAATCTCAACTTCTCATAACATCATCTCTACTT
CTGATTAGAAGAGTGGAAGTGGGGAGGTTTATTACAAAAAGACTGTTATACCTTACACAC
TTCTCCCCATGAATAGTGAAGGTGTGAGTGAAAAGACAGCAATTTTATTTTTTTTTGA
AACAGGTTCTTGCACTGTCACCCGGGCTGGAGTGCACTGTTGTGATCACTGCTCACTGCA
GCCTCCACCTCCCAGGCTCAAGTGATCCTCCTACCTCAGCCTCCTGAGTAGCTGGGACCA
CAGTTGTGCACTACCATGCCCAGCTATTTTTTTTAAGAGATGGGGTCTCACTATATTGC
TTAGGCTAGTTCTCAAACTCCTGGCCTCAAGCAGTCCTCCGACCTTGGCCTCCCAAAGGG
TTGTGATTACAGGCATAAGCCACCACACCCAGCCAGCAGTTTTAGAATAAAGGGTGAAGG
TGCTGTTGGGGAAATATAATTTAAAAAACAAAATCTTCTCTCAACCCAGAAATCCTCTCC
ATGAAGGCAGTAGAGAAAGATAAGCTTTATTATTGAATAAAAATTAAATGAGAATGTGAT
GCACATCACAGGCACTTTGCTAAGAGATCACAAAGACAGAAGGAAATTTCACCATTTTGT
ACAGCCAAGCAGGTACAGCCCATTACATGTATGTTTTCGAGATAAATAGTCCTCAACTAA
GAGAACTTGACAGCACCACTGGTCACACAGTTCATTCTAACTTTACCTGATAATTGATGT
GACCACTTGTGTTATCTAAGATATCAACTTTTCGGGGGTGGGGGAGTGTGGAAACAGCAG
TTACTTTTATAGCTTGGTGCAAGGTACTCATTAAGATTAGGCTGTTACCCTCCCACAGAA
ACTGGAAGATAGGTATGCTATCTGGTAATGTTTACATTTCCCAGATCCTTGAGAAAGACA
TTCCTAGGTCATAAAGCTGACAAAGGCTGATTCAGTTTTTAAATATATATATCTGTATA
TGTATTTCA
```

*FIG. 15F*

```
actgagagacaggactagctggatttcctaggctgactaagaatccctaagcctagctgg
||||||||||||||||||||||||||||| |||| ||||||||| |||||| ||||||||
actgagagacaggactagctcgatttcccaggccgactaagaattcctaagcctagctgg g-aaggtgaccacatccacctttaaacacggggcttgcaacttagctcacacctgaccaa
| ||||||||||| || ||||||||||| | ||||| |||| |||||||||| ||||||
ggaaggtgaccacaccctcctttaaacacagagcttgtaactcagctcacacccgaccaa tcag---------agagctcactaaaatgctaattaggc-aaagacaggaggtaaagaaa
||||         ||||||||||||||| | |||||||| ||||||||||||||||||||
tcaggtagtaaagagagctcactaaaataccaattaggctaaaaacaggaggtaaagaaa tagccaa-tcatctattgcctgagagcacagcaggaggacaatgatcgggatataaacc
|| ||| |||||||| ||||||||||||||| |||||||||||||||||||||||||||
taatcaaatcatctatcgcctgagagcacaggggagggacaatgatcgggatataaacc caagtcttcgagccggcaacggcaaccccctttgggtccctccctttgtatgggagctc
|| | || ||||  ||  || ||||| ||||||||||| | |||||||||||||||||
caggcatttgagccagatcaggtaaccctctttgggtcccctcacactgtatgggagctc tgttttcatgctatttcactctattaaatcttgcaactgcac--tcttctggtccatgtt
||||                ||||||||||||||||||||||  |||||||||||||||
tgtt-----------ttcactctattaaatcttgcaactgcacactcttctggtccatgtt tcttacggcttgagctgagcttcgctcgccatccaccactgctgtttgccgccaccgca
| || |||||  |||||||||| | ||||| |||||||||||||  ||| ||  |||||
tgttccggctcaagctgagcttttgctcgccgtccaccactgctgaatgccgccattgca gacccgccgctgactcccatccctctggatcatgcagggtgtccgctgtgctcctgatcc
|||| ||  ||||  || || ||| |||| |  | || |||||||||||||||||||||
gacctgcccttgacttccaccccttccggatccggcagagtgtccgctgcactcctgatcc agcgaggcacccattgccgctcccaatcgggctaaaggcttgccattgttcctgcatggc
||||||||||||||||||| || ||| |||||||||||||||||||||||||||| |||
agcgaggcacccattgccactcccgatcaggctaaaggcttgccattgttcctgcacagc taagtgcctgggttcatcctaattgagctgaacactagtcactgggttccatggttctct
||||||||||||||||||||||| ||| ||||||||| ||| | ||||||||| ||||||
taagtgcctgggttcatcctaatcaggctgaacactggtcgctgggttccacggttctct tctgtgaccacagcttctaatagagctataacactcaccgcatggcccaaggttccatt
|| ||||||||||||||||||||||||||||||||||| ||||||||||||||||||||
tccatgactcacagcttctaatagagctataacactcaccacatggcccaaggttccatt cctt-gaatccataaggccaagaacccaggtcagagaacacgaggcttgccaccatctt
| || |||||||| |||||||||||||||||||||||| | |||| ||| |||||||
cgttggaatccatgaggccaagaacccaggtcagagaataaaaggcccgcc-ccatctt gggag
|||||
gggag
```

*FIG. 16*

```
TCCTGTGAAC CTCTAGAGGA TTTGCGCCTG CTCTTCAAAC AACAACCAGG AGGAAAGTAA    7660
CTAAAATCAT AAATCCCCAT GGCCCTCCCT TATCATATTT TTCTCTTTAC TGTTCTTTTA    7920
CCCTCTTTCA CTCTCACTGC ACCCCCTCCA TGCCGCTGTA TGACCAGTAG CTCCCCTTAC    7980
CAAGAGTTTC TATGGAGAAT GCAGCGTCCC GGAAATATTG ATGCCCATC GTATAGGAGT    8040
CTTTCTAAGG GAACCCCCAC CTTCACTGCC CACACCCATA TGCCCGCAA CTGCTATCAC    8100
TCTGCCACTC TTTGCATGCA TGCAAATACT CATTATTGGA CAGGAAAAT GATTAATCCT    8160
AGTTGTCCTG GAGGACTTGG AGTCACTGTC TGTTGGACTT ACTTCACCCA AACTGGTATG    8220
TCTGATGGGG GTGGAGTTCA AGATCAGGCA AGAGAAAAAC ATGTAAAAGA AGTAATCTCC    8290
CAACTCACCC GGGTACATGG CACCTCTAGC CCCTACAAAG GACTAGATCT CTCAAAACTA    8340
CATGAAACCC TCCGTACCCA TACTCGCCTG GTAAGCCTAT TTAATACCAC CCTCACTGGG    8400
CTCCATGAGG TCTCGGCCCA AAACCCTACT AACTGTTGGA TATGCCTCCT CCTGAACTTC    8460
AGGCCATATG TTTCAATCCC TGTACCTGAA CAATGGAACA ACTTCAGCAC AGAAATAAAC    8520
ACCACTTCCG TTTTAGTAGG ACCTCTTGTT TCCAATCTGG AAATAACCCA TACCTCAAAC    8580
CTCACCTGTG TAAAATTTAG CAATACTACA TACACAACCA ACTCCCAATG CATCAGGTGG    8640
GTAACTCCTC CCACACAAAT AGTCTGCCTA CCCTCAGGAA TATTTTTGT CTGTGGTACC    8700
TCAGCCTATC GTTGTTTGAA TGGCTCTTCA GAATCTATGT GCTTCCTCTC ATTCTTAGTG    8760
CCCCCTATGA CCATCTACAC TGAACAAGAT TTATACAGTT ATGTCATATC TAAGCCCCGC    8820
AACAAAAGAG TACCCATTCT TCCTTTTGTT ATAGGAGCAG GAGTGCTAGG TGCACTAGGT    8880
ACTGGCATTG GCGGTATCAC AACCTCTACT CAGTTCTACT ACAAACTATC TCAAGAACTA    8940
AATGGGGACA TGGAACGGGT CGCCGACTCC CTGGTCACCT TGCAAGATCA ACTTAACTCC    9000
CTAGCAGCAG TAGTCCTTCA AAATCGAAGA GCTTTAGACT TGCTAACCGC TGAAAGAGGG    9060
GGAACCTGTT TATTTTTAGG GCAAGAATGC TGTTATTATG TTAATCAATC CGGAATCGTC    9120
ACTGAGAAAG TTAAAGAAAT TCGAGATCGA ATACAACGTA GAGCAGAGGA GCTTCGAAAC    9180
ACTGGACCCT GGGGCCTCCT CAGCCAATGG ATGCCTGGA TTCTCCCCTT CTTAGGACCT    9240
CTAGCAGCTA TAATATTGCT ACTCCTCTTT GGACCCTGTA TCTTTAACCT CCTTGTTAAC    9300
TTTGTCTCTT CCAGAATCGA AGCTGTAAAA CTACAAATGG AGCCCAAGAT GCAGTCCAAG    9360
ACTAAGATCT ACCGCAGACC CCTGGACCGG CCTGCTAGCC CACGATCTGA TGTTAATGAC    9420
ATCAAGGCA CCCCTCCTGA GGAAATCTCA GCTGCACAAC CTCTACTACG CCCCAATTCA    9480
GCAGGAAGCA GTTAGAGCGG TCTCGGCCAA CCTCCCCAAC AGCACTTAGG TTTTCCTGTT    9540
```

*FIG. 17*

```
AAGCTCCTTCAGGAGAACAAAGAACAGGCCATTACCCTGGAGAAGACTGGCAACTGATTTTACCCACAAGCCCAA
LysLeuLeuGlnGluAsnLysGluGlnAlaIleThrLeuGluLysThrGlyAsn...PheTyrProGlnAlaGln
  SerSerPheArgArgThrLysAsnArgProLeuProTrpArgArgLeuAlaThrAspPheThrHisLysProLys
   AlaProSerGlyGluGlnArgThrGlyHisTyrProGlyGluAspTrpGlnLeuIleLeuProThrSerProAsn

ACCTCAGGGATTTCAGTATCTACTAGTCTCGGGTAGATACTTTCACGGGTTGGGCAGAGGCCTTCCCCTGTAGGAC
ThrSerGlyIleSerValSerThrSerLeuGlyArgTyrPheHisGlyLeuGlyArgGlyLeuProLeu...Asp
  ProGlnGlyPheGlnTyrLeuLeuValTrpValAspThrPheThrGlyTrpAlaGluAlaPheProCysArgThr
   LeuArgAspPheSerIleTyr...SerGly...IleLeuSerArgValGlyGlnArgProSerProValGlyGln

AGAAAAGGCCCAAGAGGTAATAAAGGCACTAGTTCATGAAATAATTCCCAGATTCGGACTTCCCCGAGGCTTACA
ArgLysGlyProArgGlyAsnLysGlyThrSerSer...AsnAsnSerGlnIleArgThrSerProArgLeuThr
  GluLysAlaGlnGluValIleLysAlaLeuValHisGluIleIleProArgPheGlyLeuProArgGlyLeuGln
   LysArgProLysArg......ArgHis...PheMETLys...PheProAspSerAspPheProGluAlaTyrArg

GAGTGACAATAGCCCTGCTTTCCAGGCCACAGTAACCCAGGGAGTATCCCAGGCGTTAGGTATACGATATCACTT
Glu...Gln...ProCysPheProGlyHisSerAsnProGlySerIleProGlyValArgTyrThrIleSerLeu
  SerAspAsnSerProAlaPheGlnAlaThrValThrGlnGlyValSerGlnAlaLeuGlyIleArgTyrHisLeu
   ValThrIleAlaLeuLeuSerArgProGln...ProArgGluTyrProArgArg...ValTyrAspIleThrTyr

ACACTGCGCCTGAAGGCCACAGTCCTCAGGGAAGGTCGAGAAAATGAATGAAACACTCAAAGGACATCTAAAAAA
ThrLeuArgLeuLysAlaThrValLeuArgGluGlyArgGluAsnGlu...AsnThrGlnArgThrSerLysLys
  HisCysAla...ArgProGlnSerSerGlyLysValGluLysMETAsnGluThrLeuLysGlyHisLeuLysLys
   ThrAlaProGluGlyHisSerProGlnGlyArgSerArgLys...METLysHisSerLysAspIle...LysSer

GCAAACCCAGGAAACCCACCTCACATGGCCTGCTCTGTTGCCTATAGCCTTAAAAAGAATCTGCAACTTTCCCCA
           385       395       405       415       425       435       445
AlaAsnProGlyAsnProProHisMETAlaCysSerValAlaTyrSerLeuLysLysAsnLeuGlnLeuSerPro
  GlnThrGlnGluThrHisLeuThrTrpProAlaLeuLeuProIleAlaLeuLysArgIleCysAsnPheProGln
   LysProArgLysProThrSerHisGlyLeuLeuCysCysLeu...Pro...LysGluSerAlaThrPheProLys

AAAAGCAGGACTTAGCCCATACGAAATGCTGTATGGAAGGCCCTTCATAACCAATGACCTTGTGCTTGACCCAAG
LysSerArgThr...ProIleArgAsnAlaValTrpLysAlaLeuHisAsnGln...ProCysAla...ProLys
  LysAlaGlyLeuSerProTyrGluMETLeuTyrGlyArgProPheIleThrAsnAspLeuValLeuAspProArg
   LysGlnAspLeuAlaHisThrLysCysCysMETGluGlyProSer...ProMETThrLeuCysLeuThrGlnAsp

ACAGCCAACTTAGTTGCAGACATCACCTCCTTAGCCAAATATCAACAAGTTCTTAAAACATTACAAGGAACCTAT
ThrAlaAsnLeuValAlaAspIleThrSerLeuAlaLysTyrGlnGlnValLeuLysThrLeuGlnGlyThrTyr
  GlnProThr...LeuGlnThrSerProPro...ProAsnIleAsnLysPheLeuLysHisTyrLysGluProIle
   SerGlnLeuSerCysArgHisHisLeuLeuSerGlnIleSerThrSerSer...AsnIleThrArgAsnLeuSer

CCCTGAGAAGAGGGAAAAGAACTATTCCACCCTTGTGACATGGTATTAGTCAAGTCCCTTCCCTCTAATTCCCCA
Pro...GluGluGlyLysGluLeuPheHisProCysAspMETValLeuValLysSerLeuProSerAsnSerPro
  ProGluLysArgGluLysAsnTyrSerThrLeuValThrTrpTyr...SerSerProPheProLeuIleProHis
   LeuArgArgGlyLysArgThrIleProProLeu...HisGlyIleSerGlnValProSerLeu...PheProIle

TCCCTAGATACATCCTGGGAAGGACCCTACCCAGTCATTTTATCTACCCCAACTGCGGTTAAAGTGGCTGGAGTG
SerLeuAspThrSerTrpGluGlyProTyrProValIleLeuSerThrProThrAlaValLysValAlaGlyVal
  Pro...IleHisProGlyLysAspProThrGlnSerPheTyrLeuProGlnLeuArgLeuLysTrpLeuGluTrp
   ProArgTyrIleLeuGlyArgThrLeuProSerHisPheIleTyrProAsnCysGly...SerGlyTrpSerGly
```

*FIG. 18A*

```
GAGTCTTGGATACATCACACTTGAGTCAAATCCTGGATACTGCCAAAGGAACCTGAAAATCCAGGAGACAACGCT
GluSerTrpIleHisHisThr...ValLysSerTrpIleLeuProLysGluProGluAsnProGlyAspAsnAla
   SerLeuGlyTyrIleThrLeuGluSerAsnProGlyTyrCysGlnArgAsnLeuLysIleGlnGluThrThrLeu
      ValLeuAspThrSerHisLeuSerGlnIleLeuAspThrAlaLysGlyThr...LysSerArgArgGlnArg...

AGCTATTCCTGTGAACCTCTAGAGGATTTGCGCCTGCTCTTCAAACAACAACCAGGAGGAAAGTAACTAAAATCA
SerTyrSerCysGluProLeuGluAspLeuArgLeuLeuPheLysGlnGlnProGlyGlyLys...LeuLysSer
   AlaIleProValAsnLeu...ArgIleCysAlaCysSerSerAsnAsnAsnGlnGluSerAsn...AsnHis
      LeuPheLeu...ThrSerArgGlyPheAlaProAlaLeuGlnThrThrThrArgArgLysValThrLysIleIle

TAAATCCCCATGGCCCTCCCTTATCATATTTTTCTCTTTACTGTTCTTTTACCCTCTTTCACTCTCACTGCACCC
...IleProMETAlaLeuProTyrHisIlePheLeuPheThrValLeuLeuProSerPheThrLeuThrAlaPro
   LysSerProTrpProSerLeuIleIlePhePheSerLeuLeuPhePheTyrProLeuSerLeuSerLeuHisPro
      AsnProHisGlyProProLeuSerTyrPheSerLeuTyrCysSerPheThrLeuPheHisSerHisCysThrPro

CCTCCATGCCGCTGTATGACCAGTAGCTCCCCTTACCAAGAGTTTCTATGGAGAATGCAGCGTCCCGGAAATATT
ProProCysArgCysMETThrSerSerSerProTyrGlnGluPheLeuTrpArgMETGlnArgProGlyAsnIle
   LeuHisAlaAlaVal...ProValAlaProLeuThrLysSerPheTyrGlyGluCysSerValProGluIleLeu
      SerMETProLeuTyrAspGln...LeuProLeuProArgValSerMETGluAsnAlaAlaSerArgLysTyr...

GATGCCCCATCGTATAGGAGTCTTTCTAAGGGAACCCCCACCTTCACTGCCCACACCCATATGCCCCGCAACTGC
AspAlaProSerTyrArgSerLeuSerLysGlyThrProThrPheThrAlaHisThrHisMETProArgAsnCys
   METProHisArgIleGlyValPheLeuArgGluProProProSerLeuProThrProIleCysProAlaThrAla
      CysProIleVal...GluSerPhe...GlyAsnProHisLeuHisCysProHisProTyrAlaProGlnLeuLeu

TATCACTCTGCCACTCTTTGCATGCATGCAAATACTCATTATTGGACAGGAAAAATGATTAATCCTAGTTGTCCT
TyrHisSerAlaThrLeuCysMETHisAlaAsnThrHisTyrTrpThrGlyLysMETIleAsnProSerCysPro
   IleThrLeuProLeuPheAlaCysMETGlnIleLeuIleIleGlyGlnGluLys...LeuIleLeuValValLeu
      SerLeuCysHisSerLeuHisAlaCysLysTyrSerLeuLeuAspArgLysAsnAsp...Ser...LeuSerTrp

GGAGGACTTGGAGTCACTGTCTGTTGGACTTACTTCACCCAAACTGGTATGTCTGATGGGGGTGGAGTTCAAGAT
GlyGlyLeuGlyValThrValCysTrpThrTyrPheThrGlnThrGlyMETSerAspGlyGlyGlyValGlnAsp
   GluAspLeuGluSerLeuSerValGlyLeuThrSerProLysLeuValCysLeuMETGlyValGluPheLysIle
      ArgThrTrpSerHisCysLeuLeuAspLeuLeuHisProAsnTrpTyrVal...TrpGlyTrpSerSerArgSer

CAGGCAAGAGAAAAACATGTAAAAGAAGTAATCTCCCAACTCACCCGGGTACATGGCACCTCTAGCCCCTACAAA
GlnAlaArgGluLysHisValLysGluValIleSerGlnLeuThrArgValHisGlyThrSerSerProTyrLys
   ArgGlnGluLysAsnMET...LysLys...SerProAsnSerProGlyTyrMETAlaProLeuAlaProThrLys
      GlyLysArgLysThrCysLysArgSerAsnLeuProThrHisProGlyThrTrpHisLeu...ProLeuGlnArg

GGACTAGATCTCTAAAACTACATGAAACCCTCCGTACCCATACTCGCCTGGTAAGCCTATTTAATACCACCCTC
GlyLeuAspLeuSerLysLeuHisGluThrLeuArgThrHisThrArgLeuValSerLeuPheAsnThrThrLeu
   Asp...IleSerGlnAsnTyrMETLysProSerValProIleLeuAlaTrp...AlaTyrLeuIleProProSer
      ThrArgSerLeuLysThrThr...AsnProProTyrProTyrSerProGlyLysProIle...TyrHisProHis

ACTGGGCTCCATGAGGTCTCGGCCCAAAACCCTACTAACTGTTGGATATGCCTCCCCCTGAACTTCAGGCCATAT
ThrGlyLeuHisGluValSerAlaGlnAsnProThrAsnCysTrpIleCysLeuProLeuAsnPheArgProTyr
   LeuGlySerMETArgSerArgProLysThrLeuLeuThrValGlyTyrAlaSerPro...ThrSerGlyHisMET
      TrpAlaPro...GlyLeuGlyProLysProTyr...LeuLeuAspMETProProProGluLeuGlnAlaIleCys

GTTTCAATCCCTGTACCTGAACAATGGAACAACTTCAGCACAGAAATAAACACCACTTCCGTTTTAGTAGGACCT
ValSerIleProValProGluGlnTrpAsnAsnPheSerThrGluIleAsnThrThrSerValLeuValGlyPro
   PheGlnSerLeuTyrLeuAsnAsnGlyThrThrSerAlaGlnLys...ThrProLeuProPhe......AspLeu
      PheAsnProCysThr...ThrMETGluGlnLeuGlnHisArgAsnLysHisHisPheArgPheSerArgThrSer
```

FIG. 18B

```
CTTGTTTCCAATCTGGAAATAACCCATACCTCAAACCTCACCTGTGTAAAATTTAGCAATACTACATACACAACC
LeuValSerAsnLeuGluIleThrHisThrSerAsnLeuThrCysValLysPheSerAsnThrThrTyrThrThr
  LeuPheProIleTrpLys...ProIleProGlnThrSerProVal...AsnLeuAlaIleLeuHisThrGlnPro
   CysPheGlnSerGlyAsnAsnProTyrLeuLysProHisLeuCysLysIle...GlnTyrTyrIleHisAsnGln

AACTCCCAATGCATCAGGTGGGTAACTCCTCCCACACAAATAGTCTGCCTACCCTCAGGAATATTTTTTGTCTGT
AsnSerGlnCysIleArgTrpValThrProProThrGlnIleValCysLeuProSerGlyIlePhePheValCys
  ThrProAsnAlaSerGlyGly...LeuLeuProHisLys...SerAlaTyrProGlnGluTyrPheLeuSerVal
   LeuProMETHisGlnValGlyAsnSerSerHisThrAsnSerLeuProThrLeuArgAsnIlePheCysLeuTrp

GGTACCTCAGCCTATCGTTGTTTGAATGGCTCTTCAGAATCTATGTGCTTCCTCTCATTCTTAGTGCCCCCTATG
GlyThrSerAlaTyrArgCysLeuAsnGlySerSerGluSerMETCysPheLeuSerPheLeuValProProMET
  ValProGlnProIleValVal...METAlaLeuGlnAsnLeuCysAlaSerSerHisSer...CysProLeu...
   TyrLeuSerLeuSerLeuPheGluTrpLeuPheArgIleTyrValLeuProLeuIleLeuSerAlaProTyrAsp

ACCATCTACACTGAACAAGATTTATACAGTTATGTCATATCTAAGCCCCGCAACAAAAGAGTACCCATTCTTCCT
ThrIleTyrThrGluGlnAspLeuTyrSerTyrValIleSerLysProArgAsnLysArgValProIleLeuPro
  ProSerThrLeuAsnLysIleTyrThrValMETSerTyrLeuSerProAlaThrLysGluTyrProPhePheLeu
   HisLeuHis...ThrArgPheIleGlnLeuCysHisIle...AlaProGlnGlnLysSerThrHisSerSerPhe

TTTGTTATAGGAGCAGGAGTGCTAGGTGCACTAGGTACTGGCATTGGCGGTATCACAACCTCTACTCAGTTCTAC
PheValIleGlyAlaGlyValLeuGlyAlaLeuGlyThrGlyIleGlyGlyIleThrThrSerThrGlnPheTyr
  LeuLeu...GluGlnGluCys...ValHis...ValLeuAlaLeuAlaValSerGlnProLeuLeuSerSerThr
   CysTyrArgSerArgSerAlaArgCysThrArgTyrTrpHisTrpArgTyrHisAsnLeuTyrSerValLeuLeu

TACAAACTATCTCAAGAACTAAATGGGGACATGGAACGGGTCGCCGACTCCCTGGTCACCTTGCAAGATCAACTT
TyrLysLeuSerGlnGluLeuAsnGlyAspMETGluArgValAlaAspSerLeuValThrLeuGlnAspGlnLeu
  ThrAsnTyrLeuLysAsn...METGlyThrTrpAsnGlySerProThrProTrpSerProCysLysIleAsnLeu
   GlnThrIleSerArgThrLysTrpGlyHisGlyThrGlyArgArgLeuProGlyHisLeuAlaArgSerThr...

AACTCCCTAGCAGCAGTAGTCCTTCAAAATCGAAGAGCTTTAGACTTGCTAACCGCTGAAAGAGGGGGAACCTGT
AsnSerLeuAlaAlaValValLeuGlnAsnArgArgAlaLeuAspLeuLeuThrAlaGluArgGlyGlyThrCys
  ThrPro...GlnGln...SerPheLysIleGluGluLeu...ThrCys...ProLeuLysGluGlyGluProVal
   LeuProSerSerSerSerProSerLysSerLysSerPheArgLeuAlaAsnArg...LysArgGlyAsnLeuPhe

TTATTTTTAGGGGAAGAATGCTGTTATTATGTTAATCAATCCGGAATCGTCACTGAGAAAGTTAAAGAAATTCGA
LeuPheLeuGlyGluGluCysCysTyrTyrValAsnGlnSerGlyIleValThrGluLysValLysGluIleArg
  TyrPhe...GlyLysAsnAlaValIleMETLeuIleAsnProGluSerSerLeuArgLysLeuLysLysPheGlu
   IlePheArgGlyArgMETLeuLeuLeuCys...SerIleArgAsnArgHis...GluSer...ArgAsnSerArg

GATCGAATACAACGTAGAGCAGAGGAGCTTCGAAACACTGGACCCTGGGGCCTCCTCAGCCAATGGATGCCCTGG
AspArgIleGlnArgArgAlaGluGluLeuArgAsnThrGlyProTrpGlyLeuLeuSerGlnTrpMETProTrp
  IleGluTyrAsnValGluGlnArgSerPheGluThrLeuAspProGlyAlaSerSerAlaAsnGlyCysProGly
   SerAsnThrThr...SerArgGlyAlaSerLysHisTrpThrLeuGlyProProGlnProMETAspAlaLeuAsp

ATTCTCCCCTTCTTAGGACCTCTAGCAGCTATAATATTGCTACTCCTCTTTGGACCCTGTATCTTTAACCTCCTT
IleLeuProPheLeuGlyProLeuAlaAlaIleIleLeuLeuLeuLeuPheGlyProCysIlePheAsnLeuLeu
  PheSerProSer...AspLeu...GlnLeu...TyrCysTyrSerSerLeuAspProValSerLeuThrSerLeu
   SerProLeuLeuArgThrSerSerSerTyrAsnIleAlaThrProLeuTrpThrLeuTyrLeu...ProProCys
```

*FIG. 18C*

```
GTTAACTTTGTCTCTTCCAGAATCGAAGCTGTAAAACTACAAATGGAGCCCAAGATGCAGTCCAAGACTAAGATC
ValAsnPheValSerSerArgIleGluAlaValLysLeuGlnMETGluProLysMETGlnSerLysThrLysIle
  LeuThrLeuSerLeuProGluSerLysLeu...AsnTyrLysTrpSerProArgCysSerProArgLeuArgSer
    ...LeuCysLeuPheGlnAsnArgSerCysLysThrThrAsnGlyAlaGlnAspAlaValGlnAsp...AspLeu

TACCGCAGACCCCTGGACCGGCCTGCTAGCCCACGATCTGATGTTAATGACATCAAAGGCACCCCTCCTGAGGAA
TyrArgArgProLeuAspArgProAlaSerProArgSerAspValAsnAspIleLysGlyThrProProGluGlu
  ThrAlaAspProTrpThrGlyLeuLeuAlaHisAspLeuMETLeuMETThrSerLysAlaProLeuLeuArgLys
    ProGlnThrProGlyProAlaCys...ProThrIle...Cys......HisGlnArgHisProSer...GlyAsn

ATCTCAGCTGCACAACCTCTACTACGCCCCAATTCAGCAGGAAGCAGTTAGAGCGGTCGTCGGCCAACCTCCCCA
IleSerAlaAlaGlnProLeuLeuArgProAsnSerAlaGlySerSer...SerGlyArgArgProThrSerPro
  SerGlnLeuHisAsnLeuTyrTyrAlaProIleGlnGlnGluAlaValArgAlaValValGlyGlnProProGln
    LeuSerCysThrThrSerThrThrProGlnPheSerArgLysGlnLeuGluArgSerSerAlaAsnLeuProAsn

ACAGCACTTAGGTTTTCCTGTTGAGATGGGGG
ThrAlaLeuArgPheSerCys...AspGlyGly
  GlnHisLeuGlyPheProValGluMETGly
    SerThr...ValPheLeuLeuArgTrpGly
```

*FIG. 18D*

LysLeuLeuGlnGluAsnLysGluGlnAlaIleThrLeuGluLysThrGlyAsn...PheTyrProGlnAlaGln

ThrSerGlyIleSerValSerThrSerLeuGlyArgTyrPheHisGlyLeuGlyArgGlyLeuProLeu...Asp

ArgLysGlyProArgGlyAsnLysGlyThrSerSer...AsnAsnSerGlnIleArgThrSerProArgLeuThr

Glu...Gln...ProCysPheProGlyHisSerAsnProGlySerIleProGlyValArgTyrThrIleSerLeu

ThrLeuArgLeuLysAlaThrValLeuArgGluGlyArgGluAsnGlu...AsnThrGlnArgThrSerLysLys

AlaAsnProGlyAsnProProHisMETAlaCysSerValAlaTyrSerLeuLysLysAsnLeuGlnLeuSerPro

LysSerArgThr...ProIleArgAsnAlaValTrpLysAlaLeuHisAsnGln...ProCysAla...ProLys

ThrAlaAsnLeuValAlaAspIleThrSerLeuAlaLysTyrGlnGlnValLeuLysThrLeuGlnGlyThrTyr

Pro...GluGluGlyLysGluLeuPheHisProCysAspMETValLeuValLysSerLeuProSerAsnSerPro

SerLeuAspThrSerTrpGluGlyProTyrProValIleLeuSerThrProThrAlaValLysValAlaGlyVal

GluSerTrpIleHisHisThr...ValLysSerTrpIleLeuProLysGluProGluAsnProGlyAspAsnAla

SerTyrSerCysGluProLeuGluAspLeuArgLeuLeuPheLysGlnGlnProGlyGlyLys...LeuLysSer

...IleProMETAlaLeuProTyrHisIlePheLeuPheThrValLeuLeuProSerPheThrLeuThrAlaPro

ProProCysArgCysMETThrSerSerSerProTyrGlnGluPheLeuTrpArgMETGlnArgProGlyAsnIle

AspAlaProSerTyrArgSerLeuSerLysGlyThrProThrPheThrAlaHisThrHisMETProArgAsnCys

TyrHisSerAlaThrLeuCysMETHisAlaAsnThrHisTyrTrpThrGlyLysMETIleAsnProSerCysPro

GlyGlyLeuGlyValThrValCysTrpThrTyrPheThrGlnThrGlyMETSerAspGlyGlyGlyValGlnAsp

GlnAlaArgGluLysHisValLysGluValIleSerGlnLeuThrArgValHisGlyThrSerSerProTyrLys

GlyLeuAspLeuSerLysLeuHisGluThrLeuArgThrHisThrArgLeuValSerLeuPheAsnThrThrLeu

ThrGlyLeuHisGluValSerAlaGlnAsnProThrAsnCysTrpIleCysLeuProLeuAsnPheArgProTyr

ValSerIleProValProGluGlnTrpAsnAsnPheSerThrGluIleAsnThrThrSerValLeuValGlyPro

LeuValSerAsnLeuGluIleThrHisThrSerAsnLeuThrCysValLysPheSerAsnThrThrTyrThrThr

AsnSerGlnCysIleArgTrpValThrProProThrGlnIleValCysLeuProSerGlyIlePhePheValCys

GlyThrSerAlaTyrArgCysLeuAsnGlySerSerGluSerMETCysPheLeuSerPheLeuValProProMET

ThrIleTyrThrGluGlnAspLeuTyrSerTyrValIleSerLysProArgAsnLysArgValProIleLeuPro

PheValIleGlyAlaGlyValLeuGlyAlaLeuGlyThrGlyIleGlyGlyIleThrThrSerThrGlnPheTyr

TyrLysLeuSerGlnGluLeuAsnGlyAspMETGluArgValAlaAspSerLeuValThrLeuGlnAspGlnLeu

*FIG. 19A*

```
AsnSerLeuAlaAlaValValLeuGlnAsnArgArgAlaLeuAspLeuLeuThrAlaGluArgGlyGlyThrCys
LeuPheLeuGlyGluGluCysCysTyrTyrValAsnGlnSerGlyIleValThrGluLysValLysGluIleArg
AspArgIleGlnArgArgAlaGluGluLeuArgAsnThrGlyProTrpGlyLeuLeuSerGlnTrpMETProTrp
IleLeuProPheLeuGlyProLeuAlaAlaIleIleLeuLeuLeuLeuPheGlyProCysIlePheAsnLeuLeu
ValAsnPheValSerSerArgIleGluAlaValLysLeuGlnMETGluProLysMETGlnSerLysThrLysIle
TyrArgArgProLeuAspArgProAlaSerProArgSerAspValAsnAspIleLysGlyThrProProGluGlu
IleSerAlaAlaGlnProLeuLeuArgProAsnSerAlaGlySerSer...SerGlyArgArgProThrSerPro
ThrAlaLeuArgPheSerCys...AspGlyGly
```

*FIG. 19B*

```
SerSerPheArgArgThrLysAsnArgProLeuProTrpArgArgLeuAlaThrAspPheThrHisLysProLys
ProGlnGlyPheGlnTyrLeuLeuValTrpValAspThrPheThrGlyTrpAlaGluAlaPheProCysArgThr
GluLysAlaGlnGluValIleLysAlaLeuValHisGluIleIleProArgPheGlyLeuProArgGlyLeuGln
SerAspAsnSerProAlaPheGlnAlaThrValThrGlnGlyValSerGlnAlaLeuGlyIleArgTyrHisLeu
HisCysAla...ArgProGlnSerSerGlyLysValGluLysMETAsnGluThrLeuLysGlyHisLeuLysLys
GlnThrGlnGluThrHisLeuThrTrpProAlaLeuLeuProIleAlaLeuLysArgIleCysAsnPheProGln
LysAlaGlyLeuSerProTyrGluMETLeuTyrGlyArgProPheIleThrAsnAspLeuValLeuAspProArg
GlnProThr...LeuGlnThrSerProPro...ProAsnIleAsnLysPheLeuLysHisTyrLysGluProIle
ProGluLysArgGluLysAsnTyrSerThrLeuValThrTrpTyr...SerSerProPheProLeuIleProHis
Pro...IleHisProGlyLysAspProThrGlnSerPheTyrLeuProGlnLeuArgLeuLysTrpLeuGluTrp
SerLeuGlyTyrIleThrLeuGluSerAsnProGlyTyrCysGlnArgAsnLeuLysIleGlnGluThrThrLeu
AlaIleProValAsnLeu...ArgIleCysAlaCysSerSerAsnAsnAsnGlnGluGluSerAsn...AsnHis
LysSerProTrpProSerLeuIleIlePhePheSerLeuLeuPhePheTyrProLeuSerLeuSerLeuHisPro
LeuHisAlaAlaVal...ProValAlaProLeuThrLysSerPheTyrGlyGluCysSerValProGluIleLeu
METProHisArgIleGlyValPheLeuArgGluProProSerLeuProThrProIleCysProAlaThrAla
IleThrLeuProLeuPheAlaCysMETGlnIleLeuIleIleGlyGlnGluLys...LeuIleLeuValValLeu
GluAspLeuGluSerLeuSerValGlyLeuThrSerProLysLeuValCysLeuMETGlyValGluPheLysIle
ArgGlnGluLysAsnMET...LysLys...SerProAsnSerProGlyTyrMETAlaProLeuAlaProThrLys
Asp...IleSerGlnAsnTyrMETLysProSerValProIleLeuAlaTrp...AlaTyrLeuIleProProSer
LeuGlySerMETArgSerArgProLysThrLeuLeuThrValGlyTyrAlaSerPro...ThrSerGlyHisMET
PheGlnSerLeuTyrLeuAsnAsnGlyThrThrSerAlaGlnLys...ThrProLeuProPhe......AspLeu
LeuPheProIleTrpLys...ProIleProGlnThrSerProVal...AsnLeuAlaIleLeuHisThrGlnPro
ThrProAsnAlaSerGlyGly...LeuLeuProHisLys...SerAlaTyrProGlnGluTyrPheLeuSerVal
ValProGlnProIleValVal...METAlaLeuGlnAsnLeuCysAlaSerSerHisSer...CysProLeu...
ProSerThrLeuAsnLysIleTyrThrValMETSerTyrLeuSerProAlaThrLysGluTyrProPhePheLeu
LeuLeu...GluGlnGluCys...ValHis...ValLeuAlaLeuAlaValSerGlnProLeuLeuSerSerThr
ThrAsnTyrLeuLysAsn...METGlyThrTrpAsnGlySerProThrProTrpSerProCysLysIleAsnLeu
ThrPro...GlnGln...SerPheLysIleGluGluLeu...ThrCys...ProLeuLysGluGlyGluProVal
```

*FIG. 20A*

TyrPhe...GlyLysAsnAlaValIleMETLeuIleAsnProGluSerSerLeuArgLysLeuLysLysPheGlu
IleGluTyrAsnValGluGlnArgSerPheGluThrLeuAspProGlyAlaSerSerAlaAsnGlyCysProGly
PheSerProSer...AspLeu...GlnLeu...TyrCysTyrSerSerLeuAspProValSerLeuThrSerLeu
LeuThrLeuSerLeuProGluSerLysLeu...AsnTyrLysTrpSerProArgCysSerProArgLeuArgSer
ThrAlaAspProTrpThrGlyLeuLeuAlaHisAspLeuMETLeuMETThrSerLysAlaProLeuLeuArgLys
SerGlnLeuHisAsnLeuTyrTyrAlaProIleGlnGlnGluAlaValArgAlaValValGlyGlnProProGln
GlnHisLeuGlyPheProValGluMETGly

*FIG. 20B*

AlaProSerGlyGluGlnArgThrGlyHisTyrProGlyGluAspTrpGlnLeuIleLeuProThrSerProAsn
LeuArgAspPheSerIleTyr...SerGly...IleLeuSerArgValGlyGlnArgProSerProValGlyGln
LysArgProLysArg......ArgHis...PheMETLys...PheProAspSerAspPheProGluAlaTyrArg
ValThrIleAlaLeuLeuSerArgProGln...ProArgGluTyrProArgArg...ValTyrAspIleThrTyr
ThrAlaProGluGlyHisSerProGlnGlyArgSerArgLys...METLysHisSerLysAspIle...LysSer
LysProArgLysProThrSerHisGlyLeuLeuCysCysLeu...Pro...LysGluSerAlaThrPheProLys
LysGlnAspLeuAlaHisThrLysCysCysMETGluGlyProSer...ProMETThrLeuCysLeuThrGlnAsp
SerGlnLeuSerCysArgHisHisLeuLeuSerGlnIleSerThrSerSer...AsnIleThrArgAsnLeuSer
LeuArgArgGlyLysArgThrIleProProLeu...HisGlyIleSerGlnValProSerLeu...PheProIle
ProArgTyrIleLeuGlyArgThrLeuProSerHisPheIleTyrProAsnCysGly...SerGlyTrpSerGly
ValLeuAspThrSerHisLeuSerGlnIleLeuAspThrAlaLysGlyThr...LysSerArgArgGlnArg...
LeuPheLeu...ThrSerArgGlyPheAlaProAlaLeuGlnThrThrThrArgArgLysValThrLysIleIle
AsnProHisGlyProProLeuSerTyrPheSerLeuTyrCysSerPheThrLeuPheHisSerHisCysThrPro
SerMETProLeuTyrAspGln...LeuProLeuProArgValSerMETGluAsnAlaAlaSerArgLysTyr...
CysProIleVal...GluSerPhe...GlyAsnProHisLeuHisCysProHisProTyrAlaProGlnLeuLeu
SerLeuCysHisSerLeuHisAlaCysLysTyrSerLeuLeuAspArgLysAsnAsp...Ser...LeuSerTrp
ArgThrTrpSerHisCysLeuLeuAspLeuLeuHisProAsnTrpTyrVal...TrpGlyTrpSerSerArgSer
GlyLysArgLysThrCysLysArgSerAsnLeuProThrHisProGlyThrTrpHisLeu...ProLeuGlnArg
ThrArgSerLeuLysThrThr...AsnProProTyrProTyrSerProGlyLysProIle...TyrHisProHis
TrpAlaPro...GlyLeuGlyProLysProTyr...LeuLeuAspMETProProProGluLeuGlnAlaIleCys
PheAsnProCysThr...ThrMETGluGlnLeuGlnHisArgAsnLysHisHisPheArgPheSerArgThrSer
CysPheGlnSerGlyAsnAsnProTyrLeuLysProHisLeuCysLysIle...GlnTyrTyrIleHisAsnGln
LeuProMETHisGlnValGlyAsnSerSerHisThrAsnSerLeuProThrLeuArgAsnIlePheCysLeuTrp
TyrLeuSerLeuSerLeuPheGluTrpLeuPheArgIleTyrValLeuProLeuIleLeuSerAlaProTyrAsp
HisLeuHis...ThrArgPheIleGlnLeuCysHisIle...AlaProGlnGlnLysSerThrHisSerSerPhe
CysTyrArgSerArgSerAlaArgCysThrArgTyrTrpHisTrpArgTyrHisAsnLeuTyrSerValLeuLeu
GlnThrIleSerArgThrLysTrpGlyHisGlyThrGlyArgArgLeuProGlyHisLeuAlaArgSerThr...
LeuProSerSerSerSerProSerLysSerLysSerPheArgLeuAlaAsnArg...LysArgGlyAsnLeuPhe

*FIG. 21A*

IlePheArgGlyArgMETLeuLeuLeuCys...SerIleArgAsnArgHis...GluSer...ArgAsnSerArg
SerAsnThrThr...SerArgGlyAlaSerLysHisTrpThrLeuGlyProProGlnProMETAspAlaLeuAsp
SerProLeuLeuArgThrSerSerSerTyrAsnIleAlaThrProLeuTrpThrLeuTyrLeu...ProProCys
...LeuCysLeuPheGlnAsnArgSerCysLysThrThrAsnGlyAlaGlnAspAlaValGlnAsp...AspLeu
ProGlnThrProGlyProAlaCys...ProThrIle...Cys......HisGlnArgHisProSer...GlyAsn
LeuSerCysThrThrSerThrThrProGlnPheSerArgLysGlnLeuGluArgSerSerAlaAsnLeuProAsn
SerThr...ValPheLeuLeuArgTrpGly

*FIG. 21B*

```
TTGGTCTTAAGAACACAAATGATATGGCTCCAATGACTGGAGGAACACCAGGGTCCTTGG
TCTCACGCTGATTTAGATAAAACGACTGTCAGGCCTCTGAGCCCAAGCTAAGCCATCCTC
CCCTGTGACCTGCACGTATACATCCAGATGGCCTGAAGTAACCAAAGAATCACAAAGCA
GTGAAAATGGCCTGTTCCTGCCTTAACTGATGACATTCCACCATTGTGATTTGTTCCTGC
CCCATCTTAACTGAGCGATTAACCTTGTGAAATTCCTTCTCCTGGCTCAAAACCTCCCCC
ACTGAGCACCTTGTGACCCCCGCCCCTGCCCTAAGAGAAAACCCCCTTTGATTATAATT
TTCCACTACCCACCCAAATCCTATAAAATGGCCCCACCCCTATCTCCCTTCGCTGACTCC
TTTTTCGGACTCAGCCCGCCTGCACCCAGGTGAAATAAACAGCCTTGTTGCTCACACAAA
GCCTGTTTGGTGGACTCTCTTCACACGGACGCTCATGACATTTGGTGCCAAAACCTGGGA
TAGGAGGACTCCTTCAGGAGACCAGTCCCCTGTCCTTGCCCTCACTCTGTGAGGACATCC
ACCTACAACCTTGGGTCCTCAGACCAACCAGCCCAAGGAACAGCTCACCAATTTCAAATC
ACGTAAGCAGTCTTTTCACTCTCTTCTCCAGCCTCTCTTGCTACCCTTCAAACTCCCTCT
CTCACTACCCTTCAATCTCCCTGTCCTTCCAATTCCAGTTCTTTTTCATCTCTAGTAGAG
ACAAAGGAGACACATTTTATCCATGGACCCAAAACTCCAGCACCAGTCACGGACTTGGGA
AGACAGTCTTCCCTTGGTGTTTAATCACTCCGGGACGCCTGCCTGATTATTCACCCACA
CTCCATTGGTGTCTGATCACGGTGGGGACACCTGCCTTGGTCACTCACCCACATTCCCTT
GGTGGTACGTCAACTGCAAAAGCAGGGGACGCCTGCTTTGGCTGCTCACCCACCCCCTTC
TCTGTGTCTCTACCTTTCTCTTTAAACTTACCTCCTTCACTATGGGCAAACTTCTGCCCT
CCATTCCCCCTTCTTCTCCCTTAGCCTGTGTTCTTAAAAACCTAAAACCTCTTCAACTCA
CACCTGACCTAAACCTAAATGCCTTATTTTCTTCTGCAACACTGCGTGGCTGCAGTACA
AACTTGATAATAGCTTTAAATGGCCAGAATATGGCACTTTCAATTTCTCCATCCTACAAG
ATCTAGATAATTTTTGTGGAAAAATGGAAAAATGGTCTGAGATGCCTGACGTCCAGGCAT
TCTTTTACACATTGGTCCCTCCCTAGTCTCTGCTCCAATGCGACTCATCCCAAATCTTT
CTTCTTTCTCTCCTGTCTGTTCCTTCAGTCTCCACCCCAAGCTCTGAGTCCTTTGAATCC
TCCTTTGCTACAGACCCATCTGAACTCTCCCTCCTCCCCAGGCTGCTCCTCACCAGGCC
GAGCCAGGTCCCAATTCTTCCTCAGCCTCTGCTCCCCACCCTATAATCCTTTTATCACC
TCCTCTCCTCACACTCAGTCCGGCTTACAGTTTCGTTCTGTGACTAGCCCTCCCCCATCT
GCCCAACAATTTCCTCTTAAAGAGGTGGCTGGAGCTAAAGGCATAGTCAAGGTTAATGCT
CCTTTTTCTTTATCTGACCTCTCCCAAATCAGTTAGCGTTTACGCTCTTTTTCATCAAAT
ATAAAAACCCAGCCAGTTCATGGCCCATCTGGCAACAACCCTTACAGGCTTTACAGCCCT
AGACCCTGAAGGGTCAGAAGGCCGTCTTATTCTCAATATGCATTTTATTACCCAATCCGC
TCCCAACATTAAATAAAGCTCCAAAAATTAAATTCTGGCCCTCAAACCCCACAACAGGAC
TTAATTAACCTCACTTCAAGGTGTACAAGAATAGAGTAGAGGCAGCCAAGTAGCAACGTA
TTTGAGTTGCAATTCCTTGCCTCAACTCTGAGAGAAACCCCAGCCACATCTCCAGCAAAC
AAGAACTTCAAAACACCTGAACTGCAGCAGCCAGGCGTTCCTCCAGGACCACCTCCCCCA
GGATCTTGCTTCAAGTGCCGGAAATCTGACCATTGGGCCAAGGAATGCCTGCAGCCCAGG
ATTCCTCCTAAGCCACGTCCCATTTGTGCAGGACCCACTGGAAATCGGACTGTCCAACT
CACCCGGCAGCCAATCCCAGAGCCCCTGGAACTCTGGCCCAAGGCTCTCTGACTGACTCC
TTCCCAGATCTTCTCGGCTTAGCAGCTGAAGACTGACACTGCCCGATCACTTCAGAAGTC
CCCTGGACCATCACGGATACTGAGCTTCAGGTAACTCTCACAGTGGAGGCTAAGTCCATC
CCCTGTTTAATCGATACAGGGGCTACCCACTCCACATCACCTTCTTTTCAAGGGCCTGTT
TCCCTTTCCCCCATAACTGTTGTGGGTATTGACGGCCAAGCTTCAAAACCCCTTAAAACT
CCCCCACTCTGGTGCCAACTTGGACAACATTCTTTTATGCACTCTTTTTCAGTTATCCTC
ACCTGCCCAGTTCCCTTATTAGGCCGAGACATTTTAACCAAATTATCTGCTTCCCCGACT
ATTCCTGGGCTACAGCCACATCTCCTTGCCGCCCTTCTTCCCAACCCAAAGCCTCCTTCA
TATCTTCCTCTCATATCCCCCCACCTTAACCACAAGTATGGGACACCTCTACTCCCTCC
CTGGCAACCGATCACACGCCCATTACTATCCCATTAAAACCTAATCACCCTTACCCTGCT
CAATGCCAGTATCCCATACCACAACAGGCTTTAAAGGGATTGAAGCCTGTTATCACTTGC
```

FIG. 22A

```
CTGCTACAGCACGGGCTTCTAAACCTATAAACTCTCCATACAATTCCCCCATTTTTACCT
GTCTAAAAACCAGATAAGTCTTACAGGTTAGTTCAGAATCTGCACCTTATCAACCAAATT
GTTTTGCCTATCCACCCTGTAGCACCCAACTCGTACACTCTTTTGTCCTCAATGCCTTCC
CCCACAACTCACTATTCCGTTCTTGATCTTAAAGATGCTTTTTTCACTATTCCCCTGCAC
CCCTCATCCCAGCCTCTCTTTGCTTTTACCTGGACTGACCCTGACACCCATCAGTCCCAG
CAGCTTACCTGGGCTGTACTGCCGCAAGGCTTCAGGGACAGCCCTCATTACTTCAGCCAA
GCTCTTTCTCATGATTTACTTTCTTTCCACCTCTCTGCTTCTCACCTTATTCAATATATT
GATGACCTTCTACTTTGTAGCCCCTCCTTTAAATCTTCTAACAAGACACCCTCCTGCTC
CTTCAACATTTGTTCTCCAAGGATATCGGGTATCCCCCTCCAAAGCTCAAATTTCTTCT
CCATCTGTTACATACCTCGGCATAATTCTTCATGAAAACACATGTGCTCTCCCTGCCAAT
TGCGTCTCCAACTGATCTCTCAATCCCAACCTCTTCTACAAAACAACAACTCCTTTCCC
TCCTAGGCATGGTTGGATACTTTTGCCTTTGGATACCTGGTTTTGCCATCCTAACAAAT
CATTATATAAACTCACAAAAGGAAACCTAGCTGACCCCATAGATTCTAAATCCTTTCCCC
ACTCCTCTTTCCATTCCTTGAAGACAGCTTTAGAGACTGCTCCCACACTAGCTCTCCCTG
TCTCATCCCAACCCTTTTCATTACACACAGCCGAAGTGCAGGGCTGTGCAGTCGGAATTC
TTACACAAGGACCGGGACCATGCCCTGTAGCCTTTTGTCCAAACAACTTGACCTTACTG
TTTTAGGCTCGCCATCATGTCTCCATGCGGTAGCTTCCGCTGCCCTAATACTTTTAGAGG
CCCTCAAAATCACAAACTATGCTCAACTCACTCTCTACAGCTCTCACAACTTCCAAAATC
TATTTTCTTTCTCACACCTGACGCATATACTTTCTGCTCCCCGGCTCCTTCAGCTGTATT
CACTCTTTGTTGAGTCTCCCACAATTACCATTCTTCCTGGCCCAGACTTCAATCTGGCCT
CCCACATTATTCTGGATACCACACCTGACCCTGATGATTGTATGTCTCTGATCTACCTGA
CATTCACCCCATTTCCCCATATTTCCTTCTTTTCTGTTCCTCATGTTGATCACATTTGGT
TTACTGACGGCAGTTCCACCAGGCCTGATCGCCACTCACCAGCAAAGGCAGGCTATGCTA
TAGAATCTTCCACATCCATCATTGAGGCTACTGCTCTGCCCCCCTCCACTACCTCTCAGC
AAGCCGAACTGATTGCCTTAACTCGGGCCTTCACTCTTGCAAAGGGACTACACGTCAATA
TTTATACTGACTCTAAATATGCCTTCCATATCTTGCACCACCATGCTGTTATATGGGCTG
AAGAGGTTTCCTCACTACGCAAGGGTCCTCCATCATTAATGCCTCTTTAATAAAAACTC
TTCTCAAGGCTGCTTTACTTCCAAAGGAAGCTGGAGTCACACACTGCAAGGGCCACCAAA
AGGCGTCAGATCCCATTACTCTAGGAAATGCTTATGCTGATAAGGTAGCTAAAGAAGCAC
CTAGCGTTCCAACTTCTGTCCCTCATGGCCAGTTTTTCTCCTTCCCATCAGTCATTCCCA
CCTACTCCCCCATTGAAACTTCCGCCTATCAATCTCTTCTCACACAAGGCAAATGGTTCT
TAGACCAAGGAAAATATCTCCTTCCAGCCTCACAGGCCCATTCTATTCTGTCATCATTTC
ATAACCTCTTCCATGTAGGTTACAAGCCACTAGTCCACCTCTTAGAACCTCTCATTTCCT
TCCATCGTGGAAACATATCCTCAAGGAAATCACTTCTCAGTGTTCCATCTGCTATTCTAC
TACCCCTCAGGGATTGTTCAGGCCCCCTCCCCTCCCTACACATCAAGCTCGGGGATTTGC
CCCTGCCCAGGACTGGCAAATTGACTTTACTCACATGCCCTGAGTCAGGAAACTAAAATA
CCTCTTGGTCTGGGTAGACACTGTCACTGGATGGGTAGAGGCCTTTCCCACAGGGTCTGA
GAAGGCCACTGCAGTCATTTCTTCCCTTCTGTCAGACATAATTCCTTGGGTTGGCCTTCC
CACCTCTATACAGTCCAATAACGGAGCAGCCTTTATTAGTCAAATCACCTGAGCAGTTTT
TCAGGCTCTTGGTATTCAGTGGACCTTCGTACCCCTTACTGTCCTCAATCTTCAGGAAA
GGTAGAATGGACTAATGGTCTTTTAAAAACACACCCCACCAAACTCAGCCTCCAACTTAA
AAAGGAGGATAGAGCCCAAAAACTCGCAACCAAGCTAGTAATTATGCTGAACCCCCTTGG
GCACTCTCTAATTGGATGTCTTAGGTCCTCCCAAATCTTAGTCCTTTAATATCTGTTTTT
CTCCTTCTCTTATTCGGACCTTGTGTCTTCCGTTTAGTTTTTCAATTCATACAAAACCGC
ATCCAGGCCATCACCAATCGTTCTATACAATAAATGCTCCTTCTAACAACCCCACAATAT
CGCCCCTTACCACAAAATCTTCCTTCAGCTTAATCTCTCCCACTCTAGGTTCCCATGCCG
CCCATAATCCCTCTCGAAGCAGCCCTGAGAAACATAGCCCATTATCTCTCCATACCACCC
CCAAAATTTTTGCTGCCCCAACACTTCAACACTATTTTACATTATTTTTCTTATTAATAT
```

*FIG. 22B*

```
AAGAAGACAGCAATGTCAGGCCTCTGAGCCCAAGCCATCATATCCCCTGTGACCTGCACA
TATACATCCAGATGGCCTGAAGTAACTGAAGAATCACAAAAGAAGTGAAAATGGCCTGTT
CCTGCCTTAACCGATGACATTCCACCACTGTGATTTGTTCCTGCCCCACCTTAACTGAGC
AATTAACCTTGGGAAATTCCTTCTCCTGGCTCAAAACCTCCCCCACTGAGCACCTTGTGA
CCCCTGCCCCTCCACTACCCACCCAAATCCTATAAAATGGCCCCACCCCATCTCCCTTAG
CTGACTCCTTTTTTGGACTCAGCCCGCCTGCACCCAGGTGAAATAAACAGCCTTGTTGCT
CACACAAAGCCTGTTTGGTGGACTCTCTTCACAGGGACGGGGGTGACAACAACACGGACA
CACATGGAGTGGTTTTAAGGAGCAGAGAGTTTAATACGCAAAAAGAAGGAAGAGGCTCC
CCTGTACAGACACAGAGGGAGGGGGCTCCAAGCCGAGAGAAGGAAACCCCATGTGCAGTG
GAAAACTGGTTGATTATACTGGGAGGCTGGAGGAGGCGGTGTCTGATTTGCACAGGGCCC
AGGGGATTGGGTTGACCAGGTGTATCATTCATGTACCCCGCAAAAAACCTGGCCCTCCCA
CCTCAGCCCTTTAATATGCAAATGTGGGTTGCCATGATGTTCTGAAAACACATGAATTAT
CTGGAGGGGCCATGACACTTGGTACATGTGCTGACAAGAAGAGGGTGGGAATCGCCATG
GTGGCCATGTTGGGTGGACCTAGTTTTTAATAGCCTGCATTTGCATATCAAAGTTTGCTG
GCCTGGCTCTTTAAGCTGTCTTTTCTGTTAGAAAAGGAATGGTTTGGAATGGGTGAGGGT
TGCTTCTTATTACAAGAAAATTTCCAAAAACCTTTACTCTTTCTAGCTGCCAAAAAACTA
TTTCTTAATAACTTATGTATTACCATAATTAGGCAGCACCAAAGATCCCTGCAGGTCAGA
CCACTGCAATTAACATGCTGGCTTTACTGCTGATTATGGTAGCTGCATCCACCTAGCCTC
TCATATTGCAACTGCCTGACCTCTGCCACCCCACGAGCCACTTATCCCCACTTATAATCA
GCCCATTTCGATTGTAACATCTGCCACTTATTCCCGACGTTGTGGTATATCCTATAGATG
AATTCATTCAACATCCATTCCAACACCACCTCTCTTGCCTTCCTATACTCTCTGGAGAGT
GAATTACTGAGTCACATGATCTTCACTGCAGTCATTTGTGGCTATGTGACATAGTTCTGG
ACAGTGAACATAGACAGAAGTCCCTGGGGCGGGCTTCCTTTCTGGGATGAGGGCAAAACG
```

*FIG. 22C*

```
GATCTCTTGATCCCAGGAGGTCAAGGCTGCAATGAGCTAAGATCAAGCCACTGCATTCCA
GCCTGAGTGATAGTGGGAGACCTTGTCTTTAAAACACACACACACACACACACACACACG
AGGGCCTTTGACCACTCTTGAGTAGAAGACTCGAGAAGAACAAAGTAGAAGGCCAGAGAA
GAACAAAGTTACTTGAAAGATCTCTTATTAAAGAGAATGTACAAGCTATGAAAAAAAAAA
AACACACACACACACACAAACCTCATCTGGAATGAAAAAAACATAATGCATTTGGTTTCT
GGTTCCTTAGGCTGTTATGGAACAACCAAAGAACATTATTTTGGTTTCTGAGGTCAGAAC
TATTTTATTCCCCTCAAGCACACTATGCTTATGGTTTGAGGGAGAATGAGAAATAGGAAA
CTAGGAACAGGCTGAAATGGTCTAATCTTGACCATCTAATTCTGCAGTGTCTTATTCTCA
TTCTAAAAGAGAATGGTTATATTCGCTGTTCTAGCATAAAAAGTAATGATAAAAATAAAA
GATCCCGTATTACCAGACAATAATCCCCTAGACTGTTTTAATGCTTGGTTGAGTATTTGC
TTATGATCTCAGACTTTAAAAGATGGTCTCCCCTATGGTGAAGCTTGTTAATTATGTAG
GCATCATTAATGTCTGTTTACTTATCAAAATTTTATCATTGTTAGTTGTATTACTACTTG
ACAGTCCAATTTATTTAATTGAAAGATTGGTTAACATTTTATAGTCAAAGTAATTGTTT
CCTGTGTTTTTTCCTGTTTAGGTTATTGGAGTGATGAGTAAAGAATACATACCAAAGGGC
ACACGTTTTGGACCCCTAATAGGTGAAATCTACACCAATGACACAGTTCCTAAGAACGCC
AACAGGAAATATTTTTGGAGGGTAAGTAAGGGAAATTTCTTCAGACCCATTAAATGTTAG
GAAAAAATGGAGCTAAAAGAGCTGGGTGGCTCACCTTTCTCATCCTGTGCTGAGAAATGC
TGGGGCTCACCCATAAGTATCCAGCATCCCCATGGACACAGGGAATTCTGAACAAATGTG
ATGAAACCGATGAAATGTCTGGCCTGTAGGTGGTTAGTGATGGAGATACGGGCTATATGT
GAATCTTGATTTTTGCAATTCATTAGAGCTTTGTAATGAAAGGAAACAGTTTGTTGCTTG
CTTTAAGGATAGGTTCATTTGCATTTCTCCGCAAGGAAGTAGTAATGAGTTACCAAGCCT
TAGATTTCACCCCTTTTTGATTTCTTGCTGACTTAACTTTAATTGAATGGAAGAGTTATC
ACAAATGAATTATCTTTTTGGTTTTTTTTTTTGAGATGGAGTCTCACTCTGTCACCAG
GCTGGAGTGCAATGGCATGATCTCGGCTCACTGCAACCTCCGCCTCCCAGGTTCAAGCAA
TTGTCCTGCCTCAGCCTCCCGAGTAGCTGGGACTAAGGTGCGCGCCACCATGCCCAGTTA
ATTTTTGTATTTTTAGTAGAGACGGGGTTCCACTATGTTGGCCATGATGGTCTCGATCTC
TGGACCTCGTGATCCGCCCACCTTGGCCTCCCAAAGTGCTGGAATTACAGGCAAGAGCCA
CCGCGCCCAGCCAGGAATGACAAATGAATTACCTTATAAGTAAATGCCATTAAGGAAGGA
TAGCTGGAAGATGGGTTGAGGGGAATGGAGGACCACAGAACTAGTCCTATTTAAATACAT
GTGCATGGTAAAATGATTCCATTTGACAATAGGTTAATTATCTCATAGCATAAGGAAAAT
GCTTAACAGTCATATGCAAGATGATAAGCTTTCCTATAGCATCCAACCAAAAGATCTAGC
CAGTACAATTTCCTTTGCTATATTAGGGTTAGAAAGGCCCCAGAGGTGAACCAATTAGA
TGGAATCCTTGAATAAAACACTGGATTAGCAGTGAACAGAAAAAAGTCAGATTGCTTTCC
TTCTTCCCATAGATGTCTCAGGGATATTTAGTTTCCTCAGAAGATAAAGAATTTAGTAAG
CGTTTTTTGTGCATACTTACATGAAATGTACATTATTTGAATTCTTTAAAAAGAAACAG
CTGCATGATAACAAAATTGTGTTATGCTTGCTTTAGCTGGTATTTTGCCTAGAACGAT
TATATCGTTCGGACAAGAAGCTATTCCTAAGAAACAATATTTTAATCCAGGAAGTTTTT
CATTTTTAGAAATTTATCTTACTATTTCCCAAGCAAAAGAGGGTAGTTACAGATTCACTA
AGAATCATGTGCTCACAATTTTTATTTAATAATTATTCCTCCTTAAAATATATTAATCAC
CTGACTTACAATGGTGGAACCATGAGTGCATTTTTGCCTTTATTGTCAATAACGTCTTCT
CAGAAGTGAGCCACAAAGGTGCATAGTTCTTGGAGTTAAAGGTCTGAATTAAGACAATCC
AGCATAAGTCTCATTAATGTGTGATTATTTTGAGAAAAGGCAAGAAGTACCTAAGAATCT
CCCCGCTCACTGTCCAGTTCCCTGTTTCATTTAAAGATTCACTGTAAGTAACTGAAAGGCT
TTCCTTGGGAGGATTTATTTGAATCAGTCTTTCACATGCAAAGGATATTGTAGAACATCT
CGTTTTTGCTGGCAGGAATATGAACATCTGTTGTGAGGAAAGAAAAAGTTTCATGCAAAT
TACACTGCCAAAGAAGGGATGTTCAAGTTGAGAAACCAGTGACATTTCTTGTAACTGTAC
TATGAATCAGCGCATTTTAATCTTCTAGATAATATATGGAAGTGCAGGAAGGTGGTAGGA
AACGGTGTTCATTTTACATATGCGTTATTTTATTCTGTGTGAGTGACTTCATGGCACCGA
CATTGCTGTTTTTAAATGAGGATACAGTAAATTGCAGTCCGAGGAAGGCTAACTGGAATC
AACATACCCGTAGCTTTAGAAAGCAGTTTCCGCACCAGCGAAGAGTACAAGAGCGATGGA
ACCCCATGTTCCTGGAAGTTTGCACATCAGAGTAAACAAACTTGAAAACCCCTCTTGATA
```

*FIG. 23A*

```
GCAGAATTCACCCAGCCTTGTTCCATTTTCTCTTAACAAAACACACCGCAAAGCTCTCA
CAAGCTGCTTTGATGAAGCCACATGTATTTCCCCCTTCACAATTTACAGGAAGTTACTCT
TAAAAGAAAGTGATTCTGGTGTTTACCGCCTGTGTTAAAGGGACAGAGTTCCTTTTTATT
TCTGATAACGTTTGAGCGAAATACAGAAACTATCTGTAGACTAGCATAGTCGGTACGTGA
GTAAGGAAAAGCAATAACCTGCTGTCCGGTGAGCACAAAATTCCTGCTACGAACAGTGCC
TTACTGCTGCTTGGAGACTGCAAGTCGCAGATCACACTAGGTATTGACTGATTGTATAAG
GAAATTTCTTAAAGTCTAAAGTAAAGGTGGTACCTCCTAAAAAGAGGGGAAGAGAGAAAA
CTTTGTGTGGAAGGATAAGGAGTGTGTTTATAGTTTCACTAAGAGTGTACGTTTTAATTT
TTCTTCTTCCTCTGCCTCTTTGCCAAGTAGCCTGAGTGCATCTGTTATCCAGAAGTAGTA
TTACTCTAGGACAAACTTCAAATTCTTCATTCTGCGTTGCCTTTAAGGAACAACATACTT
TCTTCCTGTTCTTTTTCCAAAAACACACGCCTATGGCTCTGTGTGTGGTGTTTTAGCCAG
CCTCCTCCCAGATAAGGGGTTCCCTTCCCTCCTTTGCATTGAAAGGAAAGTGCAAGTCTG
GACATGTTTATCAAGAGGAAAAGTGACTTCTCAGTAATAGACTGTCAAATTCGGGCTGCT
GCCCGAGTGTTCGCTTTGTTATGGCAGGTGAAGTTCACCTTTGCCCCACCCAGTGTTTCC
ACAAAAAGGCAAGGTTCCAAGTATTCATATGAACAAGTGTTACTTTAGGACTTGGAGGGT
TGGGGGTGGAGGATGTTTGCATAGTTGAAGCCTTGGGCGGGGGTGTAGGAAACGGCGAGT
ACAGAGGCCATAGAAAAAGCTAAGACTCAGTTTGACGTCGTCAGCCGGCTTGGTCTTCTA
CCCAGTGACTCAAAGCACTAAAAGTCAGCATAATCGGAACTGAAGTCAGTAGCATCGCCC
ATTTGCCATTCACTGCAGTAGCAAAAGTAGTACTCTGTGGTGGGTTAATCGGTTTGAGGC
AGCTCCTTAAATGAACATTTGTGTTTCATTTTTCTGTTATTTTCCCGAACATGAAAAGAC
GATAAAACTGAAATGGAAAAGGTAACTGACAAAAGTGTGCCTTACCTGTTTCCGCCCTGA
TTTCTGCTGATTCAAGACTATTCTGGCTAAACTGATTGGATTCTTTTTCTAACTAGGCAG
TAGGGGATCAGAAATCACACACGGTACCGGCTGTGTTTATTCTGAGAGGTGCTGGGGAGC
TTTGGGTCTGACTTCCTTTTACATGCCTGTCTTCTCTTTTGGACAGATCTATTCCAGAGG
GGAGCTTCACCACTTCATTGACGGCTTTAATGAAGAGAAAAGCAACTGGATGCGCTATGT
GAATCCAGCACACTCTCCCCGGGAGCAAAACCTGGCTGCGTGTCAGAACGGGATGAACAT
CTACTTCTACACCATTAAGCCCATCCCTGCCAACCAGGAACTTCTTGTGTGGTATTGTCG
GGACTTTGCAGAAAGGCTTCACTACCCTTATCCCGGAGAGCTGACAATGATGAATCTCAG
TAAGTGGATTACAGAACAAAAAAATAAAAATGCCAGTAATGTCGGTTCTGCCCCTTTGA
ACTAATAACATGTTGTTTAATTATACGGCTTTGTCATGTGTTGGATGAAGTAGGTGGCTT
AAGCTAGGGACTAGGAAGAGGAAAAACATTTTTTGAGTCCCTATTAACTATTAGGAAACT
TGATCATTTAAAAGTATATATATATATGAGGAGCTACCTTGAGTTTTGAATTCAGGATGT
TACAGGAAGAAATATATGTCCAATTCTAATTTATCCAAAAGCAGTTGGGAGAATTACAGG
GATTGGTCCAGACATGCTGCGTATGCAAGGTATAGCCCTCATCTGTGGTACTTTGGCAGG
GCTTAGACTGCATCAAAATATTTATAGATGTACATTTGAGTGTACAGTTAGGATCTGATG
TGGAACATTGTAAGATCATTGCTAGAAAAACTTTGTCATAATTTTTCAATATTATTCTAA
GTGAATAACCGTAAAGATTTTACATCTTAGCTTCCTTCCTTACAGTAAAAAAACTATCTG
ATCTCTTGATCAGTATTATAGTAGCCACCTATCACTTTATCTTAACAAATTCTCAATTCC
TTAGGTTTATGTGCTTTTACTTCTTTTATTTGATTAAAATTGCTGTCATGACCTCTCTCT
GCAGAGGGCTGCATCATTTTGGTCATTCTCAAGTGATCTCTTTGAGCAATTTAAGAATTG
CCATAAGATTCTAACCTCTGCTGTAACTATGGTTGTGTGTTCTTGGTTAGACCACTAAAT
CTTATTAGCAGTTTTAAAAATTATTCCTTTTGGTTTAGAAGTTAAGACTAAATGCTGAAG
TTTTTGTAACTTTTGGTTTTGATATCATTTCAAACTTAAGAAAACATTTGAAGAAAAGGA
CAAAGAATTTCCACTTACCCTTTACCCAGGTTTACCAGTTATTGATAAGTATATCCATTT
GCTTTACCAGAAGGCTAACTTGTTTTAGTTCTCATTTTCACCTTTGAGACATTTGGAATA
AATATCAATGTTAACATAAATTGGAATTTTGACTTTGATTTTAGGACCAATGAACAAGCC
AAGTACTTACCCTAGTCATATATAATCCAACTGTATGGTTATTTGGTATTCATTCCACAC
TTCATTTTACTTGATCTCCCTTAAGATTGCAAGATTGTGTTTGCAGTTTTTCTGAAAAATC
TGGGGCTATAAAAGCATCAGGACCTCCCCCGTAGGGGAGGTCGTGTGTTTGGGGTCCTTA
CACAACAGGTTACCCTTGAGCTTCAGGAAAAGAACTGGCTCTCAGTTCCCCAGTTCCAGC
TTAATGGGTCTAATTAGGTCCTGACCAAAAGGTGGCAGTTCTTTTCCCTCATGTCTCTT
CAGCGCTCCCCGAGACTCTGGAGACTCTGTCATATCCCTAGGGCTGAGCCTCCCAGGAAC
CATTCGGCTGTTGTGGCATCTGTGTATGCCATGCCCAGTGCTGAGGACCTAGTAACAAAC
```

*FIG. 23B*

```
GACAAATGCACAGGCACAGTGGCATTTTTGTGGAACTCGTATTCCAGCTGTGCGTCTCAG
AAGAAGCGCACAGCTCCTCCTGGCTTTCTTAACATAGTGAGCCACTTCCACTTAAGGGT
CTCCTTACATTCCTTGAGTTTAATCATTCATGGATTCAGAGGAAAGTCTTTTGATTTTTG
CTTTTCTTTAAACAGTTCATTTGAGGTGACCTACCCCAGTGACTTTGCACCAACCACCAA
GAAACTTTTTTGCATGCTTCCCGCACCCTGTGCCAATCAAGGGAAGGGTTTAAAGGCCTG
GCGTTTTATTCCTCAAAGAAAGGTTTTGCACAGTATTTTAAGGTTCAAGTGCTTCTACT
TTGTGTTCAGAAGCAACTGTCATATATACTGTGAAATGACACCTTTTATTTATCCCTTTT
TATTTATGCAGTATGTCCCCTTTTATTTTGGCAGAATTTTTTCTAAATGGTGGTTTAACA
TTTTCAAGCACATTTCATTGTCCAATATTCATAGTAAAGAATGAGAGTTAACAATAACCA
GTCACATTAAAACAAGATTCCTGCTGCCAGTTGTGAAACCGGTTGTCTTAGGCGTGGCAG
CTGATGATTGAGACTGTGATCAGGAAAATTTCCACTATTTCATCAGGCCTAATAGGTAGA
TTGTGTCTCCAAATGAACTGTGTTGGTTTCCATGCTTAAAGCACAATAGAGGTGGTGCA
AGAATCTCCATGAGGGCTTAAATGGCAGTGATGGTTCAGGCGGTAGAGTTTGGAGAAGAA
GGGATTTGAAACAAACCAAAGGAAAGAAAAGTAAGTAGCCAGAAATCACAAAATGGCATT
TTTCTAAAAACAAAGGAAAAGGAATAAAAGAACTAATAAGTTTGAAACCCCTACCCCTCC
CAAATTTGGCAGGGGGGAGGTATTTTTTTTCTATCTATCTAACTAACCCATCTAGAAAA
CAGTTGACCAAATTATAGACTTCTAAATGTTAATCTGCTTTCTCAGTTTCAGTTGAAAAG
AGACTTTGTTTTGCCTACTGCAGAACTTCTAGGTTCTTTCTTATAGTCTTGGGGTTCTTA
TTATAGATCGAAAATGTGAGTCGGCATAATTAAGCCATTCGGAGTCTTCAGAAGCAGTTC
ACTCTTGAAATGACTCCGTCCGCCTACAGCCATTTAAGATTTCAGAACAAAAACAGATCT
TGATTTTCTTTTTCATGTTAACTCAAGCTGTTGCTGAGTGGGAGAGTCAGAAATGACACC
AGCTCCACTGATTACTCAGCTGCTGAAGGATGATTTTTTAAAATGCACCTTTACTGTATA
TGGACTTCCTAATTTCCACCTGTAGAGCATCTTAGGGAGGCTAACATGTCACTCTGGATG
TTCTTTTAGAATAAGATGCAAATCTATTTTTCTGAAGGCATTAGAGATAGCAAACATTTA
TTGTGAGTTTACTATATACTAGGCACTGTGCTAAGTGTTTTGCATAGAAAGTTTAAAATT
CTGGCTTTTTTGTTGGCCCAATCATAAGTTTCATATCAGTTCAACATTCAAATTATATTA
AGGTACTTAAGAAGAATCCCTGGCTAAATGTGAGGGGCAGTGCCACAGATGGACTGAAAC
TTTATGCTTATTGCACATTTATGCTATTATTATTTGTTGAATTATAGAACCAAGGGAGTG
TGGAAGCCACTGGAAAAAATATGAGACTTAGATACATAATTTGAGTAAAAATGGCTCAAA
GTCATGAGGGTAAAGTTTTTTGTATTTCCATTTTATTCGAGCGGCATCGTTTTTAAAAAT
CATTATGAATTTGACCCTATATAGATGTTTCAAATAATTCTTTTTCACCTTCATAAAAT
TCCTTCCTGTGGCTGTGAGATGCCTTGCCTATCAGTTTTCAAGCTTAGTTGTCTTTCTCA
TCCTTTACCATTTTAGCTTTAAAAAACAAAAGTGACAATTAGAACTTCCTGCCTGCTGGG
CCTCACTGAAAGACCGATATTGGCCTGATAAGGAGATATTTATTTTGTTTTAGTGGCTTC
AGAAATCCCTCTCCCTCAGCAAGCTTTCCATCACGGCCCCCCCGTCAGCATCTTCCCTGA
TAGCGTTCTTCTCTGTGTTTATTCTGGGGCTTCAGGCTCGCCCAGGAGGAACTGATAACC
GCTGGCAGGAGATAACATTCTCTAAGGGGCTCTCAAATTGGAATCGAATCCCTCAAGCCA
GTCAGCCTAGAGAATACATTTAAAGGGTTCAGTTCTGGAGTTTCACAGAGTTCATTTCTA
GACCTATCAGATAGCAAGTGTGGAGTTCTTTCTCAACTAAATTCAAGCAGAGACATTTTT
TAGACGATGAAGGATATTTGCACAAAGGCTTCAGCATGATCCCCCAAACCTGCTGCCTCT
GAAGGCATCTCCACACATTGACAGCCAATGCCTTCAGTGCGTTCCTAGGGCAGGTGTCCT
GGCTTGAGTGACTGTCCTCCAATAATCAGAGCTCAAACTAAACATCGTATGTTTTACTTT
TGGTTTCCAGGCAAGGCTGAGCAGGAATTTTCAGTTTTCCCTGCCCAGATGGGTGTTTT
TTCCTGAAGGCATCATTTATTGTGTAGCGAGGAGACAGGGCTGGCTGTGGCAGGGATAGT
CTAGAACTGTCCTCATTGCTGCTGTTCCTAAATAGTATCTTTACCAAGTAATAACGTGCC
GTCTTTGGGAATAAGTGCTTTCCTCTTAGCCTGTTCTGTTTTCTTGGGTGCGCTAAGTAA
TTGAACTGGCTCAGGAAGTACCTATTGTGGTTTGGCAGAGGTGACTGTCACGCCTTGTGA
CTCCAGGGGCCAGCACTGCTGGGATCCTGGCTAGACCAGACAGAGCCTTGGTGAAGTGCT
TAGGCTGTCTGCACATCGCGAGGAAGGTGGTATTCACTTCGCTAAGCTCCTTGGCATAGG
CAGTTTGAACAGGGCTTTATCAAATTCGTATTCAACAAGAGTAGAAGCGAAAATTGATGA
CTGTGTATTACTTGAAATGAGTCTTAATCTTTCACATTTAGTTCTCAGGGTATGCTGATT
TCCTTTAGGTAAACCATGAACATCAGAAAGACTTTTATTAACCTATGACAGGGTCCCCAC
```

*FIG. 23C*

```
CCCAGTATTTTTCCACTCCATTAAAATGGAAGTTTTTTTTTTTTTTTCTTTTTGAGAC
AGAGTTTTGCTCTTGTTGCCCAGTCTGGAGTGCAATGGCACAATCTCGGCTCACCACAAC
CTCCACCTCCCAGATTCAAGCGATTCTTCTGCCTCAGCCTCCAAGTAGCTGGGATTACA
GGTGTGCGCCACCACGCCCAGCTAATTTTGTATTTTTAGTAGAGATGGGGTTTCTCCATG
TTGGTCAGGCTGGTCTCGAACTTCCGACCTCAGGTGATCCGCCCACCTCGGCCTCCCAAA
GTGCTGGGATTACAGGCAAGAGCCACTGCATCCAGCTTAGGCTATCTTACTCCAGCCTAA
ACAGCAATTTTCTATCATAAGGTCTGTACTAATGAAAACAGAATCACCCAAGGCTGCTGT
TTGTTCTGTCTGTGCTGCCATTGTCCGCATTTTGCTGAGGAGGAAACGGAACTGCACTTT
TGAGTGAGTGGCCCAGAGCCTTCTAGAATGAGAGTGCGTTGGAAGCAGATATGTGGCGA
TTGTGTCGCCAGCTGTTACTCAGGTTTTCTCAAGAAGGAGGAGCAACTTTGGCAGTTTTG
CTTCAGTTCTCTCTAGCCCTCTGTGTAATCGCCCCTTTTTCTTTATTTCAGCACAAACAC
AGAGCAGTCTAAAGCAACCGAGCACTGAGAAAATGAACTCTGCCCAAAGAATGTCCCAA
AGAGAGAGTACAGCGTGAAAGAAATCCTAAATTGGACTCCAACCCCTCCAAAGGAAAGG
ACCTCTACCGTTCTAACATTTCACCCCTCACATCAGAAAAGGACCTCGATGACTTTAGAA
GACGTGGGAGCCCCGAAATGCCCTTCTACCCTCGGGTCGTTTACCCCATCCGGGCCCCTC
TGCCAGAAGACTTTTGAAAGCTTCCCTGGCCTACGGGATCGAGAGACCCACGTACATCA
CTCGCTCCCCATTCCATCCTCCACCACTCCAAGCCCTCTGCAAGAAGCAGCCCCGACC
AAAGCCTCAAGAGCTCCAGCCCTCACAGCAGCCCTGGGAATACGGTGTCCCCTGTGGGCC
CCGGCTCTCAAGAGCACCGGGACTCCTACGCTTACTTGAACGCGTCCTACGCACGGAAG
GTTTGGGCTCCTACCCTGGCTACGCACCCCTGCCCCACCTCCCGCCAGCTTTCATCCCCT
CGTACAACGCTCACTACCCCAAGTTCCTCTTGCCCCCCTACGGCATGAATTGTAATGGCC
TGAGCGCTGTGAGCAGCATGAATGGCATCAACAACTTTGGCCTCTTCCCGAGGCTGTGCC
CTGTCTACAGCAATCTCCTCGGTGGGGCAGCCTGCCCCACCCCATGCTCAACCCCACTT
CTCTCCCGAGCTCGCTGCCCTCAGATGGAGCCCGGAGGTTGCTCCAGCCGGAGCATCCCA
GGGAGGTGCTTGTCCCGGCGCCCCACAGTGCCTTCTCCTTTACCGGGGCCGCCGCCAGCA
TGAAGGACAAGGCCTGTAGCCCCACAAGCGGGTCTCCCACGGCGGGAACAGCCGCCACGG
CAGAACATGTGGTGCAGCCCAAAGCTACCTCAGCAGCGATGGCAGCCCCAGCAGCGACG
AAGCCATGAATCTCATTAAAAACAAAAGAAACATGACCGGCTACAAGACCCTTCCCTACC
CGCTGAAGAAGCAGAACGGCAAGATCAAGTACGAATGCAACGTTTGCGCCAAGACTTTCG
GCCAGCTCTCCAATCTGAAGGTAGGCCTTGAGAGAGAGCAGTCCAAGGGGCTGTGAGTGC
ATGCTTGTGTTTGTATTTAGCTTGCTTTCCATGGGGTATCGATTGCATTTGCAGTAGTAT
GAGCCCCGGTTGGGGATAGTGGGTATGGATTCCGCCTGGCTTTTGCCACTTCTAGCTCT
TTGACTTTGGACAAGTGACTTCCCTTCTCCTGATTTTCTTCTGAATAATAAAAAAATTAG
GGGTTTGGACTAGAAGATTAGGTGAAACTCCCTGCTAGCCTGTGATTTTTGTGCTTTTAA
GAAAAACACCATTCTGAAAACATGAAGATTTCTTCTTTTTAAGACTGTCTTGATGCTTTT
CTTAAGATATTTGCATCAACACTTGAGTCTTGGAGCAGAAATGTTAGGTCTCAGAGCCAG
CTTGAGAGCAGAGCTAACACATGTGGCTTCTTCCCAGGTCCACCTGAGAGTGCACAGTGG
AGAACGGCCTTTCAAATGTCAGACTTGCAACAAGGGCTTTACTCAGCTCGCCCACCTGCA
GAAACACTACCTGGTACACACGGGAGAAAAGCCACATGAATGCCAGGTGCGCAGTATTTT
CTGGGTAGACCTTCTGACCTTTGTAGAAAATGTCTGTGAGTCACCCTCCCATGTCCTATA
TAGCCCGTAGTTAAAGCCAACACCAGATTCTGCGTTGTCCCATCCTGGACTGATGGCACT
ATGGTCCTTCCCAGTACTTTGTATCTGCTGATGACTTGAGATGGCACAGCCAGCTTCCAG
TGGGTGGAAAATGGTAGGGAAATAAACAGCCCTCGTGTGCTGTGTGCCCACATCCCC
CCGTTTGCTTAATACCACACTGGAGGTGCCACAAGGAGGCTTCTCACCTCCTAGGTTGCT
GGGCGTTGGCCGGTAAGCCTGCCCCTCCCGTTGGCAACTCTTAATCTTCTGGCCTTCCTG
TCTCCCTTCCCTGCTGTCTCTCTCCCTACACTGTAGGTCTGCCACAAGAGATTTAGCAG
CACCAGCAATCTCAAGACCCACCTGCGACTCCATTCTGGAGAGAAACCATACCAATGCAA
GGTGTGCCCTGCCAAGTTCACCCAGTTTGTGCACCTGAAACTGCACAAGCGTCTGCACAC
CCGGGAGCGGCCCCACAAGTGCTCCCAGTGCCACAAGAACTACATCCATCTCTGTAGCCT
CAAGGTTCACCTGAAAGGGAACTGCGCTGCGGCCCCGGCGCCTGGGCTGCCCTTGGAAGA
TCTGACCCGAATCAATGAAGAAATCGAGAAGTTTGACATCAGTGACAATGCTGACCGGCT
CGAGGACGTGGAGGATGACATCAGTGTGATCTCTGTAGTGGAGAAGGAAATTCTGGCCGT
```

*FIG. 23D*

```
GGTCAGAAAAGAGAAAGAAGAAACTGGCCTGAAAGTGTCTTTGCAAAGAAACATGGGGAA
TGGACTCCTCTCCTCAGGGTGCAGCCTTTATGAGTCATCAGATCTACCCCTCATGAAGTT
GCCTCCCAGCAACCCACTACCTCTGGTACCTGTAAGGTCAAACAAGAAACAGTTGAACC
AATGGATCCTTAAGATTTTCAGAAAACACTTATTTTGTTTCTTAAGTTATGACTTGGTGA
GTCAGGGTGCCTGTAGGAAGTGGCTTGTACATAATCCCAGCTCTGCAAAGCTCTCTCGAC
AGCAAATGGTTTCCCCTCACCTCTGGAATTAAAGAAGGAACTCCAAAGTTACTGAAATCT
CAGGGCATGAACAAGGCAAAGGCCATATATATATATATATATATCTGTATACATATTA
TATATACTTATTTACACCTGTGTCTATATATTTGCCCCTGTGTATTTTGAATATTTGTGT
GGACATGTTTGCATAGCCTTCCCATTACTAAGACTATTACCTAGTCATAATTATTTTTTC
AATGATAATCCTTCATAATTTATTATACAATTTATCATTCAGAAAGCAATAATTAAAAAA
GTTTACAATGACTGGAAAGATTCCTTGTAATTTGAGTATAAATGTATTTTGTCTTGTGG
CCATTCTTTGTAGATAATTTCTGCACATCTGTATAAGTACCTAAGATTTAGTTAAACAAA
TATATGACTTCAGTCAACCTCTCTCTCTAATAATGGTTTGAAAATGAGGTTTGGGTAATT
GCCAATGTTGGACAGTTGATGTGTTCATTCCTGGATCCTATCATTTGAACAGCATTGTA
CATAACTTGGGGGTATGTGTGCAGGATTACCCAAGAATAACTTAAGTAGAAGAAACAAGA
AAGGGAATCTTGTATATTTTGTTGATAGTTCATGTTTTCCCCAGCCACAATTTTACC
GGAAGGGTGACAGGAAGGCTTTACCAACCTGTCTCTCCCTCCAAAAGAGCAGAATCCTCC
CACCGCCCTGCCCTCCCCACCGAGTCCTGTGGCCATTCAGAGCGGCCACATGACTTTTGC
ATCCATTGTATTATCAGAAAATGTGAAGAAGAAAAAATGCCATGTTTTAAAACCACTGC
GAAAATTTCCCCAAAGCATAGGTGGCTTTGTGTGTGTGCGATTTGGGGGCTTGAGTCTGG
GTGGTGTTTGTTGTTGGTTTTTGTTGCTTTTTTTTTTTTTTTTTTTAATGTCAAAAT
TGCACAAACATGGTGCTCTACCAGGAAGGATTCGAGGTAGATAGGCTCAGGCCACACTTT
AAAAACAAACACACAAACAACAAAAAACGGGTATTCTAGTCATCTTGGGGTAAAAGCGGG
TAATGAACATTCCTATCCCCAACACATCAATTGTATTTTTTCTGTAAAACTCAGATTTTC
CTCAGTATTTGTGTTTTACATTTATGGTTAATTTAATGGAAGATGAAAGGGCATTGCA
AAGTTGTTCAACAACAGTTACCTCATTGAGTGTGTCCAGTAGTGCAGGAAATGATGTCTT
ATCTAATGATTTGCTTCTCTAGAGGAGAAACCGAGTAAATGTGCTCCAGCAAGATAGACT
TTGTGTTATTCTATCTTTTATTCTGCTAAGCCCAAAGATTACATGTTGGTGTTCAAAGTG
TAGCAAAAAATGATGTATATTTATAAATCTATTTATACCACTATATCATATGTATATATA
TTTATAACCACTTAAATTGTGAGCCAAGCCATGTAAAAGATCTACTTTTTCTAAGGGCAA
AAAAAAAAAAAAAAAAAAAGAACACTCCTTTCTGAGACTTTGCTTAATACTTGGTGACC
TCACAATCACGTCGGTATGATTGGGCACCCTTGCCTACTGTAAGAGACCCTAAAACCTTG
GTGCAGTGGTGGGGACCACAAAACAACCAGGGAGGAAGAGATACATCATTTTTTAGTATT
AAGGACCATCTAAGACAGCTCTATTTTTTTTTGCCACTTTATGATTATGTGGTCACACC
CAAGTCACAGAAATAAAAAACTGACTTTACCGCTGCAATTTTTCTGTTTCCTCCTTACT
AAATACTGATACATTACTCCAATCTATTTTATAATTATATTTGACATTTTGTTCACATCA
ACTAATGTTCACCTGTAGAAGAGAACAAATTTCGAATAATCCAGGGAAACCCAAGAGCCT
TACTGGTCTTCTGTAACTTCCAAGACTGACAGCTTTTTATGTATCAGTGTTTGATAAACA
CAGTCCTTAACTGAAGGTAAACCAAAGCATCACGTTGACATTAGACCAAATACTTTTGAT
TCCCAACTACTCGTTTGTTCTTTTCTCCTTTTGTGCTTTCCCATAGTGAGAATTTTTAT
AAAGACTTCTTGCTTCTCTCACCATCCATCCTTCTCTTTTCTGCCTCTTACATGTGAATG
TTGAGCCCACAATCAACAGTGGTTTTATTTTTTCCTCTACTCAAAGTTAAAACTGACCAA
```

*FIG. 23E*

```
GTCTGGACTTGTGGTGCGCTGCCAGGGATCCGCAGCGTTGCCGGTTGTATTCGCTGGATACCAGAGGGCG
GAAGTGCAGCAGGGTTCAGCTCCGACCTCCGCGCCGGTGCTTTTTGCGGCTGCGCGGGCTTCCTGGAGTC
CTGCTACCGCGTCCCCGCAGGACAGTGTGTCAGGCGGGCAGCTTGCCCCGCCGCCCCACCGGAGCGCGGA
ATCTGGGCGTCCCCACCAGTGCGGGGAGCCGGAAGGAGGAGCCATAGCTTGGAGTAGGTTTGGCTTTGGT
TGAAATAAGAATTTAGCCTGTATGTACTGCTTTAACTCCTGGAAGAATGACAGATGACAAAGATGTGCTT
CGAGATGTGTGGTTTGGACGAATTCCAACTTGTTTCACGCTATATCAGGATGAGATAACTGAAAGGGAAG
CAGAACCATACTATTTGCTTTTGCCAAGAGTAAGTTATTTGACGTTGGTAACTGACAAAGTGAAAAAGCA
CTTTCAGAAGGTTATGAGACAAGAAGACATTAGTGAGATATGGTTTGAATATGAAGGCACACCACTGAAA
TGGCATTATCCAATTGGTTTGCTATTTGATCTTCTTGCATCAAGTTCAGCTCTTCCTTGGAACATCACAG
TACATTTTAAGAGTTTTCCAGAAAAAGACCTTCTGCACTGTCCATCTAAGGATGCAATTGAAGCTCATTT
TATGTCATGTATGAAAGAAGCTGATGCTTTAAAACATAAAAGTCAAGTAATCAATGAAATGCAGAAAAAA
GATCACAAGCAACTCTGGATGGGATTGCAAAATGACAGATTTGACCAGTTTTGGGCCATCAATCGGAAAC
TCATGGAATATCCTGCAGAAGAAAATGGATTTCGTTATATCCCCTTTAGAATATATCAGACAACGACTGA
AAGACCTTTCATTCAGAAGCTGTTTCGTCCTGTGGCTGCAGATGGACAGTTGCACACACTAGGAGATCTC
CTCAAAGAAGTTTGTCCTTCTGCTATTGATCCTGAAGATGGGGAAAAAAAGAATCAAGTGATGATTCATG
GAATTGAGCCAATGTTGGAAACACCTCTGCAGTGGCTGAGTGAACATCTGAGCTACCCGGATAATTTTCT
TCATATTAGTATCATCCCACAGCCAACAGATTGAAGGATCAACTATTTGCCTGAACAGAATCATCCTTAA
ATGGGATTTATCAGAGCATGTCACCCTTTTGCTTCAATCAGGTTTGGTGGAGGCAACCTGACCAGAAACA
CTTCGCTGCTGCAAGCCAGACAGGAAAAAGATTCCATGTCAGATAAGGCAACTGGGCTGGTCTTACTTTG
CATCACCTCTGCTTTCCTCCACTGCCATCATTAAACCTCAGCTGTGACATGAAAGACTTACCGGACCACT
GAAGGTCTTCTGTAAAATATAATGAAGCTGAAACCTTTGGCCTAAGAAGAAAATGGAAGTATGTGCCACT
CGATTTGTATTTCTGATTAACAAATAAACAGGGGTATTTCCTAAGGTGACCATGGTTGAACTTTAGCTCA
TGAAAGTGGAAACATTGGTTTAATTTTCAAGAGAATTAAGAAAGTAAAGAGAAATTCTGTTATCAATAA
CTTGCAAGTAATTTTTTGTAAAAGATTGAATTACAGTAAACCCATCTTTCCTTAACGAAAATTTCCTATG
TTTACAGTCTGTCTATTGGTATGCAATCTTGTAACTTTGATAATGAACAGTGAGAGATTTTAAATAAAG
CCTCTAAATATGTTTTGTCATTTAATAACATACAGTTTTGTCACTTTTCAAGTACTTTCTGACTCACATA
CAGTAGATCACTTTTTACTCTGTGTTACCATTTTGACTGGTCGTCATTGGCATGGGTGGATATAGGGCA
TAGGATTACTTGTCTCAGAAGCTGTCATAGAATTTCTTGCTGCCAATTAAAAAACCTGTGTTCTTACAC
ACTACACGTATAAATATTGTAACTGTTCATCTTTGTTGTTTATCACTGTAAGCCTGTCAAATCATAGTA
TCCTAAGCATCTGTAAATGCTAATTTTGCATTTTGGAAAAACCCATTCCTTCCAAGCTAGTGTTTTCA
TTGGCTCCAGGTCTAATTTTTCACTGTGGTCCCTGGCAGCCAGTCTTTTGAAGTTTAAAGATTACCTGTC
TCTTGACTGCAGTACCTTTTCTTTAATTTTTACCAAAAATATCCAGAGGTTACTGGAGTTCTTATTCAAT
ATAAGGAAAGTTTGCTGCACTTTATTACCAAGCCTCTGGGATTTTACCAGTCAAACATATTTGTGCATTA
CATTTCATTTCTTGTGAGCTAGCTGGCTGTCCATATTGAATGTTGACCCATTTGAGTACGCTAAAAGGCT
TACAGTATCAGACACGATCATGGTTTTAGATCCCATAATAAAAATGRATGTTTTCTTATAAAAATTAT
ACAAATGCTGAAGTGAGATTCTACTATTGTTCATTGCTTCCTTTTCTTTTTCCTTTTGCGATTTTCACTG
ATTAATAGCACATTTCTTCACAAAATTAGATAAAGTTGGTCAAAGACCAGATATTCTGGAATGGAAATTG
TAAAGCTTAATCAAAAAGAATAGCCAGTACAGCATACAATCTCAGAAACTTAGAAGCAAGTAGAAAATAA
TTGGTTGATGTAAACGAAAGTGCCATTTTAGTAAAGGCAGGAAAAAAATAGCAATATTTGAGTTATGTAA
GGATAAAAAATCCACTGACTTGTATTTTTGCACAAGAGGCTGGTCTGAATATGATTGTTCACATTAAGAG
TGTTTATTCGTCGGTTCATTTGGGGATTTTCCCCCTTGATGTTTTGACAGATTGAAGTGAGCTTTAGTG
AGCAAAAGGATCAGAATGCAGGGAACACTAAGCTGTGATGAAGAAAGTGTGGTAAAAAGCCAGAGTAGTT
TTATACAGACAAAACCAGTGTCAGGCCTTTGCAGTAGGCTTGAGTGAACTTCTGATCTAGATTTGAAAGT
AAATTTTATGAAGACATTGCCCATTTTTACTTCCTCATTCATTATTGTACCAGCATCATAGCTTTATTAC
TCTAATCCCAGGTAAGTCAAGCCTACAATGCCCTAGAGGAAGAGTAAAACCAGAAATTCATGCTGGCTTA
AATAATCTATTTTGTTTCTTTTCATTTGAATATTTAAATTTTATGGTTTATTAAAAAATTAAATAAAAA
AGAAAAAAAAAAAAAAAAAAA
```

*FIG. 24*

```
GAATTCCGGGAAGCCAGACGGTTAACACAGACAAAGTGCTGCCGTGACACTCGGCCCTCCAGTGTTGCGG
AGAGGCAAGAGCAGCGACCGCGCACCTGTCCGCCCGGAGCTGGGACGCGCGCCCGGCGGCCGGACGAAG
CGAGGAGGGACCGCCGAGGCTGCCCCCAAGTGTAACTCCAGCACTGTGAGGTTTCAGGGATTGGCAGAGG
GGACCAAGGGACATGAAAATGGACATGGAGGATGCGGATATGACTCTGTGGACAGAGGCTGACTTTGAT
GAGAAGTGTACATACATTGTGAACGACCACCCCTGGGATTCTGGTGCTGATGGCGGTACTTCGGTTCAGG
CGGAGGCATCCTTACCAAGGAATCTGCTTTTCAAGTATGCCACCAACAGTGAAGAGGTTATTGGAGTGAT
GAGTAAAGAATACATACCAAAGGGCACACGTTTTGGACCCCTAATAGGTGAAATCTACACCAATGACACA
GTTCCTAAGAACGCCAACAGGAAATATTTTTGGAGGATCTATTCCAGAGGGGAGCTTCACCACTTCATTG
ACGGCTTTAATGAAGAGAAAAGCAACTGGATGCGCTATGTGAATCCAGCACACTCTCCCCGGGAGCAAAA
CCTGGCTGCGTGTCAGAACGGGATGAACATCTACTTCTACACCATTAAGCCCATCCCTGCCAACCAGGAA
CTTCTTGTGTGGTATTGTCGGGACTTTGCAGAAAGGCTTCACTACCCTTATCCCGGAGAGCTGACAATGA
TGAATCTCACACAAACACAGAGCAGTCTAAAGCAACCGAGCACTGAGAAAAATGAACTCTGCCCAAAGAA
TGTCCCAAAGAGAGAGTACAGCGTGAAAGAAATCCTAAAATTGGACTCCAACCCCTCCAAAGGAAAGGAC
CTCTACCGTTCTAACATTTCACCCCTCACATCAGAAAAGGACCTCGATGACTTTAGAAGACGTGGGAGCC
CCGAAATGCCCTTCTACCCTCGGGTCGTTTACCCCATCCGGGCCCCTCTGCCAGAAGACTTTTTGAAAGC
TTCCCTGGCCTACGGGATCGAGAGACCCACGTACATCACTCGCTCCCCCATTCCATCCTCCACCACTCCA
AGCCCCTCTGCAAGAAGCAGCCCCGACCAAAGCCTCAAGAGCTCCAGCCCTCACAGCAGCCCTGGGAATA
CGGTGTCCCTGTGGGCCCCGGCTCTCAAGAGCACCGGCACTCCTACGCTTACTTGAACGCGTCCTACGG
CACGGAAGGTTTGGGCTCCTACCCTGGCTACGCACCCCTGCCCCACCTCCCGCCAGCTTTCATCCCCTCG
TACAACGCTCACTACCCCAAGTTCCTCTTGCCCCCCTACGGCATGAATTGTAATGGCCTGAGCGCTGTGA
GCAGCATGAATGGCATCAACAACTTTGGCCTCTTCCCGAGGCTGTGCCCTGTCTACAGCAATCTCCTCGG
TGGGGGCAGCCTGCCCCACCCCATGCTCAACCCCACTTCTCTCCCGAGCTCGCTGCCCTCAGATGGAGCC
CGGAGGTTGCTCCAGCCGGAGCATCCCAGGGAGGTGCTTGTCCCGGCGCCCACAGTGCCTTCTCCTTTA
CCGGGGCCGCCGCCAGCATGAAGGACAAGGCCTGTAGCCCCACAAGCGGGTCTCCCACGGCGGAACAGC
CGCCACGGCAGAACATGTGGTGCAGCCCAAAGCTACCTCAGCAGCGATGGCAGCCCCAGCAGCGACGAA
GCCATGAATCTCATTAAAAACAAAGAAACATGACCGGCTACAAGACCCTTCCCTACCCGCTGAAGAAGC
AGAACGGCAAGATCAAGTACGAATGCAACGTTTGCGCCAAGACTTTCGGCCAGCTCTCCAATCTGAAGGT
CCACCTGAGAGTGCACAGTGGAGAACGGCCTTTCAAATGTCAGACTTGCAACAAGGGCTTTACTCAGCTC
GCCCACCTGCAGAAACACTACCTGGTACACACGGGAGAAAAGCCACATGAATGCCAGGTCTGCCACAAGA
GATTTAGCAGCACCAGCAATCTCAAGACCCACCTGCGACTCCATTCTGGAGAGAAACCATACCAATGCAA
GGTGTGCCCTGCCAAGTTCACCCAGTTTGTGCACCTGAAACTGCACAAGCGTCTGCACACCCGGGAGCGG
CCCCACAAGTGCTCCCAGTGCCACAAGAACTACATCCATCTCTGTAGCCTCAAGGTTCACCTGAAAGGGA
ACTGCGCTGCGGCCCCGGCGCCTGGGCTGCCCTTGGAAGATCTGACCCGAATCAATGAAGAAATCGAGAA
GTTTGACATCAGTGACAATGCTGACCGGCTCGAGGACGTGGAGGATGACATCAGTGTGATCTCTGTAGTG
GAGAAGGAAATTCTGGCCGTGGTCAGAAAAGAGAAAGAAGAAACTGGCCTGAAAGTGTCTTTGCAAAGAA
ACATGGGGAATGGACTCCTCTCCTCAGGGTGCAGCCTTTATGAGTCATCAGATCTACCCCTCATGAAGTT
GCCTCCCAGCAACCCACTACCTCTGGTACCTGTAAAGGTCAAACAAGAAACAGTTGAACCAATGGATCCT
TAAGATTTTCAGAAAACACTTATTT
```

*FIG. 25*

```
CGCCGCCTGTGCAGCCGCTGCCGCCGCCGCCGCCGCCGCCGCCGCCGCCGCCGCCGCCGCTGCC
GCCCCGGCTGCCGCGCCGCGCCGCTGCCTCTGCCCGGCCGCCCCGCCGCCGCTGCCGCCGCCGCCCG
CAGCCAGCCAGGCGGGCGGCCCAGCCCGCCTGAGCCCGCAGCGGCTGCCGCCGCAGCGTCGGGTCGCTGG
GTGCGCGGGCTACCGCGGACCGAGCGGACCCGAGTGGGCGACCAGGCGCTTGCCCGCCCAGTGCCACTGC
CGCCGCTTCCTCGCCGGAGCACAGGACCAGACACCTCCAGCGCCCGCTGCTGCCGATGCGGCCCGGA
CACTTTTAGCTGGGCGGGAGGGCTGGAGAGCCGGGGCCGCCGAGAACCGCCAGCGAGCTGTGCCGAGAC
CCGCGCCGACCCGCTGCGATCAGGGACAGGCGCCCGCCCGCCGCCGCCCTGGCCGCTATGGATCTATT
CGACTTTTTCAGAGACTGGGACTTGGAGCAGCAGTGTCACTATGAACAAGACCGTAGTGCACTTAAAAAA
AGGGAATGGGAGCGGAGGAATCAAGAAGTCCAGCAAGAAGACGATCTCTTTTCTTCAGGCTTTGATCTTT
TTGGGGAGCCATACAAGGTAGCTGAATATACAAACAAAGGTGATGCACTTGCCAACCGAGTCCAGAACAC
GCTTGGAAACTATGATGAAATGAAGAATTTGCTAACTAACCATTCTAATCAGAATCACCTAGTGGGAATT
CCAAAGAATTCTGTGCCCCAGAATCCCAACAACAAAAATGAACCAAGCTTTTTTCCAGAACAAAAGAACA
GAATAATTCCACCTCACCAGGATAATACCCATCCTTCAGCACCAATGCCTCCACCTTCTGTTGTGATACT
GAATTCAACTCTAATACACAGCAACAGAAAATCAAACCTGAGTGGTCACGTGATAGTCATAACCCTAGC
ACTGTACTGGCAAGCCAGGCCAGTGGTCAGCCAAACAAGATGCAGACTTTGACACAGGACCAGTCTCAAG
CCAAACTGGAAGACTTCTTTGTCTACCCAGCTGAACAGCCCCAGATTGGAGAAGTTGAAGAGTCAAACCC
ATCTGCAAAGGAAGACAGTAACCCTAATTCTAGTGGAGAAGATGCTTTCAAAGAAATCTTTCAATCCAAT
TCACCGGAAGAATCTGAATTCGCCGTGCAAGCGCCTGGGTCTCCCTAGTGGCTTCCTCTTTATTAGCTC
CTAGCAGTGGCCTTTCAGTTCAAAACTTCCCACCAGGGCTTTACTGCAAAACAAGCATGGGGCAGCAAAA
GCCAACTGCATACGTCAGACCCATGGATGGCCAGGACCAGGCACCGGACATCTCACCAACACTGAAACCT
TCAATTGAATTTGAGAACAGCTTTGGGAATCTGTCATTTGGAACACTCTTGGATGGAAAACCCAGTGCAG
CCAGTTCAAAGACTAAACTGCCAAAGTTCACCATCCTCCAAACAAGTGAAGTAAGCCTTCCCAGTGATCC
AAGCTGTGTTGAAGAAATCTTGCGGGAGATGACCCATTCCTGGCCTACTCCTCTCACTTCCATGCATACT
GCTGGACACTCTGAGCAGAGCACCTTTTCCATCCCAGGACAGGAATCGCAGCATCTGACCCCAGGATTCA
CCTTACAAAAGTGGAATGACCCAACCACCAGAGCTTCTACAAAGTCAGTGTCTTTCAAATCGATGCTTGA
GGATGACCTGAAGCTGAGCAGTGATGAAGATGACCTTGAGCCTGTGAAGACCTTGACCACTCAGTGCACT
GCCACTGAGCTCTACCAGGCTGTTGAAAAGGCAAAACCTAGGAATAATCCTGTGAACCCACCCTTGGCCA
CTCCCCAGCCCCACCTGCAGTGCAAGCCAGCGGGGGTTCTGGCAGCTCCAGCGAATCGGAGAGCAGCTC
TGAGTCGGATTCAGACACTGAAAGTAGCACCACTGACAGCGAATCTAATGAGGCACCTCGTGTGGCAACT
CCAGAGCCTGAGCCACCCTCAACCAACAAGTGGCAACTGGATAAATGGCTTAACAAAGTGACATCCCAGA
ACAAGTCTTTTATTTGTGGCCCAAATGAAACACCCATGGAGACTATTTCTCTGCCTCCTCCAATCATCCA
ACCAATGGAAGTCCAGATGAAAGTGAAGACGAATGCCAGTCAGGTCCCAGCTGAACCCAAAGAAAGGCCT
CTCCTCAGTCTCATTAGGGAGAAAGCCCGTCCACGGCCCACTCAGAAAATTCCAGAAACAAAGGCTTTGA
AGCATAAGTTGTCAACAACTAGTGAGACAGTGTCTCAAAGGACAATTGGGAAAAAACAGCCCAAAAAAGT
TGAGAAGAACACCAGCACTGACGAGTTTACCTGGCCCAAACCAAATATTACCAGCAGCACTCCCAAAGAA
AAAGAAAGTGTGGAGCTTCATGACCCACCAAGAGGCCGCAACAAAGCCACTGCCCACAAACCAGCCCCTA
GGAAAGAACCAAGACCTAACATCCCTTTGGCTCCCGAGAAGAAGAAGTACAGAGGGCCTGGCAAGATTGT
GCCAAAGTCTCGGGAATTCATTGAAACAGATTCATCTACATCTGACTCCAACACAGATCAGGAAGAGACC
CTGCAAATCAAAGTCCTGCCTCCGTGCATTATTTCTGGAGGTAATACTGCCAAATCCAAGGAAATCTGTG
GTGCCAGCCTGACCCTCAGCACCTTAATGAGTAGCAGTGGCAGCAACAACAACTTATCCATCAGTAATGA
AGAGCCAACATTTTCACCTATTCCTGTCATGCAAACTGAAATCCTGTCCCCTCTGCGAGATCATGAGAAC
CTGAAAAACCTCTGGGTGAAGATTGACCTTGACTTACTCTCTAGAGTACCTGGCCACAGCTCACTCCATG
CAGCACCTGCCAAGCCAGACCACAAGGAGACTGCCACAAAACCCAAGCGTCAGACAGCTGTCACAGCTGT
GGAGAAACCAGCCCCTAAGGGCAAACGTAAGCACAAGCCAATAGAAGTTGCAGAGAAGATCCCTGAGAAG
AAGCAGCGCCTGGAGGAGGCCACAACTATCTGCTTGCTCCCTCCTTGCATCTCACCAGCCCCACCCCACA
AGCCTCCCAACACTAGAGAAAATAATTCATCCAGGAGAGCAAATAGAAGAAAGGAAGAAAAACTATTTCC
TCCTCCACTTTCCCCACTGCCAGAGGACCCTCCACGCCGCAGAAATGTCAGTGGCAATAATGGTCCCTTT
GGTCAAGACAAAAACATCGCCATGACTGGACAAATCACATCTACCAAACCTAAGAGAACTGAAGGCAAAT
TCTGTGCTACTTTCAAAGGGATATCGGTAAATGAGGAGACACTCCAAAAAAGGCATCCTCTGCCACCAT
CACTGTCACCAATACTGCTATTGCCACTGCTACTGTCACTGCTACTGCCATTGTCACCACCACTGTCACA
```

*FIG. 26A*

```
GCTACTGCCACCGCCACGGCCACCACCACAACTACTACCACTACCATTTCCACCATCACCTCTACCATCA
CTACTGGCCTCATGGATAGCAGTCACCTGGAGATGACGTCCTGGGCGGCTCTGCCCCTTCTATCCAGCAG
CAGCACTAATGTCCGGAGACCCAAGCTCACTTTTGATGACTCGGTTCACAATGCTGATTATTACATGCAA
GAAGCTAAGAAGCTGAAGCACAAAGCTGATGCACTGTTCGAGAAATTTGGCAAAGCTGTGAATTATGCTG
ATGCCGCCCTCTCCTTCACTGAATGTGGCAATGCCATGGAACGCGACCCTCTGGAAGCAAAGTCCCCATA
CACCATGTACTCTGAGACTGTGGAGCTCCTCAGGTATGCAATGAGGCTGAAGAACTTTGCAAGTCCCTTG
GCTTCGGATGGGGACAAAAAGCTAGCAGTACTATGCTACCGATGTTTATCACTCCTCTATTTGAGAATGT
TTAAGCTGAAGAAGGACCATGCTATGAAGTACTCCAGATCACTGATGGAATATTTTAAGCAAAATGCTTC
AAAAGTCGCACAGATACCCTCTCCATGGGTAAGCAATGGAAAGAACACTCCATCCCCAGTGTCTCTCAAC
AACGTCTCCCCCATCAACGCAATGGGGAACTGTAACAATGGCCCAGTCACCATTCCCAGCGCATTCACC
ACATGGCTGCCAGCCACCGTCAACATCACTAGCAATGTGTTACGGGCTATGAACACTGGGATATGGCCGA
CAAACTGACAAGAGAAAACAAAGAATTCTTTGGTGATCTGGACACGCTGATGGGGCTCTGACCCAGCAC
AGCAGCATGACCAATCTTGTCCGCTACGTTCGCCAAGGACTGTGTTGGCTGCGCATCGATGCCCACTTGT
TGTAGTGGGTGTTCTCAGATCTCTAGCATCACGACCCATCACTCTACCTCTACCAGCGCACTGATGGTCA
CTGGTGGAACTCCACTCACTGGGGAACGTTCTCTTTGGTTATGTTTGTTTTTATGCTTCTTTTGTTATCT
GTAAAAACAGAAGTCATTGTAAGTTGACACTACAACTTAAGGGCAGTGTACGTTTTATTACTTAGTCAT
TTTTTTTCTTTTAGCATTTGATATGCATTTCTCAGATTCCACCATCTTTTTGTGCTTTATGGAATGACAG
TCCCTACAATATTGTTTTAAGCCCACACTACCCAAAACAAAGAATGGGAAGCACTTGTGATAAAGACAGG
CTCCTGAGAAATGCAACAAGTGGTCTTACATATACATGAGAACTTAGACACAAGGGACCATCCCCCAAAC
TCTACTCTTATACCCAGAAAAGAACATATTTCAGAATCTGTCAAACTTTTGTGTATCCCACAGATTCAAT
CTTCAGGTGAGAATTTTCATTGTCAAAACCCACTGGTTAGATGTTGTAGCAACATCATAAAATCAAGAGT
ATCAAGAAAATAAATGAGCATAGCAATGCTACTCTTAAAAAGATGCTATGCCACACAACCAGAGGACTTT
CTTGTTAGCATCCCTTTCCTGATTCCCTATTTTGTTAATTTTAATGATAAGAAGAAAGGGTGACATTTAT
TTTGACAAGTTTTAGGCATCAGCTGGCATCAGTGTTTTTCAACTCCATTATTTGAAGTGTAAATCCTCAC
CTGGGGTTCTCTGTGTGCAAAGCTGTCCTTTTGAAGAACAGTTTGGTTGATGCATGCCTTAGTAGCCAAA
ATGCTACACTCTAGACTTACAAGTGGGAGTTAAGAGAGGTCTGGAAAGTGTCCAACAAGGAATTCACACC
TCTGCCTCCTTTGCAACAACAACATTTACACAGTTGGTAAGTGGGTCCATAACTGGCAGGATTTTTAAAT
TGTATTTTGCTCAAATCTATGGGAACAAAAGTCAAGGTATCACTACCTAGAAGTAATGATATACAGTTTT
CTTCCTAGTGGCTTGAAAATCTGGACTTCCTCAATTATTATTCACATTTTCTCTCTTATAGGTTTTCTGT
TTTCTACTTTCTTTTTTCTCTTATCTGTGTTTCCCTTTCCTTTGTTTGGCTCATTAACTTTTGACTGAAT
TACAATTACTCCTTTTATTAAAGTCCATATTATTGTGAATCATTTCCATGAAAATTTCTAAGAAAACTCC
AAACTCTCTAAATAGTAGCTAACTTTTATTTTTTTAAAATGAGTCGTGGGGTAGTGCTTCACCTTGAGAT
GCTTTGAAAGAGCCCTAAACATTGGGAACCATTCACCTAATTTGGAGACATTTCTCACTGGTTGTGACTA
CCCCCTTATGATCCTTCACATTCATTTTATGTCCCTAAACATCACAATGTAAATATCATTTTTGATGTTC
CAGCTCACCAGAAGATTCTTACACTTGGGGTAAACACTATCCATGCATTACTTACTGGTAATTACCTGCT
GGTATATAATTCCATGTAGCCTTTAATATGCTGGGTTATCAAATTCTGTTCACTGAGTTATGACCAGATA
AATAATAGATATGCACATGAAAGATGCAAACTTGTGTGATTATTAAAGCCAGCCATGCAGGTCCATGATA
GAAACAGCAGGTGATGACTCTGCACTCTCATTGTCAAGGTTAGCTATATCCCCAGTTGCAAAACAGCCAG
ACTTGAGCTGTGCTCTGGTCATCTTTGAGTTTAAGGCCTTTTGTTGTATAAGGCTGTGGAAGTTGTACTC
CAATGGCTGAAGCCATGTTGTTAATATGGCTGATGGGAGCATCCCTGCAGCTGAACCCAGCACTTTTTAT
GCTCCCACTGTGGTTGAGCTTTATGTTTACAGTGTCAGCAACAACACTTATGCATCCAAACACTCACAAA
TGAAACCTGAAAGAATCTTTTCTGAGCCTCTTAAAAGAGGAAATGATGATAACATTAAAGACTCTGAAC
ACCCAAGGTTGGTGTCACATATAAAAATTAAGCTGATGACTTTGCAGTGACTCAAGTTGTCTCTTTATCA
TGGTTTACCAGGTAGAGTGCCTGGCTATTACTATATAATGAAGCCCACTGGCTTGACTTGTAAGTTCAAC
CTAAACCACAATCCTAGACCATCATGGATTTAGGAGTAGATTCTTCTTGAAATCCCACATCCAGAAACTA
GACATTAGAATGTTGAGGCAGTTTCCCAGAGAAACAAGCATATTGCCTCATGGATGAAAGACTTGTAGTT
CTAGTTTCAGTGACTTGTTATATCTACTTACATACAACAGGGAGGCAAGAGGATTCTCTGTCATCTCTGG
TGACTGAGTGTAAAATATGTGCCAAGTCTGCAGCACAGTGACCAAATCTGACAATCGAGCTCTGGATCAC
CACTTGATTATGTAGTAGACTCATTTATAAAGCAGCTTAGGAACTAATTAAACATGGAGGATGAATTACC
TTCCTATCCCTTGAGATAAGACATCTTTCAGTTTCATGATTAAGGATTGTTGCTGTTTTATAGTTACTCT
GTTCATCACAGTGTAAATGGTGATGCGTGTCGTAGGTGTGCAGCTATTTGAGGGACTAAGGGATGGAGAT
ATTCTGTCAAATGAATCTCTTCAGTATACCAGTTTGTGGGAGGGATATGAGACATGTGGATGGCAGTGAG
```

*FIG. 26B*

```
AGATCGTGCCTCTAGATCTTGATGGAGGCTTGGTGAGACACACTTAAATAAGCACGTGGAGGTTAGAATA
GAGGGCAGAGTAAAAGGAAGCTCCATCTGAGCAAGTACACCAAATGATCTCAGCCCTGCAACTTGACCCA
GGTAGGGCCACCACTACGCCTTCACTTGTCACCCAAGCTCCAACCACAGAGAGTTTGACAAGTTTGTGTT
ATGATGTTGGCTTGGCTTTGTATTTTTAATTAACTTTGGATTTTTAGTGGTTTTGTCATATAACTGTCTG
AGTTTGGTAGGTAGGATTACTTTGAAAAGGGTTTACTAGTGTGGTCCTCCGGGTAGAATTTAGCTGTAAC
ATGTTGTTAGCCAGCCTGTAGACTGTTAATTACTTAATAATCTCATTGGAAAATACTAGTAGTTTTATA
TTTGGATGACATAATTGGAAAAGCAGATTAGCTGCTACTACTTTTAAAGACTTAAGGTCGGGATGCCT
TTTTTTCCATGTAAGGAAATGAAAAGACCCAAAATCTTCAGGCAAAAAGCAAGTTGCAAAATTAGAAACC
ATTGGCTAAAAATGTGTTTTGTTGAGTTTCCAAATGGATGAATTTCATTTGGACATTACATCACTAAAT
TCATTAGATTTTGTCTGCATTGGAAAGATACTCTTCTAGCATATCTTTCCCAAAGATATCTAATTTGGAT
TCTGTTTCATGCAAATTTGCATCCCGGAGGTTGAAGTTGGAGTTTGAGGTTGGAAAATATCTTTGAAGGC
AGAATCAGTTGAGTTGTGAGGGTGAAGCCTCACATACTTCTAACAGACATGATAAAATTCACCTGCATG
AGTTGGCAGGTGGGAGAACCAAACTGGATCACTGGGTAAGACTACTCAGTAAAGCAATGAACTGCTTGCT
TAGAGAAGCATCACTATCCCCATTGAGAAAAATGTGTGGCAAGATGATACAGCTACACAGTATCAAATGA
ATGGGTCAATTCAGCACCCCCAAATTTAATTCTGTGTGGGAAAAATTATTGAGCCAGTTGTCAGTGTTCTG
TTACATGACTGGCAGACTAAATTCTTCATCGTTGTTCTTATTCTTGTTGTTGTTTCTCATTTTCACTCGC
ACGGCCTTATTCTCATAATTAAAATCTAATTCATTTTCTCTTTAGTGTTAGTAGACTCCAACAACAGAAG
TGGCATCTGTGTATTCATAATCAGCATTTACCCTGGCAGGAGACTAATCAGATAGGCCGGTCTCAGACAT
TAATCCTACCATCTGATATTTTTGGTGAAGGAAAAAGTATTAATTCTCTTTCCATCCTCCTCCTCAGAAA
TATAGAAGCCCTCTTTACCAAAATCATCACATTTTACTCTGTAATCTACCAGCTAAAAGAAAATTGCATT
GAAGCCCCACAAAGCCAGATTGCAGTTCTTGCCCCTTTTTGCGTCTGACATGAGATGTTAAAGAATTATT
CATTGTGCTCACATTGGGTTAGGGGACACTGAACTGCTTTTTAGATCCATGATCAGTCATCATTCTTCTA
AGAGATTGGAGCTTTGCTGTTTCATTAACTGTGCAGTGTAGACTAATGGTGTTTAATAAAAATCATTCAA
AATTTCAAACTCTTTTGCCAGTGACCTCAATTTTGTTGGCTCTGTGATTTGTATCAGACTTTGAGGAGGG
AAGGGGAAGTGAAGGAAGCCTACGTCCAGGCCCCTGACAGGATGCTGCAGTAGCAAGCTCAAGCTCGCC
TGCCTGCCAGCAGTTGCTGGTGAGCAGCAGCATGCAGACCAGCTGTGGGAAGCCTCCTGAAGAATGCCCC
AGCTGATGCTTTCAGCTGGGAATAGTTTGTTCCTATTGGGGAACTCATTGTTCTCCAGTCTCTGCAGCAG
GAAGCCAGCTGTCATATTCGGAGGGAATTTCAGATGCTTTACCTTTTTGGTTTTGTCCTGCATCACTCAT
GTGGCTACGAAAGTGTCTCTGAGAATAGAGCCCAATGTGGTGACAATGGGTAGTCAAATGCACCCCAGAT
GCTCAAGCCCTGTTGTGGTTCTGCAGTGTTTATGAAATTGGGAGGAAGGAGACCCTGGACAGTAAGCAAA
ATTGGAGACACTCCAACGAGGCTAAGTTAATGCCGTGTTGCCCAGAACAAGATCTAGCTTCTCATTTGGT
CAGCCTAGCATGCAACCAGTGGTGTGCTGGTAAAATGTTTAACAACCAGCTCGCTGAGAATAGAAAGCAC
CTGGTTTGCACCATTTGCCAATTTCCATGGCATAAATACTACCACTTTAGATGATTTTAAGCTACCAACT
GTGATGTCACTGAACACATGGTTGGAAAGAGATGCACGCAGTTGGCTCTTGCAAGCCTGGGCAAAAATGC
TTCAACACGCCACTGGATGCAGCCAGTCAGAGGGTTCATATTTAATATATGTGTTCATGTGGACACACAC
AGACACACACACACAAACTCACCCTTACACACACACTTCGATGACTAAAACAATTACATAGTTTTAAGAT
ATGAATCAATGTGTGAATGTAGAAAGCTTATGATAAGGCCCTAGAGGTATGGGTTGCCCTGGAAGCCTAG
GTTTTAAGCAGGAGAATAGCTGAGAAGAATGAAGCCCTCCTGAGCTGAAAGGAGAGATGGATCAATGGAG
ATGGTTCCATCATCTCCTTCCATATCTCACAGGTAAAATGGGCACTCAGAAAACCCTCACGATTGATTTT
TTAAAAGATAAGTGAGTGTTTTTTATTTTATTATTATTGTCATCATTATTTTGATTTACAAATGCTATT
TGTAACTTTTACATGTAACTAGGATAAAGTATTTACGGGAACTCTATGGAGAATAGCACAATCCAGAATT
TACTGTGTTTTTCTTTTATGTGACGTGGAAACTCAGTAATTCTCCCACCTTCACATTGTTGTTCATAAGA
ATTTTACTTTAGTTATTAGGGAATCTAAGTTTTTTGTTAACATTTGTTTTTAGTTAAAAGTATCTACTTA
CTGTTTTAGCTCTGAACTCAAACCAGAATATCTCTGTATCAATTGCATGACTATTCAGAAACAATAATCC
AAACCAAAATAATTCTTTTTTCCACCCAGTACGAAGACGAAAACTAAGCTCAGTAACAAGAAGGCATAAACTAA
AGTATATAATGAGGCTTTCATTAAATACACACACACACACACTCACACACACACACATACACTTTTTAAA
TTTTTAAATTAGGCCTCCACACATAAATCATTTTGAAAGTAGAATAGAAAATCTCAAAGAATTCATTCTC
CTGGTCCTGTGCATCTTCTGCAGTTAATAAGAGGTTTGTATCTGGAAAGATGGAAGAACTTGTTCTAAAA
TCTTATTTTTCAAAAAAATTTCCATTTTCTCTCTGGGCCTGTATCCATGGTTGAATGTTAGCCCTGGA
GGAGATCCATGTCTTACTCGCTCTTTCTGGCCCTTCTGTCTTTTGCCTCTGCAATTCTTTTTGTAGCTGG
CACGATAGCAGGGACTGGGGGTCTATCCTTTCATGGTATTGCTACAATATTTGTCCTTACTGGAAAATGG
TAACATCCGGGTCTGATTTAATTGGCATTACACTTACACAGGGACTCTGAGCACCCCGTCACCACACCA
```

*FIG. 26C*

```
GACAGTGGACCAGTTTTCACAGCTACAAAGAGCTAGAAATGTGTTTAACATCATCCAGTGCATCCCCTAA
TTCAAAACCATCCTCACTAATCAATCATATTCACCCATAAATATTACAAATGAGATTGATTCCATCTCAA
GACAATTTGTCAAATACTTAATTTTCTTCCTGGATGATTCTACTTACTGGATATTTTAGAAAGAGAAATG
TCTGAGATAAAATCCCTCACATTTACTCAATATAACAAATTACTGTTTCTACTCCTATTCTGAGTAGTGC
TTCTGAAGATTGTTTGCTGTAGTGTTGTCTTTGATAAAATGAATGTCAGTAGTGAGCCTTTTAGAGATAC
CATGCTCAGACATCCTCTTTGGGATCAGAAGATACCTAAAATTCTCCCTTTTGCCCACTTGGTTAGATG
AGTGATATATTCTTTGGATCCTGCAAAGAAGAGATTGGTTTCTTTTCTTTTCTGGTGGTGGTAGTGGTTG
TATCTGTGGCTGTGATGGTTGTTGTTACTTGTCTCTCTCTCTCTGGCTCTGGCTTTGCTTTCCTGCT
AGTGTTCTTTCTTTCCAAACAAATAGTTAAATTAAACGTGAGCTTCTGAATTGTACTTGTTCATACTT
TCAAAACATAACAGATTAATAAAAATAGATGTGTCCTGATTTAAAACATGCCCCTGGAAAGGCATGCTG
TATTATGAAATCGTGATAATATAACTGCATTATTACATGGCAGTATAAATATTAGTCTGTTGAATTCATT
TGTCCAATTGTATAACTTTGTGGAGCAGTGTTTTGACCTTTGATACATAATTCTGGAGCAAGTGGAGTGG
TTGCAGGCAGATGAGACAGTGTTATATCAGGATTTTTCAATCAACTTTAGTTGGAGGCCTGGCAATTACA
AACATCTTCAGATGTTTCTGTAACCATTATAAATATGAAAAAAACCTCTTCAAAAAATTTCCCATAGTAC
TTCAGTCAAGACTTTTTAGGTTTATCTTTTTTTTTTCATTTCTCCTTTTCCTTTTCCATTATTTTTCGAT
GGGGGGGTTGTTATCATTGACTGAAGAAATATTTTGATTGCAATGGTCTCTCTCTCTCTCCCCTCTCTC
TCTCTCTCCTCTATTCTTTCCTCCTTCCCTCTGTCCATCACCCCTCATTAAAATATTGAAATCTGGAGTC
TTTGATAAATCTGCATTAGACCAGGCTATATGCTAGGAATGAAATCTGGGCAAATATCGATGGGTTTTCA
AAGAATGCTCCATGTTCATTGGGCCCTTTCACACCCCACAGTGATAAATGAAAAGGATAGAGGTAGTTTT
TTCAAAAGAGCACTTTAATAATATCCTCTGAGACCTAATGCAGTTTAACAAATGACTCCACCTATTTTC
CAGTAGGTAAATTGACTGAGACTTGCAAAATACCCCTGAGAGTTGTCAGGGGTGTCTTCTGCCTGGTCTA
TAGCGTGTGTGTTTGCTTTGTATCTAACAGGCACATTCACGTCTCGTGTACTCATATGAAGTATTTCCTA
ACATTCCCATTAGCCTGTATATAAGAATCAGAAAGATAATCCCAACATGTTGTAAATGAAGATGTGACTC
TATAACCTTTCTCTTCTTCCTGGAAAAAAAAGGACATTTTCATGCATATTTTAAACAGAAATTTTGTATA
TTTAAGTGTCATAGAAAATATTTATTGAGTAACTGGGACACAAATGGGAATTTAATTGTCATCATATGCT
TTGTGTGTGGGGATGCTTACCAACACCATGTCGCTGGACCATTGTGGCAAGCCATAACTGCACAAAGAGT
ACACATCGTCAGTGTGTGTGTGTGTGTGTGCGCGCACGCACGTGCGTGTGTGTCCCTGCATGTG
CAACATGTCTAGCTTGCTGTCCTTCATGGGATTTTAGCTTTCCCTTCTTGAAAAACATTATTTTACAGTT
CCAGGAGGCCCTGGTTACATTACTATATGAAGGCAGTGATTTGAAATGAAAATTCCTTTCCTCTTGGAAG
CTTTGGTCATAATATCATGGTTCAATTAAACGGATTCCACCGGACTTTGTGATGAAAAAGGCTCTGTTAA
AATCCAATTGAGTTTCCAAGAGGAAATTGTAGTAGGTCAAGATGCATGAGAGGGAAGATGGAGGCCACCT
CAGCTGGAGAACATGAGCTGAGTTGAGCCCTCAGTGTTGAAGTTGACTTGCTCCAAGCTGCAGTCTAAAA
CCCTGGGGCCCGTGCCTGGCCTATGCTCCCTCCCAAGTAAGTAGAGGAGCAGAACCATCAGGAACAGCCT
GCCTGGCTCCTATGAAGAAAACTTCCTGACGTCCTGTCCCCAAAGGAAGACCCTTTCCCCAAGGGCACCC
CAGGTGGCCATTAAATTGTGATGATCATTCAGAAAGTGCCCCCTTGGCTTTATGAGAATCCAATTAGTCT
TCTGAACCACCTTTTCTTGGGTGCAGATTTCCAACATTCATGCTCATTGCAGATCCACCAACTGTCACTG
TTCTTAACAAGCATGCTCGTCTTGTCAGAATTTCAGTAAGTTCCAATTTCCTGTACAGACCAGGGTAAAC
TGTTCTAAAATCAATCAATTAATGAAATGTTATCTGGTTTTTAAAAGCTGGTTTCATGTGCTTTATGTGT
ATAAAACTATATCTGCCTGTGTGGCTTTGCATTTCAAATGTGTGGCGCACAAGCGTTTGTTGGTGCTTT
GTTCTCAGTACAGTAACTCTGTGTACAAACATTTTAATGTGGTTTTGTTGTTTTCCAACAAGATGTCTCT
GTAAAAATGATATTGGCTGAGCTGGTGCGTTGGTTTCTCTCATAGAGGCATTAACTATACTGCCAATGCA
TTGAATTATTTAAAAATGCAAAATAAAATTTTTATGAAAATCTCA
```

*FIG. 26D*

NUCLEIC SEQUENCE AND DEDUCED PROTEIN SEQUENCE FAMILY WITH HUMAN ENDOGENOUS RETROVIRAL MOTIFS, AND THEIR USES

The present invention relates to a novel nucleic sequence and deduced protein sequence family with complete or partial human endogenous retroviral motifs, and sequences flanking or adjacent to said sequences, and controlled by the latter; modification of the expression or impairment of the structure (polyadenylation, alternative splicing and the like) of said flanking sequences.

The invention also relates to the detection and/or use of said nucleic sequences and of said corresponding protein sequences in the context of diagnostic, prophylactic and therapeutic applications, in particular for neuropathological conditions with an autoimmune component such as multiple sclerosis.

The invention also relates to the production of antisense double-stranded and single-stranded nucleic probes, of ribozymes, capable of modulating viral replication (T. R. Cech, Science, 1987, 236, 1532–1539; R. H. Symons, Trends Biochem. Sci., 1989, 14, 445–450) of the corresponding recombinant molecules, and associated antibodies.

Retroviruses are viruses which replicate solely by using the opposite route to the conventional processing of genetic information. This process, called reverse transcription, is mediated by an RNA dependent DNA polymerase or reverse transcriptase, encoded by the pol gene. Retroviruses also encode at least two additional genes. The gag gene encodes the proteins of the skeleton, matrix, nucleocapsid and capsid. The env gene encodes the envelope glycoproteins. Retroviral transcription is regulated by promoter regions or "enhancers" situated in highly repeated regions or LTR (Long Terminal Repeat) and which are present at both ends of the retroviral genome.

During the infection of a cell, polymerase makes a DNA copy of the RNA genome; this copy may then integrate into the human genome. Retroviruses do not kill the cells which they infect, but on the contrary often enhance their rate of growth. Retroviruses can infect germ cells or embryos at an early stage; they can, under these conditions, integrate the germ line and be transmitted by vertical Mendelian transmission, which constitutes the closest relationship between a host and its parasite. These endogenous viruses can degenerate during generations of the host organism and lose their initial properties. However, some of them may conserve all or part of their properties or of the properties of their constituent motifs, or acquire novel functional properties having an advantage for the host organism, which would explain the preservation of their sequence.

The existence of endogenous motifs having long open reading frames and/or subjected to a strong selection pressure can therefore be an indication of a preserved or acquired biological function, which may correspond to a benefit for the host organism. These retroviral sequences can also undergo, over the generations, discrete modifications which will be able to trigger some of their potentials and generate or promote pathological processes. It has recently appeared necessary to carry out a review and to identify these sequences so as to be able to evaluate their functional impact.

Human endogenous retroviral sequences or HERVs represent a substantial part of the human genome. These retroviral regions exist in several forms:
  complete endogenous retroviral structures combining gag, pol and env motifs, flanked by repeat nucleic sequences which exhibit a significant analogy with the LTR-gag-pol-env-LTR structure of infectious retroviruses,
  truncated retroviral sequences; for example the retrotransposons lack their env domain and the retroposons do not possess the env and LTR regions.

Up until now, the study of these regions of the genome has been neglected in humans for essentially two reasons:
  the existence of insertions/deletions which can shift the reading frame and of mutations which modify the sequence. These modifications cause impairment of the structure and consequently of the biological function of these motifs,
  the absence of confirmed associations with human pathological conditions.

The recent knowledge of fragments which are significantly representative of the human genome and an orientation of research studies toward a study of structure/function of endogenous retroviral motifs have made it possible to specify the importance of these regions. The involvement of truncated or complete endogenous sequences in pathological conditions in animals is documented; for example their association with tumor processes has been clearly demonstrated (S. K. Chattopadhyay et al., 1982, Nature, 295, 25–31). Research aimed at specifying the association or the influence of HERVs in human pathological conditions is now therefore justified.

A classification of the HERV elements has been proposed (Tönjes R. R. et al., AIDS & Hum. Retroviral., 1996, 13, p261–p267; A. M. Krieg et al., FASEB J., 1992, 6, 2537–2544). It is based on a homology of these sequences with retroviruses isolated in animals, with the aid of heterologous retroviral probes. Indeed, in general, the HERVs exhibit relatively little homology with known human infectious retroviruses.

The class I families exhibit a sequence homology with the type C mammalian retroviruses; there may be mentioned in particular the ERI superfamily, close to the MuLV virus (murine leukemia virus) and to the BaEV virus (baboon endogenous virus).

The class II families exhibit a sequence homology with the type B mammalian retroviruses such as MMTV (mouse mammary tumor virus) or the type D retroviruses such as SRV (squirrel monkey retrovirus).

Other families have also been described; among these, there may be mentioned HERVs which exceptionally exhibit partial homology with HTLV-1 (RTVL-H) or primate viruses; HRES-1, for example, exhibits sequence homology with HTLVs.

Programmes for very large sequencing of the human genome now make it possible to have available a significant number of novel retroviral sequences. The use of data processing software packages makes it possible to identify and analyse these genes. In this context, a systematic search relating to the entire information available to date has been initiated in order to identify novel human endogenous retroviral sequences as a function of certain analytical criteria:
  presence of long open reading frames conserved during evolution of the host organism and which may suggest a biological function,
  analogy with sequences already characterized outside or inside the retrovirus domain,
  location in regions of susceptibility for certain pathological conditions or close to essential genes, for example in the cancer domain, regulation of the immune system or in certain neuropathological conditions.

The work carried out by the inventors on sequence databases allowed them to identify a set of endogenous retroviral sequences or motifs whose normal or pathological expression can promote or disrupt a protective effect in relation to pathological processes, or play a role in the onset or worsening of pathological conditions.

The subject of the present invention is a purified nucleic acid fragment, characterized in that it comprises all or part of a sequence encoding a human endogenous retroviral sequence, which has at least env-type retroviral motifs, corresponding to the sequence SEQ ID NO: 1 or to a sequence exhibiting a level of homology with said sequence SEQ ID NO: 1 greater than or equal to 80% on more than 190 nucleotides or greater than or equal to 70% on more than 600 nucleotides for the env-type domains.

The expression homologous sequence is understood to mean both a sequence which exhibits complete or partial identity with the above-mentioned sequence SEQ ID NO: 1 and a sequence which exhibits partial similarity with said sequence SEQ ID NO: 1.

According to an advantageous embodiment of said fragment, it has retroviral motifs corresponding to an env domain and corresponding to the sequence SEQ ID NO: 1 and retroviral motifs corresponding to a gag domain and corresponding to the sequence SEQ ID NO: 2 or to a sequence exhibiting a level of homology greater than or equal to 80% on more than 190 nucleotides or greater than or equal to 70% on more than 600 nucleotides for the env-type domains and a level of homology greater than or equal to 90% on more than 700 nucleotides or greater than or equal to 70% on more than 1 200 nucleotides for the gag-type domains, said motifs having no insertion or deletion of more than 200 nucleotides.

Said fragments constitute a novel family of human endogenous retroviral sequences (HERV-7q family) which exhibits sequence homology with the MSRV retroviruses, as described in International Application WO 97/06260; said fragments according to the present invention have:

two repeat nucleotide motifs of 711 bp (FIG. 3), having characteristic signals identified in LTRs (Long Terminal Repeats): transcription promoters of the TATAA or CCAAT box type. These repeat domains delimit three deduced motifs of the gag, pol and env type (FIG. 2), an env-type motif (positions 6965 nt—9550 nt on the sequence SEQ ID NO: 3 or in FIG. 1) which contains a long open reading frame of 1 620 nucleotides (positions 7874–9493 of the sequence ID NO: 3 and FIG. 1) encoding a protein having an unpublished sequence of 540 amino acids called enverin (FIG. 4 and SEQ ID NO: 26) and underlined fragment in FIG. 18. There is present inside the transmembrane domain of this env domain a peptide motif of the CKS-25/CKS-17 type (FIG. 5), recognized as having immunosuppressive functions on the host lymphocytic cells (M. Mitani et al., 1987, *Proc. Natl. Acad. Sci. USA*, 84, 237–240). A zinc finger type domain $HX_{3-4}HX_{22-33}CX_2C$ (Kulkolski et al., 1992, Mol. Cell. Biol., 12, 2331–2338), which is present in integrase-type domains is identified in another reading frame. This particular env domain signatures the characteristic of novel endogenous retroviral motifs, the motif (positions 3065 nt–4390 nt on the sequence SEQ ID NO: 3) of the gag type encoding protein motifs according to FIG. 6 (SEQ ID NO: 58) (positions 3118–4198 of SEQ ID NO: 3) was identified by virtue of analogies with known gag domains. The region of major homology $QX_3EX_7R$ is for example present (Benit et al., 1997, *J. Virol.*, 71, 5652–5657). The nucleic acid binding motif $CX_2CX_{3-4}HX_4C$, situated at the C-terminal position, is identified in another reading frame (Covey et al., 1986, *Nucleic Acids Res.*, 14, 623–633). Upstream of the gag domain, a motif of 182 nucleotides is detected which is repeated twice (FIG. 1), the pol domain exhibits the conventional consensus of a retrovirus pol region at the level of the protease, reverse transcriptase and RNAse H domains. A motif close to the consensus LLDTGA is found in pol (Weber et al., 1988, Science, 243, 928–931). The motifs D and AF, LPQ and SP, and YVDD (Xiong and Eickbush, 1990, *EMBO J.*, 9, 3353–3362) are respectively found in the 3rd, 4th and 5th homology boxes. The motifs YTDGSS and TDS are present in the RNAse H region, the gag and pol regions could be considered as being joined with a passage from the gag region to the pol region by a reading frame shift.

The present invention includes the sequences belonging to the HERV-7q family as defined above (presence of the SEQ ID NO: 1 sequence or of a homologous sequence or presence of both the sequences SEQ ID NO: 1 and SEQ ID NO: 2) and in particular the sequences SEQ ID NO: 3–22, 28 and 61; it also includes the complementary nucleic sequences and the reverse sequences complementary to the preceding sequences as well as fragments derived from the coding regions of the preceding sequences corresponding to a shifting frame greater than or equal to 14 nucleotides or their complementary sequences (SEQ ID NO: 37–57, 59–60 and 121–122).

These various fragments may be advantageously used as primers or as probes (reagents A); they hybridize specifically under high stringency conditions to a sequence of the HERV-7q family.

Among these fragments, the following fragments may be preferably mentioned:

a fragment of 182 nucleotides, repeated twice, situated upstream of the gag domain at positions 2502–2611/ 2613–2865 of SEQ ID NO: 3:

Primers and Probes Specific for the gag Region a sense primer G1F located in the region upstream of the gag domain of HERV-7q: 5'GGACCATAGAGGA-CACTCCAGGACTA3' (SEQ ID NO: 37);

an antisense primer G1R located in the terminal 3' region of the gag domain: 5'CCTCAGTCCTGCTGCTGGAT-CATCT3' (SEQ ID NO: 38)

the fragment of 1505 nt amplified by the pair G1F-G1R is used in order to generate the probes capable of hybridizing the various PCR amplification products:

a nested sense primer G2F: (SEQ ID NO: 39) 5'CCTC-CAAGCAGTGGGAGGAAGAGAATT3' a nested antisense primer G2R: (SEQ ID NO: 40) 5'CCT-TCCCTGTGTTATTGTGGACATCATT3' a nested sense primer G4F: (SEQ ID NO: 41) 5'GGAA-GAAGTCTATGAATTATTCAATGATGT3' a nested sense primer G3F: (SEQ ID NO: 42) 5'GGGA-CACAGAATCAGAACATGGAGATT3' a nested antisense primer G4R: (SEQ ID NO: 43) 5'GCCTTCAGAAGAGTCAGGTGACAGAGA3' a nested antisense primer G5R: (SEQ ID NO: 44) 5'GAGCCTCCAAAGTCCACTTGCCTGA3'

Primers and Probes Specific for the env Region a sens primer E1F: (SEQ ID NO: 45) 5'GATTTCAG-TATCTACTAGTCTGGGTAGAT3' an antisense primer E1R: (SEQ ID NO: 46) 5'CTAG-GAAATCCAGCTAGTCCTGTCTCA3' the fragment of 2529 nt, amplified by the pair of primers E1F-E1R, is used to generate the probes capable of hybridizing the various PCR amplification products:

a sense primer E2F: (SEQ ID NO: 47) 5'CCAAGA-CAGCCAACTTAGTTGCAGACAT3' an antisense primer E2R: (SEQ ID NO: 48) 5'GGACGCTGCATTCTCCATAGAAACTCTT3' a sense primer E3F: (SEQ ID NO: 49) 5'GCAATACTA-CATACACAACCAACTCCCAA3' an antisense primer E3R: (SEQ ID NO: 50) 5'GGGG-GAGGCATATCCAACAGTTAGTA3' a sense primer E4F: (SEQ ID NO: 51) 5'CCATCTA-CACTGAACAAGATTTATACACTT3' an antisense primer E4R: (SEQ ID NO: 52) 5'AATGC-CAGTACCTAGTGCACCTAGCACT3' a sense primer E5F: (SEQ ID NO: 53) 5'CGAATA-CAACGTAGAGCAGAGGAGCTTCGAA3' a sense primer E6F: (SEQ ID NO: 54) 5'AGCCCAAGATGCAGTCCAAGACTAAGAT3' a primer E5R: (SEQ ID NO: 55) 5'GCGTAGTAGAGGT-TGTGCAGCTGAGAT3' a primer ExF: (SEQ ID NO: 56) CCCTTACCAA-GAGTTTCTATGGAGAAT a primer ExR: (SEQ ID NO: 57) ACCGCTCTAACT-GCTTCCTGCTGAATT All the oligonucleotides are designed to be able to generate a sense primer and an antisense primer by a shift in the sequence of the reference primer of 1 to 7 nucleotides toward the 5' side or toward the 3' side; the modification of the sequence may cause a modification of the size of the primer of 1 to 7 nucleotides depending on the cases. The primers chosen may be optimized depending on the cases by shortening or extension affecting 1 to 9 nucleotides.

Preferably, the hybridization, cloning, subcloning, production, preparation and analysis of the nucleic acids, peptides and antibodies, the sequencing of the nucleic acids and peptides, the in situ hybridization and the immunohistochemistry are carried out under the conditions described in the following books:

Current Protocols in Molecular Biology, Eds. F. M. Ausubel, R. Brent & R. E. Kingston et al. Green Publishing associates and Wiley Interscience.

Molecular Cloning: a laboratory manual. Eds. J. Sambrook, E. F. Fritsch & T. Maniatis, Cold Spring Harbor Laboratory Press, Cold Spring Harbor.

The Practical Approach series. Eds. D. Rickwood & B. D. Ames, IRL Press and Oxford University Press. In particular antibodies I & II; DNA cloning I, II, III; Nucleic acid and protein sequence analysis; Nucleic acid hybridization; Nucleic acid sequencing; Oligonucleotide synthesis; Protein purification applications; Protein purification methods; Protein sequencing; Transcription and translation; Gels electrophoresis of nucleic acids; Gels electrophoresis of proteins; Genome analysis; HPLC of macromolecules; Human genetic diseases; Microcomputing in biology; Molecular neurobiology; Mutagenicity testing; Essential molecular biology I & II.

Proteome research: New frontiers in functional genomics, Eds. M. R. Wilkins et al., Springer.

The human endogenous retroviral sequence (SEQ ID NO: 3) situated on the long arm of chromosome 7 corresponds to the HERV-7q sequence; it has 10.5 kb (FIGS. 1 and 2) and satisfies the criteria defined above.

The search for domains exhibiting total or partial similarity with the gag and env regions of HERV-7q resulted in the identification of novel endogenous retroviral sequences. These sequences may have the structure of a complete endogenous retrovirus such as the endogenous retroviral sequence situated close to the gene for the alpha and delta subunits of the T cell receptor, and consequently called HERV-TcR; by way of example, FIG. 7 shows the comparison of the nucleic alignments of the respective gag domains of HERV-7q and HERV-TcR (sequence HG12, SEQ ID NO: 19). Partial retroviral structures also exist. These retroviral domains, similar to HERV-7q, are identified in independent nucleic sequences as shown by their chromosomal location. Nucleic motifs (called here HEx or HGx, and analogous to env or gag type domains, respectively) resembling the env or gag domains of HERV-7q were found, with the aid of the above-mentioned databases:

HE2: chromosome 17 (SEQ ID NO: 4),
HE3 and HG3: chromosome 6 (SEQ ID NO: 5 and 6),
HE4: chromosome X (SEQ ID NO: 7),
HE5: chromosome X q22 (SEQ ID NO: 8),
HE6 and HG6: chromosome 1 q23.3–q24.3 (SEQ ID NO: 9 and 10),
HE7: chromosome 7 p15 (SEQ ID NO: 11),
HE8 and HG8: chromosome 19 (SEQ ID NO: 12 and 13),
HE9: chromosome X (SEQ ID NO: 14),
HE10: chromosome X q13.1–21.1 (SEQ ID NO: 15),
HE11 and HG11: chromosome 7 q21–22 (SEQ ID NO: 16 and 17),
HE12 and HG12, in HERV-TcR: chromosome 14 q11.2 (SEQ ID NO: 18 and 19),
HE13 (SEQ ID NO: 61): chromosome 6 q24.1–24.3

The present invention also includes the coding nd noncoding fragments for all or part of enverin comprising at least 14 nucleotides and in particular the fragments encoding the C-terminal part of enverin, either from amino acid 291, or from amino acid 321, starting from the first methionine.

These fragments comprise in particular a critical zone where two inserts of 12 nucleotides were characterized:

a first insert was identified (sequence A) in individuals of 2 groups (patients and controls). This insert, situated between amino acids 487 and 488, makes it possible to insert the tetrapeptide VLQM. A comparative analysis shows that this insert is identified in a homologous region situated in the sequence HE13, belonging to the HERV-7q family. The amplification of the HE13 type sequence could indicate that there is an impairment of the enverin sequence of HERV-7q, which would promote the amplification of the sequence contained in HE13. This observation also makes it possible to use this insert as a specific element for amplification of sequences of the HE13 type.

A second insert (sequence B) was identified in a patient with MS. The insert of 12 nucleotides is situated at the level of amino acid 495 and encodes the tetrapeptide MQSM. It is remarkable to observe that this insert is also identified in a homologous region situated in HE13.

Sequence A: TAAACTACAAATGG<u>TTCTTCAAATGG</u>-AGCCCA (SEQ ID NO: 59)

Sequence B: GATGCAGTCCAAGA<u>TGCAGTCCATGA</u>CTAAGA (SEQ ID NO: 60).

These observations demonstrate modifications of the enverin sequence of the HERV-7q type which constitute the basis for a detection strategy by allele-specific amplification (AS-PCR), making it possible to detect these differences in a population and which could correspond either to a mutation/deletion associated with a degree of susceptibility, or to a polymorphism, or to a mutation/deletion associated with a pathological condition such as multiple sclerosis.

The alignments of the env (FIG. 8) and gag (FIG. 9) domains explain the levels of homology observed between the sequences described above and the homologous sequences in HERV-7q. The analogies can extend to the flanking retroviral motifs.

Analysis of the sequence tags available in databases shows that transcripts belonging to some members of this family, in particular HERV-7q, are essentially expressed in tissues of foetal or placental origin.

Polypeptide sequences generated by these transcripts can therefore be potentially produced and biological functions or activities can be envisaged, by analogy with biologically active polypeptides of viral or retroviral origin; for example, the peptide motifs of the CKS-17 type (Haraguchi et al., PNAS, 1995, 92, 5568–5571) (FIG. 5) or CKS-25 type (Huang S. S. and Huang J. S., J. Biol. Chem. 1998, 273, 4815–4818) which have immuno-modulatory functions on the lymphocytic host cells. The differences in sequence which are observed and possible normal or pathological modifications are in particular responsible for modulation of the function.

HERV-7q represents the paradigm of the novel family of human endogenous retroviral sequences or of endogenous retroviral motifs.

HERV-7q and some of the endogenous retroviral sequences belonging to its family have a pol-type domain analogous to pol-type retroviral sequences such as for example the pol region identified in the MSRV retrovirus associated with multiple sclerosis and described by H. Perron et al. (1997, *Proc. Natl. Acad. Sci. USA,* 94, 7583–7588; International Application PCT WO 97/06260).

However, the sequences according to the present invention are distinguishable from the infectious exogenous retroviral sequences analogous to MSRV previously described in that the gag and env sequences according to the invention are significantly different according to the criteria defined above and as a function of certain specific characteristics, for example the long open reading frame of the env domain of HERV-7q; they would be able to allow the signaturing of a pathological condition when they have insertions, deletions, reading frame shifts or mutations.

Indeed, the differences observed between the human sequences of the HERV-7q type, which are isolated from individuals reputed to be normal, and the sequences derived from some samples of pathological origin are not randomly distributed. Comparisons carried out between the gag region obtained from infectious retroviral particles (EMBL accession No.: A60168, A60200, A60201, A60171 and the like) and the corresponding gag sequence of HERV-7q (FIG. 9), make it possible to observe that the mutations preferably affect non-sense codons. For example, two non-sense codons in HERV-7q are replaced by an arginine codon in A60200, which makes it possible to obtain a deduced sequence of 109 amino acids for HERV-7q and of 166 amino acids for A60200. The base changes consequently make it possible to extend the reading frame and to potentially encode larger sized polypeptide structures (FIG. 10).

Likewise, an env-type sequence obtained from infectious retroviral particles exhibits a significant analogy with the env domain of HERV-7q (FIG. 11). These marked analogies between exogenous and endogenous retroviral sequences could be responsible for the triggering or worsening of certain pathological processes, in particular certain autoimmune diseases such as multiple sclerosis. In this regard, it is possible to note that certain endogenous retroviral sequences described in the invention are situated close to or in regions reputed to exhibit susceptibility for multiple sclerosis: for example HERV-7q and the 7q21-22 region of chromosome 7, likewise for HE12 and HG12 in HERV-TcR and the region of the gene encoding the alpha and delta chains of the T cell receptor, HE2 and chromosome 17, or HE3, HE13 and HG3 and chromosome 6, for example, the sequences HE11 and HG11, around the region 7q 21–22 or HE4, HE5, HE6, HE9, HE10 or HG10 on the X chromosome. These sequences would therefore be capable of providing the means for locating or identifying the genes for predisposition.

No significant homology is observed with endogenous retroviral sequences already described; on the other hand, a limited homology may be noted, which makes it possible to identify a general structure of the env domain; however, said homology is less than the criteria defined according to the invention between the env domains of the sequence HERV-7q (SEQ ID NO: 1) and the sequence HERV-9 (FIG. 12). FIG. 11 shows extensive homologies between the sequence HERV-7q with an exogenous retroviral sequence (accession No. EMBL: A60170).

The human endogenous retroviral sequences belonging to the HERV-7q family can protect against attacks linked to the environment or can be beneficial for the individual. This beneficial effect could be one of the possible reasons for the selection pressure exerted on some of these sequences and the potentially functional character of the deduced protein structures identified: for example the long open reading frame capable of encoding a novel protein and corresponding to the env domain of HERV-7q.

The human endogenous retroviral sequences belonging to the HERV-7q family could be associated, for example, with pathological conditions related to processes linked to cancer, to neuropathological conditions with an autoimmune component or to any other pathological process in association or otherwise with endogenous or exogenous viruses or retroviruses. Their action could be related to the outbreak, the worsening, the modification of the time of appearance or the protection against the disease.

In the context of application to autoimmune pathological conditions (such as for example lupus, Sjöbgren's syndrome, rheumatoid arthritis, multiple sclerosis and the like), significant analogies may be detected between the endogenous retroviral motifs identified and motifs found in retroviral structures characterized in patients with autoimmune pathological conditions such as multiple sclerosis; for example, fragments of gag domain (recently available in databases) obtained from infectious retroviral particles or the complete sequence of the pol domain corresponding to the MSRV virus associated with multiple sclerosis. These retroviral motifs possess significant analogies with homologous endogenous sequences of the HERV-7q type, which makes it possible to envisage direct or indirect association with pathological processes, including multiple sclerosis, in association or otherwise with MSRV.

The importance of these sequences goes beyond the context of autoimmune diseases. Apart from the general importance of retroviral motifs in the triggering or worsening of a tumor process, which is well established in particular in murine models (H. Fan in *The retroviridiae,* 1994, ed. J. A. Levy, Plenum, New York, p. 313–353), these sequences could be present close to or inside important genes and could alter the expression thereof: for example HERV-TcR and the genes for the alpha and delta subunits of the receptor for the T cells involved in disruptions of the immune system.

The present invention includes, in addition, the use of sequences combined with the sequences of the HERV-7q family for the detection and/or prognosis of various autoimmune diseases (neuropathological conditions in particular); these sequences encode all or part of a factor whose function, the regulation/deregulation or alteration (polyadenylation, alternative splicing), is associated with the normal or pathological expression or with the regulation/deregulation of the motifs belonging to the HERV-7q family and correspond to transcripts or cDNAs of the nucleotide sequences encoding genes situated in regions flanking or delimiting retroviral sequences of the HERV-7q family.

The expression flanking region is understood to mean any region situated close to (contained in or including) an endogenous retroviral sequence belonging to the HERV-7q family, as defined above, up to and including the genes immediately contiguous and/or situated at a distance which cannot exceed 120 kb.

The inventors have now found that the presence of the retroviral sequences as defined above disrupts the expression or impairs the structure of the flanking sequences defined below.

The transcripts of said flanking sequences (and fragments thereof, in particular those underlined or in italics in FIGS. 14–16, 22–26, as defined below:

at 1021 bp upstream of HERV-7q, there is identified an endogenous retroviral sequence called RH7 (SEQ ID NO: 62 and FIG. 22); this sequence is situated in 5' of the HERV-7q sequence; in FIG. 22, the portion in italics corresponds to the beginning of the HERV-7q sequence; the RH7 sequence is underlined; two putative polyadenylation sites are in bold. This sequence SEQ ID NO: 62 exhibits significant homology, on more than 6 kb, with RGH-type endogenous retroviral sequences (FIG. 13). Sequences belonging to this family are expressed in particular in patients with rheumatoid osteoarthritis (Nakagawa et al., (1997), Arthritis, Rheum., 40, 627–638). The present invention also includes fragments of the sequence SEQ ID NO: 62, comprising between 14 and 50 nucleotides (used as primers), preferably between 14 and 25 nucleotides, or at least 25 nucleotides (used as probe), which fragments have the following characteristics: the 4 nucleotides of the 3' end are different from the corresponding motifs of the sequence RGH2 (bottom sequence in FIG. 13, GenBank accession No.: D110 18), at less than 9 kb upstream of HERV-7q, there is identified the sequence RAM75 (SEQ ID NO: 63 and FIG. 14) containing the 24 coding exons (which cover close to 41 kb) of the gene for peroxisomal ATPase PEX1. PEX1, in combination with PEX6, is responsible for the import of peroxisomal proteins and for stabilizing the PEX5 receptor. A disruption/alteration affecting PEX1 is responsible for various neuropathological conditions such as Zellweger syndrome, neonatal adrenoleukodystrophy and the infantile form of Refsum's disease (Reuber et al., (1997), Nature Genet., 17, 445–448). It can be recalled that the main function of the peroxisomes is associated with the metabolism of fatty acids, in particular by β-oxidation processes. Impairment of the gene identified in the sequence RAM75, or of its expression, by modification of the function of the regulatory 5' and 3' regions or by modification of the splicings or of the polyadenylation processes, in particular under the influence of neighboring retroviral motifs, would be able to disrupt the expression and the structure of ATPase and consequently to disrupt one of the peroxisomal functions, in particular the metabolism of lipids, in particular myelin lipids, with consequences for certain pathological conditions, including neuropathological conditions such as multiple sclerosis; the underlined portions (FIG. 14) correspond to the 24 coding exons.

The present invention also includes the fragments of the sequence SEQ ID NO: 63, included in the abovementioned 24 coding exons and comprising at least 14 nucleotides.

Analysis of the expression profile (transcripts and proteins) of the sequence RAM75 (SEQ ID NO: 63) is a good indicator for the differential diagnosis of neuropathological conditions with an autoimmune component.

In FIG. 14, the coding exons are underlined. The initiation and non-sense codons as well as the putative polyadenylation sites are in bold and underlined;

at 0.7 kb downstream of the sequence HERV-7q and on nearly 17 kb (SEQ ID NO: 64 and FIG. 15), there is identified the nucleotide sequence RAV73, where there are detected sequence tags and potential exons capable of producing one or more polypeptide sequences; the invention also includes fragments of this sequence SEQ ID NO: 64 included in the sequence tags and the potential exons as they appear (portions underlined) in FIG. 15, which fragments comprise at least 14 nucleotides, at 120 kb upstream of the sequence HG3, and on 15 kb, there is the nucleotide sequence RBP3 (SEQ ID NO: 65 and FIG. 23), which covers the 3' end of the gene encoding a transcription factor of the Blimp-1 family (SEQ ID NO: 119 and FIG. 25), a protein of 789 amino acids which is a repressor of the expression of the interferon-beta gene (Keller and Maniatis, Genes Dev., (1991), 5, 868–879), which is already associated with certain malignant pathological conditions (Mock et al., Genomics, (1996), 37, 24–28), and which could play a role in the differentiation and the pathogenesis of B cells. The possible association of the endogenous retroviral sequence containing the motifs HG3 and HE3 and of Blimp-1 has many benefits, in the case of pathological conditions, and in particular multiple sclerosis. Blimp-1 acts in particular on the B cells whose contribution in inflammatory processes associated with multiple sclerosis is known. Blimp-1 is capable of blocking the viral induction of the INFβ promoter whose capacity to reduce the frequency of attacks and the progression of lesions in patients with MS is known. Disruption in the expression or the structure of Blimp-1, in relation to a retroviral element of the HERV-7q type, is consequently associated with neuropathological conditions or with diseases having an autoimmune character, such as multiple sclerosis; this nucleotide sequence RBP3 (SEQ ID NO: 65) contains nucleotide motifs identified in the nucleic sequence encoding the Blimp-1 gene; the invention also includes the detection of the mRNA sequences for the Blimp-1 protein (SEQ ID NO: 119), the endogenous retroviral sequence of the HERV-7q type, containing HE3 and HG3, is situated in the HI3 region corresponding to an intron extending over more than 46 kb (SEQ ID NO: 66), of a gene which could encode the analogue of APS (FIG. 24), a protein of 275 amino acids specific to apoptosis, overexpressed in various cells in culture after triggering an apoptotic process (Hammond et al., FEBS Lett., (1998), 425, 391–395).

The intron is situated at the level of amino acid 231 of APS. The end of HE3 is at more than 12 kb from the 5' end of the intron, whereas HG3 is situated at more than 28 kb from the 3' end of the intron. Apoptotic processes are associated with multiple sclerosis. In particular, there has been described an apoptotic process affecting astrocytes and oligodendrocytes in the presence of a purified fraction of cerebrospinal fluid of patients suffering from multiple sclerosis (Ménard et al., J. Neurol. Sci., (1998), 154, 209–221).

Finally, it should be stressed that the nucleic region containing HE3, HG3, HI3 and RBP3 is located at the level of the short arm of chromosome 6, in 6p21, which is a proposed region of susceptibility to multiple sclerosis (The Multiple Sclerosis Genetic Group, Nature Genet., (1996), 13, 469–472).

The interaction between the HERV-7q type sequences and the flanking sequences and the importance of establishing a profile of expression including one or more of the abovementioned sequences in order to establish a differential diagnosis of a neuropathological condition is even more evident because it is observed that the sequences HG12 and HE12 are situated in an intron region of the gene encoding the alpha and delta subunits of the T cell receptors. The T cell receptors are involved in the immune regulation process and their influence has been proposed in the case of autoimmune diseases, including multiple sclerosis.

The subject of the invention is also transcripts generated from the abovementioned sequences as well as those optionally exhibiting modifications in the reference sequences described in the invention when they are expressed in certain patients.

Indeed, the systems for regulating the the expression of the retroviral proteins of HERV-7q, which are present in the LTR type motifs, could influence the expression of genes situated in the close or distant chromosomal vicinity and could induce disruptions of an immunological and/or neurological character. For example, the endogenous retroviral sequence HERV-TcR exists in the immediate vicinity of the genes for the alpha and delta subunits of the T cell receptor previously described. The LTR-type motifs could also encode superantigens (Acha-Orbea and Palmer, 1991, Immunol. Today, 12, 356–361). In general, retroviral proteins of the HERV-7q or related type, or their truncated or partial forms could be involved in cytotoxicity or superantigenicity phenomena, such as for example those derived from the long open reading frame identified in the env domain (FIG. 4).

Sequences of the HERV-7q 5' and 3' LTR type, which are highly conserved, are involved in such regulatory effects. By way of example, LTX is described, which is a sequence comparable to that of an HERV-7q LTR (SEQ ID NO: 67 and FIG. 16), and which is present in the center of an intron of more than 49 kb, but at 2 kb from the donor 5' site of the FMR2 gene associated with fragile X and encoding a protein of 1311 amino acids (FIG. 26). The LTRs modulate the alternative splicing (Kapitonov and Jurka, (1999), J. Mol. Evol., 48, 248–251), the expression of the gene, the binding to nuclear proteins (Akopov et al., (1998), FEBS Lett., 421, 229–233), or allow the production of an alternative polyadenylation signal (Goodchild et al., (1992), Gene, 121, 287–294).

In general, there may be noted the existence of several endogenous retroviral sequences of the HERV-7q type (HE4, HE5, HE9, HE10), situated at the level of chromosome X which represents the chromosome associated with the largest number of pathological conditions.

In this regard, it is possible to note that retroviral motifs derived from defective regions are capable of having biological functions; for example, the envelope protein p15E, derived from defective retroviral motifs, possesses an anti-inflammatory and immunosuppressive activity (Snyderman and Ciancolo, 1984, Immunol. Today, 5, 240–244).

These structures are probably capable of causing breaks or of amplifying deregulations in the immune defense processes. Some of the motifs of the gag, env and LTR-type domains may be associated with a particular function or may contribute to the normal or pathological function of the flanking domains as defined above (SEQ ID NO: 62–67). Recombinations with an element of exogenous, retroviral origin or otherwise can give rise to the production of nucleic or protein motifs which could either protect or trigger or promote or worsen a pathological condition. Likewise, a retroviral structure containing endogenous retroviral elements according to the invention would be capable of causing a pathological process after passing through an exogenous transient cycle followed by reintegration into a sensitive or critical region of the human genome.

It is thus possible to obtain expression profiles (transcripts and optionally proteins) which correspond to the abovementioned neuropathological conditions.

Likewise, the combination of motifs belonging to the HERV-7q family, or of elements induced by motifs belonging to the HERV-7q family, with motifs of exogenous origin or induced exogenously would be capable of triggering or worsening a pathological process or on the contrary of promoting protection or partial remission or a complete and permanent cure.

The detection made possible of the HERV-7q type domains suggests possible applications at the prophylactic, prognostic and diagnostic level; for example, immunological approaches or gene amplification, which make it possible to compare normal individuals serving as reference with patients, would be capable of promoting screening, of improving early detection of the outbreak of the disease and/or of monitoring the progression of a pathological condition in patients which may exhibit a susceptibility or in whom there has been an outbreak of the disease or in individuals considered to be normal, based on current clinical criteria.

The specific nucleic and immunological probes, as defined, in the present invention are capable of promoting the identification and detection of motifs which are abnormally expressed in the context of pathological conditions associated with cancer, or of neuropathological conditions, in particular autoimmune pathological conditions, at the forefront of which is multiple sclerosis.

The subject of the present invention is also hybrid nucleic sequences, characterized in that they comprise sequences or motifs belonging to the HERV-7q family, or of elements induced by motifs belonging to the HERV-7q family, with motifs of exogenous origin or induced exogenously (exogenous retroviral sequences); such hybrid sequences are probably capable of triggering or worsening a pathological process or on the contrary of promoting protection or partial remission or a complete and permanent cure.

The subject of the present invention is also a diagnostic reagent for the differential detection of complete or partial human endogenous nucleic sequences, having retroviral motifs, selected from the sequences SEQ ID NO: 1 and/or SEQ ID NO: 2, characterized in that it is selected from the group consisting of the sequences SEQ ID NO: 1–22, 28, 37–57, 59–61 and 121–122, the complementary nucleic sequences and the reverse sequences complementary to the preceding sequences, of nucleotide fragments capable of defining or of identifying the sequences SEQ ID NO: 1 and/or SEQ ID NO: 2 and any flanking sequence or any sequence overlapping them as well as of fragments derived from the coding regions of the sequences SEQ ID NO: 1–22 and 61, corresponding to a shifting frame greater than or equal to 14 nucleotides or their complementary sequences, optionally labeled with an appropriate marker as well as of sequences as defined in FIGS. 18–21.

The sequences of the nucleic, ribonucleic and oligonucleotide probes used will be chosen from the env and gag regions or their flanking regions; for example the oligonucleotide primers for HERV-7q will be chosen from the regions situated between nucleotides 3065 and 4390, nucleotides 6965 and 9550 or nucleotides 2502–2865 of SEQ ID NO: 3, as well as from any adjacent sequence (upstream or downstream) capable of allowing specific amplification (FIG. 1).

Among the appropriate markers, there may be mentioned radioactive isotopes, enzymes, fluorochromes, chemical markers (biotin), haptens (digoxygenin) and antibodies or appropriate base analogues.

Preferably:
said reagent is selected from the sequences SEQ ID NO: 37–57 and is capable of being used as a primer,
said reagent is selected from the following sequences:
 a fragment of 1505 nt amplified by the pair of primers SEQ ID NO: 37 and SEQ ID NO: 38 (primers G1F and G1R),
 a fragment of 2529 nt amplified by the pair of primers SEQ ID NO: 45 and SEQ ID NO: 46 (primers E1F and E1R),
 a fragment of 182 nucleotides, repeated twice, situated upstream of the gag domain at positions 2502–2611/2613–2865,
 fragments encoding or not encoding all or part of enverin, comprising at least 14 nucleotides and in particular the fragments encoding the C-terminal portion of enverin, either from amino acid 291, or from amino acid 321, starting from the first methionine,
and is capable of being used as a probe.

The subject of the present invention is also a method for the rapid and differential detection of the endogenous retroviral nucleic sequences of the env or env and gag type, their normal or pathological variants, by hybridization and/or gene amplification, carried out using a biological sample, which method is characterized in that it comprises:

(a) a step in which a biological sample to be analysed is brought into contact with at least one probe as defined above, and (b) a step in which the product(s) resulting from the nucleotide sequence-probe interaction is detected by any appropriate means.

In accordance with said method, it may comprise:
prior to step (a):
a step of preparing the relevant biological tissue or fluid,
a step of extracting the nucleic acid to be detected, and
at least one gene amplification cycle, and
subsequent to step (b):
a step of comparing the nucleic sequences obtained in said biological sample with the human endogenous retroviral sequences according to the invention by any appropriate means and in particular by sequencing, Southern blotting, restriction cleavage, SSCP or any other method which makes it possible to identify an insertion or a deletion or a single mutation between the various sequences compared.

In accordance with the invention, the human endogenous retroviral sequences according to the invention are thus compared with the nucleic sequences present in the biological sample to be analysed and allow the detection of homologous sequences from patients suffering from pathological conditions likely to involve a modification of their genome.

Advantageously, said gene comparisons are carried out using genomic DNA obtained from control individuals and from patients.

A conventional gene amplification by PCR will be carried out with the aid of 5'-sense and 3'-antisense primers delimiting or comprising the zone to be studied (env zone or gag zone).

Also advantageously, the sequences of the nucleic, ribonucleic and oligonucleotide probes used are chosen from the env and gag regions or their flanking regions; for example the oligonucleotides which are primers for HERV-7q will be chosen from the regions situated between nucleotides 3065 and 4390 and nucleotides 6965 and 9550, and from any adjacent sequence (upstream or downstream) capable of allowing specific amplification (FIG. 1), as specified above. They are preferably selected from the group consisting of
 a fragment of 1505 nt amplified by the pair of primers SEQ ID NO: 37 and SEQ ID NO: 38 (primers G1F and G1R),
 a fragment of 2529 nt amplified by the pair of primers SEQ ID NO: 45 and SEQ ID NO: 46 (primers E1F and E1R).

The gene amplification step is in particular carried out with the aid of one of the following gene amplification techniques: amplification using Qβ-replicase, PCR, LCR, ERA, CPR or SDA.

The subject of the present invention is also chimeric sequences, characterized in that they consist of a fragment of 17 to 40 nucleotides of a flanking sequence as defined above combined with an endogenous retroviral motif of the HERV-7q type comprising between 17 and 40 nucleotides, as defined above.

The subject of the present invention is also a method of detecting transcripts as defined above, characterized in that it comprises:
 collecting messenger RNAs obtained from control biological samples (biological tissues, cells or fluids) and from a similar sample collected from patients, and
 the qualitative and/or quantitative analysis of said mRNAs by in situ hybridization, by dot-blot, Northern blotting, RNAse mapping or RT-PCR, with the aid of a diagnostic reagent as defined above.

The subject of the present invention is also a method for the detection and/or evaluation of an overexpression/underexpression or of a modification of at least one of the endogenous retroviral sequences or fragments of sequences of the HERV-7q type and/or of their associated flanking sequences, characterized in that it comprises:
 depositing on an appropriate support, such as for example a nylon filter, a glass slide or their equivalent, cDNA or its equivalent obtained from clones, PCR products obtained from genomic DNA, RT-PCR products obtained from transcripts or from specific oligonucleotide sequences, said DNA sequences being endogenous retroviral sequences or fragments of sequences of the HERV-7q type and/or their flanking sequences, as defined above, consisting of transcripts and cDNAs of the genomic sequences, which encode all or part of a factor, whose function, regulation/deregulation or alteration is associated with the normal or pathological expression or with the regulation/deregulation of motifs belonging to said HERV-7q family, these sequences corresponding to nucleotide sequences encoding genes situated in flanking regions situated upstream and/or downstream of a retroviral sequence of said HERV-7q family and in which one of the ends cannot be at a distance exceeding 120 kb, and/or a chimeric sequence as defined above, the hybridization of said support with at least one appropriately labeled probe obtained, for example, by retrotransposition of an RNA mixture obtained from biological cells, tissues or fluids obtained from controls reputed to be normal, from members of various ethnic populations, from patients suffering from pathological conditions often associated with expression of retroviruses, such as tumor processes, or such as autoimmune diseases, and the detection of the hybrids formed.

According to an advantageous embodiment of said method, said transcript or cDNA is selected from the group consisting of the sequences SEQ ID NO: 62–67 and 119 and their fragments corresponding to a shifting frame greater than or equal to 14 nucleotides or their complementary sequences.

According to another advantageous embodiment of said method, said support comprises, in addition, any endogenous or exogenous retroviral sequence.

The method of DNA chips (Bowtell, (1999), Nature Genet., 21, 25–32), is used to evaluate the modification of the expression of all or part of some of the sequences of retroviral origin of the HERV-7q type and flanking sequences. Briefly, DNA obtained from clones, PCR products obtained from genomic DNA, RT-PCR products obtained from transcripts or specific oligonucleotide sequences are deposited on a support, such as for example a nylon filter, a glass slide or their equivalent. The deposited nucleic sequences cover the various retroviral domains described above, as well as the contiguous sequences and the flanking genes. In order to detect possible alternative splicing processes, specific DNAs are synthesized per step of 500–600 nucleotides with an overlap of 250–300 nucleotides on either side. The alternative splicings already identified will be the subject of a specific synthesis. The hybridization is carried out with the aid of a probe obtained, for example, by retrotransposition of an RNA mixture obtained from biological cells, tissues or fluids obtained from controls reputed to be normal, members of the various ethnic populations, patients suffering from pathological conditions often associated with expression of retroviruses, such as tumor processes, or such as autoimmune diseases, including multiple sclerosis. In this case, a $\mu$g fraction and up to a few $\mu$g of mRNA or up to a few $\mu$g or a few tens of $\mu$g of RNA, depending on the method used and the size of the DNA chip involved, are sufficient for the synthesis of the nucleic probe. The nucleic probe is suitably labeled so as to allow subsequent detection, such as for example by fluorescence or by an equivalent method.

The use of bi- or even multicolored probes makes it possible to specify the concerted expression of several genes in parallel, while taking advantage, furthermore, of a precise normalization. The results are acquired automatically, such as for example by a laser scanning system or its equivalent.

Two types of DNA chips are designed, on the one hand chips having an exhaustive set of sequences, and on the other hand specific DNA chips enabling targeting to a more specific application.

For example, a critical sequence in that it would contain a difference relating to a deletion or even a mutation is detected with the aid of specific oligonucleotides (Wang et al., (1998), Science, 280, 1077–1082). The polymorphism associated with a base or with a mutation is detected with the aid of four oligonucleotides possessing one of the four sequence possibilities at the level of a base (A, C, G or T) for each point difference, the 4 oligonucleotides are deposited and the hybridization intensities are compared. Furthermore, an alternative splicing is detected using DNAs corresponding to a single effective or putative exon; the gene is therefore analyzed exon by exon. The DNA chips also relate, by extension, to any endogenous or exogenous retroviral sequence, such as for example ERV-9, ERV-K, ERV-L, ERV-H, ERV-4, ERV-6, ERV-8, ERV-10, ERV-15, ERV-16, ERV-17, ERV-18, ERV-21, ERV-24, ERV-33, ERV-34, ERV-36, ERV-40, ERV-42, ERV-MLN, ERV-FRD, ERV-FTD and the like), as well as all the putative exon sequences (identified by the existence of sequence tags and corresponding transcripts) or effective exon sequences, and which are situated on either side up to a distance of 120 kb of the endogenous retroviral sequences of the HERV-7q type.

The comparative study is carried out between a control sample and the sample to be tested, in a prophylactic, diagnostic or therapeutic perspective, such as for example the early detection of a modification of the expression of one of the sequences, in a cell, a tissue or an organism, the identification of a sequence associated with a susceptibility or with any pathological condition, the monitoring of the progression of the pathological condition or the monitoring of a treatment and the evaluation of its efficacy.

Apart from the applications already mentioned, the advantage of the method makes it possible, more generally, to make an assessment of the changes observed in an individual, which constitutes to a certain extent an identity card, which facilitates an epidemiological approach which makes it possible to establish novel correlations between a particular observed profile and a pathological condition, in the absence of an a priori regarding this pathological condition.

The subject of the present invention is also a kit for the detection and/or evaluation of an autoimmune disease and in particular of neuropathological conditions with an autoimmune etiology, characterized in that it comprises, in addition to the buffers necessary for carrying out the methods as defined above:

diagnostic reagents A as defined above, and reagents B consisting of the transcripts and cDNAs of the genomic sequences, which encode all or part of a factor, whose function, regulation/deregulation or alteration is associated with the normal or pathological expression or with the regulation/deregulation of motifs belonging to said HERV-7q family, these sequences corresponding to nucleotide sequences encoding genes situated in flanking regions situated upstream and/or downstream of a retroviral sequence of said HERV-7q family, of which one of the ends cannot be at a distance exceeding 120 kb, which reagents are preferably attached to an appropriate support.

According to an advantageous embodiment of said kit, said reagents B are selected from the group consisting of the sequences SEQ ID NO: 62–67 and 119 and their fragments corresponding to a shifting frame greater than or equal to 14 nucleotides or their complementary sequences, as well as the sequences represented in FIGS. 13–17, 22–26.

The subject of the present invention is also products of translation, characterized in that they are encoded by a nucleotide sequence as defined above.

The subject of the present invention is also a peptide, characterized in that it is capable of being expressed with the aid of a nucleotide sequence selected from the group consisting of the sequences SEQ ID NO: 1–22, 28 and 61, as defined above, according to the combinations offered by the use of the various possible reading frames (see also FIGS. 18–21).

Said peptide also includes the derived peptides or polypeptides comprising between 5 and 540 amino acids (SEQ ID NO: 23–36 and SEQ ID NO: 58 and their fragments of at least 5 amino acids) and in particular a fragment of 538 amino acids, starting at the first methionine of the sequence SEQ ID NO: 26 (enverin).

According to an advantageous embodiment of said peptides they are in particular selected from the sequences SEQ ID NO: 23–36, 58, in particular the sequence SEQ ID NO: 26 and its C-terminal fragments, either from the amino acid 291, or from the amino acid 321, starting from the first methionine.

According to another advantageous embodiment of said peptides, they are obtained from nucleic sequences as defined above, in which at least one non-sense codon may be replaced with a codon encoding one of the following amino acids: Phe (F), Leu (L), Ser (S), Tyr (Y), Cys (C), Trp (W), Gln (O), Arg (R), Lys (K), Glu (E) or Gly (G).

The invention thus includes the deduced peptides or the deduced proteins corresponding to all or part of the nucleic sequences described in the invention, and optionally exhibiting modifications with the reference sequences described in the invention, when they are expressed in some patients. In particular, the invention includes the complete or partial sequences obtained according to the 3 sense reading frames and the 3 reverse and complementary reading frames (see FIGS. 18–21).

Advantageously, the analysis of the structure of the env domain of HERV-7q, called enverin, made it possible to demonstrate successively:

- an N-terminal signal peptide (region 1–21) and two transmembrane domains (region 320–340; 455–477), responsible for interactions with membrane lipid or protein motifs,
- an immunomodulatory motif of the CKS-17 (Haraguchi et al., (1995), 92, 5568–5571)/CKS-25 type. It is possible to note, in this regard, the presence of an Ra1D motif inside the peptide of the CKS-17/CKS-25 type of HERV-7q and a motif RvaD at position 363 which correspond to the consensus W/RxxD, proposed for the active site of the TGF-βs (Huang et al., J. Biol. Chem., 1997, 272, 27155–27159), potent factors associated with growth, with differentiation and with morphogenesis and which are associated with many human pathological conditions, such as tumor processes (Tang et al., (1998), Nat. Med., 4, 802–807) or neuro-degenerative diseases (Flanders et al., (1998), Prog. Neurobiol., 54, 71–85). The peptides according to the invention containing these motifs can advantageously serve as antagonists by inhibiting the attachment of the TGF-βs to their natural receptors,
- N-glycosylation motifs. The glycosylation of the envelope proteins of retroviruses appears to be directly associated with their functional properties, for example by influencing the number of determinants available in the T cells or by promoting recognition of antigens by the T cells. Glycosylation could play a role in the outbreak or the spread of a pathological condition with an autoimmune component. The glycosylations are necessary for maintaining the conformation of certain epitopes, in particular during the production of a recombinant envelope protein so as to develop a diagnostic reagent and to promote the efficacy of a possible vaccine. Positions 171, 210, 216, 236, 244, 283 and 411. Expected number at random: 3.2
- prenylation sites. Prenylation is an essential mechanism for attachment to the cell membrane and for the targeting of certain proteins. This targeting process could be essential for the production of specific therapeutic agents capable of interfering with the production and regulation of the traffic of cellular complexes calling into play proteins involved in the cell interactions, growth and movement. Positions 188 and 290. Expected number at random: 1.8
- targeting sites in the endoplasmic reticulum. These sites could make it possible to bring about the targeting toward the endoplasmic reticulum in order to carry out the modifications necessary for promoting membrane crossing. Positions 353 and 431. Expected number at random: 0.2

Moreover, the inventors have shown that a number of peptides derived from the env protein of HERV-7q (enverin) have a high affinity/half-life for the class I HLA alleles. CADD analysis has made it possible to select candidate peptides, for which the best scores are indicated in Table I:

TABLE I

| Location | Sequence | HLA molecule | Score | Sequence No. |
|---|---|---|---|---|
| 399 | FLGEECCYYV | A-0201 | 7214 | SEQ ID NO: 68 |
| 462 | LLFGPCIFNL | A-0201 | 1792 | SEQ ID NO: 69 |
| 189 | CLPLNFRPYV | A-0201 | 1453 | SEQ ID NO: 70 |
| 439 | GLLSQWMPWI | A-0201 | 488 | SEQ ID NO: 71 |
| 263 | CLPSGIFFV | A-0201 | 5103 | SEQ ID NO: 72 |
| 444 | WMPWILPFL | A-0201 | 897 | SEQ ID NO: 73 |
| 252 | IRWVTPPTQI | B-2705 | 3000 | SEQ ID NO: 74 |
| 432 | LRNTGPWGLL | B-2705 | 2000 | SEQ ID NO: 75 |
| 158 | LRTHTRLVSL | B-2705 | 2000 | SEQ ID NO: 76 |
| 316 | KRVPILPFVI | B-2705 | 1800 | SEQ ID NO: 77 |
| 25 | CRCMTSSSPY | B-2705 | 1000 | SEQ ID NO: 78 |
| 137 | TRVHGTSSPY | B-2705 | 1000 | SEQ ID NO: 79 |
| 124 | AREKHVKEVI | B-2705 | 600 | SEQ ID NO: 80 |
| 478 | SRIEAVKLQM | B-2705 | 600 | SEQ ID NO: 81 |
| 442 | SQWMPWILPF | B-2705 | 500 | SEQ ID NO: 82 |
| 405 | CYYVNQSGI | Kd | 2400 | SEQ ID NO: 83 |
| 346 | FYYKLSQEL | Kd | 2400 | SEQ ID NO: 84 |
| 244 | TYTTNSQCI | Kd | 2400 | SEQ ID NO: 85 |
| 291 | SFLVPPMTI | Kd | 1600 | SEQ ID NO: 86 |
| 406 | YYVNQSGIV | Kd | 1200 | SEQ ID NO: 87 |
| 167 | LFNTTLTGL | Kd | 1152 | SEQ ID NO: 88 |
| 463 | LFGPCIFNL | Kd | 960 | SEQ ID NO: 89 |
| 253 | RWVTPPTQI | Kd | 480 | SEQ ID NO: 90 |
| 449 | LPFLGPLAAI | B-5102 | 2200 | SEQ ID NO: 91 |
| 3 | LPYHIFLFTV | B-5102 | 1210 | SEQ ID NO: 92 |
| 331 | GALGTGIGGI | B-5102 | 798 | SEQ ID NO: 93 |
| 321 | LPFVIGAGVL | B-5102 | 550 | SEQ ID NO: 94 |
| 499 | RRPLDRPAS | B-2705 | 600 | SEQ ID NO: 95 |
| 194 | FRPYVSIPV | B-2705 | 600 | SEQ ID NO: 96 |
| 383 | RRALDLLTA | B-2705 | 600 | SEQ ID NO: 97 |
| 39 | WRMQRPGNI | B-2705 | 600 | SEQ ID NO: 98 |
| 423 | DRIQRRAEEL | B14 | 1800 | SEQ ID NO: 99 |
| 158 | LRTHTRLVSL | B14 | 600 | SEQ ID NO: 100 |
| 359 | ERVADSLVTL | B14 | 540 | SEQ ID NO: 101 |
| 463 | LFGPCIFNLL | Kd | 1658 | SEQ ID NO: 102 |
| 345 | QFYYKLSQEL | Kd | 1152 | SEQ ID NO: 103 |
| 443 | QWMPWILPFL | Kd | 691 | SEQ ID NO: 104 |
| 405 | CYYVNQSGIV | Kd | 500 | SEQ ID NO: 105 |
| 474 | NFVSSRIEAV | Kd | 480 | SEQ ID NO: 106 |
| 221 | GPLVSNLEI | B-5102 | 1320 | SEQ ID NO: 107 |
| 190 | LPLNFRPYV | B-5102 | 726 | SEQ ID NO: 108 |

TABLE I-continued

| Location | Sequence | HLA molecule | Score | Sequence No. |
|---|---|---|---|---|
| 449 | LPFLGPLAAI | B-5101 | 1144 | SEQ ID NO: 109 |
| 488 | EPKMQSKTKI | B-5101 | 968 | SEQ ID NO: 110 |
| 3 | LPYHIFLFTV | B-5101 | 629 | SEQ ID NO: 111 |
| 125 | REKHVKEVI | Kk | 1000 | SEQ ID NO: 112 |
| 312 | KPRNKRVPIL | B7 | 800 | SEQ ID NO: 113 |
| 378 | VVLQNRRAL | Db | 792 | SEQ ID NO: 114 |
| 377 | AVVLQNRRAL | Db | 660 | SEQ ID NO: 115 |
| 321 | LPFVIGAGV | B-5101 | 629 | SEQ ID NO: 116 |
| 304 | DLYSYVISK | A3 | 540 | SEQ ID NO: 117 |
| 301 | TEQDLYSYVI | Kk | 500 | SEQ ID NO: 118 |

This Table I indicates an estimation of the dissociation half-life of a peptide of enverin with an allele of the class I HLA system (the tables of Parker coefficients: J. Immunol, (1994), 152, 163–175). The location indicates the position of the first amino acid of the peptides tested in the enverin sequence. The one-letter code is used for the amino acid sequence. The scores around 500 or greater than 500 were selected. By way of comparison, an analysis was carried out on a concatenation of peptides (polypeptide of 4968 amino acids) reputed to bind the molecules of the class I major histocompatibility complex (Rammensee, Immunogenetics, (1995), 41, 178–228); the ten best scores recorded for nonapeptides and the HLA type A_0201 are respectively 4984, 4047, 2406, 1267, 800, 705, 607, 591, 591 and 577.

It can be seen from this Table I that some molecules of the type I major histocompatibility complex are capable of binding peptides derived from enverin, thus assimilated with peptides of viral or tumor origin, at the level of the endoplasmic reticulum. The complexes formed at the level of the endoplasmic reticulum are then transported to the cell surface, which causes the destruction of the target cell by the cytotoxic T lymphocytes. The peptides identified generally comprise 8 to 10 amino acids. Studies have shown that some alleles of the class I HLA system are thus associated with certain pathologies, in particular with an autoimmune character, such as HLA-327 with rheumatoid spondylitis or HLA-B51 with Behcet's disease.

A peptide capable of binding a particular class I molecule is consequently capable of functioning as a T cell epitope.

Consequently, the present invention also includes the fragments 399–471 and 244–271 of enverin which advantageously group together several epitopes having high affinity for various haplotypes of the class I HLA system. The use of all or some of these polypeptides is consequently capable of promoting an increase in the T cell repertoire, by allowing better efficacy of the immune response in the context of the various immunotherapeutic, prophylactic or vaccine strategies. These polypeptides may be advantageously delivered for example by the use of viral vectors, viral or synthetic particles, lipopeptides, conventional adjuvants, naked nucleic acids or nucleic acids adsorbed on particles, or liposomes.

For the purposes of the present invention, the peptides may be chemically or biochemically modified; some of the amino acids may be replaced with an analogous amino acid, according to conventional criteria for homologies (A or G; S or T; I, L or V; F, Y or W; N or Q; D or E).

The subject of the present invention is also immunogenic or vaccine compositions for protecting against autoimmune diseases, in particular in at risk subjects, characterized in that it comprises at least one peptide comprising at least one motif of the CKS type and/or at least one peptide consisting of a motif having affinity with one of the haplotypes of the class I or class II HLA system and a pharmaceutically acceptable vehicle.

According to an advantageous embodiment of said composition, said motif is selected from the group consisting of peptides, as defined in Table I above.

According to another advantageous embodiment of said composition, said peptide has the following sequence:

sequence CKH: LONRRALDLLTAERGGTclFLGEECCYYV (SEQ ID NO: 120).

It is remarkable to note at the level of position 380 of the enverin protein, the contiguousness of the motifs of the CKS-17 type (underlined) and of the peptide having the highest score (in bold; see peptide at position 399 in Table I, SEQ ID NO: 68) in the sequence CKH.

The clonal activation of the subgroups of lymphocytes, for example of cytotoxic lymphocytes, by the peptides in Table I and by extension their homologues, is blocked by conventional immunotherapy means such as for example serotherapy and vaccination.

The combination of two sequences or of the sequences analogous to the CKH peptide (SEQ ID NO: 120), is capable of causing a synergistic process in the immune response, which could bring into play additional signaling and activation pathways capable of modulating the lymphocyte activation.

The vaccination relates to the production of antibodies directed against the peptides of Table I, according to the rules of the prior art and according to the methods of release controlled by artificial or cellular implants using a composition as defined above and by using gene therapy means, such as for example expression of nucleic sequences encoding the peptides of Table I. Consequently, the subject of the invention is also immunogenic or: vaccine compositions, characterized in that they comprise a vector including at least one nucleic sequence encoding a peptide as defined in Table I, optionally combined with a sequence encoding a motif of the CKS-17 type.

The serotherapy relates to the use of neutralizing antibodies produced from the peptides of Table I and their homologues.

The protein products generated by the endogenous retroviral sequences or produced in parallel may be advantageously characterized by micro-methods of analysis and quantification of peptides and proteins: HPLC/FPLC or equivalent, capillary electrophoresis or equivalent, microsequencing techniques (Edman method or equivalent, mass spectrometry and the like).

The subject of the invention is also antibodies directed against one or more of the peptides described above and their use either for carrying out a method, in particular a differential method, of in vitro detection of the presence of such a sequence in an individual, or for the preparation of a composition capable of being used in serotherapy in neuropathological conditions with an autoimmune component.

Said antibodies are advantageously polyclonal or monoclonal antibodies obtained by an immunological reaction from a human, mammalian or avian organism or other species toward the proteins, as defined above.

The subject of the present invention is a method for the differential immunological screening of normal or pathological human endogenous retroviral sequences of the HERV-7q family, characterized in that it comprises bringing a biological sample into contact with an antibody according to the invention, the reading of the result being visualized by an appropriate means, in particular EIA, ELISA, RIA, fluorescence.

By way of illustration, such an in vitro diagnostic method according to the invention comprises bringing a biological sample collected from a patient into contact with antibodies according to the invention and detecting with the aid of any appropriate method, in particular with the aid of labeled anti-immunoglobulins, the immunological complexes formed between the proteins produced normally or pathologically and the antibodies.

Monoclonal or polyclonal antibodies, produced from antigens corresponding to synthetic peptides, or recombinant polypeptide or proteins make it possible to monitor the expression of the peptides or proteins produced normally or pathologically. The analysis is preferably carried out by ELISA or equivalent, Western blotting or equivalent, or by immunohistochemistry.

The peptides or proteins, derived from the endogenous retroviral sequences or whose expression is associated with the expression of these endogenous retroviral sequences, are tested for and identified.

The subject of the present invention is also a method for the identification and detection of endogenous retroviral motifs which are abnormally expressed in the context of pathological conditions associated with cancer, or of neuropathological conditions, in particular autoimmune neuropathological conditions, at the forefront of which is multiple sclerosis, characterized in that it comprises the comparative analysis of the sequences extracted from a biological sample and the sequences according to the invention.

The subject of the present invention is also the application of the nucleic sequences or of the protein sequences according to the invention to the diagnosis of, to the prognosis of, to the evaluation of genetic susceptibility to, any induced, congenital or acquired human diseases, in particular those with cancerous, autoimmune and/or neurological components, such as multiple sclerosis, the associated syndromes and the neurodegenerative diseases in which all or part of the nucleic sequences according to the invention and related endogenous or exogenous forms are involved.

The subject of the present invention is also hybrid nucleic sequences, characterized in that they comprise nucleic sequences or motifs according to the invention, combined with sequences or motifs of endogenous origin or of exogenous origin or induced exogenously.

The subject of the present invention is, in addition, a recombinant cloning or expression vector, characterized in that it comprises a nucleic sequence in accordance with the invention.

Therapeutic strategies may be envisaged by using some of the nucleic sequences contained in HERV-7q and the sequences of the same family or deduced polypeptide structures or by the use of peptides or proteins, or of specific antibodies.

In accordance with the invention, all or part of the endogenous retroviral nucleic sequences of the HERV-7q type may be used for use as a vector or as vector elements for therapeutic use, in particular the LTR sequences and the gag region (SEQ ID NO: 2, 21 and 22).

The advantage of such sequences lies in the safety of the vector thus formed, in the possibility of a targeted specific insertion in a well-defined region by a strategy similar to homologous recombination, in cellular targeting, which is optionally transient in the case of a placental expression in women. Another aspect relates to the possibility of combining with the genes of interest the biologically active retroviral motifs (immunomodulatory peptides, as represented in the sequences SEQ ID NO: 68–118, below, fusogenic peptide and the like).

The subject of the present invention is also transgenic animals, characterized in that they comprise all or part of a sequence of the HERV-7q type (SEQ ID NO: 1–22 and 61).

Table II below establishes the correspondences between the sequence numbers as they appear in the sequence listing and the name of the various sequences.

TABLE II

| SEQ ID NO: | DESIGNATION |
|---|---|
| 1 | Nucleic acid: 7 env |
| 2 | Nucleic acid: gag |
| 3 | Nucleic acid: HERV-7q |
| 4 | Nucleic acid: HE2 |
| 5 | Nucleic acid: HE3 |
| 6 | Nucleic acid: HG3 |
| 7 | Nucleic acid: HE4 |
| 8 | Nucleic acid: HE5 |
| 9 | Nucleic acid: HE6 |
| 10 | Nucleic acid: HG6 |
| 11 | Nucleic acid: HE7 |
| 12 | Nucleic acid: HE8 |
| 13 | Nucleic acid: HG8 |
| 14 | Nucleic acid: HE9 |
| 15 | Nucleic acid: HE10 |
| 16 | Nucleic acid: HE11 |
| 17 | Nucleic acid: HG11 |
| 18 | Nucleic acid: HE12 |
| 19 | Nucleic acid: HG12 |
| 20 | Nucleic acid: R1 |
| 21 | Nucleic acid: RIF |
| 22 | Nucleic acid + deduced env protein: HERV-7q |
| 23 | Fragment of deduced env protein according to SEQ ID NO: 22 |
| 24 | Fragment of deduced env protein according to SEQ ID NO: 22 |
| 25 | Fragment of deduced env protein according to SEQ ID NO: 22 |
| 26 | Protein: enverin |
| 27 | Fragment of deduced env protein according to SEQ ID NO: 22 |
| 28 | Nucleic acid + protein deduced from gag: HERV-7q |
| 29 | Fragment of deduced gag protein according to SEQ ID NO: 28 |
| 30 | Fragment of deduced gag protein according to SEQ ID NO: 28 |
| 31 | Fragment of deduced gag protein according to SEQ ID NO: 28 |
| 32 | Fragment of deduced gag protein according to SEQ ID NO: 28 |
| 33 | Fragment of deduced gag protein according to SEQ ID NO: 28 |
| 34 | Fragment of deduced gag protein according to SEQ ID NO: 28 |
| 35 | env protein: reading frame 1 |
| 36 | gag protein |
| 37 | Nucleic acid: G1F (primer) |
| 38 | Nucleic acid: G1R (primer) |
| 39 | Nucleic acid: G2F (primer) |
| 40 | Nucleic acid: G2R (primer) |
| 41 | Nucleic acid: G4F (primer) |
| 42 | Nucleic acid: G3F (primer) |
| 43 | Nucleic acid: G4R (primer) |
| 44 | Nucleic acid: G5R (primer) |
| 45 | Nucleic acid: E1F (primer) |
| 46 | Nucleic acid: E1R (primer) |
| 47 | Nucleic acid: E2F (primer) |
| 48 | Nucleic acid: E2R (primer) |
| 49 | Nucleic acid: E3F (primer) |
| 50 | Nucleic acid: E3R (primer) |
| 51 | Nucleic acid: E4F (primer) |
| 52 | Nucleic acid: E4R (primer) |
| 53 | Nucleic acid: E5F (primer) |
| 54 | Nucleic acid: E6F (primer) |
| 55 | Nucleic acid: E5R (primer) |
| 56 | Nucleic acid: ExF (primer) |
| 57 | Nucleic acid: ExR (primer) |
| 58 | Protein gag |
| 59 | Nucleic acid: Sequence A (insertion sequence) |
| 60 | Nucleic acid: Sequence B (insertion sequence) |
| 61 | Nucleic acid: HE13 |
| 62 | Nucleic acid: RH7 |
| 63 | Nucleic acid: RAM75 |
| 64 | Nucleic acid: RAV73 |
| 65 | Nucleic acid: RBP3 |
| 66 | Nucleic acid: HI3 |
| 67 | Nucleic acid: LTX |
| 68 | Peptide Table I |
| 69 | Peptide Table I |
| 70 | Peptide Table I |
| 71 | Peptide Table I |
| 72 | Peptide Table I |

TABLE II-continued

| SEQ ID NO: | DESIGNATION |
|---|---|
| 73 | Peptide Table I |
| 74 | Peptide Table I |
| 75 | Peptide Table I |
| 76 | Peptide Table I |
| 77 | Peptide Table I |
| 78 | Peptide Table I |
| 79 | Peptide Table I |
| 80 | Peptide Table I |
| 81 | Peptide Table I |
| 82 | Peptide Table I |
| 83 | Peptide Table I |
| 84 | Peptide Table I |
| 85 | Peptide Table I |
| 86 | Peptide Table I |
| 87 | Peptide Table I |
| 88 | Peptide Table I |
| 89 | Peptide Table I |
| 90 | Peptide Table I |
| 91 | Peptide Table I |
| 92 | Peptide Table I |
| 93 | Peptide Table I |
| 94 | Peptide Table I |
| 95 | Peptide Table I |
| 96 | Peptide Table I |
| 97 | Peptide Table I |
| 98 | Peptide Table I |
| 99 | Peptide Table I |
| 100 | Peptide Table I |
| 101 | Peptide Table I |
| 102 | Peptide Table I |
| 103 | Peptide Table I |
| 104 | Peptide Table I |
| 105 | Peptide Table I |
| 106 | Peptide Table I |
| 107 | Peptide Table I |
| 108 | Peptide Table I |
| 109 | Peptide Table I |
| 110 | Peptide Table I |
| 111 | Peptide Table I |
| 112 | Peptide Table I |
| 113 | Peptide Table I |
| 114 | Peptide Table I |
| 115 | Peptide Table I |
| 116 | Peptide Table I |
| 117 | Peptide Table I |
| 118 | Peptide Table I |
| 119 | Nucleic acid: BLIMP-1 |
| 120 | Peptide: CKH |
| 121 | Nucleic acid: F645 (primer) |
| 122 | Nucleic acid: PS5D (primer) |

In addition to the preceding arrangements, the invention also comprises other arrangements which will emerge from the description which follows, which refers to exemplary embodiments of the method which is the subject of the present invention as well as to the appended drawings, in which:

Figure 1A:
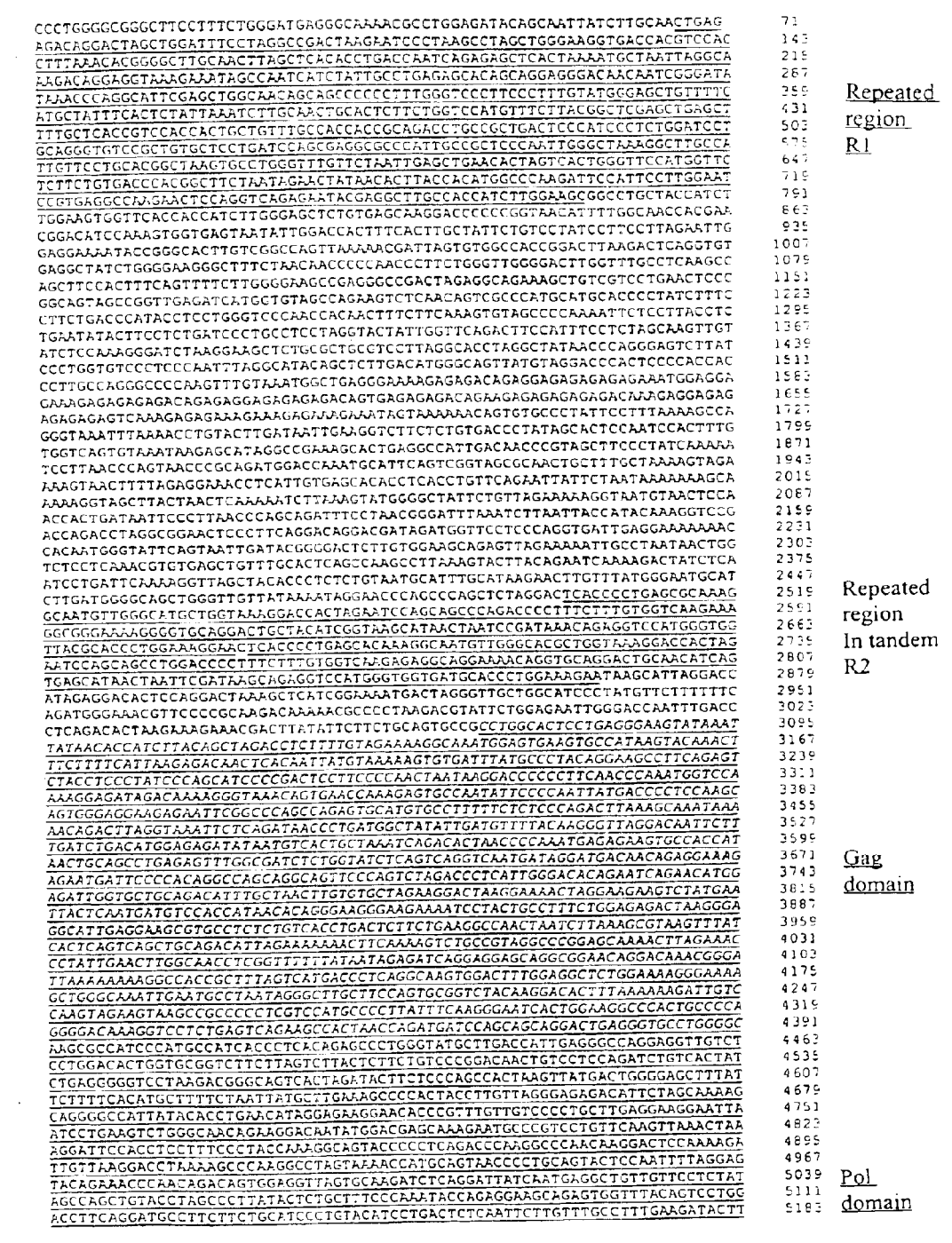

FIG. 1. Human nucleic sequence HERV-7q, whose analysis and treatment make it possible to characterize a novel endogenous retroviral structure.

The repeat nucleic regions of type R1 and R2 and the gag, pal and env domains are underlined. The gag and env type domains are in italics. The region homologous to a noncoding 3' portion of Rab7 is double underlined.

FIG. 2. Map of the human endogenous retroviral region HERV-7q. The upper part of the figure corresponds to an anonymous region of the human genome situated on the long arm of chromosome 7. The repeat domains (1), gag (2), pol (3) and env (4) of HERV-7q can be identified. The C-terminal env region (4.3) is prolonged upstream in the form of a long open reading frame (4.2). The domain 4.1 corresponds to the N-terminal region of the env domain.

FIG. 3. Comparison of the repeat nucleic sequences situated at the boundaries of HERV-7q. The 5' (top) and 3' (bottom) repeat nucleic regions are compared and the identical bases are indicated by two dots.

FIG. 4. Deduced sequence having an open reading frame in the env-type domain of HERV-7q according to the longest open reading frame rule.

FIG. 5. Sequences around the CKS-17 domain identified in various deduced env domains of the HERV-7q family and comparison with reference CKS-17 motifs.
1) HE2—2) HERV-7q —3) GenBank accession No.: M85205—4) HE7—5) HE9-6) CKS-17; the peptide motif endowed with immunomodulatory properties is underlined—7) gp20 of retrovirus type D (SRV-Pc).

FIG. 6. Possible deduced sequence of the gag-type domain identified in HERV-7q established according to the longest open reading frame rule. X and / correspond to a non-sense codon and to a reading frame shift, respectively. The underlined sequence corresponds to the beginning of the pol domain.

FIG. 7. Comparison of the nucleic regions covering the gag region of HERV-7q (top) and HERV-TcR (bottom) and their flanking regions. The identical bases are specified by two dots.

FIG. 8. Example of nucleic alignments of the env-type domain of HERV-7q with similar env-type domains present in human endogenous retroviral sequences of the same family. The non-sense codons are underlined: 1) HERV-7q—2) HE2 03) HE3—04) HE4.

FIG. 9. Nucleic alignments between the gag domain of HERV-7q and the corresponding domains belonging to the same family. Comparison with fragments of gag domains isolated from infectious retroviral agents. Sequences of infectious retroviral origin: EMBL database accession No.: 1) A60168—2) A60201—3) A60200—4) A60171. Human endogenous retroviral sequences: 5) HERV-7q—6) HG11—7) HG3. The figures indicated in the endogenous sequences correspond to the number of nucleotides inserted in order to optimize the alignment with the gag-type sequences identified in retroviruses of infectious origin.

FIG. 10. Alignment of a deduced gag protein, motif (top) belonging to an infectious retrovirus (EMBL accession No.: A60200) with the deduced gag protein motif (bottom) identified in HERV-7q. The non-sense codons are in bold and underlined. The identical amino acids are specified by 2 dashes. One dash indicates a deletion or a homologous amino acid.

FIG. 11. Alignment of an env motif (top) belonging to an infectious retrovirus (EMBL accession No.: A60170) with the env motif (bottom) identified in HERV-7q. The homologous nucleotides are specified by two dots and the deletions by a dash.

FIG. 12. Comparison between the env domain of HERV-7q (top) and the env domain of HERV-9 (bottom). The 66% homology is limited to the 3' region of the env domain of HERV-7q and HERV-9, respectively between nucleotides 8976 nt and 9500 nt of HERV-7q and nucleotides 2898 nt and 3465 nt of HERV-9 (GenBank accession No.: X57147). Numerous insertions/deletions are also observed.

FIG. 13. Homology between a portion of the sequence of the transcript encoding RH7 (top, SEQ ID NO: 62) and an RGH2 motif (bottom—GenBank accession No.: D11018).

FIG. 14. Identification of the sequence of the transcript encoding RAM75 (SEQ ID NO: 63), corresponding to the gene for an ATPase of PEX1 type. The coding exons are underlined. The initiation and non-sense codons as well as the putative poly-adenylation sites are in bold and underlined. The region in italics corresponds to the beginning of the endogenous retroviral sequence RH7.

FIG. 15. Sequence of the transcript encoding RAV73 (SEQ ID NO: 64), situated at 0.7 kb downstream of HERV-7q; the nucleic sequences capable of encoding one or more polypeptides are underlined.

FIG. 16. Comparison between the 3' LTR sequence (top) of HERV-7q and the intron sequence LTX (SEQ ID NO: 67), situated in the FMR2 gene, associated with fragile X (bottom).

FIG. 17. Detection of modifications on the nucleotide sequence (ID NO: 3), in patients suffering from MS. The modified bases, in at least one patient, are underlined. The primers used are in italics (sequences SEQ ID NO: 121 and 122). The initiation ATG and the non-sense codon are in bold.

FIG. 18. The env coding portion of the HERV-7q sequence (sequence ID NO: 3), with 3 reading frames.

FIGS. 19, 20, 21. Separate presentation of the env protein according to the 3 reading frames.

FIG. 22. Nucleic sequence containing the retroviral sequence RH7 situated in 5' of the HERV-7q sequence. The sequence in italics corresponds to the beginning of the HERV-7q sequence. The RH7 sequence is underlined. Two putative polyadenylation sites are in bold.

FIG. 23. Sequence of the transcript encoding RBP3 containing nucleotide motifs identified in the nucleic sequence encoding the Blimp-1 gene.

FIG. 24. Sequence of the transcript encoding APS.

FIG. 25. Sequence of the transcript encoding Blimp-1; the coding portion is underlined; the initiation and termination codons are in bold.

FIG. 26. Sequence of the transcript encoding FMR2. The coding portion is underlined. The initiation and non-sense codons are in bold.

It should be clearly understood, however, that these examples are given solely by way of illustration of the subject of the invention and do not in any manner constitute a limitation thereto.

EXAMPLE 1

Detection, by Gene Amplification, of a Nucleic Sequence Belonging to a Domain of the gag or env Type According to the Invention, in a Genomic DNA Sample of Human or Mammalian Origin The gene amplification is carried out using genomic DNA isolated from blood. An anticoagulant treatment is carried out with 1 ml of a citrate solution (per liter: 4.8 g of citric acid, 13.2 g of sodium citrate, 14.7 g of glucose) per 6 ml of fresh blood. After centrifugation of 20 ml of blood for 15 min at 130 000 g, the supernatant is removed and the fraction enriched with white blood cells is transferred into a new tube and then recentrifuged under the same conditions as above. The fraction enriched with white blood cells is resuspended in an extraction buffer (10 nM Tris-HCl, 0.1 M EDTA, 20 µg/ml of pancreatic RNAse treated so as to eliminate the DNAses, 0.5% SDS, pH 8.0), and then incubated for 1 hour at 37° C. Proteinase K is added at a final concentration of 100 µg/ml. The suspension of lyzed cells is incubated at 50° C. for 3 hours, with occasional stirring, and then treated with an equal volume of phenol equilibrated with 0.5 M Tris-HCl, pH 8.0. The emulsion formed is placed on a wheel for one hour and then centrifuged at 5 000 g for 15 min at room temperature. The aqueous solution is treated and deproteinized by a triple phenol extraction in order to obtain a level of purification corresponding to an absorbance A260/A280 final ratio greater than 1.75. The aqueous fraction is precipitated with 0.2 vol. of 10 M sodium acetate and 2 vol. of ethanol. The DNA is then either collected with the tip of a bent Pasteur pipette, or centrifuged at 5 000 g for 5 min at room temperature. The DNA or the DNA pellet is washed twice with 70% ethanol and then taken up in 1 ml of TE, pH 8.0 so as to be eluted, with gentle stirring, for 12 to 24 hours.

Oligonucleotides specific for the endogenous sequences described according to the invention are chosen in order to amplify the gag or env region of the endogenous retroviral regions described according to the invention. The genomic DNA studied is obtained from patients having pathological conditions such as multiple sclerosis and from individuals reputed to be healthy.

The thermostable DNA polymerases used were chosen for their high accuracy during the amplification process, such as Vent DNA polymerase (Biolabs) and the like, and are used according to the conditions recommended by the supplier.

The amplification strategy uses, depending on the case, a simple PCR, or a nested or seminested PCR.

Oligonucleotides used to amplify the gag region:
primer G1F, sense, located in the region upstream of the gag domain of HERV-7q (SEQ ID NO: 37),
primer G1R, antisense, located in the 3' terminal region of the gag domain (SEQ ID NO: 38).

The fragment of 1505 nt amplified by the pair G1F-G1R; 1505 nt is used to generate the probes capable of hybridizing the various PCR amplification products.

primer G2F, sense nested (SEQ ID NO: 39),
primer G2R, antisense nested (SEQ ID NO: 40),
primer G4F, sense nested (SEQ ID NO: 41)
primer G3F, sense nested (SEQ ID NO: 42),
primer G4R, antisense nested (SEQ ID NO: 43),
primer G5R, antisense nested (SEQ ID NO: 44).

Oligonucleotides used to amplify the env region of HERV-7q:
primer E1F, sense (SEQ ID NO: 45),
primer E1R, antisense (SEQ ID NO: 46).

The fragment of 2529 nt amplified by the pair of primers E1F-E1R is used to generate the probes capable of hybridizing the various PCR amplification products.

primer E2F, sense. (SEQ ID NO: 47),
primer E2R, antisense (SEQ ID NO: 48),
primer E3F, sense (SEQ ID NO: 49),
primer E3R, antisense (SEQ ID NO: 50),
primer E4F, sense (SEQ ID NO: 51),
primer E4R, antisense (SEQ ID NO: 52),
primer E5F, sense (SEQ ID NO: 53),
primer E6F, sense (SEQ ID NO: 54),
primer E5R (SEQ ID NO: 55),
primer ExF (SEQ ID NO: 56),
primer ExR (SEQ ID NO: 57).

The PCR is carried out using 50 to 200 ng of genomic DNA. The PCR conditions are those recommended by the supplier. The amplification cycle conditions are carried out in 50 µl: denaturation of 94° C. for 1 min, hybridization of 70° C. for 1 min, and extension at 72° C. for 1 to 2 min, depending on the amplified fragments. After 35 cycles, a terminal reaction is carried out at 72° C. for 10 min. Automated sequencing of the amplified samples is carried out with the aid of an Applied Biosystems type ABI 377 sequencer or another comparable model, according to the protocols provided by the manufacturer.

In the case of a nested or seminested PCR, the same experimental conditions are used, the only difference being that the genomic DNA sequence is replaced with 5 to 10 µl of the amplification product derived from the first PCR.

Two independent amplifications are carried out using the same sample. A control reaction is carried out by replacing the DNA sample with water in order to detect possible contaminants.

EXAMPLE 2

Detection, by Gene Amplification, of a Nucleic Sequence According to the Invention in a Biological Sample of Genomic DNA Collected from Patients Having an Existing Candidate Pathological Condition or Suspected of Having this Pathological Condition The amplification protocol is the same as in Example 1, apart from the origin of the sample which is obtained from patients having a candidate pathological condition. A genomic DNA sample reputed to be normal is systematically integrated into the set of amplified pathological samples and then analyzed.

The PCR products are separated on a 1.5% agarose gel and then transferred in the presence of 0.4 N sodium hydroxide on a charged nylon membrane. Hybridization is carried out with a specific probe corresponding to the PCR fragments amplified either with the pair G1F-G1R or the pair E1F-E1R. The probe is labeled by incorporating dUTP-digoxygenin according to the supplier's protocol (Boehringer Mannheim). The hybridization is carried out in a hybridization buffer (5×SSC, 50% formamide, 0.1% lauroylsarcosine, 0.02% SDS, 2% blocking reagent Boehringer) overnight at 42° C. The Southern is washed for twice 5 min at room temperature in a 2×SSC solution containing 0.1% SDS. Next, a high stringency wash is carried out twice for 15 min at 55° C. in a 0.1×SSC solution containing 0.1% SDS. The hybridization is visualized according to the supplier's protocol (Boehringer Mannheim), in the presence of a chemiluminescent substrate for alkaline phosphatase, of the CSPD or CDP-STAR type. The filter is visualized after a 15 min exposure at 60° C.

SSCP (single strand conformation polymorphism) analysis makes it possible to detect discrete modifications of the sequence of the fragments amplified by PCR. The PCR is carried out in the presence of dCTP labeled with $^{32}$P. The sample to be analyzed is denatured at 95° C. for 10 min in the presence of loading buffer, and then immediately loaded onto a 10% polyacrylamide gel containing 7.5% glycerol. The migration is carried out at 4° C. at 8–10 W. The gel is dried and then autoradiographed.

The PCR fragments likely to exhibit an alteration of their nucleotide sequence are sequenced according to Example 1.

Hybridization with the aid of a specific oligonucleotide (17 mers to 20 mers) corresponding to the modified nucleotide region makes it possible to identify the samples having an identical modification (ASO method). Briefly, the southern is hybridized with an oligonucleotide which is distally labeled either with $^{32}$P, or in the presence of digoxygenin (according to the Boehringer Mannheim protocol) and then washed under stringent conditions at 65° C. in a 6×SSC solution containing 0.05% sodium pyrophosphate.

For example, an automated nucleotide sequencing was carried out on six PCR fragments obtained from 5 patients suffering from MS and a control reputed to be normal, and which were amplified using the primers F645: CTTCAAA-CAACAACCAGGAGG (SEQ ID NO: 121) (situated 26 nucleotides upstream of the initiation methionine of enverin) and PS5D: TTGGGGAGGTTGGCCGACGA (SEQ ID NO: 122) (situated 6 nucleotides downstream of the non-sense codon of enverin). Modifications of the sequence of enverin were observed on the DNA from some patients (FIG. 17).

EXAMPLE 3

Detection of a Protein According to the Invention in a Biological Sample

Preparation of a purified protein fraction of cerebrospinal fluid from patients suffering from MS After a treatment at 56° C. for 30 min and removal of the immunoglobulins on a G HiTrap protein column (Pharmacia), the equivalent of 10 ml of CSF is deposited on a DEAE Sepharose CL-6B column (Pharmacia) The elution is carried out in 20 mM Tris-HCl, pH 8.8, and a gradient from 0 to 0.4 M NaCl, and then the fraction is dialyzed twice against a phosphate-NaCl buffer (PBS). After concentration on Ultrafree-MC (Millipore), the fraction is deposited on a Superose 12 column (FPLC Pharmacia) and eluted in the presence of PBS. After separation by polyacrylamide-SDS gel electrophoresis and electrotransfer onto an Immobilon-P membrane (Millipore), the protein bands are subjected to controlled trypsin hydrolysis.

Analysis of the Protein Fraction by Mass Spectrometry

The peptides digested in the presence of trypsin are analyzed by the MALDI-TOF method, which allows the analysis of peptides present in a mixture (COTTRELL J. S., Pept. Res., 1997, 7, 115–124). The peptides characterized according to their mass are compared with the proteins and with the associated proteins according to the invention.

EXAMPLE 4

Detection of Specific Antibodies to the env Domain of HERV-7q

The identification of a long open reading frame in the env sequence of HERV-7q made it possible to determine a deduced protein sequence SEQ ID NO: 22 and 35 and FIGS. 18–20 of a region of the said gene.

The protein sequences deduced from the sequences ID NO: 22, 35 and FIGS. 18–20 are positioned as follows with respect to FIG. 1 or the sequence ID NO: 3:

SEQ ID NO: 22 (reading frame 1) and FIG. 19: beginning of the coding sequence: position 7874, end of the coding sequence 1st nonsense codon (position 9493)

SEQ ID NO: 35: beginning of the coding sequence: position 7874, end of the coding sequence 1st nonsense codon (position 9493) (reading frame 1)

FIG. 19: beginning of the coding sequence: position 6970, end of the coding sequence 1st nonsense codon (position 9493) (reading frame 1)

FIG. 20: beginning of the coding sequence: position 6971, the end of the reading frame is shifted depending on the case by 1, 2 or 3 codons FIG. 21: beginning of the coding sequence: position 6972, the end of the reading frame is shifted depending on the case by 1, 2 or 3 codons Various peptides corresponding to all or part of SEQ ID NO: 22 (see SEQ ID NO: 23–27 and 35) were synthesized by genetic engineering in order to test their antigenic specificity toward sera or tissues from patients suffering from MS, for example. Briefly, all or part of the env region of HERV-7q is subcloned into the vectors pQE30, 31 and 32. The vectors pQE30, 31 and 32 contain, in 5' of the multiple cloning site, the consensus sequences for transcription (the strong T5 bacteriophage promoter, 2 operators of the lactose operon) and translation (one synthetic ribosome binding site). Likewise, pQE30, 31 and 32 possess, in 3', the phage 1 transcription terminator as well as a Stop codon for translation. The expression of the protein is carried out after transformation in E. coli M15. The plasmid pQE30, 31 and 32 possess, upstream of the multiple cloning site, the coding sequence for a succession of 6 histidines having affinity for nickel ions. This stretch allows the purification of the expressed chimeric protein by adsorption on a resin consisting of a chelating ligand, nitrotriacetic acid (NTA), charged with 4 nickel ions (NI-NTA resin, Qiagen).

The transformation is carried out by electroporation or treatment with calcium chloride. For example, an E. coli M15 colony is incubated in 100 ml of LB medium containing 250 µg of kanamycin, with stirring at 37° C. until an $OD^{600}$ of 0.5 is obtained. After centrifugation for 5 minutes at 2000 g at 4° C., the bacterial pellet is taken up in 30 ml of TFB1 solution (100 mM rubidium chloride, 50 mM manganese chloride, 30 mM potassium acetate, 10 mM $CaCl_2$, 15% glycerol, pH 5.8), at 4° C. for 90 minutes. After a centrifugation of 5 minutes at 2000 g at 4° C., the bacterial pellet is taken up in 4 ml of TFB2 solution (10 mM rubidium chloride, 10 mM MOPS, 75 mM $CaCl_2$, 15% glycerol, pH 8). The cells may be kept at −70° C. in aliquots of 500 ml. 20 µl of the ligation and 125 µl of competent cells are mixed and placed on ice for 20 minutes. After a heat shock of 42° C. for 90 seconds, the cells are stirred for 90 minutes at 37° C. in 500 ml of Psi-broth medium (LB medium supplemented with 4 mM $MgSO_4$, 10 mM potassium chloride). The transformed cells are plated on LB-agar dishes supplemented with 25 µg/ml of kanamycin and 100 µg/ml of ampicillin, and the dishes are incubated overnight at 37° C.

The potentially recombinant clones are sub-cultured in an orderly manner on a nylon filter deposited on an LB-agar dish supplemented with 25 µg/ml of kanamycin and 100 µg/ml of ampicillin. After one night at 37° C., the recombinant clones are located by hybridization of the plasmid DNA with the nucleotide probe amplified by PCR with the pair of primers according to SEQ ID NO: 45 and SEQ ID NO: 46.

An independent colony containing the insert is inoculated at 20 ml of LB medium supplemented with 25 µg/ml of kanamycin and 100 µg/ml of ampicillin. After one night at 37° C., with stirring, 500 ml of the same medium are incubated at 1/50 with this preculture until an $OD^{600}$ of 0.8 is obtained, and then 1 to 2 mM final of IPTG is added. After 5 hours, the cells are centrifuged for 20 minutes at 4 000 g.

A portion of the cellular pellet is taken up in 5 ml of sonification buffer (50 mM of sodium phosphate, pH 7.8, 300 mM NaCl) and then placed on ice. After rapid sonification, the cells are centrifuged for 20 minutes at 10 000 g. A portion of the cellular pellet is taken up in 10 ml of a 30 mM Tris/HCl-20% sucrose solution pH 8. The cells are incubated for 5 to 10 minutes, with stirring, after addition of 1 mM EDTA. After a centrifugation of 10 minutes at 8 000 g at 4° C., the pellet is taken up in 10 ml of 5 mM ice cold $MgSO_4$. After 10 minutes on the ice, with stirring, the cells are centrifuged for 10 minutes at 8 000 g at 4° C.

The pellet is taken up in 5 ml/g in buffer A (6 M GuHCl (guanidine hydrochloride), 0.1 M sodium phosphate, 0.01 M Tris/HCl, pH 8), 1 hour at room temperature. The lysate is centrifuged for 15 minutes at 10 000 g at 4° C., and the supernatant is supplemented with 8 ml of Ni-NTA resin, pre-equilibrated in buffer A. After 45 minutes at room temperature, the resin is poured into a column, washed with 10 times the column volume with buffer A and then with 5 times the column volume with buffer B (8 M urea, 0.1 M sodium phosphate, 0.01 M Tris/HCl, pH 8). The column is washed with buffer C (8 M urea, 0.1 M sodium phosphate, 0.01 M Tris/HCl, pH 6.3) until A280 is less than 0.01. The recombinant protein is eluted with 10 to 20 ml of buffer D (8 M urea, 0.1 M sodium phosphate, 0.01 M Tris/HCl, pH 5.9) and then with 10 to 20 ml of buffer E (8 M urea, 0.1 M sodium phosphate, 0.01 M Tris/HCl, pH 4.5), and then with 20 ml of buffer F (6 M HCl, 0.2 M acetic acid). After SDS-PAGE analysis, the purified fraction(s) containing the chimeric protein allowed the production of antibodies in rabbits. The antibodies obtained are tested by Western blotting after visualization with a secondary antibody coupled to alkaline phosphatase.

Antibodies are obtained in the same manner, using peptides synthesized chemically according to the Merrifield technique (G. Barany and B. Merrifield, 1980, in *The peptides*, 2, 1–284, E. Gross and J. Meienhofer, Academic Press, New York).

The specific antibodies obtained are used for detection of the serum or tissue expression of all or part of the endogenous retroviral sequences according to the invention, in normal and pathological cases.

The proteins of serum or tissue origin are separated on acrylamide-SDS gel and then transferred onto a nitrocellulose filter with the aid of a Novablot 2117–2250 apparatus (LKB). The transfer is carried out on a Hybond C-extra sheet (Amersham) using a 100 mM CAPS buffer pH 11, methanol, water (V/V/V: 1/1/8) containing 1 mM $CaCl_2$. After a transfer of 1 hour at 0.8 $mA/cm^2$, the sheet is saturated for 1 hour at room temperature in PBS-0.5% gelatin. The sheet is brought into contact with the specific antibody at the concentration of 1/1 000 in PBS-0.25% gelatin. After 2 hours, the filter is washed 3 times 15 minutes in PBS-0.1% Tween-20, and then the filter is incubated for 30 minutes in the presence of a secondary antibody coupled to alkaline phosphatase (Promega), diluted 1/7 500 in PBS-0.25% gelatin. After three washes in PBS-0.1% Tween-20, the filter is equilibrated in a buffer (100 mM Tris-HCl, pH 9.5, 100 mM NaCl, 5 mM $MgCl_2$). The visualization is carried out in the presence of 45 µl of NBT at 75 mg/ml and 35 µl of BCIP at 50 mg/ml, per 10 ml of alkaline phosphatase buffer.

The chimeric proteins obtained by genetic engineering are also used for tests of biological activity, such as for example the test for biological activity of the CKS-17-type peptide identified in the env domain-of HERV-7q (FIG. 5).

EXAMPLE 5

Production of Ribonucleic Probes Encoding the env Sequences of HERV-7q

The PCR fragments obtained are subcloned into the plasmid PGEM 4Z (Promega) which possesses on either side of its multiple cloning site, promoter sequences for the SP6 and T7 RNA polymerases.

The method of competence used is electroporation. The plasmid and the PCR fragment are hybridized in a ratio of 50 ng of vector (SmaI cleavage) to 100 ng of PCR fragment (made blunt ended by treatment with the Klenow fragment of DNA polymerase). The incubation takes place overnight at 22° C. in ligation buffer (66 mM Tris-HCl, pH 7.5, 5 mM $MgCl_2$, 1 mM dithioerythritol, 1 mM ATP) in the presence of 1 u of T4 DNA ligase and is then stopped by denaturation for 10 minutes at 65° C. In parallel, the E. coli JM 105 strain is inoculated overnight at 37° C. in LB medium. This preculture is diluted 1/500 and placed at 37° C. until an OD$^{600}$ equal to 1 is obtained. For the remainder of the procedure, the cells will always be stored at cold temperature. After centrifugation for 5 minutes at 3 500 g at 4° C., the cellular pellet is resuspended in 1/4 vol. of ultra-pure ice-cold water. This step is repeated 5 to 6 times. The pellet is then resuspended in 1/4 000 vol. of water; 10% of sterile glycerol is added, allowing preservation of the electrocompetent cells, in aliquots of 10 µl at 20° C. 1 µl of the ligation is added to 50 µl of electrocompetent cells; the mixture is subjected to an electrical discharge of 12.5 kV/cm, applied for 5.8 ms. The cells are rapidly resuspended in the SOC medium, incubated for 1 hour at 37° C. and then plated in the presence of 2% X-Gal in dimethylformamide, and 10 mM IPTG, on an LB-agar dish supplemented with ampicillin (100 µg/ml). After one night at 37° C., the potentially recombinant white clones are subcultured in an orderly manner on an LB/ampicillin dish and in parallel on a nylon filter deposited on an LB/ampicillin dish. These two dishes are incubated overnight at 37° C. The recombinant clones are then located by hybridization with a nucleic probe amplified by PCR with the pair or primers according to SEQ ID NO: 45 and SEQ ID NO: 46 and labeled with digoxygenin.

The recombinant clones are cultured in 50 ml of LB/ampicillin medium (100 µg/ml), with stirring, over night at 37° C. After centrifugation at 3 500 g for 15 minutes at 4° C., the bacterial pellet is taken up in 4 ml of P1 buffer (50 mM Tris-HCl, 10 mM EDTA, 400 µg/ml RNase A, pH 8) and 4 ml of P2 buffer (200 mm NaOH, 1% SDS). The medium is incubated at room temperature for 5 minutes. After addition of 4 ml of P3 buffer (2.55 M potassium acetate, pH 4.8), the mixture is centrifuged at 12 000 g for 30 minutes at 4° C. This supernatant is applied to a Qiagen type 100 column, pre-equilibrated with 2 ml of QBT buffer (750 mM NaCl, 50 mM MOPS, 15% ethanol, pH 7), the column is washed with twice 4 ml of QC buffer (1 M NaCl, 50 mM MOPS, 15% ethanol, pH 7) and the DNA is eluted with 2 ml of QF buffer (1.2 M NaCl, 50 mM MPOS, 15% ethanol, pH 8). The DNA is precipitated with 0.8 vol. of isopropanol and centrifuged at 12 000 g at 4° C. for 30 minutes. The pellet is washed with 70% ice-cold ethanol and then the plasmid DNA is taken up in twice 150 µl of TE buffer.

The ribonucleic probes are used as specific probes, in particular for the detection of the transcripts expressed by the endogenous retroviral sequences according to the invention.

EXAMPLE 6

Construction of a Transgenic Mouse Containing All or Part of the Gene for Enverin A transgenic mouse containing all or part of the HERV-7q sequence (SEQ ID NO: 3) is constructed so as to identify the sequences responsible for the tissue specificity, and to evaluate the role of all or part of the endogenous retroviral motifs of the HERV-7q type, in particular all or part of the peptide motifs of enverin. The microinjection technique used refers to the conventional technique (Hogan et al., (1994), Manipulating the mouse embryo, Cold Spring Harbor, Cold Spring Harbor Laboratory Press) or to its equivalents. Forms identical to the normal human molecule of motifs of the HERV-7q type, including enverin, or forms which are mutated, deleted, having insertions, or truncated are tested in order to determine the motifs which are critical both from the normal and pathological point of view, and more particularly during fetal development and during tumor processes.

BIBLIOGRAPHIC REFERENCES

Benit L. et al., 1997. Cloning of a new murine endogenous retrovirus MuERV-L, with strong similarity of the human HERV-L element and with a gag coding sequence closely related to the Fv1 restriction gene. J. Virol. 71, 5652–5657.

Coffin J. M. 1985. Endogenous retrovirus, In: "RNA tumor viruses" (Weiss R. A., Varmus H. E., Teich N. M., and Coffin J. M. eds), Cold Spring Harbor Laboratory Press, Cold Spring Harbor, N.Y.

Conrad B., Weissmahr R. N., Boni J., Arcari R., Schupbach J., and Mach B. 1997. A human endogenous retroviral superantigen as candidate autoimmunogene in type 1 diabetes. Cell 90, 303–313.

Covey S. N. 1986. Amino acid sequence homology in gag region of reverse transcribing elements and the coat protein gene of cauliflower mosaic virus, Nucleic Acids Res. 14, 623–633.

Hertig C., Coupar B. E., Gould A. R., and Boyle D. B. 1997. Field and vaccine strains of fowlpox virus carry integrated sequences from the avian retrovirus, reticuloendotheliosis virus. Virology 235, 367–376.

Hohenadl C., Leib-Mösch C., Hehlemann R., and Erfle Y. 1996. Biological significance of human endogenous retroviral sequences. J. Acqui. Imm. Def. Synd. Hum. Retrovir. 13, S268–S273.

Kulkoski J. K., Jones S., Katz R. A., Mack J. P. G., and Skalka A. M. 1992. Residues critical for retroviral integrative recombination in a region that is highly conserved among retroviral/retrotransposon integrases and bacterial insertion sequence transposases. Mol. Cell. Biol. 12, 2331–2338.

La Mantia G. et al., N. A. R., 1991, 19, 7, 1513–1520

Patience C., Wilkinson D. A., and Weiss R. A. 1997. Our retroviral heritage. Trends Genet. 13, 116–120.

Pearson W. R. 1994. Using the FASTA program to search protein and DNA sequence databases. Methods Mol. Biol. 24, 307–331.

Perron H., Garson J. A., Bedin F., Beseme F., Paranhos-Baccala G., Komurian-Pradel F., Mallet F., Tuke P. W., Voisset C., Blond J. L., Lalande B., Seigneurin J. M., Mandrand B. and the Collaborative Research Group on Multiple Scelerosis. 1997. Molecular identification of a novel retrovirus repeatedly isolated from patients with multiple sclerosis. Proc. Natl. Acad. Sci. USA 94, 7583–7588.

Tönjes R. R. et al., J. AIDS and Hum. Retrovirol. 1996, 13. S261–S267.

Vitelli R., Chiarillo M., Lattero D., Bruni C. B., and Bucci C., 1996. Molecular cloning and expression analysis of the human Rab7 GTP-ase complementary deoxyribonucleic acid. Biochem. Biophys. Res. Commun. 229, 887–890.

Weber L. T., Miller M., Jaskolski M., Leis J., Skalka M., and Wlodawer A., 1989. Molecular modeling of the HIV-1 protease and its substrate binding site. Science 243, 928–931.

Wilkinson D., Mager D. L., and Leong J. A. C. 1994. Endogenous human retroviruses. In: "The Retroviridae" (Levy J. A. ed). Plenum Press New York., Vol. 3, 465–535.

Xiong Y., and Eickbush, T. 1990. Origin and evolution of retroelements based upon their reverse transcriptase sequences. EMBO J. 9, 3353–3362.

As is evident from the above, the invention is not at all limited to its embodiments, implementations and applications which have just been described more explicitly; it embraces on the contrary all the variants which may occur to a specialist in this field, without departing from the framework or scope of the present invention.

What is claimed is:

1. An isolated polynucleotide sequence selected from the group consisting of:
   e) the polynucleotide sequence of SEQ ID NO: 3;
   f) the complementary sequence to the sequence of a);
   g) the reverse complementary sequence to the sequence of a) or b);
   h) a fragment of a coding region of the sequence of a), wherein said fragment corresponds to a coding frame of at least 14 nucleotides; and
   e) the complementary sequence to the sequence of d).

2. The isolated polynucleotide according to claim 1, wherein said fragment in d) consists of SEQ ID NO: 1 or SEQ ID NO: 2.

3. The isolated polynucleotide according to claim 1, wherein said fragment in d) consists of a sequence encoding the C-terminal portion of enverin wherein said sequence begins at the codon at positions 8749 to 8751 of SEQ ID NO: 3 and contains at least 14 nucleotides.

4. The isolated polynucleotide according to claim 1, wherein said fragment in d) consists of a sequence encoding the C-terminal portion of enverin wherein said sequence begins at the codon at positions 8839 to 8841 of SEQ ID NO: 3 and contains at least 14 nucleotides.

5. A diagnostic reagent for the differential detection of a human endogenous retroviral sequence, said diagnostic reagent comprising one or more isolated polynucleotides according to claim 1.

6. The diagnostic reagent according to claim 5, wherein said polynucleotide further comprises a label for detection.

7. The diagnostic reagent according to claim 5, wherein said polynucleotide is selected from the group consisting of nucleotides 3065–4390 of SEQ ID NO: 3, nucleotides 6965–9550 of SEQ ID NO: 3, and nucleotides 2502–2865 of SEQ ID NO: 3.

8. A method for the differential detection of a human endogenous retroviral sequence, comprising:
   (a) contacting a biological sample with at least one diagnostic reagent according to claim 5, and
   (b) detecting a nucleotide sequence-diagnostic reagent interaction; wherein the detection of a nucleotide sequence-diagnostic reagent interaction indicates the presence of the human endogenous retroviral sequence.

9. A method for the differential detection of a human endogenous retroviral sequence, comprising:
   (a) preparing a biological tissue or fluid,
   (b) extracting a nucleic acid to be detected,
   (c) contacting the nucleic acid with at least one diagnostic reagent according to claim 5,
   (d) detecting a nucleotide sequence-diagnostic reagent interaction, and
   (e) comparing the nucleotide sequences obtained from said detecting with a polynucleotide selected from the group consisting of:
      i. one of SEQ ID NO: 1, 2, and 3,
      ii. the sequence complementary to one of SEQ ID NO: 1, 2, and 3, and
      iii. a sequence that is the reverse complement to one of SEQ ID NO: 1, 2, and 3;
   wherein said comparing identifies an insertion, deletion or mutation between said sequences compared.

10. The method according to claim 9, wherein said comparing is by a technique selected from the group consisting of sequencing, Southern blotting, restriction cleavage, and SSCP.

11. A method for the differential detection of a human endogenous retroviral sequence, comprising:
   collecting messenger RNAs obtained from a control biological sample and from a sample collected from patient, and
   analyzing qualitatively and/or quantitatively said mRNAs using a diagnostic reagent according to claim 5 by a technique selected from the group consisting of in situ hybridization, by dot-blot, Northern blotting, RNAse mapping and RT-PCR.

12. A recombinant cloning or expression vector comprising the polynucleotide according to claim 1.

13. A method of making a diagnostic reagent comprising mixing the polynucleotide according to claim 1 with a suitable medium.

* * * * *

UNITED STATES PATENT AND TRADEMARK OFFICE
CERTIFICATE OF CORRECTION

| | | |
|---|---|---|
| PATENT NO. | : 6,919,438 B1 | Page 1 of 1 |
| APPLICATION NO. | : 09/719554 | |
| DATED | : July 19, 2005 | |
| INVENTOR(S) | : Patrick M. Alliel et al. | |

It is certified that error appears in the above-identified patent and that said Letters Patent is hereby corrected as shown below:

Column 229, lines 14-23, Claim 1,

" 1. An isolated polynucleotide sequence selected from the group consisting of:
  e) the polynucleotide sequence of SEQ ID NO: 3;
  f) the complementary sequence to the sequence of a);
  g) the reverse complementary sequence to the sequence of a) or b);
  h) a fragment of a coding region of the sequence of a), wherein said fragment corresponds to a coding frame of at least 14 nucleotides; and
  e) the complementary sequence to the sequence of d). "

should read

-- 1. An isolated polynucleotide sequence selected from the group consisting of:
  a) the polynucleotide sequence of SEQ ID NO: 3;
  b) the complementary sequence to the sequence of a);
  c) the reverse complementary sequence to the sequence of a) or b);
  d) a fragment of a coding region of the sequence of a), wherein said fragment corresponds to a coding frame of at least 14 nucleotides; and
  e) the complementary sequence to the sequence of d). --

Signed and Sealed this

Eighth Day of May, 2007

JON W. DUDAS
*Director of the United States Patent and Trademark Office*

SEQUENCE LISTING

<160> NUMBER OF SEQ ID NOS: 122

<210> SEQ ID NO 1
<211> LENGTH: 2599
<212> TYPE: DNA
<213> ORGANISM: Homo sapiens

<400> SEQUENCE: 1

```
atccctgcc ttaatcgcca agctccttca ggagaacaaa gaacaggcca ttaccctgga      60
gaagactggc aactgatttt acccacaagc ccaaacctca gggatttcag tatctactag     120
tctgggtaga tactttcacg ggttgggcag aggccttccc ctgtaggaca gaaaaggccc     180
aagaggtaat aaaggcacta gttcatgaaa taattcccag attcggactt ccccgaggct     240
tacagagtga caatagccct gctttccagg ccacagtaac ccagggagta tcccaggcgt     300
taggtatacg atatcactta cactgcgcct gaaggccaca gtcctcaggg aaggtcgaga     360
aaatgaatga aacactcaaa ggacatctaa aaaagcaaac ccaggaaacc cacctcacat     420
ggcctgctct gttgcctata gccttaaaaa gaatctgcaa cttcccccaa aaagcaggac     480
ttagcccata cgaaatgctg tatggaaggc ccttcataac caatgacctt gtgcttgacc     540
caagacagcc aacttagttg cagacatcac ctccttagcc aaatatcaac aagttcttaa     600
aacattacaa ggaacctatc cctgagaaga gggaaaagaa ctattccacc cttgtgacat     660
ggtattagtc aagtcccttc cctctaattc cccatcccta gatacatcct gggaaggacc     720
ctacccagtc attttatcta ccccaactgc ggttaaagtg gctggagtgg agtcttggat     780
acatcacact tgagtcaaat cctggatact gccaaaggaa cctgaaaatc caggagacaa     840
cgctagctat tcctgtgaac ctctagagga tttgcgcctg ctcttcaaac aacaaccagg     900
aggaaagtaa ctaaaatcat aaatccccat ggccctccct tatcatattt ttctctttac     960 tgttcttta ccctctttca ctctcactgc acccctcca tgccgctgta tgaccagtag    1020 ctcccttac caagagtttc tatggagaat gcagcgtccc ggaaatattg atgccccatc    1080
gtataggagt ctttctaagg gaaccccac cttcactgcc cacacccata tgccccgcaa    1140
ctgctatcac tctgccactc tttgcatgca tgcaaatact cattattgga caggaaaaat    1200
gattaatcct agttgtcctg gaggacttgg agtcactgtc tgttggactt acttcaccca    1260
aactggtatg tctgatgggg gtggagttca agatcaggca agagaaaaac atgtaaaaga    1320
agtaatctcc caactcaccc gggtacatgg cacctctagc ccctacaaag gactagatct    1380
ctcaaaacta catgaaaccc tccgtaccca tactcgcctg gtaagcctat ttaataccac    1440
cctcactggg ctccatgagg tctcggccca aaaccctact aactgttgga tatgcctccc    1500
cctgaacttc aggccatatg tttcaatccc tgtacctgaa caatggaaca acttcagcac    1560
agaaataaac accacttccg ttttagtagg acctcttgtt tccaatctgg aaataaccca    1620
tacctcaaac ctcacctgtg taaaatttag caatactaca tacacaacca actcccaatg    1680
catcaggtgg gtaactcctc ccacacaaat agtctgccta ccctcaggaa tatttttgt     1740 ctgtggtacc tcagcctatc gttgtttgaa tggctcttca gaatctatgt gcttcctctc    1800
attcttagtg cccctatga ccatctacac tgaacaagat ttatacagtt atgtcatatc     1860
```

```
taagccccgc aacaaaagag tacccattct tccttttgtt ataggagcag gagtgctagg    1920
tgcactaggt actggcattg gcggtatcac aacctctact cagttctact acaaactatc    1980
tcaagaacta aatggggaca tggaacgggt cgccgactcc ctggtcacct tgcaagatca    2040
acttaactcc ctagcagcag tagtccttca aaatcgaaga gctttagact tgctaaccgc    2100
tgaaagaggg ggaacctgtt tattttagg gaagaatgc tgttattatg ttaatcaatc     2160
cggaatcgtc actgagaaag ttaaagaaat tcgagatcga atacaacgta gagcagagga   2220
gcttcgaaac actggaccct ggggcctcct cagccaatgg atgccctgga ttctcccctt   2280
cttaggacct ctagcagcta taatattgct actcctcttt ggaccctgta tctttaacct   2340
ccttgttaac tttgtctctt ccagaatcga agctgtaaaa ctacaaatgg agcccaagat   2400
gcagtccaag actaagatct accgcagacc cctggaccgg cctgctagcc cacgatctga   2460
tgttaatgac atcaaaggca cccctcctga ggaaatctca gctgcacaac ctctactacg   2520
ccccaattca gcaggaagca gttagagcgg tctcggccaa cctccccaac agcacttagg   2580
ttttcctgtt gagatgggg                                                2599

<210> SEQ ID NO 2
<211> LENGTH: 1326
<212> TYPE: DNA
<213> ORGANISM: Homo sapiens

<400> SEQUENCE: 2
gccgcctggc actcctgagg gaagtataaa ttataacacc atcttacagc tagacctctt     60
ttgtagaaaa ggcaaatgga gtgaagtgcc ataagtacaa actttctttt cattaagaga   120
caactcacaa ttatgtaaaa agtgtgattt atgccctaca ggaagccttc agagtctacc   180
tccctatccc agcatccccg actccttccc caactaataa ggaccccct tcaacccaaa    240 tggtccaaaa ggagatagac aaaagggtaa acagtgaacc aaagagtgcc aatattcccc   300
aattatgacc cctccaagca gtgggaggaa gagaattcgg cccagccaga gtgcatgtgc   360 cttttttctct cccagactta aagcaaataa aaacagactt aggtaaattc tcagataacc   420
ctgatggcta tattgatgtt ttacaagggt taggacaatt ctttgatctg acatggagag   480
atataatgtc actgctaaat cagacactaa ccccaaatga gagaagtgcc accataactg   540
cagcctgaga gtttggcgat ctctggtatc tcagtcaggt caatgatagg atgacaacag   600
aggaaagaga atgattcccc acaggccagc aggcagttcc cagtctagac cctcattggg   660
acacagaatc agaacatgga gattggtgct gcagacattt gctaacttgt gtgctagaag   720
gactaaggaa aactaggaag aagtctatga attactcaat gatgtccacc ataacacagg   780
gaagggaaga aaatcctact gcctttctgg agagactaag ggaggcattg aggaagcgtg   840
cctctctgtc acctgactct tctgaaggcc aactaatctt aaagcgtaag tttatcactc   900
agtcagctgc agacattaga aaaaaacttc aaaagtctgc cgtaggcccg gagcaaaact   960
tagaaaccct attgaacttg gcaacctcgg ttttttataa tagagatcag gaggagcagg  1020
cggaacagga caaacgggat taaaaaaaag gccaccgctt tagtcatgac cctcaggcaa  1080
gtggactttg gaggctctgg aaaagggaaa agctgggcaa attgaatgcc taatagggct  1140
tgcttccagt gcggtctaca aggacacttt aaaaaagatt gtccaagtag aagtaagccg  1200 cccctcgtc catgcccctt atttcaaggg aatcactgga aggcccactg ccccagggga   1260
caaaggtcct ctgagtcaga agccactaac cagatgatcc agcagcagga ctgagggtgc  1320
ctgggg                                                              1326
```

<210> SEQ ID NO 3
<211> LENGTH: 10499
<212> TYPE: DNA
<213> ORGANISM: Homo sapiens

<400> SEQUENCE: 3

| | | | | | |
|---|---|---|---|---|---|
| ccctggggcg | ggcttccttt | ctgggatgag | ggcaaaacgc | ctggagatac | agcaattatc | 60 |
| ttgcaactga | gagacaggac | tagctggatt | tcctaggccg | actaagaatc | cctaagccta | 120 |
| gctgggaagg | tgaccacgtc | cacctttaaa | cacggggctt | gcaacttagc | tcacacctga | 180 |
| ccaatcagag | agctcactaa | aatgctaatt | aggcaaagac | aggaggtaaa | gaaatagcca | 240 |
| atcatctatt | gcctgagagc | acagcaggag | ggacaacaat | cgggatataa | acccaggcat | 300 |
| tcgagctggc | aacagcagcc | cccctttggg | tcccttccct | ttgtatggga | gctgttttca | 360 |
| tgctatttca | ctctattaaa | tcttgcaact | gcactcttct | ggtccatgtt | tcttacggct | 420 |
| cgagctgagc | ttttgctcac | cgtccaccac | tgctgtttgc | caccaccgca | gacctgccgc | 480 |
| tgactcccat | ccctctggat | cctgcagggt | gtccgctgtg | ctcctgatcc | agcgaggcgc | 540 |
| ccattgccgc | tcccaattgg | gctaaaggct | tgccattgtt | cctgcacggc | taagtgcctg | 600 |
| ggtttgttct | aattgagctg | aacactagtc | actgggttcc | atggttctct | tctgtgaccc | 660 |
| acggcttcta | atagaactat | aacacttacc | acatggccca | agattccatt | ccttggaatc | 720 |
| cgtgaggcca | agaactccag | gtcagagaat | acgaggcttg | ccaccatctt | ggaagcggcc | 780 |
| tgctaccatc | ttggaagtgg | ttcaccacca | tcttgggagc | tctgtgagca | aggaccccc | 840 |
| ggtaacattt | tggcaaccac | gaacggacat | ccaaagtggt | gagtaatatt | ggaccacttt | 900 |
| cacttgctat | tctgtcctat | ccttccttag | aattggagga | aaataccggg | cacttgtcgg | 960 |
| ccagttaaaa | acgattagtg | tggccaccgg | acttaagact | caggtgtgag | gctatctggg | 1020 |
| gaagggcttt | ctaacaaccc | ccaacccttc | tgggttgggg | acttggtttg | cctcaagcca | 1080 |
| gcttccactt | tcagttttct | tggggaagcc | gagggccgac | tagaggcaga | aagctgtcgt | 1140 |
| cctgaactcc | cggcagtagc | cggttgagat | catggtgtag | ccagaagtct | caacagtcgc | 1200 |
| ccatgcatgc | accctatct | ttccttctga | cccatacctc | ctgggtccca | accacaactt | 1260 |
| tcttcaaagt | gtagcccaa | aattctcctt | acctctgaat | atacttcctc | tgatccctgc | 1320 |
| ctcctaggta | ctattggttc | agacttccat | ttcctctagc | aagttgtatc | tccaagggga | 1380 |
| tctaaggaag | ctctgcgctg | cgtccttagg | cacctaggct | ataacccagg | gagtcttatc | 1440 |
| cctggtgtcc | ctcccaattt | aggcatacag | ctcttgacat | gggcagttat | gtaggaccca | 1500 |
| ctccccacca | cccttgccag | ggccccaagt | ttgtaaatgg | ctgagggaaa | agagagacag | 1560 |
| aggagagaga | gagaaatgga | ggagaaagag | agagagacag | agaggagaga | gagacagtga | 1620 |
| gagagacaga | agagagagag | agacaaagag | gagagagaga | gagtcaaaga | gagaaagaaa | 1680 |
| gagaaagaaa | tagtaaaaaa | cagtgtgccc | tattccttta | aaagccaggg | taaatttaaa | 1740 |
| acctgtactt | gataattgaa | ggtcttctct | gtgaccctat | agcactccaa | tccactttgt | 1800 |
| ggtcagtgta | aataagagca | taggccgaaa | gcactgaggc | cattgacaac | ccgtagcttc | 1860 |
| cctatcaaaa | atccttaacc | cagtaacccg | cagatggacc | aaatgcattc | agtcggtagc | 1920 |
| gcaactgctt | tgctaaaagt | agaaaagtaa | cttttagagg | aaacctcatt | gtgagcacac | 1980 |
| ctcacctgtt | cagaattatt | ctaataaaaa | aagcaaaaag | gtagcttact | aactcaaaaa | 2040 |
| tcttaaagta | tggggctatt | ctgttagaaa | aaggtaatgt | aactccaacc | actgataatt | 2100 |

| | |
|---|---|
| cccttaaccc agcagatttc ctaacgggat ttaaatctta attaccatac aaaggtccga | 2160 |
| ccagacctag gcggaactcc cttcaggaca ggacgataga tggttcctcc caggtgattg | 2220 |
| aggaaaaaaa ccacaatggg tattcagtaa ttgatacggg gactcttgtg aagcagagt | 2280 |
| tagaaaaatt gcctaataac tggtctcctc aaacgtgtga gctgtttgca ctcagccaag | 2340 |
| ccttaaagta cttacagaat caaaagacta tctcaatcct gattcaaaag gttagctaca | 2400 |
| ccctctctgt aatgcatttg cataagaact tgtttatggg aatgcatctt gatggggcag | 2460 |
| ctgggttgtt ataaaatagg aacccagccc agctctagga ctcacccctg agcgcaaagg | 2520 |
| caatgttggg catgctggta aaggaccact agaatccagc agcccagacc cctttctttg | 2580 |
| tggtcaagaa aggcgggaaa aggggtgcag gactgctaca tcggtaagca taactaatcc | 2640 |
| gataaacaga ggtccatggg tggttacgca ccctggaaag gaactcaccc ctgagcacaa | 2700 |
| aggcaatgtt gggcacgctg gtaaaggacc actagaatcc agcagcctgg acccctttct | 2760 |
| ttgtggtcaa gagaggcagg aaaacaggtg caggactgca acatcagtga gcataactaa | 2820 |
| ttcgataagc agaggtccat gggtggtgat gcaccctgga agaataagc attaggacca | 2880 |
| tagaggacac tccaggacta aagctcatcg gaaaatgact agggttgctg gcatccctat | 2940 |
| gttcttttt cagatgggaa acgttccccg caagacaaaa acgcccctaa gacgtattct | 3000 |
| ggagaattgg gaccaatttg accctcagac actaagaaag aaacgactta tattcttctg | 3060 |
| cagtgccgcc tggcactcct gagggaagta taaattataa caccatctta cagctagacc | 3120 |
| tcttttgtag aaaaggcaaa tggagtgaag tgccataagt acaaactttc ttttcattaa | 3180 |
| gagacaactc acaattatgt aaaaagtgtg atttatgccc tacaggaagc cttcagagtc | 3240 |
| tacctcccta tcccagcatc cccgactcct tccccaacta ataaggaccc cccttcaacc | 3300 |
| caaatggtcc aaaaggagat agacaaaagg gtaaacagtg aaccaaagag tgccaatatt | 3360 |
| ccccaattat gacccctcca agcagtggga ggaagagaat tcggcccagc cagagtgcat | 3420 |
| gtgccttttt ctctcccaga cttaaagcaa ataaaaacag acttaggtaa attctcagat | 3480 |
| aaccctgatg gctatattga tgttttacaa gggttaggac aattctttga tctgacatgg | 3540 |
| agagatataa tgtcactgct aaatcagaca ctaaccccaa atgagagaag tgccaccata | 3600 |
| actgcagcct gagagtttgg cgatctctgg tatctcagtc aggtcaatga taggatgaca | 3660 |
| acagaggaaa gagaatgatt ccccacaggc cagcaggcag ttcccagtct agaccctcat | 3720 |
| tgggacacag aatcagaaca tggagattgg tgctgcagac atttgctaac ttgtgtgcta | 3780 |
| gaaggactaa ggaaaactag gaagaagtct atgaattact caatgatgtc caccataaca | 3840 |
| cagggaaggg aagaaaatcc tactgccttt ctggagagac taaggaggc attgaggaag | 3900 |
| cgtgcctctc tgtcacctga ctcttctgaa ggccaactaa tcttaaagcg taagtttatc | 3960 |
| actcagtcag ctgcagacat tagaaaaaaa cttcaaaagt ctgccgtagg cccggagcaa | 4020 |
| aacttagaaa ccctattgaa cttggcaacc tcggtttttt ataatagaga tcaggaggag | 4080 |
| caggcggaac aggacaaacg ggattaaaaa aaaggccacc gctttagtca tgaccctcag | 4140 |
| gcaagtggac tttggaggct ctggaaaagg gaaaagctgg gcaaattgaa tgcctaatag | 4200 |
| ggcttgcttc cagtgcggtc tacaaggaca ctttaaaaaa gattgtccaa gtagaagtaa | 4260 |
| gccgcccct cgtccatgcc ccttatttca agggaatcac tggaaggccc actgcccag | 4320 |
| gggacaaagg tcctctgagt cagaagccac taaccagatg atccagcagc aggactgagg | 4380 |
| gtgcctgggg caagcgccat cccatgccat caccctcaca gagccctggg tatgcttgac | 4440 |
| cattgagggc caggaggttg tctcctggac actggtgcgg tcttcttagt cttactcttc | 4500 |

```
tgtcccggac aactgtcctc cagatctgtc actatctgag ggggtcctaa gacgggcagt    4560
cactagatac ttctcccagc cactaagtta tgactgggga gctttattct tttcacatgc    4620
ttttctaatt atgcttgaaa gccccactac cttgttaggg agagacattc tagcaaaagc    4680
aggggccatt atacacctga acataggaga aggaacaccc gtttgttgtc ccctgcttga    4740
ggaaggaatt aatcctgaag tctgggcaac agaaggacaa tatggacgag caaagaatgc    4800
ccgtcctgtt caagttaaac taaaggattc cacctccttt ccctaccaaa ggcagtaccc    4860
cctcagaccc aaggcccaac aaggactcca aaagattgtt aaggacctaa agcccaagg    4920 cctagtaaaa ccatgcagta acccctgcag tactccaatt ttaggagtac agaaacccaa    4980
cagacagtgg aggttagtgc aagatctcag gattatcaat gaggctgttg ttcctctata    5040
gccagctgta cctagcccct tatactctgct ttcccaaata ccagaggaag cagagtggtt    5100
tacagtcctg gaccttcagg atgccttctt ctgcatccct gtacatcctg actctcaatt    5160
cttgtttgcc tttgaagata cttcaaaccc aacatctcaa ctcacctgga ctattttacc    5220
ccaagggttc agggatagtc cccatctatt tggccaggca ttagcccaag acttgagcca    5280
atcctcatac ctggacactt gtccttcggt aggtggatga tttacttttg ccgcccatt    5340 cagaaacctt gtgccatcaa gccacccaag cgctcttcaa tttcctcgct acctgtggct    5400
acatggtttc caaaccaaag gctcaactct gctcacagca ggttacttag ggctaaaatt    5460
atccaaaggc accagggccc tcagtgagga acacatccag cctatactgg cttatcctca    5520
tcccaaaacc ctaaagcaac taaggggatt ccttggcgta ataggtttct gccgaaaatg    5580
gattcccagg tatggcgaaa tagccaggtc attaaataca ctaattaagg aaactcagaa    5640
agccaatacc catttagtaa gatggacaac tgaagtagaa gtggctttcc aggccctaac    5700
ccaagcccca gtgttaagtt tgccaacagg gcaagacttt tcttcatatg tcacagaaaa    5760
aacaggaata gctctaggag tccttacaca gatccgaggg atgagcttgc aacctgtggc    5820
atacctgact aaggaaattg atgtagtggc aaagggttga cctcattgtt tacgggtagt    5880
ggtggcagta gcagtcttag tatctgaagc agttaaaata atacagggaa gagatcttac    5940
tgtgtggaca tctcatgatg tgaatggcat actcactgct aaaggagact tgtggctgtc    6000
agacaactgt ttacttaaat gtcaggctct attacttgaa gggccagtgc tgcgactgtg    6060
cacttgtgca actcttaacc cagccacatt tcttccagac aatgaagaaa agataaaaca    6120
taactgtcaa caagtaattt ctcaaaccta tgccactcga ggggacccttt tagaggttcc    6180 tttgactgat cccgacctca acttgtatac tgatggaagt tcctttgtag aaaaaggact    6240
tcgaaaagtg gggtatgcag tggtcagtga atggaata cttgaaagta atccctcac    6300 tccaggaact agtgctcagc tagcagaact aatagccctc acttgggcac tagaattagg    6360
agaagaaaaa aggcaaata tatatacaga ctctaaatat gcttacctag tcctccatgc    6420
ccatgcagca atatggaaag aaagggaatt cctaacttct gagagaacac ctatcaaaca    6480
tcaggaagcc attaggaaat tattattggc tgtacagaaa cctaaagagg tggcagtctt    6540
acactgccgg ggtcatcaga aggaaagga aagggaaata gaagagaact gccaagcaga    6600
tattgaagcc aaaagagctg caaggcagga ccctccatta gaaatgctta taaaacaacc    6660
cctagtatag ggtaatcccc tccgggaaac caagcccag tactcagcag gagaaacaga    6720
atggggaacc tcacgaggac agttttctcc cctcgggacg gctagccact gaagaaggga    6780
aaatactttt gcctgcaact atccaatgga aattacttaa aacccttcat caaacctttc    6840
```

```
acttaggcat cgatagcacc catcagatgg ccaaatcatt atttactgga ccaggccttt   6900
tcaaaactat caagcagata gtcagggcct gtgaagtgtg ccagagaaat aatcccctgc   6960
cttatcgcca agctccttca ggagaacaaa gaacaggcca ttaccctgga gaagactggc   7020
aactgatttt acccacaagc ccaaacctca gggatttcag tatctactag tctgggtaga   7080
tactttcacg ggttgggcag aggccttccc ctgtaggaca gaaaaggccc aagaggtaat   7140
aaaggcacta gttcatgaaa taattcccag attcggactt ccccgaggct tacagagtga   7200
caatagccct gctttccagg ccacagtaac ccagggagta tcccaggcgt taggtatacg   7260
atatcactta cactgcgcct gaaggccaca gtcctcaggg aaggtcgaga aaatgaatga   7320
aacactcaaa ggacatctaa aaaagcaaac ccaggaaacc cacctcacat ggcctgctct   7380
gttgcctata gccttaaaaa gaatctgcaa cttttcccaa aaagcaggac ttagcccata   7440
cgaaatgctg tatggaaggc ccttcataac caatgacctt gtgcttgacc caagacagcc   7500
aacttagttg cagacatcac ctccttagcc aaatatcaac aagttcttaa aacattacaa   7560
ggaacctatc cctgagaaga gggaaaagaa ctattccacc cttgtgacat ggtattagtc   7620
aagtcccttc cctctaattc cccatcccta gatacatcct gggaaggacc ctacccagtc   7680
attttatcta ccccaactgc ggttaaagtg gctggagtgg agtcttggat acatcacact   7740
tgagtcaaat cctggatact gccaaaggaa cctgaaaatc caggagacaa cgctagctat   7800
tcctgtgaac ctctagagga tttgcgcctg ctcttcaaac aacaaccagg aggaaagtaa   7860
ctaaaatcat aaatcccat ggccctccct tatcatattt ttctctttac tgttcttta    7920
ccctctttca ctctcactgc accccctcca tgccgctgta tgaccagtag ctccccttac   7980
caagagtttc tatggagaat gcagcgtccc ggaaatattg atgccccatc gtataggagt   8040
cttttctaagg gaaccccac cttcactgcc cacacccata tgccccgcaa ctgctatcac   8100
tctgccactc tttgcatgca tgcaaatact cattattgga caggaaaaat gattaatcct   8160
agttgtcctg gaggacttgg agtcactgtc tgttggactt acttcaccca aactggtatg   8220
tctgatgggg gtggagttca agatcaggca agagaaaaac atgtaaaaga agtaatctcc   8280
caactcaccc gggtacatgg cacctctagc ccctacaaag gactagatct ctcaaaacta   8340
catgaaaccc tccgtaccca tactcgcctg gtaagcctat ttaataccac cctcactggg   8400
ctccatgagg tctcggccca aaaccctact aactgttgga tatgcctccc cctgaacttc   8460
aggccatatg tttcaatccc tgtacctgaa caatggaaca acttcagcac agaaataaac   8520
accacttccg ttttagtagg acctcttgtt tccaatctgg aaataaccca tacctcaaac   8580
ctcacctgtg taaaatttag caatactaca tacacaacca actcccaatg catcaggtgg   8640
gtaactcctc ccacacaaat agtctgccta ccctcaggaa tatttttgt ctgtggtacc    8700
tcagcctatc gttgtttgaa tggctcttca gaatctatgt gcttcctctc attcttagtg   8760
ccccctatga ccatctacac tgaacaagat ttatacagtt atgtcatatc taagcccgc    8820
aacaaaagag tacccattct tccttttgtt ataggagcag gagtgctagg tgcactaggt   8880
actggcattg gcggtatcac aacctctact cagttctact acaaactatc tcaagaacta   8940
aatggggaca tggaacgggt cgccgactcc ctggtcacct tgcaagatca acttaactcc   9000
ctagcagcag tagtccttca aaatcgaaga gctttagact tgctaaccgc tgaaagaggg   9060
ggaacctgtt tattttttagg ggaagaatgc tgttattatg ttaatcaatc cggaatcgtc   9120
actgagaaag ttaagaaaat tcgagatcga atacaacgta gagcagagga gcttcgaaac   9180
actggaccct ggggcctcct cagccaatgg atgccctgga ttctcccctt cttaggacct   9240
```

-continued

```
ctagcagcta taatattgct actcctcttt ggaccctgta tctttaacct ccttgttaac    9300
tttgtctctt ccagaatcga agctgtaaaa ctacaaatgg agcccaagat gcagtccaag    9360
actaagatct accgcagacc cctggaccgg cctgctagcc cacgatctga tgttaatgac    9420
atcaaaggca cccctcctga ggaaatctca gctgcacaac ctctactacg ccccaattca    9480
gcaggaagca gttagagcgg tctcggccaa cctccccaac agcacttagg ttttcctgtt    9540
gagatggggg actgagagac aggactagct ggatttccta ggctgactaa gaatccctaa    9600
gcctagctgg gaaggtgacc acatccacct ttaaacacgg ggcttgcaac ttagctcaca    9660
cctgaccaat cagagagctc actaaaatgc taattaggca aagacaggag gtaaagaaat    9720
agccaatcat ctattgcctg agagcacagc aggagggaca atgatcggga tataaaccca    9780
agtcttcgag ccggcaacgg caacccectt tgggtcccct ccctttgtat gggagctctg    9840
ttttcatgct atttcactct attaaatctt gcaactgcac tcttctggtc catgtttctt    9900
acggcttgag ctgagctttc gctcgccatc caccactgct gtttgccgcc accgcagacc    9960
cgccgctgac tcccatccct ctggatcatg caggtgtcc gctgtgctcc tgatccagcg    10020
aggcacccat tgccgctccc aatcgggcta aaggcttgcc attgttcctg catggctaag    10080
tgcctgggtt catcctaatt gagctgaaca ctagtcactg ggttccatgg ttctcttctg    10140
tgacccacag cttctaatag agctataaca ctcaccgcat ggcccaaggt tccattcctt    10200
gaatccataa ggccaagaac cccaggtcag agaacacgag gcttgccacc atcttgggag    10260
ctctgtgagc aaggaccccc aagtaacaca accatgaggg tgcaaatgca tgggccacta    10320
atggtagagc aagaaaacag aagggccctg gttcctcgaa ggcatcagtg agctgaaatg    10380
cctgccctgg atgtcctatt cctaggtgtt tttctgcctg aagcagatta aaccctttgt    10440
tcacttctcc aagtagggct tctattacag cccaaatcaa tccccacccc agatgacat     10499
```

<210> SEQ ID NO 4
<211> LENGTH: 2784
<212> TYPE: DNA
<213> ORGANISM: Homo sapiens

<400> SEQUENCE: 4

```
ctccttcagg agaacaaaga acaggccact acccaagaga agactggcaa ctagatttta     60
cccatatgcc caaatctcag ggatttcagt atctactagt ttgggtagat actttcactg    120
gttgggcaga ggccttcccc tgtaggacag aaaaggccca agaggtaata aacgttcatg    180
aaataattcc cagattcgga cttccccaag gcttacagag tgacaatggc cctgctttca    240
aggctacagt aacccaagga gtatcccagg tgttaggtat acaatatcac tcacactgcg    300
cctggaggcc acagtcctca ggaaaggtgg agaaaatgaa caaaacactc aaatgacatc    360
taaaaaagct aatccaggaa acccacctcg catggcctgc tctgttgcct atagccttac    420
taagaatccg aaactctccc caaaaagcag gacttagtcc atacaaaatg ctgtatggac    480
ggcccttcct aaccaatgaa cttgggcttg accgagagac agccaactta gttgcagaca    540
tcatctcctt agccaaatat caacaggttc ttaaaacatt acagggagcc tgtccccaag    600
aagagggaaa ggaactattc caccctggtg acatggtatt agtcaagtcc cttcctctca    660
attccccatc cctagataca tcctgggaag gaaactaccc agccatttta tctaccctaa    720
cggcagttaa agtggctgga gcggagtctt ggatacatca cactcaagtc aaaccctgga    780
tactgccaaa ggaactcaaa aatccatgag acaatgctag ctattcctgt gaacctctag    840
```

-continued

```
aggatctgcg cctgctcttc aaatgacaac caggggggaaa gtaactaaaa tcgtaaatcc    900
cctggccctc ccttatcata tttttctctt tactgttctc ttaccccctt tcactctcac    960
tgcaccccgt ccatgccact gcaccccgtc catgccccgt ccatgccagt agctcccctt   1020
agcaagagtt tctatggaga atgcagcgtc ccggaaatat tgatgcccca ttgtatagga   1080
gtttatctaa gggaaccccc accttcactg cccacaccca tatgcccac aactgctata    1140
actctgccac tctttgcatg catgcaaata ctcattattg gacaggaaaa acgattaatc   1200
ccagttgtcc tggaggactt ggaggactca cttcactcat accagtatgt ctgatggggg   1260
tggagttcaa gatcaggcaa cagaaaaaca cataaaggaa gtaatctccc aactgacctg   1320
ggtacatagc accctggcc cctacaaagg actagatctc tcaaaactac atgaaaccct    1380
ccatacccat actggcctgg taagcctatt taataccacc ctgactgggc tccatgaggt   1440
ctcggcccaa acctactga actgttggat gtgcctcccc ctgcacttta ggccatacat    1500
ttcaatccct atacctgaac aatggaacaa cttcagcaca gaaataaaca ccacttctgt   1560
tttagtaggt cctctttcca atctggaaat aacccatacc tcaaacctca cctgtgtaaa   1620
atttagcaat actatagaca cagccaactc ccaatgcatc aggtgggtaa ctcctcccac   1680
acgaatagtc tgcctaccct caggaatatt tttgtctgt ggtacctcag cctatcattg    1740
tttgaatggc tcttcagaat ctgtgtgctt cctctcattc ttagtggccc ctatgcccat   1800
ctacactgaa caagatttat acaatcatgt cataccctaag ccccgcaaca aaagagtacc   1860
cattcttcct tttgttattg gagcaggagt gctaggcgga gtagctactg gcattggcgg   1920
tatcacaacc tctactcagt tctactacaa actgtctcaa gaactaaatg gtgacatgga   1980
atgggtcgct gataccctgg tcaccttgca agatcaactt aactcccctag cagcagtagt   2040
ccttcaaaat cgaagagctt tagacttgct aaccgcggaa agcgggggaa cctttttatt   2100
tttagaggaa aaatgctgtt gttatgttaa tcaatccgga atcatcaccg agaaagttaa   2160
agaaattcaa ggtcgaatat aacgtagagc aaaggagctg caaaacactg gaccctgggg   2220
cctcctcagc caatggatgc cctggattct ccccttctta ggacctctag cagctataat   2280
attgttactc ctcttttggac cctgtatctt taacctcctt gttaagtttg tcttttccag   2340
aatcgaagca gtaaaactac aaatcgttct tcaaatggag ccccagatgc agtccatgag   2400
taaaatctac cacggacccc tggaccggcc tgctagccca tgctctgatg ttaatgacat   2460
caaaggcacc cctcccgagg aaatctcaac tgcacaacct ctactacgcc ccaattcagc   2520
aggaagcagt tagagtggtt gttggccaac ctccccaaca gcagttgggt tttcctgttg   2580
agagggggga ctgagagaca ggaataacta gatttcctag accaactaag aatccctaag   2640
actagctggg aaggtgaccg cttccacctt taaacaccgg gcttgcaact tagctcacgc   2700
ccaaccaatc agatactaaa gagagctcac taaaatgcta attaggcaaa acaggagat    2760
aaagaaatag ccaatcatct gttg                                          2784
```

<210> SEQ ID NO 5
<211> LENGTH: 1799
<212> TYPE: DNA
<213> ORGANISM: Homo sapiens

<400> SEQUENCE: 5

```
gggattctta gtcggcctag gaaatccagc taatcctgtc tctcagtccc cccactcaac     60
aggaaaaccc aagtgctgtt ggggaggttg gctgacgacc agtctaactg cttcctgcgg    120
aattggggca tagtagggt tgtgcagttg agatttcctc gggagggggtg cgttcgatat    180
```

-continued

```
cattacaatt ggagcatggg ctagtaggcc ggtccagggg tccacggtag atcttagtca      240
tggacttcat ctggggttcc atttgaagaa cgatttgtag ctttacaact ttgattctgg      300
aagagacaaa cttaacaagg aggttaaaga tacagggtcc aaagaggagt atcaatatta      360
gagctgctag agatcctaag aaggggagaa tccagggcat ccattggctg aggaggcccc      420
agggtctggt gtttttgaag ctcctctgtt ctacgttgta ttcaatctcg aatttcttca      480
actttctctg tgacaattca ggattgatta acataataac aacattcttc cgctaaaata      540
acataataac aacattcttc ccctaaaaat aaacagcttc cccctctttc agaggttagc      600
aagtctaaag ctcttcaatt ttgaaggact actgatgcta ggaagttaag ttgatcttgc      660
aaggtgacca gggagtcggc aacccattcc atgtcaccat tgagttcttg agatagtttg      720
tagtagaact gagtagaggt tgtggtaccg ccaatgccag aacctagtcc acctagcact      780
cctgctccga taacaaaagg aagaatgagt actcttttgt tgtggggctt aggtacaaca      840
taattgtata aatcttgttc agtgtaaatg gtcatggggg cactaagaat gagaggaagc      900
acatagattc tgaagagcca ttcaaacaac gataggctaa ggtaccacag acaaaaaata      960
ttcctgaggg taggcagact attcgtgtgg gaggagttac ccacctgatg cattgggagt     1020
tggttgtgtc tacagtattg ctaaatttta cacaggtgag gtttgaggta tgggttattt     1080
ccagattgga acaagaggt cctactaaaa cggaagtggt gtttatttct gtgctgtagt      1140
tgttccattg ttcaggtaca gggattgaaa tgcatggcct gaaatacagg gggaggcaca     1200
accaacagtt agtagggttt tggaccgaga cctcatggag cccagtgagg gtggtattaa     1260
ataggcttac caggcaagta tgggtatgga gggtttcatg tagttttaag agatctagtc     1320 cttttgtaggg gctaggggtg ctatgtaccc gggtcagttg ggaggttact tcctttacat     1380
gtttttctct tgcctgatct tgaactccac cccctcaga cataccagta tgggtgaagt       1440
aagtccgaca gacagtggct ccaagtcttc caggacaact aggattaatc attttccctg     1500
tccaataatg agtatttgca tgcatgcaaa gagtggcaga gttatagcag ttgtggggca     1560
tatgggtgtg ggcagtgaag gtggagtttc ctttaggtaa actcctatt gatgggcat      1620 caatatttct gggaagccgc attcttcata gaaactcttg gtaaggggag ctgctggttg     1680
tacagcagca tggaggggggt gcagtgagag tgaaagggggg taagagaaca gtaaagagaa   1740
aaatatgata agggagggcc atggggattt acgatttag ttactttcct cacggttgt       1799
```

<210> SEQ ID NO 6
<211> LENGTH: 1489
<212> TYPE: DNA
<213> ORGANISM: Homo sapiens

<400> SEQUENCE: 6

```
tggtgcttgc cccgggcact ctcagtcctg ctgctggatc atctggttag tggcttctga       60
ctcagaggac ctacgtcccc tggggcagtg ggccttacag tgattcccttt gacacgaggt      120 gcatggacga gggggcggct tatttctatt tggacaatct tttttaaagt gtccttgtag      180
accgcactgg aagcaaaccc tattaggcat ttgatttgcc tagcttttcc cttttccagt      240
gcctccaaag tccgcttgcc tgagggccat gactaaagcg gtggcctttt ttttatccca      300
tttgtcccat tctgcctgct catcctgatc tctattataa aaaactgagg ttgccaagtt      360
caatagggtt tctaagtttt gttccgggcc taaggcagac ttttgaagtt ttttcctaat      420
gtctgtagct gactgagtga taaacttatc ctttaagatt agttggcctt cagtagagtc      480
```

```
agttgacaga gagaggtatg cttcctcaat gcctccgtta gtcactccag aaaggcggta      540
ggattttctt cctttccctg tgttatagtg acatcattg aataactcac aggcttcttt      600
ctagttttcc ttagtccttc tagcacgcaa gttagcaaat gtctgcggca ccaatctcca      660
tgttctgatt ctgtgtccca gtgagggtct acactgggaa ctgcctgctg gcctgtgggg     720
aatcgttctc tttcctctgt tgtcgaccta tcattgacct gactgagata ccagagatcg     780
ccaaactctc aggctgcagt tacggcgaca cttctgtcat ttggggttag tgtctgattt     840
agcagtaaca ttatatctct ccatatcaga tcaaaggatt gtcctaaacc ttgtaaaaca     900
tcaatatagc cattagggtt atctgagaat ttacctaggt ctatttttaat ttaaagtctg    960 ggagagaaaa aggcacatgc actctggctg ggccgaattc tcttcctccc actgcgtctg    1020
agagagaaaa aggtacgtgc actctggctg ggccgaattc tcctcccacc gcttggaggg    1080
ggcataatcg gggaatattg gcattctttg gttagttgtt taccccttg tctatctcct     1140 tttgaccgt ttggggttgaa ggggggtcct tattatttgg ggaaggagtc tggggggatgc   1200 tggggtaggg aggtagactc tgagggcttc ctgtagggca taaatcacac tttttacata    1260
attgcgagtt gtctcttaat gaaaagaaag tttgtacgta tgacacttca caccatttgc    1320
cttcttttct acaaaagagg tctagctgta agatggtgtt ataatttatg cttccctcag    1380
gatgccaggt ttctccccct taaagagtat atcgttgcca gcggtactg cagaagaata     1440 tgtctttttt ttcttagcat ctgagagtca aattggtccc aattctcca                1489
```

<210> SEQ ID NO 7
<211> LENGTH: 1216
<212> TYPE: DNA
<213> ORGANISM: Homo sapiens

<400> SEQUENCE: 7

```
taaagataca gggattgaaa tgtatggcct gaagtgcagg gtcatatagg tgtgggtggt       60
gaaaatgggg tttcctttag aaaaactcct atacgatggg tcatcaatat ttccaggaag     120
ccgcattctc catagaagct cttggtaatg ggagctactg gtagtacagt ggcatggagg     180
gggtgcagtg agagtgaaag agggtaaaag aacagtaaag agaaaaatat gataagggag    240
gggttcagtg agagtgaaag ggggtaagag aacagtaaag aaaaaaatat gacaaggagg    300
gccatgagga tctacgattc tagttacttt cctcacggtt gtcgcttgaa gagcaggtgc    360
agatcctcta gaggttcaca ggaatagcta gcgttgtctc ctggattttc gggttccttt    420
ggcagtatac agagtttgac tcgagtgtga tgtattcaag actccactcc agccacttta    480
accgcagttg gggtagataa aatgactggg tagggtcctt cccaggatgt atctaaggat    540
ggggacttag aaggaaggga cttgactaat accatgtcac caggggtgcaa taattacttt   600 ccctcttctc gggaacaggt tccctgtaat gttttaagaa cttgttgata tttggccaag    660
gaggtgatgt ctgcaactaa gctggccatc tctcggtcaa gcacaaggtc cttggttagg    720
aagggccatc catacagcat tttgtatggg ctaagtcctg cttttgggg agattttgg     780 attcttagta aggctgtagg caacagagca ggccatgcaa ggtgggtttc ttgggttagc    840
ttttttaaat gtcgtttgag tgcttcattc attttcttga cttttcctga ggattgtggc   900
ctccacgcgc agtgtaagtg atattgtatg cctaatgcct gggatactcc ctgggttact    960
gtagccttga aaacggggcc attgtcactc tgtaagcctc ggggaagtcc gaatctggga   1020
attatttcat gaattagtgc ctttattaca tcttggtcct tttctgtcct acaaaggaag   1080
gcctctgccc aaccagtgaa aatatctacc cagactagta gatactgaaa tccctgagat   1140
```

```
ttgggcatgt gggtaaaatc tagttgccag tcttctcctg agtaatggcc tgttctttgt    1200
tctcctgaag gagctt                                                    1216

<210> SEQ ID NO 8
<211> LENGTH: 976
<212> TYPE: DNA
<213> ORGANISM: Homo sapiens

<400> SEQUENCE: 8
agtgataatg gaatacttga agtaatccc ctcactccag gaactagtgc tgagctggcc       60
aaactaatag ccctcactcg ggcactagaa ttaggagaag agaaagggt aaatatatat      120 acagactata agtatgctta cctagtcctt catgcccatg cagcaatatg gagagaaagg     180
gaattcctaa cttccaaagg aacacctatc aaacatcagg aagccattag gatattatta    240
ttggtggtac agaaacctaa agaggtggca gtcctacact gctggggtca tcagaaaaaa    300
aaggaaaggg aaatagaagg gaactaccaa gcagatattg aagccaaaag agccgcaagg    360
caggaccctc cattagaaat gcttatagaa ggacccctag tgtggggtaa ccccctccag    420
gaaagcaatc cccagtactc agcaggagaa ataaaatgga gaacctcacg aggacatact    480
ttcctcccct caggatggct agccaccaaa gaaggaaaaa tgcttttgcc tgcagctaac    540
caatggaaat tacttaaaac ccttcaccaa acctttcact taggattgat agcacccatc    600
agatggccaa attattattt actggatcag gccttttcaa aactatcaag caggtagtca    660
gggcctgtaa agtgtgccaa agaaataatc tcctgcactg caagccatac atttcaatcc    720
ctgtatcttt aacctccttg ttaagtttgt ctcttccaga atcaaagctg taaaactaca    780
aatggttctt caaatggagt ctcagatgca gtccatgact aagatatacc gcagccccct    840
ggagggggcc tgctagccca tgctccaatg ttaatgacat cgaaggcacc cctcccgggg    900
aaatctcaac tgcacaaccc ctactatgtc ccaattcagc aggaagcagt taaagcggtc    960
atcggccaac ctcccc                                                    976

<210> SEQ ID NO 9
<211> LENGTH: 942
<212> TYPE: DNA
<213> ORGANISM: Homo sapiens

<400> SEQUENCE: 9
agaggagaac agcagcataa gcggctggca gaggtaggga aagaccagca agaagaaaag     60
agagaaagag aaagagaaag tcagagaaag agacagagag aggaagagac aaagagacag    120
aaagtcaaag aggtagtagt cagaaacaga gacaaaaaaa aggagtcaga agagggaca    180 gacacagaaa gtcaaaaaaa aagttaagaa gaaaggaaaa gacaaagaag aagtcgaaga    240
ggagaaagag agagatagaa gtagtaaaga aaaaaacagc atatcccatt cctttaaagc    300
cagggtaaat ttctatctac ccagccaagg catattctac ttatgtggat cttcaaccca    360
tatctgcctc tcagacagtt tgcaagaaat aatgaaatct atccttactt tacaatccca    420
aatagactct ttggcagcag tgactctcca aaactgcaga ggcctagacc tcctcactgc    480
tgaaaaagga ggacactaca ccttcttagg ggaagaatgt tgttttttaca ctaaccagtc    540 ggggatagta tgagatgctg cccggagttt acaggaaaag gcttctgaaa tcagacaacg    600
cctttcaaat tcttatacca acttctggag ttaggcaaca tggcttctcc cctttctagg    660
tcctgtggca gccatcttgc tgttactcgc ctttgggccc tgtatttta accttcttgt     720
```

| | |
|---|---|
| caaatttgtt tcctctagaa tcgaggccat caagctacag atggtcttac aaatggaacc | 780 |
| ccaaaagagt tcaactaaca acttctaccg aggaccctg atcaaccca ctggcacttc | 840 |
| ccctggccta gagagttccc ctctgaagga caccgcaact gcagggccct tctttgcccc | 900 |
| atccagcagg agtagctaga gtggtcatcg gccaaattgc ca | 942 |

<210> SEQ ID NO 10
<211> LENGTH: 1375
<212> TYPE: DNA
<213> ORGANISM: Homo sapiens

<400> SEQUENCE: 10

| | |
|---|---|
| ccccaatatt ctctttctga tggggaaaaa tggccacctg agggaagcac aaattacaat | 60 |
| actatcctgc agcttgatct tttctgtaag agggaaggca aatggagtga ataccttat | 120 |
| gtccaagctt tcttttcatt gagggagaat acacaactat gcaaagcttg caatttacat | 180 |
| cccacaggag gacccctcag cttacccca tatcctagcc tccctatagc ttcccttcct | 240 |
| attgatgata ctcctcctct aatctcccct gcccagaagg aaataagcaa agaaatctcc | 300 |
| aaaggtccac aaaaccccc gggctatcgg ttatgtcccc ttcaagctgt agggggaggg | 360 |
| gaatttggcc caacccgggt gcatgtcccc ttctccctct ctgatttaaa gcagatcagg | 420 |
| cagacctggg gaagttttca gatgatcctg ataggtacat agatgtccta cagggtctag | 480 |
| ggcaaacctt tgacctcact tggagagacg tcatgctact gttagatcaa accctggcct | 540 |
| ttaatgaaaa gaatgcggct ttagctgcag cctgagagtt tggagatacc tggtatccta | 600 |
| gtcaagtaaa tgaaagaatg acagccgaag aaagggacaa cttccctact ggtcagcaag | 660 |
| ccatccccag tatggatccc cactgggact ttgactcaga tcatgggac tggagtcgta | 720 |
| aacatctgtt gatctgtgtt ctggaaggac taaggagaat tgggaaaaag cccatgaatt | 780 |
| attcaatgat atccaccata acccagggaa aggaagaaaa tccttctgcc ttcctcgagc | 840 |
| ggctacaaga ggccttaaga aaatatactc ccctgtcacc cgaatcactc gagggtcaat | 900 |
| tgattctaaa agataagttt attacccaat cagccacaga tatcaggaga aagctccaaa | 960 |
| agcaagccct gagccctgaa caaaatctag agacattatt aaacctggca accttggtgt | 1020 |
| tctataatag ggaccaagag gaacaggccc aaaaggaaaa gcgagatcag agaaaggccg | 1080 |
| cagccttagt catggccctc agacaaacaa accttggtgg ttcagagagg tcagaaaatg | 1140 |
| gagcaggcca atcacctggt acggcttgtt atcagtgcgg tttactagga cactttaaaa | 1200 |
| aagattgtcc aataagaaac aagctgcccc ctcatccgtg tccactatgc cgaggcaatc | 1260 |
| actggaaggt gcactgcccc agaggatgaa ggttccctgg gttagaagcc cccaaccaga | 1320 |
| tgatccaaca acaggactga gggtgcccgg ggcaagcacc agctcatgtc atcac | 1375 |

<210> SEQ ID NO 11
<211> LENGTH: 944
<212> TYPE: DNA
<213> ORGANISM: Homo sapiens

<400> SEQUENCE: 11

| | |
|---|---|
| acctaggagg aactgtcttc aggacaggac tatagatgct tcctcccagg cgattaaggg | 60 |
| aaaaagacac aatgggtatt cagtaagtga taggaaact cttgtagaag cagagttagg | 120 |
| aaaattgcct aataattggt ctgctcaaat gtgcgagctg tttgcactca gccaaacctt | 180 |
| aaagtatta cagaatcagg aagaagccat ctataccaat tctaagttaa tatggactga | 240 |
| acgagaactt attaatagca aagaataatt gaaatcccaa acttacaagg ttttcaacaa | 300 |

```
aagcacagtt tgctaaaagt taactgtgta acatgtatta tcctactacc acaaactctc    360
aaatgatttc tcagacagtt tgcaagaaac aatgaaacct atccttactc tacaatccca    420
aatagactct ttggcagcag tgactctcca aaaccaccaa ggcctagacc tcctcactgc    480
tgagaaagga ggactctgca ccttcttagg ggaagattgt tgttttttaca ctaaccagtc    540 agggatagtg tgagatgcca cccagcgttt acaggaaaag gcttctgaaa tcagacacaa    600
tgcttttcaa accttatagc aacctctgga gttcggcgac tggcttttcc cctttctagg    660
tcctgtgaca gccatcttgc tattactcgc cttcgggccc tgtattttta acctcctcgt    720
caaatttgtt tcctctagga tcgaggccat caagctacag atggtcttac aaatggaacc    780
ccaaatgagc tcgactaaca acttctactg gaccccctg accgaccca ctggcccttt    840 aactggctta aagagtttcc ctctggagga cactacaact gcagggcccc ttctttgccc    900
catccacagg aagttagcta gagcagtcat cacccaattc ccaa    944

<210> SEQ ID NO 12
<211> LENGTH: 963
<212> TYPE: DNA
<213> ORGANISM: Homo sapiens

<400> SEQUENCE: 12
tacaggaacc ccataatacg tccttggcaa attctattca gctccaactg ctaggagtgg     60
cccatttgtc ctgaaccctc aaatcatggg aatgagaaat gaatttagac tgaccacagc    120
ccttatgagt tttcagctac agggtgtat agaaccctga taaggagttt tctttgtgtg    180
tggaagatcc ttctatattt gcctccccac caactggaca ggaacttgta ctttagccta    240
catagtacct cctgtgactt atcctttca gaagaggcag tagctgtgcc cattcatgct    300
aagcttcagc cgagagcaat ctcactactt cctctattgg ctggtttagg atttactacc    360
acctaggaag tggactcaca gcctagatga aatctctctc caacttactc aaatccagga    420
ccaaatagac tcattagcag ctgtggttct ccgaaccagt gagcactaga tctccaatct    480
cctcactgcc gaaaggggag gaacatgcct ttttctgaac aaggaatgtt gttttatgt    540 caataaatca ggcatagtga gagatggaat taaatgactt caggatagag ctagcagact    600
acatggtggg acaaccgaaa ctacctcagg gttctcacag cctgttctcc actggcttct    660
tccattttta ggtcccttcc ttatgattat tctaggagta acctttggcc catgtctttt    720
cagttccttc atcctttcgt ttcttcctga atagaatcaa tgaaactaga atgttactg    780 cagatggaac ctcagatgac ttcaaccagc acctattatc aaggacccct aaaccagcct    840
gccggcccat acccggacgt tgacacccaa accacctctc acgaggaaac ctcagctaca    900
gaaccccttc tatgcccta ttcagcagga agcaattaga gtggtcatcc tcccacaccc    960
caa                                                                  963

<210> SEQ ID NO 13
<211> LENGTH: 1362
<212> TYPE: DNA
<213> ORGANISM: Homo sapiens

<400> SEQUENCE: 13
ccacaatatc ctcttccagg aggagaacga tggccacctg agggaagtat acactataat     60
accatcctgc aactgatctg ttttgtaaa caagaaggca gtggattta ggtaccatat    120 gttcagacct ttttctcatt aagggatgat aacccacgat tgtgtaagac atgtaacctg    180
```

-continued

```
cacccccacag ggagtcctca aattctaccc ccatacccag tcctccccac ggctcctcct      240
actaatgcca aaccctctct ggcttctaca gcccaaaagg gaacaaataa aagagccttc      300
agagagccaa gagaccccac tggcccctgg ctatgtcctc ttcaggctgt aggaggggaa      360
tttggcccaa cccgagtaca tgttcccttt tctctctctg atctaaagca aattaaggca      420
gacttggatg aaagttctca gatgacccca atagatacgt agatggcctg ctgggtctgg      480
gacaatcttt tgacctttcc tggagagaga tcatgttatt gcttgatcag acctaacctc      540
taatgagaag aatgctgctt taacaggagc ccgagagttt ggggatacct ggtacctcag      600
ttaagtaagt gatagaatga catcagaaga gagcagtttc ctactggcca gcaagcagtc      660
cccagtatgg atccccactg ggaccctgac tcggatcatg gggactggag tcacaaacat      720
ttactgacct gtatcctaga agggttaagg agaactagga aaaagcccat gaactattca      780
atgatgtcta ctataaccca agggaaggaa gaaaaccta ttgccttcct caaaaggctg      840
agggaggctt tgagaaaata tactcccctg tcaccagatt ccctcgaagg ccagttaatt      900
ttaaaggaca aatttattac tcagtcagct gcagacatta ggaaaaagct ccaaaagtta      960
gccttgggcc gagcaaaatt tggaggcatc attaaacctg caacctcag tgttctatca     1020 tagggaccaa gaggaacagg ccgaaaagga aaagcaggat aagagaaagg ctgcagattt     1080
agtcatgccc tcagacaaac cttggcggtt caaagaggag aaaaaatgga gcaggccaat     1140
cacccagcag ggcttattat cagtgcagtt tacaaggaca ctttaaacaa gattgtccaa     1200
agagaaataa gccgccctct cacccatgtc cactatgcca aggtgatcac tggaaggcac     1260
actgtcccag aggacaaagg ttctctgggc cagaagtccc caaccagatg atccagcaac     1320
aggatggagg gtgcccgggg caagcaccag ctcgtgttgt ca                         1362
```

<210> SEQ ID NO 14
<211> LENGTH: 945
<212> TYPE: DNA
<213> ORGANISM: Homo sapiens

<400> SEQUENCE: 14

```
ttgcagatca atctcagact gctgtgctag caatgagtga ggcttcgtgg gcatgggacc       60
ctctgagcca ggcatgggat ataatgtcct tgtgtgccat ttgctaagac tgttggaata      120
gcacagtatt agggtgggag tggcccgatt ttccaggtgc tgtctgtcac cgcttccctt      180
ggctaggaaa gagaattccc tgaccccttg ttcttcccag gtaaggcagt gcctcacccct     240 gcttcagctc acactcaggt gactgcaccc actgtcctgc ccccactgtc ggacaagccc      300
cagtgagatg aacctggtac ctcagttgga aatgcagaaa tcacctgtct tctgcgtcac      360
tcacactggg agctgtagac tggagctgtt cctatttggc catcttggaa ccatctccca      420
aatagactct ttggcagcag tgactctcca aaaccaccaa ggcctagacc tcctcattgc      480
tgagaaagga ggactctgca ccttcttagg ggaggagtgt tgtttttata ctgaccagtc      540
agggatggta cgagatgcca cccgatgttt acaggaaaag gcttctgaaa tcacacaaca      600
cctttcaaac tcttatacca acctctggag ttgggcaaca tggcttctcc cctttctcgg      660
tcccattgca gccatcttgc tattactcgc cttcaggctg tgtattttta acctccttgt      720
caaatttgtt tcctctagaa ttgaggccgt caagctacag atggtcttac aaatgggacc      780
ccaaatgagc tcaactaaca acttctgcca aggacccctg gaccaacctg ctggcccttt      840
cactggcctt aagagttccc ctctggaggg cactacaact gcagggcccc ttctttgccc      900
ctatccagca ggaagtagct agagcagtca tcacccaatt cccaa                      945
```

<210> SEQ ID NO 15
<211> LENGTH: 939
<212> TYPE: DNA
<213> ORGANISM: Homo sapiens

<400> SEQUENCE: 15

```
agagctacct tggcaagtac tctaggagta tgggaaaatg aaaacaacaa actcacacac      60
cattttaaca tacacaatca ggtctgccca cccagcaagg tatattcttt gtatgtggaa     120
catcgaccta tatctgcctc cccactaact agacagccac ctgaatctta gtctttctaa     180
gtcccaacag taacattgcc ccaggaaatc agaccatatc agtatccctc aaagctcaag     240
tctgtcagtg cagagccata caactaatac ccctacttat agggtaagga atggctactg     300
ctacaggaac cagaatagct agtttgttta cttcattatc ctactaccac acactctcaa     360
atgatttctc agacagtttg caagaaataa cgaaatctat ccttactcta caatcccaaa     420
tagactcctt ggcagcagtg accctccaaa acggctgagg cctagacctc tcactgcca      480
agaaaggagg actctgcatt ttcttagggg aagagtgttt ttacactaac cagtcaggga     540
cagtatgaga tgccactcgg agtttacagg aaaaggcttc tgaagtcaga caatgccttt     600
caaactctat accaaactct ggagttgggc aacatggctt ctccccttc taggtcccgt      660
gacagccatc ttgctattat ttgcctttga gccctgtatt tttaatctcc ttttcaaatt     720
tgtttcctct ggatcgaggc catcgagcta cagatggtct tcacaaatgg aaccccaaat     780
gagctcaact aacaacttct actgaggacc cctggactaa cctgctgacc ctttcactgg     840
cctgaagaat tcccctctgg aggacactac aactgcaggg ctccttcttt gcccctatcc     900
agcaggaagt agctagagct gtcattgcct aattcctaa                            939
```

<210> SEQ ID NO 16
<211> LENGTH: 979
<212> TYPE: DNA
<213> ORGANISM: Homo sapiens

<400> SEQUENCE: 16

```
agtgataatg gaatacttga aagtaatccc ctcactcccc aggaactagt gctcagctgg      60
cagaactaat agccctcact cgggtactag aatcaggaga aggaaaaagg gtaaatatat     120
atacagactc taagtgtgct tacctagtcc tccatgccca tgcagcaata tggagagaaa     180
gggaattcct aacttccgag ggaacaccta tcaaacatca ggaagccatt aggaaattat     240
tattggctgt acagaaacct aaagaggtgg cagttttaca ctgccggggt catcagaaag     300
gaaaggaaag ggaaatacaa gggagccacc aagttgatat tgaagtcaaa agagccacaa     360
ggctggaccc tccattagaa atgcttatag gaggacccct agtatggggt aatcccctcc     420
gggaagccaa gccccagtac tcagcaggag aaatagaata gggaacttca tgaggacata     480
cttccctccc ctccagatgg ctagccacca ataaggaaa atacttttg cctgcagcta      540
accaatagaa attacttaaa acccttcatc aaaccttcca cttaggcatt gatagcaccc     600
atgagatggc caaattatta tttactggac caggcctttt caaaactatc aagcagatag     660
tcagggcctg taaagtctgc aaagaaaata tccccctgca ctgcaggcca tacatttcaa     720
tccctgtatc tttaacctcc ttcttaaatt tgtctcttcc agaatcaaag ctgtaaaatt     780
acaaatagtt cttcaaatgg agccacagat gcagtccatg actaagatcc accacagacc     840
cctggaccag cctgctagcc catgctccaa tgttaatgac atcgaaggca ccccctcctg     900
```

| aggaaatctc aactgcacaa cccctactac gccccaattc agcagaaagc agttagagtg | 960 |
| gtcatcagcc aacctcccc | 979 |

<210> SEQ ID NO 17
<211> LENGTH: 1774
<212> TYPE: DNA
<213> ORGANISM: Homo sapiens

<400> SEQUENCE: 17

| catgctggta aaggaccgct agaatccagc agccaggacc actttctttg tggtcaagaa | 60 |
| aggtgggaaa acaggtgcag gactgctaca ctggtaagca taactaatcc gataagcaga | 120 |
| ggtccatggg tggttacgca ccctggaaag gaataagcat taggactata gaggacactc | 180 |
| taggactaat gctcatcgga aaatgactag gggtactggc atccctatgt tcttttttca | 240 |
| gatgggaaat gttcccccca aggcagaaat gcccctaaga tgtattctgg agaaatggga | 300 |
| ccaatctgac catcagacac taagaaagaa atgacttata ttcttctgca gtaccacctg | 360 |
| gccacaatat cttcttcaag gggcagaaac ctggcctcct gagggaagta taaattataa | 420 |
| caccatctta cagctagacc tcttttgtag aaaagaaggc aaatgagtg aagtgccata | 480 |
| tgtacaaact ttcttttcat taagagataa ctcccaatta tgtaaaaagt gtgatttatg | 540 |
| ccctacagga agccctcaga gtctacctcc cgacccagc aagaccccaa ctccttctcc | 600 |
| aactaataag gacccccctt caacccaaat ggtccaaaag gagatagaca aagggtaaa | 660 |
| caatgaacca aagagtgcca atattacacg attatactcg ctccaagcag tgggaggaga | 720 |
| atttggccca gccagcgtgc atgtaccttt ttctctctca gatttaaagc aaattaaaat | 780 |
| agacctaggt aaattctcag ataaccctga tggctatatt gatgttttac aagggttagg | 840 |
| acaatccttt gatctgacat ggagagatat aatgttactg ctaaatcaga cactaacccc | 900 |
| aaatgaaaaa agtgctgcca taacagcagc ctgagagttt ggcgaactct ggtatctcag | 960 |
| tcaggtcaat gataggatga caacagatga agagaatga ttccccacag gccagcaggc | 1020 |
| agttcccagt gtagaccctc attaggacac agaatcagaa cttggagatt ggtgccacag | 1080 |
| acatttgcta acttgcgtgc tagaaggact aaggaaaact aggaagaagc ccatgaatta | 1140 |
| ttcaatgatg tcccctataa cacagggaaa ggaagaaat cctactgcct ttctggagag | 1200 |
| actaagggaa ggattgagga agcatacctc cctgtcacct gactctatta aaggccaact | 1260 |
| aatcttaaag gataagtta tcactcagtc agctgcagag attaagaaaa aacttcaaaa | 1320 |
| gtatgcctta ggcccagagc aaaacttaga aaccctactg aacttggcaa cctcagtttt | 1380 |
| ttataataga gatcaggaag agcagggaa tgggacaaat gggataaaa aaaaaaaaa | 1440 |
| aggtgactgc tttagtcgtg gccctcaggc aaatggactt tggaggctcc agaaaaggga | 1500 |
| aaagctgagc aaattgaatg cctaacaggg cttgcttcta gtgtggtcta caaggacact | 1560 |
| ttaaaaaaga ttgtccaagt agaaacaagc tgccccttg tccatgcccc ttatgtcaag | 1620 |
| ggaatcactg gaaggcccac tgccccagga gatgaaggtc ctctgagtca gaagccacta | 1680 |
| accagataat ccagcagcag gactgaggat gcccagggca agcgccagcc catgccatca | 1740 |
| ccctcacaga gccttgggta tgcttgacca ttga | 1774 |

<210> SEQ ID NO 18
<211> LENGTH: 938
<212> TYPE: DNA
<213> ORGANISM: Homo sapiens

<400> SEQUENCE: 18

-continued

| | |
|---|---:|
| tgtaggaaga actcccttca ggacaggaca atagatggtt cctcccaggt gattaaggaa | 60 |
| aaaagacaca gtattcagta agtgataagg aaactcttgt agaagcagag ttagaaaaat | 120 |
| tgcctaataa ttggtctgct caaatgtgtg agttgtttgc actcagccaa atcttaaagt | 180 |
| acttacagaa tcaggaagca gccatctata ccaattctaa gttaatatgg actaaacgag | 240 |
| gttttattag tagcaaagaa aaattaaaat cccaaactta caaggttttc aactaaagtt | 300 |
| tgccaaaagt taacagtgta acatgtatta tcctactatc acacactctc aaaggatttc | 360 |
| tcagacagtt tgcaagaaat aacgtaatct atccttactc tacagtccca aatagactct | 420 |
| ttggtagcag tgactctcca aaactgccga ggtctagacc tcctcaatgc tgagaaagga | 480 |
| gaactctgca ccttcttagg ggaagagtgc tgtttttaca ctaaccagtc agggatagta | 540 |
| tgagatactg cctgacgttt acaggaaaag gcttctgaaa tcagacaacg cctttcaagc | 600 |
| tcttatacca acctctggag ttgggcaaca tggcttctcc ccttgctagg tcctgtggca | 660 |
| gccatcttgc tattacttgc cttcgggccc tgtattttta acctccttgt caaatttgtt | 720 |
| tcctctagga tcaaggccat caagctacag atggtcttac aaatggaacc ccaaatgagc | 780 |
| tcaactaaca acttctactg aggacacctg gactgaccca ctggcccttt cactggccta | 840 |
| aagagttccc ttctggagga cactacaact gcagggcccc gtcttcaccc ctatccagca | 900 |
| ggaagtagct agatcagtca ttgcccaatt cccaacag | 938 |

<210> SEQ ID NO 19
<211> LENGTH: 1308
<212> TYPE: DNA
<213> ORGANISM: Homo sapiens

<400> SEQUENCE: 19

| | |
|---|---:|
| gatgcttgcc ccaggcaccc tcagtcctgt tgttggatca tctggtcggg ggcttctggc | 60 |
| ccaaagaacc tttgtcctct gaggcagtgc accttccagt gattgcctca gcattgtgga | 120 |
| catgggcaag ggggcagctt gtttctcact ggacaatctt ttttaaggtg tccttccaaa | 180 |
| ccacactggt aacaagccct accaggtgat tggcctgctc tatttctgt cctctctgaa | 240 |
| ccaccaaggt ttgtctgtct gagggtcatg actaaggctg tggcctttct ctgatcttgc | 300 |
| tttttccttt tggcctgttc ctcttggtac ctattataga acactgaggt tgccaggttt | 360 |
| aacaatggct ccagattttg ttcagggcac agggctcatt ttggagcttt ctcctgatat | 420 |
| ctgcagctga ttgggtaata aacttatctt ttaggatcaa ttgactctca agagagttgg | 480 |
| gtgacagggg agtatatttc cttgaggcct cccatagccg ctctaggaag gcagaaggat | 540 |
| tttcttcctt tccctgagtt ataaaagaca tcattgaaca actcatggac ttttcccaa | 600 |
| ttctccgtag tccttctaga acacaggtca gcagatgttt acgactccag tccccatgat | 660 |
| ctgagtctag acaccagtgg ggatccatac tggggatggc ctgctgactg gtagggaatt | 720 |
| tgtccctttc tttggctgtc attctatcat ttacttgact aagataccaa gtatctccaa | 780 |
| attctcaggc tgcagctaaa gctgcattct tttcattaaa ggccagggtt tgatctaata | 840 |
| gcatgacatc tctccaagtg aggtcaaagg tttgccctag atccatagga catcagagaa | 900 |
| ggagaagggg acatacacct gagttagcca aattcccctc cctctacagc ttgaagggga | 960 |
| cataagcaat agcctgggga ttttgtggt cctttggaga tttctttgct tgtttccttc | 1020 |
| tgggtggggg agattagagg aggcttatca gtaataggaa ggggagctat agggaggcta | 1080 |
| ggatatgggg gtaagctgag aggtcatctt gtgggatgta aattgcaagc tttgcatagt | 1140 |

-continued

```
tgtggatttt ccttacaatg aaaataaagc ttggacataa ggtatttcac tccatttgcc       1200
ttccctctta cagaaaaggt caagctgcag gatagtactg taatttatac ttccttcagg      1260
tggccatttc ttcccatcag agagagaata ctggggctgg ccatagt                    1308
```

```
<210> SEQ ID NO 20
<211> LENGTH: 711
<212> TYPE: DNA
<213> ORGANISM: Homo sapiens

<400> SEQUENCE: 20
actgagagac aggactagct ggatttccta ggccgactaa gaatccctaa gcctagctgg       60
gaaggtgacc acgtccacct ttaaacacgg ggcttgcaac ttagctcaca cctgaccaat     120
cagagagctc actaaaatgc taattaggca aagacaggg gtaaagaaat agccaatcat     180
ctattgcctg agagcacagc aggagggaca acaatcggga tataaaccca ggcattcgag     240
ctggcaacag cagccccct ttgggtccct tcccttttgta tgggagctgt tttcatgcta     300
tttcactcta ttaaatcttg caactgcact cttctggtcc atgtttctta cggctcgagc     360
tgagcttttg ctcaccgtcc accactgctg tttgccacca ccgcagacct gccgctgact     420
cccatccctc tggatcctgc agggtgtccg ctgtgctcct gatccagcga ggcgcccatt     480
gccgctccca attgggctaa aggcttgcca ttgttcctgc acggctaagt gcctgggttt     540
gttctaattg agctgaacac tagtcactgg gttccatggt tctcttctgt gacccacggc     600
ttctaataga actataacac ttaccacatg gcccaagatt ccattccttg gaatccgtga     660
ggccaagaac tccaggtcag agaatacgag gcttgccacc atcttggaag c              711
```

```
<210> SEQ ID NO 21
<211> LENGTH: 711
<212> TYPE: DNA
<213> ORGANISM: Homo sapiens

<400> SEQUENCE: 21
actgagagac aggactagct ggatttccta ggctgactaa gaatccctaa gcctagctgg      60
gaaggtgacc acatccacct ttaaacacgg ggcttgcaac ttagctcaca cctgaccaat    120
cagagagctc actaaaatgc taattaggca aagacaggag gtaaagaaat agccaatcat    180
ctattgcctg agagcacagc aggagggaca atgatcggga tataaaccca agtcttcgag    240
ccggcaacgg caaccccctt tgggtcccct cctttgtat gggagctctg ttttcatgct     300
atttcactct attaaatctt gcaactgcac tcttctggtc catgtttctt acggcttgag    360
ctgagctttc gctcgccatc caccactgct gtttgccgcc accgcagacc cgccgctgac    420
tcccatccct ctggatcatg cagggtgtcc gctgtgctcc tgatcagcg aggcaccct     480 tgccgctccc aatcgggcta aaggcttgcc attgttcctg catggctaag tgcctgggtt    540
catcctaatt gagctgaaca ctagtcactg gttccatggt ttctcttctg tgacccacag    600
cttctaatag agctataaca ctcaccgcat ggcccaaggt tccattcctt gaatccataa    660
ggccaagaac cccaggtcag agaacacgag gcttgccacc atcttgggag c              711
```

```
<210> SEQ ID NO 22
<211> LENGTH: 2055
<212> TYPE: DNA
<213> ORGANISM: Homo sapiens
<220> FEATURE:
<221> NAME/KEY: CDS
<222> LOCATION: (1)..(2055)
<223> OTHER INFORMATION:
```

-continued

<400> SEQUENCE: 22

| | | | | | | | | | | | | | | | | |
|---|---|---|---|---|---|---|---|---|---|---|---|---|---|---|---|---|
| ccc | aag | aca | gcc | aac | tta | gtt | gca | gac | atc | acc | tcc | tta | gcc | aaa | tat | 48 |
| Pro | Lys | Thr | Ala | Asn | Leu | Val | Ala | Asp | Ile | Thr | Ser | Leu | Ala | Lys | Tyr | |
| 1 | | | 5 | | | | | 10 | | | | | 15 | | | |

| | | | | | | | | | | | | | | | | |
|---|---|---|---|---|---|---|---|---|---|---|---|---|---|---|---|---|
| caa | caa | gtt | ctt | aaa | aca | tta | caa | gga | acc | tat | ccc | tga | gaa | gag | gga | 96 |
| Gln | Gln | Val | Leu | Lys | Thr | Leu | Gln | Gly | Thr | Tyr | Pro | | Glu | Glu | Gly | |
| | | | 20 | | | | | 25 | | | | | | 30 | | |

| | | | | | | | | | | | | | | | | |
|---|---|---|---|---|---|---|---|---|---|---|---|---|---|---|---|---|
| aaa | gaa | cta | ttc | cac | cct | tgt | gac | atg | gta | tta | gtc | aag | tcc | ctt | ccc | 144 |
| Lys | Glu | Leu | Phe | His | Pro | Cys | Asp | Met | Val | Leu | Val | Lys | Ser | Leu | Pro | |
| | | | | 35 | | | | | 40 | | | | | 45 | | |

| | | | | | | | | | | | | | | | | |
|---|---|---|---|---|---|---|---|---|---|---|---|---|---|---|---|---|
| tct | aat | tcc | cca | tcc | cta | gat | aca | tcc | tgg | gaa | gga | ccc | tac | cca | gtc | 192 |
| Ser | Asn | Ser | Pro | Ser | Leu | Asp | Thr | Ser | Trp | Glu | Gly | Pro | Tyr | Pro | Val | |
| | | 50 | | | | | 55 | | | | | 60 | | | | |

| | | | | | | | | | | | | | | | | |
|---|---|---|---|---|---|---|---|---|---|---|---|---|---|---|---|---|
| att | tta | tct | acc | cca | act | gcg | gtt | aaa | gtg | gct | gga | gtg | gag | tct | tgg | 240 |
| Ile | Leu | Ser | Thr | Pro | Thr | Ala | Val | Lys | Val | Ala | Gly | Val | Glu | Ser | Trp | |
| 65 | | | | | 70 | | | | | 75 | | | | | | |

| | | | | | | | | | | | | | | | | |
|---|---|---|---|---|---|---|---|---|---|---|---|---|---|---|---|---|
| ata | cat | cac | act | tga | gtc | aaa | tcc | tgg | ata | ctg | cca | aag | gaa | cct | gaa | 288 |
| Ile | His | His | Thr | | Val | Lys | Ser | Trp | Ile | Leu | Pro | Lys | Glu | Pro | Glu | |
| 80 | | | | | 85 | | | | | 90 | | | | | | |

| | | | | | | | | | | | | | | | | |
|---|---|---|---|---|---|---|---|---|---|---|---|---|---|---|---|---|
| aat | cca | gga | gac | aac | gct | agc | tat | tcc | tgt | gaa | cct | cta | gag | gat | ttg | 336 |
| Asn | Pro | Gly | Asp | Asn | Ala | Ser | Tyr | Ser | Cys | Glu | Pro | Leu | Glu | Asp | Leu | |
| 95 | | | | 100 | | | | | 105 | | | | | 110 | | |

| | | | | | | | | | | | | | | | | |
|---|---|---|---|---|---|---|---|---|---|---|---|---|---|---|---|---|
| cgc | ctg | ctc | ttc | aaa | caa | caa | cca | gga | gga | aag | taa | cta | aaa | tca | taa | 384 |
| Arg | Leu | Leu | Phe | Lys | Gln | Gln | Pro | Gly | Gly | Lys | | Leu | Lys | Ser | | |
| | | | | 115 | | | | | 120 | | | | | | | |

| | | | | | | | | | | | | | | | | |
|---|---|---|---|---|---|---|---|---|---|---|---|---|---|---|---|---|
| atc | ccc | atg | gcc | ctc | cct | tat | cat | att | ttt | ctc | ttt | act | gtt | ctt | tta | 432 |
| Ile | Pro | Met | Ala | Leu | Pro | Tyr | His | Ile | Phe | Leu | Phe | Thr | Val | Leu | Leu | |
| 125 | | | | 130 | | | | | 135 | | | | | 140 | | |

| | | | | | | | | | | | | | | | | |
|---|---|---|---|---|---|---|---|---|---|---|---|---|---|---|---|---|
| ccc | tct | ttc | act | ctc | act | gca | ccc | cct | cca | tgc | cgc | tgt | atg | acc | agt | 480 |
| Pro | Ser | Phe | Thr | Leu | Thr | Ala | Pro | Pro | Pro | Cys | Arg | Cys | Met | Thr | Ser | |
| | | | | 145 | | | | | 150 | | | | | 155 | | |

| | | | | | | | | | | | | | | | | |
|---|---|---|---|---|---|---|---|---|---|---|---|---|---|---|---|---|
| agc | tcc | cct | tac | caa | gag | ttt | cta | tgg | aga | atg | cag | cgt | ccc | gga | aat | 528 |
| Ser | Ser | Pro | Tyr | Gln | Glu | Phe | Leu | Trp | Arg | Met | Gln | Arg | Pro | Gly | Asn | |
| | | | 160 | | | | | 165 | | | | | 170 | | | |

| | | | | | | | | | | | | | | | | |
|---|---|---|---|---|---|---|---|---|---|---|---|---|---|---|---|---|
| att | gat | gcc | cca | tcg | tat | agg | agt | ctt | tct | aag | gga | acc | ccc | acc | ttc | 576 |
| Ile | Asp | Ala | Pro | Ser | Tyr | Arg | Ser | Leu | Ser | Lys | Gly | Thr | Pro | Thr | Phe | |
| | | | 175 | | | | | 180 | | | | | 185 | | | |

| | | | | | | | | | | | | | | | | |
|---|---|---|---|---|---|---|---|---|---|---|---|---|---|---|---|---|
| act | gcc | cac | acc | cat | atg | ccc | cgc | aac | tgc | tat | cac | tct | gcc | act | ctt | 624 |
| Thr | Ala | His | Thr | His | Met | Pro | Arg | Asn | Cys | Tyr | His | Ser | Ala | Thr | Leu | |
| | | 190 | | | | | 195 | | | | | 200 | | | | |

| | | | | | | | | | | | | | | | | |
|---|---|---|---|---|---|---|---|---|---|---|---|---|---|---|---|---|
| tgc | atg | cat | gca | aat | act | cat | tat | tgg | aca | gga | aaa | atg | att | aat | cct | 672 |
| Cys | Met | His | Ala | Asn | Thr | His | Tyr | Trp | Thr | Gly | Lys | Met | Ile | Asn | Pro | |
| 205 | | | | 210 | | | | | 215 | | | | | 220 | | |

| | | | | | | | | | | | | | | | | |
|---|---|---|---|---|---|---|---|---|---|---|---|---|---|---|---|---|
| agt | tgt | cct | gga | gga | ctt | gga | gtc | act | gtc | tgt | tgg | act | tac | ttc | acc | 720 |
| Ser | Cys | Pro | Gly | Gly | Leu | Gly | Val | Thr | Val | Cys | Trp | Thr | Tyr | Phe | Thr | |
| | | | | 225 | | | | | 230 | | | | | 235 | | |

| | | | | | | | | | | | | | | | | |
|---|---|---|---|---|---|---|---|---|---|---|---|---|---|---|---|---|
| caa | act | ggt | atg | tct | gat | ggg | ggt | gga | gtt | caa | gat | cag | gca | aga | gaa | 768 |
| Gln | Thr | Gly | Met | Ser | Asp | Gly | Gly | Gly | Val | Gln | Asp | Gln | Ala | Arg | Glu | |
| | | | | 240 | | | | | 245 | | | | | 250 | | |

| | | | | | | | | | | | | | | | | |
|---|---|---|---|---|---|---|---|---|---|---|---|---|---|---|---|---|
| aaa | cat | gta | aaa | gaa | gta | atc | tcc | caa | ctc | acc | cgg | gta | cat | ggc | acc | 816 |
| Lys | His | Val | Lys | Glu | Val | Ile | Ser | Gln | Leu | Thr | Arg | Val | His | Gly | Thr | |
| | | | 255 | | | | | 260 | | | | | 265 | | | |

| | | | | | | | | | | | | | | | | |
|---|---|---|---|---|---|---|---|---|---|---|---|---|---|---|---|---|
| tct | agc | ccc | tac | aaa | gga | cta | gat | ctc | tca | aaa | cta | cat | gaa | acc | ctc | 864 |
| Ser | Ser | Pro | Tyr | Lys | Gly | Leu | Asp | Leu | Ser | Lys | Leu | His | Glu | Thr | Leu | |
| | | | 270 | | | | | 275 | | | | | 280 | | | |

| | | | | | | | | | | | | | | | | |
|---|---|---|---|---|---|---|---|---|---|---|---|---|---|---|---|---|
| cgt | acc | cat | act | cgc | ctg | gta | agc | cta | ttt | aat | acc | acc | ctc | act | ggg | 912 |
| Arg | Thr | His | Thr | Arg | Leu | Val | Ser | Leu | Phe | Asn | Thr | Thr | Leu | Thr | Gly | |
| 285 | | | | 290 | | | | | 295 | | | | | 300 | | |

| | |
|---|---|
| ctc cat gag gtc tcg gcc caa aac cct act aac tgt tgg ata tgc ctc<br>Leu His Glu Val Ser Ala Gln Asn Pro Thr Asn Cys Trp Ile Cys Leu<br>305 310 315 | 960 |
| ccc ctg aac ttc agg cca tat gtt tca atc cct gta cct gaa caa tgg<br>Pro Leu Asn Phe Arg Pro Tyr Val Ser Ile Pro Val Pro Glu Gln Trp<br>320 325 330 | 1008 |
| aac aac ttc agc aca gaa ata aac acc act tcc gtt tta gta gga cct<br>Asn Asn Phe Ser Thr Glu Ile Asn Thr Thr Ser Val Leu Val Gly Pro<br>335 340 345 | 1056 |
| ctt gtt tcc aat ctg gaa ata acc cat acc tca aac ctc acc tgt gta<br>Leu Val Ser Asn Leu Glu Ile Thr His Thr Ser Asn Leu Thr Cys Val<br>350 355 360 | 1104 |
| aaa ttt agc aat act aca tac aca acc aac tcc caa tgc atc agg tgg<br>Lys Phe Ser Asn Thr Thr Tyr Thr Thr Asn Ser Gln Cys Ile Arg Trp<br>365 370 375 380 | 1152 |
| gta act cct ccc aca caa ata gtc tgc cta ccc tca gga ata ttt ttt<br>Val Thr Pro Pro Thr Gln Ile Val Cys Leu Pro Ser Gly Ile Phe Phe<br>385 390 395 | 1200 |
| gtc tgt ggt acc tca gcc tat cgt tgt ttg aat ggc tct tca gaa tct<br>Val Cys Gly Thr Ser Ala Tyr Arg Cys Leu Asn Gly Ser Ser Glu Ser<br>400 405 410 | 1248 |
| atg tgc ttc ctc tca ttc tta gtg ccc cct atg acc atc tac act gaa<br>Met Cys Phe Leu Ser Phe Leu Val Pro Pro Met Thr Ile Tyr Thr Glu<br>415 420 425 | 1296 |
| caa gat tta tac agt tat gtc ata tct aag ccc cgc aac aaa aga gta<br>Gln Asp Leu Tyr Ser Tyr Val Ile Ser Lys Pro Arg Asn Lys Arg Val<br>430 435 440 | 1344 |
| ccc att ctt cct ttt gtt ata gga gca gga gtg cta ggt gca cta ggt<br>Pro Ile Leu Pro Phe Val Ile Gly Ala Gly Val Leu Gly Ala Leu Gly<br>445 450 455 460 | 1392 |
| act ggc att ggc ggt atc aca acc tct act cag ttc tac tac aaa cta<br>Thr Gly Ile Gly Gly Ile Thr Thr Ser Thr Gln Phe Tyr Tyr Lys Leu<br>465 470 475 | 1440 |
| tct caa gaa cta aat ggg gac atg gaa cgg gtc gcc gac tcc ctg gtc<br>Ser Gln Glu Leu Asn Gly Asp Met Glu Arg Val Ala Asp Ser Leu Val<br>480 485 490 | 1488 |
| acc ttg caa gat caa ctt aac tcc cta gca gca gta gtc ctt caa aat<br>Thr Leu Gln Asp Gln Leu Asn Ser Leu Ala Ala Val Val Leu Gln Asn<br>495 500 505 | 1536 |
| cga aga gct tta gac ttg cta acc gct gaa aga ggg gga acc tgt tta<br>Arg Arg Ala Leu Asp Leu Leu Thr Ala Glu Arg Gly Gly Thr Cys Leu<br>510 515 520 | 1584 |
| ttt tta ggg gaa gaa tgc tgt tat tat gtt aat caa tcc gga atc gtc<br>Phe Leu Gly Glu Glu Cys Cys Tyr Tyr Val Asn Gln Ser Gly Ile Val<br>525 530 535 540 | 1632 |
| act gag aaa gtt aaa gaa att cga gat cga ata caa cgt aga gca gag<br>Thr Glu Lys Val Lys Glu Ile Arg Asp Arg Ile Gln Arg Arg Ala Glu<br>545 550 555 | 1680 |
| gag ctt cga aac act gga ccc tgg ggc ctc ctc agc caa tgg atg ccc<br>Glu Leu Arg Asn Thr Gly Pro Trp Gly Leu Leu Ser Gln Trp Met Pro<br>560 565 570 | 1728 |
| tgg att ctc ccc ttc tta gga cct cta gca gct ata ata ttg cta ctc<br>Trp Ile Leu Pro Phe Leu Gly Pro Leu Ala Ala Ile Ile Leu Leu Leu<br>575 580 585 | 1776 |
| ctc ttt gga ccc tgt atc ttt aac ctc ctt gtt aac ttt gtc tct tcc<br>Leu Phe Gly Pro Cys Ile Phe Asn Leu Leu Val Asn Phe Val Ser Ser<br>590 595 600 | 1824 |
| aga atc gaa gct gta aaa cta caa atg gag ccc aag atg cag tcc aag<br>Arg Ile Glu Ala Val Lys Leu Gln Met Glu Pro Lys Met Gln Ser Lys<br>605 610 615 620 | 1872 |

```
act aag atc tac cgc aga ccc ctg gac cgg cct gct agc cca cga tct    1920
Thr Lys Ile Tyr Arg Arg Pro Leu Asp Arg Pro Ala Ser Pro Arg Ser
            625                 630                 635 gat gtt aat gac atc aaa ggc acc cct cct gag gaa atc tca gct gca    1968
Asp Val Asn Asp Ile Lys Gly Thr Pro Pro Glu Glu Ile Ser Ala Ala
            640                 645                 650 caa cct cta cta cgc ccc aat tca gca gga agc agt tag agc ggt cgt    2016
Gln Pro Leu Leu Arg Pro Asn Ser Ala Gly Ser Ser     Ser Gly Arg
            655                 660                 665 cgg cca acc tcc cca aca gca ctt agg ttt tcc tgt tga                2055
Arg Pro Thr Ser Pro Thr Ala Leu Arg Phe Ser Cys
            670                 675
```

<210> SEQ ID NO 23
<211> LENGTH: 28
<212> TYPE: PRT
<213> ORGANISM: Homo sapiens

<400> SEQUENCE: 23

```
Pro Lys Thr Ala Asn Leu Val Ala Asp Ile Thr Ser Leu Ala Lys Tyr
1               5                   10                  15

Gln Gln Val Leu Lys Thr Leu Gln Gly Thr Tyr Pro
            20                  25
```

<210> SEQ ID NO 24
<211> LENGTH: 55
<212> TYPE: PRT
<213> ORGANISM: Homo sapiens

<400> SEQUENCE: 24

```
Glu Glu Gly Lys Glu Leu Phe His Pro Cys Asp Met Val Leu Val Lys
1               5                   10                  15

Ser Leu Pro Ser Asn Ser Pro Ser Leu Asp Thr Ser Trp Glu Gly Pro
            20                  25                  30

Tyr Pro Val Ile Leu Ser Thr Pro Thr Ala Val Lys Val Ala Gly Val
        35                  40                  45

Glu Ser Trp Ile His His Thr
    50                  55
```

<210> SEQ ID NO 25
<211> LENGTH: 38
<212> TYPE: PRT
<213> ORGANISM: Homo sapiens

<400> SEQUENCE: 25

```
Val Lys Ser Trp Ile Leu Pro Lys Glu Pro Glu Asn Pro Gly Asp Asn
1               5                   10                  15

Ala Ser Tyr Ser Cys Glu Pro Leu Glu Asp Leu Arg Leu Leu Phe Lys
            20                  25                  30

Gln Gln Pro Gly Gly Lys
        35
```

<210> SEQ ID NO 26
<211> LENGTH: 540
<212> TYPE: PRT
<213> ORGANISM: Homo sapiens

<400> SEQUENCE: 26

```
Ile Pro Met Ala Leu Pro Tyr His Ile Phe Leu Phe Thr Val Leu Leu
1               5                   10                  15
```

-continued

```
Pro Ser Phe Thr Leu Thr Ala Pro Pro Cys Arg Cys Met Thr Ser
         20                  25                  30
Ser Ser Pro Tyr Gln Glu Phe Leu Trp Arg Met Gln Arg Pro Gly Asn
         35                  40                  45
Ile Asp Ala Pro Ser Tyr Arg Ser Leu Ser Lys Gly Thr Pro Thr Phe
 50                  55                  60
Thr Ala His Thr His Met Pro Arg Asn Cys Tyr His Ser Ala Thr Leu
 65                  70                  75                  80
Cys Met His Ala Asn Thr His Tyr Trp Thr Gly Lys Met Ile Asn Pro
             85                  90                  95
Ser Cys Pro Gly Gly Leu Gly Val Thr Val Cys Trp Thr Tyr Phe Thr
            100                 105                 110
Gln Thr Gly Met Ser Asp Gly Gly Val Gln Asp Gln Ala Arg Glu
            115                 120                 125
Lys His Val Lys Glu Val Ile Ser Gln Leu Thr Arg Val His Gly Thr
    130                 135                 140
Ser Ser Pro Tyr Lys Gly Leu Asp Leu Ser Lys Leu His Glu Thr Leu
145                 150                 155                 160
Arg Thr His Thr Arg Leu Val Ser Leu Phe Asn Thr Thr Leu Thr Gly
                165                 170                 175
Leu His Glu Val Ser Ala Gln Asn Pro Thr Asn Cys Trp Ile Cys Leu
            180                 185                 190
Pro Leu Asn Phe Arg Pro Tyr Val Ser Ile Pro Val Pro Glu Gln Trp
            195                 200                 205
Asn Asn Phe Ser Thr Glu Ile Asn Thr Thr Ser Val Leu Val Gly Pro
    210                 215                 220
Leu Val Ser Asn Leu Glu Ile Thr His Thr Ser Asn Leu Thr Cys Val
225                 230                 235                 240
Lys Phe Ser Asn Thr Thr Tyr Thr Thr Asn Ser Gln Cys Ile Arg Trp
                245                 250                 255
Val Thr Pro Pro Thr Gln Ile Val Cys Leu Pro Ser Gly Ile Phe Phe
            260                 265                 270
Val Cys Gly Thr Ser Ala Tyr Arg Cys Leu Asn Gly Ser Ser Glu Ser
            275                 280                 285
Met Cys Phe Leu Ser Phe Leu Val Pro Pro Met Thr Ile Tyr Thr Glu
    290                 295                 300
Gln Asp Leu Tyr Ser Tyr Val Ile Ser Lys Pro Arg Asn Lys Arg Val
305                 310                 315                 320
Pro Ile Leu Pro Phe Val Ile Gly Ala Gly Val Leu Gly Ala Leu Gly
                325                 330                 335
Thr Gly Ile Gly Gly Ile Thr Thr Ser Thr Gln Phe Tyr Tyr Lys Leu
            340                 345                 350
Ser Gln Glu Leu Asn Gly Asp Met Glu Arg Val Ala Asp Ser Leu Val
    355                 360                 365
Thr Leu Gln Asp Gln Leu Asn Ser Leu Ala Ala Val Val Leu Gln Asn
    370                 375                 380
Arg Arg Ala Leu Asp Leu Leu Thr Ala Glu Arg Gly Gly Thr Cys Leu
385                 390                 395                 400
Phe Leu Gly Glu Glu Cys Cys Tyr Tyr Val Asn Gln Ser Gly Ile Val
                405                 410                 415
Thr Glu Lys Val Lys Glu Ile Arg Asp Arg Ile Gln Arg Arg Ala Glu
            420                 425                 430
Glu Leu Arg Asn Thr Gly Pro Trp Gly Leu Leu Ser Gln Trp Met Pro
```

```
                435                 440                 445
Trp Ile Leu Pro Phe Leu Gly Pro Leu Ala Ala Ile Ile Leu Leu Leu
    450                 455                 460

Leu Phe Gly Pro Cys Ile Phe Asn Leu Val Asn Phe Val Ser Ser
465                 470                 475                 480

Arg Ile Glu Ala Val Lys Leu Gln Met Glu Pro Lys Met Gln Ser Lys
                485                 490                 495

Thr Lys Ile Tyr Arg Arg Pro Leu Asp Arg Pro Ala Ser Pro Arg Ser
            500                 505                 510

Asp Val Asn Asp Ile Lys Gly Thr Pro Pro Glu Glu Ile Ser Ala Ala
        515                 520                 525

Gln Pro Leu Leu Arg Pro Asn Ser Ala Gly Ser Ser
    530                 535                 540

<210> SEQ ID NO 27
<211> LENGTH: 15
<212> TYPE: PRT
<213> ORGANISM: Homo sapiens

<400> SEQUENCE: 27

Ser Gly Arg Arg Pro Thr Ser Pro Thr Ala Leu Arg Phe Ser Cys
1               5                   10                  15

<210> SEQ ID NO 28
<211> LENGTH: 1080
<212> TYPE: DNA
<213> ORGANISM: Homo sapiens
<220> FEATURE:
<221> NAME/KEY: CDS
<222> LOCATION: (1)..(1080)
<223> OTHER INFORMATION:

<400> SEQUENCE: 28 acc tct ttt gta gaa aag gca aat gga gtg aag tgc cat aag tac aaa      48
Thr Ser Phe Val Glu Lys Ala Asn Gly Val Lys Cys His Lys Tyr Lys
1               5                   10                  15 ctt tct ttt cat taa gag aca act cac aat tat gta aaa agt gtg att     96
Leu Ser Phe His     Glu Thr Thr His Asn Tyr Val Lys Ser Val Ile
            20                  25                  30 tat gcc cta cag gaa gcc ttc aga gtc tac ctc cct atc cca gca tcc    144
Tyr Ala Leu Gln Glu Ala Phe Arg Val Tyr Leu Pro Ile Pro Ala Ser
                35                  40                  45 ccg act cct tcc cca act aat aag gac ccc cct tca acc caa atg gtc    192
Pro Thr Pro Ser Pro Thr Asn Lys Asp Pro Pro Ser Thr Gln Met Val
        50                  55                  60 caa aag gag ata gac aaa agg gta aac agt gaa cca aag agt gcc aat    240
Gln Lys Glu Ile Asp Lys Arg Val Asn Ser Glu Pro Lys Ser Ala Asn
65                  70                  75 att ccc caa tta tga ccc ctc caa gca gtg gga gga aga gaa ttc ggc    288
Ile Pro Gln Leu     Pro Leu Gln Ala Val Gly Gly Arg Glu Phe Gly
80                      85                  90 cca gcc aga gtg cat gtg cct ttt tct ctc cca gac tta aag caa ata    336
Pro Ala Arg Val His Val Pro Phe Ser Leu Pro Asp Leu Lys Gln Ile
95                  100                 105                 110 aaa aca gac tta ggt aaa ttc tca gat aac cct gat ggc tat att gat    384
Lys Thr Asp Leu Gly Lys Phe Ser Asp Asn Pro Asp Gly Tyr Ile Asp
                115                 120                 125 gtt tta caa ggg tta gga caa ttc ttt gat ctg aca tgg aga gat ata    432
Val Leu Gln Gly Leu Gly Gln Phe Phe Asp Leu Thr Trp Arg Asp Ile
            130                 135                 140
```

```
atg tca ctg cta aat cag aca cta acc cca aat gag aga agt gcc acc      480
Met Ser Leu Leu Asn Gln Thr Leu Thr Pro Asn Glu Arg Ser Ala Thr
        145                 150                 155 ata act gca gcc tga gag ttt ggc gat ctc tgg tat ctc agt cag gtc      528
Ile Thr Ala Ala     Glu Phe Gly Asp Leu Trp Tyr Leu Ser Gln Val
160                     165                 170 aat gat agg atg aca aca gag gaa aga gaa tga ttc ccc aca ggc cag      576
Asn Asp Arg Met Thr Thr Glu Glu Arg Glu     Phe Pro Thr Gly Gln
    175                 180                     185 cag gca gtt ccc agt cta gac cct cat tgg gac aca gaa tca gaa cat      624
Gln Ala Val Pro Ser Leu Asp Pro His Trp Asp Thr Glu Ser Glu His
        190                 195                 200 gga gat tgg tgc tgc aga cat ttg cta act tgt gtg cta gaa gga cta      672
Gly Asp Trp Cys Cys Arg His Leu Leu Thr Cys Val Leu Glu Gly Leu
205                 210                 215                 220 agg aaa act agg aag aag tct atg aat tac tca atg atg tcc acc ata      720
Arg Lys Thr Arg Lys Lys Ser Met Asn Tyr Ser Met Met Ser Thr Ile
                225                 230                 235 aca cag gga agg gaa gaa aat cct act gcc ttt ctg gag aga cta agg      768
Thr Gln Gly Arg Glu Glu Asn Pro Thr Ala Phe Leu Glu Arg Leu Arg
            240                 245                 250 gag gca ttg agg aag cgt gcc tct ctg tca cct gac tct tct gaa ggc      816
Glu Ala Leu Arg Lys Arg Ala Ser Leu Ser Pro Asp Ser Ser Glu Gly
        255                 260                 265 caa cta atc tta aag cgt aag ttt atc act cag tca gct gca gac att      864
Gln Leu Ile Leu Lys Arg Lys Phe Ile Thr Gln Ser Ala Ala Asp Ile
    270                 275                 280 aga aaa aaa ctt caa aag tct gcc gta ggc ccg gag caa aac tta gaa      912
Arg Lys Lys Leu Gln Lys Ser Ala Val Gly Pro Glu Gln Asn Leu Glu
285                 290                 295                 300 acc cta ttg aac ttg gca acc tcg gtt ttt tat aat aga gat cag gag      960
Thr Leu Leu Asn Leu Ala Thr Ser Val Phe Tyr Asn Arg Asp Gln Glu
                305                 310                 315 gag cag gcg gaa cag gac aaa cgg gat taa aaa aaa ggc cac cgc ttt     1008
Glu Gln Ala Glu Gln Asp Lys Arg Asp     Lys Lys Gly His Arg Phe
            320                 325                 330 agt cat gac cct cag gca agt gga ctt tgg agg ctc tgg aaa agg gaa     1056
Ser His Asp Pro Gln Ala Ser Gly Leu Trp Arg Leu Trp Lys Arg Glu
        335                 340                 345 aag ctg ggc aaa ttg aat gcc taa                                     1080
Lys Leu Gly Lys Leu Asn Ala
        350
```

<210> SEQ ID NO 29
<211> LENGTH: 20
<212> TYPE: PRT
<213> ORGANISM: Homo sapiens

<400> SEQUENCE: 29

Thr Ser Phe Val Glu Lys Ala Asn Gly Val Lys Cys His Lys Tyr Lys
1               5                   10                  15

Leu Ser Phe His
            20

<210> SEQ ID NO 30
<211> LENGTH: 63
<212> TYPE: PRT
<213> ORGANISM: Homo sapiens

<400> SEQUENCE: 30

Glu Thr Thr His Asn Tyr Val Lys Ser Val Ile Tyr Ala Leu Gln Glu

-continued

```
                 1               5                  10                 15
        Ala Phe Arg Val Tyr Leu Pro Ile Pro Ala Ser Pro Thr Pro Ser Pro
                        20                  25                 30

Thr Asn Lys Asp Pro Pro Ser Thr Gln Met Val Gln Lys Glu Ile Asp
                        35                  40                 45

Lys Arg Val Asn Ser Glu Pro Lys Ser Ala Asn Ile Pro Gln Leu
                        50                  55                 60

<210> SEQ ID NO 31
<211> LENGTH: 79
<212> TYPE: PRT
<213> ORGANISM: Homo sapiens

<400> SEQUENCE: 31

Pro Leu Gln Ala Val Gly Gly Arg Glu Phe Gly Pro Ala Arg Val His
        1               5                  10                 15

Val Pro Phe Ser Leu Pro Asp Leu Lys Gln Ile Lys Thr Asp Leu Gly
                        20                  25                 30

Lys Phe Ser Asp Asn Pro Asp Gly Tyr Ile Asp Val Leu Gln Gly Leu
                        35                  40                 45

Gly Gln Phe Phe Asp Leu Thr Trp Arg Asp Ile Met Ser Leu Leu Asn
                        50                  55                 60

Gln Thr Leu Thr Pro Asn Glu Arg Ser Ala Thr Ile Thr Ala Ala
        65                      70                 75

<210> SEQ ID NO 32
<211> LENGTH: 21
<212> TYPE: PRT
<213> ORGANISM: Homo sapiens

<400> SEQUENCE: 32

Glu Phe Gly Asp Leu Trp Tyr Leu Ser Gln Val Asn Asp Arg Met Thr
        1               5                  10                 15

Thr Glu Glu Arg Glu
                        20

<210> SEQ ID NO 33
<211> LENGTH: 142
<212> TYPE: PRT
<213> ORGANISM: Homo sapiens

<400> SEQUENCE: 33

Phe Pro Thr Gly Gln Gln Ala Val Pro Ser Leu Asp Pro His Trp Asp
        1               5                  10                 15

Thr Glu Ser Glu His Gly Asp Trp Cys Cys Arg His Leu Leu Thr Cys
                        20                  25                 30

Val Leu Glu Gly Leu Arg Lys Thr Arg Lys Lys Ser Met Asn Tyr Ser
                        35                  40                 45

Met Met Ser Thr Ile Thr Gln Gly Arg Glu Glu Asn Pro Thr Ala Phe
                        50                  55                 60

Leu Glu Arg Leu Arg Glu Ala Leu Arg Lys Ala Ser Leu Ser Pro
        65                      70                 75                 80

Asp Ser Ser Glu Gly Gln Leu Ile Leu Lys Arg Lys Phe Ile Thr Gln
                        85                  90                 95

Ser Ala Ala Asp Ile Arg Lys Lys Leu Gln Lys Ser Ala Val Gly Pro
                        100                 105                110

Glu Gln Asn Leu Glu Thr Leu Leu Asn Leu Ala Thr Ser Val Phe Tyr
                        115                 120                125
```

```
Asn Arg Asp Gln Glu Glu Gln Ala Glu Gln Asp Lys Arg Asp
    130                 135                 140
```

```
<210> SEQ ID NO 34
<211> LENGTH: 29
<212> TYPE: PRT
<213> ORGANISM: Homo sapiens

<400> SEQUENCE: 34

Lys Lys Gly His Arg Phe Ser His Asp Pro Gln Ala Ser Gly Leu Trp
  1               5                  10                  15

Arg Leu Trp Lys Arg Glu Lys Leu Gly Lys Leu Asn Ala
              20                  25
```

```
<210> SEQ ID NO 35
<211> LENGTH: 685
<212> TYPE: PRT
<213> ORGANISM: Homo sapiens
<220> FEATURE:
<221> NAME/KEY: misc_feature
<222> LOCATION: (29)..(29)
<223> OTHER INFORMATION: Xaa is any amino acid
<221> NAME/KEY: misc_feature
<222> LOCATION: (85)..(85)
<223> OTHER INFORMATION: Xaa is any amino acid
<221> NAME/KEY: misc_feature
<222> LOCATION: (124)..(124)
<223> OTHER INFORMATION: Xaa is any amino acid
<221> NAME/KEY: misc_feature
<222> LOCATION: (128)..(128)
<223> OTHER INFORMATION: Xaa is any amino acid
<221> NAME/KEY: misc_feature
<222> LOCATION: (669)..(669)
<223> OTHER INFORMATION: Xaa is any amino acid
<221> NAME/KEY: misc_feature
<222> LOCATION: (685)..(685)
<223> OTHER INFORMATION: Xaa is any amino acid

<400> SEQUENCE: 35

Pro Lys Thr Ala Asn Leu Val Ala Asp Ile Thr Ser Leu Ala Lys Tyr
  1               5                  10                  15

Gln Gln Val Leu Lys Thr Leu Gln Gly Thr Tyr Pro Xaa Glu Glu Gly
              20                  25                  30

Lys Glu Leu Phe His Pro Cys Asp Met Val Leu Val Lys Ser Leu Pro
          35                  40                  45

Ser Asn Ser Pro Ser Leu Asp Thr Ser Trp Glu Gly Pro Tyr Pro Val
      50                  55                  60

Ile Leu Ser Thr Pro Thr Ala Val Lys Val Ala Gly Val Glu Ser Trp
 65                  70                  75                  80

Ile His His Thr Xaa Val Lys Ser Trp Ile Leu Pro Lys Glu Pro Glu
                  85                  90                  95

Asn Pro Gly Asp Asn Ala Ser Tyr Ser Cys Glu Pro Leu Glu Asp Leu
            100                 105                 110

Arg Leu Leu Phe Lys Gln Gln Pro Gly Gly Lys Xaa Leu Lys Ser Xaa
        115                 120                 125

Ile Pro Met Ala Leu Pro Tyr His Ile Phe Leu Phe Thr Val Leu Leu
    130                 135                 140

Pro Ser Phe Thr Leu Thr Ala Pro Pro Cys Arg Cys Met Thr Ser
145                 150                 155                 160

Ser Ser Pro Tyr Gln Glu Phe Leu Trp Arg Met Gln Arg Pro Gly Asn
                165                 170                 175

Ile Asp Ala Pro Ser Tyr Arg Ser Leu Ser Lys Gly Thr Pro Thr Phe
```

-continued

```
            180                 185                 190
Thr Ala His Thr His Met Pro Arg Asn Cys Tyr His Ser Ala Thr Leu
        195                 200                 205
Cys Met His Ala Asn Thr His Tyr Trp Thr Gly Lys Met Ile Asn Pro
        210                 215                 220
Ser Cys Pro Gly Gly Leu Gly Val Thr Val Cys Trp Thr Tyr Phe Thr
225                 230                 235                 240
Gln Thr Gly Met Ser Asp Gly Gly Val Gln Asp Gln Ala Arg Glu
                245                 250                 255
Lys His Val Lys Glu Val Ile Ser Gln Leu Thr Arg Val His Gly Thr
            260                 265                 270
Ser Ser Pro Tyr Lys Gly Leu Asp Leu Ser Lys Leu His Glu Thr Leu
        275                 280                 285
Arg Thr His Thr Arg Leu Val Ser Leu Phe Asn Thr Thr Leu Thr Gly
        290                 295                 300
Leu His Glu Val Ser Ala Gln Asn Pro Thr Asn Cys Trp Ile Cys Leu
305                 310                 315                 320
Pro Leu Asn Phe Arg Pro Tyr Val Ser Ile Pro Val Pro Glu Gln Trp
                325                 330                 335
Asn Asn Phe Ser Thr Glu Ile Asn Thr Thr Ser Val Leu Val Gly Pro
                340                 345                 350
Leu Val Ser Asn Leu Glu Ile Thr His Thr Ser Asn Leu Thr Cys Val
            355                 360                 365
Lys Phe Ser Asn Thr Thr Tyr Thr Thr Asn Ser Gln Cys Ile Arg Trp
370                 375                 380
Val Thr Pro Pro Thr Gln Ile Val Cys Leu Pro Ser Gly Ile Phe Phe
385                 390                 395                 400
Val Cys Gly Thr Ser Ala Tyr Arg Cys Leu Asn Gly Ser Ser Glu Ser
                405                 410                 415
Met Cys Phe Leu Ser Phe Leu Val Pro Pro Met Thr Ile Tyr Thr Glu
            420                 425                 430
Gln Asp Leu Tyr Ser Tyr Val Ile Ser Lys Pro Arg Asn Lys Arg Val
        435                 440                 445
Pro Ile Leu Pro Phe Val Ile Gly Ala Gly Val Leu Gly Ala Leu Gly
        450                 455                 460
Thr Gly Ile Gly Gly Ile Thr Thr Ser Thr Gln Phe Tyr Tyr Lys Leu
465                 470                 475                 480
Ser Gln Glu Leu Asn Gly Asp Met Glu Arg Val Ala Asp Ser Leu Val
                485                 490                 495
Thr Leu Gln Asp Gln Leu Asn Ser Leu Ala Ala Val Val Leu Gln Asn
                500                 505                 510
Arg Arg Ala Leu Asp Leu Leu Thr Ala Glu Arg Gly Gly Thr Cys Leu
            515                 520                 525
Phe Leu Gly Glu Glu Cys Cys Tyr Tyr Val Asn Gln Ser Gly Ile Val
        530                 535                 540
Thr Glu Lys Val Lys Glu Ile Arg Asp Arg Ile Gln Arg Arg Ala Glu
545                 550                 555                 560
Glu Leu Arg Asn Thr Gly Pro Trp Gly Leu Leu Ser Gln Trp Met Pro
                565                 570                 575
Trp Ile Leu Pro Phe Leu Gly Pro Leu Ala Ala Ile Ile Leu Leu Leu
            580                 585                 590
Leu Phe Gly Pro Cys Ile Phe Asn Leu Leu Val Asn Phe Val Ser Ser
        595                 600                 605
```

```
Arg Ile Glu Ala Val Lys Leu Gln Met Glu Pro Lys Met Gln Ser Lys
        610                 615                 620

Thr Lys Ile Tyr Arg Arg Pro Leu Asp Arg Pro Ala Ser Pro Arg Ser
625                 630                 635                 640

Asp Val Asn Asp Ile Lys Gly Thr Pro Pro Glu Glu Ile Ser Ala Ala
                645                 650                 655

Gln Pro Leu Leu Arg Pro Asn Ser Ala Gly Ser Ser Xaa Ser Gly Arg
                660                 665                 670

Arg Pro Thr Ser Pro Thr Ala Leu Arg Phe Ser Cys Xaa
        675                 680                 685

<210> SEQ ID NO 36
<211> LENGTH: 360
<212> TYPE: PRT
<213> ORGANISM: Homo sapiens
<220> FEATURE:
<221> NAME/KEY: misc_feature
<222> LOCATION: (21)..(21)
<223> OTHER INFORMATION: Xaa is any amino acid
<221> NAME/KEY: misc_feature
<222> LOCATION: (85)..(85)
<223> OTHER INFORMATION: Xaa is any amino acid
<221> NAME/KEY: misc_feature
<222> LOCATION: (165)..(165)
<223> OTHER INFORMATION: Xaa is any amino acid
<221> NAME/KEY: misc_feature
<222> LOCATION: (187)..(187)
<223> OTHER INFORMATION: Xaa is any amino acid
<221> NAME/KEY: misc_feature
<222> LOCATION: (330)..(330)
<223> OTHER INFORMATION: Xaa is any amino acid
<221> NAME/KEY: misc_feature
<222> LOCATION: (360)..(360)
<223> OTHER INFORMATION: Xaa is any amino acid

<400> SEQUENCE: 36

Thr Ser Phe Val Glu Lys Ala Asn Gly Val Lys Cys His Lys Tyr Lys
1               5                   10                  15

Leu Ser Phe His Xaa Glu Thr Thr His Asn Tyr Val Lys Ser Val Ile
                20                  25                  30

Tyr Ala Leu Gln Glu Ala Phe Arg Val Tyr Leu Pro Ile Pro Ala Ser
            35                  40                  45

Pro Thr Pro Ser Pro Thr Asn Lys Asp Pro Pro Ser Thr Gln Met Val
        50                  55                  60

Gln Lys Glu Ile Asp Lys Arg Val Asn Ser Glu Pro Lys Ser Ala Asn
65                  70                  75                  80

Ile Pro Gln Leu Xaa Pro Leu Gln Ala Val Gly Gly Arg Glu Phe Gly
                85                  90                  95

Pro Ala Arg Val His Val Pro Phe Ser Leu Pro Asp Leu Lys Gln Ile
            100                 105                 110

Lys Thr Asp Leu Gly Lys Phe Ser Asp Asn Pro Asp Gly Tyr Ile Asp
        115                 120                 125

Val Leu Gln Gly Leu Gly Gln Phe Phe Asp Leu Thr Trp Arg Asp Ile
130                 135                 140

Met Ser Leu Leu Asn Gln Thr Leu Thr Pro Asn Glu Arg Ser Ala Thr
145                 150                 155                 160

Ile Thr Ala Ala Xaa Glu Phe Gly Asp Leu Trp Tyr Leu Ser Gln Val
                165                 170                 175

Asn Asp Arg Met Thr Thr Glu Glu Arg Glu Xaa Phe Pro Thr Gly Gln
            180                 185                 190
```

```
             Gln Ala Val Pro Ser Leu Asp Pro His Trp Asp Thr Glu Ser Glu His
                 195                 200                 205

Gly Asp Trp Cys Cys Arg His Leu Leu Thr Cys Val Leu Glu Gly Leu
                 210                 215                 220

Arg Lys Thr Arg Lys Lys Ser Met Asn Tyr Ser Met Met Ser Thr Ile
             225                 230                 235                 240

Thr Gln Gly Arg Glu Glu Asn Pro Thr Ala Phe Leu Glu Arg Leu Arg
                             245                 250                 255

Glu Ala Leu Arg Lys Arg Ala Ser Leu Ser Pro Asp Ser Ser Glu Gly
                         260                 265                 270

Gln Leu Ile Leu Lys Arg Lys Phe Ile Thr Gln Ser Ala Ala Asp Ile
                     275                 280                 285

Arg Lys Lys Leu Gln Lys Ser Ala Val Gly Pro Glu Gln Asn Leu Glu
                 290                 295                 300

Thr Leu Leu Asn Leu Ala Thr Ser Val Phe Tyr Asn Arg Asp Gln Glu
             305                 310                 315                 320

Glu Gln Ala Glu Gln Asp Lys Arg Asp Xaa Lys Lys Gly His Arg Phe
                             325                 330                 335

Ser His Asp Pro Gln Ala Ser Gly Leu Trp Arg Leu Trp Lys Arg Glu
                         340                 345                 350

Lys Leu Gly Lys Leu Asn Ala Xaa
                     355                 360
```

<210> SEQ ID NO 37
<211> LENGTH: 26
<212> TYPE: DNA
<213> ORGANISM: Homo sapiens

<400> SEQUENCE: 37
ggaccataga ggacactcca ggacta                                        26

<210> SEQ ID NO 38
<211> LENGTH: 25
<212> TYPE: DNA
<213> ORGANISM: Homo sapiens

<400> SEQUENCE: 38
cctcagtcct gctgctggat catct                                         25

<210> SEQ ID NO 39
<211> LENGTH: 27
<212> TYPE: DNA
<213> ORGANISM: Homo sapiens

<400> SEQUENCE: 39
cctccaagca gtgggaggaa gagaatt                                       27

<210> SEQ ID NO 40
<211> LENGTH: 28
<212> TYPE: DNA
<213> ORGANISM: Homo sapiens

<400> SEQUENCE: 40
ccttccctgt gttattgtgg acatcatt                                      28

<210> SEQ ID NO 41
<211> LENGTH: 30
<212> TYPE: DNA
<213> ORGANISM: Homo sapiens -continued

```
<400> SEQUENCE: 41
ggaagaagtc tatgaattat tcaatgatgt                                      30

<210> SEQ ID NO 42
<211> LENGTH: 27
<212> TYPE: DNA
<213> ORGANISM: Homo sapiens

<400> SEQUENCE: 42
gggacacaga atcagaacat ggagatt                                         27

<210> SEQ ID NO 43
<211> LENGTH: 27
<212> TYPE: DNA
<213> ORGANISM: Homo sapiens

<400> SEQUENCE: 43
gccttcagaa gagtcaggtg acagaga                                         27

<210> SEQ ID NO 44
<211> LENGTH: 25
<212> TYPE: DNA
<213> ORGANISM: Homo sapiens

<400> SEQUENCE: 44
gagcctccaa agtccacttg cctga                                           25

<210> SEQ ID NO 45
<211> LENGTH: 29
<212> TYPE: DNA
<213> ORGANISM: Homo sapiens

<400> SEQUENCE: 45
gatttcagta tctactagtc tgggtagat                                       29

<210> SEQ ID NO 46
<211> LENGTH: 27
<212> TYPE: DNA
<213> ORGANISM: Homo sapiens

<400> SEQUENCE: 46
ctaggaaatc cagctagtcc tgtctca                                         27

<210> SEQ ID NO 47
<211> LENGTH: 28
<212> TYPE: DNA
<213> ORGANISM: Homo sapiens

<400> SEQUENCE: 47
ccaagacagc caacttagtt gcagacat                                        28

<210> SEQ ID NO 48
<211> LENGTH: 28
<212> TYPE: DNA
<213> ORGANISM: Homo sapiens

<400> SEQUENCE: 48
ggacgctgca ttctccatag aaactctt                                        28

<210> SEQ ID NO 49
<211> LENGTH: 29
<212> TYPE: DNA
<213> ORGANISM: Homo sapiens
```

```
<400> SEQUENCE: 49
gcaatactac atacacaacc aactcccaa                                    29

<210> SEQ ID NO 50
<211> LENGTH: 26
<212> TYPE: DNA
<213> ORGANISM: Homo sapiens

<400> SEQUENCE: 50
gggggaggca tatccaacag ttagta                                       26

<210> SEQ ID NO 51
<211> LENGTH: 30
<212> TYPE: DNA
<213> ORGANISM: Homo sapiens

<400> SEQUENCE: 51
ccatctacac tgaacaagat ttatacactt                                   30

<210> SEQ ID NO 52
<211> LENGTH: 28
<212> TYPE: DNA
<213> ORGANISM: Homo sapiens

<400> SEQUENCE: 52
aatgccagta cctagtgcac ctagcact                                     28

<210> SEQ ID NO 53
<211> LENGTH: 31
<212> TYPE: DNA
<213> ORGANISM: Homo sapiens

<400> SEQUENCE: 53
cgaatacaac gtagagcaga ggagcttcga a                                 31

<210> SEQ ID NO 54
<211> LENGTH: 28
<212> TYPE: DNA
<213> ORGANISM: Homo sapiens

<400> SEQUENCE: 54
agcccaagat gcagtccaag actaagat                                     28

<210> SEQ ID NO 55
<211> LENGTH: 27
<212> TYPE: DNA
<213> ORGANISM: Homo sapiens

<400> SEQUENCE: 55
gcgtagtaga ggttgtgcag ctgagat                                      27

<210> SEQ ID NO 56
<211> LENGTH: 27
<212> TYPE: DNA
<213> ORGANISM: Homo sapiens

<400> SEQUENCE: 56
cccttaccaa gagtttctat ggagaat                                      27

<210> SEQ ID NO 57
<211> LENGTH: 27
<212> TYPE: DNA
```

-continued

```
<213> ORGANISM: Homo sapiens

<400> SEQUENCE: 57
accgctctaa ctgcttcctg ctgaatt                                           27

<210> SEQ ID NO 58
<211> LENGTH: 420
<212> TYPE: PRT
<213> ORGANISM: Homo sapiens
<220> FEATURE:
<221> NAME/KEY: misc_feature
<222> LOCATION: (21)..(21)
<223> OTHER INFORMATION: Xaa is any amino acid
<221> NAME/KEY: misc_feature
<222> LOCATION: (86)..(86)
<223> OTHER INFORMATION: Xaa is any amino acid
<221> NAME/KEY: misc_feature
<222> LOCATION: (166)..(166)
<223> OTHER INFORMATION: Xaa is any amino acid
<221> NAME/KEY: misc_feature
<222> LOCATION: (188)..(188)
<223> OTHER INFORMATION: Xaa is any amino acid
<221> NAME/KEY: misc_feature
<222> LOCATION: (331)..(331)
<223> OTHER INFORMATION: Xaa is any amino acid
<221> NAME/KEY: misc_feature
<222> LOCATION: (361)..(361)
<223> OTHER INFORMATION: Xaa is any amino acid
<221> NAME/KEY: misc_feature
<222> LOCATION: (362)..(362)
<223> OTHER INFORMATION: Xaa is any amino acid
<221> NAME/KEY: misc_feature
<222> LOCATION: (374)..(374)
<223> OTHER INFORMATION: Xaa is any amino acid
<221> NAME/KEY: misc_feature
<222> LOCATION: (380)..(380)
<223> OTHER INFORMATION: Xaa is any amino acid
<221> NAME/KEY: misc_feature
<222> LOCATION: (382)..(382)
<223> OTHER INFORMATION: Xaa is any amino acid
<221> NAME/KEY: misc_feature
<222> LOCATION: (408)..(408)
<223> OTHER INFORMATION: Xaa is any amino acid
<221> NAME/KEY: misc_feature
<222> LOCATION: (413)..(413)
<223> OTHER INFORMATION: Xaa is any amino acid

<400> SEQUENCE: 58

Thr Ser Phe Val Glu Lys Ala Asn Gly Val Lys Cys His Lys Tyr Lys
1               5                   10                  15

Leu Ser Phe His Xaa Glu Thr Thr His Asn Tyr Val Lys Ser Val Ile
            20                  25                  30

Tyr Ala Leu Gln Glu Ala Phe Arg Val Tyr Leu Pro Ile Leu Pro Ala
        35                  40                  45

Ser Pro Thr Pro Ser Pro Thr Asn Lys Asp Pro Ser Thr Gln Met
    50                  55                  60

Val Gln Lys Glu Ile Asp Lys Arg Val Asn Ser Glu Pro Lys Ser Ala
65                  70                  75                  80

Asn Ile Pro Gln Leu Xaa Pro Leu Gln Ala Val Gly Gly Arg Glu Phe
                85                  90                  95

Gly Pro Ala Arg Val His Val Pro Phe Ser Leu Pro Asp Leu Lys Gln
            100                 105                 110

Ile Lys Thr Asp Leu Gly Lys Phe Ser Asp Asn Pro Asp Gly Tyr Ile
        115                 120                 125

Asp Val Leu Gln Gly Leu Gly Gln Phe Phe Asp Leu Thr Trp Arg Asp
    130                 135                 140

Ile Met Ser Leu Leu Asn Gln Thr Leu Thr Pro Asn Glu Arg Ser Ala
```

```
                145                 150                 155                 160
Thr Ile Thr Ala Ala Xaa Glu Phe Gly Asp Leu Trp Tyr Leu Ser Gln
                    165                 170                 175
Val Asn Asp Arg Met Thr Thr Glu Glu Arg Glu Xaa Phe Pro Thr Gly
                180                 185                 190
Gln Gln Ala Val Pro Ser Leu Asp Pro His Trp Asp Thr Glu Ser Glu
                195                 200                 205
His Gly Asp Trp Cys Cys Arg His Leu Leu Thr Cys Val Leu Glu Gly
            210                 215                 220
Leu Arg Lys Thr Arg Lys Lys Ser Met Asn Tyr Ser Met Met Ser Thr
225                 230                 235                 240
Ile Thr Gln Gly Arg Glu Glu Asn Pro Thr Ala Phe Leu Glu Arg Leu
                245                 250                 255
Arg Glu Ala Leu Arg Lys Arg Ala Ser Leu Ser Pro Asp Ser Ser Glu
                260                 265                 270
Gly Gln Leu Ile Leu Lys Arg Lys Phe Ile Thr Gln Ser Ala Ala Asp
            275                 280                 285
Ile Arg Lys Lys Leu Gln Lys Ser Ala Val Gly Pro Glu Gln Asn Leu
290                 295                 300
Glu Thr Leu Leu Asn Leu Ala Thr Ser Val Phe Tyr Asn Arg Asp Gln
305                 310                 315                 320
Glu Glu Gln Ala Glu Gln Asp Lys Arg Asp Xaa Lys Lys Gly His Arg
                325                 330                 335
Phe Ser His Asp Pro Gln Ala Ser Gly Leu Trp Arg Leu Trp Lys Arg
            340                 345                 350
Glu Lys Leu Gly Lys Leu Asn Ala Xaa Xaa Gly Leu Leu Pro Val Arg
            355                 360                 365
Ser Thr Arg Thr Leu Xaa Lys Arg Leu Ser Lys Xaa Lys Xaa Ala Ala
        370                 375                 380
Pro Ser Ser Met Pro Leu Ile Ser Arg Glu Ser Leu Glu Gly Pro Leu
385                 390                 395                 400
Pro Gln Gly Thr Lys Val Leu Xaa Val Arg Ser His Xaa Pro Asp Ser
                405                 410                 415
Ser Ser Arg Thr
            420

<210> SEQ ID NO 59
<211> LENGTH: 32
<212> TYPE: DNA
<213> ORGANISM: Homo sapiens

<400> SEQUENCE: 59
taaactacaa atggttcttc aaatggagcc ca                                        32

<210> SEQ ID NO 60
<211> LENGTH: 32
<212> TYPE: DNA
<213> ORGANISM: Homo sapiens

<400> SEQUENCE: 60
gatgcagtcc aagatgcagt ccatgactaa ga                                        32

<210> SEQ ID NO 61
<211> LENGTH: 1740
<212> TYPE: DNA
<213> ORGANISM: Homo sapiens
```

<400> SEQUENCE: 61

```
aggttggctg acaaccgctc ttaactgctt catgctgaat tggggcatag tagggtcgt      60
gcagttgaga tttccttggg aggggtgcct tcaatgtcat caacattgga gcatgggcta    120
gcaggccagt ccagggggtcc gcggtagatc ttagtcatgg actgcatctg gggctccatt    180
tgaagaacca tttgtagttt tacagcttcg attctggaag agacaaacgt aacaaggagg    240
ttaaagatac aaggattgaa atgtacggcc tgaagtgcag gggcatatga gtgtgggcgg    300
tgcaagtggg gtttcccttta gaaaaactcc gatacaatag gcatcaata tttctaggaa    360
gccacattct ccatagaagc tctcggtaag gggagctact ggtagtacag cagcatacag    420
ggggtgcagt gagagtgaaa gggggtaaga gaacagtaaa aagaaaaata tgacaaggga    480
gggccaagag gatctacgat tctagttact ttcctcacgg ttgtcgcctg aagagcaggc    540
gcagatcctc tagaggttca caggaataagc tagcattgtc tgctggattt tcgggttcct    600
ttggcagtat ccagggtttg gctcgagtgt gacttatcca agactccact ccagccactt    660
aactgcggtt agggtagata aaatgactgg gtagggtcct tcccaggatg tgtgtaggga    720
tggggaatta aaggggaagg gacttgacta ataccatgtc accagggtgg aataattcct    780
ttccctcctc tcagggacag gttccctgta atgttttaag aactcgttga tatttggcta    840
aggaggtgat gtctgcaact aagttggccg tctctcagtc aagcacaagg tcattggtta    900
ggaagggctg tccatacagc atctcatatg gactaagtcc tgcttttttgg ggacagtttc    960
ggattcttag taaggctata ggcaacagag caggccatgc aaggtgggtt tcttgggtta   1020
gcttttttag atgtcgtttg agtgtttcat tcatttttctc aacttttcct gaggatcgtg   1080
gcctccaggc acagtgtaag tgatattgta tacctaacgc ctgggatact ccctgcgtta   1140
ctgcagcctt gaaattgggg ccattgtcac tctgtaaacc tcagggaagt ccgaatctgg   1200
gaattatttc atgaattagt acttttatta cctcttgggc cttttctgtc ctacaaggga   1260
aggcctccac ccaaccagtg aaagtaccca gattagtaga tactgaaatc tctgagattt   1320
gggcatgtgg gtaaaatcta gttgctagtc ttctcctggg taatggcctg ttctttgttc   1380
tcctgaagga gcttggcaat aaggcagggg attatttctt tggcacactt cacaggccct   1440
gactatctgc ttgacagttt tgaaaaggcc tggtccagta aataatgatt tggccatctg   1500
atgggtgctg tcaatgccta agtgaaaggt ctggtgaagg gttttaagta atttccattg   1560
gttagctgca ggcaaaagta tttttttcttt ggtggctggc catcctgagg agaggaaact   1620
atgtcctcgt gagtttcccc attccatttc ttctgctgag tactggagct tggtttccca   1680
gagggggatta ccccatacta ggggtccttc tgtaagcatt tctaatggag agtcctgcct   1740
```

<210> SEQ ID NO 62
<211> LENGTH: 7140
<212> TYPE: DNA
<213> ORGANISM: Homo sapiens

<400> SEQUENCE: 62

```
ttggtcttaa gaacacaaat gatatggctc caatgactgg aggaacacca gggtccttgg     60
tctcacgctg atttagataa aacgactgtc aggcctctga gcccaagcta agccatcctc    120
ccctgtgacc tgcacgtata catccagatg gcctgaagta accaaagaat cacaaaagca    180
gtgaaaatgg cctgttcctg ccttaactga tgacattcca ccattgtgat tgttcctgc     240
cccatcttaa ctgagcgatt aaccttgtga aattccttct cctggctcaa aacctccccc    300
actgagcacc ttgtgacccc cgcccctgcc cctaagagaa aaccccccttt gattataatt   360
```

-continued

```
ttccactacc cacccaaatc ctataaaatg gccccacccc tatctccctt cgctgactcc      420
tttttcggac tcagcccgcc tgcacccagg tgaaataaac agccttgttg ctcacacaaa      480
gcctgtttgg tggactctct tcacacggac gctcatgaca tttggtgcca aaacctggga      540
taggaggact ccttcaggag accagtcccc tgtccttgcc ctcactctgt gaggacatcc      600
acctacaacc ttgggtcctc agaccaacca gcccaaggaa cagctcacca atttcaaatc      660
aggtaagcag tcttttcact ctcttctcca gcctctcttg ctacccttca aactccctct      720
ctcactaccc ttcaatctcc ctgtccttcc aattccagtt cttttcatc tctagtagag       780
acaaaggaga cacattttat ccatggaccc aaaactccag caccagtcac ggacttggga      840
agacagtctt cccttggtgt ttaatcactg cggggacgcc tgcctgatta ttcacccaca      900
ctccattggt gtctgatcac ggtggggaca cctgccttgg tcactcaccc acattccctt      960
ggtggtacgt caactgcaaa agcaggggac gcctgctttg gctgctcacc cacccccttc     1020
tctgtgtctc tacctttctc tttaaactta cctccttcac tatgggcaaa cttctgccct     1080
ccattccccc ttcttctccc ttagcctgtg ttcttaaaaa cctaaaacct cttcaactca     1140
cacctgacct aaaacctaaa tgccttattt tcttctgcaa cactgcgtgg ctgcagtaca     1200
aacttgataa tagctttaaa tggccagaat atggcacttt caatttctcc atcctacaag     1260
atctagataa ttttttgtgga aaaatggaaa atggtctga gatgcctgac gtccaggcat     1320
tcttttacac attggtccct ccctagtctc tgctcccaat gcgactcatc ccaaatcttt     1380
cttctttctc tcctgtctgt tccttcagtc tccaccccaa gctctgagtc ctttgaatcc     1440
tcctttgcta cagacccatc tgaactctcc cctcctcccc aggctgctcc tcaccaggcc     1500
gagccaggtc ccaattcttc ctcagcctct gctcccccac cctataatcc ttttatcacc     1560
tcctctcctc acactcagtc cggcttacag tttcgttctg tgactagccc tcccccatct     1620
gcccaacaat ttcctcttaa agaggtggct ggagctaaag gcatagtcaa ggttaatgct     1680
ccttttttctt tatctgacct ctcccaaatc agttagcgtt tacgctcttt ttcatcaaat     1740
ataaaacccc agccagttca tggcccatct ggcaacaacc cttacaggct ttacagccct     1800
agaccctgaa gggtcagaag gccgtcttat tctcaatatg cattttatta cccaatccgc     1860
tcccaacatt aaataaagct ccaaaaatta aattctggcc ctcaaacccc acaacaggac     1920
ttaattaacc tcacttcaag gtgtacaaga atagagtaga ggcagccaag tagcaacgta     1980
tttgagttgc aattccttgc ctcaactctg agagaaaccc cagccacatc tccagcaaac     2040
aagaacttca aaacacctga actgcagcag ccaggcgttc ctccaggacc acctccccca     2100
ggatcttgct tcaagtgccg gaaatctgac cattgggcca aggaatgcct gcagcccagg     2160
attcctccta agccacgtcc catttgtgca ggaccccact ggaaatcgga ctgtccaact     2220
cacccggcag ccaatcccag agccctgga actctggccc aaggctctct gactgactcc      2280
ttcccagatc ttctcggctt agcagctgaa gactgacact gcccgatcac ttcagaagtc     2340
ccctggacca tcacggatac tgagcttcag gtaactctca cagtggaggc taagtccatc     2400
ccctgtttaa tcgatacagg ggctacccac tccacatcac cttcttttca agggcctgtt     2460
tcccttttccc ccataactgt tgtgggtatt gacggccaag cttcaaaacc ccttaaaact     2520
ccccactct ggtgccaact tggacaacat tcttttatgc actcttttc agttatcctc       2580
acctgcccag ttcccttatt aggccgagac attttaacca aattatctgc ttccccgact     2640
attcctgggc tacagccaca tctccttgcc gcccttcttc ccaacccaaa gcctccttca     2700
```

```
tatcttcctc tcatatcccc ccaccttaac ccacaagtat gggacacctc tactccctcc    2760
ctggcaaccg atcacacgcc cattactatc ccattaaaac ctaatcaccc ttaccctgct    2820
caatgccagt atcccatacc acaacaggct ttaaagggat tgaagcctgt tatcacttgc    2880
ctgctacagc acgggcttct aaaacctata aactctccat acaattcccc cattttacct    2940
gtctaaaaac cagataagtc ttacaggtta gttcagaatc tgcacccttat caaccaaatt    3000 gttttgccta tccaccctgt agcacccaac tcgtacactc ttttgtcctc aatgccttcc    3060
cccacaactc actattccgt tcttgatctt aaagatgctt ttttcactat tccctgcac    3120 ccctcatccc agcctctctt tgcttttacc tggactgacc ctgacacccca tcagtcccag    3180 cagcttacct gggctgtact gccgcaaggc ttcagggaca gccctcatta cttcagccaa    3240
gctctttctc atgatttact ttcttccac ctctctgctt ctcaccttat tcaatatatt    3300
gatgaccttc tactttgtag cccctccttt aaatcttctc aacaagacac cctcctgctc    3360
cttcaacatt tgttctccaa aggatatcgg gtatcccccct ccaaagctca aatttcttct    3420
ccatctgtta catacctcgg cataattctt catgaaaaca catgtgctct ccctgccaat    3480
tgcgtctcca actgatctct caaatcccaa cctcttctac aaaacaacaa ctcctttccc    3540
tcctaggcat ggttggatac ttttgccttt ggatacctgg ttttgccatc ctaacaaaat    3600
cattatataa actcacaaaa ggaaacctag ctgaccccat agattctaaa tcctttcccc    3660
actcctcttt ccattccttg aagacagctt tagagactgc tcccacacta gctctccctg    3720
tctcatccca acccttttca ttacacacag ccgaagtgca gggctgtgca gtcggaattc    3780
ttacacaagg accgggacca tgccctgtag ccttttttgtc caaacaactt gaccttactg    3840
ttttaggctc gccatcatgt ctccatgcgg tagcttccgc tgccctaata cttttagagg    3900
ccctcaaaat cacaaactat gctcaactca ctctctacag ctctcacaac ttccaaaatc    3960
tattttcttt ctcacacctg acgcatatac tttctgctcc ccggctcctt cagctgtatt    4020
cactctttgt tgagtctccc acaattacca ttcttcctgg cccagacttc aatctggcct    4080
cccacattat tctggatacc acacctgacc ctgatgattg tatgtctctg atctacctga    4140
cattcacccc atttccccat atttccttct tttctgttcc tcatgttgat cacatttggt    4200
ttactgacgg cagttccacc aggcctgatc gccactcacc agcaaaggca ggctatgcta    4260
tagaatcttc cacatccatc attgaggcta ctgctctgcc cccctccact acctctcagc    4320
aagccgaact gattgcctta actcgggcct tcactcttgc aaagggacta cacgtcaata    4380
tttatactga ctctaaatat gccttccata tcttgcacca ccatgctgtt atatgggctg    4440 aaagagggttt cctcactacg caagggtcct ccatcattaa tgcctctttta ataaaaactc    4500 ttctcaaggc tgctttactt ccaaaggaag ctggagtcac acactgcaag ggccaccaaa    4560
aggcgtcaga tcccattact ctaggaaatg cttatgctga taaggtagct aaagaagcac    4620
ctagcgttcc aacttctgtc cctcatggcc agttttttctc cttcccatca gtcattccca    4680
cctactcccc cattgaaact tccgcctatc aatctcttct cacacaaggc aaatggttct    4740
tagaccaagg aaaatatctc cttccagcct cacaggccca ttctattctg tcatcatttc    4800
ataacctctt ccatgtaggt tacaagccac tagtccacct cttagaacct ctcatttcct    4860
tccatcgtgg aaacatatcc tcaaggaaat cacttctcag tgttccatct gctattctac    4920 taccccctcag ggattgttca ggccccctcc cctccctaca catcaagctc ggggatttgc    4980
ccctgcccag gactggcaaa ttgactttac tcacatgccc tgagtcagga aactaaaata    5040
cctcttggtc tgggtagaca ctgtcactgg atgggtagag gcctttccca cagggtctga    5100
```

```
gaaggccact gcagtcattt cttcccttct gtcagacata attccttggg ttggccttcc    5160
cacctctata cagtccaata acggagcagc ctttattagt caaatcacct gagcagtttt    5220
tcaggctctt ggtattcagt ggaaccttcg taccccttac tgtcctcaat cttcaggaaa    5280
ggtagaatgg actaatggtc ttttaaaaac acaccccacc aaactcagcc tccaacttaa    5340
aaaggaggat agagcccaaa aactcgcaac caagctagta attatgctga accccttgg     5400 gcactctcta attggatgtc ttaggtcctc ccaaatctta gtcctttaat atctgttttt    5460
ctccttctct tattcggacc ttgtgtcttc cgtttagttt ttcaattcat acaaaaccgc    5520
atccaggcca tcaccaatcg ttctatacaa taaatgctcc ttctaacaac cccacaatat    5580
cgccccttac cacaaaatct tccttcagct taatctctcc cactctaggt tcccatgccg    5640
cccataatcc ctctcgaagc agccctgaga acatagccc attatctctc cataccaccc    5700
ccaaaatttt tgctgcccca cacttcaac actattttac attattttc ttattaatat     5760 aagaagacag caatgtcagg cctctgagcc caagccatca tatcccctgt gacctgcaca    5820
tatacatcca gatggcctga gtaactgaa gaatcacaaa agaagtgaaa atggcctgtt     5880
cctgccttaa ccgatgacat tccaccactg tgatttgttc ctgccccacc ttaactgagc    5940
aattaacctt gggaaattcc ttctcctggc tcaaaacctc ccccactgag caccttgtga    6000
cccctgcccc tccactaccc acccaaatcc tataaaatgg ccccacccca tctcccttag    6060
ctgactcctt ttttggactc agcccgcctg cacccaggtg aaataaacag ccttgttgct    6120
cacacaaagc ctgtttggtg gactctcttc acagggacgg gggtgacaac aacacggaca    6180
cacatggagt ggttttaagg agcagagagt ttaatacgca aaaagaagg aagaggctcc     6240 cctgtacaga cacagaggga gggggctcca agccgagaga aggaaacccc atgtgcagtg    6300
gaaaagtggt tgattatact gggaggctgg aggaggcggt gtctgatttg cacagggccc    6360
aggggattgg gttgaccagg tgtatcattc atgtaccccg caaaaaacct ggccctccca    6420
cctcagccct ttaatatgca aatgtgggtt gccatgatgt tctgaaaaca catgaattat    6480
ctggaggggg ccatgacact tggtacatgt gctgacaaga agagggtggg aatcgccatg    6540
gtggccatgt tgggtggacc tagttttttaa tagcctgcat ttgcatatca aagtttgctg    6600
gcctggctct ttaagctgtc ttttctgtta gaaaaggaat ggtttggaat gggtgagggt    6660
tgcttcttat tacaagaaaa tttccaaaaa cctttactct ttctagctgc caaaaaacta    6720
tttcttaata acttatgtat taccataatt aggcagcacc aaagatccct gcaggtcaga    6780
ccactgcaat taacatgctg gctttactgc tgattatggt agctgcatcc acctagcctc    6840
tcatattgca actgcctgac ctctgccacc ccacgagcca cttatcccca cttataatca    6900
gcccatttcg attgtaacat ctgccactta ttcccgacgt tgtggtatat cctatagatg    6960
aattcattca acatccattc caacaccacc tctcttgcct tcctatactc tctgagagt     7020 gaattactga gtcacatgat cttcactgca gtcatttgtg gctatgtgac atagttctgg    7080
acagtgaaca tagacagaag tccctggggc gggcttcctt tctgggatga gggcaaaacg    7140
```

<210> SEQ ID NO 63
<211> LENGTH: 44100
<212> TYPE: DNA
<213> ORGANISM: Homo sapiens

<400> SEQUENCE: 63

```
tgcctttatt tccgtaggct ggtcatatgg cgctagcact cacataaagc taccgaggag      60
```

-continued

| | | | | |
|---|---|---|---|---|
| agcgaatgaa | accaaaatca | ctttaccttc | acagcacgag | gccgtcgtcc ctctcgatat | 120 |
| ttggcccgtg | tgtcgcatac | cgccctctgg | acgtggtgat | caaataaact ccctagctcc | 180 |
| ccgccgctcg | acgccatctt | gcctactttg | atcctcgcag | ggaggacaac atccgcccta | 240 |
| ctgagctccc | ttttatccaa | taagagagcg | ggatgagtta | aggagtgcca ggattggctg | 300 |
| gagaatcgac | agcgtcggcc | atcgtttcct | gcgtgcgaag | atttgatgaa cgaggtgccg | 360 |
| cccccgagcg | gctcggcgga | gaggcgcggt | gggtgacaga | agctttcttg tcccacccac | 420 |
| tacaggctta | cggcaggatg | cgcagcgggg | agaggggggcg | gggccgcagg gggcggggcc | 480 |
| gatcgatctc | ctccggctcc | gacgtcctcg | gcctgccggg | tcccgggtcc tttgcggcgc | 540 |
| tagggtgggc | gaacccagag | cgacgctccg | ggacgatgtg | gggcagcgat cgcctggcgg | 600 |
| gtgctggggg | aggcggggcg | gcagtgactg | tggccttcac | caacgctcgc gactgcttcc | 660 |
| tccacctgcc | gcggcgtctc | gtggcccagc | tgcatctgct | gcaggtaacc tgccggcccc | 720 |
| gagccacctg | atcttcagcc | tggggtcgga | cgaggccgaa | gcctctcagg acgcggcgg | 780 |
| gacaccggct | gccacccggg | cgccgccgaa | gcgcgcagag | atcagggtcc ctcgacggca | 840 |
| gggcccttct | gggtagtctc | tggatcccac | aagtccagtg | cagccctggg ctcgtcttat | 900 |
| cccaggtctt | ttcacttggt | gaaactgaac | ctagaaacgt | cctaatattc taccactgtt | 960 |
| tttataaata | ttccttattc | caggctggaa | aagctcctga | gaagtggttt gtttttatta | 1020 |
| ttttaaaagg | tgttttcctt | gccagccatt | tccagttaac | ctgcgctgct gccgtccggg | 1080 |
| ccgcgagagc | gggacgcaga | gttgttggcg | gagcccctgt | cggttcccgg ggactaagca | 1140 |
| ccgcgtccca | tgagcgggaa | aggttaatac | aatgatggtt | ctgccctgcg tcgctgacgc | 1200 |
| ggaacacagc | tgtagtgtgt | taggaacaca | taacgtagtt | aagatcactt gaagctctgc | 1260 |
| gatcagtcgc | ccttctggac | gttgtggtta | ggatgtttca | cagttctaac cactggtgga | 1320 |
| gatacagcgt | ccatattttc | ataattaaaa | atagaggcac | atggtctcac gagtttgagt | 1380 |
| gtacttatgg | gggcaaaagg | acggcgtatt | tgaaatcctc | ataaatcctg gatgcatggt | 1440 |
| acccaccagt | ggctaatcta | tgcaatgaat | agagtttgca | ataatttcaa gcatcccttc | 1500 |
| tttccacttg | agttacttcc | ccatacctag | gggaagatat | ttttggtcca ctgaaaacat | 1560 |
| gagttcagca | gaatcctcct | atcatcgtcg | ttattatttt | ttaccactaa gtagacaatc | 1620 |
| ttttggtttt | tgatgggctt | tatggctaga | gacaaatcag | tcactgtcac caagttccag | 1680 |
| gtagaagttg | gttcagtgct | ctgtcagctt | cgatgggatt | tttcaacatg ttttcaaatc | 1740 |
| tgcacttaat | agtaggaatg | ctttcttaca | gtaactctaa | tttgatccta agatgtagtt | 1800 |
| gttaccttac | attcatcact | gtttaagaat | ttagtggtct | tgatctttgt tttaaatttt | 1860 |
| gagccttcgg | gaagtactta | taagaattaa | ttcatgcata | tcttttttgaa atgtaaatgt | 1920 |
| ctttagccct | ggaacaaatt | gctgtttctg | ttcagcccat | attagcagaa taggtcaact | 1980 |
| ttactttcta | attatcaatg | taataagttt | attactttat | agattccata aatctataca | 2040 |
| tttattcctc | gatgaattat | ataaatttat | agaatttatg | ttttatagaa aatttggaaa | 2100 |
| gcatggaaaa | ttattaacaa | gaaataagt | tacccataat | cccagaactt agaggtgact | 2160 |
| aatgttgaca | gtttggatca | aatcttccag | ttttgtttct | aatctttatt tttaacataa | 2220 |
| atgaggtcct | gtatacacac | gtacagtttt | tgtgtcctggt | gtttttattt aatgttatta | 2280 |
| tgagtgttttt | attttgttaa | aaggtcatca | ttttaagttg | ttaattagta ttctagcaca | 2340 |
| aatttgccat | aatttattta | attgtttact | atgattgacc | atttagattg tacttaattt | 2400 |
| ttaggcatta | gaagtgataa | actatatttt | aatcagacgt | tgaaaataac acatctttgt | 2460 |

```
ttagaaaaca tcattttatt tctggttgtc taggatagat tcccagaatt cttgggttag    2520
aggccataga taattatgaa agcagaaaga ttcacaagtt gggagttaat acttgaatta    2580
ctttatttgg ggtgaagcat tgagtgcata atacagatca tgcagtaatg ggaagaaggg    2640
ttggaacaat ggttttctgg cctatgtcag acttaccttg aagcttttaa gaatacagat    2700
gttctgatca accctcagac ctattaaatc agacctaaaa tcttagggaa taggcttttag   2760 gcatctctaa ttttaaaaaa tttattcagg ctacttggat gcacaaaaga gttgagacct    2820
actgtcctag aatcatagaa ttttaatgac gatagagacc ttaagcatct aggtcgtttc    2880 tgtacttta  catgtaagga aactggcatt cctaggccag taccattgcc atgcagctaa    2940
tttgccctct tgtctatagc tcactctgca tcacccaacc taccgttctc actgtttctt    3000
ctataaccaa tctccttccc acttctgttc tcttactcat gccattcttc cctcagtcat    3060 tttcttcct  tccatacaaa ttccatgtct ttaaaaagga ataatcctac ctcctccaca    3120
tagctttcca attctctgtt gcccacattt gtctcccttt caatacttct ctgttgtgtt    3180
atgtgacaca tcacatttga tatactctgt actgtgtttc aagtattgta ttctcttgtt    3240
tactcaagtc attatttcag gactgactac ccagtagatg ctttaagtca ggatttctca    3300
accttggcac tgttgacatt ttgagctgga taatttttg ttttggggggc tctcctgtac    3360 attttaagat gtttaacagc acccttggcc tctatccagt agacgcctgt actgcctccc    3420
cctatctgtg acaaccaaaa aggtcttcag acattgtcag atgtctactg aaggacaaaa    3480
tcacctctgg ttgagaacca ccgcttcaac taagttatct tctctgtact cagaacttga    3540
tgtgattgca gcaggggggag aggattcata tacacagtga atgcaaacga acctaaatca    3600
ccattcggat atggccacac aattttcatt tcccttgtgt tagcaagaga taccctaggc    3660
tttggacctg attattccta aggcattctg atgtatggtt ttacctgcag atttcctggt    3720
aatactgata cctcagtttg ggtcaaagaa ggtcaattaa ttgattgatt tgatttgact    3780
cctggaaaag acgctccttt ctagctgtct cttttcttctc tttacctgaa tagccagggc    3840
tctgtggttc aagtgaagta ttttgacata aaaattaact tagaacattg gtctgcagag    3900
tttgctcaat ataactgagc acatattgtg gctttatgga gctggttact acttttgac    3960 caaataaata attagaagta ttttcctcc tcaataaggt tcattttcc tttttcagt      4020 gagctggtag agtttccttt tttgatattt cagggcatct ttcatatttc catctcttaa   4080
gtttcttcat atgaagtaga atttatctgg attatgtatt gctgactctg atgaaaaccc   4140
atagaaagca tctggggctt gatcaccttc attcttgtaa tagctcacac ggttacagct   4200
gatatggtaa cttaagactt ttgattccaa atctaggcaa aatacactca gttgaaagaa   4260
tttgtcagcc agaacagttg gactgttctg tgaaaattgt gagaaaaatt acacaactaa   4320
gtgatacatg atgatggctt tcttaaatat aaaattgtaa taacatggtt aatttccagt   4380
acgttatatt gtcccagaag tggctccaac attgtttgaa atttgtctca tttaaagaaa   4440
cataagctgg ctatggtggc tcacgcctgt aatcccagca ctttgggagg ctgaggcagg   4500
cagatcacct gaggtcagga gttcgagacc agcctggcca acatggtaaa accccatctc   4560
tactaaaaat acaaaaatta gccgggcatt tggtggggggc ctgtaatccc agctacttgg   4620
gaggctgagg caggagaatt gcttgaatct gggaggtgga ggttgcagtg agccgagatt   4680
gtgccactgc cctccagcct gggtgacaga gtgagtctcc gtctcaagaa aaaaaaaaa    4740 aaaagcaaga aacataaaga ctgggcatgt tggctcatgc ctgtaatccc agcactttga    4800
```

```
gagactgagg tgggaagatc acttgagccc aggaggttaa ggctgcagtg agccgtgatt    4860
ttgccactgt actcgagcct gggcaacaca gtgagatcct gtctcaggaa aaaaaaaatt    4920
gcatgtaaat gaatgaattt gatatttaat attttaaatt atgaaaactg ttctgtagag    4980
atgtagatct tgccatgttg cccaggctgg ctttgaactt ctgggctcaa acaatcctcc    5040
tgtctcagtc tcccaaagta taaagattac acatgtgagc cactgcacct ggcctaatat    5100
ttttaactta atgaatttat tttgatataa ataaattaat aacactgaag cttcctgata    5160
taataagtct ttttgtgtgt gtgacgggtt ctcactctgt tgcccagact ggagtgtaat    5220
ggcactatca tggctcactg tagcctcaac ctccctgact caagtgatcc tcccacctcg    5280
gcttcctgag tagatgggac cacaggcgta tgccaccaca cctggctgat ttttaaaatt    5340
tattattgat acatattaat aaaattattt ttattttaaa aatgatatat gtggctgggc    5400
atggtggctc atgcctgtaa tcccgacagt ttgggaggcc gaggtgggag gatcacttga    5460
gaccaggagc ttaagaccag cctaagcaac atagtgagat cccatctcta tagaaaaaaa    5520
aaatggctag gtgtggtggt gtatgcctat attcccagct actcaggaga ctgaggtgag    5580
aggattgcta gagcccagga gtttcaagtt acagtgacct atgattgtgc cagtgcactc    5640
cagcctgggc aacagagcaa atcctgtct caaaaaaaa aaagttcga aatgcttat      5700 gatgcaatat aagtagtgga aaaggatatt aaattgtgcc tatatgaaca caactatatg    5760
aaaaacttgc acatagagaa aaggattaac aagaaataga ccaaattgtt cacatggttg    5820
tcttgtttgt ggagagaata tcagtagttc atttgtttcc ttccaagttt atatgttttc    5880
cgaggtctct ataatgagtt tgtaattgtt taatcataga aaacccttt ttggtccttg    5940 gccacaaact tacatgtttt aatgtaattg cttttttaat gagaataaat gttatatttt    6000
gcttttttaa aacctatatt cccatagtta tatgagccct tacaattatt aagaggctgc    6060
ataatataac gtttctggaa gggtacagaa gaaacagcag taattacctc tgagaacaga    6120
gacatggctt cacattttac ccttttgtac gtttttgtgct tttgccacat gcatttatta    6180
ttcttccaat aaataagtaa ataaatatgg attgtatact ccatctggtt ggtgtttcat    6240
aattctaaaa ttatattgct acattttta agatgatatg tgtttctact tattaacgta    6300
tatgttaaaa tagtaaattt atatcttatt taataatttc cctattgata gacatttaag    6360
acagtctcaa gtgttcacta tcatagaaaa tactgcacag atagcttttg ctatagtttc    6420
ttttttcttt gaatcgttaa ttgggaataa atgctcaaat agttatatgt ggctcaactg    6480
ctatttaagt ttattgactg actgctgcca ttttgaattc tgaaggggtt gattaaattt    6540
ataatgctgc cataagaata taagggtatt ggcttcatta gcatccacca gcattgggtg    6600
ttggaaatga ttatagattt ttaaatgcta caacaaatgt agataacaga gaactatcta    6660
tagaactctt tttggacatg tgaattgtaa taatagttta ttttcatgtg aatccagaaa    6720
aatgtatacg aaaacctttt ttcctctcat ttcttatatg aatagaatca agctatagaa    6780
gtggtctgga gtcaccagcc tgcattcttg agctgggtgg aaggcaggca ttttagtgat    6840
gggggacagg taagcacatg tgatggcaat aactttcttc taatatcaca taatatagca    6900
atagaaataa aattaaaagt ttagatttt tgttaaagga ggtgagatgt cacctaattt    6960
gtatgctatt atgtaactag tctaggatat tgaagctgac tatactctgt ttttaggtca    7020
ttatcttgta gtttaccata ctccctactt gcttcttatt ctactattta actcattttc    7080
cacatcccct aattttggtt tcatgaaatt attttttcctt ctgaattact aggttctact    7140
tactattatt aaactttatt tctgacatat tttataacct tccatggtct cacttgatta    7200
```

-continued

```
aaaataaaaa attcagctgg gtgcggtggc tcacacctat aatcccagca ctttgggagg    7260
ccaaggtggg cggataattt gaggtcagga gttggagacc agcctgccca acgtggtgaa    7320
accccccctc tctactaaaa attcaaaaat tagctgggca tggtggcagg tgcctgtaat    7380
cccagctact caggaggctg aggcaggaga attgcttgaa cctgggaggt ggaggttgca    7440
gtgagctgag attgcactgc tgcacttcag ctgggtgaca gagcgaaac aatgtcttga     7500 aaaaaataa aaaataaaaa attctacaac acaggttat tattttttcca tttttgtttt    7560 cccttatgag tttaatatgt ttagattata aacctgaaag cttgaatacc tatgtctatc    7620
ttttgttttc ttatgtttat caagttattc ctttaaacat tttctaaact gtaagaataa    7680
tgtgaggctg ggctcaatgg cttatgcctg taatcccagt gctttgggag gccaaggtgg    7740
gaggaccact tgaggccacg agttcaagat tagcctggct aggcaacata gcaagaccct    7800
atctctataa aaaattaaa aaattagct gggcatggta gcaaatgctt gtagtcccag     7860
ctactcagca gactgaggta ggaggaatgc ttgagaccag gaatttgagt gacctatgat    7920
tatgcactcc agcccgggca atagcaagac cctatctctt aaaagaagaa gatgtagtaa    7980
taatacatat tcattataac tattttacca ttgaaagtaa aaaatgagtt tttacctttt    8040
cccagtccca tcctcagaat gggatctca gtagacctt  aggattggaa gaatgagatc    8100 attcatatttt tctgcaatta ttaccccaca aaatatttca gataccttc catgtattac     8160 aaacaatgtg catttaacat gtctctctct ttctctctct ctctgtgtgc gtcttcatga    8220
tcctctgttg cagccctgcc agtaagacac tatctcctga agaatcactg ataggaacag    8280
aaagtggact ggctaggcca ggagtcctta gcttcttagg gggcaggagc tgctttgtgc    8340
tttctcagaa tcagatatat atgtggactg aaacatttaa aaacagaata gccaagggtg    8400
ctatacgttt aaaacttata tagatggggc tacattgctc tctattacta atttcccatg    8460
acaatacacg agagtgccat gtctttttaa cttgttttga gcacagacta atcttgttta    8520
tgcatgtttt ttgatgagaa taggctactc atgagaaatc tgtaaaccta acactagtcc    8580
cttgcatact ctaaattgtt gctagaatct taaaatttta gcaccagacg gaccttagaa    8640
atcattaact ttggtgcttt gttctacaat acaaggagat ggaatatttt acccaggatt    8700
gcttagcagg ttacagttct gccctctgag tacccagcac ttccctgtgg gcaacatcaa    8760
cttcctgatt ttcaagtctt aattagtact ctgaagaatc ctacttgttt ttaactccca    8820
tttgctttga agtgacttta cctgattttt ttagatccct tattgcagca atgccactaa    8880
gaaactgagt ctctagcttc ttggtgggca ggagctgctt tgtgcttgct cagaatcatc    8940
cttttcagta aggagatat tgaagagaaa tctactgagg agtctggggg tgaggcactc     9000
agggaaatcc tgctccagtc cacaaaagca gagaggaagg gttggttacc tagagtattt    9060
aacatgcaga ggctttggat tttactcctt taatccttgg aaatgcctat ggaaggggaa    9120
aggaagtaag atggtgactc cagcttatag acatactagt gttacatata tttaaactat    9180
aataggaggg tattattagt tttacttaac tttcaactgt gaaggattat acttctcaat    9240
atttgtctcc agtgtctatt tcagtgtatt tttcactttt cttgaagcag catgtctgtt    9300
gcaaaacttc tagaaataat gagaatattt atatattaga tcaagccata acttgatgat    9360
atagtcattt cttcttatat tttttactta cattttaca ttttaatgat tactttcatt     9420
tttgaaaaac atgtcatgct gagatgtatt tttcttcatt ctgtaattag ttatgaaaca    9480 gttttttccta aaatgctgag tatatcaagt cttggctaag aataagtaat aaatatttgc    9540
```

```
cacatgaaag actacacata tagccaggtg cagtggcttg cacctgtttt cccagctacc    9600
caggaggctg aggcaggagg attgcttgag cccagggttt ccaggctgca gtgaactatg    9660
attgtaccac tctactccag aatgggtgac agagccaggc cccatctctc aaaacagaaa    9720
agaaagatta catagactac atatacaccc ccatccaaaa catacacaca catctactta    9780
acctaaaatg gtaagaagat aacttcttat tttctaatat atgacacaga aaagttttt     9840 taaagtagtt ttaaatttt aatttttct aggtatttct caagccatgt tcccatgtgg     9900
tatcttgtca acaagttgag gtggaacccc tctcagcaga tgattgggag atactggtaa    9960
agaaaaccaa ataagaacta tctcatttaa ggttaaatta cttcacaata tcaatgtctt   10020
tagctttctc taagctttat tatatattct gagttggttt tgaattataa gaatgaattg   10080
gggccaggca cagtagctca tgcctatagt cccagcactt tgggaggcca aggcaggtgg   10140
attgcttgag tccaggagtt caagaccagg ctgggcaaca tggtgaaacc ccgtatctac   10200
taaaaataca aaaattagcc aggcatggta gtgcatgcca ttagtcccag tcacttggga   10260
ggctgaggca ggagaatcgc ttgagcccgt aaagtcaagg ctgcagtgag tcaggatctt   10320
gccattgtac tccagtctgg aaaacagagt gagaccttgt ctcaaataaa aaagaatga    10380 attgatagag atctaatgta caacctgaca actataggta ataaaattgt attggggatt   10440
catgttaaat gagtagattt taactactct taccacaaaa acacaaaagt gggtaactgt   10500
gagatgatgt atatgttaat ttacttcact atagtaacca ttatactatc tatatgtagc   10560
tcataacacc atgtcgtgta tattaaatat gcacattaaa atttgttttt taaaaaaga    10620 attgagattt ttttaacta gatatggagt ggacaaaatg taaagtgaat tgatcttttc    10680
gtctgttggt tctaggagct gcatgctgtt tcccttgaac aacatcttct agatcaaatt   10740
cgaatagttt ttccaaaagc cattttcct gtttgggttg atcaacaaac gtacatattt    10800
atccaaattg gtaggtgcta ttgtaatatt tgctgtcata ttctacacta tagcattgag   10860
tccaaagtag aaatgaatgt gcactaatga gctttatttt ctacacagtt gcactaatac   10920
cagctgcctc ttatgaagg ctggaaactg acaccaaact ccttattcag ccaaagacac    10980
gccgagccaa agagaataca ttttcaaaag ctgatgctga atataaaaaa cttcatagtt   11040
atggaagaga ccagaaagga atgatgaaag aacttcaaac caagcaactt cagtcaaata   11100
ctgtgggaat cactgaatct aatgaaaacg agtcagagat tccagttgac tcatcatcag   11160
tagcaagttt atggactatg ataggaagca tttttttctt tcaatctgag aagaaacaag   11220
agacatcttg gggtttaact gaaatcaatg cattcaaaaa tatgcagtca aaggttgttc   11280
ctctagacaa tatttcaga gtatgcaaat ctcaacctcc tagtatatat aacgcgtcag    11340
caacctctgt ttttcataaa cactgtgcca ttcatgtatt tccatgggac caggaatatt   11400
ttgatgtaga gcccagcttt actgtgacat atggaaagct agttaagcta ctttctccaa   11460
agcaacagca aagtaaaaca aaacaaaatg tgttatcacc tgaaaagag aagcagatgt     11520 cagagccact agatcaaaaa aaaattaggt cagatcataa tgaagaagat gagaaggcct   11580
gtgtgctaca agtagtctgg aatggacttg aagaattgaa caatgccatc aaatatacca   11640
aaaatgtaga agttctccat cttgggaaag tctgggttag tataaatttt ataacttggg   11700 agaaattta tgtggcttaa acatcccaa attatgaatt agaatagtat ttcatatata    11760
aattgaaaat caattaaaaa gaaacacagt gcctaaaggc acttggggga cacatttacg   11820
ctttgcagta aagtccttgt ttggataaag attgtatgtt ttctggccaa gtaagcttga   11880
ataggtacaa gcttagatag gttcaggcca gagaggtcaa aattacttgc ctgagattgc   11940
```

```
atagctagtg ttacaactag gattcaaacc caggcagatt gacttggggg ttcatcagga    12000
tggagtgccc tacaaagcct cccatcttta atgcttgcag atttgttccc cagttaccga    12060
aagcaacttg ttaatattag ggaaaagggc cagtgtaggg agagatccat ggcatgaggt    12120
aaccttcctg ctgcatgtgg tggcacctgg attggaatgc atccaggagc tgcttaccct    12180
gccggtgtct gctctttaat ttgtgtataa cggagaggaa gtagacaggg caactagtgc    12240
tccagcccct catcctggcc acaaatatta atgctacctt tatatgacat aagtcactag    12300
tccatttatt ggaacctaaa tttgaaccac tgtaaagtaa gacttcatag tgataaagag    12360
aggaacttgt taggaaagag aataaaatag aaagagaagg ttgtctcctt ttgtagattt    12420 ttttttttc tccaacagtt ttacctgtga cctttataca ataactgac aaagcattaa      12480 tctctttggc ctacatcatt ttcttttcta tttttttttt ccacaagatg gagtttcact    12540
cttcttgccc aagctggagt gcagtggcat gatctggctc actgcaacct ccgcctccca    12600
cgttcaagtg gttctcctgc ctcagcctcc tgagtagctg ggactacagg catgcaccac    12660
cacgcctggc taattttttg tattttttagt agaaactggg tttcaccatg ttagccagcc    12720
tggtctggaa ctcctgacct caggtgatct gcctgcctcg gcctcccaaa gtgctgggat    12780
tacaggcatg agccactgct cctggccggc tacatcatt ttctaaagct ccagaccatt     12840
cttttctttt cttttctttt cttttctttt cttttctttt cttttctttt cttttttctc    12900
ttctcttctc ttctcttctc ttctcttctc ttctcttctc ttttctttc ttttttttgag    12960 ttagaagctt gctttgttgc ccaggctgga gtgcagtggc accacctcca ctcactacaa    13020
cctccacctc ccaggttcaa atgattctcc tgcctcagcc ttcagagtag ctgggactac    13080
aagtgtgcgc caccactcct ggctaatttt tgtattttta gtagggacga ggtttcacca    13140
tgttggccag gctagtcttg aactcctggt ctcaagtgat ccgcctgcct cagtctccca    13200
aggtgctggg attacaggcg tgagccactg tgcctggcct cagatcatta ttttctgtta    13260 gctttaaaact gtccgttcag gagatcccac tgcatcctca aattcaaaat atctaacact    13320
gagcttatga tttagctggt tctgtcatta gatgggaata ccttttatt tccttgaaat     13380 tatatggtga gaacagggag aagtgctgat ggtaaagtcc tgtgattaag atagcaataa    13440
ggactccgcc cttcccactc cactgaaggt tgaagagcca tggacaatga gaagtcacag    13500
taggtgaaat caggtactaa aatggacttg gcttgagaga tcaaaattga tcacttggtg    13560
atacaactaa caaattcatg ttaacttgaa ccctttattac cctgtgaagc atggtgatta    13620
aaaaaaaaca acaaacaaac aggaaacttg attgttaaat tctctttaag tcagaatatg    13680
taccttagag ttttttattta tgcttttgtc taccattaat atgtctgcac ctgctctttta   13740 gaagttaata gagagtaaag tcgtctttat gtctttcagt gcttacttat atttgggaag    13800
ttgagaaaaa ttttttaacat cattattgat atatatatat atatatatat atatatatat    13860
atatatatat atatatatat atagataatt ttttttttt tcttgagacg gagtctcact      13920
ctgtcgccca ggccggagtg tggtggcgat ctccactcaa tgcaagctct gcctcccagg    13980
ttcaagcgat tctcttgcct cagcctcccg agtagctagg atacaggctc ccaccaccac    14040
gcctggctaa ttttttgtagt tttagtagag acgaggtttc accatattgg ccacgctggt    14100
ctcaaactcc tgaccttgtg atccgcccac ctcggcctcc caaagtgctg ggattacagg    14160
cgtgagccac tgcgcccggc tgaggtaaaa tttaaagtgt acaattcagt catttttagt    14220
atatttatac tagttgtaca gccatcacca caatctaagt ttagaacatt ttcattaggg    14280
```

```
ggtgggagaa attttactct gcttttaga ttaagtttct gtctggatct aatcatttaa      14340
tcagacaatc aggcagattg tctgtgatta gttttggcca ttccagcttc ttcattggtt      14400
gttaactttc acaaataaag gctgctcaaa gattagaaat aacatttaat ttgaatgtaa      14460
atgtgccata gtttaaaaga tgggtttggt gaatacagtc aaatacatac atttaaagct      14520
ctaattctga agattatgta aagaaaagga agaaatgta gggagaggat tgaaatgttc       14580
atggtataac aatatctgaa catccatctg gtcacaccgt tggtatttga atgttttgtc      14640
ctcctcaaat tcatatgtcg aaatcccaac tcccaaggtg atcgtattag gaggtgtggt      14700 cttttgggaag tgattaggtc atgaaggtga agccttcatg aatgggattc gtgctcttat     14760
aaaagagaac tgtgagaaat aagtttctgt cgtttgttag ccacccagtt taggatattt      14820
tgatatagca gcctgcatgg actgagacaa ctatgagtta ttatgatagc ttctgttatt     14880
tcacctaaat tcatagaagc taatatatca atatttatgc tatgaaatat ttcttaacca     14940
agctttgaat atatttatat ttttgtttat ttttaaattt cagattccag atgacctgag     15000
gaagagacta aatatagaaa tgcatgccgt agtcaggata actccagtgg aagttacccc     15060
taaaattcca agatctctaa agttacaacc tagagagaat ttagtgagtt caaatatata     15120
tgttacatca aaattctttt acacgttttg taagatttct agttgctta gctaagtaat     15180 aagaatgttg tattccttt tgatacaaat cttttttat tgtgttaaac tatatataac       15240
ataaaatatg ccatgttcgc cattttaag tgtataattc aaaggcatta attacattca      15300
taatattgta caaccatcac cactatctat atccagaact tttccatcac cccaaagaga     15360
aacttggtac ccattaaaca ataattcccc gtccactcct ttccccagtc cctggtaatc     15420
tctaatgtat attgtgtctc tatgaattta cttattctag atatttcata taaagtaga     15480 agtatgcatt tgtcttatgt atctgactta tttcatttaa cataatgttt tcaaggctca    15540
tctgtgttgt atgtatcaga atgttattcc ttttcatggc tgaatactat tccattgact    15600
gcatatacca catttgttta tccattcatc tgttgatgga cacttgggtt gtttccacat    15660
ttttggctgc tgtgaataat gctacagtga acattggtgt acaagtatct gtttgagttc     15720
ctcttttcag ctcctttggg atatacctag gaattatgtt taacttttg agaagctgag     15780 aaatctttaa taaatgataa cacaaatact tatatttgcc aatgcaaata tgaatatttt    15840
tggcttttaa gagattgatc attttgccac gtggttgtaa ttaaaaaaaa ttgtcccatg     15900
ttgtttcagt attaatattg tagcctaaaa gagtgctaga ctgttttact ttttactcag    15960
ttaattcttt ggatactggt agagtcagga aatgagatat tgaacttaaa gatctttgca    16020 ggtgggtcc agtggctcac acctgtaatc ctagcacttt gggaagctga ggtgggagga     16080
ttgcttgagg ccaagagttt gagaatagcc tgggcaacat agcaagaccc catctctaca    16140
aaaaaattaa aaaaaaatt aagccaggcg tggtagctca cgcctgttat cccaacactt    16200
cgggaggctg agatgggtgg atcacttgag gtcaggagtt ggagaccagc ctggccaaca     16260
tggtgaaacc ccatctctac taaaaatacc aaaattatcg gggcgtggtg ctaatcctgt     16320
aatctcagct actcaggagg ctgaggcagg agaaccactt gaactgagga ggtggaagtt    16380
gcagtgagcc tagatctcac cactgcactc cagcctgggt aacagagcga gactctattt    16440
caaaaaaagt aaaaataaaa attagacaca tgtggtggca catgcctgta gtcctagcta    16500
ctcaggaggc tgactgaagt gggaggatct cttgagccca ggagttccac actgcagtga     16560
gctatgattg tgccactgca ctccagccta ggcaatatct caaaaaaaat tttttaaat    16620 agattattag gccagacgtg gtggctcatg ccagtaatcc cagcactttg gaaggccaag     16680
```

```
gcaggcggat cacctgaggc caggagtttg agaccagcct ggccaacatg gtgaaacccc   16740
atgtctacca aaaatacaaa aattagctgc aatgtctata atcccagcta cttgggagcc   16800
tgaggcaagc gaatcgcttg aacccgggag gcagaggttg cagtgagtgg agactgcgcc   16860
actgcactcc agcctgggcg atacagcgag attctgtctc aaagaaaaag gaatttgttt   16920
tcctgtcttt atcgtagagg gaggaaaggg agaatgggt tggaatggtt attgagtgag   16980
ccacattatg gtagatgtat cactgggcat agagaaaagg agcatttaaa acttttccgc   17040
ctaacagatg tttcttcagg ctacactgca ctcattgtgc taactgtaat gtcaaatccc   17100
agacctgtgc ctatagaaca tgaacatcct tcattggatt tgtttggtca ggcttacact   17160
ttattaggaa gatcagatgt taaaataagg gtgttaaagt taagttcaga tatgaggata   17220
attcattact attccttttt ctggcagcct aaagacataa gtgaagaaga cataaaaact   17280
gtattttatt catggctaca gcagtctact accaccatgc ttcctttggt aatatcagag   17340
gaagaattta ttaagctgga aactaaagat ggtgagtaca tttgttattt tgacttttt   17400 ttctatttaa atagttgtac attttaatt gttcttgcaa cctgtcatac ctgtgaacag   17460
tatgtgaata gtgaaatata attatgataa ttaaacagta gtttttatgt attgaaaaat   17520
atctttggcc gggtgcagtg gctcatgcct gtaatcccag cactttggga ggccgaggca   17580
ggcggatcac ttgaggccag gagttcgaga gcagcctgcc aacatggcgc aaccctatct   17640
atacaaaaaa atacaaaaat tagcctgaca tagtggtgta tgcctgtagt cccagctact   17700
tgggaggctg aggcagaagg atcacttgag cccaggagg ctgtgttcct gccactgcac   17760
tccagcctgg gcagcagagt gagacccctgt tgggggaaa aaaaaaaaag tctttaactt   17820
aaataaattt gacatttaaa atcttaaatt atttcatctc tgtttcagta ctaactctgc   17880
atttattact ttctttttaa taggactgaa ggaattttct ctgagtatag ttcattcttg   17940
ggaaaaagaa aaagataaaa atatttttct gttgagtccc aatttgctgc agaagactac   18000
aatacaagta atagcatgtt attgaatatt taataaaata ctatttgtta catatgattg   18060
ataataaagt atgaagttcc ttgtaacacc ttgcattgtg aagtgtatta aaaacctgct   18120
aagagtaagg aataacttga tttaaaatat tttattctgt aatctcttta aattatctgt   18180
acaaattatt gacttaacct aaatttaaaa atgaatgcct tagcacaatt aagttccaag   18240
aatagagttg atcatgttaa ctggtaaatg gatcatgatt taaaattctt ctaggattga   18300
aacaaatgaa aacgtagttt taagggtttg atttttttaaa ttcctatttt tacatgcaat   18360
tttactgcac aacccatctt attttgacag ttcttaaatt cgcaactctt cagaaatatt   18420
atcagatcac ttttctttgc ttccataagt tttttttatta ttatattatt attttttttt   18480
tttaaaagac ggtgtctcac tttgtcgccc aggctggagt gcagtggcat gatcatggct   18540
cactgcagcc tcgacctccc aggctcaggt gattctccca cctcagcctc ccaagtagct   18600
gggaccacag gcgaatgcca tgatgcctgg ctaatttttg tatgttttgt agagataggg   18660
tttcaccatg ttgcccagaa ttgtcttgaa ctcctgggtt caagcagttg ttctgccttg   18720
cccacccaaa gttgtgggat tacaagtgtg agccactgcg cccagctatt ctagaagtat   18780
tttaagagtc atcttttttt tttttttgag atggagtctc actctgtcac ccaggctgga   18840
gtgcagtggc acactctcgg ctcactgcaa cctccacctc ctgggttcaa gtgattctcc   18900
tgcctcagct tccctagtag ctaggattac aggcgcatgc caccatgccc tgctattttt   18960 tgtagttttta gtagagacga gatttcacca tgttggccag gctgctcttg aactcctgac   19020
```

-continued

```
ctcaagtgat ctgccctcct cagcctccca aagtgctggg attctaagtg taaaccacca   19080
cacccagcca agagtggtct ttttacaata ttattttttg attaggacat tcattcttgt   19140
cataaaattg aagatactct agtcatttag aatttcattg ttttggaact agacattgtt   19200
tctttatttt tgaaatgtta ttgaaggaat accatttgga gaagatacaa atgtaagaat   19260
tgtgaaaagg ataattgtga cacaaatcaa aattatagat aaaatatac ctgtaaaatg    19320 tattaaggca ataacattct ttctgcttgt tgaccataaa tatttatatt ccctggatgg   19380
gtacattgtt attgtcaagg gtgtttaaat aatgatcttg catgcataat ttattctctc   19440
tggtataaca gaatcagcaa tttagttttc tgggacccga gaaaaacatg caaaagacat   19500
actttgaaat gtaaaactga ttttccttg caactgtagg tccttctaga tcctatggta    19560
aaagaagaaa acagtgagga aattgacttt attcttcctt ttttaaagct gagctctttg   19620
gggtaagaag ttatggccaa actagcatgt tagacatgtt tttaacacta tatctggcag   19680
agttttcaat gtaaatatta aagtagatgt taatgtcaat aagtgatctt aataatgcat   19740
cagtagatat ttttcaagg attgtctcta tcttcacgcc tagcttataa tttgccttgt    19800 cgtcttttt ttttctctt tattttatg ttttatcca tccctggtgg taggggataa       19860
ccttgtcttc ttcgataaca agaagtctga agcttattag aaattttact ttgagaattg   19920
atcgatgaga agaaagcaac tagatatcac gtggatcata tatgcttgaa taaaacaata   19980
attcttagaa caaataaata cattttaaaa gttaaagcca aaaacattag ttgaatgttt   20040
aaaaatattt caaattaagt tattccttca ctgtcttgta ttactgtaat aatttggatt   20100
atttgtgttt ttctcaactt ttaaaacaaa tatttaaaaa attcctcttt tgattaagta   20160
gggctagata aaatataaaa aatatttttt aaactcctct taatttccat atttcttata   20220
taatatgaga atctcttata aacactacct cttagaagtc tccacagaag ctttggtaga   20280
tgtagtagta gggattttgat ttcttagaat ggtataatct gtaaatgttt tagtaaaagg  20340
attaaacgat aaagtcaaaa tgtttatagc acagtgttta ttaatataaa ataaaatctc   20400
tttttttttt tttgagatgg actctcactt tgtcactcag gctggagtgc agtgttgcaa   20460
tctcagctca ttgcaacctc cgcctcctgg gttcaagcaa tccttccgca tcagcctcct   20520
aagtagctgg gattacaagc atgcaccacc acacctgcct aattttttgt attttagta    20580 gagatggggt ttcaccatgt tggccaggct ggtctcaagt gatccgcctg cctcagcctc   20640
ccaaagtgct gggattacag gcgtgaacca ctgtgcccag cataaagtaa aatctcttca   20700
gactctcatg tgatcatgta aagtggcagg cagtcacagt caagaagtag tttaaagttc   20760
atgtttgtaa aatataatct acagattgat actggatttc ataggtaatg tttaagagaa   20820
aataagtttt tagttatcct cagtacttca aaagcaccca tttatgatta tgttgattac   20880
taaactaaat catttgggggg ctagaggtgt ttttttatgt gttaagattc cttaaggagt  20940
tctattaggg caaaactttt agtaactgca tattttaaaa gtaataaaac taattttaaa   21000
agcttggagg ctgggcgcgg tggctcacac ctgtaattcc agcactttgg gaggccaagg   21060
cgggtggatc acttgaggtc aggagtttga gacgagcctg agcaacatgg tgaaaccttg   21120
tctctactaa aaatacagaa attagccagg tgtggtggtg ggcacctgta atcccagcta   21180
ctcgggaggc taaggcagga gaattgctcg aacttgggag gcagaggttg cagtgagccg   21240
agatcatgcc actgcactcc agcctgggtg acagagcaag actccgtctc aaaaaaaaaa   21300
aaaaaaaaaa gcttgaagtc agattcgaca ttaatcagta tactttctct caagtagggg   21360
acaatttcta agattttagt cttttaaaat ttattaacta gtctgagcat ggtggcttgt   21420
```

```
gtctataatc ccagcactttt gtggggccga ggcagatgga tcacttgagc ccaggagttg   21480
gagactagcc tgggcaacat ggcaaaaccc cgtctctaca acaaatgcac acacaaaaaa   21540
cccaatcagc tgggtgtggt gttacactcc tgaagtccca gctactcggg aggctgaggc   21600
aggaggatca cctttgccag ggcgtttgag gctgcaggga gctgggttca caccactgcg   21660
ctccagcctg gatgacacag caagccccctt tctcaaaaaa aaaaagataa aaaattaaat   21720
taaattaatt aactacactg ggaaggcaaa attcagcatt ttttttatagc taaattttat   21780 cctgcttcag tcttttatca tgtaactatg tatattttt acagaggagt gaattcctta   21840
ggcgtatcct ccttggagca catcactcac agcctcctgg gacgcccttt gtctcggcag   21900
ctgatgtctc ttgttgcagg acttaggaat ggagctcttt tactcacagg aggaaaggta   21960
agtggttaag gtgtgttcat ttttctgtaa catttaataa cttttcattt atctttcttt   22020
gggttttgac catctattat ataggggtggg ttttgaccat ctattatata gggtttatac   22080
gacatatgga aagcattcat ttattcacta atatttctgt gtgtctgctt ttaggtgttg   22140
ggggagtgat gacgaataag actgatgttc tccatgccct ttttctgtgt cagttgatac   22200
aattatatgg tttttctttt ttaggctatt aggtgttgat agggttgagt aacttacaaa   22260
tgttgaacca gccttgcata cctgtgataa ataccacgta gttgtggtgt atcattcttt   22320
ctacattgct gagttttatc tgctaatgtt ctgttgagct tttgtccatt taagtttgaa   22380
agtgattagt ttgcagtttt ctgttttgt gttgtctttg tctggttttg ctatccgtgt   22440
aaatctggcc tcataaaatg agatgggaag tattctctcc tcttcttttg ttttttttgga   22500 agaggttgta taaaattgag gctgaatctt ggtggttgcc acaatgacag gaactatttc   22560
tgtgactgaa tatattggga attcctataa agcaattatt ttctagggaa gtggaaaatc   22620
aactttagcc aaagcaatct gtaaagaagc atttgacaaa ctggatgccc atgtggagag   22680
agttgactgt aaagctttac gaggtatgag tatggtaaca ctctatataa atcccttttt   22740
cattagaaag acaggaatgt tatacataat gctgtcaatc taataaatac acatatcatc   22800 tagtcttttaa cttttctgtt tatcatttag tcattaaaat ttctttggct ttctaatgtt   22860
tttgataaaa tttctaaaac tctccatatt taatggaggc ctatttttt ttctagccag   22920 aacttttttgt agactacatt tctggaagtg ctcactgaca ccactctgaa aaattagtac   22980
ttagaatata ctctaattgg tataaatgat ctctgaattg ctatggaaaa ctgggagaat   23040
ggttgcttca ggggagagaa agtagggaggc tgtggacagc aatgaggaga attacagttc   23100
accatataac acttttgtac ttttaaagtc cttaacattt acattattat ctattcaatt   23160
aaaaaatatt gggaagattt tactttgaac agttaatttt tccccatgg gtaccgctgt   23220 catatagttc caactaatca tgaacttgtg tatttcctgt tctttgtaaa tttaaacttt   23280
gtaactcacc aggaagtttg aagccaaatt tgtgtttcaa atatagcaac tccaggatct   23340
ctaggcagat gcatttgcat ttgatttttaa atgaatcttg atcccttact ctcacttatg   23400
ttttcccaca tcctacttttt tttattttgt tgtaagccat ctaaaattct caatgggatg   23460
aaactgggta taaatgaata catgcataca ggaattatag tagcatattc cttttctttt   23520 ttctttttt tttttttga cacagagtct tgctctgtag cccaggctgg agtgcagtgg   23580
tgcgatctcg gctcactata gcctccacct cccaggttca agcaattctc gtgcctcaac   23640
ctcccgagta attgggacta caggtgcatg ccaccacacc tggctaattt ttgtattttt   23700
tagtagagat ggggtttcac catgttggcc aggctgatct caaactcctg acctcaaagt   23760
```

```
gatctgcctg ccttggtttc ccaaagtgct gggattacta gcataagcca ctgcacctgg   23820
cctccttttc tgagttttat aaaatttgat actttactgc acgctttgag actgtattaa   23880
ttgaaccatg ttgatgaaca agttttttgtg atgggtatat taataaaata tagatcaaat   23940
ttttatagtt aaatcaatat cgagcttttc tagtgctttc aaaaggacaa cctgaattt    24000 cccagcactg aaatgatact gaaaccattt catatcttct gtattaagga aaaaggcttg   24060
aaaacataca aaaaccccta gaggtggctt tctcagaggc agtgtggatg cagccatctg   24120
ttgtcctgct ggatgacctt gacctcattg ctggactgcc tgctgtcccg aacatgagc    24180 acagtcctga tgcggtgcag agccagcggc ttgctcatgg taaatgcatc caccactggc   24240
ttaaggtctt gttcttttgt cagtcagcat ttttagtctt aacaataaat ctactctctt   24300
cagagaataa tatatgtgtt atgttaagtg ttgtgtttga ggcccctgat ggcattctac   24360
agttgtccta tagactgtaa tagcaaaatt ggtagagtaa aaacagtgtg aaaattctgc   24420
aacttcatgg ttagtccttt agggttttc attctcccctt acttattgtt taatttacag    24480
atttactctt ttgttcattt gacaaatatt tgtcaaatgc ttgtgcacag tctgtattct   24540
caaattctag gagaaaaaga agggtgaaca gtattagcgc agaacgatac taataatgat   24600
ggctactgtg tatgagtagc cagccctttc ttggctttct tggattgctt tgtattctac   24660
atgaagatat tccctgggct ttacaggtca ataaatggaa attcagagag attaatttga   24720
ccagggtgac caacaaggag atgacagcat acactatgcg agaagtatac acagagtagt   24780
gtaggagcat ataacctaaa ctgggggtga ggtgggataa ggagttatca gggaaggctt   24840
tttggaggag ttgacaactg agccgagttt tgatggaaga gtagaaatta gcatgaacca   24900
atttcatgct aataaagaag caaggaagc gtggtctaca ggcaaaagca cagaggtaca    24960
ggaagtaatg atatgttggg gaatacccctg ttgactggag cttagagtgc aaggagagga   25020
gtgctaggga ggtgaggttg gagggtttgg cagcattgac ttgcttcaag gttcttaaga   25080
gctgaaatag atataaaatg caactaagag tggcttggat tattattacc tagtgtgtta   25140
atctcaaatt ttgaaatcta tagcatctat aggactggtg ttactaatct tacactcgat   25200
ctgttactgt tcttatacta gatctattag tccagtgttt aagggagtgg tgcagatttc   25260
taggtcagga caggactcag atgtacatta ttaatgccta tttcagttct gaccttctca   25320
tatgaaacct tataagacct gggggtaggaa gagattgttc tggaagtcat aggaatatga   25380
actgtatttt gtttaacaaa caatacagta tggaaattta tcacccttcc agaatattta   25440
tttcagagac aaattttat cattcgttca tttatttcat aagatccacg agtagggaac    25500
ctcactagac attgctctga gtatatggtc tgagtttgca gtacctcttg tgtctccatt   25560
agatttatta ggtcctcaat agataaatca gggaataact agatggattc attttttaaa   25620
gacatgaaag agcgatacca tacatactgc accttaaagg tcaaccttag agtatcatta   25680
tttttaatga atgtataatt tttaaatttc atgtttactt ttcctaagct tttgcactat   25740
attgcttaat tccagctttg aatgatatga taaaagagtt tatctccatg ggaagtttgg   25800
ttgcactgat tgccacaagt cagtctcagc aatctctaca tcctttactt gtttctgctc   25860
aaggagttca catatttcag tgcgtccaac acattcagcc tcctaatcag gtaatacact   25920
acttgtaagg attattgaat tatgtccctt ttatagaaat tatttttcaa ttttattagt   25980
aattcgtggc tttaaattta tgcttctctt aatgatttta aggatatgta agtcaacatt   26040
tggtgcatat tgtgctagag gcataaaatta aatttatag ccacctgaaa tgttagtatg    26100
cgcttttcca gaaaatgact ttttgaaaa tggtatttct ttgaatgaga aagaacagag   26160
```

-continued

```
agaaatagat agatggcttt taaacacttc attaattaaa ctttttttt ccaccatcac    26220 ataatggcac ttagtcccct ttgggaactc atgagggttt tagtggtagt gagctgaaag   26280
aaatatgttc caggactggc aaacatattc taaattcttt aaaattttca cctagcatct   26340
accctaaata ttcagaccct gtgctagtta actgctattg aagaacaaag gtattatatc   26400
tattattaag gataatagaa tggtatttga gatattggtc attgaatatg aatatgtttt   26460
gagaaataag ttttatagga accaaaaaaa aattcttaaa ggaaccatat attactaaaa   26520
atgcttctta ttggagaaag aaatgacaat catttattaa tgtgattttt tcacaacttt   26580
attaagatat aatttaagta caacaaactc acataaagtg tacaatttga tcagttttaa   26640
catatgtaga tgccatgaaa ccatcaccac aattaaggaa acaaacattt tcatcactcc   26700
agaagtctcc tagcccttt actacccatt cctcccctgc tccatcccca gacaactacc    26760
aatttgcttt ctgtcactat agatttgtca acctgatttt ctccaaatat acattcaaaa   26820
atatacagtt gaatacaatt ggaaattcga attttgtgtt ttttctta ggaacaaaga     26880 tgtgaaattc tgtgtaatgt aataaaaaat aaattggact gtgatataaa caagttcacc   26940
gatcttgacc tgcagcatgt agctaaagaa actggcgggt ttgtggctag agattttaca   27000
gtacttgtgg atcgagccat acattctcga ctctctcgtc agagtatatc caccagagaa   27060
agtatgtttt actattaaaa cctgaacttg gaatcttctt tctattgtgg agaaatgtaa   27120
ttgtagtaag acaagaatta aatatattcc attgtagtat ttgaataagc agttatttga   27180
gtagaaaatt agtgtttcca gctaagatga tggcatattt tgaaaattca tatagtgaat   27240
ataactagta aaagaagttt tgtttatttt taaacagaat tagttttaac aacattggac   27300
ttccaaaagg ctctccgcgg atttcttcct gcgtctttgc gaagtgtcaa cctgcataaa   27360
cctagagacc tgggttggga caagattggt gggttacatg aagttaggca gatactcatg   27420
gatactatcc agttacctgc caaggtatgt ttaaaaaaag aaaaagtgaa tacttactcc   27480
cagaagaacc actgtattat tggctttggc tttatgtgtc agcttgccca atctccgtgt   27540
gagtcaacaa gtgtttactg agttaccaaa taaatgtctt aacactattt taggtacttt   27600
aacaaatttt aatttattaa ttaattttt tattagaatt gagacctcac tctgtcatct    27660
aggctggagt acactcacag ctcactgcaa cctcaaactc ctgggctcaa gcaatcctcc   27720
tgcctcagcc tccccagtag ctagaactac aggcatgaac caccatgccc ggccaactct   27780
ttaattttct tagagacgga gtcttgctat gttgcccagg cagacagatt ttaatgtgta   27840
tgatgcagtc tttgatgata agaaacttat aatggaaagc tgaggtgata gttacagtaa   27900
atacattttg atgtataatt ctgtttgctt taatcattca aattgtagta aagcaagatg   27960
aactgtctgc tgggatttga gcagaaatgg ataggaataa actaggaggt agaagagtta   28020
tcaaggttca caggactgat gggtgaagct agatttccag acccgggatg tcagtccttg   28080
aaaagcagac ttggcaggca tagacgaggc agatagcagg ataaaggaga caaatgtaga   28140
ttgttcttca gaagatcaga tggtagagtc taggaggtag tgtgttttaa tcagagatct   28200
gagaggcaaa gatcattgca tgagatcagg gacccatgca aaggagtgag aaaaaaaact   28260
gggttaagga gcctgctgca tggcaactcc tgggaacagt ggccactggg gcctgggaca   28320
tgttgattgc agcccaggac tgttaaaacc agtgtgagag aacatgggta tggaagtact   28380
agctagcagg atcatgaccc cgatgctggg atgggcatc aagcattagt acatggagat    28440
tcagtacatc cagatgcagt acatggagac tatatgcgta actgctgact ttgggcttct   28500
```

```
ttcagattgg agcagaggta gaggtgagtg ggaatattct caatagaggg aactaaatag    28560
gcatacctaa taaaggagac caggatattg cagacagtag cctcatgttt ggctcacctg    28620
ttcaaaaagt tctcttgttc ttgagcagtg gtgccttaaa aggtaacttg agaagcagtc    28680
gattatttgt tcagcctgga gactcttggg atatttact  atctttgatt gaatagattt    28740
aaatgtacac agctctcata acttgcccca tgaagcatat ccatgaaagg cactatactt    28800
gttaaaagat tggtttgtac ttttaaatg  tagtactttt aataaaacag gaaaatagaa    28860
agttctgatg cagttatatg cattttatat agaatgtgtt cttaattgga aaaaatttgt    28920
cgtagttcct ttgagttcat ttacagtttt tagtaggaat tgtattttct actgttgtac    28980
ttgctgttac taaagaaaga tggtcgtgat taccatctga attttttttc tatacattga    29040
tctttagctg ctacttagtc atttctgttt agacttgagc tcttttcat  atttttttt     29100 tttgtttctc agtatccaga attatttgca aacttgccca tacgacaaag aacaggaata    29160
ctgttgtatg gtccgcctgg aacaggaaaa accttactag ctgggtaat  tgcacgagag    29220 agtagaatga attttataag tgtcaaggta tgttgtctac ttatcttctt ttttatttaa    29280
ggtaaaatta acataaatgc agttagccat ttcaaagtgt aaattcactg gcatttagtg    29340
cattcacaat gctatgcaac caccacctct ctctaatttc aaacttttt  cattccactc    29400 ctcctcttgc ttatcccctg gcaaccattc atctgctttt tgtctctatg gatttgcctt    29460
ttctgtatat ttcatataaa acaaatcatg caatatgtga ccttttttgt ctggcttctt    29520
tcacttatgt aatgttttca tggttcatcc aggtagtagc atgtatcagt acttcattcc    29580
tttgcatgac tgaataatgt taccatactt tgtttatcca cttatcagtg gtgaacatt     29640 gaattgtttc tacctttga  ctattatgaa taatgttgct gtaaatattc atgcacaaat    29700
ttctccacgg atatgttttc atttctcttg ggtataaact gaggagtaga attcttgggt    29760
cttagggtaa ttctctaact tttcaaagaa ccaccaaact gtctttcaca ccaactgcac    29820
cattcccact agcagtgtgg ggggttcctg attctccaca tctttaccaa caccattatg    29880
tttctcaatt gtgggctagt ctcacatttg gaaagctagt gggagcagcg atccatctat    29940
taaaagttgt atgaaattga gtaatgagcc acctctctct tgtagggctt attatgttct    30000
tgcttaaggc aatcttcatg cattgtgaac agaattatac ataaatgctc agataaaagg    30060
gcaaaccatt cttaaaggga gtagacaact agaggcagga gaccatactg aggcaggaag    30120
ctggggtttt tatggttctg ttacttttga ctatatctca ccattgcttt tgtcaaagtg    30180
agactaggtc taagtttttt tcaggtataa ggtgagtgtg gtaattaagg ggcatgctag    30240
cagatcattt tgggtaatgc ttcacagtcc accactggtg tgtcattgtg gtcgcagatc    30300
cagtatctta gctgtgtaat ttcagacatc agcaatatta gtttaacaaa gggcaattag    30360
attccaagac aaaggaatcg tgtattattc tagccttatt caaacttgat ttataaatca    30420
gtttagtaat ttatttattt gtttctgtat ttatttttat ttcttgaga  tggagtctca    30480 ctctattggc caggctggag tgtagtgatg caatcttggc ttactgcaac ctctgcctcc    30540
tgggttcaag ctattctcct gcctcagcct cccgagtagc tgggattaca ggctaatttt    30600 tgtatttta  gtagagatgg ggtttcacca tgttggccag gctggtcttg aactcctgac    30660
ctcgagtgat ctgcccgcct tggcctccca aagttctggg attacagacg tgagctaccg    30720
tgcccagctc agtttagtaa tgtataactg ggttttaccc agttgtaaat tactcttttg    30780
tcgtgttttt ttgagaactg gcaatgacgg agaaactaaa agtgccaggc tgttgccttg    30840
ttcctgttat tttgccttag ttttttttt  ttttttttt  ttctctgaga ctgagtcttg    30900
```

```
ttgtgttacc aggctagagt ggagtggcat gatctcggct cactgcaacc tctgcctcct   30960
gggttcaagt gattcctgcc tcagcctccc gagtagctgg gattacaggc gcctgccacc   31020
gcacccggtg aattttttgta tttttagtag agacgggatt ttaccatgtt ggccaggctg   31080
gcctcgacct cctgacctca tgatccacca gcttcggcct cccaaagtgc tgggattaca   31140
ggcgagaacc accgtgcccg gtcttgcctt agttatttct tgttccctcc tctagtccta   31200
tagttctctg actgtattga ggaaatgtaa ttaaatatta ttatgttaat agatatttat   31260
gtggttgaat attagaaatt ccttattttg gtcacatatc ctgatcagta gttggtcttc   31320
tggagatagt gattttttcac tagagatgac tttaggacct attcaggttt tttttaagat   31380
cccaatttaa ggaaagacta ttctcattat tgattttgct atatgcaggg aaatttattt   31440
cgaaaggttt ttcagttggc ttttagggaa gattatatat tctctttttt ttttttggc   31500 cttttcccac atgttctaaa aatgatatat tctttaactc ctatgaaaat acattgtttc   31560
agtaattgaa gatgctgatt aaagtcatat ctctacacat ttttaaaat ttgagataga   31620 tgggactttg tcccttctta caccattcac ttattcactt ggaaaaacta ttatccaata   31680
cttatgtggc agacactgtt tctggcacaa gggattcagc agtgaacaaa actgcctttt   31740
tggagtttac attctactag tggaaagcga caacaagcag atagacacat tcagtatata   31800
attcactgtc agatggtggt ggtaagtcct atgtaggaag aaaagcaggg taaggaggct   31860
tggagtaact ggagtgagtc atagatggac ttgtcaggaa agggtttctg aagaggtggt   31920
atttgggcag agatctaaat aaaatgaagc aacaagccat gagaatatcc gggggaaaat   31980
gttctgggca gaagcatcaa gcatagaact tgtggtatga tatttattct agcacacatt   32040
aattttaaaa atgtataaaa gacatccatt taatcatatt aaagatttcc atgattcatt   32100
tagacttagt cagaaaccaa atttatattt tcttttttaaa taattttatc tcaactctta   32160
ttttacccaa taggggccag agttactcag caaatacatt ggagcaagtg aacaagctgt   32220
tcgggatatt tttattaggt tggtagccta tgaatgtttt taaagtaact gactctgtta   32280
ttatttatca atcagtgctt ttttttggtct tgttttttga agaactgata tttgaaacct   32340
gtggtttatg tgaattatta ataagctaga ggacgtggat tctctatttc atcaaataat   32400
acaaaacatt ttagatatta aattttggaa attatttggt tttgttttac aatagaaata   32460
ctcctcaaag tggaatcgaa gtggttattc aaagaaatct cagagtagat tcttatatga   32520
agcaaataat tgcccctaat ttatctctaa atttttgtaag ttctaaattc tttttttcccc   32580 cagtttctaa tttatctctt ataagtcaag agtccatctg gccaatttaa tttcagtgag   32640
tgtaactatt ttgcatatat taaaaaactg tatatgaata cagaagatgg tatttaagga   32700
tgaaaataat tattcaaatg tgatagcatt atggggagtt ttaaaataaa agttactgtt   32760
ttattcttcc aaaaattta ttataaagta tacagttaag agaatataca taaaatacat   32820
atgcagctta aggaagaata ataaaatgaa tacttcatgt attcaccacc gagtttacca   32880
ggaaaaagca taaacaaaat aaacctcttc cacgtaattc ctgggttaaa gagaagttat   32940
agtggaaaat atttgggagc aaacgataat gaaaatacta tccattaaaa ttgttagatg   33000
ttgcaaaact gatttcaagg aaaatttata gtgttaaatg tttagaaaag aaaaaaggtt   33060
agaagttaac cacttatgta tctatctcat gaaattagga aaattataga tataaactaa   33120
aaaatatgtt aaaagggaaa taataaagat aagaatgaag tttaatgaaa cacaaaacag   33180
agaagctcac aaagccaaga tttattttttt gaacaccgag tacaattgac aaatctctaa   33240
```

```
caagtttgat taagaaaaaa gaaagcatga ataaacaatt ttagggataa aaagggaaac   33300
atcgctaaag atatcccaga aatgtaaaag ataataaggg aatattatga aaatattcat   33360
gccaatacat ttgaaaactt aggtgacata gacaaaaaca aaattgacca aaattgagca   33420 aaaagaaac aaaatctgag tagtcctgta acttagtaaa aattgagtta gaaaagttaa    33480
agaagtcttt acacaaatca aacatcagac tcagttttct aggagagttt tgccaaacat   33540
tcaagtagca gataattctg gtctattttt ggccccagaa gatatatttt acttgccatg   33600
catttaatga gatagctgtt gatttttttc aatcaccgtg acaggtgttt tatattaggt   33660
gttattcgcc agacatctag tccacctgtt gccagatatg gaattaatat tcacttattt   33720
tgaattaaaa tttgttaata aattaataaa acaaagtcaa agttcaaatt attaaaaaag   33780
taaaagaaat aaaatatatt ttatagagag cccttacaaa acagtaccaa cataatgagc   33840
tttccaaatt ttgaatgggc aaaataaatg aataggcatt tcacaaaaga aggaagggtg   33900
gccaataagt atatattaat ataaaatgg ttacttgtaa taggaatcaa aagtgtttga    33960
cttattgact aagagtcagt ttttgttttg atccctgtta gtctatccag aaggcatggg   34020
tcttaataaa caccttgacc tcaacagttt actgaataca agggtaattt catatgcctt   34080
gccttcttta agggtttgtt gtaaagatta aaataaatac ataaatatat ataaatacat   34140
ttatatgtat ttatatgtaa ttacatacaa cttgccttct ttaagggttt gttgtaaaaa   34200
ttaaaagaag tatataaata tatataaata cataaaataa atacattcat atatgtatat   34260
gaaatcactt tgccaactat gaagcctgat tcaaatatga aatgttgttt gttttcccca   34320
gagcacaggc tgcaaagccc tgcattcttt tctttgatga atttgaatcc attgctcctc   34380 ggcgggtca tgataataca ggagttacag accgagtagt taaccagttg ctgactcagt    34440
tggatggagt agaaggctta cagggtaata attataaata cagaaataga atgttataac   34500
aaaatgtcat catgtcatca gattttggta aaaaaatgtt cttttttcct ctaggtgttt   34560
atgtattggc tgctactagt cgccctgact tgattgaccc tgccctgctt aggcctggtc   34620
gactagataa atgtgtatac tgtcctcctc ctgatcaggt gacaatttca tatttagagt   34680 ccaaaccca acaaatgcta cactctttcc ttgtgagctt tacttctgcc aggtaatggc    34740
aattgtcctt agaagaccag ctttcttagg gaaaagcttt agccactgtt tgctcaaagc   34800
ataaaaagat tctgaattag atgcaaagcc ttttttggc ccagtgcaag tctgaaaact    34860
ttgtaatcct tctgtgttgg ctgattgggg aaaaaaaat gcaagaaacc taatgtatta    34920
tattttcaca ttatcttctg ttcaaagatt acatacttcc attatcctgt caaaaaaaaa   34980
actctgatac agaatcaagc atgtgaatcg taagcatgta agcaggtttc atagagataa   35040
tttttcaact cttccttgtc ctgtgttgtt ccaactctta ttctccaatt tagaagcaaa   35100
caaataaatg aatgaaagaa cagatagaca aatgaatagt caaaggtata agtatctgt    35160 atatatgtta catgtagcta ttatttaaat tatttagatt ttcctttga aataccttct    35220 tggcacactt gcctaaatct agaaaataag cactgtgtga ataagaaatt atttacactg   35280
aatattttgt aggtttttgg gttttttgttt ttcagacaag gtctcacttt gtcacccagg   35340
ctggagtaca ctggtacgat cacaactcac tgcagcctct atggcccagg ctcaagcaat   35400 ctcccccacct cagcctcccg agtagctggg accacaggca cacgctacca tgcccagata   35460
attttattat taattttgt atagagatgg ggtctccctg tgttgcccag gctttcttga    35520
actccagggc tcaagtgatc ctcccacctc aacctcccaa agtgttggga ttacaggcgt   35580
gagccaccat gcccagcctt aagagtgttt gattttcatt cattttccta tatatattat   35640
```

```
ttctgttggg gaaaaaattc caaggaagat aaatagtagg ctgttggtac atttctcaac   35700
ttacttataa agctttttag atatataagg ttaatttatg aagaaaatca taagatacac   35760
aatttaagat aatatttta atttattttt ttatttgtta aataaatttt tctcctttca    35820
ggtgtcacgt cttgaaattt taaatgtcct cagtgactct ctacctctgg cagatgatgt   35880
tgaccttcag catgtagcat cagtaactga ctccttact ggagctgatc tgaaagcttt    35940
actttacaat gcccaattgg aggccttaca tggaatgctg ctctcgagtg gactccaggc   36000
aagttatatg aggaagttgt tatgacattt tatgagtgat aaaagaagta caatgtcaaa   36060
atttccacct taaaaatgc tattttttaa acaactttgg taaaactgta tagaaacata    36120
aatttacctt tagttgaatg ttccatagtt ggaatatggg ttttgcagag aatttataat   36180
tatgaagttt gatgtctgtt tctttaacat taccttaata ttggcaaaaa catgttggtg   36240
tttgcaagga tattatttaa attgggatac catgaattaa atactacaaa caaaaataat   36300
tagagttttt tgtttgtttg tactttaact tttaaaaaat aatcagttaa agttgttgtt   36360
ttgaagctca cattgttcca atctggccaa taggagcccc ttttgtatgg ctcctgtatc   36420
tttatgacat gtcctcatca ttcttgaatc acttcctcac ttccagatac agtaagttat   36480
tcttggccag gtgcagtggt tcacgcctgt aatcccagca ctttggcagg ccaaggcagg   36540
aggatcattt gggcctagtt tgagaccaaa tcatggttgc acaaactgta cccactatgg   36600
acaacagagt gggatcttgt ctctgtgaaa aatttaaaaa ttagctgggc atggtggcac   36660
atacctgtag tcctagcttc ttgggagagg ctgtggcagg aggatcgctt gagtaaatcc   36720
aggatgcagt gagccatgct tgtgccactg cactccagca tggatgacag aatgagaccc   36780
tgcccccaaa aagaaaaat attcttggtt tatcttgtac tttctgtatc ccagccctag    36840
catcagcctt ttctctaaag acagtattat gattttaata tttacagtag atatttgaac   36900
tgttacatta tagactttac catatatttt ctaggaagga ttattctatt actcttcttt   36960
accacatttg tttggaatgt ctacagaacc tacagtttct aaatcagaaa ctccctaggt   37020
ttttgctatt ttgcaagcc attgaagttc ttccctctcc ctttactacc agaaaggtgt    37080
gtatttgtag agctctctat aatgagaaag cactctataa catggttgat tcatcatttt   37140
ggagtagaaa agtatgaatg gaaagtcaga gacataaaaa taaagcccag aggtctgagt   37200
cttagcttca ttacagactt tcttggggga tggttggtaa attatctaca cattctatct   37260
tgtctttata attttaatag ttaaattttt accatgtgcc tcaaaaccgt tagagaatta   37320
atgagctctt tgaaaaatgc ttctaagttt cttgtattgc tctaatagaa tgctatctat   37380
gttattattt atttctgaga ctaaaattgt ttacatcttt aaactggttg tccttttgtg   37440
tatttaggga tggaagttcc agctctgata gtgacctaag tctgtcttca atggtctttc   37500
ttaaccatag cagtggctct gacgattcag ctggagatgg agaatgtggc ttagatcagt   37560
cccttgtttc tttagagatg tccgagatcc ttccagatga atcaaaattc aatatgtacc   37620
ggctctactt tggaagctct tatgaatcag aacttggaaa tggaacctct tctgatttgg   37680
tatcttgtgc agtcatcatt atacagttct gaaatataaa gctatatgtt ggtgtaaagt   37740
tgcagtgatt tctctcctaa ccagccccac atattcttcc tggttggttg gttcttcagt   37800
aaaatagtct tgtttcttgc ttacactaat tggtaatttg cattccttgt taagattttc   37860
aagacagggc tgggagcaag gaaccaaagt agcgcgtggt tgtgattacc tttggtttct   37920
ttgaggtttc tcttacctag tggctttaaa acatctttag gagcagttcc attttatagt   37980
```

```
aaacttaaat tctgttatca tgaacagttg aggataatga ataatttgat acaataatgt   38040
aagaaattcc tgaaaacaaa gtgttatctg tgatacttttt gctgcatagt aagcacaatg   38100
aagtgtactg ataatgtttc aacaggaaag tgttttgatt aaatgtgggc agtatcactg   38160
ttctactagc attcaacatc tcttctaaaa attaatagtg gttcactgta attttattgg   38220
tacatgtaac atctgtacat gtgtttggtt atctatatgt ttcctggttt tttgtacatt   38280
tgctttatta atttaggctt ttttttttttt tttttttga cagtctca ctctatcatc     38340 cagactagag tgcagtggca caattatggc tcactgcagc cttgacctcc tgggcttagg   38400
tgattcttcc acctcagcct cctgagtagc tgggactaca ggcacatgcc accatgccca   38460
gctaattttt gtatgttttg tagagacgag gtttcaccat attgcccagg ctggtctcaa   38520
actcctgggc tcaagctatc tgcgtgcctt gacctcccaa agtgctagga ttacaggtgt   38580
gagccactat gcctagccta actcagactt taaaaatata aagcaattc attttattc     38640 ccaagaacag taaggtggtg gtttaatttt agtctttaat tctgttttta atttattcta   38700
tttagaaatg tcccagaaac ttagtataac tttactttct gaaaatgaag aaacctgtcc   38760
ttgggcatta gtgtgttgga tttaagcaac aaagttaaaa aaacctaccc tgtgttatgg   38820
caattttcac ttgatggtgg ttctataaca caggtatcag tgaaccttta taaaagatga   38880 acaactttc agcttgctta atttcagtta attaacatgt atacttatct atgttaatgt   38940
tttattgctt aaaatgttta atttttatat ttggtaaaca gatagttttt tctctcccc    39000 tcttccttcc atctttcatt actacaattt accatgcaga gctcacaatg tctctctgca   39060
ccaagctcca tgactcagga tttgcctgga gttcctggga agaccagtt gttttcacag    39120 cctccagtgt taaggacagc ttcacaagag ggttgccaag aacttacaca agaacaaaga   39180
gatcaactga gggcagatat cagtattatc aaaggcagat accggagcca agtggagta    39240 tggcttttttc cccctcatta taattgttaa aacttcttaa aaattgttttc accccttgga  39300 tatatatttc tttgacttat aaacgagcta tatttataaa caagggacca gaacacatta   39360
actcagtcat ggttatgtgc ttccttgctt tcaatgtttc attatcttat aaggaagaga   39420
acgtatggtc tcttgaaaaa actgacaata agaagtaaca actggactac cacattttt    39480 tttacatcct taatttaact cttcgtcaat ttctttttttt acttaaggag gacgaatcca   39540
tgaaccaacc aggaccaatc aaaaccagac tggctattag tcagtcacat ttaatgactg   39600
cacttggtca cacaagacca tccattagtg aagatgactg gaagaatttt gctgagctgt   39660
aagtaacaga ttctgttttg gaagtacagc tactattaca agtgacatag tattacactt   39720
aaacctttaa agttcgtgtt taaaataaaa atattttgaa tatttaaaag ctaattcaaa   39780
aaatatgtgt cgtagctatg cattaaaaaa ccccaaaatg tcagaagtac agaagtcaaa   39840
attgagtttt cattaaccag ttcatttgat tatatttgaa ttattcataa tggactcatt   39900
taattttagt aactttgggc tggtgctgt ggctcatgcc tgtaatccca gctctttggg   39960
aggccaaggc aggtggatca cctgaggtca ggagttcgag gcaagcctaa ccaacacggg   40020
gaaaccccat ctctactaaa aatacaaaaa ttagccaggt gtggtggcat gtgcctgtag   40080
tcccagctac ttgggaggct gagacaggag aattgcttga acccaggagg tggaggttgc   40140
agtgagccga gattgcacca ctgcactcca tccagcctgg gccacagagc gagactgtgt   40200
ctcaaaaaaa aaaaaaaaaa atttagtaac ttcgaagaaa taagaaggaa aattaaaagt   40260
tgaaagtgat tctaatgtat agtttataaa attttgttat aaaaatacct gttttgcctt   40320
caaaataatt tatattaata tttttattgac ctcaagaaca tttaaataca ttcagattta   40380
```

-continued

```
ttcatttgtg gaccacattt gttatacatt ggatttaaag gatccttgca attgagttta    40440
tggccaccta tgcatctgag acccatggac tgggaaccat tctaggtcaa tgattcagtg    40500
tgattcaatt taagagatgt ttattcctgg tctttagaag ctgctacctt ttgttatcta    40560
attttgcagt actttgaagt atgtatgtat gtgtacatac gttagtgcta tgtatttatt    40620
aaagaagaat cagaaaacag aggtaaggaa aataaggaa acaaatttct gttaagccca     40680
ccacctccca aagcatattt gtttatatgc ttatatatgt tttcctatta tggtaagaac    40740
agtctgtaca tattgctata tagcagtccc cctttatcca catacatcct gaaaattgtt    40800
ttacatttta aatgttaact actttattgt ttttaaatgt cattttatag tgtagctatg    40860
ccacaatatc caattttag acatttaaat tgctcccagg caatgtggta atgaacattc     40920
ttgcagctga atatatgcac atatctaatt gtttcactag gatagaggtg gaattgtata    40980
acagggagct cacattttt aaggcttttg aaatgtattg ccaaattgcc tgccagatat     41040
actgcaccat cactaacatt gtgtgttgca gtattttct aaacttggcc cttttgattt     41100
tagaaaaatg atatcaataa tttacatttc tttgattaaa gtgtagaagt tataattttt    41160
catattattc attgtcattt gtattttatc ttttctaact tgtctcttca tccccttttgc   41220
tccgttttct attggagtgc aactttattt gtaagaattc tttttaattt ctgtgactgg    41280
aatttttttt tctagtttgt tatttcccgt tcatttctta aaatataatt gtgtttgcca    41340
acaatccatt atcttttgtt ttgtaatggt agtattttata catattaaat tatctctttc   41400
ttttttcaga tatgaaagct ttcaaaatcc aagaggaga aaaaatcaaa gtggaacaat     41460
gtttcgacct ggacagaaag taactttagc ataaaatata cttcttttg atttggttct     41520
gttaagtttt ttgatggctt ttccatatgt tgtaacagga aaaaaatggt gtctatgaat    41580
ttcttcttaa tttaacaaat ttggttaatt tataaaatca cagattggta aatgctataa    41640
ttatgtaatg atcaggattg agattaatac tgtagtataa attgggacat tataacagat   41700
tccatatttt atttcctaaa atctaaattc agtctttaat gaaataatat tagccaaatg    41760
gtggaactaa tttatttctt ttgaggaaaa gataataaag aatgtaatta aatttaaatt    41820
tcttggaatt cccagttgta tattcatcac ctttgtagca tttgacaaat tttatgctta    41880
gcagcttctt cactgttttg aaataaaata tcctattacc tactgataca attatctgtt    41940
cttttgtatat caaaaaatgt gaaatttaca cataattcaa atacatttaa ttatccgctc   42000
aaccagaaat gaaatcacat ccctctacta tactacatcc agctccaagc ccaagatatt    42060
taaatgacat ccattcctct cctagttcca gttatgattt tatcttgata ttctctcata    42120
tatgaactaa attataaagt tagccaccat caatacaatc tgcgtatcta atatcttaac    42180
tatatagtaa tggggtaagg gaacagcaaa aaggagaaca ttaattaaaa tatacaagta    42240
agcctgggca acatagtgag accccatctc ttaaaaaaaa aattagccat gcatgatggt    42300
atgcctctag tcccagctac ttgggaggct gaggtaggag gatcacttgc tcccaggagg    42360
ttcaaggttc taaccagca aagctcagaa tcccagggga tagaaacaaa gacttagtgg     42420
atcactagta ttaaactgag acacgtcacc ctgcattgca ctttgtttct cagttctttg    42480
atgaaatcac tgagctgaca tacctgcccct cttttcacca taaagtgagt ttcatgatca   42540
gaagcaatgt ctatgggata gcctaacaaa caatgtaaaa accatttagt aagttcatga    42600
agggtggtgg tggtaaaaat ttggagaaca tacaaaacaa atacaattcc aaggtgtgtc    42660
ccctccagga aggacaaatt gctgcctgct ctgtgataga agaggatcag atgtaatcaa    42720
```

```
cctgccgtca gacttgggct gttctctcct gggtgtggac ttgcctggtt ggtcactgct   42780
gctgacaagt aggctgtcaa tatagctggg ttgtcatgtc agctgtggtg aggggggaagt  42840
ccacattgtg gaggccacat ccctgcactc ttggccaatt tgaccatgaa tcttaagcac   42900
tggggtggct ggaaaagaca gccgattgac atccatacag aggtcatctt gaccacttga   42960
ttagtataag cactgaaggc ttttaactga gcattcacat aggacacaaa tattctgatt   43020
ctttgggccc attccaagaa ctctgggcat acttttcctc cagacctcat acccagttgt   43080
gttctttcca aatttctggt catctggtta tgttattagc cactatctgt gaatcagcat   43140
agatttttat atcagacatc tctacctcct gacagaatgg aggagatatg ttacttaaca   43200
attctgttcc cttggaagat ttcctgtctc cactgtttgt aagggctact ccctcaatgt   43260
agcagtaatg ctttcactct gatgggaagt cacagtggaa ttctgggtct caagaatta    43320
gtgttagtgc atacacagtg tctgataatc cccagagtgt ctggtgccct tggatcctgt   43380
gaagaaggct tggagaaaag aagattcatg gcaagaactt gtgatgtgat gacagggcct   43440
tttctctggc tcttcattct tagtctgacc taggtgtgag aattaggtca ggggccatga   43500
ctatattgtg gtgactcaaa ccaggccttt gtttactaac tggagatttt ttacattgta   43560
agaatcaagt aggatctttg cccatgtatt ttggtcttaa gaacacaaat gatatggctc   43620
caatgactgg aggaacacca gggtccttgg tctcacgctg atttagataa aacgactgtc   43680
aggcctctga gcccaagcta agccatcctc ccctgtgacc tgcacgtata catccagatg   43740
gcctgaagta accaaagaat cacaaaagca gtgaaaatgg cctgttcctg ccttaactga   43800
tgacattcca ccattgtgat ttgttcctgc cccatcttaa ctgagcgatt aaccttgtga   43860
aattccttct cctggctcaa aacctccccc actgagcacc ttgtgacccc cgcccctgcc   43920
cctaagagaa aaccccctttt gattataatt ttccactacc cacccaaatc ctataaaatg   43980
gccccacccc tatctccctt cgctgactcc ttttttcggac tcagcccgcc tgcacccagg   44040
tgaaataaac agccttgttg ctcacacaaa gcctgtttgg tggactctct tcacacggac   44100
```

<210> SEQ ID NO 64
<211> LENGTH: 16869
<212> TYPE: DNA
<213> ORGANISM: Homo sapiens

<400> SEQUENCE: 64

```
aagctttagt agagatctca aaaatggttg gatggtagca aattactaag aactctcaaa     60
gtttctaaag ccttagtttc agcttgctag aaaacctatg ttgagtatta tggctagttc    120
catagttgag ttgggaaatg tctttgagga gacactttttt cactttgtat tcatctgtac  180
attttctgtt acttgcattc tgtcatgctc aggctattag agcaggtaca ttttttataac   240
tggaatgttt atgtgtagtg aagctctgag aggactttgc attagatctc agcagcataa   300
tcagaaggtt gtcctttgtc tcagcaattt ttaagctaat agtagcagaa attgcagtgg    360
aaatagactg ctttgccaca acattcagaa aatcatttat cttttttattg cagttccttgt  420
caccaaacaa tacattttag tacttctcaa attgcagaac tctcataggg ctgggaaaat   480
gcctgtagac acatacatac tatgaatgtg ctaatgtttt ttgtatttc atagcccatc   540
aaagctcctg agtcagtttc cactataatc actgcagaat caatcttcta caaggtaagc   600
ttttgtagag ttactgaagg aagagttggg cctagtgggg aatgtgccac taaaatgttg   660
gattagtcta aaggtctctg ctactctttta tttgtataag gtgtgattat acttttgtt    720
```

```
cccttcttag ctgttttccc ccataagtgg ctgttattaa aacatctcat ctagagctga      780
agtgggagga gaaagtgcct actgacacat gatgtgagga tcttaagtat ttttttttag     840
tgtagattgt aggaattatt cttaaaatgc tgattgtata gtgtggagcc atggaagact     900
gagccgttag tgcgatggca ttgaagaatg agaaggacag agacaggatt tggactagta     960
gaggttgtcg actgtggtgt caaatgggta gagtaggccc agagattcta aaatgccttt    1020
aagtggagtt gagctgagta aaggcagtag tgaggattaa cacctactag aaattcatag    1080
tgagaggaat tccaagatgt tttgataaaa gaatgaggag gtcaggtttc ccagggccaa    1140
agtccatgaa catctgatac ctcagtgaga gaagtgacag attgttgtgt ttaaaccaga    1200
agtcttagga aaggaattag aacatagacc cccaaggctc ggcaggcctg gcacggcaca    1260
ggcagcaacc attgaaggct atttggtgtt tcgggatctg aactgtcatt taggggacag    1320
tggtgtgagt tagtacttta tacttgaccc aggtggactg agaaactcaa gtgatgatgc    1380
ccttaagtat acttttttttt aagcccacaa tctatatagt cgaagtctgt tcctcccaac    1440
aggggtacac tggcattcct cagcagggct gggaaaaacc aacaacaaaa aaagtctgta    1500
cacaggcaaa catctctctt attttttccaa catttaatac attgttaata aaatatctaa    1560
agtttagcaa acagttgctg tgtatcagtg gctgagcatt ttgcatgctt tatttcattc    1620
agttcactct atgaggtgga tactactatc cccattttct agatgagaac attgaggcac    1680
agcgaggtta attaacttgt ccaagatcac atagccaaca agtcatggag tgaggcagtc    1740
tcatgccaga gcttaagcct agagcatagt tcctggctct acagctttag caagtgactg    1800
gctatgtgac gaggaccaac ctctctaatg tctcatctgt aaaataggaa ttgtaaatag    1860
ttactacctc agtgggtcaa atgaaatcat atgtgttaag cacttagcag agtaagcact    1920
caatgaatag taggagttat cacatcttcg tatttgtgca ttaccttcac agtttacaga    1980
ttaaggccag aagcaacttg ttgagctacg ggtttagtgt actaacagtt tccatgtgtg    2040
tctccatgga agggtgtgtg ggacctgtta ttgtgactgt ctgtactttc gtattgttgt    2100
ctgccaccca tgtttattaa atgataagga caataatgca acaaagtagt caagtaatgt    2160
tgcaaatgcc cagtattgta gtggctatca cagcagtgcc actggcaggc agcaccatgg    2220
tggcaagttc aagaggtcac tgccagccac tgagctagag cccagatcag gcatgcaaga    2280
ggagcctgag tgggagccac tggggatcac ggccaagagt gtgaccaccc aagacccaga    2340
atggctgagt ggcctccctg gagcatggca gtggcagaac aactccatga actcagatct    2400
ggtgatgcct aaactagtgc tgttctcgtg tggaccccctt ttctctacca gaaaccttga    2460
atcctctcag caaatgagga gactactcag atcagtgact tagtcctgtt tggtgttata    2520
tatgtgtaca caacacagca catattaata aatacctact atgtgccagg cactgcctac    2580
cactggaatc tttcactaag acattgtttt tactttgcat ttctgccttt acactatgaa    2640
agtagatgtt ttggattcat attcattcag catacatttg aatatgctgt gttatgcata    2700
gtaagcctat gataagcaag tattctcatt tagaatttgg gaatattgat tatacatgtg    2760
gacaaacaaa ccataaatgc aaactattta tatgataaat aactttggac tgatggctgg    2820
gaggaaggac cagctattga tgggtaggaa ctagcaagta gcggactgtg gcctgcatag    2880
accagaccca tccgtagtga tccagatgaa acagccaccc tcagacactt ggataaaggg    2940
tccaccagga aaaaactcct ggcctatcag gtgctatgtt acagttcagt tactggaagt    3000
atttcctcaa aagtgttttt atggttgagg tacacattcc tacagcttta cctgctgcca    3060
agtccctgtt tcaagggaag cagcaatgaa ttacactgtt cccgtagtca aggacagtat    3120
```

```
atcttaccaa gaactatacc cacttaagga ggtgctggat gtcataaaga tttggatcaa    3180
ccattatggg tgttcagagg agagattatt tccagctcaa gacccaggga agaggacata    3240
ggatggatac cagagtcata gggaggattt aacacaggac atgtacacat tagttagttg    3300
ggtataaagt ggaacagaaa tgaatgagac acaaagcctt gaatgccaga aatactagta    3360
gtcctgttgt ggaaggatat aaaactcaac tgggagtgga agagaaaggc agcagtgagt    3420
ctaggagatg tacagtaggt tgaggtaaac atatcctgaa gactataatc caaagattat    3480
ttttggtttt aatttgtttt ggtttgaatt catggtatct attttctttg agtggatggt    3540
tggggagggt ggcatgtaga atgcattctt accaaatcag catgattttc aagacagtac    3600
agagaaaaga ctgctgagct gatgtaggag ctttggctgc agtctctatg gctttcagca    3660
agccgtttaa ccttactact gcttcatgac tgtggctaac aaagtaggga tagtacggag    3720
cacagaggat tttagggcg tgaaactat taatactctc tttgtatgat actataatgg      3780
tgggtacatg tcattataca tttgcccaac cccacagaat acacagcacc aagagtgaac    3840
cctaatgtga actctggtct tgatgatgc tatgtcagtg tacgttcatc cgtgtaacaa     3900
gtgtaccact ctagtggtgg gagggttat tgataatagg ggaggatgtg catgtgtggg     3960
ggcaggaagt atatgggaaa tctctctact tctgctcaat tttgctgtaa acctaaaacc    4020
tctgtaaaaa ataaagtcta ttttttaaaa agtggggatg gtattacggc aatataaaat    4080
caaaatactt tatgaacaaa tcttttctcc agatgtaaac tgtcatatat gcaccctcgt    4140
atgtgtatgt ataattttca ttcaaacgtg aaacaacttt agaattggca ccaaacatat    4200
aaacactgat acattagact atctcgaaca ccttttactg accactttga aaacttgctt    4260
acctattaag gttcattcat agctgtgatg ttctatttttatttcaatg tgggattatc      4320
ttctgttttcc cccagggagt atattaccaa attggtgatg ttgtttctgt gattgatgaa   4380
caagatggaa agccctacta tgctcaaatc agaggtttta tccaggacca gtattgcgag    4440
aagagtgcag cactgacgtg gctcattcct accctctcta gccccagaga ccaatttgat    4500
cccgcctcct atatcatagg taagtttgac aaatggcaca ggttttttt taacttagtt     4560
aactctccaa tattatgtaa aagagtgtgt tagtcagctt gggctgtcag gacaaaatat    4620
cacagactga gtggcttaaa aacacagaaag tcactttctc acagttgtgg aggctgaagt   4680
ccaacatcaa ggtgctggca aacacggattt ctggggaggc ttttcttcct ggcatataga   4740
tggtcacctt cttgctgtgt cctcacatgg ccttttcatgg agtgagagct ctttggtgta   4800
tcttcttata aggacaccat ttctgtcaga tgagggcccc acccttatgg tttcatttaa    4860
ccttaattgc ctccctaaag gtctcatctc caagtaccat cacattgggg attagggctt    4920
caacatataa atttggaggg tggcgggggg ggatgcaatt cagtccataa caaaaaaagc    4980
atgagtatta ttaagtacaa aaaaattaga gagctttata gaaaatatga ggcattttat    5040
gtagctggag tgtgagtgct atcagttatt ttgagttaga gcaatgtgca tctactaaga    5100
agtggtatgg ataagatttt tttggagtga cccagggtta aactgtacta caagaatgta   5160
ttgctcagga actaggttat ttaggttact tatttataca aacctattca aaaataattt    5220
aggaaagaac tatcccagtt atcccatact tgcaaattct caatatgtgt gcctctgcat    5280
gctacacatg tcatcttagg cctttatagt ataaggctg atagttgaaa tggcagctgc     5340
tgtgcttttg ttaatttcaa agctgccaaa acagttgtga gatagactca caagaattta    5400
ctgattaata caattttttaa agttttcaga ttttacagt tacttcagac tttttatctt    5460
```

```
tctgcagtga gcatgcatca ttacttttgc atcctgagaa caagcataag tgtgtttttg   5520
gagagaactc cagggacaaa taatatacca ctgttattct cacctatatg tcaagtttga   5580
tacattacca aacaattcta gccttctgct tataagtata tagaattttt atttaccttg   5640
tctatggatc aggatctcag cagaggcagt gatgtatcag aatcaccttc gggattcctc   5700
tactgcctcc tctttctaat ccccagattc tgatatgcat ccttgtccta cagcgaggca   5760
gcatggcatg aggtcagaac accagttctg gagccagact gtctaggttc acagcctgcc   5820
atttaccggc catgtgactt tggcaagttt cttagtctct cttgcctcac tttcctcata   5880
tgtaaaatgg gaataataat agtgcctacc tcagaaggtt gatgtgagga atgaaggtat   5940
tgatacatgt aaacttagag cagtgtgggt acaaaataaa catgatgcaa gtgttcaatc   6000
actgtttttg ggagaatgcc atattcttta agccgttaaa aagaaaaaa tgattaagaa   6060 taatttcaaa gtaatgcatg tttcaagggc taatgccagg ttgctcccag agtggtctct   6120
cccagtgtct agaaattta acatcttatg aaaatgatat atatggtcaa aaatgtattt   6180
aacctttccc ttggctgcct tccagggcca gaggaagatc ttccaaggaa gatggaatac   6240
ttggaatttg tttgtcatgc accttctgag tatttcaagt cacggtcatc accatttccc   6300
acagttccca ccagaccaga gaagggctac atatggactc atgttgggcc tactcctgca   6360
ataacaatta aggaatcagt tgccaaccat ttgtagttca caaattaaaa ctgggtttcc   6420
aggcctggtg tggtggctca cgcctgtagc cccagctatt gcaccactgc tctccaagct   6480
gggcaatgga gtcagattct ctttcttaaa aaaccacaaa aaaactggat tccagttct   6540 ctaatattct tagtaccaca agatatgtca taggtatctt taaatgaaat tcttagctgg   6600
aaaagtgact aaaaagtttt tctcctgcta cctagtaata aacaaatcat tgtttattac   6660
tggtcactta gaaaattaaa agggataggg ccaggcacag tggcttatgc ctgtaattgc   6720 agcacttta gaggccgagg caggcggatc acctgaggtc gggaagtgga tcgcctgagg   6780
tcaggagttc gagaccagcc tggccaacat ggcgaaaccc cgtcgctact aaaaatacaa   6840
aaattagcca ggtgtggtgg catgtgcctg taatcccagc tatttgggag gctgaggcag   6900
gagaatcgcc taaacccagg aggtggaggt tgtagtgagc caagattgca ccgctgtgct   6960
ccagcctggg caacagagtg agactcttgt ctcggaaaaa aaaaaaaaa aaaaggctg   7020 ggcacagtgg ctcacgcctt taatcccagc actttgggag gctgaggcag atggatcgcc   7080
tgaggttggg agttcgagac cagcctggcc agcatggtga aaccctgtct ctactaaaaa   7140
tacaaaaatt agccaggtgt ggtggcgcac acctgtagtc ccagctactc gggaggctga   7200
ggcaggagaa ttggttgaac ccaggaggcg gaggttgcag tgagcagaga tcgtgccact   7260
gcactccagc ctgggtggac agagcaagac tccgtctcaa agaaacaaac aaaaaattaa   7320
aagggataga atataatgaa atatattttg aacttaaatt atattctata tgtgtatctt   7380
cctaggcaaa agctgtaatt tccagagaga ccattaggaa caggtagtat ctattttct   7440 ccattattta tttctagaaa ctcataaaat ggattgtatt tttctataag aacaaaatat   7500
taattaaggt atagatgact gaccaagggc ttaatcaaat aaaatgacta acagcatcta   7560
tcataaagcc acacaagcct tatgttctca tctcaaaaat gctgtgacag cttttggct   7620 gctttaacca taagaaaaat gattggtgga tgattttatt agcccaggct tttaaaaact   7680
ttcatctagg ccacgtgcgg tggctcatgc ctgtaatccc ggcactttgg gaggcctgag   7740
tggatggatc acttgaggtc aggagttcag gaccagcctg ccaacatga tgaaaccctg   7800 tctctactaa atatacaaaa attagttggg tgttatggtg catgcctgta atcccagcta   7860
```

-continued

```
ctcgggaggc tgaggcagga gaattgcttg aactcgggag gtggagattg cagtaagccg    7920
agatcgtgcc actgcactcc agcctgggtg atagagcaag actgtctcaa aaagaaaaa     7980
aaagaaaaaa ttttaattta atccttctgt agaaacaggc attcagaacc attccattga    8040
tcttaataaa gctgctcttt actgtttcta gtcaaaaatg agacttcgat caaaccataa    8100
gatttttatac tgcagatagt cagcttcacc aaagccgcag aggaaacatg tcgagatcag   8160
gcttcctgct tgatagtctc ttgactacca ttaaaacgaa tattgggagg tcatgaaagt    8220
cattggtagg ccattagcat tgatatcttt aaaacatcta ccctaaacca tctgctatgg    8280
acccataata agaggcctgt tgtatatgaa attgtctaga attcaggtgc aggtctttgc    8340
cggttaagta agggagcaac acgtaaaatg ggagaggagt ggggtgtact cacttgcctc    8400
ctcttttgtc ctgatttaac cagcattttt caaccctggg aaaatttgca gaatctaagt    8460
tgattgtaat gattttgagc tgcagcagct ttaactctta cccttttttcc acatagttat   8520
ggtgtttgag ttggaaagaa acaactatag gtagctacac gtacataatt atctctttat    8580
tcacaaaggg tatagtaaaa ttgattgtaa ataactttct aagtgccaat attcaaaact    8640
tttggattaa aatgtatttt tcaccgtgca tttactttgg atgtatttat ttcatttaaa    8700
caatttaaat ggggctcttt aaccaaaaat ggtatttaaa accaaaacag tatcgtactt    8760
agaatttgga gtagaggccg ggcacagtgg ctcacgcctg taatcccagc actttggaag    8820
gctgaggcag gcggatcacc tgaggtcagg agttcgagac cagcctggtc aacatgaaac    8880
cccgtctcta ctaaaaatac aaaaattagc tgggcgtggt ggcgtgcgcc tataatccca    8940
gctagtctac tcgggaggct gaggcaggag aatcgctgga actcaggagg cagagactgc    9000
agtgagccga gatcgcgcca ctgcactcca gtctgggtga cggcatgact ccatctccaa    9060
aaaaaaaaaa aaaagatttt ggagtagatt catcattaat aagtaacaga ttttaggaaa    9120
atcaaaaaat ggctaataaa atgaacacaa tgtaaaacat ttattaaaat gtagactttt    9180
aaaaatctat aaattgatca tctgtttata aattggcaga tggttgtgta ccatctttta    9240
aaataaagat tgaatttcac ccagtgtgat ggttcccatt gcttatattt ctcctgctga    9300
ggccggacct gatatggccc tggtctgtgt tcccagcctt gtttcctcat taccactaaa    9360
atctttcccc tgtatgcccg cccaattttt ctggctctga gtccttgttc atactgttct    9420
ctccaattct accttccaaa ggcctttctt aacaccttcg gattctttct ttgagaactt    9480
tccagattcc catgccttttt tggaatcaat ctctatccta ttgtcatcac atttaagttt   9540
ctacttccat catcctcact cctatcccttt tggtcctggg atgacaggga tgctgtgttt   9600
tatttactca tcttttgtaac ttccacataa cctaaccccg gttcttgctt atgggagatg   9660
ctgattgtag ggtctgagtt agatactgtt aactaaaatg cttgttgata ttttagttat    9720
taattcatat taactttggc tgaaactttt aaattctatt gtgaatagtc aagtaaaatt    9780
tagattgtta cattctgggt tagtattaga ttgtttttaa gattgtttta aacaagatgt    9840
ttttaagatg agtttttaaat agttctctta acacaaataa agcttaatat gagtatttga   9900
aggaaattat cccaaaccat tccagttcct ggctgtgaaa ggcttttcca ggcctaataa    9960
gttttccact tcagccgtaa gtaggtgaaa tcaaatgaac aatagaggga aatgtatttta  10020
tttgctttat acacatgcat gtgtgttgtg tctacatata aacattgcac acgcttagaa   10080
tgaagtttct gtcatgccca gaaagggag aggcattttt gtggattttg tctggctgcc   10140
ctggggatgt ttgaagaact gtgctgttta cttcatacca ggtgtgtgag ccatacctttt  10200
```

-continued

```
ggtaggaggg tatacctcct acacccaaga aatataagcc aggagaaggt ctgtgccaag      10260
agaaggaacc caaatgaccc acaagaggtg ggccattaat tattgggtca gatgcataaa      10320
tgcacagtaa tttatttaag cacctcttaa tggtgaccca caaggaagat tgctcgtagt      10380
agcggaaagg ttcacaataa ataagagaaa aaagcagaat gtagaactgt atgatagcaa      10440
ttctgcaaac aagaagcatc ttttataaaa gatggaagga gcccaggcac agtagctcat      10500
gcctgtaatc ccagcacttt aagaggctga ggtggaggat cacttgagct gcagtgaccc      10560
atgattgtgc caccactcca gcctgggtga tagaagtgag accttctctc aaaaaaaaaa      10620 aaaaaaaaa aaagacggaa attcctccag aattttaaca tgtcaacaga ggttttctgc      10680
agctactttt ttcagcttta tacttcgcag tattttccaa attttctcta caagcagta       10740 ttttccaaat tttttacaat aagcacacac acacacacac gtttgtttgc ataagtgccc      10800
aactggtggt gaacaaccgc tggctttttag tctatacata tctagaatat tttataaata    10860
gtagttctta aacccttgaa agggagtgaa tgaccagctg agaaaataaa gtcagtgatt      10920
tcattatttt cctatattca catcatgatt ctaggaaaga acttgggagt gacttccttc      10980
agcttcagcc actcctgggc caggcgcatg cttagctctg tggtaaaggt caccagcttc      11040
ttctgcaggg tgcctgtatc atctgaattg gaggtttggc gagggtaaga gactgatgta      11100
ggttcaagtt tttctttcct gtcctccact tgaaatctgt cttcccttcc agactgcctg      11160
cgctgctgac ttaaggcccc aacaccaaac acagaagcaa cagccttaca cagagtgttc      11220
agcaagctcc aacaattgtg taaggtaaag tttcctttat agattccttt tctatatcgc      11280
tcctagtggt tctgtttctc tgatcgaatt ctggctgata acagttgctg agactctgaa      11340
agagaaggca aggaactact gtttctcatt ataaactgtt tagaattatt tggccatctt      11400
tttgctatga atatgtagtg ctttgataca ttttttaaat caaaaagtaa tgaaagagat      11460 cacatagga aagatagatt ggattatttt taaagtttat atactaaatt gaaaagcaaa       11520
gaataaaatg ggagaaacag ctccctcatg tggctgttgg caggaagctt ccattcctct      11580
ctgtgggcct ccacaggttt gctcacagca aatggtccgt gacagaaaga cgcaagggca     11640
gttgcaccca agatggaagc caccatcttt tctataacct aatctgaaag aagggacata      11700
ccagcacttc tgccatatgc tgttgggtca cacagaccaa ctctggtaca gtgtgaacac      11760
aggaccacac aagggcgtga attccaaggg cagagaccac tagggaccac ctcagaggca     11820
cagagggaca ccctatccag ctggtggcca atgtaaatta acatagcttt ttagaatagc      11880
aatatgtatc tataatctta aaagtattaa aagtacttct tgatccagta atttcatttc      11940
taagaatcca tgctaagagg atttaaaatg tggaccaaaa aatgggtata aaaagaagtt      12000
gttaacagta tttaaagttg tgaaaaacca gaaacaatct aaaggtccaa caataggaaa      12060
atgaattttg atattttct  aatagaattt tatgctgtca tcagaaatac catttacaaa      12120 taattttaa taacgcaaaa aaaagtttat aaaatgttta gtgtaaaacc tggacacaac       12180
tacataatga ttctgatttt gtaaaaaaaa aaacaaaaa cacacacata tacacatgca       12240
tacatatgca tataaagaaa actggaacaa acaaaataac aagcatagtt ggaattacag      12300
tcattttaat attctttatg cttttaaaaa ttttgaagtt tgtattacta gcatccacta      12360
cttacgtagt caggaaaaaa atacaacttt aaaatagata tttaggtcca aagatggtaa      12420
tctaaatggt gttacaggct gaatgtgtgc ctgatcccca tgccccaagt tcatatgtta      12480
aagccctggc ccccaaggca atggtattag gggagtaggg cctttgggag gtaatcagat      12540
ttctacgagg tcatgagggt ggagcccgca tagtggaatt agtgtccttt taggaagagg      12600
```

-continued

```
agaacagacc aaagccttcc tttctctcct cactatgtaa gaagacagcc agaaggtggc    12660
cacagccagg aagagagctc tcaccagaac ccaaatctgc tagcaccttg ctcttgggtt    12720
ctcagcatcc agaactgtga gaaatgaatg tgtgttgttt aaaccactca ggctacggta    12780
ttttgttgca gcagcccaag ctgacagaga tagaaacaac acaaggaccc atcagcagac    12840
gaatggatga tcaaaacgtg gtgaggtcgt gcagtgggat attattcagc cgtagaagga    12900
atgaaattct gatacatgct ataatgatga accttgaaaa catgttaatg gaaataagcc    12960
aaacttaaaa ggacaaatat tgtataattc cacttatatg agttagttac ctagaatagg    13020
caaattatgt catagataca gaacattaga ggttaccagg gttgtgggaa gagggtatt     13080 gtgggtacaa attttcggtt tggagtgatt ttgaaaaaat tctggaaatg ggtagtgaca    13140
gtagtcaaca tgatgaatgt acttaatgac actaaattgt acacttaaaa atggttaata    13200
ctgggctggc gcagtggctc atgcctgtaa atcccagaac tttgggaggc caagacaggc    13260
ggatcatgag gtcaggagat tgagaccatt ctggctaaca tggtgaaacc ctgtctctac    13320 taaaaataa aaacaaataa aaaaaaatt agccgggcat ggtggcaggc acctgtagtc    13380
ccagctactc gggaggctga ggcaggagaa tggtgtgacc tgggagtcgg agcttgcagt    13440
gagctgagat cgcgccactg cactccagcc tgggcaacag agccagattc cgtctcaaaa    13500 aaaaaaaaa aaaggttgat acctgggtgc ggtggctcat gcctgtaatt tcagcacttt    13560
gggaggccaa ggcaggcaga tcagttgagg tcaagagtta aggaccagcc tggccaacgt    13620
ggcgaaaccc catctctatt aaaaatacaa aaattagtcg agtgtggtgg tgggtgcctg    13680
tagtcccagc tgctgggagg atgaggccta ggaattgctt gaacccagga ggcagaggtt    13740
gcagtgagtt gagattgcgc cactgcactc cagcctgggg gacagagcga gacttagtct    13800 caaaaaaag gttaaaattg taagttttgt tatgcatatt ttaccataat ctttaaaaaa    13860
tagatatata ggagataaag tcaacagaat ttaataacca gttgtaaata gagactgagt    13920
gaggaggatg aattaaggaa gacattgagt acaacttttt ggtaggtgaa aaactcttaa    13980
aaaaatacgt gggcaaagat cctacttgat tcttataatt taaaaatctc ccagttagta    14040
aacaaggcta ggtggagatt tgcatgtgat gtgaggtgtg tgttctgttt tgtaatgtga    14100
ggactgtgag ccatctcctg gacttgaata tccattagat aattgaaaat acggatttga    14160
gaactcagga gacgtgcaat gcagtaacaa aactctgcac ctagttgatt tctgtctcct    14220
aatttaatgc ttttatggga caaactgtta ggcaggtggg caagatggac agccatattt    14280
ttgtgggttt ctggcctgtg ggccagcctc agtgctcact ctgaggtcat gtccaaactt    14340
agaacacatt caggcctacc acagtcaagg ctcccttttct caactctagt cctctgcaca    14400
aatatccgaa gcctagaaat aataatcatc tgtccttgtg tcttgcatta tgaaagccta    14460
ggaaagggcc ttgggaatta agaagaatgg aaaaactggt ctaactgctg catgcttcag    14520
cttgcagggg aatcactgaa atggggacag gccataaaag gacaaccaga agagtggctt    14580
cagcaaaggc atcgtttttc agagcaagct agagaatcct gccagcgtcc tcaggcaggg    14640
cccctgggca cagaggttag gcaagggagt gtcccagcat gttgatgccc tgagcatcag    14700
aataatgcca tagaggagct tccaaagagt tcatttcagg ttttgtaagc cgaacatttc    14760
taggcaaata aaatttgatt ttgtgaataa agcttgtttc ttcaactcca gtgcagattc    14820
tcatagattg atagtggctt gtgatccaga taaagaaaac aattttttcaa agattcatat    14880 tctttgtaga tgtacggatt tagagaccat ctaatctaac tccctcattc tacagatagg    14940
```

-continued

```
aaaaatgagg cctaaagaag ttaagaaaat accatggaaa tgtcactgct gaactgccat      15000
acgtaggatc cgaaagaaat tgggtaaatg ctactgtgag aaatacagta ctaggtccaa      15060
agaatctaat acaaattaaa aatctaaatg ttatttctaa agcatccctg cacatggctg      15120
aacttacata gtttcatttt ctttcttttc tgttgaagaa gaggcaattg gctgggtgca      15180
gtggctcatg cctgtaatcc tggcactttg agaggccgag gcgggtggat cacctgaggt      15240
caggagtttg agaccagcct ggccaacatg gtgaaacccc atctctacta aaaatacaaa      15300
aattagctgg ctgtggtggc gcctgcctgt aatcccagct actccagagg ctgaggcagg      15360
agaattactt gaatctggga ggtggaggtt gcagtgagcc aagatcacgc cattgcactc      15420
tagcctggat gacaagaggg aaactccatc tcaaaaaaaa aagaaaaaa agcaatcact       15480 aacctgtgtt gtttattaaa catgacagac tggcatgaag taattaccaa actgtaaaca      15540
aaaaagctac aatctgccag gcatggtggc tcatgcctgt aatccccac cttgggaggc        15600 caggttgggg gatcacctga ggcctggagt tcaagactag cctggtcaac atggtgaaac      15660
ctcgtctcta ctaaaaatac aaaaattagc ccggcgtggt ggcacatccc tgtaatccca      15720
gttactcagg aggctgaggc aggagaatca cttgaacctg ggcagtgggg aggttgcagt      15780
gagccaagat cgcaccgttg tactccagtc tgggccgaca gagtgagact cggtctcaaa      15840
aaaaagaaaa aagaaaagct acaaccttaa tctcaacttc tcataacatc atctctactt      15900
ctgattagaa gagtggaagt ggggaggttt attacaaaaa gactgttata ccttacacac      15960
ttctccccat gaatagtgaa ggtgtgagtg aaaaagacag caattttatt ttttttttga      16020
aacaggttct tgcactgtca cccgggctgg agtgcactgt tgtgatcact gctcactgca      16080
gcctccacct cccaggctca agtgatcctc ctacctcagc ctcctgagta gctgggacca      16140
cagttgtgca ctaccatgcc cagctatttt ttttttaagag atggggtctc actatattgc      16200
ttaggctagt tctcaaactc ctggcctcaa gcagtcctcc gaccttggcc tcccaaaggg      16260
ttgtgattac aggcataagc caccacaccc agccagcagt tttagaataa agggtgaagg      16320
tgctgttggg gaaatataat ttaaaaaaca aaatcttctc tcaacccaga atcctctcc       16380 atgaaggcag tagagaaaga taagctttat tattgaataa aaattaaatg agaatgtgat      16440
gcacatcaca ggcactttgc taagagatca caaagacaga aggaaatttc accattttgt      16500
acagccaagc aggtacagcc cattacatgt atgttttcga gataaatagt cctcaactaa      16560
gagaacttga cagcaccact ggtcacacag ttcattctaa ctttacctga taattgatgt      16620
gaccacttgt gttatctaag atatcaactt ttcgggggtg ggggagtgtg gaaacaggag      16680
ttacttttat agcttggtgc aaggtactca ttaagattag gctgttaccc tcccacagaa      16740
actggaagat aggtatgcta tctggtaatg tttacatttc ccagatcctt gagaaagaca      16800
ttcctaggtc ataaagctga caaaggctg attcagtttt taaatatata tatctgtata       16860
tgtatttca                                                               16869
```

<210> SEQ ID NO 65
<211> LENGTH: 15000
<212> TYPE: DNA
<213> ORGANISM: Homo sapiens

<400> SEQUENCE: 65

```
gatctcttga tcccaggagg tcaaggctgc aatgagctaa gatcaagcca ctgcattcca        60
gcctgagtga tagtgggaga ccttgtcttt aaaacacaca cacacacaca cacacacacg       120
agggcctttg accactcttg agtagaagac tcgagaagaa caaagtagaa ggccagagaa       180
```

```
gaacaaagtt acttgaaaga tctcttatta aagagaatgt acaagctatg aaaaaaaaaa    240
aacacacaca cacacacaaa cctcatctgg aatgaaaaaa acataatgca tttggtttct    300
ggttccttag gctgttatgg aacaaccaaa gaacattatt ttggtttctg aggtcagaac    360
tattttattc ccctcaagca cactatgctt atggtttgag ggagaatgag aaataggaaa    420
ctaggaacag gctgaaatgg tctaatcttg accatctaat tctgcagtgt cttattctca    480
ttctaaaaga gaatggttat attcgctgtt ctagcataaa aagtaatgat aaaaataaaa    540
gatcccgtat taccagacaa taatcccta gactgtttta atgcttggtt gagtatttgc     600
ttatgatctc agactttaaa agatggtctc cccctatggt gaagcttgtt aattatgtag    660
gcatcattaa tgtctgttta cttatcaaaa ttttatcatt gttagttgta ttactacttg    720
acagtccaat ttatttaatt gaaagattg gttaacattt tatagtcaaa gtaattgttt    780
cctgtgtttt ttcctgttta ggttattgga gtgatgagta aagaatacat accaaagggc    840
acacgttttg gacccctaat aggtgaaatc tacaccaatg acacagttcc taagaacgcc    900
aacaggaaat attttggag ggtaagtaag ggaaatttct tcagacccat aaatgttag      960 gaaaaatgg agctaaaaga gctgggtggc tcacctttct catcctgtgc tgagaaatgc    1020
tggggctcac ccataagtat ccagcatccc catggacaca gggaattctg aacaaatgtg    1080
atgaaaccga tgaaatgtct ggcctgtagg tggttagtga tggagatacg ggctatatgt    1140
gaatcttgat ttttgcaatt cattagagct ttgtaatgaa aggaaacagt ttgttgcttg    1200
ctttaaggat aggttcattt gcatttctcc gcaaggaagt agtaatgagt taccaagcct    1260
tagatttcac cccttttttga tttcttgctg acttaacttt aattgaatgg aagagttatc   1320
acaaatgaat tatcttttg gtttttttttt ttttgagatg gagtctcact ctgtcaccag   1380
gctggagtgc aatggcatga tctcggctca ctgcaacctc cgcctcccag gttcaagcaa    1440
ttgtcctgcc tcagcctccc gagtagctgg gactaaggtg cgcgccacca tgcccagtta    1500 attttttgtat ttttagtaga cacggggttc cactatgttg gccatgatgg tctcgatctc  1560
tggacctcgt gatccgccca ccttggcctc ccaaagtgct ggaattacag gcaagagcca    1620
ccgcgcccag ccaggaatga caaatgaatt accttataag taaatgccat taaggaagga    1680
tagctggaag atgggttgag gggaatggag gaccacagaa ctagtcctat ttaaatacat    1740
gtgcatggta aaatgattcc atttgacaat aggttaatta tctcatagca taaggaaaat    1800
gcttaacagt catatgcaag atgataagct ttcctatagc atccaaccaa aagatctagc    1860
cagtacaatt tcctttgcta tattagggtt agaaaggccc ccagaggtga accaattaga    1920
tggaatcctt gaataaaaca ctggattagc agtgaacaga aaaagtcag attgcttcc     1980 ttcttcccat agatgtctca gggatattta gtttcctcag aagataaaga atttagtaag   2040 cgttttttg tgcatactta catgaaatgt acattatttg aattctttaa aaagaaacag    2100
ctgcatgata acaaaaattg tgttatgctt gctttagctg gtattttgc ctagaacgat    2160 tatatcgttc ggacaagaag ctattcctaa gaaacaatat ttttaatcca ggaagttttt   2220 cattttaga aatttatctt actatttccc aagcaaaaga gggtagttac agattcacta     2280
agaatcatgt gctcacaatt tttatttaat aattattcct ccttaaaata tattaatcac    2340
ctgacttaca atggtggaac catgagtgca ttttgcctt tattgtcaat aacgtcttct    2400
cagaagtgag ccacaaaggt gcatagttct tggagttaaa ggtctgaatt aagacaatcc    2460
agcataagtc tcattaatgt gtgattattt tgagaaaagg caagagtac ctaagaatct     2520
```

```
ccccctcact gtccagttcc ctgtttcatt taaagattca ctgtaagtaa ctgaaaggct    2580
ttccttggga ggatttatttt gaatcagtct ttcacatgca aaggatattg tagaacatct   2640 cgttttttgct ggcaggaata tgaacatctg ttgtgaggaa agaaaaagtt tcatgcaaat   2700
tacactgcca aagaagggat gttcaagttg agaaaccagt gacatttctt gtaactgtac    2760
tatgaatcag cgcattttaa tcttctagat aatatatgga agtgcaggaa ggtggtagga    2820
aacggtgttc attttacata tgcgttattt tattctgtgt gagtgacttc atggcaccga    2880
cattgctgtt tttaaatgag gatacagtaa attgcagtcc gaggaaggct aactggaatc    2940
aacatacccg tagcttttaga aagcagtttc cgcaccagcg aagagtacaa gagcgatgga   3000
accccatgtt cctggaagtt tgcacatcag agtaaacaaa cttgaaaacc cctcttgata    3060
gcagaattca cccagccttg ttccattttc tcttaacaaa acacaccgca aaagctctca    3120
caagctgctt tgatgaagcc acatgtattt ccccttcac aatttacagg aagttactct     3180
taaaagaaag tgattctggt gtttaccgcc tgtgttaaag ggacagagtt ccttttttatt  3240 tctgataacg tttgagcgaa atacagaaac tatctgtaga ctagcatagt cggtacgtga    3300
gtaaggaaaa gcaataaccct gctgtccggt gagcacaaaa ttcctgctac gaacagtgcc   3360
ttactgctgc ttggagactg caagtcgcag atcacactag gtattgactg attgtataag    3420
gaaatttctt aaagtctaaa gtaaaggtgg tacctcctaa aaagagggga agagagaaaa    3480
ctttgtgtgg aaggataagg agtgtgttta tagtttcagt aagagtgtac gttttaatttt  3540 ttcttcttcc tctgcctctt tgccaagtag cctgagtgca tctgttatcc agaagtagta    3600
ttactctagg acaaacttca aattcttcat tctgcgttgc ctttaaggaa caacatactt    3660
tcttcctgtt ctttttccaa aaacacacgc ctatggctct gtgtgtggtg ttttagccag    3720
cctcctccca gataaggggt tcccttccct cctttgcatt gaaaggaaag tgcaagtctg    3780
gacatgttta tcaagaggaa aagtgacttc tcagtaatag actgtcaaat tcgggctgct    3840
gcccgagtgt tcgctttgtt atggcaggtg aagttcacct ttgccccacc cagtgttttcc   3900 acaaaaaggc aaggttccaa gtattcatat gaacaagtgt tactttagga cttggagggt    3960
tgggggtgga ggatgtttgc atagttgaag ccttgggcgg gggtgtagga aacggcgagt    4020
acagaggcca tagaaaaagc taagactcag tttgacgtcg tcagccggct tggtcttcta    4080
cccagtgact caaagcacta aaagtcagca taatcggaac tgaagtcagt agcatcgccc    4140
atttgccatt cactgcagta gcaaaagtag tactctgtgg tgggttaatc ggtttgaggc    4200
agctccttaa atgaacattt gtgtttcatt ttctgttat tttcccgaac atgaaaagac     4260
gataaaactg aaatgaaaaa ggtaactgac aaaagtgtgc cttacctgtt tccgccctga    4320
tttctgctga ttcaagacta ttctggctaa actgattgga ttcttttttct aactaggcag   4380 taggggatca gaaatcacac acggtaccgg ctgtgtttat tctgagaggt gctggggagc    4440 tttggtctg acttcctttt acatgcctgt cttctctttt ggacagatct attccagagg     4500
ggagcttcac cacttcattg acggctttaa tgaagagaaa agcaactgga tgcgctatgt    4560
gaatccagca cactctcccc gggagcaaaa cctggctgcg tgtcagaacg ggatgaacat    4620
ctacttctac accattaagc ccatccctgc caaccaggaa cttcttgtgt ggtattgtcg    4680
ggactttgca gaaaggcttc actacccctta tcccggagag ctgacaatga tgaatctcag   4740
taagtggatt acagaacaaa aaaataaaaa atgccagtaa tgtcggttct gccccttttga   4800 actaataaca tgttgtttaa ttatacggct ttgtcatgtg ttggatgaag taggtggctt    4860
aagctaggga ctaggaagag gaaaaacatt tttgagtcc ctattaacta ttaggaaact     4920
```

```
tgatcattta aaagtatata tatatatgag gagctacctt gagttttgaa ttcaggatgt    4980
tacaggaaga aatatatgtc caattctaat ttatccaaaa gcagttggga gaattacagg    5040
gattggtcca gacatgctgc gtatgcaagg tatagccctc atctgtggta ctttggcagg    5100
gcttagactg catcaaaata tttatagatg tacatttgag tgtacagtta ggatctgatg    5160
tggaacattg taagatcatt gctagaaaaa ctttgtcata attttcaat attattctaa     5220 gtgaataacc gtaaagattt tacatcttag cttccttcct tacagtaaaa aaactatctg    5280
atctcttgat cagtattata gtagccacct atcactttat cttaacaaat tctcaattcc    5340
ttaggtttat gtgcttttac ttcttttatt tgattaaaat tgctgtcatg acctctctct    5400
gcagagggct gcatcatttt ggtcattctc aagtgatctc tttgagcaat ttaagaattg    5460
ccataagatt ctaacctctg ctgtaactat ggttgtgtgt tcttggttag accactaaat    5520
cttattagca gtttaaaaa ttattccttt tggtttagaa gttaagacta aatgctgaag     5580
tttttgtaac ttttggtttt gatatcattt caaacttaag aaaacatttg aagaaaagga    5640
caaagaattt ccacttaccc tttacccagg tttaccagtt attgataagt atatccattt    5700
gctttaccag aaggctaact tgttttagtt ctcattttca cctttgagac atttggaata    5760
aatatcaatg ttaacataaa ttggaatttt gactttgatt ttaggaccaa tgaacaagcc    5820
aagtacttac cctagtcata tataatccaa ctgtatggtt atttggtatt cattccacac    5880
ttcattttac ttgatctccc ttaagattgc aagattgtgt ttgcagtttt tctgaaaatc    5940
tggggctata aaagcatcag gacctccccc gtaggggagg tcgtgtgttt ggggtcctta    6000
cacaacaggt tacccttgag cttcaggaaa agaactggct ctcagttccc cagttccagc    6060
ttaatgggtc taattaggtc ctgaccaaaa aggtggcagt tcttttccct catgtctctt    6120
cagcgctccc cgagactctg gagactctgt catatcccta gggctgagcc tcccaggaac    6180
cattcggctg ttgtggcatc tgtgtatgcc atgcccagtg ctgaggacct agtaacaaac    6240
gacaaatgca caggcacagt ggcatttttg tggaactcgt attccagctg tgcgtctcag    6300
aagaagcgca cagctcccct ctggctttct taacatagtg agccacttcc acttaagggt    6360
ctccttacat tccttgagtt taatcattca tggattcaga ggaaagtctt ttgattttg     6420 cttttctta aacagttcat ttgaggtgac ctaccccagt gactttgcac caaccaccaa     6480
gaaacttttt tgcatgcttc ccgcaccctg tgccaatcaa gggaagggtt taaaggcctg    6540 gcgttttat tcctcaaaga aaggttttgc acagtatttt aaggttcaag tgcttctact     6600
ttgtgttcag aagcaactgt catatatact gtgaaatgac acctttatt tatcccttt     6660 tattatgca gtatgtcccc tttattttg gcagaatttt ttctaaatgg tggtttaaca    6720
ttttcaagca catttcattg tccaatattc atagtaaaga atgagagtta acaataacca   6780
gtcacattaa aacaagattc ctgctgccag ttgtgaaacc ggttgtctta ggcgtggcag    6840
ctgatgattg agactgtgat caggaaaatt tccactattt catcaggcct aataggtaga    6900
ttgtgtctcc aaatgaactg tgttgggttt ccatgcttaa agcacaatag aggtggtgca    6960
agaatctcca tgagggctta aatggcagtg atggttcagg cggtagagtt tggagaagaa    7020
gggatttgaa acaaaccaaa ggaaagaaaa gtaagtagcc agaaatcaca aaatggcatt    7080
tttctaaaaa caaaggaaaa ggaataaaag aactaataag tttgaaaccc ctacccctcc    7140
caaatttggc agggggggag gtatttttt tctatctatc taactaaccc atctagaaaa     7200
cagttgacca aattatagac ttctaaatgt taatctgctt tctcagtttc agttgaaaag    7260
```

```
agactttgtt ttgcctactg cagaacttct aggttctttc ttatagtctt ggggttctta    7320
ttatagatcg aaaatgtgag tcggcataat taagccattc ggagtcttca gaagcagttc    7380
actcttgaaa tgactccgtc cgcctacagc catttaagat ttcagaacaa aaacagatct    7440
tgattttctt tttcatgtta actcaagctg ttgctgagtg ggagagtcag aaatgacacc    7500
agctccactg attactcagc tgctgaagga tgattttta aaatgcacct ttactgtata    7560
tggacttcct aatttccacc tgtagagcat cttagggagg ctaacatgtc actctggatg    7620 ttctttaga ataagatgca aatctatttt tctgaaggca ttagagatag caaacattta    7680
ttgtgagttt actatatact aggcactgtg ctaagtgttt tgcatagaaa gtttaaaatt    7740
ctggcttttt tgttggccca atcataagtt tcatatcagt tcaacattca aattatatta    7800
aggtacttaa gaagaatccc tggctaaatg tgaggggcag tgccacagat ggactgaaac    7860
tttatgctta ttgcacattt atgctattat tatttgttga attatagaac caagggagtg    7920
tggaagccac tggaaaaaat atgagactta gatacataat ttgagtaaaa atggctcaaa    7980
gtcatgaggg taaagttttt tgtatttcca ttttattcga gcggcatcgt ttttaaaaat    8040
cattatgaat ttgaccctat atagatgttt ccaaataatt cttttttcacc ttcataaaat    8100 tccttcctgt ggctgtgaga tgccttgcct atcagttttc aagcttagtt gtctttctca    8160
tcctttacca ttttagcttt aaaaaacaaa agtgacaatt agaacttcct gcctgctggg    8220
cctcactgaa agaccgatat tggcctgata aggagatatt tattttgttt tagtggcttc    8280
agaaatccct ctccctcagc aagctttcca tcacggcccc ccgtcagca tcttccctga    8340 tagcgttctt ctctgtgttt attctggggc ttcaggctcg cccaggagga actgataacc    8400
gctggcagga gataacattc tctaaggggc tctcaaattg gaatcgaatc cctcaagcca    8460
gtcagcctag agaatacatt taaagggttc agttctggag tttcacagag ttcatttcta    8520
gacctatcag atagcaagtg tggagttctt tctcaactaa attcaagcag agacattttt    8580
tagacgatga aggatatttg cacaaaggct tcagcatgat ccccccaaaccc tgctgcctct    8640 gaaggcatct ccacacattg acagccaatg ccttcagtgc gttcctaggg caggtgtcct    8700
ggcttgagtg actgtcctcc aataatcaga gctcaaacta aacatcgtat gttttacttt    8760
tggtttccag gcaaggctga gcagggaatt ttcagttttc cctgcccaga tgggtgtttt    8820
ttcctgaagg catcatttat tgtgtagcga ggagacaggg ctggctgtgg cagggatagt    8880
ctagaactgt cctcattgct gctgttccta aatagtatct ttaccaagta ataacgtgcc    8940
gtctttggga ataagtgctt tcctcttagc ctgttctgtt ttcttgggtg cgctaagtaa    9000
ttgaactggc tcaggaagta cctattgtgg tttggcagag gtgactgtca cgccttgtga    9060
ctccaggggc cagcactgct gggatcctgg ctagaccaga cagagccttg gtgaagtgct    9120
taggctgtct gcacatcgcg aggaaggtgg tattcacttc gctaagctcc ttggcatagg    9180
cagtttgaac agggctttat caaattcgta ttcaacaaga gtagaagcga aaattgatga    9240
ctgtgtatta cttgaaatga gtcttaatct ttcacattta gttctcaggg tatgctgatt    9300
tcctttaggt aaaccatgaa catcagaaag acttttatta acctatgaca gggtccccac    9360
cccagtattt ttccactcca ttaaaatgga gttttttt ttttttttct tttttgagac    9420
agagttttgc tcttgttgcc cagtctggag tgcaatggca caatctcggc tcaccacaac    9480
ctccacctcc cagattcaag cgattcttct gcctcagcct cccaagtagc tgggattaca    9540
ggtgtgcgcc accacgccca gctaattttg tatttttagt agagatgggg tttctccatg    9600
ttggtcaggc tggtctcgaa cttccgacct caggtgatcc gcccacctcg gcctcccaaa    9660
```

```
gtgctgggat tacaggcaag agccactgca tccagcttag gctatcttac tccagcctaa   9720
acagcaattt tctatcataa ggtctgtact aatgaaaaca gaatcaccca aggctgctgt   9780
ttgttctgtc tgtgctgcca ttgtccgcat tttgctgagg aggaaacgga actgcacttt   9840
tgagtgagtg gcccagagcc ttctagaatg agagtgcgtt ggaagccaga tatgtggcga   9900
ttgtgtcgcc agctgttact caggttttct caagaaggag gagcaacttt ggcagttttg   9960
cttcagttct ctctagccct ctgtgtaatc gccccttttt ctttatttca gcacaaacac  10020
agagcagtct aaagcaaccg agcactgaga aaatgaact ctgcccaaag aatgtcccaa   10080
agagagagta cagcgtgaaa gaaatcctaa aattggactc caacccctcc aaaggaaagg  10140
acctctaccg ttctaacatt tcaccctca catcagaaaa ggacctcgat gactttagaa    10200
gacgtgggag ccccgaaatg cccttctacc ctcgggtcgt ttaccccatc cgggcccctc  10260
tgccagaaga cttttgaaa gcttccctgg cctacgggat cgagagaccc acgtacatca    10320
ctcgctcccc cattccatcc tccaccactc caagcccctc tgcaagaagc agccccgacc  10380
aaagcctcaa gagctccagc cctcacagca gccctgggaa tacggtgtcc cctgtgggcc  10440
ccggctctca agagcaccgg gactcctacg cttacttgaa cgcgtcctac ggcacggaag  10500
gtttgggctc ctaccctggc tacgcacccc tgccccacct cccgccagct ttcatcccct  10560
cgtacaacgc tcactacccc aagttcctct gccccccta cggcatgaat tgtaatggcc    10620
tgagcgctgt gagcagcatg aatggcatca acaactttgg cctcttcccg aggctgtgcc  10680
ctgtctacag caatctcctc ggtgggggca gcctgcccca ccccatgctc aaccccactt  10740
ctctcccgag ctcgctgccc tcagatggag cccggaggtt gctccagccg gagcatccca  10800
gggaggtgct tgtcccggcg ccccacagtg ccttctcctt taccggggcc gccgccagca  10860
tgaaggacaa ggcctgtagc cccacaagcg ggtctcccac ggcgggaaca gccgccacgg  10920
cagaacatgt ggtgcagccc aaagctacct cagcagcgat ggcagccccc agcagcgacg  10980
aagccatgaa tctcattaaa aacaaaagaa acatgaccgg ctacaagacc cttccctacc  11040
cgctgaagaa gcagaacggc aagatcaagt acgaatgcaa cgtttgcgcc aagactttcg  11100
gccagctctc caatctgaag gtaggccttg agagagagca gtccaagggg ctgtgagtgc  11160
atgcttgtgt ttgtatttag cttgctttcc atggggtatc gattgcattt gcagtagtat  11220 gagccccgg ttggggatag tgggtatgga ttccgcctgg cttttgccac ttctagctct    11280
ttgactttgg acaagtgact tcccttctcc tgattttctt ctgaataata aaaaattag    11340 gggtttggac tagaagatta ggtgaaactc cctgctagcc tgtgattttt gtgcttttaa   11400
gaaaaacacc attctgaaaa catgaagatt tcttcttttt aagactgtct tgatgctttt  11460
cttaagatat ttgcatcaac acttgagtct tggagcagaa atgttaggtc tcagagccag  11520
cttgagagca gagctaacac atgtggcttc ttcccaggtc cacctgagag tgcacagtgg  11580
agaacggcct ttcaaatgtc agacttgcaa caagggcttt actcagctcg cccacctgca  11640
gaaacactac ctggtacaca cgggagaaaa ggccacatgaa tgccaggtgc gcagtatttt  11700
ctgggtagac cttctgacct ttgtagaaaa tgtctgtgag tcaccctccc atgtcctata  11760
tagcccgtag ttaaagccaa caccagattc tgcgttgtcc catcctggac tgatggcact  11820
atggtccttc ccagtacttt gtatctgctg atgacttgag atggcacagc cagcttccag  11880
tgggtgggaa aatggtaggg gaaataaaca gcccctcgtg tgctgtgtgc ccacatcccc  11940
ccgtttgctt aataccacac tggaggtgcc acaaggaggc ttctcacctc ctaggttgct  12000
```

```
gggcgttggc cggtaagcct gcccctcccg ttggcaactc ttaatcttct ggccttcctg    12060
tctcccttcc ctgctgtctc tctccccctac actgtaggtc tgccacaaga gatttagcag   12120
caccagcaat ctcaagaccc acctgcgact ccattctgga gagaaaccat accaatgcaa    12180
ggtgtgccct gccaagttca cccagtttgt gcacctgaaa ctgcacaagc gtctgcacac    12240
ccgggagcgg ccccacaagt gctcccagtg ccacaagaac tacatccatc tctgtagcct    12300
caaggttcac ctgaaaggga actgcgctgc ggccccggcg cctgggctgc ccttggaaga    12360
tctgacccga atcaatgaag aaatcgagaa gtttgacatc agtgacaatg ctgaccggct    12420
cgaggacgtg gaggatgaca tcagtgtgat ctctgtagtg gagaaggaaa ttctggccgt    12480
ggtcagaaaa gagaagaag aaactggcct gaaagtgtct ttgcaaagaa acatggggaa     12540
tggactcctc tcctcagggt gcagccttta tgagtcatca gatctacccc tcatgaagtt    12600
gcctcccagc aacccactac ctctggtacc tgtaaaggtc aaacaagaaa cagttgaacc    12660
aatggatcct taagattttc agaaaacact tattttgttt cttaagttat gacttggtga    12720
gtcagggtgc ctgtaggaag tggcttgtac ataatcccag ctctgcaaag ctctctcgac    12780
agcaaatggt ttcccctcac ctctggaatt aagaaggaa ctccaaagtt actgaaatct     12840
caggggcatga acaaggcaaa ggccatatat atatatatat atatatctgt atacatatta   12900
tatatactta tttacacctg tgtctatata tttgccccctg tgtattttga atatttgtgt   12960
ggacatgttt gcatagcctt cccattacta agactattac ctagtcataa ttattttttc    13020
aatgataatc cttcataatt tattatacaa tttatcattc agaaagcaat aattaaaaaa    13080
gtttacaatg actggaaaga ttccttgtaa tttgagtata aatgtatttt tgtcttgtgg    13140
ccattctttg tagataattt ctgcacatct gtataagtac ctaagattta gttaaacaaa    13200
tatatgactt cagtcaacct ctctctctaa taatggtttg aaaatgaggt ttgggtaatt    13260
gccaatgttg gacagttgat gtgttcattc ctgggatcct atcatttgaa cagcattgta    13320
cataacttgg gggtatgtgt gcaggattac ccaagaataa cttaagtaga agaaacaaga    13380
aagggaatct tgtatatttt tgttgatagt tcatgttttt cccccagcca caatttttacc   13440
ggaagggtga caggaaggct ttaccaacct gtctctccct ccaaaagagc agaatcctcc    13500
caccgccctg ccctcccccac cgagtcctgt ggccattcag agcggccaca tgacttttgc    13560
atccattgta ttatcagaaa atgtgaagaa gaaaaaaatg ccatgttta aaaccactgc    13620
gaaaattttcc ccaaagcata ggtggctttg tgtgtgtgcg atttgggggc ttgagtctgg   13680
gtggtgttttt gttgttggtt tttgttgctt tttttttttt tttttttta atgtcaaaat    13740
tgcacaaaca tggtgctcta ccaggaagga ttcgaggtag ataggctcag gccacacttt    13800
aaaaacaaac acacaaacaa caaaaaacgg gtattctagt catcttgggg taaaagcggg    13860
taatgaacat tcctatcccc aacacatcaa ttgtatttt tctgtaaaac tcagattttc     13920
ctcagtattt gtgttttttac attttatggt taatttaatg gaagatgaaa gggcattgca    13980
aagttgttca acaacagtta cctcattgag tgtgtccagt agtgcaggaa atgatgtctt    14040
atctaatgat ttgcttctct agaggagaaa ccgagtaaat gtgctccagc aagatagact    14100
ttgtgttatt ctatctttta ttctgctaag cccaaagatt acatgttggt gttcaaagtg    14160
tagcaaaaaa tgatgtatat ttataaatct atttataccca ctatatcata tgtatatata   14220
tttataacca cttaaattgt gagccaagcc atgtaaaaga tctactttttt ctaagggcaa   14280
aaaaaaaaaa aaaaaaaaaa gaacactcct ttctgagact ttgcttaata cttggtgacc    14340
tcacaatcac gtcggtatga ttgggcaccc ttgcctactg taagagaccc taaaaccttg    14400
```

-continued

| | | | |
|---|---|---|---|
| gtgcagtggt | gggggaccaca | aaacaaccag | ggaggaagag | atacatcatt | ttttagtatt | 14460 |
| aaggaccatc | taagacagct | ctatttttt | tttgccactt | tatgattatg | tggtcacacc | 14520 |
| caagtcacag | aaataaaaaa | ctgactttac | cgctgcaatt | tttctgtttt | cctccttact | 14580 |
| aaatactgat | acattactcc | aatctatttt | ataattatat | ttgacatttt | gttcacatca | 14640 |
| actaatgttc | acctgtagaa | gagaacaaat | ttcgaataat | ccagggaaac | ccaagagcct | 14700 |
| tactggtctt | ctgtaacttc | caagactgac | agcttttat | gtatcagtgt | ttgataaaca | 14760 |
| cagtccttaa | ctgaaggtaa | accaaagcat | cacgttgaca | ttagaccaaa | tacttttgat | 14820 |
| tcccaactac | tcgtttgttc | tttttctcct | tttgtgcttt | cccatagtga | gaatttttat | 14880 |
| aaagacttct | tgcttctctc | accatccatc | cttctctttt | ctgcctctta | catgtgaatg | 14940 |
| ttgagcccac | aatcaacagt | ggttttattt | tttcctctac | tcaaagttaa | aactgaccaa | 15000 |

<210> SEQ ID NO 66
<211> LENGTH: 46340
<212> TYPE: DNA
<213> ORGANISM: Homo sapiens

<400> SEQUENCE: 66

| | | | | | | |
|---|---|---|---|---|---|---|
| tattttactt | cagtaacaga | aaatgaaaga | aatgttttaa | tgttgctgat | tgtattacct | 60 |
| tcaggatcaa | tagcagaagg | acaaacttct | ttgaggagat | ctcctagtgt | gtgcaactgt | 120 |
| ccatctgcag | ccacaggacg | aaacagcttc | tgaatgaaag | gtctttcagt | cgttgtctat | 180 |
| ttgaaaaagg | aaaaaatgat | tcaagcaatt | aagtctttgt | tgctgccaat | tacaaattta | 240 |
| tatatcataa | actttatgtt | ggcattaggt | gccttttgat | acggtgttag | cataattaca | 300 |
| caacatcaca | gatgtggtat | cactgtgaaa | aatgtttaac | atgataaatt | caggtaaatc | 360 |
| taattctgag | gaaacagaca | aatccaaagt | tgggtgggac | attctaaaga | taattggctg | 420 |
| ggacccttca | aaaacttaaa | gacattaaaa | agcaaacaac | acaaaaagat | atcaacaaaa | 480 |
| gcatttttc | tcagtatctc | ttaaagagac | taacaaagca | aatacaaaac | ataaaccatg | 540 |
| gctgaatact | aaattgaaga | aggacatttt | ttagaaatcc | aactatgaaa | cacagtttg | 600 |
| ggataaatgg | ggaaatacag | aatggacaac | tgataatatt | attgagttaa | tgtcaaattt | 660 |
| cttaggtaca | ataaggacaa | tccttatttt | taagaaattc | attgttcaag | tgtttaggaa | 720 |
| agaagtgcca | tgatatccaa | aacttaatct | tctttctctt | tttttggaga | cagagtctcg | 780 |
| ctctgccacc | ccggctggag | tgcagtggcg | cgatctcagc | tcactgcaac | ctctactttc | 840 |
| caggttcaag | tgattctcat | ggctcagcct | cccaagtagc | tgggactaca | ggagtgcgcc | 900 |
| accatgtcca | gctaactttt | tgtattttta | ctagagatgg | ggtttcacca | tgttgcccag | 960 |
| gctggtctca | aactcctgag | ctcaggcaat | ctgccggctt | cggcctccca | gagtgttagg | 1020 |
| gttacaggcg | tgagccaacc | gctcctggcc | ccaaaactta | accatctaat | ggttgagaga | 1080 |
| gagacagaga | gagagagaaa | gagagagaca | gagaatgtgt | gtgtgtgtga | agacaaagca | 1140 |
| aaaataaaaa | aatattaact | aatggtgatt | ctaggtagag | ggtgtatgat | tttagtagtt | 1200 |
| tcattatttc | aacttttcga | taggtttcac | aatttccaaa | acagcagatc | cagccatttc | 1260 |
| atctgacaaa | aactgttagc | agcactacat | cgtaattat | tgctaataat | ctcattgttt | 1320 |
| tactcttaaa | attgtttcat | ttactaaatt | tccttagtga | tgatggaggc | tttatcatga | 1380 |
| cagagtacag | aggctctgaa | atgagccagt | gtctatgaag | agcaccactg | tttgcaagat | 1440 |
| ctatgatctt | gtacccagtt | tcctttatct | gttaatttgg | gacattccat | atctcttgag | 1500 |

| | | | | | |
|---|---|---|---|---|---|
| tttgttgtgg | aaataaatga | gcaactttgc | caaccacaga | gtaaataaat | aaatgttaaa | 1560 |
| gagaataaaa | gcattttac | ctcctctctc | cctcttaacg | gttatttcac | tttaagatgg | 1620 |
| taaattttaa | gctttctgag | atgaaaaatc | attaaaactt | aacaagaaca | gagaaatgcc | 1680 |
| atacatacat | attttttgtt | tgcttgtttc | ctgagacaag | gtttcactct | gtcacccagg | 1740 |
| ttgaattgca | gtggtgcaac | ccccaagttg | caatcctcca | cctaagcctc | cagagtagct | 1800 |
| gggactacag | gtgtgagcca | ccatgctcag | ctaatttttt | tactttttg | tagaaggggg | 1860 |
| tctcactatg | ttgcccaggc | tgcctcatat | tttataagaa | tatgacttca | aacacttagg | 1920 |
| cattagcgac | aaggttttgt | ttttgtcttt | taatgacaga | ggtatacctc | aacatatttg | 1980 |
| acacaactgt | tagagatttg | gtttaaaaag | aaatagacat | ggatgaagct | ggaaactatc | 2040 |
| attctcagca | aactaacaca | ggaacagaaa | accaaacacc | tcatgttctc | actcacaact | 2100 |
| gggagctgaa | caacgagaac | acatggacac | aggcagggga | acatcacaca | ccaaggcctg | 2160 |
| tcggggagta | gggggctagg | ggagggatag | cattaggaga | aataacctaac | gtagatgagg | 2220 |
| ggctgatggg | tgcagcaaac | caccatggca | catgcatatc | tatgtaacaa | acctgcacat | 2280 |
| tctgcacatg | tattccagaa | cttaaagtat | aatacaaaat | gaaaaaataa | ataaaaataa | 2340 |
| gtagaaaaaa | taaacatgta | agcatgtgag | ctgccttttcc | taattctatg | tttatgtatt | 2400 |
| cactgaatac | atagtatttt | aaaatagtaa | tccaataata | tatttgagtg | tttgtgacaa | 2460 |
| gtatgaaaat | tgtaattttt | aaaaaatctt | gataatatgc | attgaatatg | atttaattca | 2520 |
| cttcactatt | tgaactcttt | agggattatt | tttaaaaata | tgattgatat | cctttgatat | 2580 |
| gttttggctc | tgtgtttcca | tccaaatctc | atctcaaatt | gtaatcccca | cccgtctagg | 2640 |
| gagggactgt | aatccccatg | tgtcgaggga | gggaggtgat | tgggtcatag | gggtggtttt | 2700 |
| cctcatgttg | ttctcgtgat | actgagtgaa | ttctcatgag | atctgatggt | tttaaaagtg | 2760 |
| gcagttttc | ctgcactctc | atctctcttt | cctgctggct | tgtgaaggtg | cctgcttccc | 2820 |
| tttctgccat | gattttaagt | ttcctgaggc | ccccacaagc | catacggaac | tgtgagtcaa | 2880 |
| ttaaaccttt | tgccttata | aattatccag | tctcagatat | ttctttaaag | cagagtgaaa | 2940 |
| acagactaat | acattcttca | atttaaaaag | ccatactttc | tcatacaagt | tgaaaccaag | 3000 |
| aacaatatca | tgcataatca | agtgattaac | tgtgtaaaga | taataaggtt | gaggagttca | 3060 |
| gagaagaaaa | gaaatgaata | gggaactgta | gtgataattt | aaaatagcca | tccctcactc | 3120 |
| agggttttg | atcttcaggc | catgaagaag | cttttaatgc | tttttagcaa | aggaagtaat | 3180 |
| gttggtgaaa | ggcttttct | gacgactaat | ggaaagcagt | gctatgtatg | gtgacttggt | 3240 |
| tatgaaccaa | aaccagaatg | actggtgaga | ggctgactga | atacagcaag | cttatgtgaa | 3300 |
| gacaactgga | gctggtgcag | tggaaaagga | agacagcagg | actgtaccca | caactcaaag | 3360 |
| aaaaaagtca | gaaggtacct | cccgcagtcc | aacctgaaaa | caacaaagtc | aaaggaatct | 3420 |
| tttcaagaat | ttggagctct | cattcatatc | ctaattagtg | tatgaaatgt | gaggtggctt | 3480 |
| tgctataatg | aaattacctg | gaatatttct | aacacaaaga | aataataaat | gcttgaggtg | 3540 |
| gtgaatatcc | tcatttgatc | attacacatt | gcatgcttat | agcaaaagat | tacatgtacc | 3600 |
| ccataaataa | ttgcaactat | tatgtatcca | taataattaa | aactaaaaga | ttaaaaatta | 3660 |
| cctgaaaaaa | aatgctaaac | aggaaaggcc | aactagtctt | ggttacatat | taaaaaacag | 3720 |
| aaattcttct | ctaacctcac | tattggagaa | atatcctgtt | attttatat | atcttttttt | 3780 |
| tcacccttc | ccaaatctga | gcaagtatta | taaaggtata | accttcaaca | atctttatg | 3840 |
| atgaggtatt | tgcttactgg | ggacaaagcc | ccagtgctat | tacatagtgt | agctaaacgc | 3900 |

```
tgtagaatgg taaaaacaag aaaatgctca gcaaagtgtt gtttctcatt taatgaaaat    3960
cttattttaa aacacaaaaa ctcaatatac cccaaccaaa aatctgatga acattttctg    4020
tttaatattt attatacagt acctttaaaa acgtaatatt cttattctta aaaatttagt    4080
gtgctagcaa atagcaatta agtacctaag tcaatcagga cgacaaaaaa atactcaatt    4140
tggggagtta gttacttcta tcatctgaat gcgtccctcc aaaattcatg ctgaaaccta    4200
ttcctcatca tggcagtatt aagaggtgaa gcctttgaga ggtaattagg tcatgagggc    4260
agagtcctca agaatgggat caatgctctt ataaaagagg ccccagggag cttgtaaggc    4320
ttttgcccct tctgccatgt tgggggggtg gggtggggg cgcagcaacc agtgctaact    4380
ctgaagcaga gagcagccct caccagaaac cgaatctgtt gaagccttga tctctgactt    4440
cccagcctcc agaactgtga gaaataattt tctgttgttt ataaattacc cagtctaggc    4500
tgggcgtggt ggatcacctg aggtcaggag ttcaagacca gcctggccaa tatggtgaaa    4560
ccccatctct actaaaaata cagaaaatta gctgggcata gttgtgggcg cctgtaatcc    4620
cagctactca ggaggctgag gcaggagaat cacttgaacc cagaaggcag aggttgcagt    4680
gaatcaagat catgccattg aactccagcc tgggcaacaa gagggaaact gtctcaaaaa    4740
aaaaaaaaaa aagtacacac tctaacatat tttggtatag cagcccaaat ggaatggact    4800
aagacaatta cccttaaaat aaaagctccc atagagagat catgcattca agtacagagg    4860
ttcttaaggg caatgggaat ggaggacata ttcctgcaaa cttttcaaca gctctcatta    4920
gcccgatgtt agagctctgc aaagaagact aaattatact gagaaatatt tttaaatctc    4980
cacaaatagg aatgctgtaa acgttgattt agtatatata aaattagaca agactaacaa    5040
tatccaatgc aatctaaatc ttaggttgac agacaagaaa gccactgcaa acaggaatat    5100
accacaatac ctgatcttgc cacatatttg taaatatgca agtatttca ataacttcca    5160 agaaacagta ttactctcat gagaaataac atgatgtaag tcacctttga aactgtcctt    5220 gttactttt caaatgtatg ttagtcattt cttaacacca aatgaaatga aaaactgagg    5280
tggtaatggc tggctgctcc catctctcct ctactcatgt gccttcacca atacagcaat    5340 catttttct tatatgggaa atttacagtg ttgatatagc tcagagatat attgaagaaa    5400
agcagaaaaa cgaaacttat aaacatttta ggaaacctta tgtatttct taaatagttc    5460 aagtgtaaaa cttagaattc ttataaataa tgtgtgttac agctatattg taaatggtgg    5520
ctcatgcctg taatcccagc acttcaggag accgaggtgg gaggagagct tgagcccatg    5580
agtttgagac tcacccgggc aacacagaga gacctcatct cttaaaaaaa aagaaagaa    5640 agaaagaaat gaaatgcaaa gaaaaagtct ctatttcaaa tgtagccagt agagccaata    5700
ggttaaccaa tattaacatt aacgttgata aaacaagaaa tgatgattta ctataagctg    5760
aaaatcagac aatgtatgga ctttaagagt aacaggcacg atcatcacaa acttaaatca    5820
ggtttgagtc ctatgagtta tatacagtta catgatgcaa caaagatgc cagccagttg    5880 ttaaagagta ttagattcgg ctgggggtgg tggctcatgc ctgtaattcc agcactttgg    5940
gaggccgagg agggaggatc acgaggtcgg gagtccgaga ccagcctggc caatatagtg    6000
aaacctgatc tctactaaaa atacaaaaac tagtcaggca tggtggcacg tgcctgtaat    6060
cccagctact cgggaggctg aggcaggaga attgcttgaa cccaggggc ggaggttgca    6120 gtgagccgaa atcgcgccac tgcactctag cctgggcaac agagcaagac tctgtctcaa    6180
aaaagagtat tagattcaag tcctgttcct gtcatttatt atggaaccat ggacacaact    6240
```

```
acctatcttt cctgaacctc agtttttca  actgcaaaac aggaatatat acatatgtgt  6300
atatatacat ctgtgtaaac acatatgtgt atatatacat ctgtgtaaac acatatgtat  6360
atgtataaat ggagataata cctacattat agtttctgag ataataaaat gcacaacaca  6420
attctgacac ataacaattt gtaacttaaa acataccatc accagggcca ctagttttag  6480
aacactgtaa tgcatagtct aatttaatac tatgcaaact gtgttcactc aaggttttat  6540
ttccttttaa tttcattcat ttactcttca gttgtttgta agctaaaaag tccagaatca  6600
tgaaattcag aagtttacgt tttaatgttt ttctatatgg caaggaaaaa aaaaagggca  6660
aagtcatttt aacactactt tcaaaatcag cctagaactt aacactaaag gcatgaccca  6720
taaaagggaa tactaataaa tagacttaat taaaattaaa caacaacaac aacagctaag  6780
cttttgttct gcaaaagatc ctgtgaagag aatgaaaaca taagccgcag gctgggagaa  6840
aatatttgca aaccatattt ccgagaaagg tcttgtgtct ataatatata agaactccca  6900
aaattcaaca gttttaaaa  aaagcaaata atccaattag aaaatgggca aaagacatga  6960
acagacattt taccaaagag aatatatagg tggcaaataa gcatatgaaa acatatctca  7020
cacatcatta gccattaaag aaatgcaaat taaaaccaca atgtgatatc attacacacc  7080
taccaaaata tccaaaataa aaattagtgg taacaccaaa tgctggtgcg catgtggaaa  7140
aatagtcctt cacacactga tggtacaaat gcaaaacagt acagtccctc aggaaaggag  7200
tatggcagtt tcttacaaaa ctaaacatgc acttaccata tgaccaagta attatactct  7260
tgaatattcc cagaagtaaa aatgtcttct ccaaaaaact tatacatgaa cgttcatagc  7320
tgttttattc gtgagagtca aaaacagaaa gcaatcccag ggctacccat taaaacaggt  7380
gaatgcttat aaactgactg taataggtct gtcccacgga atactactca gcaataaaaa  7440
ggaacaaact actggtatat gcaacaactt ggatagatct caagggagtt atgttatgtg  7500
aaaaaagtca atctcaaaag gttacacact gcatgactcc actgatataa cattagtgaa  7560
atgacaaaaa ttttagaaat ggaaaacaaa ttagtagttg tcagaggtta gggaagaaat  7620
gcagtaaggt aggtggctgt ggctataaaa gggtagccta agagatcctt ctgttgaaac  7680
gggtatattt tgaatatagg gtgaatttac atatgtgata aagattgcat agaactaaat  7740
acacacacac agtatatgta aaactaagga aatctgagta aggtttgtgg attatattaa  7800
tacaatttcc tggttgtgat actgtactgt aattatgcaa gatgttagaa ttgggggaaa  7860
ctagatgaag ggtatgtaga tcttttctgta ttatttctta caattgcatg tgaatctgta  7920
attatctcaa aataaaaatt tttttcaaaa tttcaaaaca actagtctag agctttgtta  7980
atcaaagttt tctctgagga cctgtagcat tttggttatc acctggatct tattaaaatg  8040
tagattctca ggctgcatat tggaattcct gaattggaat ccgcatttta acaagatttc  8100
caagtgattc atgtttaaag tttgagaagc actagtctac aacaatgact tttaacctttt  8160
caacctactc taacacactt gaaggccata acaaaattca catcaataac agttgctcgg  8220
ttggacagtg actctcaaca caaatgagtg aggaaaggtg gggactcaag actcaggtag  8280
caggaaaagc cccttaggtg atcctgatga aatgttttct ccatcctggc tgaaaaaccc  8340
agaacagtca attaaggctc aaaacaaaag taatgtttat aatactggag atctttaaaa  8400
ggcagataat atatactata acagagcaaa ggtaattatt acaatgtata aatcttataa  8460
gaaccaaaat cagaattaaa atcactaagc acataatgaa aatcctttaa aaagtataaa  8520
aatgaatgta gtctaagtaa atactaataa tggcagttat agtgagaaaa gctctagagt  8580
cttttactct tcatacttcc tagtcacaaa catctatttc caaaactgac ccttcgtatt  8640
```

```
tcaaataatt tatggcctgg tacagtaata agagcatgat atttaaagcc agtcagaaga    8700
cacatattct agctctggat ggcacttgat gacgatggat tcagcttatg gttccaatcc    8760
cagctctgtc aattagtacc tatatgaccc tagtcaaata cttaaaccttt cttgtgttac   8820
ttgtgtgtca attgtatcat ctataaaatg aggatattaa cagtatatac ctcatagatt    8880
tttttgtgaa ggttatacaa ttaattcata taaagtattt agaacaatgt ctagcacagt    8940
gaattctcaa tgagtgttat aattgttctt tttaaatgtg acttgactct caacagaact    9000
ctactgaatt ctaatatgta ttctgtattg agctgtcaaa aaaataagg attataataa     9060
catatactat tcttgtagtc aaccctgtta ctatgttatt actagtgtca gttttgttgt    9120
tttggtcata catattgttt tacatacatt aagaattatt agaaatgttg gtttattaaa    9180
aatgaccatt tatggctaga agggtatata tctggctcac tgactgtgga gtcaatgtcc    9240
ataaagagga ggaagaatgc catcagagta aaaggagatt ctattcactg aaacaaagtg    9300
ataaaaagct atgaaagaga aaaacataaa ataaccaaag gggtgaaact taacagatgc    9360
ccagtagatg cacaatgcac tgggttgtaa aacttaaaat ggccttaatt aaaagccaag    9420
cacggatgga ggtgctgggg gagtctccta cggacacagc aggcagaatg taacaatgac    9480
aaggggctca agtttattta aaaagagatt ggacaggccg ggcgtggtgg ctcacgcctg    9540
taatcccagc actttgggag gctgaggcgg gtggatcatg aggtcgggag ttcgaggcca    9600
gcctggccaa catggcgaaa cctcatctct actaaaaata aaaaaatta gccgggagtg     9660
gtggcgtgca tctgtagtcc cagctactca ggaggctgag gcaggagaat cacttgaacc    9720
tgggaggcaa aggttgcagt gagctgagat catgtcactg cactccagcc tgggcaacag    9780
agtgagactg ctcaggatct cccaaagacc caaatccctg taaactgaat gcataatatc    9840
atttgctcca gtgaggctta gatggacatt ctagtcttct tggttagct gaagaaacaa     9900
atattatatt gataatttat gtatgttgta tttttcaagg tatagcaaca agttttatt    9960
catcagctac tttgtgtgtg tgctttgttt ttaagtcttt tgaaacagga tggtgattta   10020
ctacatttat aagtaaaatt tatttgattt acaagggttg cttaagtgta tcacaggatt   10080
tcacttgtta tatttgcagg tgcttaaaaa atcagctata ctaaactata actggaatta   10140
gcaaagttca tttattgatt aatcaagaat ataattgat ttgcctaact atataagtag    10200
tactatgtgt tatttaagaa ttaaatctag aaaagggatg gactctggaa atatcaagaa   10260
gtgaaaaaga ctgctctcat ttttgtacaa caattactaa atttctaagt agcattaatt   10320
gaactgaaaa ggcattttag aaaaactaga ttttacaatt tataactcta ataaaacaca   10380
actaactatg agtgtgcttg ttcatgccca aaagctacct tccaaaatta aaaccctat    10440
tggatggctg ggtgcagagg ctcatgcctg taattccagc actttgggag gccaaggcgg   10500
gcggatcacc tgaggtcagg agttcgagat cagcctggcc aatatggtga acccgtctct   10560
aacaaaaata caaaaattag ccgggcgctg tggcgggtgc ttgtaatccc agctactcgg   10620
gaggctgagg caggagaatc acttgatcct gtgaggcgga ggttgcagtg agctgacacc   10680
gtcccactgc actccagcct gggcgagagc ccagagcgag actccgtata ttaaacaaaa   10740
caaaacaaaa ctcaaaaaac cctattggca attactaggg ccatcaaatc agtatatttt   10800
cacttgacac acaattttga gataatgaac cgaacttact atttttgaaa atattacata   10860
ataaatatta gtgaagcttc attgctgaaa tggtgacaaa gatgaatagc aataaaactt   10920
ttcttataga tctttagcaa aaacaaaaaa accccaagca tactatggta cattacttta   10980
```

```
gagaatcaag tagctgctag ttgagtaata gtggtaatag gcactacaat gatataaaca   11040
aattacaaca aagaatattg tttttatttc ctgtccatgt tttaaaaaag ctttggtttt   11100
acctatgttt aacaaaagca taggtacaac aacgactact actactaaca tataagtagc   11160
ctggatagaa ttatcttaat agtagtaccc aagtgcagga tctctaagta atgatcagaa   11220
ggcaggaata aattttatca gaaatcttca ttcattacat atttactatg catttaccag   11280
ggtatcacta tgctaatgga tacaaagata aataacatgc aaacaactgt aatacagtgt   11340
tatgtgataa cagaaatatg tacaaagcac tatgaaaaaa attacaaagc ttgagcacaa   11400 atttttaactc tggacttact ggcatttaga gcaaaaccaa acaatcctaa actggttaat   11460 ttcatttttct aagagttgga agctatatca gtaggtacaa agtaaaatat gctaattgtg   11520
gtagaaagta aaatattaca acagtagaga atttcaaaag aagataaaaa taatggaggg   11580
aatatagaag gtcttcaagc ttccagcttg aaatacatat ttttttttaa atagagaaag   11640
agataaagtc atttgagtat tcagagggca gactgaatat aatggtactt ctgagaaatc   11700
agtggataag gagagaaaag tggactaaag gccatagcat atagagcttg aatgtcaaa    11760 tgtagtggaa ataacaaagg tttggttgga atcccaactc ccaacaacgt actgtgtatc   11820
tagagcaaat tacatcaacc tttgggagta ctgtttctga atctgaaaaa tgaggaaaac   11880
ttatctttga acaattgatg tgataattaa atgagatata tgaaatatct aatgtaacaa   11940
gtgcttaaca atgactagtt cttttcattc ctctcttgaa ccattgtgaa acgtagaacc   12000
aagaaaggta acagtattta gttgttacag aacccattaa gagagaataa aaaataactg   12060
gtattctaac ttcagtttcc tttgaagtct tgttaatgag aataaatatt atgtggcaca   12120
aagaaaaaga aaacaggggt ttacacagga tatgctgcca gactttacca acaatgacac   12180
atgatatctg cttcaactgt cccatgcata tttggcttaa gatatattca tgcatatcaa   12240
attttacatc acatggtttt caaaagaaga ttcattaaaa ttagcttaag aatgtacaca   12300
atatacaata cctcattaaa taaaaagaac agaccatttc caaatgaatg ctttttagagc  12360 tttacagtaa acagtctttt ggtggtagaa agagggggaa cagagagggg agtgggtggg   12420
agtctgtagc acttatcaga ctactttttat cctttatgta gagaaatagg agagttgaaa   12480
ataagcactt tctgtactta tgttgagagt ctgaagccca cttttaatag tcttgacaac   12540 actaaaaat aataattaac atttgaaaag ctgtcattat tatagtcagg gacacttaat    12600
ctccaaagga gaagtttctt aattgatact atgattaaat aaaagcatcc atcagaatta   12660
tatccacaat ctggtttgga gtttatgttt tgtcttatttt aaattgttat acttattata   12720
attctgtcta gacagtgcca aatgtacttt gtcatacaaa cacttgaggc aaattttctt   12780
caaataagcg caacactttg tttcctcttc gtatcctttg actgaataac gtgtggtaca   12840
gagaagtaat acttcccttt cttgggatcg agatcaattt gatgcttgtt ataagcccat   12900
ttacagaaca aatggtattg cttttaaatt tttatatgaa cttatcagta gactagccaa   12960
aaaagaagct tcatataaaa gtgctaggat tgatattctt agtaataatt aggtaaattc   13020
tctaaaattt tctcccaaaa gatctgaaaa atcataccaa gggaagtata gtttaaattt   13080
cattatatat aatagcttta aaatatcttt gctaattcta cccaaagcca cactaaaaag   13140
actaatacaa aaagaatgta attaataaac tattttcctc tgaagaatca aagggcactt   13200
ctgcatatga acatgtttta tccttttggt gtacttacat aaaataatta agaaacactt   13260
ttaattagta taaacaaaga aatcaaaata gcaagaagaa atgtctgagt aaaagcagct   13320
gtgctgacct caaaagtgaa attctgttct cttgatgccc agttaagtgt ctaacccagg   13380
```

```
gaaaagtgat tctaaacctg ggctaggagc tagtggagct cttcaaacag tctcacctac   13440
cctcacccct caaggaatgg tctatgggtt ctgtggtgaa cgctaaagtt tataacatgg   13500
gaatatttat tattttgttt ctaacacaaa taatttttaa aaatttattc tactaaagta   13560
acatcaaagg gaaatttcat aaaaattctt ttgaaatttt tagaagtagc aaataaaggc   13620
aagtgataaa tattttacag atttcaccac ttacgtaatc tgatcaacaa attttaaaaa   13680
catagcactt gaatactatt aaaaatatat taaaaaggta acatagtaaa actataaaat   13740
tctttaaaaa aaatataaga ggaaaccttc gtgaccttgg attaggaaat ggtttcttac   13800
atacggcaac ctaaaaatac aagcaaccaa agaaaaaaac agacaaactg gacttcatca   13860
aagttaaaaa cttttgttct tcaaatgaca tcatcaagaa aataaatccc acagaatggg   13920
acaaaatatt tgcaaaccat atctgataag agaccactat tcagaatatg taaagaattt   13980
gtaaaactta taaataaaaa gttaaagaag tcaattttaa aatgagcaaa ggatctgaag   14040
acaattctcc taagaaatac gaatggctag ttaaatgcat gaaaagatgt ttagcatcac   14100
tggtcattag gaaagagcaa aaaccaaaat gatatactcc ttcatacccca ctaagactgc   14160 tgtaattaaa actatagaaa ataagcgttg gcaaggatgt ggacaaattg gaaccctcct   14220
catacactga tggtagaaat gtaaaatggt gcagatgctt tggaaaacag tctgacaata   14280
ccccaaaggt ttaaacgtgg aattaccatg caacccagca attctactcc taagtatcta   14340
cccaagagaa atgaaaatat atgttcacca aaacatttgt acataaatat taactgcagc   14400
ttttattcat aatagccaaa aagtggagac aatcccacatg tctatcaatt ggtgaattga   14460
taaacaaaat gtggtatctt catacaacta ttactgggcc ataaaagaa tgatgtattg   14520 atacatgcta caaaatgaat gaaccttaaa aacaatatgc aagcaaaaga aaccagacac   14580
aaaaggccat atattacatg atgctaatta cataaaatgt ccagaaggga gaaataaatt   14640
agtagttgcc aagggctgga gggagggggga atgatataag tgactgccaa tgggcatggg   14700
gtttcttttt agggtgatga aaatgttctg aaattttatc acgggaatgg ttgcacaact   14760
ctgtgtaact tagaattcag tgactcctaa aaccaatgaa tagcatgctt taaaaggtga   14820
cctttgctga gcatagtggc tatagtccta gctacttggg aagctgaggc aagaggatca   14880
cttgagccag gagttccagg ctgtactgca ctatgatcat acctgtaaat agccaccata   14940
cacaccagcc tgggcaacac agaccatgtc tctaaataaa taaacaaata aataaataaa   15000
agggtgacct ctgtagtatt gagattatac ttcaagtaag ctgttattaa aaaaaaaaaa   15060
gttatcatat gggtggcagg ggaaatcatt ctgggatgat ggctaacttc atcagtatt    15120 gatttatacc tatgcatcat acctatgtt tgttttatgc attttgtggg ttttttaaaa   15180
aaattatatt tcataaaaac aaattttaaa aaattaaag tcaagaaccc caaaacaaca    15240
aagatcagag atacatttct accttatcaa ttcagaaaaa ttacaagttt ttttcttaaa   15300
aattgtatag catcatggtg attttaagtt acctgtagga atttaaataa ctttgtctta   15360
actgttcacc aaaactcatt taatattcat gttctgatac tgaaaatgaa gctgaaaagt   15420
tttgaaatta caatatgcta gtttaaaaag gtttactaaa atacataatt tcattataag   15480
gagtaatatg aaataaaagt atcaaatatg ggaccattaa aaatgtcctt actaacaaat   15540
tgctacccac attgtggact cactgcgtcc actgtttgcg agcttttcca gaacgctcgc   15600
caccagttag ggtagccaag aactcctcat cttcactttc ttcctcacta gcttggaacc   15660
tctggattcc cacccacact gctgtgacct gaatggggaa gagaaacgcc atagtaaggg   15720
```

```
aactcttcct tttatagatt tctgaattag aatctggcat tacaaaagaa caatgttata    15780
aatccaggtc agagtttata gttctatttc actattactt atatggcttg tcctaggaac    15840
ttaactatta tttacaatgt aagtacctat ttccacaaaa aaattcaaaa ttttggaata    15900
caatatctga agagagaatg gtctattgaa tccaaagtag gctgatacat cccaacagta    15960
tttcagattg agataataat aataccacca attcatcaag tcaaattata tgcttatttt    16020
ccacaatgga agttttaaaa tagtataaac attttaatat atagcaggct taacttatga    16080
ttattaaaca gggttctaag aaaatagtat acatcaaata ttaatgtgct tcttgtataa    16140
tttaggtgac aatttatcca tctgagaaat gcaaaagaga ctttggtaag gggttgagta    16200
aggagcattc tgtgtcaaag aattcactag caaagaggg tatactgtag ttacaagcta    16260
taatcactgt acttatttta aatccctctt cagaaccagg tcttaaaaga tgataaacat    16320
ggcctcatga ataactatca accaaactat agaaagagt gcaagagtgt ggtgttctaa    16380
cttaaaatat ggtgttttat tcaaataatt ttatttaagg ctccaaaagc agcagcctca    16440
ttccccagaa atcatagtta aatgaaatct tccttactaa aggaaaaatg aatcacaata    16500
tttaacgtga acattttaaa aacactctaa agcaacaaaa ctattcaatt gtatgtgata    16560
tggcttagaa aggcatgtag gtaaaaagga ctaaaaactc taataatggt tgggccaaaa    16620
gtaaatttgt tagttctact ccattaagca ttccctcaagc agtgtaaaaa tcagagttca    16680
agttacactt tgatgtgtag atcctttgaa agccactcta ccctgtttta tatgaagcat    16740
ccgcagctaa aatgaacacc tagtgaagag tatgaatgct gcaatacata agcagacgtc    16800
agaattgtcc caagctgatt ctaagttact ttaaacatgt atgcagagtc agaatatgac    16860
ttacttctta gaagtaacag ataattacct ttggcataat gaaaaaaact ttaaatgtaa    16920
gttaatacag gtattttccc tttagcaaag ctttgctttt aaaagaaaac ttcaaaactt    16980
aaattaaaat aggaaatgct ctactatgta gtaaaaatac ttttttagatt actgaagcaa    17040 agaaaaggaa ggattctatg agggaggaaa agtgggagaa aaatgtaaag aaaaaaagga    17100
agaaggaaag aaaagagaaa aggaggaaag aacacaagga cagaaaggcc tattgaaata    17160
tattatttct ttcaaatttt aaacgagcag aataaattct tttgttttat aactatgaaa    17220
taatctatgt tcctcttatc tatgcttgga aaatttagac aaaatgttaa gagtaagtac    17280
tacattggat ttccgggtct tcagctctga aaacaagctg tttcttaaca tacgtcaatt    17340
ttctatattt catgtcattt ctatttgcaa atgttataaa gttcaatatg atgtaaaaca    17400
tggttaaatg aagttcaaaa ataagtataa catacattag tttggctatt ccaaatttca    17460
tgcacattaa ctcagccaca catctaacac agtcagccct ccctatccag gggttctgca    17520
tctgcagatt caactaacca tgggtcgaaa atgttttgt accaaacatg tacaggcttt    17580
ttttcttgtt atcattccct aactacagta taacaactat tttcacagtg tgtacatgtg    17640
tatgaaatat tataagtaat ctacagataa tttaaagtat acaagagggt atgcataggt    17700
tatatgcaaa tactacacca ttttatatca gactctcaaa catcagtaga atttggtaac    17760
ccagggaggt cctggaacta atcacccaga ggtatcgaca gatggctata tataaatcac    17820
tcagtgaatt caggattcac attatttcac aactagtata attttatgtt gttcacataa    17880
ttgtgtcaca acatatacat gcagacaggt gactttcatg aaaagattac acccaagata    17940
gacatatggt ctactcaaat acggtttcca aatgtgtatc caatcttgtt taattataat    18000
caaactcacc attccattga taagcgacct ctaccaacct gcttatcccc tccaagcaat    18060
ataacagtgg ttctctgaac caatattgac cctccttttaa attgatagcc ttttttttaaa    18120
```

```
aagctaacca ttgagaagta catactgttg aagacagaac atattctgta aaatgctccc   18180
aagatatcaa agtcagatga tacaactgaa tgtttatgct agattatatt tctaagctga   18240
gaattacatt ttaatatacc ataagcaatc tgcaaaagaa gcaacttgcc taaagatttc   18300
aggagtttca agtatgcata tgtcaatatc tgtatcaata tgtaatatca atataatcaa   18360
tgcacacaac aatacgtaac tgtacttata tcatctcctt agcactaatt attacaaaca   18420
atctgcatgc actgcaaagc aaaagtataa tataaaatcc caaaaaacct tgaaaattta   18480
ataaaaccaa aaaacaggca tcacacacaa gaactgaggc gtatacttca ttaatgagta   18540
tgatatcctg atatgaaatg tcaaacaaaa ttacccaggc tcaggttaga aataaagata   18600
ggacattagt ctttgtattt ttaaattgat tttttcttct aatattcctt aatgataacc   18660
ctatatatta cctacttaaa attattagca aatagttatt ttaaaagtat gagtaattag   18720
accaaaagca actctcatat ttacccaaaa gaaggaacca ctaccaagaa tcaaagccta   18780
gtaattctgt tcttaacaga caggtgttgt gtattctggc atgttacatg aaaatcactt   18840
atgagaagaa cagaaaaaaa aattagaagg tagttttcac tatggaaata ggtaagtgat   18900
taagcagatt ttcttacacc atgaaattgt cagcagactc aataatcacc ctaaggggca   18960
tcattctgga tgccgacatt ctctatgatg gaaagggact gaaagtaaaa tgcactaatg   19020
acataaagaa accaatatcc aatagtaaag ttgaagaaat aaacattctt tggacaggaa   19080
ctaagctgaa gtttgcaact accaagaatg tattatgcca gcagtaaatt aggaaactaa   19140
agcccatgtc aaccaatgaa aaatggggagg actgaaatca atcattaaag cagcagcaag   19200
gttctaacta ttctaaggta taggctacct ctggcgtata ttatcagagt tgacaattct   19260
tccaagaaat tctaacatca actgtaatct gaggtccttt aaaaaataat ataaaccagg   19320
cagtagactt acattttgta atattttctt ctaagagctg tacattaaga ttttatttgt   19380
gatataaata ctatcaaata attagctata gaacagctct attttcaaca gttataacat   19440
tttaagccat ctcacattta acctaaactt ttatcaaatg tcaaaactga ggccgggtac   19500
ggtggctaac acctgtagtc ccagcacttt gggaggccaa gatgggcgga tcacttgagc   19560
ccaggaattc gagaccaacc tgggcaacat ggtgaaaccc catctctata aaaatacaa   19620 aaattagctg cgcctggtgg tgtgcgcctg tagtcccagc tactagagag gctgaggag   19680 gagaatcacc agggcctggg agatcaaagc tgcagtgagc tgagatcgtg ccactgcact   19740
ccaccctggg tgacagagtg agaccctgtc tcaaaaaaaa aaaaaaaag aaagaaagaa   19800 aaaaaaatca aaactgatca cttgaggtcc aacttatgtt tactatatct acttatattc   19860
ccaaagacat cttaaggaga gatgaaatca taaaaggtg aggatgagaa agaaaatagt   19920
aagtcagtaa ggtcaatttt tacatatatt aggctagcat aataaaaata tgagtgtctt   19980
attattattt ttttttgaga cagagtcttg ctctgttgcc caggctggag tgcagtggtg   20040
caatcatggc ttactgcaat gtctgccttc caggttcaag caatccttgt gcctcagcct   20100
cctgagtagc tgggattaca ggtgtgcgtc accctgccca gctaattttt gtattttcag   20160
tagagacagg gtttcaccac gttaaaccat gagtttggcc aggatggtct caaactccca   20220
aagtgctagg attacatgcg tgagccactg cgtctggcct aaagtgtctt attataacca   20280
agaatttatt tgtggagaga ggtaaagaaa actcattttt agtgaaataa ttaaaactgc   20340
atcattcaca atctatcttt caaaatgagg tattaactat tttggcttct aaaattaccc   20400
catatactac atgcatgagc atgggaattg aagttatttt attcctaagt ttgagacttc   20460
```

```
atgttttaat gtgatcacta aaaatttcct aattgatgat taggaaaata actttctgta   20520
aaattccaga attttagctg tttcaatctc ttcatattaa ggggagaaca ttatgttttt   20580
actttctgtg catgcacttt ctttattaga agaaaatgga ctgagggcag taagcaaccg   20640
aaaaggaaga gtaataagaa gcctgatgtg tgtgaaaact ggagaacagt ctcaaatcat   20700
aaaaagttat gacagaagag gcataaaaaa taaaagtaat gaacttaata tatgaaaggt   20760
aataatgatt aagagcatag gctataaagc cagactggac tccctggatt caaatcctgg   20820
ctcttctaat tactaggtag gtaaccctga gcaagtttca atgaccaatc tttttctcaa   20880
ttacctcagg tatataaagg ggacagtaac agcatttaac ccagaggaca ataaggatta   20940
aataaataca tgtaaaataa tttaaaacag tacctggtat tcaataaagc gcaataaatg   21000
ttagctgcta ttattattca tctaaacttt actttcatta ccagcaatat ttttaatct   21060
taaaaatatt gaataaaaca atgacctagc ttagtaaata aattcataat gagaaaatgt   21120
tgatttcatt taataataac tttagtagtt tgggataaca ctttgcatat tttaatttcc   21180
ccagctataa ataactcaaa taatttgcca tcagatgatc tgttatttg aagttaacaa    21240
ataaagcatt tcctaaaaaa gttctaatac ataacttttg ctctcatctt atgttttaaa   21300
aacaaaatgg caaatcatct gcatcaaata gttcctactc ttataacatg acaattgttt   21360
taaaatatat ctgctggaaa aagcaactga agtcctagaa aatagaaatg taattttaaa   21420
ctattccaat aaagctggag gaggaagggg aaaaacatat ctgccaaata agcttataat   21480
taatagttgt tttcagtttt caaaaatcca cataggaagc aatttaagcc taaattgcct   21540
aagtctcaat ctcagcgtag tagatagctt agggcaatca aaacttgctg tgttgggctg   21600
ccccctacag gactcaattt acctatttct tttaaaaggt gtgtaagtag gaaatatgat   21660
tcaagtttta cattaacaat attaatgcta aagcagatga ttatcattca cgcattcact   21720
ataggaggaa acagtctctg agaaccatct atagagatac agagagaaat gaaacaatcc   21780
ttgtccttga ggaattaata gtttactgct tacagagaaa ctacatacat ggtgaaatat   21840
ttaaaaatag ctcatgatat cctctatgat attatgtttg ctatagaaaa agaacaaggc   21900
tgaagatcta agatccaagt tctactgttg gctctgccat caaacaataa gctaaacaat   21960
gtacaagtca gttttgggga agctgtctta ttcccaaaat gaggaggtta aattagttaa   22020
ttcttccagc ctctatggct ctaatattcc acagttacat ttgtcaaaac aaaaggtaga   22080
aggaaatgtt tcaaaaacag acttcgcaga aagaacatct atatgatatg aagggctggg   22140
gcatatgtga agaaatcaag gaagacttct tgaggaaggt gacatctgaa gtaactttag   22200
aagcactctg ggagccaagg ctattcccag gagttaacag agtcagataa taaaagatca   22260
aagatgttta ggggaatagc atgcagtgtt atttggttgc agtctagcta tattttagga   22320
aacatcaaat taatatcagt ataaaactca acagaatgga gggagaaaaa gcaggtagaa   22380
aaatctaaga accactaaaa tagttcatct agaagataaa ggaccatga gctaaatcag    22440
tgcaaatggc aagaagggaa taaatgaaga cagttctggt ccattagaac tgcaactcaa   22500
caaaagtgat caaaagagtt attccaaagt attgacctgg taacttgaag aaaagtaaag   22560
aaagaggaaa ctggacactg aaacagaaga agtagattat gtatttggta gtgaatggaa   22620
gtagattggt gggaccagtt agaacctcac agagaagaac tatgttaaga ccagaaatac   22680
ggccaggtgc ggtggctcat gcctgtaatc ccagcacttt gggaggcctg ggtgggcgga   22740
tcacctgagg tcaggagttc aagaccagcc tgacaaagat ggagaaaccc tgtctcccct   22800
gtctgtacta atacaaaatt agccaggtgt ggtggtgcat gcctgtaatc ccagctactc   22860
```

-continued

```
aggaggctga ggtaggagaa tcgcttgaac ccgggaggcg gaggttgcag tgagctgaga    22920
tcgcaccatt gcactccagg ctgggcaaaa agagcgaaac tcttgtctca aaaaacaaac    22980
aaacaaaaca aaacaaaaca cagaaataca tcaattaaaa aagtgagcta ttcaccagat    23040
atgttccact ggtcataaaa caaaagaata caggaggcat gacaagccat catcattgct    23100
gttaaaataa ctcacagcaa aattataatg atttaagtca ataacatcta ataattccag    23160
ctatagtgtg caatttaatt tattatgtgc caggcacaat agtttattaa aggtattacc    23220
tctaattttc acaataaccc tattttacag attataaaat ggaggcccag agatgtaagg    23280
tgaacgagcc aaatcaccta gttacctgga atataaactc agaactgcct aaatcaaaag    23340
ctctcaatct taaccacatg ctatactgat gcatgtcaaa gattcaattc attcagattt    23400
ttcaaggtta tcggaaaacc tatgtagata aaaatttcca aaataatcaa ggatatgtaa    23460
cttttacaga aagcaatcac tgatcatcta ttgcaatact catgttctta agcaatatac    23520
tgagttgaaa tttttatatt ttataaataa ttagaaagaa tacatttttt aaaactttaa    23580
aaaacacctc agtttttatt ctcttcccca aatttcaaca aaatccattt atccaaactt    23640
gaggttgaat cattaaagtg gtgatatcat cagtaatagc agagtgagga ccctgaatat    23700
actctcctcc ataaaagcaa caagaacaca aaaattctca aaatgaactt tttctgaaat    23760
cttttcaaaag ccccactctc agaaaactgt cattatttga tctgccagtt ccctagaaaa    23820
acctccctca taggacatta tttgacttga ctcagagctc actcagtgca aacaatttta    23880
tcaccaggag agtttgtgga aaatcagtgg caattgttaa acatcacatc tgccatgaga    23940
tagcaataac agatgggaca aacaagctaa ccaaaaaatt aaaagaaaaa cctgggaaat    24000
aagaaatcca aaggggtct gaaaagttct aacatatttc tgataatcca gaaagccata    24060
cacatgtata gagctgtgta cacgctcaaa aaacatctac gaaggcccta aactctcacc    24120
tatgggaaac cctgaggctc tgtacaagaa gaaagtaaaa tccagttata aattgcttgc    24180
cgtatcattg aaggcaatgc cccaacattc acacataggc ccctggcaaa gattggaaga    24240
tactctagtt ctaggcattc aagaaaatct cttctaatca tcagatgatc actaaactca    24300
ccaagcagta actttagggg cctgtgtgat aaaaaataaa aacctgaaag aattagttca    24360
ggaaagaaac taaacaagca acagcaacaa caaaaacaga ccttgggaaa ggggggaagc    24420
atctggtttc cagagttatt ctgttatact atataaaata ttcaggtctc aacaacaaca    24480
aaattacaaa gacatgcaaa gaaacaagta taagccacaa actgggggga aaaagcagca    24540
gaaactggcc ctgaaaaaga ccagatgctg gacttactgg acaaagactt taagagagtt    24600
attttaaata tgcgcaaaga actaaaaaaa agtttatcta aagaactaca ggaaagtatc    24660
agaacaatat ttctgatcct tcagaagaac cacttttttgt cactacagat tagttctgtc    24720
tggtctagaa cttcttaaaa acagaatcat agagtatatt ctctttatat cagctctttt    24780
tactcaacac aatgttgtgt gagatttatc catgttgttg catgtatcat tcccaaacag    24840
aaatagaaat tatagagata aataggagtt acaaaaaagt accaaacaaa aattctggag    24900
ttgaaaagca caaaaactga attaacttga ggggctcaac agctgatttg ggcagccaga    24960
agaatgaatc agcaaatcta aagataggtc aattgcgaga aagagaggga agaaggaagg    25020
aaggaaggaa aggaggctca gagacccaag agacaccatc aggcatacca atatacatat    25080
aatgagaggc ccagaagaag atgcagaaaa agggtcagag tatctgaaaa aataatggcc    25140
ctaaacttcc cgaacttgac cccaaaaatt aatctacaca tccaagaaga taaacaaact    25200
```

```
aaaaagaata aaatcaaagc gatccacacc taggtacatc ataatcaaat gactgaaata    25260
taaagagaga ctctcaaaac aggcaaggga cttatgtaca aaacatcttc agattaataa    25320
caaatttctc atcagaaatg atgttgtcaa taggcaatca gatgacataa tcaaagcact    25380
gaaagaagta gaatgtctgg gacctggaat gctggtggac acctgtaatc tcagtatttt    25440
gggtggccaa ggtgggagga tcacttgagg caaggagttg aagaccagcc tgggcagcag    25500
aaagaggctc tgtctctaca aagaataaaa agattggctg aatgtggtgg tgtggacctg    25560
tagtcccagc tactcaggcg gctaaggtgg aaagatcgct tgagcccagg agttggaggc    25620
tgcagtgagc tatgactgtg ccactgcact cttgcagtgg agaccctgtc tctataaaga    25680
aaaaatgtca accaaaaact acatgcagaa aaactgcact tcaagaaatg atcagtacct    25740
tgaagctctg aaggtgctta agactgtaga tcaataccat agaaaataat ttagtattta    25800
ggaatgtaag aaaattaaga cagccttgtt tgataactac acataatact gtaactgttc    25860
ttgcactgtt ctggttattg tcaagctatg agcacaaact gatgactgaa atacagaata    25920
cagaacagga tataaaatct tatcaggtaa agttaggcaa gcaattacta gttgtaattc    25980
aacttgaagg agaaggaata aggaaccaac tcaaaccagg cagcaatgaa ttgtaaaaaa    26040
gcttaaggta aaacaaacag ggaaataaaa caactcagaa cctaagcata tcgtaagaac    26100
ctaatctaac aaggaggggc ttaaactgat tattttacag cttgggtgca attatcccac    26160
aaaaaacttt caggagtttc accagtccat aaactatttg gttattagaa aatagcttta    26220
ttgggctacc ctctttgggt cccctccctt tgtatgggag ctctgttttc actctattaa    26280
atcttgcaac tgcactcttc tggtccgtgt ttgttacggc tcgagctgag cttycactct    26340
ccatccacca ctgctgtttg ccgccatcgc aggcctgcca ctgacttcca tccctctgga    26400
tctagcaggg tgtccgttgt gctcctgatc cagtgagacg cccattgccg atcccgactg    26460
ggctaaagac ttgccattgt tcctacgcgg ctaagtgccc gggttcatcc taattgagct    26520
gaacactagt cactgggttc cacggttctc ttctgtgacc cgtggcttct aatagagcta    26580
taacactcac cgcgtggccc aagattccat ttattggaat ccatgaggcc aagaacccca    26640
ggtcagagaa cacgaggctt gccatcatct tagaagcagc ccgccaccat cttcggagtt    26700 ctggagcaa ggaccccctg gtaacaattt ggcgaccaca aagggacctg aacccgcaac    26760
catgaaggga tctccaaagc ggtaatattg gaccactttt gcttgctact ctggcctatc    26820
ccttagaatt ggaggaaaat actgggcacc tgtcggccgg ttaaaaacga ttagcatggc    26880
cgccagactt tagactcagg tatgaggcta tctgggaag ggctttctaa caaccctcaa    26940
cccttctggg ttgggaacct tggtctgcct ggagccagct tccactttca attttcctgg    27000
ggaagccaag ggctgactag aggcagaaag ctgtcgtccc gaactccggg cattagccgg    27060
ttgagatcat gtcgcagcca gaagtctcta ctcaacagtc gcccatgcgt gcgctcctac    27120
cttcccttct gtcccacacc tcctgggtcc caaccacgac tttcttgaaa gtgtagcccc    27180
aaaattctcc ttacctctga atctacttcc tctgatccct gcctcctagg tactaatggt    27240
tgagactttc atttcctcta gcaagttgta tctccaaagg gatctaagga agctctatgc    27300
tgcgccctta ggcatctagg ctataaaccc agggagtctt gtccctggtg tccctcctga    27360
tttaggtata cagctctaga catgggcagt tatgtggcac ctgttcccca ccaccttgc    27420 cagggcccca agtttgtaaa tggctaagag aggaaacaga gagagacaga gagaaagaga    27480
cagtgagaga cagacagaga cagagagaga gagagacaga gaggagagag agagagacag    27540
ggaggacagg gagagagaca gagaggagag ggagagagac aaagaggaga aagaggcaga    27600
```

-continued

```
gagacaaaca gggagtcaga gaaagaaaga caaagataga aatagtaaaa aaaaacagtg    27660
tgccctattc ctttaaaagc cagggtaaat gtaaaaccta taattgataa ttgaaggtct    27720
tctccgcgac cctataacac tccaatacta ccttgttgtc agcgtaaaca agggcgtagc    27780
ctgaaaacac taagaccact gacaacccat agccttccta tcaaaaatcc ttaacatcca    27840
gtgacctgcg gatggcccaa atgcattcaa tctgtagcgg caactgcttt gctaacagaa    27900
aaaagtagaa aagtaacttt tagaggaaac ctcattgtga gcacacctca ccggttcaga    27960
attattctaa gtcaaaaaag caaaaaggta gcttattaac tcaaaaatat taaagtatgg    28020
ggctattctg tcagaaaaag gtaatttaac actaaccact gataattccc ttaaccctgc    28080
agatttcctt acaggggatt taaatcttaa ttaccataca aaggtccgac cagacctagg    28140
aggaactccc ttcaggacag gatgatagat ggttcctccc aaatgactga ggaaaaaacc    28200
acaatgggta ttcagtaatt gatagggaga ctcttgtgga agcagagtta gaaaaattgc    28260
ctaataattg gtctcctcaa atgtcagagc tgtttgcact cagccaagcc ttaacgtact    28320
taccgaatca aaaagactat ctcaatcctg actcaaaagc ttacttatac cctctctgaa    28380
acgaatttgc ctaagaactg ttgtttatgg gaatgcatct tgatggagca gctgggttgt    28440
tatgaaatac tcaggaactc agcctagctc taggactcac ccctgagcac aaaggcaatg    28500
ttgggcacgc tggtaaagga ccactagaat ccagcagccc ggaccccttt ctttgtgatc    28560
aagaaaggcg ggaaaagggg tgagggctgc tacatcagtg agcataacta atccgataag    28620
cagaggtcca tgggtggtta cacccccgg aaaggaataa gcattaggac catagaggac    28680
gctctaggac taatgctcat cggaaaatga ctagtggtgc tggcatccct atgttctttt    28740
ttcagatagg aaacgttccc ctcaaggcaa aaacacccct aagatgtatt ctggagaatt    28800
gggaccaatt tgactctcag atgctaagaa aaaaagaca tattcttctg cagtaccgcc    28860
tggcaacgat atactcttta aggggagaa acctggcatc ctgagggaag cataaattat    28920
aacaccatct tacagctaga cctcttttgt agaaagaag gcaaatggtg tgaagtgtca    28980
tacgtacaaa ctttctttc attaagagac aactcgcaat tatgtaaaaa gtgtgattta    29040
tgccctacag gaagccctca gagtctacct ccctacccca gcatccccca gactccttcc    29100
ccaaataata aggaccccc ttcaacccaa acggtccaaa aggagataga caagggggta    29160
aacaactaac caaagaatgc caatattccc cgattatgcc ccctccaagc ggtgggagga    29220
gaattcggcc cagccagagt gcacgtacct ttttctctct cagactttaa attaaaatag    29280
acctaggtaa attctcagat aaccctaatg gctatattga tgttttacaa ggtttaggac    29340
aatcctttga tctgatatgg agagatataa tgttactgct aaatcagaca ctaaccccaa    29400
atgacagaag tgtcgccgta actgcagcct gagagtttgg cgatctctgg tatctcagtc    29460
aggtcaatga taggtcgaca acagaggaaa gagaacgatt ccccacaggc cagcaggcag    29520
ttcccagtgt agaccctcac tgggacacag aatcagaaca tggagattgg tgccgcagac    29580
atttgctaac ttgcgtgcta gaaggactaa ggaaaactag aaagaagcct gtgagttatt    29640
caatgatgtc cactataaca cagggaaagg aagaaaatcc taccgccttt ctggagtgac    29700
taacggaggc attgaggaag cataacctctc tctgtcaact gactctactg aaggccaact    29760
aatcttaaag gataagtttta tcactcagtc agctacagac attaggaaaa aacttcaaaa    29820
gtctgcctta ggcccggaac aaaacttaga acccctattg aacttggcaa cctcagtttt    29880
ttataataga gatcaggatg agcaggcaga atggacaaa tgggataaaa aaaaggccac    29940
```

```
cgctttagtc atggccctca ggcaagcgga cttttggaggc actggaaaag ggaaaagcta   30000
ggcaaatcaa atgcctaata gggtttgctt ccagtgcgt  ctacaaggac actttaaaaa   30060
agattgtcca aatagaaata agccgccccc tcgtccatgc acctcgtgtc aagggaatca   30120
ctgtaaggcc cactgcccca ggggacgtag gtcctctgag tcagaagcca ctaaccagat   30180
gatccagcag caggactgag agtgcccggg gcaagcacca gcccatgcca tcaccctcac   30240
agagccctgg gtatgcttga ccattgacgg ccaggaggct aactgtctcc tggacactgg   30300
tgtggcctct tcagtcttat tttcctgtcc cagacaacgg tcctccagag ctgtcactat   30360 ccaagggggtc ctaggacagc cagtcactag atacttctcc cagccactaa gttgtgactg   30420
gggaacttca ctcttttcac atgcttttct aattatgcct gaaagcccaa ctcccttgtt   30480
agggagagac attctagcaa aagcaggggc cattatacac ctgaacatag gagaacaccc   30540
gtttgttgtc ccctgcttga ggaaggaatt aatcttgaag actgggcaac agaaggacaa   30600
tatggacgag caaagaatgc ccgtcctgtt caagttaaac taaaggattc tgcctccttt   30660
ccccaccaaa ggcagtaccc ccttagaccc gaggctcaac aaggactcca aaagattaag   30720
gacctaaaag cccaaggcct agtaaaagca tgcaatagcc cctacaataa tccaacttta   30780
ggagtacaga aacccagtgg acagtggagg ttagtgcaag atctcaggat tatcaatgag   30840
gtcactgtcc ctctatacct agctgtacct aaccctttata ttctgctttc ccaaatacca   30900
gaggaagcag agtggtttac agacctggac cttaaggatg cctttttctg catccctgta   30960
catcctgact ctcaattctt atttgccttt gaagatcctt caaacccaat gtctcaactc   31020
acctggactg tttcacccca agggttcagg gatagccccc atctatttgg ccaggcatta   31080
gcccaagact tgagccggtt ctcatacctg ggcactcttg tccttttggta tgtggatgat   31140 ttttactttt agccgccagt tcagaaacct tgtgccatca agtcacccaa gtgctcttaa   31200
attttctcgc tacctgtggc tacaaggttt ccaaaccaaa ggctcagctc tgctcacagc   31260
aggttaaata cttagggcta aaattatcca aaggcaccag ggccctcagt gcctattctg   31320
gcttatcctc atcccaaaac cctaaagcaa ctaagaggat tccttgacat aacaggtttc   31380
tgccaaatat ggattcccag gtacggcgaa atagccagac cattatatac actaattaag   31440
gaaactcaga aagccaatac ccatttagta agatggacac ctgaagcaga agcggctttc   31500
caggccctaa agaaggccct aacccaagcc ccagtgttta gcttgccaac ggggcaagac   31560
ttttctttac atgtcacaga aaaaaacaga aatagctcta ggagtcctta cacaggtcga   31620
tgagcttgca acccatggca tacctgagta aggaaattga tgtagtggca aagggttggc   31680
ctcattgttt atgggtagtg gcggcagtag cagtcttagt atctgaagca gttaaaataa   31740
tacaaggaag agatctgtgt agacatctca taacgtgaac ggcatactca ctgctaaagg   31800
agacttgtgg ctgtcagaca accgtgagga agtaactaa aatcgtaaat ccccatggcc   31860
ctcccttatc atattttcct ctttactgtt ctcttacccc cttcactct  cactgcaccc   31920 cctccatgct gctgtacaac cagcagctcc ccttaccaag agtttctatg aagaatgcgg   31980
cttcccagaa atattgatgc cccatcaaat aggagtttac ctaaaggaaa ctccaccttc   32040
actgcccaca cccatatgcc ccacaactgc tataactctg ccactctttg catgcatgca   32100
aatactcatt attggacagg gaaatgatt  aatcctagtt gtcctggaag acttggagcc   32160
actgtctgtc ggacttactt cacccatact ggtatgtctg agggggggtgg agttcaagat   32220 caggcaagag aaaaacatgt aaaggaagta acctcccaac tgacccgggt acatagcacc   32280
cctagcccct acaaaggact agatctctta aaactacatg aaaccctcca tacccatact   32340
```

```
tgcctggtaa gcctatttaa taccaccctc actgggctcc atgaggtctc ggcccaaaac    32400
cctactaact gttggatgtg cctcccctg tatttcaggc catgcatttc aatccctgta    32460
cctgaacaat ggaacaacta cagcacagaa ataaacacca cttccgtttt agtaggacct    32520
cttgtttcca atctggaaat aacccatacc tcaaacctca cctgtgtaaa atttagcaat    32580
actgtagaca caaccaactc ccaatgcatc aggtgggtaa ctcctcccac acgaatagtc    32640
tgcctaccct caggaatatt ttttgtctgt ggtaccttag cctatcgttg tttgaatggc    32700
tcttcagaat ctatgtgctt cctctcattc ttagtgcccc catgaccatt tacactgaac    32760
aagatttata caattatgtt gtacctaagc cccacaacaa aagagtactc attcttcctt    32820
ttgttatcgg agcaggagtg ctaggtggac taggttctgg cattggcggt accacaacct    32880
ctactcagtt ctactacaaa ctatctcaag aactcaatgg tgacatggaa tgggttgccg    32940
actccctggt caccttgcaa gatcaactta acttcctagc atcagtagtc cttcaaaatt    33000
gaagagcttt agacttgcta acctctgaaa gagggggaag ctgtttattt ttaggggaag    33060
aatgttgtta ttatgttatt ttagcggaag aatgttgtta ttatgttaat caatcctgaa    33120
ttgtcacaga gaaagttgaa gaaattcgag attgaataca acgtagaaca gaggagcttc    33180
aaaaacacca gaccctgggg cctcctcagc caatggatgc cctggattct ccccttctta    33240
ggatctctag cagctctaat attgatactc ctctttggac cctgtatctt taacctcctt    33300
gttaagtttg tctcttccag aatcaaagtt gtaaagctac aaatcgttct tcaaatggaa    33360
ccccagatga agtccatgac taagatctac cgtggacccc tggaccggcc tactagccca    33420
tgctccaatt gtaatgatat cgaacgcacc cctcccgagg aaatctcaac tgcacaaccc    33480
ctactatgcc ccaattccgc aggaagcagt tagactggtc gtcagccaac ctccccaaca    33540
gcacttgggt tttcctgttg agtgggggga ctgagagaca ggattagctg gatttcctag    33600
gccgactaag aatcccaaag cctagctggg aaggtgacca catccaacctt taaacactgg    33660 gcttgcaact tagctcacac ccgaccaatc aggtagtaaa gagagctcac taaaatgcta    33720
attagacaaa aacaggaggt aaaaaaatag ccaatcatct atcgcctgag agcacagcgg    33780
gaaggacaat gatcgggata taaacccagg cattcaagcc ggcaacggct accttctttg    33840
ggtcccctcc ctttgtatgg gagctctctc tgtcttcact ctattaaata ttgcaactgc    33900
aaaaaaaaaa tagcttaatt gaagaataaa ttaatacaat aaaaggaata cattttaagt    33960
atacagttca aactgtaaca gtgttacagt ttcaagagga ccccttcaac aagatattgg    34020
gcatttccat catgccctaa aagttccttc ttgtcccta ctggttgggt ccatctctac    34080
tacaccctcc tgacctggcc cagacttgg cctcagaaga atcattttt tgtcactaca    34140 tattagtttt gtctgttcta gaacttctta aaaacagaat catagagtat gttctctttg    34200
tattggttct ttttactcaa tgtaatgttc tgtgacattt atccatatta ttgcatgtat    34260
tattcctttt aatcctgaat agtatgctgt tttaggaata taatgcaatt gtttattcat    34320
ttacctgttg acagatatct gagctattat gatggatatt atgaataatt ctgctatgaa    34380
cacttctgta caatgttttc tcggacatat atttttcattt ttcttgagtg gagctgttag    34440
aactgttgga tcagaaagta agcatatgtt gaattttgaa agaaactggt aaactcttgt    34500
ctaaagtgat ttgtaccatt ttacactcct actaataatg tatgagagtt atatttgctc    34560
cacagccttt ttactacttt gttaatcttt ttagtactgt caacctttt aatttatcca    34620 atctagggaa cgtgaagtag tatctcactg ttatttcat tttcctgatg agtaacaata    34680
```

```
                                                       -continued
tcgtgtatct tttcatgtgc ttattagcca ttcctatatc ttttgtgaaa tagttaactt  34740
aaatttgtaa ctaaaggtgc tttcctgagt ttcaggtagt aagcctattt ccctcaagtg  34800
aataaactac agtcttggaa tgaaaaatta aacacagtgg agacattttt tgtataagtt  34860
gttttactct gtgtatgtct ggtttgctta gtctattatt atatgcccca tgaaagcaaa  34920
cacagtgctt atttcactaa tgagtatcac tagcacatag aactgtgctt gcccaaagca  34980
tgaactcaat aaatatgtta atgtgtatgc atgcacatac atctacatgc atgtacatct  35040
atacacacat ataaacatat attaattttt agacccacaa atctaagaaa actaattctt  35100
gagcctctgg tttgaagaat tctcaaatta ttaacatatc tttatgttcc actccacatc  35160
cactgtacct gaaatagccc tactgttcta ctttggtaaa tcaggcaaat ttaattttt   35220 aaataattaa gattccaact aattttaaaa tataatttga agttaacaa tgaaatacat   35280 tacataaaaa gaaaatttta aataaaagca aaactaaacc caataagagg aagaaagtt   35340 gggctgtatt tctttaatcc tttaaaattc aaatcacaca atgctccaat gaaatcttca  35400
ttaactgaac caaactatgc ccatgaaaga tctcatatgc aactgctaaa acctcaataa  35460
acatattcat cttcttgcaa aaaagatatt tctttataat atgcacatgc agtatatact  35520
attttgaggc agatttgtac tttagtcctt gttccattgc ttaccggctg gctgtccttt  35580
gtctggtcat tgacctccaa cttaaaaaat aatacttgcc ttgtctaccc cacagaagtg  35640
ttatgaaagt caaacaaggt agcataaagg tattttacaa gatataaagt gctataatac  35700
agatttaaaa aatcactcta catcccataa tactttgttg tacaatttta gagcaatagt  35760
agaaaataac aattattgcc taattgaaaa tccagtcccg aattccataa aatgtatgat  35820
atgaacatta tagtacatca tattacgagc cccaaataat cactgcttat atagttggtt  35880
aggatttcct tagtttgttc atatagttta tatatttatg cagtccctat tttgtgagag  35940
gcattgtgag gagcataaag acataagcac agtacagagc cttagcttct ctacatttac  36000
taaagaagac ttcttcttgg gtatttaatc aatatttaaa gtattctggg aagaaatgaa  36060
attaacttca tagactgacc ttagattact atcattacaa aaagatgcct gagtgatctg  36120
tctttaacat accagtattt atcttataac tgttatattt acttgaatca gaagtgaagt  36180 cctttaagc actaagcatc cattctatac tttcttgtct ttacatatga gatacaaatc  36240
atatttttaa aacttttatt tacttttatt ttttagagac ggagtcttgc tctgtagccc  36300
aggctggagt acagtggcat gatcttggct caccacaatc tccacctcca cttcccaggg  36360
ttcaagtgaa caaatcatac ttttaagcac agattctcaa catgtatcct agcatgctac  36420
tgccataact agggtgtgaa ttaagtatta aagacagctt accccaaata ttactgtaac  36480
atatatctct aaatgaaaaa gaacatatta caaactatac ttggatggga ttctgggagc  36540
taacccatcc ctctctcccc tttcctccaa attccatctc ctattaacac accagctctc  36600
ctgagctaag cagctcctgg ggttgggaa gggtgtacat ggagaaagct agaacctcta   36660
cagtgttttc ctctctggga ggaactagca ggcatacgaa cagaaaaagc tgaataaaag  36720
gctgaatcct ttctattcct gaggcagaca gagagaagac cagggaacaa agagacttcg  36780
accaagagcc ctgccaggta ttgataccct tgatactgag aaaatatctg ggatatgaaa  36840
tacaaatgct aaataagtat ctttgaaata ggggtaaaag aataaagggt cttgatgagt  36900
aaaatgggta gtatttttta ataacctgat aatgagcttt aggaaaaggg aaggtcaacg  36960
ttatggaatg aaaacacaga ggtaccaaat ttaaaagcat aaaaaaagt ggagggggg    37020 aacccaataa cttcatcaaa ctagcaaata acttagtatc atttctaatt agaaacgcta  37080
```

```
gaaggaaatc acttagatct gataaagact aggctataat tctaactgat gaaacactta    37140
aactgtatca attaatacca gaaaacaaac acagaaaagt ctactagaac catcattatt    37200
cagcacagtc ttggtaatgc aatactataa tagcaatgca ataaagcaag aaaaaaaaaa    37260
gtttgtaaaa acacaatagg atgagatttt tgttttttcca atgccataaa taactagaaa    37320
tggaaacaaa ataagaaaa acaaaatcta caaaacacct ggaaataaaa agaaaaatgg    37380
tctatttgaa gaaaaccta aaatctatgc agaacataaa acaaaatctg aataaaaga    37440 aatatcatgt tcttgtctgg gaagacttaa tatcataaga aagtgaatta tatcaaaatt    37500
taaatcgaaa tttaatgtat ttccatctct aatcagacag gacactatgg ggaactgaat    37560
aagtgatttt aaaagtcatg gaaaattaat aactgagaat aaccatgaaa agtatgaaaa    37620
aaggagacaa atgaattgct ccaacagata tcagaacgct aaaattaaat aaaatacta    37680 ctaggataag aaaatacata tactgatgta atgaataaag aatccagaat tagattccag    37740
taagtcaaac tactttacta taaaccaggg gtggcatatt catccagtgg gaaaaggaca    37800
gtaagaagtg agtaaactat ggcccactgg ccaaattgtg gcctctgcct attttttgcaa    37860 ataaagtttt actgggacaa agccaagcct atcatttgca aattgtctat aaatattttc    37920
atgttacaga atcacacagt ttcaacagag accatcttgt ctacaaagct gaaaatatct    37980
actatctggc ccttgaagaa agtttgccaa accttagttt atataataaa agatcagcta    38040
tctcatagac acctatctca cacaacacat tgtgggaaag gaccttcttt tttttttgag    38100 acgggtctt gctctgttga ccaggctgga ctgtagtggc atgatcatgg ctcactgcag    38160
cctcaacctc ccaggttcaa gtaatgctcc caccacagaa tcccaaacag ctgggagaga    38220
tgtgtgccac tacgcctggc taaggggcct ttttaacaga gaaagaaatc cacatactac    38280
taagaaaaag aagggcatat ttgatatata tttatatttt ttatatagat atcataaaaa    38340
tcaagatgaa ttatacagtt atattttgca atgtgtttga cggtaaaagt ttaatatcta    38400
taaaaattat tttataaaat atctttaata tatttataga tattataata taaaatatct    38460
ataaaattat tttataaaat aaaaagttaa gaagaaaaga taggcaaaac aaaatacagt    38520
gcaatttaca gaaaaccaag tccaaatggt caacaaagat aaaacagatt tataaactca    38580
ctaagtgtga gagaattatt agttaaagta aaaatatctc tctataccca caatactact    38640
aaaaatcaga gttataatgc cctattgctg gtggagatgt aagggagaa gcatgctctc    38700 atatactgtt agtgaaaatt taaactaata catttttgaa aagtaagctg gcaatttttt    38760
ttttaatctc taccttttga tgcaaaaact cattttggg tacctattcc ataccttaaa    38820
aaaaatacat atgcttactg tagtactgtt tataatggta aaaactagaa aaaagaaaa    38880 cttgatagtg aatactgaac aaattacagt gcatctacag attaaacata atgcagccat    38940
taaaaaagaa taaattaggc tgggtgcggt ggctcatgcc cgtaatccca gcactttggg    39000
aggccaaagc aggcggatca cttgaggcca ggagttcgag accagcctgg ccaacatggc    39060
aaaaccctgg ctctacaaaa aatacaaaaa ttagtcgggc atggtggtgg gcacctgtag    39120
tcccagctac tcaggaggct gaggcaggag aatcacttga gcctgggaga cagagattgc    39180
agtgagccaa gatcatgcca cagcattcca gtccaggtga cagaacgaga ctctgtctca    39240
acaaaaagaa caaattaaac cctacaactc atcaacaaaa atacccaaac ccaattcaaa    39300
aatgggcaaa ggacttgaat agacatttct tcaaggatga taaacaagca catgaaaaga    39360
tgcagagcac tattcattag tgattacatc ccacatgcat taggatggct agtatgaaga    39420
```

```
acagaaaata ataaatattg gtgaagatct gaaaaacaga aacctttgtg cactgttggt    39480
gggaatgtaa agtggtacag ctactacgga aaacagtatg gccattcctc aagaaaataa    39540
aaataaaatt atcttatgat aggaatatgc atttctgggt aaatacccca ataactgaa     39600 aacagggtgt acacccattt caacatttac atgtcaattc aactgggcca gaatacccag    39660
atatttgttc aaatattctt ctggatgctt ctatatatat gttttttggc tgaggttaac    39720
atttaaattg gtggattctg agtacagcag attaccatcc acaatgtagg tgggcctcat    39780
ctactcagtt gaaggtctta cagaaaaaga ctgacctccc ttgagcaaga aagaattcag    39840
gcaacagact gcctttggac tcaactgcaa ctcttccttg agtcaacagc ccatcccatc    39900
accctggctt ggtgagtcca gggtctgatg aggtaggctg cagactcaag gaagagctgc    39960 caaaccagg aaagccaatt cattaaaata aatctctctc tacacaaaca cacacacaca     40020
ctaccaccac caccatgatg gttctgtttc tctggagaat gctaatacac ccctgttcat    40080
ggcagcatta ttcacaatag ccaaaaggtg gaagcaactc cagcagatga atggagaagc    40140 aaatgtggt atgtatatac aatggaatat tattaagcct ttaaaaagtg gaaattatat     40200
ctatctatat ctatacacac atactcacac acacacacac acatttatag aagacagggt    40260
ttcaccatgt tgtcaaggct ggtctcgaac tcctgggctc aagcaaaccg cctgcctcag    40320
cttcccaaag tgctgagatt acatgtgtga gccaccacac ccagccaaaa aaggacatt     40380 ctgacacata atacaatata gataaacaat gaggacatca tgatatgcga ataagcctg     40440 tcacaaaaag gcaattagtg tatgattcct cttgtatgag gtacctatgg atgtcaaatc    40500
cataaagtag aatggggaaa cagagagttg tttaatgggt atagagtttg ttttgcaaga    40560
agaaaagagt tttggagaat gaatgtacaa cagtgtgaac ataattaaca ctactgaaaa    40620
tggttaagat tataaatttt atgttacatt tattttacca tgattaaaaa ttaaaacaaa    40680
ataatattaa ggaaaaatac tataaataac aacaacaaaa aaaacacctc aagcaactta    40740
cattcacctg ggaaacagaa tacatcctat tctgctagag atatatctgc agttcaaaat    40800
ttattacaaa tgatgttgtg tatcttttg aaatgactga aaaactaaat taaaagcaat     40860
aatattcagt ttactaacca gtaagtcctt ctttcatggt tcctgacttt tctgtaagat    40920
gttattgcaa gatatctact aaaatggaaa acaactgaaa aggcaaaatt ataatttctt    40980
atcaacatcg ctaaaaccct ggaggggaag aatcctaaca aacatggcca taatttgcca    41040
catatttcta ctgtcctcac ttttcaaaat ccagaaaatca acatttctgg aaacaaaaca    41100
gagtctaaaa tttggctcct tcttcagttt agaaggtgcc aagttaatcc ctgacatcct    41160
agtttccatt ttcaaaaatg tacttttct ctccccaaac cggtatctag attcttaaat     41220 attttttagca catagaagtt aaatagattt gcttaaccaa aatagccagt aaacctccca    41280
aaagaattaa aatattaatg gcgctttaat gatacaaatg aacaacttta cattcaatcg    41340
tcaatgggaa aggaagcaga attctgagga ttatgaaagt aaacaaaacg aagttcaaat    41400
tctactttat tttactttt tgtaactaat gaacaacttc ttccaaagac aagtaggaaa     41460
tacaaaaatt agccaggcat ggcacatgcc tgtagtcctg gttacttgga aggctgaagt    41520
gggtggatcg cttgagccgg gaaggcagag gctgtagtga gctgagatca catcactgca    41580
ctcaagcctg ggtgacagag caagaccctc tctgggaaaa aaaaaaaaaa aaataggctg    41640
ggcgcagtgg ctcacacttg taattccagc actttgggag gctgaggcag gtggttcacc    41700
tgaggtcagg agttctagac cagcctgacc aatatggtga aaccctgtct ctactaaaaa    41760
tacaaaaatt agccaggcat ggtggtgggc aattgtaatc ctagctactc gggaggctga    41820
```

-continued

```
ggcaggaaaa tcgcctgaac ccaagaggcg gaggtttcag tgagccgaga ttgcactagt   41880
gcactccagc ctgggcgaca gagcaagact tcatctcaaa ataaataaat aagtaagtaa   41940
ataaaattaa aaaatatata aaaataaaac aaagataagt aggaaccatc cttttttttt   42000
tttttttttt ttttttttaa agatagggtc tgtttctgat gcccaggctt gagtgtagtg   42060
gcatgatcat ggctcactgc aaccttgacc tctcaaatac aagtgactct cctacctcag   42120
cctcccaagt agctgggact acaggtgctt accaccccat ccggctcatt taaaaaaatt   42180
tttttgtaga ggtggggtct cactatgttg tatccaggct ggtctcattt taactttatt   42240
agaaaacaag cattgtttta tcagcttctt gttttttaa aactaaaaat aacactgcta   42300
ggttgtttct atgaagattc tctaaattta tttataacct taagaataac atgtagaaca   42360
aagtagatga ctgaatgatc tttgttgaat aaatatgaat ggatattcaa ataattaaaa   42420
atctcttaag atctcccatt ctttacagga tacagaaaa actcgttaat atggcctgac   42480 ttttacctttt gcagccttat ccaaactctg tggtcaagac aaacaggttg tccttatact   42540
tacaacgtcc ccctttgcct acaaagctct tctcatgact ctttgcctat cttaagttca   42600
cctatctgtc aaatctctgg gaatgcaaca tttcctcaag gtagccttct ctcctcccaa   42660
actagaacaa attcttcctg gggcattagg ttttttattgc actgtatgtc tcttcttcac   42720
agcaatcaca gttccaatgt tatatttgta ttcttagttg atttgtttct ttccaccttt   42780
agactataac cttctaaggg gtcacacata atatcgatca tcagttgtat cccttgtgca   42840
tagcacaggg catggcaggc aaatatgtgt gtaaataaac ttgttgaatg aatcaatgag   42900
acacactttt cttacccaaa gtataatggc aggataacat ttatcaatct attgcttctt   42960
gaaaaacaga tatgatgtgc ttaattttca ttttacatct caaataccaa tgcctaagga   43020
attcacagtc attttacaaa tctttttgac aaatgccttc attaatcacc acctgtttac   43080
aagtgctaaa taacatttttg gttacattct gtaaacatttc ctgcacttaa tgtcatctct   43140
agaatactgg ctaatatgaa gcacctggac ttcaggaaca caaacctgaa actaacacac   43200
caaactaaac tgttatgtaa atgacagaaa tgacacattt tggtctgcaa catctctaga   43260
tggcttttgg accaattcaa ctttaccac taaaaatcgg tcacctgact atagtcattt   43320
tgagctcatg ataaatgaat tacagatgaa aaataaatag tttgatgaca atctttacaa   43380
aagtttatct tcaaagaata ccaccagtca caggtattct aggctcctat caacttattt   43440
ggtcagggca gacttcactt ttcatgataa ttatgttctg aaaattctac aaacttaatg   43500
attacaaaca aaagtcatag tttgctcata aatcaggcct aggtctggat tctagttctt   43560 ccattttttca tttgttcact gaggcaagtg acttaaaatt ccctagcctc agtttcctca   43620
catgtaaaat cagataatga ttcctattcc taagatggtt ttgaggcttc aacaagataa   43680
gatgggcctc actcaagcat gctcagtact ctgtctctct ctctccggtt atgcagaaat   43740
tctattagga ttctgcaaag taaaataaat atttcagtaa aaattatgcc ctttattaat   43800
gaatctagat tttcagattt tccttaaatt tacttagtaa cttaagggct caaatattat   43860
agagatttgt atctagtatt ttaaagaaat gaaggtgtt aatcaaaatg ctgcacaaat   43920
aaatgctaca tttaacaaac agaatatcac aaccatacaa actaatcaga tataagaag   43980 tcagcaacag aaatctgatg ttgccttttag atcacacaat taggcaaaca aaaatagagt   44040
tccatcctcc tttggtcaag gccatggttg aagactgaat accaaatagg gaaataggaa   44100
aagccaggaa atggcaaatt agcaaaaact ggactcctta atttttatat tcattttcat   44160
```

-continued

```
atctcacttc taaaacttta attaaattca aataaaaacc aaaatggaac tgagataaag    44220
ccaaaaggaa agttatgtag gtcaaatgag aacctatatt gtccttaggc tctttgttgc    44280
tttctgttta aggaaaaact gcccaagtgc cttgacacat taaagatcaa gcaggaggtt    44340
ctgccgagag tccccatctg gcagccaggt tttgtcaagc aaattttgag aattctctac    44400
cctcccactt tctatctaat tatagcactt tataaaaacc attctctctc tgtctctgtc    44460
tctctctctc tctctctctc acacacacac acacacacac acacacacac acacacaccc    44520
tttctctctc tctctctctg aaacttatct gtattataat aacacaacac taggtatgga    44580
ttaatctgac aattttcccc taaaacagaa taaattcaaa aaggaaaacc tttcctctgt    44640
acacatgcac tatattctga caataataat tcctaaatta agtataatac attttcccta    44700
caggagttta aagaagttac agtaaagaat ctcttgtata aatatatatg ccagaacttg    44760
acccaaataa gtgctgagag gtataaatct caaaacagtt tccggactct tgtgaaatg     44820
tcttcagagt ctgcgatata ttttcttcaa ctaaattata caagtaagat attttgctgg    44880
gctgtgggaa tgccttacgg catgttactg tggagctcat ggtaaaatag aagaatata    44940
aataattaaa ataaaattga caaatgataa atgatttaat aaattagaaa ttcaaatgcc    45000
gggcactttt ctagaacctg gacacaaagc atgaacctaa caataacccc gccttcatga    45060
aaaatatgga ctatttgaaa attataacctg caacactaaa taaatattct tcattcttcc    45120
agtatattga gatgtttact ttcaattaga caatttgctt tcctctctga acacatagtt    45180
atgtgatggc tctataaaag atttaaaat aactatagaa ggaactattg gtaaagactg     45240
tgggatacta aaaatggcta caaagaaagt tatgacaaaa cctctgagtt tgaatggaag    45300
tcctactaga ttagagtcta agcctgtgac attatgcttc tggttcttgt tcttaaatgc    45360
ttttctcatt aatagtatgt aacttacttc ctggaatgcc attcattaaa aaaatattta    45420
atatttgcta aatgtcaata tttatgccag cacttttaaa gtacagaaac atggagtttc    45480
tttacctcat gcaaatatgc tgtgagaaag acttaagagc ctattgccta ctttgtggta    45540
caacactgaa gactcaccat ccaaaacaaa cagacttagt aaattcttgt gatttgcagt    45600
agttctgttc tataaggtta ccacaaacac tgaaatcatc gctcctgggg gaatacaagg    45660
ttatgtttcc gtgagccctc ggtcacaaca tgttcattaa ctgatcaata cataaccttg    45720
ttctatgtgt gtttctgttt aaaaagagca cttcagtgct acatttggag tctgttttaa    45780
acagcaaaat cactaataaa aagcacaaaa atgtaaaagc atggcactac atacactgtg    45840
acaagaaggc ttgtttatag tatgacagct gagacaagaa ggtagagcct cgctttgatc    45900
aacctctgct gggaaatgag catcaggtga atcaattttt caccactctg aatgaccgta    45960
aaagtgctcc aagtactgac tttggggtta cacataaatt ttagtaagca tgtgaatctg    46020
ccaatatgaa atctacaaat aatgagtacc aaatgcatat gagtcaaata tttcagtgcg    46080
gtatctgact tgattgccac tgaaagacac agtttggaaa acccctaata aataccgttt    46140
agttactatg cagacaaaga gttctacact agagtgcttc aattaagatg tctgaggctt    46200
tcataaatgg atgtttttta aaatgttatt tcctacctga tatattctaa agggatata     46260
acgaaatcca ttttcttctg caggatattc catgagtttc cgattgatgg cccaaaactg    46320
gtcaaatctg tctgtaatga                                                46340
```

<210> SEQ ID NO 67
<211> LENGTH: 773
<212> TYPE: DNA
<213> ORGANISM: Homo sapiens -continued

```
<400> SEQUENCE: 67
actgagagac aggactagct ggatttccta ggctgactaa gaatccctaa gcctagctgg      60
gaaggtgacc acatccacct ttaaacacgg ggcttgcaac ttagctcaca cctgaccaag     120
gaaggtgacc acaccctcct ttaaacacag agcttgtaac tcagctcaca cccgaccaat     180
caggtagtaa agagagctca ctaaaatacc aattaggcta aaaacaggag gtaaagaaat     240
aatcaaatca tctatcgcct gagagcacag ggggagggac aatgatcggg atataaaccc     300
aggcatttga gccagatcag gtaaccctct ttgggtcccc tcacactgta tgggagctct     360
gttttcactc tattaaatct tgcaactgca cactcttctg gtccatgttt gttccggctc     420
aagctgagct tttgctcgcc gtccaccact gctgaatgcc gccattgcag acctgccctt     480
gacttccacc cctccggatc cggcagagtg tccgctgcac tcctgatcca gcgaggcacc     540
cattgccact cccgatcagg ctaaaggctt gccattgttc ctgcacagct aagtgcctgg     600
gttcatccta atcaggctga acactggtcg ctgggttcca cggttctctt ccatgactca     660
cagcttctaa tagagctata acactcacca catgggccaa ggttccattc gttggaatcc     720
atgaggccaa gaaccccagg tcagagaata aaaggcccgc cccatcttgg gag            773

<210> SEQ ID NO 68
<211> LENGTH: 10
<212> TYPE: PRT
<213> ORGANISM: Homo sapiens

<400> SEQUENCE: 68

Phe Leu Gly Glu Glu Cys Cys Tyr Tyr Val
1               5                   10

<210> SEQ ID NO 69
<211> LENGTH: 10
<212> TYPE: PRT
<213> ORGANISM: Homo sapiens

<400> SEQUENCE: 69

Leu Leu Phe Gly Pro Cys Ile Phe Asn Leu
1               5                   10

<210> SEQ ID NO 70
<211> LENGTH: 10
<212> TYPE: PRT
<213> ORGANISM: Homo sapiens

<400> SEQUENCE: 70

Cys Leu Pro Leu Asn Phe Arg Pro Tyr Val
1               5                   10

<210> SEQ ID NO 71
<211> LENGTH: 10
<212> TYPE: PRT
<213> ORGANISM: Homo sapiens

<400> SEQUENCE: 71

Gly Leu Leu Ser Gln Trp Met Pro Trp Ile
1               5                   10

<210> SEQ ID NO 72
<211> LENGTH: 9
<212> TYPE: PRT
<213> ORGANISM: Homo sapiens
```

```
<400> SEQUENCE: 72

Cys Leu Pro Ser Gly Ile Phe Phe Val
1               5

<210> SEQ ID NO 73
<211> LENGTH: 9
<212> TYPE: PRT
<213> ORGANISM: Homo sapiens

<400> SEQUENCE: 73

Trp Met Pro Trp Ile Leu Pro Phe Leu
1               5

<210> SEQ ID NO 74
<211> LENGTH: 10
<212> TYPE: PRT
<213> ORGANISM: Homo sapiens

<400> SEQUENCE: 74

Ile Arg Trp Val Thr Pro Pro Thr Gln Ile
1               5                   10

<210> SEQ ID NO 75
<211> LENGTH: 10
<212> TYPE: PRT
<213> ORGANISM: Homo sapiens

<400> SEQUENCE: 75

Leu Arg Asn Thr Gly Pro Trp Gly Leu Leu
1               5                   10

<210> SEQ ID NO 76
<211> LENGTH: 10
<212> TYPE: PRT
<213> ORGANISM: Homo sapiens

<400> SEQUENCE: 76

Leu Arg Thr His Thr Arg Leu Val Ser Leu
1               5                   10

<210> SEQ ID NO 77
<211> LENGTH: 10
<212> TYPE: PRT
<213> ORGANISM: Homo sapiens

<400> SEQUENCE: 77

Lys Arg Val Pro Ile Leu Pro Phe Val Ile
1               5                   10

<210> SEQ ID NO 78
<211> LENGTH: 10
<212> TYPE: PRT
<213> ORGANISM: Homo sapiens

<400> SEQUENCE: 78

Cys Arg Cys Met Thr Ser Ser Ser Pro Tyr
1               5                   10

<210> SEQ ID NO 79
<211> LENGTH: 10
<212> TYPE: PRT
<213> ORGANISM: Homo sapiens

<400> SEQUENCE: 79
```

-continued

Thr Arg Val His Gly Thr Ser Ser Pro Tyr
1               5                   10

<210> SEQ ID NO 80
<211> LENGTH: 10
<212> TYPE: PRT
<213> ORGANISM: Homo sapiens

<400> SEQUENCE: 80

Ala Arg Glu Lys His Val Lys Glu Val Ile
1               5                   10

<210> SEQ ID NO 81
<211> LENGTH: 10
<212> TYPE: PRT
<213> ORGANISM: Homo sapiens

<400> SEQUENCE: 81

Ser Arg Ile Glu Ala Val Lys Leu Gln Met
1               5                   10

<210> SEQ ID NO 82
<211> LENGTH: 10
<212> TYPE: PRT
<213> ORGANISM: Homo sapiens

<400> SEQUENCE: 82

Ser Gln Trp Met Pro Trp Ile Leu Pro Phe
1               5                   10

<210> SEQ ID NO 83
<211> LENGTH: 9
<212> TYPE: PRT
<213> ORGANISM: Homo sapiens

<400> SEQUENCE: 83

Cys Tyr Tyr Val Asn Gln Ser Gly Ile
1               5

<210> SEQ ID NO 84
<211> LENGTH: 9
<212> TYPE: PRT
<213> ORGANISM: Homo sapiens

<400> SEQUENCE: 84

Phe Tyr Tyr Lys Leu Ser Gln Glu Leu
1               5

<210> SEQ ID NO 85
<211> LENGTH: 9
<212> TYPE: PRT
<213> ORGANISM: Homo sapiens

<400> SEQUENCE: 85

Thr Tyr Thr Thr Asn Ser Gln Cys Ile
1               5

<210> SEQ ID NO 86
<211> LENGTH: 9
<212> TYPE: PRT
<213> ORGANISM: Homo sapiens

<400> SEQUENCE: 86

Ser Phe Leu Val Pro Pro Met Thr Ile
1               5

<210> SEQ ID NO 87
<211> LENGTH: 9
<212> TYPE: PRT
<213> ORGANISM: Homo sapiens

<400> SEQUENCE: 87

Tyr Tyr Val Asn Gln Ser Gly Ile Val
1               5

<210> SEQ ID NO 88
<211> LENGTH: 9
<212> TYPE: PRT
<213> ORGANISM: Homo sapiens

<400> SEQUENCE: 88

Leu Phe Asn Thr Thr Leu Thr Gly Leu
1               5

<210> SEQ ID NO 89
<211> LENGTH: 9
<212> TYPE: PRT
<213> ORGANISM: Homo sapiens

<400> SEQUENCE: 89

Leu Phe Gly Pro Cys Ile Phe Asn Leu
1               5

<210> SEQ ID NO 90
<211> LENGTH: 9
<212> TYPE: PRT
<213> ORGANISM: Homo sapiens

<400> SEQUENCE: 90

Arg Trp Val Thr Pro Pro Thr Gln Ile
1               5

<210> SEQ ID NO 91
<211> LENGTH: 10
<212> TYPE: PRT
<213> ORGANISM: Homo sapiens

<400> SEQUENCE: 91

Leu Pro Phe Leu Gly Pro Leu Ala Ala Ile
1               5                   10

<210> SEQ ID NO 92
<211> LENGTH: 10
<212> TYPE: PRT
<213> ORGANISM: Homo sapiens

<400> SEQUENCE: 92

Leu Pro Tyr His Ile Phe Leu Phe Thr Val
1               5                   10

<210> SEQ ID NO 93
<211> LENGTH: 10
<212> TYPE: PRT
<213> ORGANISM: Homo sapiens

<400> SEQUENCE: 93

Gly Ala Leu Gly Thr Gly Ile Gly Gly Ile
1               5                   10

```
<210> SEQ ID NO 94
<211> LENGTH: 10
<212> TYPE: PRT
<213> ORGANISM: Homo sapiens

<400> SEQUENCE: 94

Leu Pro Phe Val Ile Gly Ala Gly Val Leu
1               5                   10

<210> SEQ ID NO 95
<211> LENGTH: 9
<212> TYPE: PRT
<213> ORGANISM: Homo sapiens

<400> SEQUENCE: 95

Arg Arg Pro Leu Asp Arg Pro Ala Ser
1               5

<210> SEQ ID NO 96
<211> LENGTH: 9
<212> TYPE: PRT
<213> ORGANISM: Homo sapiens

<400> SEQUENCE: 96

Phe Arg Pro Tyr Val Ser Ile Pro Val
1               5

<210> SEQ ID NO 97
<211> LENGTH: 9
<212> TYPE: PRT
<213> ORGANISM: Homo sapiens

<400> SEQUENCE: 97

Arg Arg Ala Leu Asp Leu Leu Thr Ala
1               5

<210> SEQ ID NO 98
<211> LENGTH: 9
<212> TYPE: PRT
<213> ORGANISM: Homo sapiens

<400> SEQUENCE: 98

Trp Arg Met Gln Arg Pro Gly Asn Ile
1               5

<210> SEQ ID NO 99
<211> LENGTH: 10
<212> TYPE: PRT
<213> ORGANISM: Homo sapiens

<400> SEQUENCE: 99

Asp Arg Ile Gln Arg Arg Ala Glu Glu Leu
1               5                   10

<210> SEQ ID NO 100
<211> LENGTH: 10
<212> TYPE: PRT
<213> ORGANISM: Homo sapiens

<400> SEQUENCE: 100

Leu Arg Thr His Thr Arg Leu Val Ser Leu
1               5                   10

<210> SEQ ID NO 101
<211> LENGTH: 10
```

```
<212> TYPE: PRT
<213> ORGANISM: Homo sapiens

<400> SEQUENCE: 101

Glu Arg Val Ala Asp Ser Leu Val Thr Leu
1               5                   10

<210> SEQ ID NO 102
<211> LENGTH: 10
<212> TYPE: PRT
<213> ORGANISM: Homo sapiens

<400> SEQUENCE: 102

Leu Phe Gly Pro Cys Ile Phe Asn Leu Leu
1               5                   10

<210> SEQ ID NO 103
<211> LENGTH: 10
<212> TYPE: PRT
<213> ORGANISM: Homo sapiens

<400> SEQUENCE: 103

Gln Phe Tyr Tyr Lys Leu Ser Gln Glu Leu
1               5                   10

<210> SEQ ID NO 104
<211> LENGTH: 10
<212> TYPE: PRT
<213> ORGANISM: Homo sapiens

<400> SEQUENCE: 104

Gln Trp Met Pro Trp Ile Leu Pro Phe Leu
1               5                   10

<210> SEQ ID NO 105
<211> LENGTH: 10
<212> TYPE: PRT
<213> ORGANISM: Homo sapiens

<400> SEQUENCE: 105

Cys Tyr Tyr Val Asn Gln Ser Gly Ile Val
1               5                   10

<210> SEQ ID NO 106
<211> LENGTH: 10
<212> TYPE: PRT
<213> ORGANISM: Homo sapiens

<400> SEQUENCE: 106

Asn Phe Val Ser Ser Arg Ile Glu Ala Val
1               5                   10

<210> SEQ ID NO 107
<211> LENGTH: 9
<212> TYPE: PRT
<213> ORGANISM: Homo sapiens

<400> SEQUENCE: 107

Gly Pro Leu Val Ser Asn Leu Glu Ile
1               5

<210> SEQ ID NO 108
<211> LENGTH: 9
<212> TYPE: PRT
<213> ORGANISM: Homo sapiens
```

```
<400> SEQUENCE: 108

Leu Pro Leu Asn Phe Arg Pro Tyr Val
1               5

<210> SEQ ID NO 109
<211> LENGTH: 10
<212> TYPE: PRT
<213> ORGANISM: Homo sapiens

<400> SEQUENCE: 109

Leu Pro Phe Leu Gly Pro Leu Ala Ala Ile
1               5                   10

<210> SEQ ID NO 110
<211> LENGTH: 10
<212> TYPE: PRT
<213> ORGANISM: Homo sapiens

<400> SEQUENCE: 110

Glu Pro Lys Met Gln Ser Lys Thr Lys Ile
1               5                   10

<210> SEQ ID NO 111
<211> LENGTH: 10
<212> TYPE: PRT
<213> ORGANISM: Homo sapiens

<400> SEQUENCE: 111

Leu Pro Tyr His Ile Phe Leu Phe Thr Val
1               5                   10

<210> SEQ ID NO 112
<211> LENGTH: 9
<212> TYPE: PRT
<213> ORGANISM: Homo sapiens

<400> SEQUENCE: 112

Arg Glu Lys His Val Lys Glu Val Ile
1               5

<210> SEQ ID NO 113
<211> LENGTH: 10
<212> TYPE: PRT
<213> ORGANISM: Homo sapiens

<400> SEQUENCE: 113

Lys Pro Arg Asn Lys Arg Val Pro Ile Leu
1               5                   10

<210> SEQ ID NO 114
<211> LENGTH: 9
<212> TYPE: PRT
<213> ORGANISM: Homo sapiens

<400> SEQUENCE: 114

Val Val Leu Gln Asn Arg Arg Ala Leu
1               5

<210> SEQ ID NO 115
<211> LENGTH: 10
<212> TYPE: PRT
<213> ORGANISM: Homo sapiens

<400> SEQUENCE: 115
```

Ala Val Val Gln Asn Arg Arg Ala Leu
1               5                   10

<210> SEQ ID NO 116
<211> LENGTH: 9
<212> TYPE: PRT
<213> ORGANISM: Homo sapiens

<400> SEQUENCE: 116

Leu Pro Phe Val Ile Gly Ala Gly Val
1               5

<210> SEQ ID NO 117
<211> LENGTH: 9
<212> TYPE: PRT
<213> ORGANISM: Homo sapiens

<400> SEQUENCE: 117

Asp Leu Tyr Ser Tyr Val Ile Ser Lys
1               5

<210> SEQ ID NO 118
<211> LENGTH: 10
<212> TYPE: PRT
<213> ORGANISM: Homo sapiens

<400> SEQUENCE: 118

Thr Glu Gln Asp Leu Tyr Ser Tyr Val Ile
1               5                   10

<210> SEQ ID NO 119
<211> LENGTH: 2615
<212> TYPE: DNA
<213> ORGANISM: Homo sapiens

<400> SEQUENCE: 119

```
gaattccggg aagccagacg gttaacacag acaaagtgct gccgtgacac tcggccctcc      60
agtgttgcgg agaggcaaga gcagcgaccg cgcacctgtc cgcccggagc tgggacgcgc     120
gcccgggcgg ccggacgaag cgaggaggga ccgccgaggc tgcccccaag tgtaactcca     180
gcactgtgag gtttcaggga ttggcagagg ggaccaaggg gacatgaaaa tggacatgga     240
ggatgcggat atgactctgt ggacagaggc tgagtttgaa gagaagtgta catacattgt     300
gaacgaccac ccctgggatt ctggtgctga tggcggtact tcggttcagg cggaggcatc     360
cttaccaagg aatctgcttt tcaagtatgc caccaacagt gaagaggtta ttggagtgat     420
gagtaaagaa tacataccaa agggcacacg ttttggaccc ctaataggtg aaatctacac     480
caatgacaca gttcctaaga cgccaacaga gaaatatttt tggaggatct attccagagg     540
ggagcttcac cacttcattg acggctttaa tgaagagaaa agcaactgga tgcgctatgt     600
gaatccagca cactctcccc gggagcaaaa cctggctgcg tgtcagaacg ggatgaacat     660
ctacttctac accattaagc ccatccctgc caaccaggaa cttcttgtgt ggtattgtcg     720
ggactttgca gaaaggcttc actaccccta tcccggagag ctgacaatga tgaatctcac     780
acaaacacag agcagtctaa agcaaccgag cactgagaaa atgaactct  gcccaaagaa     840
tgtcccaaag agagagtaca gcgtgaaaga atcctaaaa ttggactcca accctccaa      900
aggaaaggac ctctaccgtt ctaacatttc acccctcaca tcagaaaagg acctcgatga     960
ctttagaaga cgtgggagcc ccgaaatgcc cttctaccct cgggtcgttt accccatccg    1020
```

```
ggcccctctg ccagaagact ttttgaaagc ttccctggcc tacgggatcg agagacccac    1080
gtacatcact cgctccccca ttccatcctc caccactcca agccctctg caagaagcag     1140 ccccgaccaa agcctcaaga gctccagccc tcacagcagc cctgggaata cggtgtcccc    1200
tgtgggcccc ggctctcaag agcaccggga ctcctacgct tacttgaacg cgtcctacgg    1260
cacggaaggt ttgggctcct accctggcta cgcacccctg ccccacctcc cgccagcttt    1320
catcccctcg tacaacgctc actacccaa gttcctcttg cccccctacg gcatgaattg     1380
taatggcctg agcgctgtga gcagcatgaa tggcatcaac aactttggcc tcttcccgag    1440
gctgtgccct gtctacagca atctcctcgg tgggggcagc ctgccccacc ccatgctcaa    1500
ccccacttct ctcccgagct cgctgccctc agatggagcc cggaggttgc tccagccgga    1560
gcatcccagg gaggtgcttg tcccggcgcc ccacagtgcc ttctccttta ccggggccgc    1620
cgccagcatg aaggacaagg cctgtagccc cacaagcggg tctcccacgg cgggaacagc    1680
cgccacggca gaacatgtgg tgcagcccaa agctacctca gcagcgatgg cagcccccag    1740
cagcgacgaa gccatgaatc tcattaaaaa caaaagaaac atgaccggct acaagaccct    1800
tccctacccg ctgaagaagc agaacggcaa gatcaagtac gaatgcaacg tttgcgccaa    1860
gactttcggc cagctctcca atctgaaggt ccacctgaga gtgcacagtg gagaacggcc    1920
tttcaaatgt cagacttgca acaagggctt tactcagctc gcccacctgc agaaacacta    1980
cctggtacac acgggagaaa agccacatga atgccaggtc tgccacaaga gatttagcag    2040
caccagcaat ctcaagaccc acctgcgact ccattctgga gagaaaccat accaatgcaa    2100
ggtgtgccct gccaagttca cccagtttgt gcacctgaaa ctgcacaagc gtctgcacac    2160
ccgggagcgg ccccacaagt gctcccagtg ccacaagaac tacatccatc tctgtagcct    2220
caaggttcac ctgaaaggga actgcgctgc ggccccggcg cctgggctgc ccttggaaga    2280
tctgacccga atcaatgaag aaatcgagaa gtttgacatc agtgacaatg ctgaccggct    2340
cgaggacgtg gaggatgaca tcagtgtgat ctctgtagtg gagaaggaaa ttctggccgt    2400
ggtcagaaaa gagaagaag aaactggcct gaaagtgtct ttgcaaagaa acatggggaa    2460
tggactcctc tcctcagggt gcagccttta tgagtcatca gatctacccc tcatgaagtt    2520
gcctcccagc aacccactac ctctggtacc tgtaaaggtc aaacaagaaa cagttgaacc    2580
aatggatcct taagatttc agaaaacact tattt                               2615
```

<210> SEQ ID NO 120
<211> LENGTH: 29
<212> TYPE: PRT
<213> ORGANISM: Homo sapiens

<400> SEQUENCE: 120

Leu Gln Asn Arg Arg Ala Leu Asp Leu Leu Thr Ala Glu Arg Gly Gly
1               5                   10                  15

Thr Cys Leu Phe Leu Gly Glu Glu Cys Cys Tyr Tyr Val
            20                  25

<210> SEQ ID NO 121
<211> LENGTH: 21
<212> TYPE: DNA
<213> ORGANISM: Homo sapiens

<400> SEQUENCE: 121
cttcaaacaa caaccaggag g                                               21

```
-continued

<210> SEQ ID NO 122
<211> LENGTH: 20
<212> TYPE: DNA
<213> ORGANISM: Homo sapiens

<400> SEQUENCE: 122
ttggggaggt tggccgacga                                              20
```